US011608362B2

(12) United States Patent
Brough et al.

(10) Patent No.: US 11,608,362 B2
(45) Date of Patent: Mar. 21, 2023

(54) HEPATITIS B VACCINES AND USES OF THE SAME

(71) Applicant: Precigen, Inc., Germantown, MD (US)

(72) Inventors: Douglas E. Brough, Germantown, MD (US); Cheryl G. Bolinger, Germantown, MD (US); Ramya Yarlagadda, Blacksburg, VA (US); Vinodhbabu Kurella, Blacksburg, VA (US); Prabakaran Ponraj, Blacksburg, VA (US); Simon Metenou, Germantown, MD (US); Kuan-Fu Ding, Blacksburg, VA (US)

(73) Assignee: Precigen, Inc., Germantown, MD (US)

( * ) Notice: Subject to any disclaimer, the term of this patent is extended or adjusted under 35 U.S.C. 154(b) by 0 days.

(21) Appl. No.: 16/978,570

(22) PCT Filed: Mar. 6, 2019

(86) PCT No.: PCT/US2019/020930

§ 371 (c)(1),
(2) Date: Sep. 4, 2020

(87) PCT Pub. No.: WO2019/173463

PCT Pub. Date: Sep. 12, 2019

(65) Prior Publication Data

US 2021/0015911 A1 Jan. 21, 2021

Related U.S. Application Data

(60) Provisional application No. 62/639,354, filed on Mar. 6, 2018.

(51) Int. Cl.

| | |
|---|---|
| ***C07K 14/02*** | (2006.01) |
| ***A61K 39/29*** | (2006.01) |
| ***C12N 15/86*** | (2006.01) |
| ***C07K 14/005*** | (2006.01) |
| ***A61K 39/12*** | (2006.01) |
| ***C12N 7/00*** | (2006.01) |
| ***A61K 48/00*** | (2006.01) |
| ***C12N 15/861*** | (2006.01) |

(52) U.S. Cl.

CPC ............ *C07K 14/005* (2013.01); *A61K 39/12* (2013.01); *A61K 39/292* (2013.01); *A61K 48/0066* (2013.01); *C07K 14/02* (2013.01); *C12N 7/00* (2013.01); *C12N 15/861* (2013.01); *C07K 2319/33* (2013.01); *C12N 2710/20022* (2013.01); *C12N 2710/20034* (2013.01)

(58) Field of Classification Search

None

See application file for complete search history.

(56) References Cited

U.S. PATENT DOCUMENTS

| | | | |
|---|---|---|---|
| 4,985,461 | A | 1/1991 | Hsu et al. |
| 5,117,057 | A | 5/1992 | Hsu et al. |
| 5,122,464 | A | 6/1992 | Wilson et al. |
| 5,225,443 | A | 7/1993 | Murphy et al. |
| 5,283,173 | A | 2/1994 | Fields et al. |
| 5,350,674 | A | 9/1994 | Boenisch et al. |
| 5,378,726 | A | 1/1995 | Yanagi et al. |
| 5,530,028 | A | 6/1996 | Lidert et al. |
| 5,585,362 | A | 12/1996 | Wilson et al. |
| 5,770,359 | A | 6/1998 | Wilson et al. |
| 5,837,511 | A | 11/1998 | Falck-Pedersen et al. |
| 5,851,806 | A | 12/1998 | Kovesdi et al. |
| 5,880,333 | A | 3/1999 | Goff et al. |
| 5,885,827 | A | 3/1999 | Wabl et al. |
| 5,994,106 | A | 11/1999 | Kovesdi et al. |
| 5,994,128 | A | 11/1999 | Fallaux et al. |
| 5,998,205 | A | 12/1999 | Hallenbeck et al. |
| 6,013,836 | A | 1/2000 | Hsu et al. |
| 6,033,908 | A | 3/2000 | Bout et al. |
| 6,127,175 | A | 10/2000 | Vigne et al. |
| 6,225,289 | B1 | 5/2001 | Kovesdi et al. |
| 6,265,173 | B1 | 7/2001 | Evans et al. |
| 6,482,616 | B1 | 11/2002 | Kovesdi et al. |
| 6,489,458 | B2 | 12/2002 | Hackett et al. |
| 6,514,943 | B2 | 2/2003 | Kovesdi et al. |
| 6,613,752 | B2 | 9/2003 | Kay et al. |
| 6,677,156 | B2 | 1/2004 | Brough et al. |
| 6,682,929 | B2 | 1/2004 | Brough et al. |
| 7,091,038 | B2 | 8/2006 | Palli et al. |
| 7,148,203 | B2 | 12/2006 | Hackett et al. |
| 7,195,896 | B2 | 3/2007 | Kovesdi et al. |

(Continued)

FOREIGN PATENT DOCUMENTS

| | | | |
|---|---|---|---|
| EP | 0234994 | B1 | 9/1991 |
| EP | 0461809 | B1 | 12/1994 |

(Continued)

OTHER PUBLICATIONS

Stahl et al. Immunogenicity of peptide fusions to hepatitis B virus core antigen. Proc. Natl. Acad Sci. USA 86 (1989), 86: 6283-6287.*
Chen et al. Fusion protein linkers: Property, design and functionality. Advanced Drug Delivery Reviews 65 (2013) 1357-1369.*
Altschul, S.F., et al., "Basic Local Alignment Search Tool," Journal of Molecular Biology 215(3):403-410, Elsevier, United Kingdom (Oct. 1990).
Altschul, S.F., et al., "Gapped BLAST and PSI-Blast: A New Generation of Protein Database Search Programs," Nucleic Acids Research 25(17):3389-3402, Oxford University Press, United Kingdom (Sep. 1997).

(Continued)

*Primary Examiner* — Nianxiang Zou
(74) *Attorney, Agent, or Firm* — Sterne, Kessler, Goldstein & Fox P.L.L.C.

(57) ABSTRACT

Provided herein are engineered hepatitis B virus (HBV) molecular vaccine constructs. Vaccine constructs can also include ligand-inducible engineered gene switch systems for modulating expression of heterologous genes, such as a cytokines, in host cells.

16 Claims, 26 Drawing Sheets

Specification includes a Sequence Listing.

(56) References Cited

U.S. PATENT DOCUMENTS

| | | | | |
|---|---|---|---|---|
| 7,531,326 | B2 | 5/2009 | Kapitskaya et al. | |
| 7,563,879 | B2 | 7/2009 | Palli | |
| 7,601,508 | B2 | 10/2009 | Palli et al. | |
| 7,776,587 | B2 | 8/2010 | Palli et al. | |
| 7,807,417 | B2 | 10/2010 | Palli et al. | |
| 7,829,676 | B2 | 11/2010 | Zhang et al. | |
| 7,919,269 | B2 | 4/2011 | Zhang et al. | |
| 7,935,510 | B2 | 5/2011 | Palli et al. | |
| 7,985,739 | B2 | 7/2011 | Kay et al. | |
| 8,021,878 | B2 | 9/2011 | Palli | |
| 8,030,067 | B2 | 10/2011 | Zhang et al. | |
| 8,076,454 | B2 | 12/2011 | Palli et al. | |
| 8,076,517 | B2 | 12/2011 | Hormann et al. | |
| 8,105,825 | B2 | 1/2012 | Dhadialla et al. | |
| 8,168,426 | B2 | 5/2012 | Dhadialla et al. | |
| 8,202,718 | B2 | 6/2012 | Palli et al. | |
| 8,227,432 | B2 | 7/2012 | Hackett et al. | |
| 8,236,556 | B2 | 8/2012 | Kapitskaya et al. | |
| 8,293,233 | B2 | 10/2012 | Tanha | |
| 8,497,093 | B2 | 7/2013 | Palli | |
| 8,598,409 | B2 | 12/2013 | Kapitskaya et al. | |
| 8,603,950 | B2 | 12/2013 | Bowers et al. | |
| 8,715,959 | B2 | 5/2014 | Palli et al. | |
| 9,228,180 | B2 | 1/2016 | Izsvak et al. | |
| 9,249,207 | B2 | 2/2016 | Palli et al. | |
| 9,402,919 | B2 | 8/2016 | Roeth et al. | |
| 9,492,482 | B2 | 11/2016 | Beech et al. | |
| 9,493,540 | B2 | 11/2016 | Palli et al. | |
| 2004/0049037 | A1 | 3/2004 | Tice et al. | |
| 2004/0171651 | A1 | 9/2004 | Hormann et al. | |
| 2005/0209283 | A1 | 9/2005 | Hormann et al. | |
| 2005/0287161 | A1 | 12/2005 | Dubin et al. | |
| 2006/0020146 | A1 | 1/2006 | Hormann et al. | |
| 2006/0100416 | A1 | 5/2006 | Palli et al. | |
| 2007/0203326 | A1 | 8/2007 | Dedhar et al. | |
| 2008/0233650 | A1 | 9/2008 | Gall et al. | |
| 2009/0123441 | A1 | 5/2009 | Braughler et al. | |
| 2009/0136465 | A1 | 5/2009 | Merenick et al. | |
| 2010/0175141 | A1 | 7/2010 | Collins et al. | |
| 2011/0117072 | A1 | 5/2011 | Izsvak et al. | |
| 2011/0212528 | A1 | 9/2011 | Palli et al. | |
| 2011/0268766 | A1 | 11/2011 | Beech et al. | |
| 2012/0167239 | A1 | 6/2012 | Palli et al. | |
| 2013/0195800 | A1 | 8/2013 | Roeth et al. | |
| 2013/0243805 | A1 * | 9/2013 | Apelian | A61K 36/12 435/254.2 |
| 2016/0208285 | A1 | 7/2016 | Roeth et al. | |
| 2018/0002719 | A1 | 1/2018 | Roeth et al. | |
| 2021/0024586 | A1 | 1/2021 | Brough et al. | |

FOREIGN PATENT DOCUMENTS

| | | | |
|---|---|---|---|
| JP | 2008536490 | A | 9/2008 |
| JP | 2013501038 | A | 1/2013 |
| JP | 2013527753 | A | 7/2013 |
| JP | 2014507144 | A | 3/2014 |
| JP | 2014527404 | A | 10/2014 |
| JP | 2017518051 | A | 7/2017 |
| WO | WO-9208796 | A1 | 5/1992 |
| WO | WO-9428143 | A1 | 12/1994 |
| WO | WO-9428152 | A1 | 12/1994 |
| WO | WO-9502697 | A1 | 1/1995 |
| WO | WO-9516772 | A1 | 6/1995 |
| WO | WO-9534671 | A1 | 12/1995 |
| WO | WO-9622378 | A1 | 7/1996 |
| WO | WO-9700326 | A1 | 1/1997 |
| WO | WO-9712986 | A2 | 4/1997 |
| WO | WO-9721826 | A2 | 6/1997 |
| WO | WO-9738117 | A1 | 10/1997 |
| WO | WO-9902683 | A1 | 1/1999 |
| WO | WO-9958155 | A1 | 11/1999 |
| WO | WO-0000628 | B1 | 3/2000 |
| WO | WO-0034444 | A2 | 6/2000 |
| WO | WO-0170816 | A2 | 9/2001 |
| WO | WO-0198333 | A2 | 12/2001 |
| WO | WO-0229075 | A2 | 4/2002 |
| WO | WO-02066612 | A2 | 8/2002 |
| WO | WO-02066613 | A2 | 8/2002 |
| WO | WO-02066614 | A2 | 8/2002 |
| WO | WO-02066615 | A2 | 8/2002 |
| WO | WO-03020879 | A2 | 3/2003 |
| WO | WO-03022311 | A1 | 3/2003 |
| WO | WO-03027266 | A2 | 4/2003 |
| WO | WO-03027289 | A1 | 4/2003 |
| WO | WO-2005108617 | A2 | 11/2005 |
| WO | WO-2008145745 | A1 | 12/2008 |
| WO | WO-2008153801 | A1 | 12/2008 |
| WO | WO-2009045370 | A2 | 4/2009 |
| WO | WO-2009048560 | A1 | 4/2009 |
| WO | WO-2010042189 | A2 | 4/2010 |
| WO | WO-2011015656 | A3 | 2/2011 |
| WO | WO-2011119773 | A1 | 9/2011 |
| WO | WO-2012109404 | A1 | 8/2012 |
| WO | WO-2012122025 | A2 | 9/2012 |
| WO | WO-2013007772 | A1 | 1/2013 |
| WO | WO-2013052799 | A2 | 4/2013 |
| WO | WO-2013052811 | A2 | 4/2013 |
| WO | WO-2013052832 | A2 | 4/2013 |
| WO | WO-2015095249 | A1 | 6/2015 |
| WO | WO-2015187009 | A1 | 12/2015 |
| WO | WO-2016020538 | A1 | 2/2016 |
| WO | WO-2016048903 | A1 | 3/2016 |
| WO | WO-2016145146 | A1 | 9/2016 |
| WO | WO-2017037280 | A1 | 3/2017 |
| WO | WO-2017062953 | A1 | 4/2017 |
| WO | WO-2017070284 | A1 | 4/2017 |
| WO | WO-2017083750 | A1 | 5/2017 |
| WO | WO-2017096432 | A1 | 6/2017 |
| WO | WO-2019173463 | A1 | 9/2019 |
| WO | WO-2019173465 | A1 | 9/2019 |

OTHER PUBLICATIONS

Bai, M., et al., "Mutations That Alter an Arg-gly-asp (Rgd) Sequence in the Adenovims Type 2 Penton Base Protein Abolish its Cell-rounding Activity and Delay Virus Reproduction in Flat Cells," Journal of Virology 67(9):5198-5205, American Society for Microbiology, United States (Sep. 1993).

Biegert, A., and Soding, J., "Sequence Context-specific Profiles for Homology Searching," Proc Natl Acad Sci USA 106(10):3770-3775, National Academy of Sciences, United States (Mar. 2009).

Bird, R.E., et al., "Single-chain Antigen-binding Proteins," Science 242(4877):423-426, Association for the Advancement of Science, United States (Oct. 1988).

Boulanger, P., et al., "Characterization of Adenovirus Protein Ix," The Journal of General Virology 44(3):783-800, Press for the Society for General Microbiology, United Kingdom (Sep. 1979).

Brash, D.E., et al., "Strontium Phosphate Transfection of Human Cells in Primary Culture: Stable Expression of the Simian Virus 40 Large-T-Antigen Gene in Primary Human Bronchial Epithelial Cells," Molecular and Cellular Biology, 7(5):2031-2034, American Society for Microbiology, United States (May 1987).

Brough, D.E., et al., "Activation of Transgene Expression by Early Region 4 is Responsible for a High Level of Persistent Transgene Expression From Adenovirus Vectors in Vivo," Journal of Virology 71(12):9206-9213, American Society for Microbiology, United States (Dec. 1997).

Chen, H.H., et al., "Persistence in Muscle of an Adenoviral Vector that Lacks all Viral Genes," Proc Natl Acad Sci USA 94(5):1645-1650, National Academy of Sciences, United States (Mar. 1997).

Christopherson, K.S., et al., "Ecdysteroid-dependent Regulation of Genes in Mammalian Cells by a *Drosophila ecdysone* Receptor and Chimeric Transactivators," Proc Natl Acad Sci USA 89(14):6314-6318, National Academy of Sciences, United States (1992).

Chroboczek, J., et al., "The Sequence of the Genome of Adenovims Type 5 and its Comparison With the Genome of Adenovirus Type 2," Virology 186(1):280-285, Academic Press, United States (Jan. 1992).

(56) References Cited

OTHER PUBLICATIONS

Colbere-Garapin, F., et al., "A New Dominant Hybrid Selective Marker for Higher Eukaryotic Cells," Journal of Molecular Biology 150(1):1-14, Academic Press, United Kingdom (Jul. 1981).
Conese, M., et al., "Gene therapy progress and prospects: episomally maintained selfreplicating systems," Gene Therapy 11(24):1735-41, Nature Publishing Group, United Kingdom (2004).
Corpet, F, "Multiple Sequence Alignment With Hierarchical Clustering," Nucleic Acids Research 16(22):10881-10890, Oxford University Press, United Kingdom (Nov. 1988).
Crawford-Miksza, L.C., and Schnurr, D.P., "Analysis of 15 Adenovims Hexon Proteins Reveals the Location and Structure of Seven Hypervariable Regions Containing Serotype-specific Residues," Journal of Virology 70(3): 1836-1844, American Society for Microbiology, United States (Mar. 1996).
Curiel, D.T., et al., "High-efficiency gene transfer mediated by adenovirus coupled to DNA-polylysine complexes," *Hum Gene Ther 3*(2):147-54, Mary Ann Liebert Inc., United States (1992).
Devaux, C., et al., "Structure of Adenovims Fibre. I. Analysis of Crystals of Fibre From Adenovirus Serotypes 2 and 5 by Electron Microscopy and X-ray Crystallography," Journal of Molecular Biology 215(4):567-588, Academic Press, United Kingdom (Oct. 1990).
Field, J., et al., "Properties of the Adenovirus DNA Polymerase," The Journal of Biological Chemistry 259(15):9487-9495, American Society for Biochemistry and Molecular Biology, United States (Aug. 1984).
Funston, G.M., et al., "Expression of Heterologous Genes in Oncolytic Adenoviruses Using Picomaviral 2a Sequences That Trigger Ribosome Skipping," The Journal of General Virology 89(Pt 2): 389-396, Cambridge Univ. Press for the Society for General Microbiology, United Kingdom (Feb. 2008).
Gall, J.G.D., et al., "Construction and Characterization of Hexon-chimeric Adenoviruses: Specification of Adenovims Serotype," Journal of Virology 72(12):10260-10264, American Society for Microbiology, United States (Sep. 1998).
Genbank, "E3 14.7K [Human adenovirus 5]," Accession No. AP 000224.1, accessed at https://www.ncbi.nlm.nih.gov/protein/AP_000224, accessed on Dec. 10, 2020, 1 page.
GenBank,"E3 12.5K [Human adenovims 5]," Accession No. AP_000218.1, accessed at https://www.ncbi.nlm.nih.gov/protein/56160551/, accessed on Dec. 10, 2020, 1 page.
Ghosh-Choudhury, G., et al., "Protein Ix, A Minor Component of the Human Adenovirus Capsid, is Essential for the Packaging of Full Length Genomes," The EMBO Journal 6(6):1733-1739, Wiley Blackwell, United Kingdom (Jun. 1987).
Ginsberg, H.S., et al., "A Proposed Terminology for the Adenovirus Antigens and Virion Morphological Subunits," Virology 28(4):782-783, Academic Press, United States (Apr. 1966).
Graham, F.L., et al., "Characteristics of a Human Cell Line Transformed by Dna From Human Adenovirus Type," The Journal of General Virology 36(1):59-74, Microbiology Society, United Kingdom (Jul. 1977).
Green, N.M., et al., "Evidence for a Repeating Cross Sheet Structure in the Adenovirus Fibre," The EMBO Journal 2(8):1357-1365, IRL Press Limited, United Kingdom (Jun. 1983).
Henikoff, S. and Henikoff, J.G., "Amino Acid Substitution Matrices from Protein Blocks," Proc Natl Acad Sci USA 89(22):10915-10919, National Academy of Sciences, United States (Nov. 1992).
Henry, L.J., et al., "Characterization of the Knob Domain of the Adenovirus Type 5 Fiber Protein Expressed in *Escherichia coli*," Journal of Virology 68(8): 5239-5246, American Society for Microbiology, United States (Aug. 1994).
Higgins, D.G and Sharp, P.M, "Clustal: A Package for Performing Multiple Sequence Alignment on a Microcomputer," Gene 73(1):237-244, Elsevier, Netherlands (Dec. 1988).
Higgins, D.G., and Sharp, P.M., "Fast and Sensitive Multiple Sequence Alignments on a Microcomputer," Computer Applications in the Biosciences 5(2):151-153, Oxford University Press, United Kingdom (Apr. 1989).
Holliger, P, and Hudson, P.J., "Engineered Antibody Fragments and the Rise of Single Domains," Nature Biotechnology 23(9):1126-1136, Nature Publishing Group, United Kingdom (2005).
Horwitz, M.S., "Adenoviridae and their replication" in *Fields Virology*, 2nd Edition, pp. 1679-1721, Fields B.N., Knipe D.M., et al., eds., Raven Press, Ltd., United States (1990).
Huang, X., et al., "Parallelization of a Local Similarity Algorithm," Computer Applications in the Biosciences 8(2):155-165, Oxford University Press, United Kingdom (Apr. 1992).
Hurton, L.V., et al., "Tethered I1-15 Augments Antitumor Activity and Promotes a Stem-cell Memory Subset in Tumor-specific T Cells," Proc Natl Acad Sci USA 113(48): E7788-E7791, National Academy of Sciences, United States (Nov. 2016).
Huston, J.S., et al., "Protein Engineering of Antibody Binding Sites: Recovery of Specific Activity in an Anti-digoxin Single-chain Fv Analogue Produced in *Escherichia coli*," Proc Natl Acad Sci USA 85(16):5879-5883, National Academy of Sciences, United States (Aug. 1988).
International Search Report and Written Opinion for International Application No. PCT/US2019/020930, ISA/US, Alexandria, VA, dated Jul. 22, 2019, 13 pages.
International Search Report and Written Opinion for International Application No. PCT/US2019/020933, ISA/US, Alexandria, VA, dated Jul. 23, 2019, 13 pages.
Ivics, Z., et al., "Molecular Reconstruction of Sleeping Beauty, a Tcl-like Transposon From Fish, and its Transposition in Human Cells," Cell 91(4):501-510, MIT Press, United States (Nov. 1997).
Jin, Z., et al., "The Hyperactive Sleeping Beauty Transposase Sb100x Improves the Genetic Modification of T Cells to Express a Chimeric Antigen Receptor," Gene Therapy 18(9):849-856, Macmillan Press Ltd, United Kingdom (Sep. 2011).
Johnston, S.A., "Biolistic Transformation: Microbes to Mice," Nature 346(6286):776-777, Nature Publishing Group, United Kingdom (Aug. 1990).
Jornvall, H., et al., "The Adenovirus Hexon Protein. The Primary Structure of the Polypeptide and its Correlation With the Hexon Gene," The Journal of Biological Chemistry 256(12):6181-6186, American Society for Biochemistry and Molecular Biology, United States (Jun. 1981).
Kent, R.B., et al., "Ouabain resistance conferred by expression of the cDNA for a murine Na+, K+-ATPase alpha subunit," Science 237(4817):901-903, American Association for the Advancement of Science, United States (Aug. 1987).
Kochanek, S., "High-capacity Adenoviral Vectors for Gene Transfer and Somatic Gene Therapy," Human Gene Therapy 10(15):2451-2459, Mary Ann Liebert Inc., United States (Oct. 1999).
Lowy, I., et al., "Isolation of Transforming DNA: Cloning the Hamster aprt Gene," Cell 22(3):817-823, Cell Press, United States (Dec. 1980).
Lutz, P., et al., "The Product of the Adenovirus Intermediate Gene Ix is a Transcriptional Activator," Journal of Virology 71(7): 5102-5109, American Society For Microbiology, United States (Jul. 1997).
Mates, L., et al., "Molecular Evolution of a Novel Hyperactive Sleeping Beauty Transposase Enables Robust Stable Gene Transfer in Vertebrates," Nature Genetics 41(6):753-761, Nature Publishing Group, United Kingdom (Jun. 2009).
Mattila, P.S.,et al., "The Actions of Cyclosporin A and FK506 Suggest a Novel Step in the Activation of T Lymphocytes," EMBO J 9(13):4425-4433, Wiley Blackwell, United Kingdom (Dec. 1990).
Mitra, R., et al., "Functional Characterization of Piggybat from the Bat Myotis Lucifugus Unveils an Active Mammalian DNA Transposon," Proc Natl Acad Sci USA 110(1):234-239, National Academy of Sciences, United States (Jan. 2013).
Morsy, M.A., et al., "An adenoviral vector deleted for all viral coding sequences results in enhanced safety and extended expression of a leptin transgene," Proc Natl Acad Sci USA 95(14):7866-71, National Academy of Sciences, United States (1998).
Mountford, P.S and Smith, A.G., "Internal Ribosome Entry Sites and Dicistronic Rnas In Mammalian Transgenesis," Trends in Genetics 11(5): 179-184, Elsevier Trends Journals, United Kingdom (May 1995).

(56) References Cited

OTHER PUBLICATIONS

Mulligan, R.C. and Berg, P., "Selection for Animal Cells that Express the *Escherichia coli* Gene Coding for Xanthine-guanine Phosphoribosyltransferase," Proc Natl Acad Sci USA 78(4):2072-2076, National Academy of Sciences, United States (Apr. 1981).
Mumtaz, S., et al., "Design of Liposomes for Circumventing the Reticuloendothelial Cells," Glycobiology 1(5):505-510, IRL Press at Oxford University Press, United Kingdom (Nov. 1991).
Needleman S.B., et al., "A General Method Applicable to the Search for Similarities in the Amino Acid Sequence of Two Proteins," Journal of Molecular Biology 48(3):443-453, Academic Press Inc., United States (Mar. 1970).
Neumann, R., et al., "Determination of the Nucleotide Sequence for the Penton-Base Gene of Human Adenovirus Type 5," Gene 69(1): 153-157, Elsevier B.V., Netherlands (Sep. 1988).
No, D., et al., "Ecdysone-inducible Gene Expression in Mammalian Cells and Transgenic Mice," Proc Natl Acad Sci USA 93(8):3346-3351, National Academy of Sciences, United States (Apr. 1996).
Novelli, A., and Boulanger, P. A., "Deletion analysis of functional domains in baculovirus-expressed adenovirus type 2 fiber," Virology 185(1):365-76, Elsevier, Netherlands (1991).
Nuclear Receptors Nomenclature Committee, "A Unified Nomenclature System for the Nuclear Receptor Superfamily," Cell 97(2):161-163, Cell Press, United States (Apr. 1999).
O'Hare, K., et al., "Transformation of Mouse Fibroblasts to Methotrexate Resistance by a Recombinant Plasmid Expressing a Prokaryotic Dihydrofolate Reductase," Proc Natl Acad Sci USA 78(3):1527-1531, National Academy of Sciences, United States (Mar. 1981).
Osbourn, J.K., et al., "Directed Selection of Mip-1 Alpha Neutralizing Ccr5 Antibodies from a Phage Display Human Antibody Library," Nature Biotechnology 16(8):778-781, Nature Publishing Group, United Kingdom (Aug. 1998).
Paul, W. E., ed., "Fundamental Immunology," 3rd Edition, pp. 353-363, Raven Press, United States (1993).
Pearson, W.R. and Lipman, D.J., "Improved Tools for Biological Sequence Comparison," Proc Natl Acad Sci USA 85(8):2444-2448, National Academy of Sciences, United States (Apr. 1988).
Pearson, W.R., "Using the FASTA Program to Search Protein and DNA Sequence Databases," Methods in Molecular Biology 24:307-331, Humana Press, United States (Feb. 1994).
Roberts, M.M., et al., "Three-Dimensional Structure of the Adenovirus Major Coat Protein Hexon," Science 232(4754):1148-1151, American Association for the Advancement of Science, United States (May 1986).
Rux, J. J., et al., "Structural and Phylogenetic Analysis of Adenovirus Hexons by Use of High-Resolution X-Ray Crystallographic, Molecular Modeling, and Sequence-Based Methods," Journal of Virology 77(17): 9553-9566, American Society for Microbiology, United States (Sep. 2003).
Santerre, R.F., et al., "Expression of Prokaryotic Genes for Hygromycin B and G418 Resistance as Dominant-selection Markers in Mouse L Cells," Gene 30(1-3): 147-156, Elsevier, Netherlands (Oct. 1984).
Schirmbeck, R., et al., "Targeting Murine Immune Responses to Selected T Cell- or Antibody-Defined Determinants of the Hepatitis B Surface Antigen By Plasmid DNA Vaccines Encoding Chimeric Antigen," Journal of Immunology 166(2):1405-1413, American Association of Immunologists, United States (Jan. 2001).
Signas, C., et al., "Adenovirus 3 Fiber Polypeptide Gene: Implications forthe Structure of the Fiber Protein," Journal of Virology 53(2):672-678, American Society For Microbiology, United States (Feb. 1985).
Smith, T.F., and Waterman, M.S., "Comparison of biosequences," *Advances in Applied Mathematics 2*(4):482-498, Academic Press Inc., United States (19 81).
Soding, J., "Protein Homology Detection by Hmm-hmm Comparison," Bioinformatics 21(7):951-960, Oxford University Press, United Kingdom (Apr. 2005).
Soleimanjahi, H., et al., "Antitumor Response to a Codon-Optimized HPV-16 E7/HSP70 Fusion Antigen DNA Vaccine," Iranian Journal of Immunology 14(3):180-191, Shiraz University of Medical Sciences, Iran (Sep. 2017).
Stewart , P.L., et al., "Image Reconstruction Reveals the Complex Molecular Organization of Adenovirus," Cell 67(1): 145-154, Cell Press, United States (Oct. 1991).
Stewart, P.L., et al., "Difference Imaging of Adenovirus: Bridging the Resolution Gap between X-Ray Crystallography and Electron Microscopy," EMBO Journal 12(7):2589-2599, Wiley Blackwell, United Kingdom (Jul. 1993).
Suhr, S.T., et al., "High Level Transactivation by a Modified Bombyx Ecdysone Receptor in Mammalian Cells Without Exogenous Retinoid X Receptor," Proc Natl Acad Sci USA 95(14):7999-8004, National Academy of Sciences, United States (1998).
Szybalska, E.H. and Szybalski, W., "Genetics of Human Cess Line IV DNA-mediated Heritable Transformation of a Biochemical Trait," Proc Natl Acad Sci USA 48:2026-2034, National Academy of Sciences, United States (Dec. 1962).
Ui-Tei, K., et al., "Sensitive Assay of RNA Interference in *Drosophila* and Chinese Hamster Cultured Cells Using Firefly Luciferase Gene as Target," FEBS Letters 479(3): 79-82, John Wiley & Sons, Inc., United States (Aug. 2000).
Van Oostrum, J., et al., "Molecular Composition of the Adenovirus Type 2 Virion," Journal of Virology 56(2):439-448, American Society for Microbiology, United States (Nov. 1985).
Wieking, B.G., et al., "A non-oncogenic HPV 16 E6/E7 vaccine enhances treatment of HPV expressing tumors," Cancer Gene Therapy 19(10):667-674, Nature Publishing Group, United Kingdom (Oct. 2012).
Wigler, M., et al., "Transfer of Purified Herpes Virus Thymidine Kinase Gene to Cultured Mouse Cells," Cell 11(1):223-232, Cell Press, United States (May 1977).
Wigler, M., et al., "Transformation of Mammalian Cells with an Amplifiable Dominant-Acting Gene," Proc Natl Acad Sci USA 77(6):3567-3570, National Academy of Sciences, United States (Jun. 1980).
Wilson, M.H., et al., "Piggybac Transposon-Mediated Gene Transfer in Human Cells," Molecular Therapy 15(1):139-145, Cell Press, United States (Jan. 2007).
Yan, J., et al., "Induction of antitumor immunity in vivo following delivery of a novel HPV-16 DNA vaccine encoding an E6/E7 fusion antigen," Vaccine 27(3):431-440, Elsevier Science, Netherlands (2009).
Yeh, H.Y., et al., "Human adenovims type 41 contains two fibers," Virus Res 33(2):179-98, Elsevier, Netherlands (Aug. 1994).
Co-pending Application, U.S. Appl. No. 16/978,573, inventors Brough, D.E., et al., filed Mar. 6, 2019 (Not Published).
Martin, P., et al., "TG1050, an immunotherapeutic to treat chronic hepatitis B, induces robust T cells and exerts an antiviral effect in HBV-persistent mice," Gut 64(12): 1961-1971, Elsevier, Netherlands (published online Nov. 2014, published in print Dec. 2015).
Li, J., et al., "Research progress of therapeutic vaccines for treating chronic hepatitis B," Hum Vaccin Immunother 13(5): 986-997, Taylor & Francis, United States (published online Jan. 2017, published in print May 2017).
Supplementary European Search Report for EP Application No. EP 19 76 4606, Munich, Germany, dated Feb. 28, 2022, 12 pages.
Rostami, A., et al., "Design and expression of a chimeric vaccine candidate for avian necrotic enteritis," Protein Engingeering, Design & Selection 30(1):39-45, Oxford University Press, United Kingdom (Jan. 2017).

* cited by examiner

Linkers

| | |
|---|---|
| HBx-1 | VLHKRTLGL |
| HBx-2 | LPKVLHKRTL |
| HBx-3 | HKRTLGLSAM |
| HBx-4 | QFLPKVLHKR |
| HBx-5 | TVNAHQFLPK |
| HBx-6 | LSAMSTTDL |

ILPKVLHKRTLGLS

DDB1 in Complex with the H-Box Motif of HBX (PDB 3I7H)

EYIKDCVFKDWEELGEEIR
LKVFVLG

Bcl-2 in complex with HBx-BH3 motif (PDB 3FCG)

Newly identified epitope V60 from HBV core protein complexed with HLA-A*0201 (PDB 4K7F)

Structure of HLA-A2 P130 ~ HBc 123-129 complexed with HLA-A*02 (PDB 5E00)

Crystal structures of HLAs A*02:06/02:07/02:03 bound to HBV Core 18-27 (PDB 3OXR, 3OXS, 3OX8)

Structure of HLA-A*0201 complexed with HBc141~149 (Protein Cell 2014, 5(4):317~327)

```
TG1050 (MOD-1755595) HBV D Core   MDIDPYKEFGASVELLSFLPSDFFPSVRDLLDTATALYRDALESPEHCTPHHTALRhvcL
TG1050 GB  Y07587.1               MDIDPYKEFGATVELLSFLPSDFFPSVRDLLDTASALYREALESPEHCSPHHTALRqaiL

TG1050 (MOD-1755595) HBV D Core   CWGDLMnLATWVGtNLEDqaSRDLVVSYVNTNMGLKFRQLLWFHISCLTFGRDlVLEYLV
TG1050 GB  Y07587.1               CWGELMTLATWVGgNLEDpiSRDLVVSYVNTNMGLKFRQLLWFHISCLTFGREtVIEYLV

TG1050 (MOD-1755595) HBV D Core   SFGVWIRTPPAYRPsNAPILSTLPETTVmplsyqhfrrllllddeagpleeelprladeg
TG1050 GB  Y07587.1               SFGVWIRTPPAYRPpNAPILSTLPETTV--------------------------------

TG1050 (MOD-1755595) HBV D Core   lnrrvaedlnlgnlnvsipwthkvgnftglysstvpvfnphwktpsfpnihlhqdiikkc
TG1050 GB  Y07587.1               ------------------------------------------------------------

TG1050 (MOD-1755595) HBV D Core   eqfvgpltvnekrrlqlimparfypnvtkylpldkgikpyypehlvnhyfqtrhylhtlw
TG1050 GB  Y07587.1               ------------------------------------------------------------

TG1050 (MOD-1755595) HBV D Core   kagilykretthsasfcgspysweqklqhgaesfhqqssgilsrppvgsslqskhrksrl
TG1050 GB  Y07587.1               ------------------------------------------------------------
```

FIG. 15A

▼ Polymerase deletions -- 538 -- 544aa, 710-742aa

SEQUENCE LISTING

```
<160> NUMBER OF SEQ ID NOS: 148

<210> SEQ ID NO 1
<211> LENGTH: 30
<212> TYPE: DNA
<213> ORGANISM: Artificial Sequence
<220> FEATURE:
<223> OTHER INFORMATION: Adenovirus pIX fragment nucleotides

<400> SEQUENCE: 1

agctctttgg tggcgagcgg cgcggcctct                                     30


<210> SEQ ID NO 2
<211> LENGTH: 439
<212> TYPE: DNA
<213> ORGANISM: Artificial Sequence
<220> FEATURE:
<223> OTHER INFORMATION: Adenovirus DNA polymerase fragment nucleotides

<400> SEQUENCE: 2

aacatcaata cctcaaagtc atggtcaggg acactttcgc cctcacccac acctccctcc     60

gcaaggcggc gcaggcctac gcgctgcccg tggagaaggg ctgttgcccc taccaggccg    120

tcaaccagtt ctacatgcta ggctcttacc gttcggacac ggacgggttt cccctccaag    180

agtactggaa agaccgcgaa gagttcgtcc tcaaccgcga gctgtggaaa aagaaggggg    240

aggataagta tgacatcatc cgcgagaccc tcgactactg cgcgctcgac gtccaggtca    300

ccgccgagct ggtgcacaag ctgcgcgagt cctacgcctc cttcgtcagg gactcggtgg    360

gcttgcaaga agcaagcttc aacgtcttcc agcggcccac catctcctcc aactcccatg    420

ccatcttcag gcagatcgc                                                 439
```

<210> SEQ ID NO 3
<211> LENGTH: 34
<212> TYPE: DNA
<213> ORGANISM: Artificial Sequence
<220> FEATURE:
<223> OTHER INFORMATION: Adenovirus penton base protein fragment nucleotides

<400> SEQUENCE: 3
actgaggctg cggctaaggc tgaggtcgaa gcca 34

<210> SEQ ID NO 4
<211> LENGTH: 45
<212> TYPE: DNA
<213> ORGANISM: Artificial Sequence
<220> FEATURE:
<223> OTHER INFORMATION: Adenovirus hexon protein fragment nucleotides

<400> SEQUENCE: 4
ataggtgtgg atgccacaca ggcgggagat aaccctatat atgct 45

<210> SEQ ID NO 5
<211> LENGTH: 30
<212> TYPE: DNA
<213> ORGANISM: Artificial Sequence
<220> FEATURE:
<223> OTHER INFORMATION: Adenovirus fiber protein fragment nucleotides

<400> SEQUENCE: 5
gtagcaggcc ccctagctgt ggccaatggc 30

<210> SEQ ID NO 6
<211> LENGTH: 399
<212> TYPE: DNA
<213> ORGANISM: Artificial Sequence
<220> FEATURE:
<223> OTHER INFORMATION: Adenovirus pIX nucleotides

<400> SEQUENCE: 6
atgagcgaca ccggcaacag ctttgatgga agcatcttta gcccctatct gacagtgcgc 60
atgcctcact gggctggagt gcgtcagaat gtgatgggtt ccaacgtgga tggacgcccc 120
gttctgcctt caaattcgtc tacaatggcc tacgcgaccg tgggaggaac tccgctggac 180
gccgcgacct ccgccgccgc ctccgccgcc gccgcgaccg cgcgcagcat ggctacggac 240
ctttacagct ctttggtggc gagcggcgcg gcctctcgcg cgtctgctcg ggatgagaaa 300
ctgaccgctc tgctgcttaa actggaagac ttgacccggg agctgggtca actgacccag 360
caggtctcca gcttgcgtga gagcagcctt gcctccccc 399

<210> SEQ ID NO 7
<211> LENGTH: 3168
<212> TYPE: DNA
<213> ORGANISM: Artificial Sequence
<220> FEATURE:
<223> OTHER INFORMATION: Adenovirus DNA polymerase nucleotides

<400> SEQUENCE: 7
atggacagct ccaatgtgcg cgatgtcgtc atcaaactcc gcccgccgag cgccgagatc 60
tggacctgcg gctctcgcgg cgtggtggtc tgctccacca tcgccctcca ggagacagat 120
gctggcggcc agacaaccaa agtagaagac caccagccac acgggacccc aggcggggga 180
cttagattcc cgctgcgctt cctcgtcaga ggtcgccagg ttcacctcgt gcaagatata 240
caacccgtgc agcgctgcca gtactgcggt cgcttttaca aaagccagca cgagtgctcg 300
gcccgcagac gggacttcta ctttcaccac atcaacagcc aatcctccaa ctggtggcgg 360
gagatccagt tcttcccgat cggctctcat cctcgcacgg agcgcctctt tgtcacctac 420
gatgtagaga cctacacttg gatgggagcc tttggcaagc agctcgtgcc cttcatgctg 480
gtcatgaaac tgggggggcga cgaggctctg gtcgccgccg cgcgcgacct cgcccgagag 540
ctcagatggg accccctggga gaaagacccc ctcaccttct actgcatcac ccccgaaaag 600
atggccgtgg ggcgacagtt cagaaccttc cgcgaccgcc tgcagaccct catggcccgc 660
gacctctggc gatccttcct ggcggccaac cctcacttgc aagactgggc cctggaggag 720
cacggcctgg aatcgcccga ggagctcacc tacgaggaac tcaaaaagct cccctccatc 780
aagggccagc cccgcttttt ggagctctac atcgtgggcc acaacataaa cggctttgac 840
gagatcgtcc tggccgccca ggtcatcaac aaccgctcct cggtcccagg gccctttcgc 900
atcaccagaa acttcatgcc tcgagcgggg aagatcctct tcaatgacct caccttctcc 960
ctgcccaacc cgcgctccaa aaagcgcacg gactacaccc tgtgggaaca gggcggctgc 1020
gatgacacag acttcaaaca tcaatacctc aaagtcatgg tcagggacac tttcgccctc 1080
acccacacct ccctccgcaa ggcggcgcag gcctacgcgc tgcccgtgga gaagggctgt 1140
tgcccctacc aggccgtcaa ccagttctac atgctaggct cttaccgttc ggacacggac 1200
gggtttcccc tccaagagta ctggaaagac cgcgaagagt tcgtcctcaa ccgcgagctg 1260
tggaaaaaga agggggagga taagtatgac atcatccgcg agaccctcga ctactgcgcg 1320
ctcgacgtcc aggtcaccgc cgagctggtg cacaagctgc gcgagtccta cgcctccttc 1380
gtcagggact cggtgggctt gcaagaagca agcttcaacg tcttccagcg gcccaccatc 1440
tcctccaact cccatgccat cttcaggcag atcgccttcc gcgccgagcg cccccagcgc 1500
accaacctcg ggcccaacat gctggccccc tcccacgagc tctatgacta cgtgcgcgcc 1560
agcatccgcg gggggcgctg ctaccccacc tacctcggca tcctcaggga accccctgtac 1620
gtgtatgaca tctgcggcat gtacgcctcc gcgctcaccc accccatgcc ctggggcccg 1680
cccctcaacc cctacgagcg cgcgctcgcc gcccgcgaat ggcagcgggc tctggacatg 1740
caagcttgca agatcgacta ctttgacccg cgcttgctcc ccggggtctt caccatcgac 1800
gcggaccccc caaacgagga ccagctggac cccctacccc ccttctgctc gcgcaagggc 1860
ggccgcctct gctggaccaa cgagcgcctg cgcggcgagg tcgccaccag cgtcgacatg 1920
gtcaccctgc acaaccgagg ctggagggtg cgcctaatcc cagacgagcg caccaccgtc 1980
ttccccgagt ggaagtgcgt ggcccgcgag tacgtgcaac tcaacatcgc ggccaaggag 2040
cgagccgacc gcgacaaaaa ccagaccctg cgctccatcg ccaagctgct ctccaacgcc 2100
ctctacgggt cgttcgccac caagcttgac aacaaaaaaa tagtgttttc tgaccagatg 2160
gacccaggta ccctcaaagg tatcacctcc ggacaggtga acatcaaatc ctcctcattt 2220
ttagaaactg acaacctgag cgctgaggtc atgcccgcct tcgagaggga atacttaccc 2280
cagcagctgg ccctcgcaga cagcgatgcg gaagagagtg aagatgaaag ggcgcccacc 2340
cccttttata cccccccgtc gggaaccccc ggtcacgtgt cctacaccta caagccaatc 2400
acttttctgg acgcggagga gggggacatg tgcctgcaca ccctggagaa ggtggacccg 2460
ctagtggaca acgaccgcta cccctcccac gtggcctcct tcgtcctggc ctggacgcgg 2520
gccttcgtct cagagtggtc agagtttctc tacgaggagg acagaggcac tccgctggaa 2580

-continued

```
gacaggcccc tgaagtcggt ctacggggac acggacagcc tcttcgtcac cgagaaggga   2640

caccgcctca tggagagccg aggtaagaaa cgcatcaaaa agcatggggg caacctggtt   2700

tttgaccctg accgcccgga gctcacttgg ctggtggaat gcgagacggt ctgcgcttcc   2760

tgcggcgcgg acgcctactc cccagagtcc gtgtttctcg ctcccaagct ctacgccctg   2820

aagagcctgc agtgcccctc gtgcggcgcc acctccaagg gaaagctccg cgccaagggg   2880

cacgccgccg agggtctcga ctacgagacc atggtcaaat gctacctggc cgacgcgcag   2940

ggcgaagagc ggcagcgatt cagcaccagc agaaccagcc tcaagcgcac cctggccagc   3000

gcccaacccg gagcgcaccc cttcaccgtg acccagacca ccctgacgag gaccctgcgc   3060

ccatggaagg acatgactct ggccccgctg gacgcccatc ggctggtgcc ctacagcgaa   3120

agccgcccca acccgcgaaa cgaggagatc tgctggatcg agatgccg                 3168
```

<210> SEQ ID NO 8
<211> LENGTH: 1974
<212> TYPE: DNA
<213> ORGANISM: Artificial Sequence
<220> FEATURE:
<223> OTHER INFORMATION: Adenovirus penton base protein nucleotides

<400> SEQUENCE: 8

```
atgcggcgcg cggcgatgtt cgaggagggg cctccccccct cttacgagag cgcgatgggg     60

atttctcctg cggcgcccct gcagcctccc tacgtgcctc ctcggtacct gcaacctaca    120

ggggggagaa atagcatctg ttactctgag ctgcagcccc tgtacgatac caccagactg    180

tacctggtgg acaacaagtc cgcggacgtg gcctccctga actaccagaa cgaccacagc    240

gatttttga ccacggtgat ccaaaacaac gacttcaccc caaccgaggc cagcacccag    300

accataaacc tggataacag gtcgaactgg ggcggcgacc tgaagaccat cttgcacacc    360

aacatgccca acgtgaacga gttcatgttc accaactctt ttaaggcgcg ggtgatggtg    420

gcgcgcgagc agggggaggc gaagtacgag tgggtggact tcacgctgcc cgagggcaac    480

tactcagaga ccatgactct cgacctgatg aacaatgcga tcgtggaaca ctatctgaaa    540

gtgggcaggc agaacggggt gaaggaaagc gatatcgggg tcaagtttga caccagaaac    600

ttccgtctgg gctgggaccc cgtgaccggg ctggtcatgc cgggggtcta caccaacgag    660

gcctttcatc ccgacatagt gcttctgccc ggctgtgggg tggacttcac ccagagccgg    720

ctgagcaacc tgctgggcat tcgcaagcgg cagcctttcc aggagggttt caagatcacc    780

tatgaggatc tgaagggggg caacattccc gcgctccttg atctggacgc ctacgaggag    840

agcttgaaac ccgaggagag cgctggcgac agcggcgaga gtggcgagga gcaagccggc    900

ggcggtggcg gcgcgtcggt agaaaacgaa agtacgcccg cagtggcggc ggacgctgcg    960

gaggtcgagc cggaggccat gcagcaggac gcagaggagg gcgcacagga gggcgcgcag   1020

aaggacatga acgatgggga gatcagggga gacacattcg ccacccgggg cgaagaaaaa   1080

gaggcagagg cggcggcggc ggcgacggcg gaggccgaaa ccgaggttga ggcagaggca   1140

gagcccgaga ccgaagttat ggaagacatg aatgatggag aacgtagggg cgacacgttc   1200

gccacccggg gcgaagagaa ggcggcggag gcagaagccg cggctgagga ggcggctgcg   1260

gctgcggcca agactgaggc tgcggctaag gctgaggtcg aagccaatgt tgcggttgag   1320

gctcaggctg aggaggaggc ggcggctgaa gcagttaagg aaaaggccca ggcagagcag   1380

gaagagaaaa aacctgtcat tcaacctcta aaagaagata gcaaaaagcg cagttacaac   1440

gtcatcgagg gcagcacctt tacccagtac cgcagctggt acctggcgta caactacggc   1500
```

```
gacccggtca agggggtgcg ctcgtggacc ctgctctgca cgccggacgt cacctgcggc   1560

tccgagcaga tgtactggtc gctgccgaac atgatgcaag acccggtgac cttccgctcc   1620

acgcggcagg ttagcaactt cccggtggtg ggcgccgaac tgctgcccgt gcactccaag   1680

agtttttaca acgagcaggc cgtctactcc cagctgatcc gccaggccac ctctctgacc   1740

cacgtgttca atcgctttcc cgagaaccag attttggcgc gcccgccggc ccccaccatc   1800

accaccgtga gtgaaaacgt tcctgccctc acagatcacg ggacgctacc gctgcgcaac   1860

agcatctcag gagtccagcg agtgaccatt actgacgcca gacgccggac ctgcccctac   1920

gtttacaagg ccttgggcat agtctcgccg cgcgtcctct ccagtcgcac tttt         1974
```

```
<210> SEQ ID NO 9
<211> LENGTH: 2877
<212> TYPE: DNA
<213> ORGANISM: Artificial Sequence
<220> FEATURE:
<223> OTHER INFORMATION: Adenovirus hexon protein nucleotides

<400> SEQUENCE: 9
```

```
atggcgaccc catcgatgat gcctcagtgg tcgtacatgc acatctcggg ccaggacgct     60

tcggagtacc tgagccccgg gctggtgcag ttcgcccgcg ccacagacac ctacttcaac    120

atgagtaaca agttcaggaa ccccactgtg gcgcccaccc acgatgtgac cacggaccgg    180

tcgcagcgcc tgacgctgcg gttcatcccc gtggatcggg aggacaccgc ctactcttac    240

aaggcgcggt tcacgctggc cgtgggcgac aaccgcgtgc tggacatggc ctccacttac    300

tttgacatca ggggggtgct ggacaggggc cccaccttca agccctactc gggtactgcc    360

tacaactccc tggcccccaa gggcgctccc aattcttgcg agtgggaaca agatgaacca    420

gctcaggcag caatagctga agatgaagaa gaacttgaag aagaacaagc tcaggacgaa    480

caggcgccca ctaagaaaac ccatgtatac gcccaggcac ctctttctgg tgaaaaaatt    540

actaaggatg gtttgcaaat aggtgtggat gccacacagg cgggagataa ccctatatat    600

gctgataaaa cattccaacc cgaacctcag ataggtgagt ctcagtggaa cgaggctgat    660

gccacagtag caggaggcag agtcttaaaa aagaccaccc ctatgagacc ttgctatgga    720

tcctatgcca aacctactaa tgccaatggc ggtcaaggga tcatggtggc caatgatcag    780

ggagcgcttg aatctaaagt tgagatgcaa tttttctcca ccacaacgtc tcttaatgta    840

agggaaggtg aaaacaatct tcagccaaaa gtagtgctat acagcgaaga tgttaacttg    900

gaatcccctg acactcattt gtcttacaaa cctaaaaagg atgacaccaa ctctaaaatc    960

atgttgggtc agcaagccat gcccaacaga cccaacctca ttgcttttag ggacaacttt   1020

attggactta tgtactacaa cagcacaggc aacatgggag tgctggcagg acaggcctcc   1080

cagctaaacg ctgtggtaga cttgcaagac agaaacacag agctgtcata ccaactgatg   1140

cttgattcca ttggagacag atcaagatac ttttccatgt ggaaccaggc agtggacagc   1200

tatgacccag atgtcagaat cattgaaaac catggggttg aagatgagct gcccaactat   1260

tgctttcccc tgggcggtat tggaattaca gacacatacc agtgcataaa accaaccgca   1320

gctgctaata acactacatg gtctaaggat gaagaattta gtgatcgcaa tgaaataggg   1380

gtgggaaaca acttcgccat ggagatcaac atccaggcca acctctggag gaacttcctc   1440

tatgcgaacg tggggctcta cctgccagac aagctcaagt acaaccccac caacgtggac   1500

atctctgaca accccaacac ctatgactac atgaacaagc gtgtggtggc tcccggcctg   1560
```

-continued gtggactgct ttgtcaatgt gggagccagg tggtccctgg actacatgga caacgtcaac 1620
cccttcaacc accaccgcaa tgcgggtctg cgctaccgct ccatgatcct gggcaacggg 1680
cgctacgtgc ccttccacat tcaggtgccc cagaagttct ttgccatcaa gaacctcctc 1740
ctcctgccgg gctcctacac ttacgagtgg aacttcagga aggatgtcaa catggtcctg 1800
cagagctctc tgggcaatga ccttagggtg gacggggcca gcatcaagtt tgacagcgtc 1860
accctctatg ctaccttctt ccccatggct cacaacaccg cctccacgct cgaggccatg 1920
ctgaggaacg acaccaacga ccagtccttc aatgactacc tctctggggc caacatgctc 1980
taccccatcc ccgccaaggc caccaacgtg cccatctcca ttccctctcg caactgggcc 2040
gccttcagag gctgggcctt tacccgcctt aagaccaagg aaacccccct cctgggctcg 2100
ggttttgacc cctactttgt ctactcggga tccatcccct acctggatgg caccttctac 2160
ctcaaccaca cttttaagaa gatatccatc atgtatgact cctccgtcag ctggccgggc 2220
aatgaccgcc tgctcacccc caatgagttc gaggtcaagc gcgccgtgga cggcgagggc 2280
tacaacgtgg cccagtgcaa catgaccaag gactggttcc tggtgcagat gctggccaac 2340
tacaacatag gctaccaggg cttctacatc ccagagagct acaaggacag gatgtactcc 2400
ttcttcagaa atttccaacc catgagcagg caggtggtgg acgagaccaa atacaaggac 2460
tatcaggcca ttggcatcac tcaccagcac aacaactcgg gattcgtggg ctacctggct 2520
cccaccatgc gcgaggggca ggcctacccc gccaacttcc cctacccgtt gataggcaaa 2580
accgcggtcg acagcgtcac ccagaaaaag ttcctctgcg accgcaccct ctggcgcatc 2640
cccttctcta gcaacttcat gtccatgggt gcgctcacgg acctgggcca gaacctgctc 2700
tatgccaact ccgcccatgc gctggacatg acttttgagg tggaccccat ggacgagccc 2760
acccttctct atattgtgtt tgaagtgttc gacgtggtca gagtgcacca gccgcaccgc 2820
ggtgtcatcg agaccgtgta cctgcgcacg cccttctcgg ccggcaacgc caccacc 2877

<210> SEQ ID NO 10
<211> LENGTH: 1749
<212> TYPE: DNA
<213> ORGANISM: Artificial Sequence
<220> FEATURE:
<223> OTHER INFORMATION: Adenovirus fiber protein nucleotides

<400> SEQUENCE: 10
atgaaacgcg cgagatcgtc tgacgagacc ttcaaccccg tgtaccccta cgataccgag 60
atcgctccga cttctgtccc tttccttacc cctccctttg tgtcatccgc aggaatgcaa 120
gaaaatccag ctggggtgct gtccctgcac ttgtcagagc cccttaccac ccacaatggg 180
gccctgactc taaaaatggg gggcggcctg accctggaca aggaagggaa tctcacttcc 240
caaaacatca ccagtgtcga tccccctctc aaaaaaagca agaacaacat cagccttcag 300
accgccgcac ccctcgccgt cagctccggg gccctaacac tttttgccac tcccccccta 360
gcggtcagtg gtgacaacct tactgtgcag tctcaggccc ctctcacttt ggaagactca 420
aaactaactc tggccaccaa aggaccccta actgtgtccg aaggcaaact tgtcctagaa 480
acagaggctc ccctgcatgc aagtgacagc agcagcctgg gccttagcgt tacggcccca 540
cttagcatta acaatgacag cctaggacta gatctgcagg cacccattgt ctctcaaaat 600
ggaaaactgg ctctaaatgt agcaggcccc ctagctgtgg ccaatggcat taatgctttg 660
acagtaggca caggcaaagg tattggtcta aatgaaacca gcactcactt gcaagcaaag 720
ttggtcgccc ccctaggctt tgataccaat ggcaacatta agctaagcgt tgcaggaggc 780

```
atgagactaa ataatgacac acttatacta gatgtaaact acccatttga agctcaaggc      840

caactaagtc taagagtggg ccagggtccg ctgtatgtag attctagcag ccataacctg      900

accattagat gccttagagg attatacata acatcgtcta ataaccaaac cggtctagag      960

gccaacataa aactaacaaa aggccttgtc tatgatggaa atgccatagc agtcaatgtt     1020

ggtcaaggat tgcaatacag cactactgcc acatcggaag gtgtgtatcc tatacagtct     1080

aagataggtt tgggaatgga atatgatacc aacggagcca tgatgacaaa actaggctct     1140

ggactaagct ttgacaattc aggagccatt gtagtgggaa acaaaaatga tgacaggctt     1200

actctgtgga ctacaccaga cccatctcct aactgtagaa tttattctga aaaagatact     1260

aaactaacct tggtgctgac taagtgtggc agccaaatcc taggcacagt atctgccctt     1320

gctgtcagag gcagccttgc gcccatcact aatgcatcca gcatagtcca aatatttcta     1380

agatttgatg aaaatggact attgatgagc aactcatcgc tagacggtga ttactggaat     1440

tacagaaatg gggactccac taatagcaca ccatatacaa atgcagtagg ctttatgcct     1500

aatctagcag cctatcctaa aggtcaggct acagctgcaa aaagcagtat tgtaagccag     1560

gtatacatgg atggtgacac tactaaacct ataacactaa aaataaactt caatggcatt     1620

gatgaaacaa cagaaaatac ccctgttagt aaatattcca tgacattctc atggagctgg     1680

cccaccgcaa gctacatagg ccacactttt gcaacaaact cttttacttt ctcctacatc     1740

gcccaagaa                                                              1749
```

<210> SEQ ID NO 11
<211> LENGTH: 10
<212> TYPE: PRT
<213> ORGANISM: Artificial Sequence
<220> FEATURE:
<223> OTHER INFORMATION: Adenovirus pIX protein fragment

<400> SEQUENCE: 11

Ser Ser Leu Val Ala Ser Gly Ala Ala Ser
1               5                   10

<210> SEQ ID NO 12
<211> LENGTH: 147
<212> TYPE: PRT
<213> ORGANISM: Artificial Sequence
<220> FEATURE:
<223> OTHER INFORMATION: Adenovirus DNA polymerase fragment

<400> SEQUENCE: 12

Lys His Gln Tyr Leu Lys Val Met Val Arg Asp Thr Phe Ala Leu Thr
1               5                   10                  15

His Thr Ser Leu Arg Lys Ala Ala Gln Ala Tyr Ala Leu Pro Val Glu
            20                  25                  30

Lys Gly Cys Cys Pro Tyr Gln Ala Val Asn Gln Phe Tyr Met Leu Gly
        35                  40                  45

Ser Tyr Arg Ser Asp Thr Asp Gly Phe Pro Leu Gln Glu Tyr Trp Lys
    50                  55                  60

Asp Arg Glu Glu Phe Val Leu Asn Arg Glu Leu Trp Lys Lys Lys Gly
65                  70                  75                  80

Glu Asp Lys Tyr Asp Ile Ile Arg Glu Thr Leu Asp Tyr Cys Ala Leu
                85                  90                  95

Asp Val Gln Val Thr Ala Glu Leu Val His Lys Leu Arg Glu Ser Tyr
            100                 105                 110

```
Ala Ser Phe Val Arg Asp Ser Val Gly Leu Gln Glu Ala Ser Phe Asn
        115                 120                 125

Val Phe Gln Arg Pro Thr Ile Ser Ser Asn Ser His Ala Ile Phe Arg
    130                 135                 140

Gln Ile Ala
145


<210> SEQ ID NO 13
<211> LENGTH: 15
<212> TYPE: PRT
<213> ORGANISM: Artificial Sequence
<220> FEATURE:
<223> OTHER INFORMATION: Adenovirus penton base protein fragment

<400> SEQUENCE: 13

Lys Thr Glu Ala Ala Ala Lys Ala Glu Val Glu Ala Asn Val Ala
1               5                   10                  15


<210> SEQ ID NO 14
<211> LENGTH: 15
<212> TYPE: PRT
<213> ORGANISM: Artificial Sequence
<220> FEATURE:
<223> OTHER INFORMATION: Adenovirus hexon protein fragment

<400> SEQUENCE: 14

Ile Gly Val Asp Ala Thr Gln Ala Gly Asp Asn Pro Ile Tyr Ala
1               5                   10                  15


<210> SEQ ID NO 15
<211> LENGTH: 15
<212> TYPE: PRT
<213> ORGANISM: Artificial Sequence
<220> FEATURE:
<223> OTHER INFORMATION: Adenovirus fiber protein fragment

<400> SEQUENCE: 15

Leu Asn Val Ala Gly Pro Leu Ala Val Ala Asn Gly Ile Asn Ala
1               5                   10                  15


<210> SEQ ID NO 16
<211> LENGTH: 133
<212> TYPE: PRT
<213> ORGANISM: Artificial Sequence
<220> FEATURE:
<223> OTHER INFORMATION: Adenovirus pIX amino acids

<400> SEQUENCE: 16

Met Ser Asp Thr Gly Asn Ser Phe Asp Gly Ser Ile Phe Ser Pro Tyr
1               5                   10                  15

Leu Thr Val Arg Met Pro His Trp Ala Gly Val Arg Gln Asn Val Met
            20                  25                  30

Gly Ser Asn Val Asp Gly Arg Pro Val Leu Pro Ser Asn Ser Ser Thr
        35                  40                  45

Met Ala Tyr Ala Thr Val Gly Gly Thr Pro Leu Asp Ala Ala Thr Ser
    50                  55                  60

Ala Ala Ala Ser Ala Ala Ala Ala Thr Ala Arg Ser Met Ala Thr Asp
65                  70                  75                  80

Leu Tyr Ser Ser Leu Val Ala Ser Gly Ala Ala Ser Arg Ala Ser Ala
                85                  90                  95

Arg Asp Glu Lys Leu Thr Ala Leu Leu Leu Lys Leu Glu Asp Leu Thr
            100                 105                 110
```

Arg Glu Leu Gly Gln Leu Thr Gln Gln Val Ser Ser Leu Arg Glu Ser
115 120 125

Ser Leu Ala Ser Pro
130

<210> SEQ ID NO 17
<211> LENGTH: 1056
<212> TYPE: PRT
<213> ORGANISM: Artificial Sequence
<220> FEATURE:
<223> OTHER INFORMATION: Adenovirus DNA polymerase amino acids

<400> SEQUENCE: 17

Met Asp Ser Ser Asn Val Arg Asp Val Val Ile Lys Leu Arg Pro Pro
1 5 10 15

Ser Ala Glu Ile Trp Thr Cys Gly Ser Arg Gly Val Val Val Cys Ser
20 25 30

Thr Ile Ala Leu Gln Glu Thr Asp Ala Gly Gly Gln Thr Thr Lys Val
35 40 45

Glu Asp His Gln Pro His Gly Thr Pro Gly Gly Gly Leu Arg Phe Pro
50 55 60

Leu Arg Phe Leu Val Arg Gly Arg Gln Val His Leu Val Gln Asp Ile
65 70 75 80

Gln Pro Val Gln Arg Cys Gln Tyr Cys Gly Arg Phe Tyr Lys Ser Gln
85 90 95

His Glu Cys Ser Ala Arg Arg Arg Asp Phe Tyr Phe His His Ile Asn
100 105 110

Ser Gln Ser Ser Asn Trp Trp Arg Glu Ile Gln Phe Phe Pro Ile Gly
115 120 125

Ser His Pro Arg Thr Glu Arg Leu Phe Val Thr Tyr Asp Val Glu Thr
130 135 140

Tyr Thr Trp Met Gly Ala Phe Gly Lys Gln Leu Val Pro Phe Met Leu
145 150 155 160

Val Met Lys Leu Gly Gly Asp Glu Ala Leu Val Ala Ala Ala Arg Asp
165 170 175

Leu Ala Arg Glu Leu Arg Trp Asp Pro Trp Glu Lys Asp Pro Leu Thr
180 185 190

Phe Tyr Cys Ile Thr Pro Glu Lys Met Ala Val Gly Arg Gln Phe Arg
195 200 205

Thr Phe Arg Asp Arg Leu Gln Thr Leu Met Ala Arg Asp Leu Trp Arg
210 215 220

Ser Phe Leu Ala Ala Asn Pro His Leu Gln Asp Trp Ala Leu Glu Glu
225 230 235 240

His Gly Leu Glu Ser Pro Glu Glu Leu Thr Tyr Glu Glu Leu Lys Lys
245 250 255

Leu Pro Ser Ile Lys Gly Gln Pro Arg Phe Leu Glu Leu Tyr Ile Val
260 265 270

Gly His Asn Ile Asn Gly Phe Asp Glu Ile Val Leu Ala Ala Gln Val
275 280 285

Ile Asn Asn Arg Ser Ser Val Pro Gly Pro Phe Arg Ile Thr Arg Asn
290 295 300

Phe Met Pro Arg Ala Gly Lys Ile Leu Phe Asn Asp Leu Thr Phe Ser
305 310 315 320

Leu Pro Asn Pro Arg Ser Lys Lys Arg Thr Asp Tyr Thr Leu Trp Glu
325 330 335

-continued

```
Gln Gly Gly Cys Asp Asp Thr Asp Phe Lys His Gln Tyr Leu Lys Val
            340                 345                 350

Met Val Arg Asp Thr Phe Ala Leu Thr His Thr Ser Leu Arg Lys Ala
        355                 360                 365

Ala Gln Ala Tyr Ala Leu Pro Val Glu Lys Gly Cys Cys Pro Tyr Gln
    370                 375                 380

Ala Val Asn Gln Phe Tyr Met Leu Gly Ser Tyr Arg Ser Asp Thr Asp
385                 390                 395                 400

Gly Phe Pro Leu Gln Glu Tyr Trp Lys Asp Arg Glu Glu Phe Val Leu
                405                 410                 415

Asn Arg Glu Leu Trp Lys Lys Lys Gly Glu Asp Lys Tyr Asp Ile Ile
            420                 425                 430

Arg Glu Thr Leu Asp Tyr Cys Ala Leu Asp Val Gln Val Thr Ala Glu
        435                 440                 445

Leu Val His Lys Leu Arg Glu Ser Tyr Ala Ser Phe Val Arg Asp Ser
    450                 455                 460

Val Gly Leu Gln Glu Ala Ser Phe Asn Val Phe Gln Arg Pro Thr Ile
465                 470                 475                 480

Ser Ser Asn Ser His Ala Ile Phe Arg Gln Ile Ala Phe Arg Ala Glu
                485                 490                 495

Arg Pro Gln Arg Thr Asn Leu Gly Pro Asn Met Leu Ala Pro Ser His
            500                 505                 510

Glu Leu Tyr Asp Tyr Val Arg Ala Ser Ile Arg Gly Gly Arg Cys Tyr
        515                 520                 525

Pro Thr Tyr Leu Gly Ile Leu Arg Glu Pro Leu Tyr Val Tyr Asp Ile
    530                 535                 540

Cys Gly Met Tyr Ala Ser Ala Leu Thr His Pro Met Pro Trp Gly Pro
545                 550                 555                 560

Pro Leu Asn Pro Tyr Glu Arg Ala Leu Ala Ala Arg Glu Trp Gln Arg
                565                 570                 575

Ala Leu Asp Met Gln Ala Cys Lys Ile Asp Tyr Phe Asp Pro Arg Leu
            580                 585                 590

Leu Pro Gly Val Phe Thr Ile Asp Ala Asp Pro Pro Asn Glu Asp Gln
        595                 600                 605

Leu Asp Pro Leu Pro Pro Phe Cys Ser Arg Lys Gly Gly Arg Leu Cys
    610                 615                 620

Trp Thr Asn Glu Arg Leu Arg Gly Glu Val Ala Thr Ser Val Asp Met
625                 630                 635                 640

Val Thr Leu His Asn Arg Gly Trp Arg Val Arg Leu Ile Pro Asp Glu
                645                 650                 655

Arg Thr Thr Val Phe Pro Glu Trp Lys Cys Val Ala Arg Glu Tyr Val
            660                 665                 670

Gln Leu Asn Ile Ala Ala Lys Glu Arg Ala Asp Arg Asp Lys Asn Gln
        675                 680                 685

Thr Leu Arg Ser Ile Ala Lys Leu Leu Ser Asn Ala Leu Tyr Gly Ser
    690                 695                 700

Phe Ala Thr Lys Leu Asp Asn Lys Lys Ile Val Phe Ser Asp Gln Met
705                 710                 715                 720

Asp Pro Gly Thr Leu Lys Gly Ile Thr Ser Gly Gln Val Asn Ile Lys
                725                 730                 735

Ser Ser Ser Phe Leu Glu Thr Asp Asn Leu Ser Ala Glu Val Met Pro
            740                 745                 750

Ala Phe Glu Arg Glu Tyr Leu Pro Gln Gln Leu Ala Leu Ala Asp Ser
```

```
        755                 760                 765

Asp Ala Glu Glu Ser Glu Asp Glu Arg Ala Pro Thr Pro Phe Tyr Thr
    770                 775                 780

Pro Pro Ser Gly Thr Pro Gly His Val Ser Tyr Thr Tyr Lys Pro Ile
785                 790                 795                 800

Thr Phe Leu Asp Ala Glu Glu Gly Asp Met Cys Leu His Thr Leu Glu
                805                 810                 815

Lys Val Asp Pro Leu Val Asp Asn Asp Arg Tyr Pro Ser His Val Ala
            820                 825                 830

Ser Phe Val Leu Ala Trp Thr Arg Ala Phe Val Ser Glu Trp Ser Glu
        835                 840                 845

Phe Leu Tyr Glu Glu Asp Arg Gly Thr Pro Leu Glu Asp Arg Pro Leu
    850                 855                 860

Lys Ser Val Tyr Gly Asp Thr Asp Ser Leu Phe Val Thr Glu Lys Gly
865                 870                 875                 880

His Arg Leu Met Glu Ser Arg Gly Lys Lys Arg Ile Lys Lys His Gly
                885                 890                 895

Gly Asn Leu Val Phe Asp Pro Asp Arg Pro Glu Leu Thr Trp Leu Val
            900                 905                 910

Glu Cys Glu Thr Val Cys Ala Ser Cys Gly Ala Asp Ala Tyr Ser Pro
        915                 920                 925

Glu Ser Val Phe Leu Ala Pro Lys Leu Tyr Ala Leu Lys Ser Leu Gln
    930                 935                 940

Cys Pro Ser Cys Gly Ala Thr Ser Lys Gly Lys Leu Arg Ala Lys Gly
945                 950                 955                 960

His Ala Ala Glu Gly Leu Asp Tyr Glu Thr Met Val Lys Cys Tyr Leu
                965                 970                 975

Ala Asp Ala Gln Gly Glu Glu Arg Gln Arg Phe Ser Thr Ser Arg Thr
            980                 985                 990

Ser Leu Lys Arg Thr Leu Ala Ser  Ala Gln Pro Gly Ala  His Pro Phe
        995                 1000                1005

Thr Val  Thr Gln Thr Thr Leu  Thr Arg Thr Leu Arg  Pro Trp Lys
    1010                1015                1020

Asp Met  Thr Leu Ala Pro Leu  Asp Ala His Arg Leu  Val Pro Tyr
    1025                1030                1035

Ser Glu  Ser Arg Pro Asn Pro  Arg Asn Glu Glu Ile  Cys Trp Ile
    1040                1045                1050

Glu Met  Pro
    1055


<210> SEQ ID NO 18
<211> LENGTH: 658
<212> TYPE: PRT
<213> ORGANISM: Artificial Sequence
<220> FEATURE:
<223> OTHER INFORMATION: Adenovirus penton base protein

<400> SEQUENCE: 18

Met Arg Arg Ala Ala Met Phe Glu Glu Gly Pro Pro Pro Ser Tyr Glu
1               5                   10                  15

Ser Ala Met Gly Ile Ser Pro Ala Ala Pro Leu Gln Pro Pro Tyr Val
            20                  25                  30

Pro Pro Arg Tyr Leu Gln Pro Thr Gly Gly Arg Asn Ser Ile Cys Tyr
        35                  40                  45

Ser Glu Leu Gln Pro Leu Tyr Asp Thr Thr Arg Leu Tyr Leu Val Asp
```

-continued

```
    50                  55                  60

Asn Lys Ser Ala Asp Val Ala Ser Leu Asn Tyr Gln Asn Asp His Ser
65                  70                  75                  80

Asp Phe Leu Thr Thr Val Ile Gln Asn Asn Asp Phe Thr Pro Thr Glu
                85                  90                  95

Ala Ser Thr Gln Thr Ile Asn Leu Asp Asn Arg Ser Asn Trp Gly Gly
            100                 105                 110

Asp Leu Lys Thr Ile Leu His Thr Asn Met Pro Asn Val Asn Glu Phe
        115                 120                 125

Met Phe Thr Asn Ser Phe Lys Ala Arg Val Met Val Ala Arg Glu Gln
    130                 135                 140

Gly Glu Ala Lys Tyr Glu Trp Val Asp Phe Thr Leu Pro Glu Gly Asn
145                 150                 155                 160

Tyr Ser Glu Thr Met Thr Leu Asp Leu Met Asn Asn Ala Ile Val Glu
                165                 170                 175

His Tyr Leu Lys Val Gly Arg Gln Asn Gly Val Lys Glu Ser Asp Ile
            180                 185                 190

Gly Val Lys Phe Asp Thr Arg Asn Phe Arg Leu Gly Trp Asp Pro Val
        195                 200                 205

Thr Gly Leu Val Met Pro Gly Val Tyr Thr Asn Glu Ala Phe His Pro
    210                 215                 220

Asp Ile Val Leu Leu Pro Gly Cys Gly Val Asp Phe Thr Gln Ser Arg
225                 230                 235                 240

Leu Ser Asn Leu Leu Gly Ile Arg Lys Arg Gln Pro Phe Gln Glu Gly
                245                 250                 255

Phe Lys Ile Thr Tyr Glu Asp Leu Lys Gly Gly Asn Ile Pro Ala Leu
            260                 265                 270

Leu Asp Leu Asp Ala Tyr Glu Glu Ser Leu Lys Pro Glu Glu Ser Ala
        275                 280                 285

Gly Asp Ser Gly Glu Ser Gly Glu Glu Gln Ala Gly Gly Gly Gly Gly
    290                 295                 300

Ala Ser Val Glu Asn Glu Ser Thr Pro Ala Val Ala Ala Asp Ala Ala
305                 310                 315                 320

Glu Val Glu Pro Glu Ala Met Gln Gln Asp Ala Glu Glu Gly Ala Gln
                325                 330                 335

Glu Gly Ala Gln Lys Asp Met Asn Asp Gly Glu Ile Arg Gly Asp Thr
            340                 345                 350

Phe Ala Thr Arg Gly Glu Glu Lys Glu Ala Glu Ala Ala Ala Ala Ala
        355                 360                 365

Thr Ala Glu Ala Glu Thr Glu Val Glu Ala Glu Ala Glu Pro Glu Thr
    370                 375                 380

Glu Val Met Glu Asp Met Asn Asp Gly Glu Arg Arg Gly Asp Thr Phe
385                 390                 395                 400

Ala Thr Arg Gly Glu Glu Lys Ala Ala Glu Ala Glu Ala Ala Ala Glu
                405                 410                 415

Glu Ala Ala Ala Ala Ala Ala Lys Thr Glu Ala Ala Ala Lys Ala Glu
            420                 425                 430

Val Glu Ala Asn Val Ala Val Glu Ala Gln Ala Glu Glu Glu Ala Ala
        435                 440                 445

Ala Glu Ala Val Lys Glu Lys Ala Gln Ala Glu Gln Glu Glu Lys Lys
    450                 455                 460

Pro Val Ile Gln Pro Leu Lys Glu Asp Ser Lys Lys Arg Ser Tyr Asn
465                 470                 475                 480
```

```
Val Ile Glu Gly Ser Thr Phe Thr Gln Tyr Arg Ser Trp Tyr Leu Ala
                485                 490                 495

Tyr Asn Tyr Gly Asp Pro Val Lys Gly Val Arg Ser Trp Thr Leu Leu
            500                 505                 510

Cys Thr Pro Asp Val Thr Cys Gly Ser Glu Gln Met Tyr Trp Ser Leu
        515                 520                 525

Pro Asn Met Met Gln Asp Pro Val Thr Phe Arg Ser Thr Arg Gln Val
    530                 535                 540

Ser Asn Phe Pro Val Val Gly Ala Glu Leu Leu Pro Val His Ser Lys
545                 550                 555                 560

Ser Phe Tyr Asn Glu Gln Ala Val Tyr Ser Gln Leu Ile Arg Gln Ala
                565                 570                 575

Thr Ser Leu Thr His Val Phe Asn Arg Phe Pro Glu Asn Gln Ile Leu
            580                 585                 590

Ala Arg Pro Pro Ala Pro Thr Ile Thr Thr Val Ser Glu Asn Val Pro
        595                 600                 605

Ala Leu Thr Asp His Gly Thr Leu Pro Leu Arg Asn Ser Ile Ser Gly
    610                 615                 620

Val Gln Arg Val Thr Ile Thr Asp Ala Arg Arg Arg Thr Cys Pro Tyr
625                 630                 635                 640

Val Tyr Lys Ala Leu Gly Ile Val Ser Pro Arg Val Leu Ser Ser Arg
                645                 650                 655

Thr Phe


<210> SEQ ID NO 19
<211> LENGTH: 959
<212> TYPE: PRT
<213> ORGANISM: Artificial Sequence
<220> FEATURE:
<223> OTHER INFORMATION: Adenovirus hexon protein

<400> SEQUENCE: 19

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Asn Met Ser Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ser Leu Ala Pro Lys Gly
        115                 120                 125

Ala Pro Asn Ser Cys Glu Trp Glu Gln Asp Glu Pro Ala Gln Ala Ala
    130                 135                 140

Ile Ala Glu Asp Glu Glu Glu Leu Glu Glu Glu Gln Ala Gln Asp Glu
145                 150                 155                 160

Gln Ala Pro Thr Lys Lys Thr His Val Tyr Ala Gln Ala Pro Leu Ser
                165                 170                 175
```

-continued

Gly Glu Lys Ile Thr Lys Asp Gly Leu Gln Ile Gly Val Asp Ala Thr
180 185 190

Gln Ala Gly Asp Asn Pro Ile Tyr Ala Asp Lys Thr Phe Gln Pro Glu
195 200 205

Pro Gln Ile Gly Glu Ser Gln Trp Asn Glu Ala Asp Ala Thr Val Ala
210 215 220

Gly Gly Arg Val Leu Lys Lys Thr Thr Pro Met Arg Pro Cys Tyr Gly
225 230 235 240

Ser Tyr Ala Lys Pro Thr Asn Ala Asn Gly Gly Gln Gly Ile Met Val
245 250 255

Ala Asn Asp Gln Gly Ala Leu Glu Ser Lys Val Glu Met Gln Phe Phe
260 265 270

Ser Thr Thr Thr Ser Leu Asn Val Arg Glu Gly Glu Asn Asn Leu Gln
275 280 285

Pro Lys Val Val Leu Tyr Ser Glu Asp Val Asn Leu Glu Ser Pro Asp
290 295 300

Thr His Leu Ser Tyr Lys Pro Lys Lys Asp Asp Thr Asn Ser Lys Ile
305 310 315 320

Met Leu Gly Gln Gln Ala Met Pro Asn Arg Pro Asn Leu Ile Ala Phe
325 330 335

Arg Asp Asn Phe Ile Gly Leu Met Tyr Tyr Asn Ser Thr Gly Asn Met
340 345 350

Gly Val Leu Ala Gly Gln Ala Ser Gln Leu Asn Ala Val Val Asp Leu
355 360 365

Gln Asp Arg Asn Thr Glu Leu Ser Tyr Gln Leu Met Leu Asp Ser Ile
370 375 380

Gly Asp Arg Ser Arg Tyr Phe Ser Met Trp Asn Gln Ala Val Asp Ser
385 390 395 400

Tyr Asp Pro Asp Val Arg Ile Ile Glu Asn His Gly Val Glu Asp Glu
405 410 415

Leu Pro Asn Tyr Cys Phe Pro Leu Gly Gly Ile Gly Ile Thr Asp Thr
420 425 430

Tyr Gln Cys Ile Lys Pro Thr Ala Ala Ala Asn Asn Thr Thr Trp Ser
435 440 445

Lys Asp Glu Glu Phe Ser Asp Arg Asn Glu Ile Gly Val Gly Asn Asn
450 455 460

Phe Ala Met Glu Ile Asn Ile Gln Ala Asn Leu Trp Arg Asn Phe Leu
465 470 475 480

Tyr Ala Asn Val Gly Leu Tyr Leu Pro Asp Lys Leu Lys Tyr Asn Pro
485 490 495

Thr Asn Val Asp Ile Ser Asp Asn Pro Asn Thr Tyr Asp Tyr Met Asn
500 505 510

Lys Arg Val Val Ala Pro Gly Leu Val Asp Cys Phe Val Asn Val Gly
515 520 525

Ala Arg Trp Ser Leu Asp Tyr Met Asp Asn Val Asn Pro Phe Asn His
530 535 540

His Arg Asn Ala Gly Leu Arg Tyr Arg Ser Met Ile Leu Gly Asn Gly
545 550 555 560

Arg Tyr Val Pro Phe His Ile Gln Val Pro Gln Lys Phe Phe Ala Ile
565 570 575

Lys Asn Leu Leu Leu Leu Pro Gly Ser Tyr Thr Tyr Glu Trp Asn Phe
580 585 590

Arg Lys Asp Val Asn Met Val Leu Gln Ser Ser Leu Gly Asn Asp Leu 595 600 605

Arg Val Asp Gly Ala Ser Ile Lys Phe Asp Ser Val Thr Leu Tyr Ala
610 615 620

Thr Phe Phe Pro Met Ala His Asn Thr Ala Ser Thr Leu Glu Ala Met
625 630 635 640

Leu Arg Asn Asp Thr Asn Asp Gln Ser Phe Asn Asp Tyr Leu Ser Gly
645 650 655

Ala Asn Met Leu Tyr Pro Ile Pro Ala Lys Ala Thr Asn Val Pro Ile
660 665 670

Ser Ile Pro Ser Arg Asn Trp Ala Ala Phe Arg Gly Trp Ala Phe Thr
675 680 685

Arg Leu Lys Thr Lys Glu Thr Pro Ser Leu Gly Ser Gly Phe Asp Pro
690 695 700

Tyr Phe Val Tyr Ser Gly Ser Ile Pro Tyr Leu Asp Gly Thr Phe Tyr
705 710 715 720

Leu Asn His Thr Phe Lys Lys Ile Ser Ile Met Tyr Asp Ser Ser Val
725 730 735

Ser Trp Pro Gly Asn Asp Arg Leu Leu Thr Pro Asn Glu Phe Glu Val
740 745 750

Lys Arg Ala Val Asp Gly Glu Gly Tyr Asn Val Ala Gln Cys Asn Met
755 760 765

Thr Lys Asp Trp Phe Leu Val Gln Met Leu Ala Asn Tyr Asn Ile Gly
770 775 780

Tyr Gln Gly Phe Tyr Ile Pro Glu Ser Tyr Lys Asp Arg Met Tyr Ser
785 790 795 800

Phe Phe Arg Asn Phe Gln Pro Met Ser Arg Gln Val Val Asp Glu Thr
805 810 815

Lys Tyr Lys Asp Tyr Gln Ala Ile Gly Ile Thr His Gln His Asn Asn
820 825 830

Ser Gly Phe Val Gly Tyr Leu Ala Pro Thr Met Arg Glu Gly Gln Ala
835 840 845

Tyr Pro Ala Asn Phe Pro Tyr Pro Leu Ile Gly Lys Thr Ala Val Asp
850 855 860

Ser Val Thr Gln Lys Lys Phe Leu Cys Asp Arg Thr Leu Trp Arg Ile
865 870 875 880

Pro Phe Ser Ser Asn Phe Met Ser Met Gly Ala Leu Thr Asp Leu Gly
885 890 895

Gln Asn Leu Leu Tyr Ala Asn Ser Ala His Ala Leu Asp Met Thr Phe
900 905 910

Glu Val Asp Pro Met Asp Glu Pro Thr Leu Leu Tyr Ile Val Phe Glu
915 920 925

Val Phe Asp Val Val Arg Val His Gln Pro His Arg Gly Val Ile Glu
930 935 940

Thr Val Tyr Leu Arg Thr Pro Phe Ser Ala Gly Asn Ala Thr Thr
945 950 955

<210> SEQ ID NO 20
<211> LENGTH: 583
<212> TYPE: PRT
<213> ORGANISM: Artificial Sequence
<220> FEATURE:
<223> OTHER INFORMATION: Adenovirus fiber protein

<400> SEQUENCE: 20

Met Lys Arg Ala Arg Ser Ser Asp Glu Thr Phe Asn Pro Val Tyr Pro

-continued

```
1               5                   10                  15

Tyr Asp Thr Glu Ile Ala Pro Thr Ser Val Pro Phe Leu Thr Pro Pro
            20                  25                  30

Phe Val Ser Ser Ala Gly Met Gln Glu Asn Pro Ala Gly Val Leu Ser
        35                  40                  45

Leu His Leu Ser Glu Pro Leu Thr Thr His Asn Gly Ala Leu Thr Leu
    50                  55                  60

Lys Met Gly Gly Gly Leu Thr Leu Asp Lys Glu Gly Asn Leu Thr Ser
65                  70                  75                  80

Gln Asn Ile Thr Ser Val Asp Pro Pro Leu Lys Lys Ser Lys Asn Asn
                85                  90                  95

Ile Ser Leu Gln Thr Ala Ala Pro Leu Ala Val Ser Ser Gly Ala Leu
            100                 105                 110

Thr Leu Phe Ala Thr Pro Pro Leu Ala Val Ser Gly Asp Asn Leu Thr
        115                 120                 125

Val Gln Ser Gln Ala Pro Leu Thr Leu Glu Asp Ser Lys Leu Thr Leu
    130                 135                 140

Ala Thr Lys Gly Pro Leu Thr Val Ser Glu Gly Lys Leu Val Leu Glu
145                 150                 155                 160

Thr Glu Ala Pro Leu His Ala Ser Asp Ser Ser Ser Leu Gly Leu Ser
                165                 170                 175

Val Thr Ala Pro Leu Ser Ile Asn Asn Asp Ser Leu Gly Leu Asp Leu
            180                 185                 190

Gln Ala Pro Ile Val Ser Gln Asn Gly Lys Leu Ala Leu Asn Val Ala
        195                 200                 205

Gly Pro Leu Ala Val Ala Asn Gly Ile Asn Ala Leu Thr Val Gly Thr
    210                 215                 220

Gly Lys Gly Ile Gly Leu Asn Glu Thr Ser Thr His Leu Gln Ala Lys
225                 230                 235                 240

Leu Val Ala Pro Leu Gly Phe Asp Thr Asn Gly Asn Ile Lys Leu Ser
                245                 250                 255

Val Ala Gly Gly Met Arg Leu Asn Asn Asp Thr Leu Ile Leu Asp Val
            260                 265                 270

Asn Tyr Pro Phe Glu Ala Gln Gly Gln Leu Ser Leu Arg Val Gly Gln
        275                 280                 285

Gly Pro Leu Tyr Val Asp Ser Ser Ser His Asn Leu Thr Ile Arg Cys
    290                 295                 300

Leu Arg Gly Leu Tyr Ile Thr Ser Ser Asn Asn Gln Thr Gly Leu Glu
305                 310                 315                 320

Ala Asn Ile Lys Leu Thr Lys Gly Leu Val Tyr Asp Gly Asn Ala Ile
                325                 330                 335

Ala Val Asn Val Gly Gln Gly Leu Gln Tyr Ser Thr Thr Ala Thr Ser
            340                 345                 350

Glu Gly Val Tyr Pro Ile Gln Ser Lys Ile Gly Leu Gly Met Glu Tyr
        355                 360                 365

Asp Thr Asn Gly Ala Met Met Thr Lys Leu Gly Ser Gly Leu Ser Phe
    370                 375                 380

Asp Asn Ser Gly Ala Ile Val Val Gly Asn Lys Asn Asp Asp Arg Leu
385                 390                 395                 400

Thr Leu Trp Thr Thr Pro Asp Pro Ser Pro Asn Cys Arg Ile Tyr Ser
                405                 410                 415

Glu Lys Asp Thr Lys Leu Thr Leu Val Leu Thr Lys Cys Gly Ser Gln
            420                 425                 430
```

```
Ile Leu Gly Thr Val Ser Ala Leu Ala Val Arg Gly Ser Leu Ala Pro
        435                 440                 445

Ile Thr Asn Ala Ser Ser Ile Val Gln Ile Phe Leu Arg Phe Asp Glu
    450                 455                 460

Asn Gly Leu Leu Met Ser Asn Ser Ser Leu Asp Gly Asp Tyr Trp Asn
465                 470                 475                 480

Tyr Arg Asn Gly Asp Ser Thr Asn Ser Thr Pro Tyr Thr Asn Ala Val
                485                 490                 495

Gly Phe Met Pro Asn Leu Ala Ala Tyr Pro Lys Gly Gln Ala Thr Ala
            500                 505                 510

Ala Lys Ser Ser Ile Val Ser Gln Val Tyr Met Asp Gly Asp Thr Thr
        515                 520                 525

Lys Pro Ile Thr Leu Lys Ile Asn Phe Asn Gly Ile Asp Glu Thr Thr
    530                 535                 540

Glu Asn Thr Pro Val Ser Lys Tyr Ser Met Thr Phe Ser Trp Ser Trp
545                 550                 555                 560

Pro Thr Ala Ser Tyr Ile Gly His Thr Phe Ala Thr Asn Ser Phe Thr
                565                 570                 575

Phe Ser Tyr Ile Ala Gln Glu
            580
```

<210> SEQ ID NO 21
<211> LENGTH: 32739
<212> TYPE: DNA
<213> ORGANISM: Artificial Sequence
<220> FEATURE:
<223> OTHER INFORMATION: Adenovirus vector nucleotide sequences

<400> SEQUENCE: 21

```
catcatcaat aatatacctt attttggatt gtggccaata tgataatgag gtgggcgggg     60

agaggcgggg cgggtgacgt aggacgcgcg agtagggttg ggaggtgtgg cggaagtgtg    120

gcatttgcaa gtgggaggag ctcacatgca agcttccgtc gcggaaaatg tgacgttttt    180

gatgagcgcc gcctacctcc ggaagtgcca attttcgcgc gcttttcacc ggatatcgta    240

gtaattttgg gcgggaccat gtaagatttg gccattttcg cgcgaaaagt gaaacgggga    300

agtgaaaact gaataatagg gcgttagtca tagcgcgtaa tatttaccga gggccgaggg    360

actttgaccg attacgtgga ggactcgccc aggtgttttt tacgtgaatt tccgcgttcc    420

gggtcaaagt ctccgttttt attgtcaccg tcatttgacg cggagggtat ttaaacccgc    480

tgcgctcctc aagaggccac tcttgagtgc cagcgagaag agttttctcc tctgctccgc    540

ttcggtgatc gaaaaatgag acacatagcc tgcactccgg gtcttttgtc cggtcgggcg    600

gcggccgagc ttttggacgc tttgatcaat gatgtcctaa gcgatgattt tccgtctact    660

acccacttta gcccacctac tcttcacgaa ctgtacgatc tggatgtact ggtggatgtg    720

aacgatccca acgaggaggc ggtttctgcg tttttcccg agtctgcgct gttggccgct    780

caggagggat ttgacctaca cactccgccg cctattttag agtctccgct gccggagccc    840

agtggtatac cttatatgcc tgaactgctt cccgaagtgg tagacctgac ctgccacgag    900

cctggctttc cgcccagcga cgatgagggt gagccttttg ttttagactt tgctgagata    960

cctgggcacg gttgcaggtc ttgtgcatat catcagaggg ttaccggaga ccccgaggtt   1020

aagtgttcgc tgtgctatat gaggatgacc tcttccttta tctacagtaa gtttttgtct   1080

aggtgggctt ttgggtaggt gggttttgtg tcagaacagg tgtaaacgtt gcttgtgttt   1140
```

-continued

```
tttgtacctg taggtccggt gtccgagcca gacccggagc ccgaccgcga tcccgagccg   1200
gatcccgagc ctcctcgcag gacaaggaaa ctaccttcca ttctgtgcaa gtctcagaca   1260
cctgtaagga ccagcgaggc agacagcacc gactctggca cttctacctc tccccctgaa   1320
attcacccag tggttcctct gggtatacat aaacctgttg ctgttaaagt ttgcgggcga   1380
cgccctgcag tacagtgcat tgaggacttg cttcacgatc ccgaggaacc tttggacttg   1440
agccttaaac gccctaggca ataaacccca cctaagtaat aaaccccacc taagtaataa   1500
accctgccgc ccttggttat tgagatgacg cccaatgttt gcttttgaat gacttcatgt   1560
gtgtaataaa agtgagtgtg atcataggtc tcttgtttgt ctgggcgggg cttaagggta   1620
tataagtctc ttggggctaa acttggttac acttgacccc aatggaggcg tgggggtgct   1680
tggaggagtt tgcggacgtg cgccgtttgc tggacgagag ctctagcaat acctatacta   1740
tttggaggta tctgtggggc tctactcagg ccaagttggt ttccagaatt aagcaggatt   1800
acaagtgcga ttttgaagag ctttttagtt cctgcggtga gcttttgcaa tccttgaatc   1860
tgggccatca ggctattttc caggaaaagg ttctctcgac tttggatttt tccactcccg   1920
ggcgcaccgc cgcttgtgtg gcttttgtgt cttttgtgca agataaatgg agcgaggaga   1980
cccacctgag tcacggctac gtactggatt tcatggcgat ggctctttgg agggctcaca   2040
acaaatggaa gattcagaag gaactgtacg gttccgccct acgtcgtcca cttctgtcgc   2100
gacaggggct gaggtttccc gaccatcggc agcatcagaa tctggaagac gagtcggagg   2160
agcgagcgga ggagaagatc agcttgagag ccggcctgga ccctcctcag gaggaatgaa   2220
tctcccgcag gtggttgacc tgtttccaga actgagacgg gtcctgacta tcagggagga   2280
tggtcagttt gtgaagaagt ttaagaggga tcggggtgag ggagatgatg aggcggctag   2340
caatttagct tttagtctga tgactcgcca ccgaccggaa tgtattacct atcagcagat   2400
taaggagagt tgtgccaacg agctggatct tttgggtcag aagtatagca tagaacagct   2460
taccacttac tggcttcagc ctggggatga ttgggaagag gcgatcaggg tgtatgcaaa   2520
ggtggccctg cggcccgatt gcaagtataa gattactaag ttggttaata ttagaaactg   2580
ctgctatatt tctgggaacg gggccgaagt ggagatagat actcaggaca gggtggcttt   2640
taggtgttgc atgataaaca tgtggcccgg gatactgggg atggatgggg tggtattcat   2700
gaatgtgagg tttacgggcc ccaactttaa tggcacggtg ttcatgggca acaccaactt   2760
gctcctgcat ggtgcgagtt tctatgggtt taataacacc tgtatagagg cctggaccga   2820
tgtaaaggtt cgaggttgtt ccttttatag ctgttggaag gcggtggtgt gtcgccctaa   2880
aagcaggggt tctgtgaaaa aatgcttgtt tgaaaggtgc accttaggca tcctctctga   2940
gggcaactcc agggtgcgcc ataatgtggc ttcgaactgc ggttgcttca tgcaagtgaa   3000
gggggtgagc gttatcaagc ataactcggt gtgtggaaac tgcgaggatc gcgcctccca   3060
gatgctgacc tgctttgatg gcaactgtca cctgttgaag accattcata taagcagcca   3120
ccccagaaag gcctggcccg tgtttgagca taacatcttg acccgctgct ccttgcatct   3180
gggggtcagg aggggtatgt tcctgcctta ccagtgtaac tttagccaca ctaaaatcct   3240
gctggaaccc gagtgcatga ccaaggtcag cctgaatggt gtgtttgatg tgactctgaa   3300
aatctggaag gtgctgaggt atgatgagac caggaccagg tgccgaccct gcgagtgcgg   3360
cggcaagcac atgagaaatc agcctgtgat gttggatgtg accgaggagc ttaggcctga   3420
ccatctggtg ctggcctgca ccagggccga gtttgggtct agcgatgagg ataccgattg   3480
aggtgggtaa ggtgggcgtg gctagaaggg tggggcgtgt ataaattggg ggtctaaggg   3540
```

```
tctctctgtt ttgtcttgca acagccgccg ccatgagcga caccggcaac agctttgatg   3600
gaagcatctt tagcccctat ctgacagtgc gcatgcctca ctgggctgga gtgcgtcaga   3660
atgtgatggg ttccaacgtg gatggacgcc ccgttctgcc ttcaaattcg tctacaatgg   3720
cctacgcgac cgtgggagga actccgctgg acgccgcgac ctccgccgcc gcctccgccg   3780
ccgccgcgac cgcgcgcagc atggctacgg acctttacag ctctttggtg gcgagcggcg   3840
cggcctctcg cgcgtctgct cgggatgaga aactgaccgc tctgctgctt aaactggaag   3900
acttgacccg ggagctgggt caactgaccc agcaggtctc cagcttgcgt gagagcagcc   3960
ttgcctcccc ctaatggccc ataatataaa taaaagccag tctgtttgga ttaagcaagt   4020
gtatgttctt tatttaactc tccgcgcgcg gtaagcccgg gaccagcggt ctcggtcgtt   4080
tagggtgcgg tggattcttt ccaacacgtg gtacaggtgg ctctggatgt ttagatacat   4140
gggcatgagt ccatccctgg ggtggaggta gcaccactgc agagcttcgt gctcgggggt   4200
ggtgttgtat atgatccagt cgtagcagga gcgctgggcg tggtgctgaa aaatgtcctt   4260
aagcaagagg cttatagcta gggggaggcc cttggtgtaa gtgtttacaa atctgctcag   4320
ttgggagggg tgcatccggg gggatataat gtgcatcttg gactggattt ttaggttggc   4380
tatgttccca cccagatccc ttctgggatt catgttgtgc aggaccacca gcacggtata   4440
tccagtgcac ttgggaaatt tatcgtggag cttagacggg aatgcatgga agaacttgga   4500
gacgcccttg tggcctccca gattttccat acattcgtcc atgatgatgg caatgggccc   4560
gtgggaagct gcctgagcaa aaatgtttct gggatcgctc acatcgtagt tatgttccag   4620
ggtgaggtca tcataggaca tctttacgaa tcgggggcgg agggtcccgg actgggggat   4680
gatggtaccc tcgggccccg gggcgtagtt cccctcacag atctgcatct cccaggcttt   4740
catttcagag ggagggatca tatccacctg cggagcgatg aaaaacacag tttctggcgc   4800
aggggagatt aactgggatg agagcaggtt tctgagcagc tgtgactttc cacagccggt   4860
gggcccatat atcacgccta tcaccggctg cagctggtag ttaagagagc tgcagctgcc   4920
gtcctcccgg agcagggggg ccacctcgtt cagcatatcc ctgacgtgga tgttctccct   4980
gaccaattcc gccagaaggc gctcgccgcc cagcgaaagc agctcttgca aggaagcaaa   5040
atttttcagc ggttttaggc cgtcggccgt gggcatgttt ttcagcgtct gggtcagcag   5100
ttccagcctg tcccacagct cggtgatgtg ctctacggca tctcgatcca gcagatctcc   5160
tcgtttcgcg ggttggggcg gctttcgctg tagggcacca gccgatgggc gtccagcggg   5220
gccagagtca tgtccttcca tgggcgcagg gtcctcgtca gggtggtctg ggtcacggtg   5280
aaggggtgcg ctccgggttg ggcgctggcc agggtgcgct tgaggctggt tctgctggtg   5340
ctgaatcgct gccgctcttc gccctgcgcg tcggccaggt agcatttgac catggtctcg   5400
tagtcgagac cctcggcggc gtgccccttg gcgcggagct ttcccttgga ggtggcgccg   5460
cacgaggggc actgcaggct cttcagggcg tagagcttgg gagcgagaaa cacggactct   5520
ggggagtagg cgtccgcgcc gcaggaagcg cagaccgtct cgcattccac cagccaagtg   5580
agctccgggc ggtcagggtc aaaaaccagg ttgcccccat gctttttgat gcgtttctta   5640
cctcggctct ccatgaggcg gtgtcccttc tcggtgacga agaggctgtc cgtgtccccg   5700
tagaccgact tcaggggcct gtcttccagc ggagtgcctc tgtcctcctc gtagagaaac   5760
tctgaccact ctgagacgaa ggcccgcgtc caggccagga cgaaggaggc cacgtgggag   5820
gggtagcggt cgttgtccac tagcgggtcc accttctcca gggtgtgcag gcacatgtcc   5880
```

-continued

```
ccctcctccg cgtccagaaa agtgattggc ttgtaggtgt aggacacgtg accgggggtt   5940
cccgacgggg gggtataaaa gggggtgggc gccctttcat cttcactctc ttccgcatcg   6000
ctgtctgcga gggccagctg ctggggtaag tattccctct cgaaggcggg catgacctca   6060
gcgctcaggt tgtcagtttc taaaaatgag gaggatttga tgttcacctg tccggaggtg   6120
ataccttga gggtacctgg gtccatctgg tcagaaaaca ctattttttt gttgtcaagc   6180
ttggtggcga acgacccgta gagggcgttg gagagcagct tggcgatgga gcgcagggtc   6240
tggtttttgt cgcggtcggc tcgctccttg gccgcgatgt tgagttgcac gtactcgcgg   6300
gccacgcact tccactcggg gaagacggtg gtgcgctcgt ctgggattag gcgcaccctc   6360
cagcctcggt tgtgcagggt gaccatgtcg acgctggtgg cgacctcgcc gcgcaggcgc   6420
tcgttggtcc agcagaggcg gccgcccttg cgcgagcaga aggggggtag ggggtccagc   6480
tggtcctcgt ttgggggggtc cgcgtcgatg gtgaagaccc cggggagcaa gcgcgggtca   6540
aagtagtcga tcttgcaagc ttgcatgtcc agagcccgct gccattcgcg ggcggcgagc   6600
gcgcgctcgt aggggttgag gggcgggccc cagggcatgg ggtgggtgag cgcggaggcg   6660
tacatgccgc agatgtcata cacgtacagg ggttccctga ggatgccgag gtaggtgggg   6720
tagcagcgcc ccccgcggat gctggcgcgc acgtagtcat agagctcgtg ggagggggcc   6780
agcatgttgg gcccgaggtt ggtgcgctgg gggcgctcgg cgcggaaggc gatctgcctg   6840
aagatggcat gggagttgga ggagatggtg ggccgctgga agacgttgaa gcttgcttct   6900
tgcaagccca ccgagtccct gacgaaggag gcgtaggact cgcgcagctt gtgcaccagc   6960
tcggcggtga cctggacgtc gagcgcgcag tagtcgaggg tctcgcggat gatgtcatac   7020
ttatcctccc ccttcttttt ccacagctcg cggttgagga cgaactcttc gcggtctttc   7080
cagtactctt ggaggggaaa cccgtccgtg tccgaacggt aagagcctag catgtagaac   7140
tggttgacgg cctggtaggg gcaacagccc ttctccacgg gcagcgcgta ggcctgcgcc   7200
gccttgcgga gggaggtgtg ggtgagggcg aaagtgtccc tgaccatgac tttgaggtat   7260
tgatgtttga agtctgtgtc atcgcagccg ccctgttccc acagggtgta gtccgtgcgc   7320
tttttggagc gcgggttggg cagggagaag gtgaggtcat tgaagaggat cttccccgct   7380
cgaggcatga agtttctggt gatgcgaaag ggccctggga ccgaggagcg gttgttgatg   7440
acctgggcgg ccaggacgat ctcgtcaaag ccgtttatgt tgtggcccac gatgtagagc   7500
tccaaaaagc ggggctggcc cttgatggag gggagctttt tgagttcctc gtaggtgagc   7560
tcctcgggcg attccaggcc gtgctcctcc agggcccagt cttgcaagtg agggttggcc   7620
gccaggaagg atcgccagag gtcgcgggcc atgagggtct gcaggcggtc gcggaaggtt   7680
ctgaactgtc gccccacggc catcttttcg gggtgatgc agtagaaggt gagggggtct   7740
ttctcccagg ggtcccatct gagctctcgg gcgaggtcgc gcgcggcggc gaccagagcc   7800
tcgtcgcccc ccagtttcat gaccagcatg aagggcacga gctgcttgcc aaaggctccc   7860
atccaagtgt aggtctctac atcgtaggtg acaaagaggc gctccgtgcg aggatgagag   7920
ccgatcggga agaactggat ctcccgccac cagttggagg attggctgtt gatgtggtga   7980
aagtagaagt cccgtctgcg ggccgagcac tcgtgctggc ttttgtaaaa gcgaccgcag   8040
tactggcagc gctgcacggg ttgtatatct tgcacgaggt gaacctggcg acctctgacg   8100
aggaagcgca gcgggaatct aagtcccccg cctggggtcc cgtgtggctg gtggtcttct   8160
actttggttg tctggccgcc agcatctgtc tcctggaggg cgatggtgga gcagaccacc   8220
acgccgcgag agccgcaggt ccagatctcg gcgctcggcg ggcggagttt gatgacgaca   8280
```

-continued

```
tcgcgcacat tggagctgtc catggtctcc agctcccgcg gcggcaggtc agctgggagt   8340
tcctggaggt tcacctcgca gagacgggtc aaggcgcggg cagtgttgag atggtatctg   8400
atttcaaggg gcgtgttggc ggcggagtcg atggcttgca ggaggccgca gccccggggg   8460
gccacgatgg ttccccgcgg ggcgcgaggg gaggcggaag ctgggggtgt gttcagaagc   8520
ggtgacgcgg gcgggccccc ggaggtaggg ggggttccgg ccccacaggc atgggcggca   8580
ggggcacgtc ttcgccgcgc gcgggcaggg gctggtgctg gctccgaaga gcgcttgcgt   8640
gcgcgacgac gcgacggttg gtgtcctgta tctgacgcct ctgagtgaag accacgggtc   8700
ccgtgacctt gaacctgaaa gagagttcga cagaatcaat ctcggcatcg ttgacagcgg   8760
cctggcgcag gatctcctgc acgtcgcccg agttgtcctg gtaggcgatc tctgccatga   8820
actgctcgat ctcttcttcc tggagatctc ctcgtccggc gcgctccacg gtggccgcca   8880
ggtcgttgga gatgcgaccc atgagctgtg agaaggcgtt gagcccgccc tcgttccaga   8940
cccggctgta gaccacgccc ccctcggcgt cgcgagcgcg catgaccacc tgggccaggt   9000
tgagctccac gtgtcgcgtg aagacggcgt agttgcgcag gcgctggaaa aggtagttca   9060
gggtggtggc ggtgtgctcg gcgacgaaga agtacatgac ccagcgccgc aacgtggatt   9120
cattgatgtc ccccaaggcc tccaggcgct ccatggcctc gtagaagtcc acggcgaagt   9180
tgaaaaactg ggagttgcga gcggacacgg tcaactcctc ctccagaaga cggatgagct   9240
cggcgacagt gttgcgcacc tcgcgctcga aggccacggg gggcgcttct tcctcttcca   9300
cctcttcttc catgatcgct tcttcttctt cctcagccgg gacgggaggg ggcggcggcg   9360
gcgggggagg ggcgcggcgg cggcggcggc gcaccgggag gcggtcgatg aagcgctcga   9420
tcatctcccc ccgcatgcgg cgcatggtct cggtgacggc gcggccgttc tcccgggggc   9480
gcagctcgaa gacgccgcct ctcatctcgc cgcggggcga gcggccgtga ggtagcgaga   9540
cggcgctgac tatgcatctt aacaattgct gtgtaggtac accgccgagg gacctgattg   9600
agtccagatc caccggatcc gaaaaccttt ggaggaaagc gtctatccag tcgcagtcgc   9660
aaggtaggct gagcaccgtg gcgggcgggg gcgggtctgg agagttcctg gcggagatgc   9720
tgctgatgat gtaattaaag taggcggtct tgagaaggcg gatggtggac aggagcacca   9780
tgtctttggg tccggcctgt tggatgcgga ggcggtcggc catgccccag gcctcgttct   9840
gacaccggcg caggtctttg tagtagtctt gcatgagtct ttccaccggc acctcttctc   9900
cttcctcttc tccatctcgc cggtggtttc tcgcgccgcc catgcgcgtg accccaaagc   9960
ccctgagcgg ctgcagcagg gccaggtcgg cgaccacgcg ctcggccaag atggcctgct  10020
gcacctgagt gagggtcctc tcgaagtcat ccatgtccac gaagcggtgg taggcgcccg  10080
tgttgatggt gtaggtgcag ttggccatga cggaccagtt gacggtctgg tgtcccggct  10140
gcgagagctc cgtgtaccgc aggcgcgaga aggcgcggga atcgaacacg tagtcgttgc  10200
aagtccgcac cagatactgg tagcccacca ggaagtgcgg cggaggttgg cgatagaggg  10260
gccagcgctg ggtggcgggg gcgccgggcg ccaggtcttc cagcatgagg cggtggtatc  10320
cgtagatgta cctggacatc caggtgatgc cggcggcggt ggtggtggcg cgcgcgtagt  10380
cgcggacccg gttccagatg tttcgcaggg gcgagaagtg ttccatggtc ggcacgctct  10440
ggccggtgag gcgcgcgcag tcgttgacgc tctatacaca cacaaaaacg aaagcgttta  10500
cagggctttc gttctgtagc ctggaggaaa gtaaatgggt tgggttgcgg tgtgccccgg  10560
ttcgagacca agctgagctc ggccggctga agccgcagct aacgtggtat tggcagtccc  10620
```

```
gtctcgaccc aggccctgta tcctccagga tacggtcgag agccctttttg ctttcttggc  10680
caagcgcccg tggcgcgatc tgggatagat ggtcgcgatg agaggacaaa agcggctcgc  10740
ttccgtagtc tggagaaaca atcgccaggg ttgcgttgcg gcgtaccccg gttcgagccc  10800
ctatggcggc ttgaatcggc cggaaccgcg gctaacgagg gccgtggcag ccccgtcctc  10860
aggaccccgc cagccgactt ctccagttac gggagcgagc cccttttgtt ttttattttt  10920
tagatgcatc ccgtgctgcg gcagatgcgc ccctcgcccc ggcccgatca gcagcagcaa  10980
cagcaggcat gcagaccccc ctctcccctt tccgccccgg tcaccacggc cgcggcggcc  11040
gtgtcgggcg cggggggcgc gctggagtca gatgagccac cgcggcggcg acctaggcag  11100
tatctggact tggaagaggg cgagggactg gcgcggctgg gggcgaactc tccagagcgc  11160
cacccgcggg tgcagttgaa aagggacgcg cgcgaggcgt acctgccgcg gcagaacctg  11220
tttcgcgacc gcgggggcga ggagcccgag gagatgcgag actgcaggtt ccaagcgggg  11280
cgcgagctgc ggcgcgggct ggacagacag cgcctgctgc gcgaggagga ctttgagccc  11340
gacacgcaga cgggcatcag ccccgcgcgc gcgcacgtag ccgcggccga cctggtgacc  11400
gcctacgagc agacggtaaa ccaggagcgc aacttccaaa agagcttcaa caaccacgtg  11460
cgcacgctgg tggcgcgcga ggaggtgacc ctgggtctca tgcatctgtg ggacctggtg  11520
gaggcgatcg tgcagaaccc cagcagcaag cccctgaccg cgcagctgtt cctggtggtg  11580
cagcacagca gggacaacga ggccttcagg gaggcgctgc tgaacatcac cgagccggag  11640
gggcgctggc tcctggacct gataaacatc ctgcagagca tagtggtgca ggagcgcagc  11700
ctgagcctgg ccgagaaggt ggcggccatc aactactcta tgctgagcct gggcaagttc  11760
tacgcccgca agatctacaa gaccccctac gtgcccatag acaaggaggt gaagatagac  11820
agcttctaca tgcgcatggc gctgaaggtg ctgaccctga gcgacgacct gggagtgtac  11880
cgcaacgagc gcatccacaa ggccgtgagc gccagccggc ggcgcgagct gagcgaccgc  11940
gagctgatgc acagtctgca gcgcgcgctg accggcgcgg gcgagggcga cagggaggtc  12000
gagtcctact tcgacatggg ggccgacctg cactggcagc cgagccgccg cgccctggag  12060
gcggcggggg cgtacggcgg ccccctggcg gccgatgacc aggaagagga ggactatgag  12120
ctagaggagg gcgagtacct ggaggactga cctggctggt ggtgttttgg tatagatgca  12180
agatccgaac gtggcggacc cggcggtccg ggcggcgctg caaagccagc cgtccggcat  12240
taactcctct gacgactggg ccgcggccat gggtcgcatc atggccctga ccgcgcgcaa  12300
ccccgaggct ttcaggcagc agcctcaggc caaccggctg gcggccatct tggaagcggt  12360
agtgcccgcg cgctccaacc ccacccacga gaaggtgctg gccatagtca acgcgctggc  12420
ggagagcagg gccatccgcg cggacgaggc cggactggtg tacgatgcgc tgctgcagcg  12480
ggtggcgcgg tacaacagcg gcaacgtgca gaccaacctg gaccgcctgg tgacggacgt  12540
gcgcgaggcc gtggcgcagc gcgagcgctt gcatcaggac ggtaacctgg gctcgctggt  12600
ggcgctaaac gccttcctca gcacccagcc ggccaacgta ccgcgggggc aggaggacta  12660
caccaacttt ttgagcgcgc tgcggctgat ggtgaccgag gtccctcaga gcgaggtgta  12720
ccagtcgggg cccgactact tcttccagac cagcagacag ggcttgcaaa ccgtgaacct  12780
gagccaggct ttcaagaacc tgcgggggct gtggggagtg aaggcgccca ccggcgaccg  12840
ggctacggtg tccagcctgc taacccccaa ctcgcgcctg ctgctgctgc tgatcgcgcc  12900
cttcacggac agcgggagcg tctcgcggga gacctatctg ggccacctgc tgacgctgta  12960
ccgcgaggcc atcgggcagg cgcaggtgga cgagcacacc ttccaagaga tcaccagcgt  13020
```

-continued

```
gagccacgcg ctggggcagg aggacacggg cagcctgcag gcgaccctga actacctgct  13080
gaccaacagg cggcagaaga ttcccacgct gcacagcctg acccaggagg aggagcgcat  13140
cttgcgctac gtgcagcaga gcgtgagcct gaacctgatg cgcgacggcg tgacgcccag  13200
cgtggcgctg gacatgaccg cgcgcaacat ggaaccgggc atgtacgcct cccaccggcc  13260
gtttatcaac cgcctgatgg actacttgca tcgggcggcg gccgtgaacc ccgagtactt  13320
cactaatgcc attctgaatc cccactggat gcccccctccg ggtttctaca acggggactt  13380
tgaggtgccc gaggtcaacg acgggttcct ctgggatgac atggatgaca gtgtgttctc  13440
acccaacccg ctgcgcgccg cgtctctgcg attgaaggag ggctctgaca gggaaggacc  13500
gaggagtctg gcctcctccc tggctctggg agcggtgggc gccacgggcg cggcggcgcg  13560
gggcagtagc cccttcccca gcctggcaga ctctctgaac agcgggcggg tgagcaggcc  13620
ccgcttgcta ggcgaggagg agtatctgaa caactccctg ctgcagcccg cgagggacaa  13680
gaacgctcag cggcagcagt ttcccaacaa tgggatagag agcctggtgg acaagatgtc  13740
cagatggaag acgtatgcgc aggagtacaa ggagtgggag gaccgccagc cgcggccctt  13800
gccgcccccct aggcagcgct ggcagcggcg cgcgtccaac cgccgctgga ggcaggggcc  13860
cgaggacgat gatgactctg cagatgacag cagcgtgttg gacctgggcg ggagcgggaa  13920
ccccttttcg cacctgcgcc cacgcctggg caagatgttt taaaagaaaa aaaaaataaa  13980
actcaccaag gccatggcga cgagcgttgg ttttttgttc ccttccttag tatgcggcgc  14040
gcggcgatgt tcgaggaggg gcctcccccc tcttacgaga gcgcgatggg gatttctcct  14100
gcggcgcccc tgcagcctcc ctacgtgcct cctcggtacc tgcaacctac agggggggaga  14160
aatagcatct gttactctga gctgcagccc ctgtacgata ccaccagact gtacctggtg  14220
gacaacaagt ccgcggacgt ggcctccctg aactaccaga acgaccacag cgattttttg  14280
accacggtga tccaaaacaa cgacttcacc ccaaccgagg ccagcaccca gaccataaac  14340
ctggataaca ggtcgaactg gggcggcgac ctgaagacca tcttgcacac caacatgccc  14400
aacgtgaacg agttcatgtt caccaactct tttaaggcgc gggtgatggt ggcgcgcgag  14460
cagggggagg cgaagtacga gtgggtggac ttcacgctgc ccgagggcaa ctactcagag  14520
accatgactc tcgacctgat gaacaatgcg atcgtggaac actatctgaa agtgggcagg  14580
cagaacgggg tgaaggaaag cgatatcggg gtcaagtttg acaccagaaa cttccgtctg  14640
ggctgggacc ccgtgaccgg gctggtcatg ccgggggtct acaccaacga ggcctttcat  14700
cccgacatag tgcttctgcc cggctgtggg gtggacttca cccagagccg gctgagcaac  14760
ctgctgggca ttcgcaagcg gcagcctttc caggagggtt tcaagatcac ctatgaggat  14820
ctgaaggggg gcaacattcc cgcgctcctt gatctggacg cctacgagga gagcttgaaa  14880
cccgaggaga gcgctggcga cagcggcgag agtggcgagg agcaagccgg cggcggtggc  14940
ggcgcgtcgg tagaaaacga aagtacgccc gcagtggcgg cggacgctgc ggaggtcgag  15000
ccggaggcca tgcagcagga cgcagaggag ggcgcacagg agggcgcgca gaaggacatg  15060
aacgatgggg agatcagggg agacacattc gccacccggg gcgaagaaaa agaggcagag  15120
gcggcggcgg cggcgacggc ggaggccgaa accgaggttg aggcagaggc agagcccgag  15180
accgaagtta tggaagacat gaatgatgga gaacgtaggg gcgacacgtt cgccacccgg  15240
ggcgaagaga aggcggcgga ggcagaagcc gcggctgagg aggcggctgc ggctgcggcc  15300
aagactgagg ctgcggctaa ggctgaggtc gaagccaatg ttgcggttga ggctcaggct  15360
```

```
gaggaggagg cggcggctga agcagttaag gaaaaggccc aggcagagca ggaagagaaa  15420
aaacctgtca ttcaacctct aaaagaagat agcaaaaagc gcagttacaa cgtcatcgag  15480
ggcagcacct ttacccagta ccgcagctgg tacctggcgt acaactacgg cgacccggtc  15540
aagggggtgc gctcgtggac cctgctctgc acgccggacg tcacctgcgg ctccgagcag  15600
atgtactggt cgctgccgaa catgatgcaa gacccggtga ccttccgctc cacgcggcag  15660
gttagcaact tcccggtggt gggcgccgaa ctgctgcccg tgcactccaa gagtttttac  15720
aacgagcagg ccgtctactc ccagctgatc cgccaggcca cctctctgac ccacgtgttc  15780
aatcgctttc ccgagaacca gattttggcg cgcccgccgg cccccaccat caccaccgtg  15840
agtgaaaacg ttcctgccct cacagatcac gggacgctac cgctgcgcaa cagcatctca  15900
ggagtccagc gagtgaccat tactgacgcc agacgccgga cctgccccta cgtttacaag  15960
gccttgggca tagtctcgcc gcgcgtcctc tccagtcgca ctttttaaaa cacatctacc  16020
cacacgttcc aaaatcatgt ccgtactcat ctcacccagc aacaacaccg gctgggggct  16080
gcgcgcgccc agcaagatgt ttggaggggc gaggaagcgc tccgaccagc accctgtgcg  16140
cgtgcgcggc cactaccgcg cgccctgggg agcgcacaag cgcgggcgca cagggcgcac  16200
cactgtggac gacgtcattg actccgtagt ggagcaagcg cgccactaca cacccggcgc  16260
gccgaccgcc cccgccgtgt ccaccgtgga ccaggcgatc gaaagcgtgg tacagggcgc  16320
gcggcactat gccaacctta aaagtcgccg ccgccgcgtg gcccgccgcc atcgccggag  16380
accccgggcc accgccgccg cgcgccttac taaggctctg ctcaggcgcg ccaggcgaac  16440
tggccaccgg gccgccatga gggccgcacg gcgggctgcc gctgccgcaa gcgtcgtggc  16500
cccgcgggca cgaaggcgcg cggccgctgc cgccgccgcc gccatttcca gcttggcctc  16560
gacgcggcgc ggtaacatat actgggtgcg cgactcggta accggcacgc gggtacccgt  16620
gcgctttcgc cccccgcgga attagcacaa gacaacatac acactgagtc tcctgctgtt  16680
gtgtatccca gcggcgaccg tcagcagcgg cgacatgtcc aagcgcaaaa ttaaagaaga  16740
gatgctccag gtcatcgcgc cggagatcta tgggcccccg aagaaggagg aggatgatta  16800
caagccccgc aagctaaagc gggtcaaaaa gaaaaagaaa gatgatgatg acgaggcggt  16860
ggagtttgtc cgccgcatgg cacccaggcg ccccgtgcag tggaagggcc ggcgcgtgca  16920
gcgcgttttg cgccccggca ccgcggtggt cttcacgccc ggcgagcgct ccacgcgcac  16980
tttcaagcgg gtgtacgatg aggtgtacgg cgacgaggac ctgttggagc aggccaacca  17040
gcgctttggg gagtttgcat atgggaaacg gccccgcgag agtctaaaag aggacctgct  17100
ggcgctaccg ctggacgagg gcaatcccac cccgagtctg aagccggtaa ccctgcaaca  17160
ggtgctgcct ttgagcgcgc ccagcgagca taagcgaggg ttgaagcgcg aaggcgggga  17220
cctggcgccc accgtgcagt tgatggtgcc caagcggcag aagctggagg acgtgctgga  17280
gaaaatgaaa gtagagcccg ggatccagcc cgagatcaag gtccgcccca tcaagcaggt  17340
ggcgcccggc gtgggagtcc agaccgtgga cgttaggatt ccccacggag agatggaaac  17400
ccaaaccgcc actccctctt cggcggccag cgccaccacc ggcaccgctt cggtagaggt  17460
gcagacggac ccctggctac ccgccaccgc tgttgccgcc gccgcccccc gttcgcgcgg  17520
gcgcaagaga aattatccag cggccagcgc gctcatgccc cagtacgcac tgcatccatc  17580
catcgtgccc acccccggct accgcgggta ctcgtaccgc ccgcgcagat cagccggcac  17640
tcgcggccgc cgccgccgtg cgaccacaac cagccgccgc cgtcgccgcc gccgccagcc  17700
agtgctgacc cccgtgtctg taaggaaggt ggctcgctcg gggagcacgc tggtggtgcc  17760
```

```
cagagcgcgc taccacccca gcatcgttta aagccggtct ctgtatggtt cttgcagata  17820
tggccctcac ttgtcgcctc cgcttcccgg tgccgggata ccgaggaaga actcaccgcc  17880
gcagaggcat ggcgggcagc ggtctccgcg gcggccgtcg ccatcgccgg cgcgcaaaaa  17940
gcaggcgcat gcgcggcggt gtgctgcctc tgctaatccc gctaatcgcc gcggcgatcg  18000
gtgccgtacc cgggatcgcc tccgtggccc tgcaggcgtc ccagaaacgt tgactcttgc  18060
aaccttgcaa gcttgcattt tttggaggaa aaataaaaaa aagtctagac tctcacgctc  18120
gcttggtcct gtgactattt tgtagaaaaa aagatggaag acatcaactt tgcgtcgctg  18180
gccccgcgtc acggctcgcg cccgttcatg ggagactgga cagatatcgg caccagcaat  18240
atgagcggtg gcgccttcag ctggggcagt ctgtggagcg gccttaaaaa ttttggttcc  18300
accattaaga actatggcaa caaagcgtgg aacagcagca cgggccagat gctgagagac  18360
aagttgaaag agcagaactt ccaggagaag gtggcgcagg gcctggcctc tggcatcagc  18420
ggggtggtgg acatagctaa ccaggccgtg cagaaaaaga taaacagtca tctggacccc  18480
cgtcctcagg tggaggaaat gcctccagcg atggagacgg tgtctcccga gggcaaaggc  18540
gaaaagcgcc cgcggcccga cagagaagag accctggtgt cacacaccga ggagccgccc  18600
tcttacgagg aggcagtcaa ggccggcctg cccaccactc gccccatagc ccccatggcc  18660
accggtgtgg tgggccacag gcaacacact cccgcaacac tagatctgcc cccgccgtcc  18720
gagccgccgc gccagccaaa ggcggcgacg gtgcccgctc cctccacttc cgccgccaac  18780
agagtgcccc tgcgccgcgc cgcgagcggc ccccgggcct cgcgagttag cggcaactgg  18840
cagagcacac tgaacagcat cgtgggcctg ggagtgagga gtgtgaagcg ccgccgttgc  18900
tactgaatga gcaagctagc taacgtgttg tatgtgtgta tgcgtcctat gtcgccgcca  18960
gaggagctgt tgagccgccg gcgccgtctg cactccagcg aatttcaaga tggcgacccc  19020
atcgatgatg cctcagtggt cgtacatgca catctcgggc caggacgctt cggagtacct  19080
gagccccggg ctggtgcagt tcgcccgcgc cacagacacc tacttcaaca tgagtaacaa  19140
gttcaggaac cccactgtgg cgcccaccca cgatgtgacc acggaccggt cgcagcgcct  19200
gacgctgcgg ttcatccccg tggatcggga ggacaccgcc tactcttaca aggcgcggtt  19260
cacgctggcc gtgggcgaca accgcgtgct ggacatggcc tccacttact ttgacatcag  19320
gggggtgctg gacaggggcc ccaccttcaa gccctactcg ggtactgcct acaactccct  19380
ggcccccaag ggcgctccca attcttgcga gtgggaacaa gatgaaccag ctcaggcagc  19440
aatagctgaa gatgaagaag aacttgaaga agaacaagct caggacgaac aggcgcccac  19500
taagaaaacc catgtatacg cccaggcacc tctttctggt gaaaaaatta ctaaggatgg  19560
tttgcaaata ggtgtggatg ccacacaggc gggagataac cctatatatg ctgataaaac  19620
attccaaccc gaacctcaga taggtgagtc tcagtggaac gaggctgatg ccacagtagc  19680
aggaggcaga gtcttaaaaa agaccacccc tatgagacct tgctatggat cctatgccaa  19740
acctactaat gccaatggcg gtcaagggat catggtggcc aatgatcagg gagcgcttga  19800
atctaaagtt gagatgcaat tttctccac cacaacgtct cttaatgtaa gggaaggtga  19860
aaacaatctt cagccaaaag tagtgctata cagcgaagat gttaacttgg aatcccctga  19920
cactcatttg tcttacaaac ctaaaaagga tgacaccaac tctaaaatca tgttgggtca  19980
gcaagccatg cccaacagac ccaacctcat tgcttttagg gacaacttta ttggacttat  20040
gtactacaac agcacaggca acatgggagt gctggcagga caggcctccc agctaaacgc  20100
```

-continued

```
tgtggtagac ttgcaagaca gaaacacaga gctgtcatac caactgatgc ttgattccat  20160
tggagacaga tcaagatact tttccatgtg gaaccaggca gtggacagct atgacccaga  20220
tgtcagaatc attgaaaacc atggggttga agatgagctg cccaactatt gctttcccct  20280
gggcggtatt ggaattacag acacatacca gtgcataaaa ccaaccgcag ctgctaataa  20340
cactacatgg tctaaggatg aagaatttag tgatcgcaat gaaatagggg tgggaaacaa  20400
cttcgccatg gagatcaaca tccaggccaa cctctggagg aacttcctct atgcgaacgt  20460
ggggctctac ctgccagaca agctcaagta caaccccacc aacgtggaca tctctgacaa  20520
ccccaacacc tatgactaca tgaacaagcg tgtggtggct cccggcctgg tggactgctt  20580
tgtcaatgtg ggagccaggt ggtccctgga ctacatggac aacgtcaacc ccttcaacca  20640
ccaccgcaat gcgggtctgc gctaccgctc catgatcctg ggcaacgggc gctacgtgcc  20700
cttccacatt caggtgcccc agaagttctt tgccatcaag aacctcctcc tcctgccggg  20760
ctcctacact tacgagtgga acttcaggaa ggatgtcaac atggtcctgc agagctctct  20820
gggcaatgac cttagggtgg acggggccag catcaagttt gacagcgtca ccctctatgc  20880
taccttcttc cccatggctc acaacaccgc ctccacgctc gaggccatgc tgaggaacga  20940
caccaacgac cagtccttca atgactacct ctctggggcc aacatgctct accccatccc  21000
cgccaaggcc accaacgtgc ccatctccat tccctctcgc aactgggccg ccttcagagg  21060
ctgggccttt acccgcctta agaccaagga aaccccctcc ctgggctcgg gttttgaccc  21120
ctactttgtc tactcgggat ccatccccta cctggatggc accttctacc tcaaccacac  21180
ttttaagaag atatccatca tgtatgactc ctccgtcagc tggccgggca atgaccgcct  21240
gctcaccccc aatgagttcg aggtcaagcg cgccgtggac ggcgagggct acaacgtggc  21300
ccagtgcaac atgaccaagg actggttcct ggtgcagatg ctggccaact acaacatagg  21360
ctaccagggc ttctacatcc cagagagcta caaggacagg atgtactcct tcttcagaaa  21420
tttccaaccc atgagcaggc aggtggtgga cgagaccaaa tacaaggact atcaggccat  21480
tggcatcact caccagcaca acaactcggg attcgtgggc tacctggctc ccaccatgcg  21540
cgaggggcag gcctaccccg ccaacttccc ctacccgttg ataggcaaaa ccgcggtcga  21600
cagcgtcacc cagaaaaagt tcctctgcga ccgcaccctc tggcgcatcc ccttctctag  21660
caacttcatg tccatgggtg cgctcacgga cctgggccag aacctgctct atgccaactc  21720
cgcccatgcg ctggacatga cttttgaggt ggaccccatg gacgagccca cccttctcta  21780
tattgtgttt gaagtgttcg acgtggtcag agtgcaccag ccgcaccgcg gtgtcatcga  21840
gaccgtgtac ctgcgcacgc ccttctcggc cggcaacgcc accacctaag gagacagcgc  21900
cgccgcctgc atgacgggtt ccaccgagca agagctcagg gccatcgcca gagacctggg  21960
atgcggaccc tatttttttgg gcacctatga caaacgcttc ccgggcttca tctcccgaga  22020
caagctcgcc tgcgccatcg tcaacacggc cgcgcgcgag accgggggcg tgcactggct  22080
ggcctttggc tgggacccgc gctccaaaac ctgctacctc ttcgacccct ttggcttctc  22140
cgatcagcgc ctcagacaga tctatgagtt tgagtacgag gggctgctgc gccgcagcgc  22200
gcttgcctcc tcgcccgacc gctgcatcac ccttgagaag tccaccgaga ccgtgcaggg  22260
gccccactcg gccgcctgcg gtctcttctg ctgcatgttt ttgcacgcct ttgtgcgctg  22320
gccccagagt cccatggatc gcaaccccac catgaacttg ctcaagggag tgcccaacgc  22380
catgctccag agcccccagg tccagcccac cctgcgccac aaccaggaac agctctaccg  22440
cttcctggag cgccactccc cctacttccg cagtcacagc gcgcacatcc ggggggccac  22500
```

ctctttctgc cacttgcaag aaaacatgca agacggaaaa tgatgtacag ctcgcttttt 22560
aataaatgta aagactgtgc actttattta tacacgggct ctttctggtt atttattcaa 22620
caccgccgtc gccatctaga aatcgaaagg gttctgccgc gcgtcgccgt gcgccacggg 22680
cagagacacg ttgcgatact ggaagcggct cgcccactta aactcgggca ccaccatgcg 22740
gggcagtggt tcctcgggga agttctcgcc ccacagggtg cgggtcagct gcagcgcgct 22800
caggaggtcg ggagccgaga tcttgaagtc gcagttgggg ccggaaccct gcgcgcgcga 22860
gttgcggtac acggggttgc agcactggaa caccagcagg gccggattat gcacgctggc 22920
cagcaggctc tcgtcgctga tcatgtcgct gtccagatcc tccgcgttgc tcagggcgaa 22980
cggggtcatc ttgcagacct gcctgcccag gaaaggcggc agcccgggct tgccgttgca 23040
gtcgcagcgc aggggcatca gcaggtgccc gcggcccgac tgcgcctgcg ggtacagcgc 23100
gcgcatgaag gcttcgatct gcctgaaagc cacctgcgtc ttggctccct ccgaaaagaa 23160
catcccacag gacttgctgg agaactggtt cgcgggacag ctggcatcgt gcaggcagca 23220
gcgcgcgtcg gtgttggcga tctgcaccac gttgcgaccc caccggttct tcactatctt 23280
ggccttggaa gcctgctcct tcagcgcgcg ctggccgttc tcgctggtca catccatctc 23340
tatcacctgc tccttgttga tcatgtttgt accgtgcaga cacttcaggt cgccctccgt 23400
ctgggtgcag cggtgctccc acagcgcgca accggtgggc tcccaatttt tgtgggtcac 23460
ccccgcgtag gcctgcaggt aggcctgcaa gaagcgcccc atcatggcca caaaggtctt 23520
ctggctcgta aaggtcagct gcaggccgcg atgctcttcg ttcagccagg tcttgcagat 23580
ggcggccagc gcctcggtct gctcgggcag catcctaaaa tttgtcttca ggtcgttatc 23640
cacgtggtac ttgtccatca tggcgcgcgc cgcctccatg cccttctccc aggcggacac 23700
catgggcagg cttagggggt ttatcacttc caccggcgag gacaccgtac tttcgatttc 23760
ttcttcctcc ccctcttccc ggcgcgcgcc cacgctgctg cgcgctctca ccgcctgcac 23820
caaggggtcg tcttcaggca agcgccgcac cgagcgcttg ccgcccttga cctgcttaat 23880
cagcaccggc gggttgctga agcccaccat ggtcagcgcc gcctgctctt cttcgtcttc 23940
gctgtctacc actatctctg gggaagggct tctccgctct gcggcggcgc gcttcttttt 24000
tttcttggga gcggccgtga tggagtccgc cacggcgacg gaggtcgagg gcgtggggct 24060
gggggtgcgc ggtaccaggg cctcgtcgcc ctcggactct tcctctgact ccaggcggcg 24120
gcggagtcgc ttctttgggg gcgcgcgcgt cagcggcggc ggagacgggg acggggacgg 24180
ggacgggacg ccctccacag gggtggtct tcgcgcagac ccgcggccgc gctcgggggt 24240
cttctcgagc tggtcttggt cccgactggc cattgtatcc tcctcctcct aggcagagag 24300
acataaggag tctatcatgc aagtcgagaa ggaggagagc ttaaccaccc cctctgagac 24360
cgccgatgcg cccgccgtcg ccgtcgcccc cgctgccgcc gacgcgcccg ccacaccgag 24420
cgacaccccc gcggaccccc ccgccgacgc acccctgttc gaggaagcgg ccgtggagca 24480
ggacccgggc tttgtctcgg cagaggagga tttgcgagag gaggaggata aggagaagaa 24540
gccctcagtg ccaaaagatg ataaagagca agacgagcac gacgcagatg cacaccaggg 24600
tgaagtcggg cggggggacg gagggcatga cggcgccgac tacctagacg aagggaacga 24660
cgtgctcttg aagcacctgc atcgtcagtg cgccattgtt tgcgacgctc tgcaggagcg 24720
cagcgaagtg cccctcagcg tggcggaggt cagccacgcc tacgagctca gcctcttctc 24780
cccccgggtg ccccccccgcc gccgcgaaaa cggcacatgc gagcccaacc cgcgcctcaa 24840

```
cttctacccc gcctttgtgg tacccgaggt cctggccacc tatcacatct tctttcaaaa  24900
ttgcaagatc cccctctcgt gccgcgccaa ccgtagccgc gccgataaga tgctggccct  24960
gcgccagggc gaccacatac ctgatatcgc cgctttggaa gatgtaccaa agatcttcga  25020
gggtctgggt cgcaacgaga agcgggcagc aaactctctg caacaggaaa acagcgaaaa  25080
tgagagtcac accggggtac tggtggagct cgagggcgac aacgcccgcc tggcggtggt  25140
caagcgcagc atcgaggtca cccactttgc ctaccccgcg ctaaacctgc cccccaaagt  25200
catgaacgcg gccatggacg ggctgatcat gcgccgcggc cggcccctcg ctccagatgc  25260
aaacttgcat gaggagaccg aggacggcca gcccgtggtc agcgacgagc agctggcgcg  25320
ctggctggag accgcggacc ccgccgaact ggaggagcgg cgcaagatga tgatggccgt  25380
ggtgctggtc accgtagagc tggagtgtct gcagcgcttc ttcggcgacc ccgagatgca  25440
gagaaaggtc gaggagaccc tgcactacac cttccgccag ggctacgtgc gccaggcttg  25500
caagatctcc aacgtggagc tcagcaacct ggtgtcctac ctgggcatct tgcatgagaa  25560
ccgcctcggg cagagcgtgc tgcactccac cctgcgcggg gaggcgcgcc gcgactacgt  25620
gcgcgactgc gtttacctct tcctctgcta cacctggcag acggccatgg gggtctggca  25680
gcagtgcctg gaggagcgca acctcaagga gctggagaag ctcctgcagc gcgcgctcaa  25740
agatctctgg acgggctaca acgagcgctc ggtggccgcc gcgctggccg acctcatctt  25800
ccccgagcgc ctgctcaaaa ccctccagca ggggctgccc gacttcacca gccaaagcat  25860
gttgcaaaac ttcaggaact ttatcctgga gcgttctggc atcctacccg ccacctgctg  25920
cgccctgccc agcgactttg tcccccctcgt gtaccgcgag tgcccccccgc cgctgtgggg  25980
tcactgctac ctgttccaac tggccaacta cctgtcctac cacgcggacc tcatggagga  26040
ctccagcggc gaggggctca tggagtgcca ctgccgctgc aacctctgca cgccccaccg  26100
ctccctggtc tgcaacaccc aactgctcag cgagagtcag attatcggta ccttcgagct  26160
acagggtccg tcctcctcag acgagaagtc cgcggctccg gggctaaaac tcactccggg  26220
gctgtggact tccgcctacc tgcgcaaatt tgtacctgaa gactaccacg cccacgagat  26280
caggttttac gaagaccaat cccgcccgcc caaggcggag ctgaccgcct gcgtcatcac  26340
ccagggcgag atcctaggcc aattgcaagc catccaaaaa gcccgccaag actttttgct  26400
gaagaagggt cggggggtgt atctggaccc ccagtcgggt gaggagctca acccggttcc  26460
cccgctgccg ccgccgcggg accttgcttc ccaggataag catcgccatg gctcccagaa  26520
agaagcagca gcggccgcca ctgccgccac ccccacatgct ggaggaagag gaggaatact  26580
gggacagtca ggcagaggag gtttcggacg aggaggagcc ggagacggag atggaagagt  26640
gggaggagga cagcttagac gaggaggctt ccgaagccga agaggcagac gcaacaccgt  26700
caccctcggc cgcagccccc tcgcaggcgc ccccgaagtc cgctcccagc atcagcagca  26760
acagcagcgc tataacctcc gctcctccac cgccgcgacc cacggccgac cgcagaccca  26820
accgtagatg ggacaccacc ggaaccgggg ccggtaagtc ctccgggaga ggcaagcaag  26880
cgcagcgcca aggctaccgc tcgtggcgcg ctcacaagaa cgccatagtc gcttgcttgc  26940
aagactgcgg ggggaacatc tccttcgccc gccgcttcct gctcttccac cacggtgtgg  27000
ccttcccccg taacgtcctg cattactacc gtcatctcta cagcccctac tgcggcggca  27060
gtgagccaga gacggtcggc ggcggcggcg gcgcccgttt cggcgcctag gaagacccag  27120
ggcaagactt cagccaagaa actcgcggcg gccgcggcga acgcggtcgc gggggccctg  27180
cgcctgacgg tgaacgaacc cctgtcgacc cgcgaactga ggaaccgaat cttccccact  27240
```

ctctatgcca tcttccagca gagcagaggg caggatcagg aactgaaagt aaaaaacagg 27300
tctctgcgct ccctcacccg cagctgtctg tatcacaaga gcgaagacca gcttcggcgc 27360
acgctggagg acgctgaggc actcttcagc aaatactgcg cgctcactct taaggactag 27420
ctccgcgccc ttctcgaatt taggcgggaa cgcctacgtc atcgcagcgc cgccgtcatg 27480
agcaaggaca ttcccacgcc atacatgtgg agctatcagc cgcagatggg actcgcggcg 27540
ggcgcctccc aagactactc cacccgcatg aactggctca gtgccggccc acacatgatc 27600
tcacaggtta atgatatccg cacccatcga aaccaaatat tggtggagca ggcggcaatt 27660
accaccacgc cccgcaataa tcccaacccc agggagtggc ccgcgtccct ggtgtatcag 27720
gaaattcccg gccccaccac cgtactactt ccgcgtgatt cccaggccga agtccaaatg 27780
actaactcag ggcacagct cgcgggcggc tgtcgtcaca gggtgcggcc tcctcgccag 27840
ggtataactc acctggagat ccgaggcaga ggtattcagc tcaacgacga gtcggtgagc 27900
tcctcgctcg gtctcagacc tgacgggacc ttccagatag ccggagccgg ccgatcttcc 27960
ttcacgcccc gccaggcgta cctgactctg caaagctcgt cctcggcgcc gcgctcgggc 28020
ggcatcggga ctctccagtt cgtgcaggag tttgtgccct cggtctactt caacccccttc 28080
tcgggctctc ccggtcgcta cccggaccag ttcatctcga actttgacgc cgcgagggac 28140
tcggtggacg gctacgactg aatgtcgggt ggacccggtg cagagcaact tcgcctgaag 28200
cacctcgacc actgccgccg ccctcagtgc tttgcccgct gtcagaccgg tgagttccag 28260
tacttttccc tgcccgactc gcacccggac ggcccggcgc acggggtgcg ctttttcatc 28320
ccgagtcagg tgcgctctac cctaatcagg gagtttaccg cccgtcccct actggcggag 28380
ttggaaaagg ggccttctat cctaaccatt gcctgcatct gctctaaccc tggattgcac 28440
caagatcttt gctgtcattt gtgtgctgag tataataaag gctgagatca gaatctactc 28500
gggctcctgt cgccatcctg tcaacgccac cgtccaagcc cggcccgatc agcccgaggt 28560
gaacctcacc tgcggtctgc accggcgcct gaggaaatac ctagcttggt actacaacag 28620
cactcccttt gtggtttaca acagctttga ccaggacggg gtctcactga gggataacct 28680
ctcgaacctg agctactcca tcaggaagaa cagcaccctc gagctacttc ctccttacct 28740
gcccgggact taccagtgtg tcaccggtcc ctgcacccac acccacctgt tgatcgtaaa 28800
cgactctctt ccgagaacag acctcaataa ctcctcttcg cagttcccca gaacaggagg 28860
tgagctcagg aaaccccggg taaagaaggg tggacgagag ttaacacttg tggggtttct 28920
ggtgtatgtg acgctggtgg tggctctttt gattaaggct tttccttcca tgtctgaact 28980
ctccctcttc ttttatgaac aactcgacta gtgctaacgg gaccctaccc aacgaatcgg 29040
gattgaatat cggtaaccag gttgcagttt cacttttgat taccttcata gtcctcttcc 29100
tgctagtgct gtcgcttctg tgcctgcgga tcgggggctg ctgcatccac gtttatatct 29160
ggtgctggct gtttagaagg ttcggagacc atcgcaggta gaataaacat gctgctgctt 29220
accctctttg tcctggcgct ggccgccagc tgccaagcct tttccgaggc tgactttata 29280
gagccccagt gtaatgtgac ttttaaagcc catgcacagc gttgtcatac tataatcaaa 29340
tgtgccaccg aacacgatga ataccttatc cagtataaag ataaatcaca caaagtggca 29400
cttgttgaca tctggaaacc cgaagaccct ttggaataca atgtgaccgt tttccagggt 29460
gacctcttca aaatttacaa ttacactttc ccatttgacc agatgtgtga ctttgtcatg 29520
tacatggaaa agcagcacaa gctgtggcct ccgactcccc agggctgtgt ggaaaatcca 29580

-continued

```
ggctctttct gcatgatctc tctctgtgta actgtgctgg cactaatact cacgcttttg  29640
tatatcagat ttaaatcaag gcaaagcttc attgatgaaa agaaaatgcc ttaatcgctt  29700
tcacgcttga ttgctaacac cgggttttta tccgcagaat gattggaatc accctactaa  29760
tcacctccct ccttgcgatt gcccatgggt tggaacgaat cgaagtccct gtgggggcca  29820
atgttaccct ggtggggcct gtcggcaatg ctacattaat gtgggaaaaa tatactaaaa  29880
atcaatgggt ctcttactgc actaacaaaa atagccacaa gcccagagcc atctgcgatg  29940
ggcaaaatct aaccttgatt gatgttcaat tgctggatgc gggctactat tatgggcagc  30000
tgggtacaat gattaattac tggagacccc acagagatta catgctccac gtagtaaagg  30060
gtccccttag cagcccaccc actaccacct ctactacccc cactaccacc actactccca  30120
ccaccagcac tgccgcccag cctcctcata gcagaacaac cacttttatc aattccaagt  30180
cccactcccc ccacattgcc ggcgggccct ccgcctcaga ctccgaaacc accgagatct  30240
gcttctgcaa atgctctgac gccattgccc aggatttgga agatcacgag gaagatgagc  30300
atgacttcgc agatgcatgc caggcatcag agccagaagc gctgccggtg gccctcaaac  30360
agtatgcaga cccccacacc acccccgacc ttcctccacc ttcccagaag ccaagtttcc  30420
tgggggaaaa tgaaactctg cctctctcca tactcgctct gacatctgtt gctatgttga  30480
ccgctctgct ggtgcttcta tgctctatat gctacctgat ctgctgcaga aagaaaaaat  30540
ctcacggcca tgctcaccag cccctcatgc acttccctta ccctccagag ctgggcgacc  30600
acaaacttta agtctgcagt aactatctgc ccatcccttg tcagtcgaca gcgatgagcc  30660
ccactaatct aacggcctct ggacttacaa catcgtctct taatgagacc accgctcctc  30720
aagacctgta cgatggtgtc tccgcgctgg ttaaccagtg ggatcacctg ggcatatggt  30780
ggctcctcat aggagcagtg accctgtgcc taatcctggt ctggatcatc tgctgcatca  30840
aaagcagaag acccaggcgg cggcccatct acaggccctt tgtcatcaca cctgaagatg  30900
atgatgacac cacttccagg ctgcagaggc taaagcagct actcttctct tttacagcat  30960
ggtaaattga atcatgcctc gcattttcat ctacttgtct ctccttccac tttttctggg  31020
ctcttctaca ttggccgctg tgtcccacat cgaggtagac tgcctcacgc ccttcacagt  31080
ctacctgctt ttcggctttg tcatctgcac ctttgtctgc agcgttatca ctgtagtgat  31140
ctgcttcata cagtgcatcg actacgtctg cgtgcgggtg gcttacttta gacaccaccc  31200
ccagtatcgc aacagggaca tagcggctct cctaagactt gtttaaaatc atggccaaat  31260
taactgtgat tggtcttctg atcatctgct gcgtcctagc cgcgattggg actcaagctc  31320
ctaccaccac cagcgctccc agaaagagac atgtatcctg cagcttcaag cgtccctgga  31380
atatacccca atgctttact gatgaacctg aaatctcttt ggcttggtac ttcagcgtca  31440
ccgcccttct tatcttctgc agtacggtta ttgcccttgc catctaccct tcccttgacc  31500
tgggctggaa tgctgtcaac tctatggaat atcccacctt cccagaacca gacctgccag  31560
acctggttgt tctaaacgcg tttcctcctc ctgctcccgt tcaaaatcag tttcgccctc  31620
cgtcccccac gcccactgag gtcagctact ttaatctaac aggcggagat gactgaaaac  31680
ctagacctag aaatggacgg tctctgcagc gagcaacgca cactagagag gcgccggcaa  31740
aaagagctcg agcgtcttaa acaagagctc caagacgcgg tggccataca ccagtgcaaa  31800
aaaggtgtct tctgtctggt aaaacaggcc acgctcacct atgaaaaaac aggtgacacc  31860
caccgcctag gatacaagct gcccacacag cgccaaaagt tcgccctcat gataggcgaa  31920
caacccatca ccgtgaccca gcactccgtg gagacagaag gctgcataca tgctccctgt  31980
```

aggggcgctg actgcctcta caccttgatc aaaaccctct gcggtctcag agaccttatc 32040
cctttcaatt aatcataact gtaatcaata aaaaatcact tacttgaaat ctgatagcaa 32100
gcctctgtcc aatttttttca gcaacacttc cttcccctcc tcccaactct ggtactctag 32160
gcgcctccta gctgcaaact tcctccacag tctgaaggga atgtcagatt cctcctcctg 32220
tccctccgca cccacgatct tcatgttgtt gcagatgaaa cgcgcgagat cgtctgacga 32280
gaccttcaac cccgtgtacc cctacgatac cgagatcgct ccgacttctg tccctttcct 32340
tacccctccc tttgtgtcat ccgcaggaat gcaagaaaat ccagctgggg tgctgtccct 32400
gcacttgtca gagccccttta ccacccacaa tggggccctg actctaaaaa tgggggggcgg 32460 cctgaccctg gacaaggaag ggaatctcac ttcccaaaac atcaccagtg tcgatccccc 32520
tctcaaaaaa agcaagaaca acatcagcct tcagaccgcc gcacccctcg ccgtcagctc 32580
cggggcccta acactttttg ccactccccc cctagcggtc agtggtgaca accttactgt 32640
gcagtctcag gcccctctca ctttggaaga ctcaaaacta actctggcca ccaaaggacc 32700
cctaactgtg tccgaaggca aacttgtcct agaaacaga 32739

<210> SEQ ID NO 22
<211> LENGTH: 32739
<212> TYPE: DNA
<213> ORGANISM: Artificial Sequence
<220> FEATURE:
<223> OTHER INFORMATION: Adenovirus vector nucleotide sequences

<400> SEQUENCE: 22
catcatcaat aatatacctt attttggatt gtggccaata tgataatgag gtgggcgggg 60
agaggcgggg cgggtgacgt aggacgcgcg agtagggttg ggaggtgtgg cggaagtgtg 120
gcatttgcaa gtgggaggag ctcacatgca agcttccgtc gcggaaaatg tgacgttttt 180
gatgagcgcc gcctacctcc ggaagtgcca attttcgcgc gcttttcacc ggatatcgta 240
gtaattttgg gcgggaccat gtaagatttg gccattttcg cgcgaaaagt gaaacgggga 300
agtgaaaact gaataatagg gcgttagtca tagcgcgtaa tatttaccga gggccgaggg 360
actttgaccg attacgtgga ggactcgccc aggtgttttt tacgtgaatt tccgcgttcc 420
gggtcaaagt ctccgttttt attgtcaccg tcatttgacg cggagggtat ttaaacccgc 480
tgcgctcctc aagaggccac tcttgagtgc cagcgagaag agttttctcc tctgctccgc 540
ttcggtgatc gaaaaatgag acacatagcc tgcactccgg gtcttttgtc cggtcgggcg 600
gcggccgagc ttttggacgc tttgatcaat gatgtcctaa gcgatgattt tccgtctact 660
acccacttta gcccacctac tcttcacgaa ctgtacgatc tggatgtact ggtggatgtg 720
aacgatccca acgaggaggc ggtttctgcg ttttttcccg agtctgcgct gttggccgct 780
caggagggat ttgacctaca cactccgccg cctattttag agtctccgct gccggagccc 840
agtggtatac cttatatgcc tgaactgctt cccgaagtgg tagacctgac ctgccacgag 900
cctggctttc cgcccagcga cgatgagggt gagccttttg ttttagactt tgctgagata 960
cctgggcacg gttgcaggtc ttgtgcatat catcagaggg ttaccggaga ccccgaggtt 1020
aagtgttcgc tgtgctatat gaggatgacc tcttccttta tctacagtaa gtttttgtct 1080
aggtgggctt ttgggtaggt gggttttgtg tcagaacagg tgtaaacgtt gcttgtgttt 1140
tttgtacctg taggtccggt gtccgagcca gacccggagc ccgaccgcga tcccgagccg 1200
gatcccgagc ctcctcgcag gacaaggaaa ctaccttcca ttctgtgcaa gtctcagaca 1260

-continued

```
cctgtaagga ccagcgaggc agacagcacc gactctggca cttctacctc tccccctgaa   1320
attcacccag tggttcctct gggtatacat aaacctgttg ctgttaaagt ttgcgggcga   1380
cgccctgcag tacagtgcat tgaggacttg cttcacgatc ccgaggaacc tttggacttg   1440
agccttaaac gccctaggca ataaacccca cctaagtaat aaaccccacc taagtaataa   1500
accctgccgc ccttggttat tgagatgacg cccaatgttt gcttttgaat gacttcatgt   1560
gtgtaataaa agtgagtgtg atcataggtc tcttgtttgt ctgggcgggg cttaagggta   1620
tataagtctc ttggggctaa acttggttac acttgacccc aatggaggcg tgggggtgct   1680
tggaggagtt tgcggacgtg cgccgtttgc tggacgagag ctctagcaat acctatacta   1740
tttggaggta tctgtggggc tctactcagg ccaagttggt ttccagaatt aagcaggatt   1800
acaagtgcga ttttgaagag ctttttagtt cctgcggtga gcttttgcaa tccttgaatc   1860
tgggccatca ggctattttc caggaaaagg ttctctcgac tttggatttt tccactcccg   1920
ggcgcaccgc cgcttgtgtg gcttttgtgt cttttgtgca agataaatgg agcgaggaga   1980
cccacctgag tcacggctac gtactggatt tcatggcgat ggctctttgg agggctcaca   2040
acaaatggaa gattcagaag gaactgtacg gttccgccct acgtcgtcca cttctgtcgc   2100
gacaggggct gaggtttccc gaccatcggc agcatcagaa tctggaagac gagtcggagg   2160
agcgagcgga ggagaagatc agcttgagag ccggcctgga ccctcctcag gaggaatgaa   2220
tctcccgcag gtggttgacc tgtttccaga actgagacgg gtcctgacta tcagggagga   2280
tggtcagttt gtgaagaagt ttaagaggga tcggggtgag ggagatgatg aggcggctag   2340
caatttagct tttagtctga tgactcgcca ccgaccggaa tgtattacct atcagcagat   2400
taaggagagt tgtgccaacg agctggatct tttgggtcag aagtatagca tagaacagct   2460
taccacttac tggcttcagc ctggggatga ttgggaagag gcgatcaggg tgtatgcaaa   2520
ggtggccctg cggcccgatt gcaagtataa gattactaag ttggttaata ttagaaactg   2580
ctgctatatt tctgggaacg gggccgaagt ggagatagat actcaggaca gggtggcttt   2640
taggtgttgc atgataaaca tgtggcccgg gatactgggg atggatgggg tggtattcat   2700
gaatgtgagg tttacgggcc ccaactttaa tggcacggtg ttcatgggca acaccaactt   2760
gctcctgcat ggtgcgagtt tctatgggtt taataacacc tgtatagagg cctggaccga   2820
tgtaaaggtt cgaggttgtt ccttttatag ctgttggaag gcggtggtgt gtcgccctaa   2880
aagcaggggt tctgtgaaaa aatgcttgtt tgaaaggtgc accttaggca tcctctctga   2940
gggcaactcc agggtgcgcc ataatgtggc ttcgaactgc ggttgcttca tgcaagtgaa   3000
gggggtgagc gttatcaagc ataactcggt gtgtggaaac tgcgaggatc gcgcctccca   3060
gatgctgacc tgctttgatg gcaactgtca cctgttgaag accattcata taagcagcca   3120
ccccagaaag gcctggcccg tgtttgagca taacatcttg acccgctgct ccttgcatct   3180
gggggtcagg aggggtatgt tcctgcctta ccagtgtaac tttagccaca ctaaaatcct   3240
gctggaaccc gagtgcatga ccaaggtcag cctgaatggt gtgtttgatg tgactctgaa   3300
aatctggaag gtgctgaggt atgatgagac caggaccagg tgccgaccct gcgagtgcgg   3360
cggcaagcac atgagaaatc agcctgtgat gttggatgtg accgaggagc ttaggcctga   3420
ccatctggtg ctggcctgca ccagggccga gtttgggtct agcgatgagg ataccgattg   3480
aggtgggtaa ggtgggcgtg gctagaaggg tggggcgtgt ataaattggg ggtctaaggg   3540
tctctctgtt ttgtcttgca acagccgccg ccatgagcga caccggcaac agctttgatg   3600
gaagcatctt tagcccctat ctgacagtgc gcatgcctca ctgggctgga gtgcgtcaga   3660
```

-continued atgtgatggg ttccaacgtg gatggacgcc ccgttctgcc ttcaaattcg tctacaatgg 3720
cctacgcgac cgtgggagga actccgctgg acgccgcgac ctccgccgcc gcctccgccg 3780
ccgccgcgac cgcgcgcagc atggctacgg acctttacag ctctttggtg gcgagcggcg 3840
cggcctctcg cgcgtctgct cgggatgaga aactgaccgc tctgctgctt aaactggaag 3900
acttgacccg ggagctgggt caactgaccc agcaggtctc cagcttgcgt gagagcagcc 3960
ttgcctcccc ctaatggccc ataatataaa taaaagccag tctgtttgga ttaagcaagt 4020
gtatgttctt tatttaactc tccgcgcgcg gtaagcccgg gaccagcggt ctcggtcgtt 4080
tagggtgcgg tggattcttt ccaacacgtg gtacaggtgg ctctggatgt ttagatacat 4140
gggcatgagt ccatccctgg ggtggaggta gcaccactgc agagcttcgt gctcgggggt 4200
ggtgttgtat atgatccagt cgtagcagga gcgctgggcg tggtgctgaa aaatgtcctt 4260
aagcaagagg cttatagcta gggggaggcc cttggtgtaa gtgtttacaa atctgctcag 4320
ttgggagggg tgcatccggg ggatataat gtgcatcttg gactggattt ttaggttggc 4380
tatgttccca cccagatccc ttctgggatt catgttgtgc aggaccacca gcacggtata 4440
tccagtgcac ttgggaaatt tatcgtggag cttagacggg aatgcatgga agaacttgga 4500
gacgcccttg tggcctccca gattttccat acattcgtcc atgatgatgg caatgggccc 4560
gtgggaagct gcctgagcaa aaatgtttct gggatcgctc acatcgtagt tatgttccag 4620
ggtgaggtca tcataggaca tctttacgaa tcgggggcgg agggtcccgg actgggggat 4680
gatggtaccc tcgggccccg gggcgtagtt cccctcacag atctgcatct cccaggcttt 4740
catttcagag ggagggatca tatccacctg cggagcgatg aaaaacacag tttctggcgc 4800
aggggagatt aactgggatg agagcaggtt tctgagcagc tgtgactttc cacagccggt 4860
gggcccatat atcacgccta tcaccggctg cagctggtag ttaagagagc tgcagctgcc 4920
gtcctcccgg agcagggggg ccacctcgtt cagcatatcc ctgacgtgga tgttctccct 4980
gaccaattcc gccagaaggc gctcgccgcc cagcgaaagc agctcttgca aggaagcaaa 5040
atttttcagc ggttttaggc cgtcggccgt gggcatgttt ttcagcgtct gggtcagcag 5100
ttccagcctg tcccacagct cggtgatgtg ctctacggca tctcgatcca gcagatctcc 5160
tcgtttcgcg ggttggggcg gctttcgctg tagggcacca gccgatgggc gtccagcggg 5220
gccagagtca tgtccttcca tgggcgcagg gtcctcgtca gggtggtctg ggtcacggtg 5280
aaggggtgcg ctccgggttg ggcgctggcc agggtgcgct tgaggctggt tctgctggtg 5340
ctgaatcgct gccgctcttc gccctgcgcg tcggccaggt agcatttgac catggtctcg 5400
tagtcgagac cctcggcggc gtgccccttg gcgcggagct ttcccttgga ggtggcgccg 5460
cacgaggggc actgcaggct cttcagggcg tagagcttgg gagcgagaaa cacggactct 5520
ggggagtagg cgtccgcgcc gcaggaagcg cagaccgtct cgcattccac cagccaagtg 5580
agctccgggc ggtcagggtc aaaaaccagg ttgcccccat gctttttgat gcgtttctta 5640
cctcggctct ccatgaggcg gtgtcccttc tcggtgacga agaggctgtc cgtgtccccg 5700
tagaccgact tcaggggcct gtcttccagc ggagtgcctc tgtcctcctc gtagagaaac 5760
tctgaccact ctgagacgaa ggcccgcgtc caggccagga cgaaggaggc cacgtgggag 5820
gggtagcggt cgttgtccac tagcgggtcc accttctcca gggtgtgcag gcacatgtcc 5880
ccctcctccg cgtccagaaa agtgattggc ttgtaggtgt aggacacgtg accgggggtt 5940
cccgacgggg gggtataaaa gggggtgggc gccctttcat cttcactctc ttccgcatcg 6000

-continued

```
ctgtctgcga gggccagctg ctggggtaag tattccctct cgaaggcggg catgacctca   6060
gcgctcaggt tgtcagtttc taaaaatgag gaggatttga tgttcacctg tccggaggtg   6120
ataccttttga gggtacctgg gtccatctgg tcagaaaaca ctattttttt gttgtcaagc   6180
ttggtggcga acgacccgta gagggcgttg gagagcagct tggcgatgga gcgcagggtc   6240
tggtttttgt cgcggtcggc tcgctccttg gccgcgatgt tgagttgcac gtactcgcgg   6300
gccacgcact tccactcggg gaagacggtg gtgcgctcgt ctgggattag gcgcaccctc   6360
cagcctcggt tgtgcagggt gaccatgtcg acgctggtgg cgacctcgcc gcgcaggcgc   6420
tcgttggtcc agcagaggcg gccgcccttg cgcgagcaga aggggggtag ggggtccagc   6480
tggtcctcgt ttgggggggtc cgcgtcgatg gtgaagaccc cggggagcaa gcgcgggtca   6540
aagtagtcga tcttgcaagc ttgcatgtcc agagcccgct gccattcgcg ggcggcgagc   6600
gcgcgctcgt aggggttgag gggcgggccc cagggcatgg ggtgggtgag cgcggaggcg   6660
tacatgccgc agatgtcata cacgtacagg ggttccctga ggatgccgag gtaggtgggg   6720
tagcagcgcc ccccgcggat gctggcgcgc acgtagtcat agagctcgtg ggagggggcc   6780
agcatgttgg gcccgaggtt ggtgcgctgg gggcgctcgg cgcggaaggc gatctgcctg   6840
aagatggcat gggagttgga ggagatggtg ggccgctgga agacgttgaa gcttgcttct   6900
tgcaagccca ccgagtccct gacgaaggag gcgtaggact cgcgcagctt gtgcaccagc   6960
tcggcggtga cctggacgtc gagcgcgcag tagtcgaggg tctcgcggat gatgtcatac   7020
ttatcctccc ccttcttttt ccacagctcg cggttgagga cgaactcttc gcggtctttc   7080
cagtactctt ggaggggaaa cccgtccgtg tccgaacggt aagagcctag catgtagaac   7140
tggttgacgg cctggtaggg gcaacagccc ttctccacgg gcagcgcgta ggcctgcgcc   7200
gccttgcgga gggaggtgtg ggtgagggcg aaagtgtccc tgaccatgac tttgaggtat   7260
tgatgtttga agtctgtgtc atcgcagccg ccctgttccc acagggtgta gtccgtgcgc   7320
tttttggagc gcgggttggg cagggagaag gtgaggtcat tgaagaggat cttccccgct   7380
cgaggcatga agtttctggt gatgcgaaag ggccctggga ccgaggagcg gttgttgatg   7440
acctgggcgg ccaggacgat ctcgtcaaag ccgtttatgt tgtggcccac gatgtagagc   7500
tccaaaaagc ggggctggcc cttgatggag gggagctttt tgagttcctc gtaggtgagc   7560
tcctcgggcg attccaggcc gtgctcctcc agggcccagt cttgcaagtg agggttggcc   7620
gccaggaagg atcgccagag gtcgcgggcc atgagggtct gcaggcggtc gcggaaggtt   7680
ctgaactgtc gccccacggc catcttttcg gggtgatgc agtagaaggt gagggggtct   7740
ttctcccagg ggtcccatct gagctctcgg gcgaggtcgc gcgcggcggc gaccagagcc   7800
tcgtcgcccc ccagtttcat gaccagcatg aagggcacga gctgcttgcc aaaggctccc   7860
atccaagtgt aggtctctac atcgtaggtg acaaagaggc gctccgtgcg aggatgagag   7920
ccgatcggga agaactggat ctcccgccac cagttggagg attggctgtt gatgtggtga   7980
aagtagaagt cccgtctgcg ggccgagcac tcgtgctggc ttttgtaaaa gcgaccgcag   8040
tactggcagc gctgcacggg ttgtatatct tgcacgaggt gaacctggcg acctctgacg   8100
aggaagcgca gcgggaatct aagtcccccg cctggggtcc cgtgtggctg gtggtcttct   8160
actttggttg tctggccgcc agcatctgtc tcctggaggg cgatggtgga gcagaccacc   8220
acgccgcgag agccgcaggt ccagatctcg gcgctcggcg ggcggagttt gatgacgaca   8280
tcgcgcacat tggagctgtc catggtctcc agctcccgcg gcggcaggtc agctgggagt   8340
tcctggaggt tcacctcgca gagacgggtc aaggcgcggg cagtgttgag atggtatctg   8400
```

```
atttcaaggg gcgtgttggc ggcggagtcg atggcttgca ggaggccgca gccccggggg   8460
gccacgatgg ttccccgcgg ggcgcgaggg gaggcggaag ctgggggtgt gttcagaagc   8520
ggtgacgcgg gcgggccccc ggaggtaggg ggggttccgg ccccacaggc atgggcggca   8580
ggggcacgtc ttcgccgcgc gcgggcaggg gctggtgctg gctccgaaga gcgcttgcgt   8640
gcgcgacgac gcgacggttg gtgtcctgta tctgacgcct ctgagtgaag accacgggtc   8700
ccgtgacctt gaacctgaaa gagagttcga cagaatcaat ctcggcatcg ttgacagcgg   8760
cctggcgcag gatctcctgc acgtcgcccg agttgtcctg gtaggcgatc tctgccatga   8820
actgctcgat ctcttcttcc tggagatctc ctcgtccggc gcgctccacg gtggccgcca   8880
ggtcgttgga gatgcgaccc atgagctgtg agaaggcgtt gagcccgccc tcgttccaga   8940
cccggctgta gaccacgccc ccctcggcgt cgcgagcgcg catgaccacc tgggccaggt   9000
tgagctccac gtgtcgcgtg aagacggcgt agttgcgcag gcgctggaaa aggtagttca   9060
gggtggtggc ggtgtgctcg gcgacgaaga agtacatgac ccagcgccgc aacgtggatt   9120
cattgatgtc ccccaaggcc tccaggcgct ccatggcctc gtagaagtcc acggcgaagt   9180
tgaaaaactg ggagttgcga gcggacacgg tcaactcctc ctccagaaga cggatgagct   9240
cggcgacagt gttgcgcacc tcgcgctcga aggccacggg gggcgcttct tcctcttcca   9300
cctcttcttc catgatcgct tcttcttctt cctcagccgg gacgggaggg ggcggcggcg   9360
gcgggggagg ggcgcggcgg cggcggcggc gcaccgggag gcggtcgatg aagcgctcga   9420
tcatctcccc ccgcatgcgg cgcatggtct cggtgacggc gcggccgttc tcccgggggc   9480
gcagctcgaa gacgccgcct ctcatctcgc cgcggggcga gcggccgtga ggtagcgaga   9540
cggcgctgac tatgcatctt aacaattgct gtgtaggtac accgccgagg gacctgattg   9600
agtccagatc caccggatcc gaaaaccttt ggaggaaagc gtctatccag tcgcagtcgc   9660
aaggtaggct gagcaccgtg gcgggcgggg gcgggtctgg agagttcctg gcggagatgc   9720
tgctgatgat gtaattaaag taggcggtct tgagaaggcg gatggtggac aggagcacca   9780
tgtctttggg tccggcctgt tggatgcgga ggcggtcggc catgccccag gcctcgttct   9840
gacaccggcg caggtctttg tagtagtctt gcatgagtct ttccaccggc acctcttctc   9900
cttcctcttc tccatctcgc cggtggtttc tcgcgccgcc catgcgcgtg accccaaagc   9960
ccctgagcgg ctgcagcagg gccaggtcgg cgaccacgcg ctcggccaag atggcctgct  10020
gcacctgagt gagggtcctc tcgaagtcat ccatgtccac gaagcggtgg taggcgcccg  10080
tgttgatggt gtaggtgcag ttggccatga cggaccagtt gacggtctgg tgtcccggct  10140
gcgagagctc cgtgtaccgc aggcgcgaga aggcgcggga atcgaacacg tagtcgttgc  10200
aagtccgcac cagatactgg tagcccacca ggaagtgcgg cggaggttgg cgatagaggg  10260
gccagcgctg ggtggcgggg gcgccgggcg ccaggtcttc cagcatgagg cggtggtatc  10320
cgtagatgta cctggacatc caggtgatgc cggcggcggt ggtggtggcg cgcgcgtagt  10380
cgcggacccg gttccagatg tttcgcaggg gcgagaagtg ttccatggtc ggcacgctct  10440
ggccggtgag gcgcgcgcag tcgttgacgc tctatacaca cacaaaaacg aaagcgttta  10500
cagggctttc gttctgtagc ctggaggaaa gtaaatgggt tgggttgcgg tgtgccccgg  10560
ttcgagacca agctgagctc ggccggctga agccgcagct aacgtggtat tggcagtccc  10620
gtctcgaccc aggccctgta tcctccagga tacggtcgag agccctttg  ctttcttggc  10680
caagcgcccg tggcgcgatc tgggatagat ggtcgcgatg agaggacaaa agcggctcgc  10740
```

ttccgtagtc tggagaaaca atcgccaggg ttgcgttgcg gcgtaccccg gttcgagccc 10800
ctatggcggc ttgaatcggc cggaaccgcg gctaacgagg gccgtggcag ccccgtcctc 10860
aggaccccgc cagccgactt ctccagttac gggagcgagc cccttttgtt ttttattttt 10920
tagatgcatc ccgtgctgcg gcagatgcgc ccctcgcccc ggcccgatca gcagcagcaa 10980
cagcaggcat gcagaccccc ctctcccctt tccgccccgg tcaccacggc cgcggcggcc 11040
gtgtcgggcg cggggggcgc gctggagtca gatgagccac cgcggcggcg acctaggcag 11100
tatctggact tggaagaggg cgagggactg gcgcggctgg gggcgaactc tccagagcgc 11160
cacccgcggg tgcagttgaa aagggacgcg cgcgaggcgt acctgccgcg gcagaacctg 11220
tttcgcgacc gcgggggcga ggagcccgag gagatgcgag actgcaggtt ccaagcgggg 11280
cgcgagctgc ggcgcgggct ggacagacag cgcctgctgc gcgaggagga ctttgagccc 11340
gacacgcaga cgggcatcag ccccgcgcgc gcgcacgtag ccgcggccga cctggtgacc 11400
gcctacgagc agacggtaaa ccaggagcgc aacttccaaa agagcttcaa caaccacgtg 11460
cgcacgctgg tggcgcgcga ggaggtgacc ctgggtctca tgcatctgtg ggacctggtg 11520
gaggcgatcg tgcagaaccc cagcagcaag cccctgaccg cgcagctgtt cctggtggtg 11580
cagcacagca gggacaacga ggccttcagg gaggcgctgc tgaacatcac cgagccggag 11640
gggcgctggc tcctggacct gataaacatc ctgcagagca tagtggtgca ggagcgcagc 11700
ctgagcctgg ccgagaaggt ggcggccatc aactactcta tgctgagcct gggcaagttc 11760
tacgcccgca agatctacaa gaccccctac gtgcccatag acaaggaggt gaagatagac 11820
agcttctaca tgcgcatggc gctgaaggtg ctgaccctga gcgacgacct gggagtgtac 11880
cgcaacgagc gcatccacaa ggccgtgagc gccagccggc ggcgcgagct gagcgaccgc 11940
gagctgatgc acagtctgca gcgcgcgctg accggcgcgg gcgagggcga cagggaggtc 12000
gagtcctact tcgacatggg ggccgacctg cactggcagc cgagccgccg cgccctggag 12060
gcggcggggg cgtacggcgg ccccctggcg gccgatgacc aggaagagga ggactatgag 12120
ctagaggagg gcgagtacct ggaggactga cctggctggt ggtgttttgg tatagatgca 12180
agatccgaac gtggcggacc cggcggtccg ggcggcgctg caaagccagc cgtccggcat 12240
taactcctct gacgactggg ccgcggccat gggtcgcatc atggccctga ccgcgcgcaa 12300
ccccgaggct ttcaggcagc agcctcaggc caaccggctg gcggccatct tggaagcggt 12360
agtgcccgcg cgctccaacc ccacccacga gaaggtgctg gccatagtca acgcgctggc 12420
ggagagcagg gccatccgcg cggacgaggc cggactggtg tacgatgcgc tgctgcagcg 12480
ggtggcgcgg tacaacagcg gcaacgtgca gaccaacctg gaccgcctgg tgacggacgt 12540
gcgcgaggcc gtggcgcagc gcgagcgctt gcatcaggac ggtaacctgg gctcgctggt 12600
ggcgctaaac gccttcctca gcacccagcc ggccaacgta ccgcgggggc aggaggacta 12660
caccaacttt ttgagcgcgc tgcggctgat ggtgaccgag gtccctcaga gcgaggtgta 12720
ccagtcgggg cccgactact tcttccagac cagcagacag ggcttgcaaa ccgtgaacct 12780
gagccaggct ttcaagaacc tgcgggggct gtggggagtg aaggcgccca ccggcgaccg 12840
ggctacggtg tccagcctgc taacccccaa ctcgcgcctg ctgctgctgc tgatcgcgcc 12900
cttcacggac agcgggagcg tctcgcggga gacctatctg ggccacctgc tgacgctgta 12960
ccgcgaggcc atcgggcagg cgcaggtgga cgagcacacc ttccaagaga tcaccagcgt 13020
gagccacgcg ctggggcagg aggacacggg cagcctgcag gcgaccctga actacctgct 13080
gaccaacagg cggcagaaga ttcccacgct gcacagcctg acccaggagg aggagcgcat 13140

```
cttgcgctac gtgcagcaga gcgtgagcct gaacctgatg cgcgacggcg tgacgcccag  13200
cgtggcgctg gacatgaccg cgcgcaacat ggaaccgggc atgtacgcct cccaccggcc  13260
gtttatcaac cgcctgatgg actacttgca tcgggcggcg gccgtgaacc ccgagtactt  13320
cactaatgcc attctgaatc cccactggat gccccctccg ggtttctaca acggggactt  13380
tgaggtgccc gaggtcaacg acgggttcct ctgggatgac atggatgaca gtgtgttctc  13440
acccaacccg ctgcgcgccg cgtctctgcg attgaaggag ggctctgaca gggaaggacc  13500
gaggagtctg gcctcctccc tggctctggg agcggtgggc gccacgggcg cggcggcgcg  13560
gggcagtagc cccttcccca gcctggcaga ctctctgaac agcgggcggg tgagcaggcc  13620
ccgcttgcta ggcgaggagg agtatctgaa caactccctg ctgcagcccg cgagggacaa  13680
gaacgctcag cggcagcagt ttcccaacaa tgggatagag agcctggtgg acaagatgtc  13740
cagatggaag acgtatgcgc aggagtacaa ggagtgggag gaccgccagc cgcggccctt  13800
gccgcccccct aggcagcgct ggcagcggcg cgcgtccaac cgccgctgga ggcaggggcc  13860
cgaggacgat gatgactctg cagatgacag cagcgtgttg gacctgggcg ggagcgggaa  13920
cccctttttcg cacctgcgcc cacgcctggg caagatgttt taaaagaaaa aaaaaaataa  13980
aactcaccaa ggccatggcg acgagcgttg gtttttttgtt cccttcctta gtatgcggcg  14040
cgcggcgatg ttcgaggagg ggcctccccc ctcttacgag agcgcgatgg ggatttctcc  14100
tgcggcgccc ctgcagcctc cctacgtgcc tcctcggtac ctgcaaccta caggggggag  14160
aaatagcatc tgttactctg agctgcagcc cctgtacgat accaccagac tgtacctggt  14220
ggacaacaag tccgcggacg tggcctccct gaactaccag aacgaccaca gcgatttttt  14280
gaccacggtg atccaaaaca acgacttcac ccccaaccgag gccagcaccc agaccataaa  14340
cctggataac aggtcgaact ggggcggcga cctgaagacc atcttgcaca ccaacatgcc  14400
caacgtgaac gagttcatgt tcaccaactc ttttaaggcg cgggtgatgg tggcgcgcga  14460
gcagggggag gcgaagtacg agtgggtgga cttcacgctg cccgagggca actactcaga  14520
gaccatgact ctcgacctga tgaacaatgc gatcgtggaa cactatctga aagtgggcag  14580
gcagaacggg gtgaaggaaa gcgatatcgg ggtcaagttt gacaccagaa acttccgtct  14640
gggctgggac cccgtgaccg ggctggtcat gccgggggtc tacaccaacg aggcctttca  14700
tcccgacata gtgcttctgc ccggctgtgg ggtggacttc acccagagcc ggctgagcaa  14760
cctgctgggc attcgcaagc ggcagccttt ccaggagggt ttcaagatca cctatgagga  14820
tctgaagggg ggcaacattc ccgcgctcct tgatctggac gcctacgagg agagcttgaa  14880
acccgaggag agcgctggcg acagcggcga gagtggcgag gagcaagccg gcggcggtgg  14940
cggcgcgtcg gtagaaaacg aaagtacgcc cgcagtggcg gcggacgctg cggaggtcga  15000
gccggaggcc atgcagcagg acgcagagga gggcgcacag gagggcgcgc agaaggacat  15060
gaacgatggg gagatcaggg gagacacatt cgccacccgg ggcgaagaaa aagaggcaga  15120
ggcggcggcg gcggcgacgg cggaggccga aaccgaggtt gaggcagagg cagagcccga  15180
gaccgaagtt atggaagaca tgaatgatgg agaacgtagg ggcgacacgt tcgccacccg  15240
gggcgaagag aaggcggcgg aggcagaagc cgcggctgag gaggcggctg cggctgcggc  15300
caagactgag gctgcggcta aggctgaggt cgaagccaat gttgcggttg aggctcaggc  15360
tgaggaggag gcggcggctg aagcagttaa ggaaaaggcc caggcagagc aggaagagaa  15420
aaaacctgtc attcaacctc taaaagaaga tagcaaaaag cgcagttaca acgtcatcga  15480
```

-continued gggcagcacc tttacccagt accgcagctg gtacctggcg tacaactacg gcgacccggt 15540
caagggggtg cgctcgtgga ccctgctctg cacgccggac gtcacctgcg gctccgagca 15600
gatgtactgg tcgctgccga acatgatgca agacccggtg accttccgct ccacgcggca 15660
ggttagcaac ttcccggtgg tgggcgccga actgctgccc gtgcactcca agagttttta 15720
caacgagcag gccgtctact cccagctgat ccgccaggcc acctctctga cccacgtgtt 15780
caatcgcttt cccgagaacc agattttggc gcgcccgccg gcccccacca tcaccaccgt 15840
gagtgaaaac gttcctgccc tcacagatca cgggacgcta ccgctgcgca acagcatctc 15900
aggagtccag cgagtgacca ttactgacgc cagacgccgg acctgcccct acgtttacaa 15960
ggccttgggc atagtctcgc cgcgcgtcct ctccagtcgc actttttaaa acacatctac 16020
ccacacgttc caaaatcatg tccgtactca tctcacccag caacaacacc ggctgggggc 16080
tgcgcgcgcc cagcaagatg tttggagggg cgaggaagcg ctccgaccag caccctgtgc 16140
gcgtgcgcgg ccactaccgc gcgccctggg gagcgcacaa gcgcgggcgc acagggcgca 16200
ccactgtgga cgacgtcatt gactccgtag tggagcaagc gcgccactac acacccggcg 16260
cgccgaccgc ccccgccgtg tccaccgtgg accaggcgat cgaaagcgtg gtacagggcg 16320
cgcggcacta tgccaacctt aaaagtcgcc gccgccgcgt ggcccgccgc catcgccgga 16380
gaccccgggc caccgccgcc gcgcgcctta ctaaggctct gctcaggcgc gccaggcgaa 16440
ctggccaccg ggccgccatg agggccgcac ggcgggctgc cgctgccgca agcgtcgtgg 16500
ccccgcgggc acgaaggcgc gcggccgctg ccgccgccgc cgccatttcc agcttggcct 16560
cgacgcggcg cggtaacata tactgggtgc gcgactcggt aaccggcacg cgggtacccg 16620
tgcgctttcg ccccccgcgg aattagcaca agacaacata cacactgagt ctcctgctgt 16680
tgtgtatccc agcggcgacc gtcagcagcg gcgacatgtc caagcgcaaa attaaagaag 16740
agatgctcca ggtcatcgcg ccggagatct atgggccccc gaagaaggag gaggatgatt 16800
acaagccccg caagctaaag cgggtcaaaa agaaaaagaa agatgatgat gacgaggcgg 16860
tggagtttgt ccgccgcatg gcacccaggc gccccgtgca gtggaagggc cggcgcgtgc 16920
agcgcgtttt gcgccccggc accgcggtgg tcttcacgcc cggcgagcgc tccacgcgca 16980
ctttcaagcg ggtgtacgat gaggtgtacg gcgacgagga cctgttggag caggccaacc 17040
agcgctttgg ggagtttgca tatgggaaac ggccccgcga gagtctaaaa gaggacctgc 17100
tggcgctacc gctggacgag ggcaatccca ccccgagtct gaagccggta accctgcaac 17160
aggtgctgcc tttgagcgcg cccagcgagc ataagcgagg gttgaagcgc gaaggcgggg 17220
acctggcgcc caccgtgcag ttgatggtgc ccaagcggca gaagctggag gacgtgctgg 17280
agaaaatgaa agtagagccc gggatccagc ccgagatcaa ggtccgcccc atcaagcagg 17340
tggcgcccgg cgtgggagtc cagaccgtgg acgttaggat tcccacggag gagatggaaa 17400
cccaaaccgc cactccctct tcggcggcca gcgccaccac cggcaccgct tcggtagagg 17460
tgcagacgga cccctggcta cccgccaccg ctgttgccgc cgccgccccc cgttcgcgcg 17520
ggcgcaagag aaattatcca gcggccagcg cgctcatgcc ccagtacgca ctgcatccat 17580
ccatcgtgcc cacccccggc taccgcgggt actcgtaccg cccgcgcaga tcagccggca 17640
ctcgcggccg ccgccgccgt gcgaccacaa ccagccgccg ccgtcgccgc cgccgccagc 17700
cagtgctgac cccgtgtct gtaaggaagg tggctcgctc ggggagcacg ctggtggtgc 17760
ccagagcgcg ctaccacccc agcatcgttt aaagccggtc tctgtatggt tcttgcagat 17820
atggccctca cttgtcgcct ccgcttcccg gtgccgggat accgaggaag aactcaccgc 17880

```
cgcagaggca tggcgggcag cggtctccgc ggcggccgtc gccatcgccg gcgcgcaaaa  17940

agcaggcgca tgcgcggcgg tgtgctgcct ctgctaatcc cgctaatcgc cgcggcgatc  18000

ggtgccgtac ccgggatcgc ctccgtggcc ctgcaggcgt cccagaaacg ttgactcttg  18060

caaccttgca agcttgcatt ttttggagga aaaaataaaa aaaaagtcta gactctcacg  18120

ctcgcttggt cctgtgacta ttttgtagaa aaaaagatgg aagacatcaa ctttgcgtcg  18180

ctggccccgc gtcacggctc gcgcccgttc atgggagact ggacagatat cggcaccagc  18240

aatatgagcg gtggcgcctt cagctggggc agtctgtgga gcggccttaa aaattttggt  18300

tccaccatta agaactatgg caacaaagcg tggaacagca gcacgggcca gatgctgaga  18360

gacaagttga aagagcagaa cttccaggag aaggtggcgc agggcctggc ctctggcatc  18420

agcggggtgg tggacatagc taaccaggcc gtgcagaaaa agataaacag tcatctggac  18480

ccccgtcctc aggtggagga aatgcctcca gcgatggaga cggtgtctcc cgagggcaaa  18540

ggcgaaaagc gcccgcggcc cgacagagaa gagaccctgg tgtcacacac cgaggagccg  18600

ccctcttacg aggaggcagt caaggccggc ctgcccacca ctcgccccat agcccccatg  18660

gccaccggtg tggtgggcca caggcaacac actcccgcaa cactagatct gcccccgccg  18720

tccgagccgc cgcgccagcc aaaggcggcg acggtgcccg ctccctccac ttccgccgcc  18780

aacagagtgc ccctgcgccg cgccgcgagc ggcccccggg cctcgcgagt tagcggcaac  18840

tggcagagca cactgaacag catcgtgggc ctgggagtga ggagtgtgaa gcgccgccgt  18900

tgctactgaa tgagcaagct agctaacgtg ttgtatgtgt gtatgcgtcc tatgtcgccg  18960

ccagaggagc tgttgagccg ccggcgccgt ctgcactcca gcgaatttca agatggcgac  19020

cccatcgatg atgcctcagt ggtcgtacat gcacatctcg ggccaggacg cttcggagta  19080

cctgagcccc gggctggtgc agttcgcccg cgccacagac acctacttca acatgagtaa  19140

caagttcagg aaccccactg tggcgcccac ccacgatgtg accacggacc ggtcgcagcg  19200

cctgacgctg cggttcatcc ccgtggatcg ggaggacacc gcctactctt acaaggcgcg  19260

gttcacgctg gccgtgggcg acaaccgcgt gctggacatg gcctccactt actttgacat  19320

caggggggtg ctggacaggg gccccacctt caagccctac tcgggtactg cctacaactc  19380

cctggccccc aagggcgctc ccaattcttg cgagtgggaa caagatgaac cagctcaggc  19440

agcaatagct gaagatgaag aagaacttga agaagaacaa gctcaggacg aacaggcgcc  19500

cactaagaaa acccatgtat acgcccaggc acctctttct ggtgaaaaaa ttactaagga  19560

tggtttgcaa ataggtgtgg atgccacaca ggcgggagat aaccctatat atgctgataa  19620

aacattccaa cccgaacctc agataggtga gtctcagtgg aacgaggctg atgccacagt  19680

agcaggaggc agagtcttaa aaaagaccac ccctatgaga ccttgctatg gatcctatgc  19740

caaacctact aatgccaatg gcggtcaagg gatcatggtg gccaatgatc agggagcgct  19800

tgaatctaaa gttgagatgc aatttttctc caccacaacg tctcttaatg taagggaagg  19860

tgaaaacaat cttcagccaa aagtagtgct atacagcgaa gatgttaact tggaatcccc  19920

tgacactcat ttgtcttaca aacctaaaaa ggatgacacc aactctaaaa tcatgttggg  19980

tcagcaagcc atgcccaaca gacccaacct cattgctttt agggacaact ttattggact  20040

tatgtactac aacagcacag gcaacatggg agtgctggca ggacaggcct cccagctaaa  20100

cgctgtggta gacttgcaag acagaaacac agagctgtca taccaactga tgcttgattc  20160

cattggagac agatcaagat acttttccat gtggaaccag gcagtggaca gctatgaccc  20220
```

agatgtcaga atcattgaaa accatggggt tgaagatgag ctgcccaact attgctttcc 20280
cctgggcggt attggaatta cagacacata ccagtgcata aaaccaaccg cagctgctaa 20340
taacactaca tggtctaagg atgaagaatt tagtgatcgc aatgaaatag ggtgggaaa 20400
caacttcgcc atggagatca acatccaggc caacctctgg aggaacttcc tctatgcgaa 20460
cgtggggctc tacctgccag acaagctcaa gtacaacccc accaacgtgg acatctctga 20520
caaccccaac acctatgact acatgaacaa gcgtgtggtg gctcccggcc tggtggactg 20580
ctttgtcaat gtgggagcca ggtggtccct ggactacatg gacaacgtca accccttcaa 20640
ccaccaccgc aatgcgggtc tgcgctaccg ctccatgatc ctgggcaacg ggcgctacgt 20700
gcccttccac attcaggtgc cccagaagtt ctttgccatc aagaacctcc tcctcctgcc 20760
gggctcctac acttacgagt ggaacttcag gaaggatgtc aacatggtcc tgcagagctc 20820
tctgggcaat gaccttaggg tggacggggc cagcatcaag tttgacagcg tcaccctcta 20880
tgctaccttc ttccccatgg ctcacaacac cgcctccacg ctcgaggcca tgctgaggaa 20940
cgacaccaac gaccagtcct tcaatgacta cctctctggg gccaacatgc tctaccccat 21000
ccccgccaag gccaccaacg tgcccatctc cattccctct cgcaactggg ccgccttcag 21060
aggctgggcc tttacccgcc ttaagaccaa ggaaaccccc tccctgggct cgggttttga 21120
cccctacttt gtctactcgg gatccatccc ctacctggat ggcaccttct acctcaacca 21180
cacttttaag aagatatcca tcatgtatga ctcctccgtc agctggccgg gcaatgaccg 21240
cctgctcacc cccaatgagt tcgaggtcaa gcgcgccgtg gacggcgagg gctacaacgt 21300
ggcccagtgc aacatgacca aggactggtt cctggtgcag atgctggcca actacaacat 21360
aggctaccag ggcttctaca tcccagagag ctacaaggac aggatgtact ccttcttcag 21420
aaatttccaa cccatgagca ggcaggtggt ggacgagacc aaatacaagg actatcaggc 21480
cattggcatc actcaccagc acaacaactc gggattcgtg ggctacctgg ctcccaccat 21540
gcgcgagggg caggcctacc ccgccaactt cccctacccg ttgataggca aaaccgcggt 21600
cgacagcgtc acccagaaaa agttcctctg cgaccgcacc ctctggcgca tccccttctc 21660
tagcaacttc atgtccatgg gtgcgctcac ggacctgggc cagaacctgc tctatgccaa 21720
ctccgcccat gcgctggaca tgacttttga ggtggacccc atggacgagc ccacccttct 21780
ctatattgtg tttgaagtgt tcgacgtggt cagagtgcac cagccgcacc gcggtgtcat 21840
cgagaccgtg tacctgcgca cgcccttctc ggccggcaac gccaccacct aaggagacag 21900
cgccgccgcc tgcatgacgg gttccaccga gcaagagctc agggccatcg ccagagacct 21960
gggatgcgga ccctattttt tgggcaccta tgacaaacgc ttcccgggct tcatctcccg 22020
agacaagctc gcctgcgcca tcgtcaacac ggccgcgcgc gagaccgggg gcgtgcactg 22080
gctggccttt ggctgggacc cgcgctccaa aacctgctac ctcttcgacc cctttggctt 22140
ctccgatcag cgcctcagac agatctatga gtttgagtac gaggggctgc tgcgccgcag 22200
cgcgcttgcc tcctcgcccg accgctgcat cacccttgag aagtccaccg agaccgtgca 22260
ggggccccac tcggccgcct gcggtctctt ctgctgcatg tttttgcacg cctttgtgcg 22320
ctggccccag agtcccatgg atcgcaaccc caccatgaac ttgctcaagg gagtgcccaa 22380
cgccatgctc cagagccccc aggtccagcc caccctgcgc cacaaccagg aacagctcta 22440
ccgcttcctg gagcgccact ccccctactt ccgcagtcac agcgcgcaca tccgggggc 22500
cacctctttc tgccacttgc aagaaaacat gcaagacgga aatgatgta cagctcgctt 22560
tttaataaat gtaaagactg tgcactttat ttatacacgg gctctttctg gttatttatt 22620
caacaccgcc gtcgccatct agaaatcgaa agggttctgc cgcgcgtcgc cgtgcgccac 22680
gggcagagac acgttgcgat actggaagcg gctcgcccac ttaaactcgg gcaccaccat 22740
gcggggcagt ggttcctcgg ggaagttctc gccccacagg gtgcgggtca gctgcagcgc 22800
gctcaggagg tcgggagccg agatcttgaa gtcgcagttg gggccggaac cctgcgcgcg 22860
cgagttgcgg tacacggggt tgcagcactg gaacaccagc agggccggat tatgcacgct 22920
ggccagcagg ctctcgtcgc tgatcatgtc gctgtccaga tcctccgcgt tgctcagggc 22980
gaacggggtc atcttgcaga cctgcctgcc caggaaaggc ggcagcccgg gcttgccgtt 23040
gcagtcgcag cgcaggggca tcagcaggtg cccgcggccc gactgcgcct gcgggtacag 23100
cgcgcgcatg aaggcttcga tctgcctgaa agccacctgc gtcttggctc cctccgaaaa 23160
gaacatccca caggacttgc tggagaactg gttcgcggga cagctggcat cgtgcaggca 23220
gcagcgcgcg tcggtgttgg cgatctgcac cacgttgcga ccccaccggt tcttcactat 23280
cttggccttg gaagcctgct ccttcagcgc gcgctggccg ttctcgctgg tcacatccat 23340
ctctatcacc tgctccttgt tgatcatgtt tgtaccgtgc agacacttca ggtcgccctc 23400
cgtctgggtg cagcggtgct cccacagcgc gcaaccggtg ggctcccaat ttttgtgggt 23460
cacccccgcg taggcctgca ggtaggcctg caagaagcgc cccatcatgg ccacaaaggt 23520
cttctggctc gtaaaggtca gctgcaggcc gcgatgctct tcgttcagcc aggtcttgca 23580
gatggcggcc agcgcctcgg tctgctcggg cagcatccta aaatttgtct tcaggtcgtt 23640
atccacgtgg tacttgtcca tcatggcgcg cgccgcctcc atgcccttct cccaggcgga 23700
caccatgggc aggcttaggg ggtttatcac ttccaccggc gaggacaccg tactttcgat 23760
ttcttcttcc tcccccctctt cccggcgcgc gcccacgctg ctgcgcgctc tcaccgcctg 23820
caccaagggg tcgtcttcag gcaagcgccg caccgagcgc ttgccgccct tgacctgctt 23880
aatcagcacc ggcgggttgc tgaagcccac catggtcagc gccgcctgct cttcttcgtc 23940
ttcgctgtct accactatct ctggggaagg gcttctccgc tctgcggcgg cgcgcttctt 24000
ttttttcttg ggagcggccg tgatggagtc cgccacggcg acggaggtcg agggcgtggg 24060
gctgggggtg cgcggtacca gggcctcgtc gccctcggac tcttcctctg actccaggcg 24120
gcggcggagt cgcttctttg ggggcgcgcg cgtcagcggc ggcggagacg ggacgggga 24180
cggggacggg acgccctcca cagggggtgg tcttcgcgca gacccgcggc cgcgctcggg 24240
ggtcttctcg agctggtctt ggtcccgact ggccattgta tcctcctcct cctaggcaga 24300
gagacataag gagtctatca tgcaagtcga gaaggaggag agcttaacca ccccctctga 24360
gaccgccgat gcgcccgccg tcgccgtcgc ccccgctgcc gccgacgcgc ccgccacacc 24420
gagcgacacc cccgcggacc cccccgccga cgcacccctg ttcgaggaag cggccgtgga 24480
gcaggacccg ggctttgtct cggcagagga ggatttgcga gaggaggagg ataaggagaa 24540
gaagccctca gtgccaaaag atgataaaga gcaagacgag cacgacgcag atgcacacca 24600
gggtgaagtc gggcgggggg acggagggca tgacggcgcc gactacctag acgaagggaa 24660
cgacgtgctc ttgaagcacc tgcatcgtca gtgcgccatt gtttgcgacg ctctgcagga 24720
gcgcagcgaa gtgcccctca gcgtggcgga ggtcagccac gcctacgagc tcagcctctt 24780
ctccccccgg gtgccccccc gccgccgcga aaacggcaca tgcgagccca acccgcgcct 24840
caacttctac cccgcctttg tggtacccga ggtcctggcc acctatcaca tcttctttca 24900
aaattgcaag atccccctct cgtgccgcgc caaccgtagc cgcgccgata agatgctggc 24960
cctgcgccag ggcgaccaca tacctgatat cgccgctttg gaagatgtac caaagatctt 25020
cgagggtctg ggtcgcaacg agaagcgggc agcaaactct ctgcaacagg aaaacagcga 25080
aaatgagagt cacaccgggg tactggtgga gctcgagggc gacaacgccc gcctggcggt 25140
ggtcaagcgc agcatcgagg tcacccactt tgcctacccc gcgctaaacc tgccccccaa 25200
agtcatgaac gcggccatgg acgggctgat catgcgccgc ggccggcccc tcgctccaga 25260
tgcaaacttg catgaggaga ccgaggacgg ccagcccgtg gtcagcgacg agcagctggc 25320
gcgctggctg gagaccgcgg accccgccga actggaggag cggcgcaaga tgatgatggc 25380
cgtggtgctg gtcaccgtag agctggagtg tctgcagcgc ttcttcggcg accccgagat 25440
gcagagaaag gtcgaggaga ccctgcacta caccttccgc cagggctacg tgcgccaggc 25500
ttgcaagatc tccaacgtgg agctcagcaa cctggtgtcc tacctgggca tcttgcatga 25560
gaaccgcctc gggcagagcg tgctgcactc caccctgcgc ggggaggcgc gccgcgacta 25620
cgtgcgcgac tgcgtttacc tcttcctctg ctacacctgg cagacggcca tgggggtctg 25680
gcagcagtgc ctggaggagc gcaacctcaa ggagctggag aagctcctgc agcgcgcgct 25740
caaagatctc tggacgggct acaacgagcg ctcggtggcc gccgcgctgg ccgacctcat 25800
cttccccgag cgcctgctca aaaccctcca gcaggggctg cccgacttca ccagccaaag 25860
catgttgcaa aacttcagga actttatcct ggagcgttct ggcatcctac ccgccacctg 25920
ctgcgccctg cccagcgact ttgtccccct cgtgtaccgc gagtgccccc cgccgctgtg 25980
gggtcactgc tacctgttcc aactggccaa ctacctgtcc taccacgcgg acctcatgga 26040
ggactccagc ggcgaggggc tcatggagtg ccactgccgc tgcaacctct gcacgcccca 26100
ccgctccctg gtctgcaaca cccaactgct cagcgagagt cagattatcg gtaccttcga 26160
gctacagggt ccgtcctcct cagacgagaa gtccgcggct ccggggctaa aactcactcc 26220
ggggctgtgg acttccgcct acctgcgcaa atttgtacct gaagactacc acgcccacga 26280
gatcaggttt tacgaagacc aatcccgccc gcccaaggcg gagctgaccg cctgcgtcat 26340
cacccagggc gagatcctag gccaattgca agccatccaa aaagcccgcc aagacttttt 26400
gctgaagaag ggtcgggggg tgtatctgga cccccagtcg ggtgaggagc tcaacccggt 26460
tcccccgctg ccgccgccgc gggaccttgc ttcccaggat aagcatcgcc atggctccca 26520
gaaagaagca gcagcggccg ccactgccgc caccccacat gctggaggaa gaggaggaat 26580
actgggacag tcaggcagag gaggtttcgg acgaggagga gccggagacg gagatggaag 26640
agtgggagga ggacagctta gacgaggagg cttccgaagc cgaagaggca gacgcaacac 26700
cgtcaccctc ggccgcagcc ccctcgcagg cgcccccgaa gtccgctccc agcatcagca 26760
gcaacagcag cgctataacc tccgctcctc caccgccgcg acccacggcc gaccgcagac 26820
ccaaccgtag atgggacacc accggaaccg gggccggtaa gtcctccggg agaggcaagc 26880
aagcgcagcg ccaaggctac cgctcgtggc gcgctcacaa gaacgccata gtcgcttgct 26940
tgcaagactg cggggggaac atctccttcg cccgccgctt cctgctcttc caccacggtg 27000
tggccttccc ccgtaacgtc ctgcattact accgtcatct ctacagcccc tactgcggcg 27060
gcagtgagcc agagacggtc ggcggcggcg gcggcgcccg tttcggcgcc taggaagacc 27120
cagggcaaga cttcagccaa gaaactcgcg gcggccgcgg cgaacgcggt cgcgggggcc 27180
ctgcgcctga cggtgaacga acccctgtcg acccgcgaac tgaggaaccg aatcttcccc 27240
actctctatg ccatcttcca gcagagcaga gggcaggatc aggaactgaa agtaaaaaac 27300
aggtctctgc gctccctcac ccgcagctgt ctgtatcaca agagcgaaga ccagcttcgg 27360
cgcacgctgg aggacgctga ggcactcttc agcaaatact gcgcgctcac tcttaaggac 27420
tagctccgcg cccttctcga atttaggcgg gaacgcctac gtcatcgcag cgccgccgtc 27480
atgagcaagg acattcccac gccatacatg tggagctatc agccgcagat gggactcgcg 27540
gcgggcgcct cccaagacta ctccacccgc atgaactggc tcagtgccgg cccacacatg 27600
atctcacagg ttaatgatat ccgcacccat cgaaaccaaa tattggtgga gcaggcggca 27660
attaccacca cgccccgcaa taatcccaac cccagggagt ggcccgcgtc cctggtgtat 27720
caggaaattc ccggccccac caccgtacta cttccgcgtg attcccaggc cgaagtccaa 27780
atgactaact caggggcaca gctcgcgggc ggctgtcgtc acagggtgcg gcctcctcgc 27840
cagggtataa ctcacctgga gatccgaggc agaggtattc agctcaacga cgagtcggtg 27900
agctcctcgc tcggtctcag acctgacggg accttccaga tagccggagc cggccgatct 27960
tccttcacgc cccgccaggc gtacctgact ctgcaaagct cgtcctcggc gccgcgctcg 28020
ggcggcatcg ggactctcca gttcgtgcag gagtttgtgc cctcggtcta cttcaacccc 28080
ttctcgggct ctcccggtcg ctacccggac cagttcatct cgaactttga cgccgcgagg 28140
gactcggtgg acggctacga ctgaatgtcg ggtggacccg gtgcagagca acttcgcctg 28200
aagcacctcg accactgccg ccgccctcag tgctttgccc gctgtcagac cggtgagttc 28260
cagtactttt ccctgcccga ctcgcacccg gacggcccgg cgcacggggt gcgctttttc 28320
atcccgagtc aggtgcgctc taccctaatc agggagttta ccgcccgtcc cctactggcg 28380
gagttggaaa aggggccttc tatcctaacc attgcctgca tctgctctaa ccctggattg 28440
caccaagatc tttgctgtca tttgtgtgct gagtataata aaggctgaga tcagaatcta 28500
ctcgggctcc tgtcgccatc ctgtcaacgc caccgtccaa gcccggcccg atcagcccga 28560
ggtgaacctc acctgcggtc tgcaccggcg cctgaggaaa tacctagctt ggtactacaa 28620
cagcactccc tttgtggttt acaacagctt tgaccaggac ggggtctcac tgagggataa 28680
cctctcgaac ctgagctact ccatcaggaa gaacagcacc ctcgagctac ttcctcctta 28740
cctgcccggg acttaccagt gtgtcaccgg tccctgcacc cacacccacc tgttgatcgt 28800
aaacgactct cttccgagaa cagacctcaa taactcctct tcgcagttcc ccagaacagg 28860
aggtgagctc aggaaacccc gggtaaagaa gggtggacga gagttaacac ttgtggggtt 28920
tctggtgtat gtgacgctgg tggtggctct tttgattaag gcttttcctt ccatgtctga 28980
actctccctc ttcttttatg aacaactcga ctagtgctaa cgggacccta cccaacgaat 29040
cgggattgaa tatcggtaac caggttgcag tttcactttt gattaccttc atagtcctct 29100
tcctgctagt gctgtcgctt ctgtgcctgc ggatcggggg ctgctgcatc cacgtttata 29160
tctggtgctg gctgtttaga aggttcggag accatcgcag gtagaataaa catgctgctg 29220
cttaccctct ttgtcctggc gctggccgcc agctgccaag ccttttccga ggctgacttt 29280
atagagcccc agtgtaatgt gacttttaaa gcccatgcac agcgttgtca tactataatc 29340
aaatgtgcca ccgaacacga tgaataccttt atccagtata aagataaatc acacaaagtg 29400
gcacttgttg acatctggaa acccgaagac cctttggaat acaatgtgac cgttttccag 29460
ggtgacctct tcaaaattta caattacact ttcccatttg accagatgtg tgactttgtc 29520
atgtacatgg aaaagcagca caagctgtgg cctccgactc cccagggctg tgtggaaaat 29580
ccaggctctt tctgcatgat ctctctctgt gtaactgtgc tggcactaat actcacgctt 29640
ttgtatatca gatttaaatc aaggcaaagc ttcattgatg aaaagaaaat gccttaatcg 29700

```
ctttcacgct tgattgctaa caccgggttt ttatccgcag aatgattgga atcaccctac  29760
taatcacctc cctccttgcg attgcccatg ggttggaacg aatcgaagtc cctgtggggg  29820
ccaatgttac cctggtgggg cctgtcggca atgctacatt aatgtgggaa aaatatacta  29880
aaaatcaatg ggtctcttac tgcactaaca aaaatagcca caagcccaga gccatctgcg  29940
atgggcaaaa tctaaccttg attgatgttc aattgctgga tgcgggctac tattatgggc  30000
agctgggtac aatgattaat tactggagac cccacagaga ttacatgctc cacgtagtaa  30060
agggtcccct tagcagccca cccactacca cctctactac ccccactacc accactactc  30120
ccaccaccag cactgccgcc cagcctcctc atagcagaac aaccactttt atcaattcca  30180
agtcccactc cccccacatt gccggcgggc cctccgcctc agactccgaa accaccgaga  30240
tctgcttctg caaatgctct gacgccattg cccaggattt ggaagatcac gaggaagatg  30300
agcatgactt cgcagatgca tgccaggcat cagagccaga agcgctgccg gtggccctca  30360
aacagtatgc agaccccac accaccccg accttcctcc accttcccag aagccaagtt  30420
tcctggggga aaatgaaact ctgcctctct ccatactcgc tctgacatct gttgctatgt  30480
tgaccgctct gctggtgctt ctatgctcta tatgctacct gatctgctgc agaaagaaaa  30540
aatctcacgg ccatgctcac cagcccctca tgcacttccc ttaccctcca gagctgggcg  30600
accacaaact ttaagtctgc agtaactatc tgcccatccc ttgtcagtcg acagcgatga  30660
gccccactaa tctaacggcc tctggactta caacatcgtc tcttaatgag accaccgctc  30720
ctcaagacct gtacgatggt gtctccgcgc tggttaacca gtgggatcac ctgggcatat  30780
ggtggctcct cataggagca gtgaccctgt gcctaatcct ggtctggatc atctgctgca  30840
tcaaaagcag aagacccagg cggcggccca tctacaggcc ctttgtcatc acacctgaag  30900
atgatgatga caccacttcc aggctgcaga ggctaaagca gctactcttc tcttttacag  30960
catggtaaat tgaatcatgc ctcgcatttt catctacttg tctctccttc cactttttct  31020
gggctcttct acattggccg ctgtgtccca catcgaggta gactgcctca cgcccttcac  31080
agtctacctg cttttcggct ttgtcatctg cacctttgtc tgcagcgtta tcactgtagt  31140
gatctgcttc atacagtgca tcgactacgt ctgcgtgcgg gtggcttact ttagacacca  31200
cccccagtat cgcaacaggg acatagcggc tctcctaaga cttgtttaaa atcatggcca  31260
aattaactgt gattggtctt ctgatcatct gctgcgtcct agccgcgatt gggactcaag  31320
ctcctaccac caccagcgct cccagaaaga gacatgtatc ctgcagcttc aagcgtccct  31380
ggaatatacc ccaatgcttt actgatgaac ctgaaatctc tttggcttgg tacttcagcg  31440
tcaccgccct tcttatcttc tgcagtacgg ttattgccct tgccatctac ccttcccttg  31500
acctgggctg gaatgctgtc aactctatgg aatatcccac cttcccagaa ccagacctgc  31560
cagacctggt tgttctaaac gcgtttcctc ctcctgctcc cgttcaaaat cagtttcgcc  31620
ctccgtcccc cacgcccact gaggtcagct actttaatct aacaggcgga gatgactgaa  31680
aacctagacc tagaaatgga cggtctctgc agcgagcaac gcacactaga gaggcgccgg  31740
caaaaagagc tcgagcgtct taaacaagag ctccaagacg cggtggccat acaccagtgc  31800
aaaaaaggtg tcttctgtct ggtaaaacag gccacgctca cctatgaaaa aacaggtgac  31860
acccaccgcc taggatacaa gctgcccaca cagcgccaaa agttcgccct catgataggc  31920
gaacaaccca tcaccgtgac ccagcactcc gtggagacag aaggctgcat acatgctccc  31980
tgtaggggcg ctgactgcct ctacaccttg atcaaaaccc tctgcggtct cagagacctt  32040
atccctttca attaatcata actgtaatca ataaaaaatc acttacttga aatctgatag  32100
```

caagcctctg tccaattttt tcagcaacac ttccttcccc tcctcccaac tctggtactc 32160
taggcgcctc ctagctgcaa acttcctcca cagtctgaag ggaatgtcag attcctcctc 32220
ctgtccctcc gcacccacga tcttcatgtt gttgcagatg aaacgcgcga gatcgtctga 32280
cgagaccttc aaccccgtgt acccctacga taccgagatc gctccgactt ctgtcccttt 32340
ccttacccct ccctttgtgt catccgcagg aatgcaagaa aatccagctg ggtgctgtc 32400 cctgcacttg tcagagcccc ttaccaccca caatggggcc ctgactctaa aaatgggggg 32460
cggcctgacc ctggacaagg aagggaatct cacttcccaa aacatcacca gtgtcgatcc 32520
ccctctcaaa aaaagcaaga acaacatcag ccttcagacc gccgcacccc tcgccgtcag 32580
ctccggggcc ctaacacttt ttgccactcc ccccctagcg gtcagtggtg acaaccttac 32640
tgtgcagtct caggcccctc tcactttgga agactcaaaa ctaactctgg ccaccaaagg 32700
acccctaact gtgtccgaag gcaaacttgt cctagaaac 32739

<210> SEQ ID NO 23
<211> LENGTH: 32739
<212> TYPE: DNA
<213> ORGANISM: Artificial Sequence
<220> FEATURE:
<223> OTHER INFORMATION: Adenovirus vector nucleotide sequences

<400> SEQUENCE: 23 ataaatatacc ttattttgga ttgtggccaa tatgataatg aggtgggcgg ggagaggcgg 60
ggcgggtgac gtaggacgcg cgagtagggt tgggaggtgt ggcggaagtg tggcatttgc 120
aagtgggagg agctcacatg caagcttccg tcgcggaaaa tgtgacgttt ttgatgagcg 180
ccgcctacct ccggaagtgc caattttcgc gcgcttttca ccggatatcg tagtaatttt 240
gggcgggacc atgtaagatt tggccatttt cgcgcgaaaa gtgaaacggg gaagtgaaaa 300
ctgaataata gggcgttagt catagcgcgt aatatttacc gagggccgag ggactttgac 360
cgattacgtg gaggactcgc ccaggtgttt tttacgtgaa tttccgcgtt ccgggtcaaa 420
gtctccgttt ttattgtcac cgtcatttga cgcggagggt atttaaaccc gctgcgctcc 480
tcaagaggcc actcttgagt gccagcgaga agagttttct cctctgctcc gcttcggtga 540
tcgaaaaatg agacacatag cctgcactcc gggtcttttg tccggtcggg cggcggccga 600
gcttttggac gctttgatca atgatgtcct aagcgatgat tttccgtcta ctacccactt 660
tagcccacct actcttcacg aactgtacga tctggatgta ctggtggatg tgaacgatcc 720
caacgaggag gcggtttctg cgtttttcc cgagtctgcg ctgttggccg ctcaggaggg 780
atttgaccta cacactccgc cgcctatttt agagtctccg ctgccggagc ccagtggtat 840
accttatatg cctgaactgc ttcccgaagt ggtagacctg acctgccacg agcctggctt 900
tccgcccagc gacgatgagg gtgagccttt tgttttagac tttgctgaga tacctgggca 960
cggttgcagg tcttgtgcat atcatcagag ggttaccgga gaccccgagg ttaagtgttc 1020
gctgtgctat atgaggatga cctcttcctt tatctacagt aagtttttgt ctaggtgggc 1080
ttttgggtag gtgggttttg tgtcagaaca ggtgtaaacg ttgcttgtgt tttttgtacc 1140
tgtaggtccg gtgtccgagc cagacccgga gcccgaccgc gatcccgagc cggatcccga 1200
gcctcctcgc aggacaagga aactaccttc cattctgtgc aagtctcaga cacctgtaag 1260
gaccagcgag gcagacagca ccgactctgg cacttctacc tctccccctg aaattcaccc 1320
agtggttcct ctgggtatac ataaacctgt tgctgttaaa gtttgcgggc gacgccctgc 1380

-continued

```
agtacagtgc attgaggact tgcttcacga tcccgaggaa cctttggact tgagccttaa   1440
acgccctagg caataaaccc cacctaagta ataaacccca cctaagtaat aaaccctgcc   1500
gcccttggtt attgagatga cgcccaatgt ttgcttttga atgacttcat gtgtgtaata   1560
aaagtgagtg tgatcatagg tctcttgttt gtctgggcgg ggcttaaggg tatataagtc   1620
tcttggggct aaacttggtt acacttgacc ccaatggagg cgtgggggtg cttggaggag   1680
tttgcggacg tgcgccgttt gctggacgag agctctagca atacctatac tatttggagg   1740
tatctgtggg gctctactca ggccaagttg gtttccagaa ttaagcagga ttacaagtgc   1800
gattttgaag agctttttag ttcctgcggt gagcttttgc aatccttgaa tctgggccat   1860
caggctattt tccaggaaaa ggttctctcg actttggatt tttccactcc cgggcgcacc   1920
gccgcttgtg tggcttttgt gtcttttgtg caagataaat ggagcgagga gacccacctg   1980
agtcacggct acgtactgga tttcatggcg atggctcttt ggagggctca caacaaatgg   2040
aagattcaga aggaactgta cggttccgcc ctacgtcgtc cacttctgtc gcgacagggg   2100
ctgaggtttc ccgaccatcg gcagcatcag aatctggaag acgagtcgga ggagcgagcg   2160
gaggagaaga tcagcttgag agccggcctg gaccctcctc aggaggaatg aatctcccgc   2220
aggtggttga cctgtttcca gaactgagac gggtcctgac tatcagggag gatggtcagt   2280
ttgtgaagaa gtttaagagg gatcggggtg agggagatga tgaggcggct agcaatttag   2340
cttttagtct gatgactcgc caccgaccgg aatgtattac ctatcagcag attaaggaga   2400
gttgtgccaa cgagctggat cttttgggtc agaagtatag catagaacag cttaccactt   2460
actggcttca gcctggggat gattgggaag aggcgatcag ggtgtatgca aaggtggccc   2520
tgcggcccga ttgcaagtat aagattacta agttggttaa tattagaaac tgctgctata   2580
tttctgggaa cggggccgaa gtggagatag atactcagga cagggtggct tttaggtgtt   2640
gcatgataaa catgtggccc gggatactgg ggatggatgg ggtggtattc atgaatgtga   2700
ggtttacggg ccccaacttt aatggcacgg tgttcatggg caacaccaac ttgctcctgc   2760
atggtgcgag tttctatggg tttaataaca cctgtataga ggcctggacc gatgtaaagg   2820
ttcgaggttg ttccttttat agctgttgga aggcggtggt gtgtcgccct aaaagcaggg   2880
gttctgtgaa aaaatgcttg tttgaaaggt gcaccttagg catcctctct gagggcaact   2940
ccagggtgcg ccataatgtg gcttcgaact gcggttgctt catgcaagtg aagggggtga   3000
gcgttatcaa gcataactcg gtgtgtggaa actgcgagga tcgcgcctcc cagatgctga   3060
cctgctttga tggcaactgt cacctgttga agaccattca tataagcagc caccccagaa   3120
aggcctggcc cgtgtttgag cataacatct tgacccgctg ctccttgcat ctgggggtca   3180
ggaggggtat gttcctgcct taccagtgta actttagcca cactaaaatc ctgctggaac   3240
ccgagtgcat gaccaaggtc agcctgaatg gtgtgtttga tgtgactctg aaaatctgga   3300
aggtgctgag gtatgatgag accaggacca ggtgccgacc ctgcgagtgc ggcggcaagc   3360
acatgagaaa tcagcctgtg atgttggatg tgaccgagga gcttaggcct gaccatctgg   3420
tgctggcctg caccagggcc gagtttgggt ctagcgatga ggataccgat tgaggtgggt   3480
aaggtgggcg tggctagaag ggtggggcgt gtataaattg gggtctaag ggtctctctg   3540
ttttgtcttg caacagccgc cgccatgagc gacaccggca acagctttga tggaagcatc   3600
tttagcccct atctgacagt gcgcatgcct cactgggctg gagtgcgtca gaatgtgatg   3660
ggttccaacg tggatggacg ccccgttctg ccttcaaatt cgtctacaat ggcctacgcg   3720
accgtgggag gaactccgct ggacgccgcg acctccgccg ccgcctccgc cgccgccgcg   3780
```

accgcgcgca gcatggctac ggacctttac agctctttgg tggcgagcgg cgcggcctct 3840
cgcgcgtctg ctcgggatga gaaactgacc gctctgctgc ttaaactgga agacttgacc 3900
cgggagctgg gtcaactgac ccagcaggtc tccagcttgc gtgagagcag ccttgcctcc 3960
ccctaatggc ccataatata aataaaagcc agtctgtttg gattaagcaa gtgtatgttc 4020
tttatttaac tctccgcgcg cggtaagccc gggaccagcg gtctcggtcg tttagggtgc 4080
ggtggattct ttccaacacg tggtacaggt ggctctggat gtttagatac atgggcatga 4140
gtccatccct ggggtggagg tagcaccact gcagagcttc gtgctcgggg gtggtgttgt 4200
atatgatcca gtcgtagcag gagcgctggg cgtggtgctg aaaaatgtcc ttaagcaaga 4260
ggcttatagc taggggaggg cccttggtgt aagtgtttac aaatctgctc agttgggagg 4320
ggtgcatccg gggggatata atgtgcatct tggactggat tttaggttg gctatgttcc 4380
cacccagatc ccttctggga ttcatgttgt gcaggaccac cagcacggta tatccagtgc 4440
acttgggaaa tttatcgtgg agcttagacg ggaatgcatg gaagaacttg gagacgccct 4500
tgtggcctcc cagattttcc atacattcgt ccatgatgat ggcaatgggc ccgtgggaag 4560
ctgcctgagc aaaaatgttt ctgggatcgc tcacatcgta gttatgttcc agggtgaggt 4620
catcatagga catctttacg aatcgggggc ggagggtccc ggactggggg atgatggtac 4680
cctcgggccc cggggcgtag ttcccctcac agatctgcat ctcccaggct ttcatttcag 4740
agggagggat catatccacc tgcggagcga tgaaaaacac agtttctggc gcaggggaga 4800
ttaactggga tgagagcagg tttctgagca gctgtgactt tccacagccg gtgggcccat 4860
atatcacgcc tatcaccggc tgcagctggt agttaagaga gctgcagctg ccgtcctccc 4920
ggagcagggg ggccacctcg ttcagcatat ccctgacgtg gatgttctcc ctgaccaatt 4980
ccgccagaag gcgctcgccg cccagcgaaa gcagctcttg caaggaagca aaatttttca 5040
gcggttttag gccgtcggcc gtgggcatgt ttttcagcgt ctgggtcagc agttccagcc 5100
tgtcccacag ctcggtgatg tgctctacgg catctcgatc cagcagatct cctcgtttcg 5160
cgggttgggg cggctttcgc tgtagggcac cagccgatgg gcgtccagcg ggggccagagt 5220
catgtccttc catgggcgca gggtcctcgt cagggtggtc tgggtcacgg tgaaggggtg 5280
cgctccgggt tgggcgctgg ccagggtgcg cttgaggctg gttctgctgg tgctgaatcg 5340
ctgccgctct tcgccctgcg cgtcggccag gtagcatttg accatggtct cgtagtcgag 5400
accctcggcg gcgtgcccct tggcgcggag ctttcccttg gaggtggcgc cgcacgaggg 5460
gcactgcagg ctcttcaggg cgtagagctt gggagcgaga aacacggact ctggggagta 5520
ggcgtccgcg ccgcaggaag cgcagaccgt ctcgcattcc accagccaag tgagctccgg 5580
gcggtcaggg tcaaaaacca ggttgccccc atgctttttg atgcgtttct tacctcggct 5640
ctccatgagg cggtgtccct tctcggtgac gaagaggctg tccgtgtccc cgtagaccga 5700
cttcaggggc ctgtcttcca gcggagtgcc tctgtcctcc tcgtagagaa actctgacca 5760
ctctgagacg aaggcccgcg tccaggccag gacgaaggag gccacgtggg aggggtagcg 5820
gtcgttgtcc actagcgggt ccaccttctc cagggtgtgc aggcacatgt ccccctcctc 5880
cgcgtccaga aaagtgattg gcttgtaggt gtaggacacg tgaccggggg ttcccgacgg 5940
gggggtataa aagggggtgg gcgccctttc atcttcactc tcttccgcat cgctgtctgc 6000
gagggccagc tgctggggta agtattccct ctcgaaggcg ggcatgacct cagcgctcag 6060
gttgtcagtt tctaaaaatg aggaggattt gatgttcacc tgtccggagg tgataccttt 6120

-continued

```
gagggtacct gggtccatct ggtcagaaaa cactattttt ttgttgtcaa gcttggtggc   6180
gaacgacccg tagagggcgt tggagagcag cttggcgatg gagcgcaggg tctggttttt   6240
gtcgcggtcg gctcgctcct tggccgcgat gttgagttgc acgtactcgc gggccacgca   6300
cttccactcg gggaagacgg tggtgcgctc gtctgggatt aggcgcaccc tccagcctcg   6360
gttgtgcagg gtgaccatgt cgacgctggt ggcgacctcg ccgcgcaggc gctcgttggt   6420
ccagcagagg cggccgccct tgcgcgagca gaagggggggt aggggggtcca gctggtcctc   6480
gtttgggggg tccgcgtcga tggtgaagac cccggggagc aagcgcgggt caaagtagtc   6540
gatcttgcaa gcttgcatgt ccagagcccg ctgccattcg cgggcggcga gcgcgcgctc   6600
gtaggggttg aggggcgggc cccagggcat ggggtgggtg agcgcggagg cgtacatgcc   6660
gcagatgtca tacacgtaca ggggttccct gaggatgccg aggtaggtgg ggtagcagcg   6720
ccccccgcgg atgctggcgc gcacgtagtc atagagctcg tgggaggggg ccagcatgtt   6780
gggcccgagg ttggtgcgct gggggcgctc ggcgcggaag gcgatctgcc tgaagatggc   6840
atgggagttg gaggagatgg tgggccgctg gaagacgttg aagcttgctt cttgcaagcc   6900
caccgagtcc ctgacgaagg aggcgtagga ctcgcgcagc ttgtgcacca gctcggcggt   6960
gacctggacg tcgagcgcgc agtagtcgag ggtctcgcgg atgatgtcat acttatcctc   7020
ccccttcttt ttccacagct cgcggttgag gacgaactct tcgcggtctt tccagtactc   7080
ttggagggga aacccgtccg tgtccgaacg gtaagagcct agcatgtaga actggttgac   7140
ggcctggtag gggcaacagc ccttctccac gggcagcgcg taggcctgcg ccgccttgcg   7200
gagggaggtg tgggtgaggg cgaaagtgtc cctgaccatg actttgaggt attgatgttt   7260
gaagtctgtg tcatcgcagc cgccctgttc ccacagggtg tagtccgtgc gctttttgga   7320
gcgcgggttg ggcagggaga aggtgaggtc attgaagagg atcttccccg ctcgaggcat   7380
gaagtttctg gtgatgcgaa agggccctgg gaccgaggag cggttgttga tgacctgggc   7440
ggccaggacg atctcgtcaa agccgtttat gttgtggccc acgatgtaga gctccaaaaa   7500
gcggggctgg cccttgatgg aggggagctt tttgagttcc tcgtaggtga gctcctcggg   7560
cgattccagg ccgtgctcct ccagggccca gtcttgcaag tgagggttgg ccgccaggaa   7620
ggatcgccag aggtcgcggg ccatgagggt ctgcaggcgg tcgcggaagg ttctgaactg   7680
tcgccccacg gccatctttt cgggggtgat gcagtagaag gtgagggggt ctttctccca   7740
ggggtcccat ctgagctctc gggcgaggtc gcgcgcggcg gcgaccagag cctcgtcgcc   7800
ccccagtttc atgaccagca tgaagggcac gagctgcttg ccaaaggctc ccatccaagt   7860
gtaggtctct acatcgtagg tgacaaagag gcgctccgtg cgaggatgag agccgatcgg   7920
gaagaactgg atctcccgcc accagttgga ggattggctg ttgatgtggt gaaagtagaa   7980
gtcccgtctg cgggccgagc actcgtgctg gcttttgtaa aagcgaccgc agtactggca   8040
gcgctgcacg ggttgtatat cttgcacgag gtgaacctgg cgacctctga cgaggaagcg   8100
cagcgggaat ctaagtcccc cgcctggggt cccgtgtggc tggtggtctt ctactttggt   8160
tgtctggccg ccagcatctg tctcctggag ggcgatggtg gagcagacca ccacgccgcg   8220
agagccgcag gtccagatct cggcgctcgg cgggcggagt ttgatgacga catcgcgcac   8280
attggagctg tccatggtct ccagctcccg cggcggcagg tcagctggga gttcctggag   8340
gttcacctcg cagagacggg tcaaggcgcg ggcagtgttg agatggtatc tgatttcaag   8400
gggcgtgttg gcggcggagt cgatggcttg caggaggccg cagccccggg gggccacgat   8460
ggttccccgc ggggcgcgag gggaggcgga agctgggggt gtgttcagaa gcggtgacgc   8520
```

gggcgggccc ccggaggtag ggggggttcc ggccccacag gcatgggcgg caggggcacg 8580
tcttcgccgc gcgcgggcag gggctggtgc tggctccgaa gagcgcttgc gtgcgcgacg 8640
acgcgacggt tggtgtcctg tatctgacgc ctctgagtga agaccacggg tcccgtgacc 8700
ttgaacctga aagagagttc gacagaatca atctcggcat cgttgacagc ggcctggcgc 8760
aggatctcct gcacgtcgcc cgagttgtcc tggtaggcga tctctgccat gaactgctcg 8820
atctcttctt cctggagatc tcctcgtccg gcgcgctcca cggtggccgc caggtcgttg 8880
gagatgcgac ccatgagctg tgagaaggcg ttgagcccgc cctcgttcca gacccggctg 8940
tagaccacgc ccccctcggc gtcgcgagcg cgcatgacca cctgggccag gttgagctcc 9000
acgtgtcgcg tgaagacggc gtagttgcgc aggcgctgga aaaggtagtt cagggtggtg 9060
gcggtgtgct cggcgacgaa gaagtacatg acccagcgcc gcaacgtgga ttcattgatg 9120
tcccccaagg cctccaggcg ctccatggcc tcgtagaagt ccacggcgaa gttgaaaaac 9180
tgggagttgc gagcggacac ggtcaactcc tcctccagaa gacggatgag ctcggcgaca 9240
gtgttgcgca cctcgcgctc gaaggccacg gggggcgctt cttcctcttc cacctcttct 9300
tccatgatcg cttcttcttc ttcctcagcc gggacgggag gggcggcggc cggcgggggga 9360
ggggcgcggc ggcggcggcg gcgcaccggg aggcggtcga tgaagcgctc gatcatctcc 9420
ccccgcatgc ggcgcatggt ctcggtgacg gcgcggccgt tctcccgggg gcgcagctcg 9480
aagacgccgc ctctcatctc gccgcggggc gagcggccgt gaggtagcga gacggcgctg 9540
actatgcatc ttaacaattg ctgtgtaggt acaccgccga gggacctgat tgagtccaga 9600
tccaccggat ccgaaaacct ttggaggaaa gcgtctatcc agtcgcagtc gcaaggtagg 9660
ctgagcaccg tggcgggcgg gggcgggtct ggagagttcc tggcggagat gctgctgatg 9720
atgtaattaa agtaggcggt cttgagaagg cggatggtgg acaggagcac catgtctttg 9780
ggtccggcct gttggatgcg gaggcggtcg gccatgcccc aggcctcgtt ctgacaccgg 9840
cgcaggtctt tgtagtagtc ttgcatgagt ctttccaccg gcacctcttc tccttcctct 9900
tctccatctc gccggtggtt tctcgcgccg cccatgcgcg tgaccccaaa gcccctgagc 9960
ggctgcagca gggccaggtc ggcgaccacg cgctcggcca agatggcctg ctgcacctga 10020
gtgagggtcc tctcgaagtc atccatgtcc acgaagcggt ggtaggcgcc cgtgttgatg 10080
gtgtaggtgc agttggccat gacggaccag ttgacggtct ggtgtcccgg ctgcgagagc 10140
tccgtgtacc gcaggcgcga gaaggcgcgg gaatcgaaca cgtagtcgtt gcaagtccgc 10200
accagatact ggtagcccac caggaagtgc ggcggaggtt ggcgatagag gggccagcgc 10260
tgggtggcgg gggcgccggg cgccaggtct tccagcatga ggcggtggta tccgtagatg 10320
tacctggaca tccaggtgat gccggcggcg gtggtggtgg cgcgcgcgta gtcgcggacc 10380
cggttccaga tgtttcgcag ggcgagaaag tgttccatgg tcggcacgct ctggccggtg 10440
aggcgcgcgc agtcgttgac gctctataca cacacaaaaa cgaaagcgtt tacagggctt 10500
tcgttctgta gcctggagga aagtaaatgg gttgggttgc ggtgtgcccc ggttcgagac 10560
caagctgagc tcggccggct gaagccgcag ctaacgtggt attggcagtc ccgtctcgac 10620
ccaggccctg tatcctccag gatacggtcg agagcccttt tgctttcttg gccaagcgcc 10680
cgtggcgcga tctgggatag atggtcgcga tgagaggaca aaagcggctc gcttccgtag 10740
tctggagaaa caatcgccag ggttgcgttg cggcgtaccc cggttcgagc ccctatggcg 10800
gcttgaatcg gccggaaccg cggctaacga gggccgtggc agccccgtcc tcaggacccc 10860

-continued

```
gccagccgac ttctccagtt acgggagcga gccccttttg ttttttattt tttagatgca  10920
tcccgtgctg cggcagatgc gcccctcgcc ccggcccgat cagcagcagc aacagcaggc  10980
atgcagaccc ccctctcccc tttccgcccc ggtcaccacg gccgcggcgg ccgtgtcggg  11040
cgcggggggc gcgctggagt cagatgagcc accgcggcgg cgacctaggc agtatctgga  11100
cttggaagag ggcgagggac tggcgcggct gggggcgaac tctccagagc gccacccgcg  11160
ggtgcagttg aaaagggacg cgcgcgaggc gtacctgccg cggcagaacc tgtttcgcga  11220
ccgcgggggc gaggagcccg aggagatgcg agactgcagg ttccaagcgg ggcgcgagct  11280
gcggcgcggg ctggacagac agcgcctgct gcgcgaggag gactttgagc ccgacacgca  11340
gacgggcatc agccccgcgc gcgcgcacgt agccgcggcc gacctggtga ccgcctacga  11400
gcagacggta aaccaggagc gcaacttcca aaagagcttc aacaaccacg tgcgcacgct  11460
ggtggcgcgc gaggaggtga ccctgggtct catgcatctg tgggacctgg tggaggcgat  11520
cgtgcagaac cccagcagca agcccctgac cgcgcagctg ttcctggtgg tgcagcacag  11580
cagggacaac gaggccttca gggaggcgct gctgaacatc accgagccgg aggggcgctg  11640
gctcctggac ctgataaaca tcctgcagag catagtggtg caggagcgca gcctgagcct  11700
ggccgagaag gtggcggcca tcaactactc tatgctgagc ctgggcaagt tctacgcccg  11760
caagatctac aagacccccct acgtgcccat agacaaggag gtgaagatag acagcttcta  11820
catgcgcatg gcgctgaagg tgctgaccct gagcgacgac ctgggagtgt accgcaacga  11880
gcgcatccac aaggccgtga gcgccagccg gcggcgcgag ctgagcgacc gcgagctgat  11940
gcacagtctg cagcgcgcgc tgaccggcgc gggcgagggc gacagggagg tcgagtccta  12000
cttcgacatg ggggccgacc tgcactggca gccgagccgc cgcgccctgg aggcggcggg  12060
ggcgtacggc ggcccccctgg cggccgatga ccaggaagag gaggactatg agctagagga  12120
gggcgagtac ctggaggact gacctggctg gtggtgtttt ggtatagatg caagatccga  12180
acgtggcgga cccggcggtc cgggcggcgc tgcaaagcca gccgtccggc attaactcct  12240
ctgacgactg ggccgcggcc atgggtcgca tcatggccct gaccgcgcgc aaccccgagg  12300
ctttcaggca gcagcctcag gccaaccggc tggcggccat cttggaagcg gtagtgcccg  12360
cgcgctccaa ccccacccac gagaaggtgc tggccatagt caacgcgctg gcggagagca  12420
gggccatccg cgcggacgag gccggactgg tgtacgatgc gctgctgcag cgggtggcgc  12480
ggtacaacag cggcaacgtg cagaccaacc tggaccgcct ggtgacggac gtgcgcgagg  12540
ccgtggcgca gcgcgagcgc ttgcatcagg acggtaacct gggctcgctg gtggcgctaa  12600
acgccttcct cagcacccag ccggccaacg taccgcgggg gcaggaggac tacaccaact  12660
ttttgagcgc gctgcggctg atggtgaccg aggtccctca gagcgaggtg taccagtcgg  12720
ggcccgacta cttcttccag accagcagac agggcttgca aaccgtgaac ctgagccagg  12780
ctttcaagaa cctgcggggg ctgtggggag tgaaggcgcc caccggcgac cgggctacgg  12840
tgtccagcct gctaaccccc aactcgcgcc tgctgctgct gctgatcgcg cccttcacgg  12900
acagcgggag cgtctcgcgg gagacctatc tgggccacct gctgacgctg taccgcgagg  12960
ccatcgggca ggcgcaggtg gacgagcaca ccttccaaga gatcaccagc gtgagccacg  13020
cgctggggca ggaggacacg ggcagcctgc aggcgaccct gaactacctg ctgaccaaca  13080
ggcggcagaa gattcccacg ctgcacagcc tgacccagga ggaggagcgc atcttgcgct  13140
acgtgcagca gagcgtgagc ctgaacctga tgcgcgacgg cgtgacgccc agcgtggcgc  13200
tggacatgac cgcgcgcaac atggaaccgg gcatgtacgc ctcccaccgg ccgtttatca  13260
```

```
accgcctgat ggactacttg catcgggcgg cggccgtgaa ccccgagtac ttcactaatg  13320
ccattctgaa tccccactgg atgccccctc cgggtttcta caacggggac tttgaggtgc  13380
ccgaggtcaa cgacgggttc ctctgggatg acatggatga cagtgtgttc tcacccaacc  13440
cgctgcgcgc cgcgtctctg cgattgaagg agggctctga cagggaagga ccgaggagtc  13500
tggcctcctc cctggctctg ggagcggtgg gcgccacggg cgcggcggcg cggggcagta  13560
gccccttccc cagcctggca gactctctga acagcgggcg ggtgagcagg ccccgcttgc  13620
taggcgagga ggagtatctg aacaactccc tgctgcagcc cgcgagggac aagaacgctc  13680
agcggcagca gtttcccaac aatgggatag agagcctggt ggacaagatg tccagatgga  13740
agacgtatgc gcaggagtac aaggagtggg aggaccgcca gccgcggccc ttgccgcccc  13800
ctaggcagcg ctggcagcgg cgcgcgtcca accgccgctg gaggcagggg cccgaggacg  13860
atgatgactc tgcagatgac agcagcgtgt tggacctggg cgggagcggg aacccctttt  13920
cgcacctgcg cccacgcctg ggcaagatgt tttaaaagaa aaaaaaaata aaactcacca  13980
aggccatggc gacgagcgtt ggtttttgt tcccttcctt agtatgcggc gcgcggcgat  14040
gttcgaggag gggcctcccc cctcttacga gagcgcgatg ggatttctc ctgcggcgcc  14100
cctgcagcct ccctacgtgc ctcctcggta cctgcaacct acaggggga gaaatagcat  14160
ctgttactct gagctgcagc ccctgtacga taccaccaga ctgtacctgg tggacaacaa  14220
gtccgcggac gtggcctccc tgaactacca gaacgaccac agcgattttt tgaccacggt  14280
gatccaaaac aacgacttca ccccaaccga ggccagcacc cagaccataa acctggataa  14340
caggtcgaac tggggcggcg acctgaagac catcttgcac accaacatgc ccaacgtgaa  14400
cgagttcatg ttcaccaact cttttaaggc gcgggtgatg gtggcgcgcg agcaggggga  14460
ggcgaagtac gagtgggtgg acttcacgct gcccgagggc aactactcag agaccatgac  14520
tctcgacctg atgaacaatg cgatcgtgga acactatctg aaagtgggca ggcagaacgg  14580
ggtgaaggaa agcgatatcg gggtcaagtt tgacaccaga aacttccgtc tgggctggga  14640
ccccgtgacc gggctggtca tgccggggt ctacaccaac gaggcctttc atcccgacat  14700
agtgcttctg cccggctgtg ggtggactt cacccagagc cggctgagca acctgctggg  14760
cattcgcaag cggcagcctt tccaggaggg tttcaagatc acctatgagg atctgaaggg  14820
gggcaacatt cccgcgctcc ttgatctgga cgcctacgag gagagcttga aacccgagga  14880
gagcgctggc gacagcggcg agagtggcga ggagcaagcc ggcggcggtg gcggcgcgtc  14940
ggtagaaaac gaaagtacgc ccgcagtggc ggcggacgct gcggaggtcg agccggaggc  15000
catgcagcag gacgcagagg agggcgcaca ggagggcgcg cagaaggaca tgaacgatgg  15060
ggagatcagg ggagacacat tcgccacccg gggcgaagaa aaagaggcag aggcggcggc  15120
ggcggcgacg gcggaggccg aaaccgaggt tgaggcagag gcagagcccg agaccgaagt  15180
tatggaagac atgaatgatg gagaacgtag gggcgacacg ttcgccaccc ggggcgaaga  15240
gaaggcggcg gaggcagaag ccgcggctga ggaggcggct gcggctgcgg ccaagactga  15300
ggctgcggct aaggctgagg tcgaagccaa tgttgcggtt gaggctcagg ctgaggagga  15360
ggcggcggct gaagcagtta aggaaaaggc ccaggcagag caggaagaga aaaaacctgt  15420
cattcaacct ctaaaagaag atagcaaaaa gcgcagttac aacgtcatcg agggcagcac  15480
ctttacccag taccgcagct ggtacctggc gtacaactac ggcgacccgg tcaagggggt  15540
gcgctcgtgg accctgctct gcacgccgga cgtcacctgc ggctccgagc agatgtactg  15600
```

gtcgctgccg aacatgatgc aagacccggt gaccttccgc tccacgcggc aggttagcaa 15660
cttcccggtg gtgggcgccg aactgctgcc cgtgcactcc aagagttttt acaacgagca 15720
ggccgtctac tcccagctga tccgccaggc cacctctctg acccacgtgt tcaatcgctt 15780
tcccgagaac cagattttgg cgcgcccgcc ggcccccacc atcaccaccg tgagtgaaaa 15840
cgttcctgcc ctcacagatc acgggacgct accgctgcgc aacagcatct caggagtcca 15900
gcgagtgacc attactgacg ccagacgccg gacctgcccc tacgtttaca aggccttggg 15960
catagtctcg ccgcgcgtcc tctccagtcg cactttttaa aacacatcta cccacacgtt 16020
ccaaaatcat gtccgtactc atctcaccca gcaacaacac cggctggggg ctgcgcgcgc 16080
ccagcaagat gtttggaggg gcgaggaagc gctccgacca gcaccctgtg cgcgtgcgcg 16140
gccactaccg cgcgccctgg ggagcgcaca agcgcgggcg cacagggcgc accactgtgg 16200
acgacgtcat tgactccgta gtggagcaag cgcgccacta cacacccggc gcgccgaccg 16260
cccccgccgt gtccaccgtg gaccaggcga tcgaaagcgt ggtacagggc gcgcggcact 16320
atgccaacct taaaagtcgc cgccgccgcg tggcccgccg ccatcgccgg agaccccggg 16380
ccaccgccgc cgcgcgcctt actaaggctc tgctcaggcg cgccaggcga actggccacc 16440
gggccgccat gagggccgca cggcgggctg ccgctgccgc aagcgtcgtg gccccgcggg 16500
cacgaaggcg cgcggccgct gccgccgccg ccgccatttc cagcttggcc tcgacgcggc 16560
gcggtaacat atactgggtg cgcgactcgg taaccggcac gcgggtaccc gtgcgctttc 16620 gcccccgcg gaattagcac aagacaacat acacactgag tctcctgctg ttgtgtatcc 16680
cagcggcgac cgtcagcagc ggcgacatgt ccaagcgcaa aattaaagaa gagatgctcc 16740
aggtcatcgc gccggagatc tatgggcccc cgaagaagga ggaggatgat tacaagcccc 16800
gcaagctaaa gcgggtcaaa aagaaaaaga aagatgatga tgacgaggcg gtggagtttg 16860
tccgccgcat ggcacccagg cgccccgtgc agtggaaggg ccggcgcgtg cagcgcgttt 16920
tgcgccccgg caccgcggtg gtcttcacgc ccggcgagcg ctccacgcgc actttcaagc 16980
gggtgtacga tgaggtgtac ggcgacgagg acctgttgga gcaggccaac cagcgctttg 17040
gggagtttgc atatgggaaa cggccccgcg agagtctaaa agaggacctg ctggcgctac 17100
cgctggacga gggcaatccc accccgagtc tgaagccggt aaccctgcaa caggtgctgc 17160
ctttgagcgc gcccagcgag cataagcgag ggttgaagcg cgaaggcggg gacctggcgc 17220
ccaccgtgca gttgatggtg cccaagcggc agaagctgga ggacgtgctg gagaaaatga 17280
aagtagagcc cgggatccag cccgagatca aggtccgccc catcaagcag gtggcgcccg 17340
gcgtgggagt ccagaccgtg gacgttagga ttcccacgga ggagatggaa acccaaaccg 17400
ccactccctc ttcggcggcc agcgccacca ccggcaccgc ttcggtagag gtgcagacgg 17460
acccctggct acccgccacc gctgttgccg ccgccgcccc ccgttcgcgc gggcgcaaga 17520
gaaattatcc agcggccagc gcgctcatgc cccagtacgc actgcatcca tccatcgtgc 17580
ccacccccgg ctaccgcggg tactcgtacc gcccgcgcag atcagccggc actcgcggcc 17640
gccgccgccg tgcgaccaca accagccgcc gccgtcgccg ccgccgccag ccagtgctga 17700
cccccgtgtc tgtaaggaag gtggctcgct cggggagcac gctggtggtg cccagagcgc 17760
gctaccaccc cagcatcgtt taaagccggt ctctgtatgg ttcttgcaga tatggccctc 17820
acttgtcgcc tccgcttccc ggtgccggga taccgaggaa gaactcaccg ccgcagaggc 17880
atggcgggca gcggtctccg cggcggccgt cgccatcgcc ggcgcgcaaa aagcaggcgc 17940
atgcgcggcg gtgtgctgcc tctgctaatc ccgctaatcg ccgcggcgat cggtgccgta 18000
cccgggatcg cctccgtggc cctgcaggcg tcccagaaac gttgactctt gcaaccttgc 18060
aagcttgcat tttttggagg aaaaataaaa aaaagtctag actctcacgc tcgcttggtc 18120
ctgtgactat tttgtagaaa aaaagatgga agacatcaac tttgcgtcgc tggccccgcg 18180
tcacggctcg cgcccgttca tgggagactg gacagatatc ggcaccagca atatgagcgg 18240
tggcgccttc agctggggca gtctgtggag cggccttaaa aattttggtt ccaccattaa 18300
gaactatggc aacaaagcgt ggaacagcag cacgggccag atgctgagag acaagttgaa 18360
agagcagaac ttccaggaga aggtggcgca gggcctggcc tctggcatca gcggggtggt 18420
ggacatagct aaccaggccg tgcagaaaaa gataaacagt catctggacc cccgtcctca 18480
ggtggaggaa atgcctccag cgatggagac ggtgtctccc gagggcaaag gcgaaaagcg 18540
cccgcggccc gacagagaag agaccctggt gtcacacacc gaggagccgc cctcttacga 18600
ggaggcagtc aaggccggcc tgcccaccac tcgccccata gcccccatgg ccaccggtgt 18660
ggtgggccac aggcaacaca ctcccgcaac actagatctg cccccgccgt ccgagccgcc 18720
gcgccagcca aaggcggcga cggtgcccgc tccctccact tccgccgcca acagagtgcc 18780
cctgcgccgc gccgcgagcg gcccccgggc ctcgcgagtt agcggcaact ggcagagcac 18840
actgaacagc atcgtgggcc tgggagtgag gagtgtgaag cgccgccgtt gctactgaat 18900
gagcaagcta gctaacgtgt tgtatgtgtg tatgcgtcct atgtcgccgc cagaggagct 18960
gttgagccgc cggcgccgtc tgcactccag cgaatttcaa gatggcgacc ccatcgatga 19020
tgcctcagtg gtcgtacatg cacatctcgg gccaggacgc ttcggagtac ctgagccccg 19080
ggctggtgca gttcgcccgc gccacagaca cctacttcaa catgagtaac aagttcagga 19140
accccactgt ggcgcccacc cacgatgtga ccacggaccg gtcgcagcgc ctgacgctgc 19200
ggttcatccc cgtggatcgg gaggacaccg cctactctta caaggcgcgg ttcacgctgg 19260
ccgtgggcga caaccgcgtg ctggacatgg cctccactta ctttgacatc aggggggtgc 19320
tggacagggg ccccaccttc aagccctact cgggtactgc ctacaactcc ctggccccca 19380
agggcgctcc caattcttgc gagtgggaac aagatgaacc agctcaggca gcaatagctg 19440
aagatgaaga agaacttgaa gaagaacaag ctcaggacga acaggcgccc actaagaaaa 19500
cccatgtata cgcccaggca cctctttctg gtgaaaaaat tactaaggat ggtttgcaaa 19560
taggtgtgga tgccacacag gcgggagata accctatata tgctgataaa acattccaac 19620
ccgaacctca gataggtgag tctcagtgga acgaggctga tgccacagta gcaggaggca 19680
gagtcttaaa aaagaccacc cctatgagac cttgctatgg atcctatgcc aaacctacta 19740
atgccaatgg cggtcaaggg atcatggtgg ccaatgatca gggagcgctt gaatctaaag 19800
ttgagatgca atttttctcc accacaacgt ctcttaatgt aagggaaggt gaaaacaatc 19860
ttcagccaaa agtagtgcta tacagcgaag atgttaactt ggaatcccct gacactcatt 19920
tgtcttacaa acctaaaaag gatgacacca actctaaaat catgttgggt cagcaagcca 19980
tgcccaacag acccaacctc attgctttta gggacaactt tattggactt atgtactaca 20040
acagcacagg caacatggga gtgctggcag gacaggcctc ccagctaaac gctgtggtag 20100
acttgcaaga cagaaacaca gagctgtcat accaactgat gcttgattcc attggagaca 20160
gatcaagata cttttccatg tggaaccagg cagtggacag ctatgaccca gatgtcagaa 20220
tcattgaaaa ccatggggtt gaagatgagc tgcccaacta ttgctttccc ctgggcggta 20280
ttggaattac agacacatac cagtgcataa aaccaaccgc agctgctaat aacactacat 20340
ggtctaagga tgaagaattt agtgatcgca atgaaatagg ggtgggaaac aacttcgcca 20400
tggagatcaa catccaggcc aacctctgga ggaacttcct ctatgcgaac gtggggctct 20460
acctgccaga caagctcaag tacaacccca ccaacgtgga catctctgac aaccccaaca 20520
cctatgacta catgaacaag cgtgtggtgg ctcccggcct ggtggactgc tttgtcaatg 20580
tgggagccag gtggtccctg gactacatgg acaacgtcaa ccccttcaac caccaccgca 20640
atgcgggtct gcgctaccgc tccatgatcc tgggcaacgg gcgctacgtg cccttccaca 20700
ttcaggtgcc ccagaagttc tttgccatca agaacctcct cctcctgccg ggctcctaca 20760
cttacgagtg gaacttcagg aaggatgtca acatggtcct gcagagctct ctgggcaatg 20820
accttagggt ggacggggcc agcatcaagt ttgacagcgt caccctctat gctaccttct 20880
tccccatggc tcacaacacc gcctccacgc tcgaggccat gctgaggaac gacaccaacg 20940
accagtcctt caatgactac ctctctgggg ccaacatgct ctaccccatc cccgccaagg 21000
ccaccaacgt gcccatctcc attccctctc gcaactgggc cgccttcaga ggctgggcct 21060
ttacccgcct taagaccaag gaaacccccct ccctgggctc gggttttgac ccctactttg 21120
tctactcggg atccatcccc tacctggatg gcaccttcta cctcaaccac acttttaaga 21180
agatatccat catgtatgac tcctccgtca gctggccggg caatgaccgc ctgctcaccc 21240
ccaatgagtt cgaggtcaag cgcgccgtgg acggcgaggg ctacaacgtg gcccagtgca 21300
acatgaccaa ggactggttc ctggtgcaga tgctggccaa ctacaacata ggctaccagg 21360
gcttctacat cccagagagc tacaaggaca ggatgtactc cttcttcaga aatttccaac 21420
ccatgagcag gcaggtggtg gacgagacca aatacaagga ctatcaggcc attggcatca 21480
ctcaccagca caacaactcg ggattcgtgg gctacctggc tcccaccatg cgcgaggggc 21540
aggcctaccc cgccaacttc ccctacccgt tgataggcaa aaccgcggtc gacagcgtca 21600
cccagaaaaa gttcctctgc gaccgcaccc tctggcgcat ccccttctct agcaacttca 21660
tgtccatggg tgcgctcacg gacctgggcc agaacctgct ctatgccaac tccgcccatg 21720
cgctggacat gacttttgag gtggacccca tggacgagcc caccccttctc tatattgtgt 21780
ttgaagtgtt cgacgtggtc agagtgcacc agccgcaccg cggtgtcatc gagaccgtgt 21840
acctgcgcac gcccttctcg gccggcaacg ccaccaccta aggagacagc gccgccgcct 21900
gcatgacggg ttccaccgag caagagctca gggccatcgc cagagacctg ggatgcggac 21960
cctatttttt gggcacctat gacaaacgct tcccgggctt catctcccga gacaagctcg 22020
cctgcgccat cgtcaacacg gccgcgcgcg agaccggggg cgtgcactgg ctggcctttg 22080
gctgggaccc gcgctccaaa acctgctacc tcttcgaccc ctttggcttc tccgatcagc 22140
gcctcagaca gatctatgag tttgagtacg aggggctgct gcgccgcagc gcgcttgcct 22200
cctcgcccga ccgctgcatc acccttgaga agtccaccga gaccgtgcag gggccccact 22260
cggccgcctg cggtctcttc tgctgcatgt tttgcacgc ctttgtgcgc tggccccaga 22320
gtcccatgga tcgcaacccc accatgaact tgctcaaggg agtgcccaac gccatgctcc 22380
agagccccca ggtccagccc accctgcgcc acaaccagga acagctctac cgcttcctgg 22440
agcgccactc cccctacttc cgcagtcaca gcgcgcacat ccgggggggcc acctctttct 22500
gccacttgca agaaaacatg caagacggaa aatgatgtac agctcgcttt ttaataaatg 22560
taaagactgt gcactttatt tatacacggg ctctttctgg ttatttattc aacaccgccg 22620
tcgccatcta gaaatcgaaa gggttctgcc gcgcgtcgcc gtgcgccacg ggcagagaca 22680
cgttgcgata ctggaagcgg ctcgcccact taaactcggg caccaccatg cggggcagtg 22740

-continued

```
gttcctcggg gaagttctcg ccccacaggg tgcgggtcag ctgcagcgcg ctcaggaggt  22800
cgggagccga gatcttgaag tcgcagttgg ggccggaacc ctgcgcgcgc gagttgcggt  22860
acacggggtt gcagcactgg aacaccagca gggccggatt atgcacgctg gccagcaggc  22920
tctcgtcgct gatcatgtcg ctgtccagat cctccgcgtt gctcagggcg aacggggtca  22980
tcttgcagac ctgcctgccc aggaaaggcg gcagcccggg cttgccgttg cagtcgcagc  23040
gcaggggcat cagcaggtgc ccgcggcccg actgcgcctg cgggtacagc gcgcgcatga  23100
aggcttcgat ctgcctgaaa gccacctgcg tcttggctcc ctccgaaaag aacatcccac  23160
aggacttgct ggagaactgg ttcgcgggac agctggcatc gtgcaggcag cagcgcgcgt  23220
cggtgttggc gatctgcacc acgttgcgac cccaccggtt cttcactatc ttggccttgg  23280
aagcctgctc cttcagcgcg cgctggccgt tctcgctggt cacatccatc tctatcacct  23340
gctccttgtt gatcatgttt gtaccgtgca gacacttcag gtcgccctcc gtctgggtgc  23400
agcggtgctc ccacagcgcg caaccggtgg gctcccaatt tttgtgggtc acccccgcgt  23460
aggcctgcag gtaggcctgc aagaagcgcc ccatcatggc cacaaaggtc ttctggctcg  23520
taaaggtcag ctgcaggccg cgatgctctt cgttcagcca ggtcttgcag atggcggcca  23580
gcgcctcggt ctgctcgggc agcatcctaa aatttgtctt caggtcgtta tccacgtggt  23640
acttgtccat catggcgcgc gccgcctcca tgcccttctc ccaggcggac accatgggca  23700
ggcttagggg gtttatcact tccaccggcg aggacaccgt actttcgatt tcttcttcct  23760
ccccctcttc ccggcgcgcg cccacgctgc tgcgcgctct caccgcctgc accaaggggt  23820
cgtcttcagg caagcgccgc accgagcgct tgccgccctt gacctgctta atcagcaccg  23880
gcgggttgct gaagcccacc atggtcagcg ccgcctgctc ttcttcgtct tcgctgtcta  23940
ccactatctc tggggaaggg cttctccgct ctgcggcggc gcgcttcttt tttttcttgg  24000
gagcggccgt gatggagtcc gccacggcga cggaggtcga gggcgtgggg ctgggggtgc  24060
gcggtaccag ggcctcgtcg ccctcggact cttcctctga ctccaggcgg cggcggagtc  24120
gcttctttgg gggcgcgcgc gtcagcggcg gcggagacgg ggacggggac ggggacggga  24180
cgccctccac agggggtggt cttcgcgcag acccgcggcc gcgctcgggg gtcttctcga  24240
gctggtcttg gtcccgactg gccattgtat cctcctcctc ctaggcagag agacataagg  24300
agtctatcat gcaagtcgag aaggaggaga gcttaaccac cccctctgag accgccgatg  24360
cgcccgccgt cgccgtcgcc cccgctgccg ccgacgcgcc cgccacaccg agcgacaccc  24420
ccgcggaccc ccccgccgac gcacccctgt tcgaggaagc ggccgtggag caggacccgg  24480
gctttgtctc ggcagaggag gatttgcgag aggaggagga taaggagaag aagccctcag  24540
tgccaaaaga tgataaagag caagacgagc acgacgcaga tgcacaccag ggtgaagtcg  24600
ggcgggggga cggagggcat gacggcgccg actacctaga cgaagggaac gacgtgctct  24660
tgaagcacct gcatcgtcag tgcgccattg tttgcgacgc tctgcaggag cgcagcgaag  24720
tgcccctcag cgtggcggag gtcagccacg cctacgagct cagcctcttc tccccccggg  24780
tgcccccccg ccgccgcgaa aacggcacat gcgagcccaa cccgcgcctc aacttctacc  24840
ccgcctttgt ggtacccgag gtcctggcca cctatcacat cttctttcaa aattgcaaga  24900
tcccccctctc gtgccgcgcc aaccgtagcc gcgccgataa gatgctggcc ctgcgccagg  24960
gcgaccacat acctgatatc gccgctttgg aagatgtacc aaagatcttc gagggtctgg  25020
gtcgcaacga gaagcgggca gcaaactctc tgcaacagga aaacagcgaa aatgagagtc  25080
```

-continued

```
acaccggggt actggtggag ctcgagggcg acaacgcccg cctggcggtg gtcaagcgca  25140
gcatcgaggt cacccacttt gcctaccccg cgctaaacct gccccccaaa gtcatgaacg  25200
cggccatgga cgggctgatc atgcgccgcg gccggcccct cgctccagat gcaaacttgc  25260
atgaggagac cgaggacggc cagcccgtgg tcagcgacga gcagctggcg cgctggctgg  25320
agaccgcgga ccccgccgaa ctggaggagc ggcgcaagat gatgatggcc gtggtgctgg  25380
tcaccgtaga gctggagtgt ctgcagcgct tcttcggcga ccccgagatg cagagaaagg  25440
tcgaggagac cctgcactac accttccgcc agggctacgt gcgccaggct tgcaagatct  25500
ccaacgtgga gctcagcaac ctggtgtcct acctgggcat cttgcatgag aaccgcctcg  25560
ggcagagcgt gctgcactcc accctgcgcg gggaggcgcg ccgcgactac gtgcgcgact  25620
gcgtttacct cttcctctgc tacacctggc agacggccat gggggtctgg cagcagtgcc  25680
tggaggagcg caacctcaag gagctggaga agctcctgca gcgcgcgctc aaagatctct  25740
ggacgggcta caacgagcgc tcggtggccg ccgcgctggc cgacctcatc ttccccgagc  25800
gcctgctcaa aaccctccag caggggctgc ccgacttcac cagccaaagc atgttgcaaa  25860
acttcaggaa ctttatcctg gagcgttctg gcatcctacc cgccacctgc tgcgccctgc  25920
ccagcgactt tgtcccccctc gtgtaccgcg agtgcccccc gccgctgtgg ggtcactgct  25980
acctgttcca actggccaac tacctgtcct accacgcgga cctcatggag gactccagcg  26040
gcgaggggct catggagtgc cactgccgct gcaacctctg cacgccccac cgctccctgg  26100
tctgcaacac ccaactgctc agcgagagtc agattatcgg taccttcgag ctacagggtc  26160
cgtcctcctc agacgagaag tccgcggctc cggggctaaa actcactccg gggctgtgga  26220
cttccgccta cctgcgcaaa tttgtacctg aagactacca cgcccacgag atcaggtttt  26280
acgaagacca atcccgcccg cccaaggcgg agctgaccgc ctgcgtcatc acccagggcg  26340
agatcctagg ccaattgcaa gccatccaaa aagcccgcca agactttttg ctgaagaagg  26400
gtcggggggt gtatctggac ccccagtcgg gtgaggagct caacccggtt cccccgctgc  26460
cgccgccgcg ggaccttgct tcccaggata agcatcgcca tggctcccag aaagaagcag  26520
cagcggccgc cactgccgcc accccacatg ctggaggaag aggaggaata ctgggacagt  26580
caggcagagg aggtttcgga cgaggaggag ccggagacgg agatggaaga gtgggaggag  26640
gacagcttag acgaggaggc ttccgaagcc gaagaggcag acgcaacacc gtcaccctcg  26700
gccgcagccc cctcgcaggc gcccccgaag tccgctccca gcatcagcag caacagcagc  26760
gctataacct ccgctcctcc accgccgcga cccacggccg accgcagacc caaccgtaga  26820
tgggacacca ccggaaccgg ggccggtaag tcctccggga gaggcaagca agcgcagcgc  26880
caaggctacc gctcgtggcg cgctcacaag aacgccatag tcgcttgctt gcaagactgc  26940
gggggggaaca tctccttcgc ccgccgcttc ctgctcttcc accacggtgt ggccttcccc  27000
cgtaacgtcc tgcattacta ccgtcatctc tacagcccct actgcggcgg cagtgagcca  27060
gagacggtcg gcggcggcgg cggcgcccgt ttcggcgcct aggaagaccc agggcaagac  27120
ttcagccaag aaactcgcgg cggccgcggc gaacgcggtc gcgggggccc tgcgcctgac  27180
ggtgaacgaa cccctgtcga cccgcgaact gaggaaccga atcttcccca ctctctatgc  27240
catcttccag cagagcagag ggcaggatca ggaactgaaa gtaaaaaaca ggtctctgcg  27300
ctccctcacc cgcagctgtc tgtatcacaa gagcgaagac cagcttcggc gcacgctgga  27360
ggacgctgag gcactcttca gcaaatactg cgcgctcact cttaaggact agctccgcgc  27420
ccttctcgaa tttaggcggg aacgcctacg tcatcgcagc gccgccgtca tgagcaagga  27480
```

```
cattcccacg ccatacatgt ggagctatca gccgcagatg ggactcgcgg cgggcgcctc  27540
ccaagactac tccacccgca tgaactggct cagtgccggc ccacacatga tctcacaggt  27600
taatgatatc cgcacccatc gaaaccaaat attggtggag caggcggcaa ttaccaccac  27660
gccccgcaat aatcccaacc ccagggagtg gcccgcgtcc ctggtgtatc aggaaattcc  27720
cggccccacc accgtactac ttccgcgtga ttcccaggcc gaagtccaaa tgactaactc  27780
aggggcacag ctcgcgggcg gctgtcgtca cagggtgcgg cctcctcgcc agggtataac  27840
tcacctggag atccgaggca gaggtattca gctcaacgac gagtcggtga gctcctcgct  27900
cggtctcaga cctgacggga ccttccagat agccggagcc ggccgatctt ccttcacgcc  27960
ccgccaggcg tacctgactc tgcaaagctc gtcctcggcg ccgcgctcgg gcggcatcgg  28020
gactctccag ttcgtgcagg agtttgtgcc ctcggtctac ttcaacccct tctcgggctc  28080
tcccggtcgc tacccggacc agttcatctc gaactttgac gccgcgaggg actcggtgga  28140
cggctacgac tgaatgtcgg gtggacccgg tgcagagcaa cttcgcctga agcacctcga  28200
ccactgccgc cgccctcagt gctttgcccg ctgtcagacc ggtgagttcc agtacttttc  28260
cctgcccgac tcgcacccgg acggcccggc gcacggggtg cgctttttca tcccgagtca  28320
ggtgcgctct accctaatca gggagtttac cgcccgtccc ctactggcgg agttggaaaa  28380
ggggccttct atcctaacca ttgcctgcat ctgctctaac cctggattgc accaagatct  28440
ttgctgtcat ttgtgtgctg agtataataa aggctgagat cagaatctac tcgggctcct  28500
gtcgccatcc tgtcaacgcc accgtccaag cccggcccga tcagcccgag gtgaacctca  28560
cctgcggtct gcaccggcgc ctgaggaaat acctagcttg gtactacaac agcactccct  28620
ttgtggttta caacagcttt gaccaggacg gggtctcact gagggataac ctctcgaacc  28680
tgagctactc catcaggaag aacagcaccc tcgagctact tcctccttac ctgcccggga  28740
cttaccagtg tgtcaccggt ccctgcaccc acacccacct gttgatcgta aacgactctc  28800
ttccgagaac agacctcaat aactcctctt cgcagttccc cagaacagga ggtgagctca  28860
ggaaaccccg ggtaaagaag ggtggacgag agttaacact tgtggggttt ctggtgtatg  28920
tgacgctggt ggtggctctt ttgattaagg cttttccttc catgtctgaa ctctccctct  28980
tcttttatga acaactcgac tagtgctaac gggaccctac ccaacgaatc gggattgaat  29040
atcggtaacc aggttgcagt ttcacttttg attaccttca tagtcctctt cctgctagtg  29100
ctgtcgcttc tgtgcctgcg gatcgggggc tgctgcatcc acgtttatat ctggtgctgg  29160
ctgtttagaa ggttcggaga ccatcgcagg tagaataaac atgctgctgc ttaccctctt  29220
tgtcctggcg ctggccgcca gctgccaagc cttttccgag gctgacttta tagagcccca  29280
gtgtaatgtg acttttaaag cccatgcaca gcgttgtcat actataatca aatgtgccac  29340
cgaacacgat gaatacctta tccagtataa agataaatca cacaaagtgg cacttgttga  29400
catctggaaa cccgaagacc ctttggaata caatgtgacc gttttccagg gtgacctctt  29460
caaaatttac aattacactt tcccatttga ccagatgtgt gactttgtca tgtacatgga  29520
aaagcagcac aagctgtggc ctccgactcc ccagggctgt gtggaaaatc caggctcttt  29580
ctgcatgatc tctctctgtg taactgtgct ggcactaata ctcacgcttt tgtatatcag  29640
atttaaatca aggcaaagct tcattgatga aaagaaaatg ccttaatcgc tttcacgctt  29700
gattgctaac accgggtttt tatccgcaga atgattggaa tcaccctact aatcacctcc  29760
ctccttgcga ttgcccatgg gttggaacga atcgaagtcc ctgtgggggc caatgttacc  29820
```

```
ctggtggggc ctgtcggcaa tgctacatta atgtgggaaa aatatactaa aaatcaatgg  29880
gtctcttact gcactaacaa aaatagccac aagcccagag ccatctgcga tgggcaaaat  29940
ctaaccttga ttgatgttca attgctggat gcgggctact attatgggca gctgggtaca  30000
atgattaatt actggagacc ccacagagat tacatgctcc acgtagtaaa gggtcccctt  30060
agcagcccac ccactaccac ctctactacc cccactacca ccactactcc caccaccagc  30120
actgccgccc agcctcctca tagcagaaca accactttta tcaattccaa gtcccactcc  30180
ccccacattg ccggcgggcc ctccgcctca gactccgaaa ccaccgagat ctgcttctgc  30240
aaatgctctg acgccattgc ccaggatttg gaagatcacg aggaagatga gcatgacttc  30300
gcagatgcat gccaggcatc agagccagaa gcgctgccgg tggccctcaa acagtatgca  30360
gacccccaca ccacccccga ccttcctcca ccttcccaga agccaagttt cctgggggaa  30420
aatgaaactc tgcctctctc catactcgct ctgacatctg ttgctatgtt gaccgctctg  30480
ctggtgcttc tatgctctat atgctacctg atctgctgca gaaagaaaaa atctcacggc  30540
catgctcacc agcccctcat gcacttccct taccctccag agctgggcga ccacaaactt  30600
taagtctgca gtaactatct gcccatccct tgtcagtcga cagcgatgag ccccactaat  30660
ctaacggcct ctggacttac aacatcgtct cttaatgaga ccaccgctcc tcaagacctg  30720
tacgatggtg tctccgcgct ggttaaccag tgggatcacc tgggcatatg gtggctcctc  30780
ataggagcag tgaccctgtg cctaatcctg gtctggatca tctgctgcat caaaagcaga  30840
agacccaggc ggcggcccat ctacaggccc tttgtcatca cacctgaaga tgatgatgac  30900
accacttcca ggctgcagag gctaaagcag ctactcttct cttttacagc atggtaaatt  30960
gaatcatgcc tcgcattttc atctacttgt ctctccttcc actttttctg ggctcttcta  31020
cattggccgc tgtgtcccac atcgaggtag actgcctcac gcccttcaca gtctacctgc  31080
ttttcggctt tgtcatctgc acctttgtct gcagcgttat cactgtagtg atctgcttca  31140
tacagtgcat cgactacgtc tgcgtgcggg tggcttactt tagacaccac ccccagtatc  31200
gcaacaggga catagcggct ctcctaagac ttgtttaaaa tcatggccaa attaactgtg  31260
attggtcttc tgatcatctg ctgcgtccta gccgcgattg ggactcaagc tcctaccacc  31320
accagcgctc ccagaaagag acatgtatcc tgcagcttca agcgtccctg gaatataccc  31380
caatgcttta ctgatgaacc tgaaatctct ttggcttggt acttcagcgt caccgccctt  31440
cttatcttct gcagtacggt tattgccctt gccatctacc cttcccttga cctgggctgg  31500
aatgctgtca actctatgga atatcccacc ttcccagaac cagacctgcc agacctggtt  31560
gttctaaacg cgtttcctcc tcctgctccc gttcaaaatc agtttcgccc tccgtccccc  31620
acgcccactg aggtcagcta ctttaatcta acaggcggag atgactgaaa acctagacct  31680
agaaatggac ggtctctgca gcgagcaacg cacactagag aggcgccggc aaaaagagct  31740
cgagcgtctt aaacaagagc tccaagacgc ggtggccata caccagtgca aaaaaggtgt  31800
cttctgtctg gtaaaacagg ccacgctcac ctatgaaaaa acaggtgaca cccaccgcct  31860
aggatacaag ctgcccacac agcgccaaaa gttcgccctc atgataggcg aacaacccat  31920
caccgtgacc cagcactccg tggagacaga aggctgcata catgctccct gtaggggcgc  31980
tgactgcctc tacaccttga tcaaaaccct ctgcggtctc agagacctta tccctttcaa  32040
ttaatcataa ctgtaatcaa taaaaaatca cttacttgaa atctgatagc aagcctctgt  32100
ccaatttttt cagcaacact tccttcccct cctcccaact ctggtactct aggcgcctcc  32160
tagctgcaaa cttcctccac agtctgaagg gaatgtcaga ttcctcctcc tgtccctccg  32220
```

```
cacccacgat cttcatgttg ttgcagatga aacgcgcgag atcgtctgac gagaccttca  32280

accccgtgta cccctacgat accgagatcg ctccgacttc tgtccctttc cttacccctc  32340

cctttgtgtc atccgcagga atgcaagaaa atccagctgg ggtgctgtcc ctgcacttgt  32400

cagagcccct taccacccac aatggggccc tgactctaaa aatgggggc ggcctgaccc  32460

tggacaagga agggaatctc acttcccaaa acatcaccag tgtcgatccc cctctcaaaa  32520

aaagcaagaa caacatcagc cttcagaccg ccgcacccct cgccgtcagc tccggggccc  32580

taacactttt tgccactccc cccctagcgg tcagtggtga caaccttact gtgcagtctc  32640

aggcccctct cactttggaa gactcaaaac taactctggc caccaaagga ccccctaactg  32700

tgtccgaagg caaacttgtc ctagaaacag aggctcccc                         32739
```

<210> SEQ ID NO 24
<211> LENGTH: 32739
<212> TYPE: DNA
<213> ORGANISM: Artificial Sequence
<220> FEATURE:
<223> OTHER INFORMATION: Adenovirus vector nucleotide sequences

<400> SEQUENCE: 24

```
ataatatacc ttattttgga ttgtggccaa tatgataatg aggtgggcgg ggagaggcgg     60

ggcgggtgac gtaggacgcg cgagtagggt tgggaggtgt ggcggaagtg tggcatttgc    120

aagtgggagg agctcacatg caagcttccg tcgcggaaaa tgtgacgttt ttgatgagcg    180

ccgcctacct ccggaagtgc caattttcgc gcgcttttca ccggatatcg tagtaatttt    240

gggcgggacc atgtaagatt tggccatttt cgcgcgaaaa gtgaaacggg gaagtgaaaa    300

ctgaataata gggcgttagt catagcgcgt aatatttacc gagggccgag ggactttgac    360

cgattacgtg gaggactcgc ccaggtgttt tttacgtgaa tttccgcgtt ccgggtcaaa    420

gtctccgttt ttattgtcac cgtcatttga cgcggagggt atttaaaccc gctgcgctcc    480

tcaagaggcc actcttgagt gccagcgaga agagttttct cctctgctcc gcttcggtga    540

tcgaaaaatg agacacatag cctgcactcc gggtcttttg tccggtcggg cggcggccga    600

gcttttggac gctttgatca atgatgtcct aagcgatgat tttccgtcta ctacccactt    660

tagcccacct actcttcacg aactgtacga tctggatgta ctggtggatg tgaacgatcc    720

caacgaggag gcggtttctg cgtttttttcc cgagtctgcg ctgttggccg ctcaggaggg    780

atttgaccta cacactccgc cgcctatttt agagtctccg ctgccggagc ccagtggtat    840

accttatatg cctgaactgc ttcccgaagt ggtagacctg acctgccacg agcctggctt    900

tccgcccagc gacgatgagg gtgagccttt tgttttagac tttgctgaga tacctgggca    960

cggttgcagg tcttgtgcat atcatcagag ggttaccgga gaccccgagg ttaagtgttc   1020

gctgtgctat atgaggatga cctcttcctt tatctacagt aagtttttgt ctaggtgggc   1080

ttttgggtag gtgggtttg tgtcagaaca ggtgtaaacg ttgcttgtgt tttttgtacc   1140

tgtaggtccg gtgtccgagc cagacccgga gcccgaccgc gatcccgagc cggatcccga   1200

gcctcctcgc aggacaagga aactaccttc cattctgtgc aagtctcaga cacctgtaag   1260

gaccagcgag gcagacagca ccgactctgg cacttctacc tctccccctg aaattcaccc   1320

agtggttcct ctgggtatac ataaacctgt tgctgttaaa gtttgcgggc gacgccctgc   1380

agtacagtgc attgaggact tgcttcacga tcccgaggaa cctttggact tgagccttaa   1440

acgccctagg caataaaccc cacctaagta ataaacccca cctaagtaat aaaccctgcc   1500
```

-continued

```
gcccttggtt attgagatga cgcccaatgt ttgcttttga atgacttcat gtgtgtaata   1560
aaagtgagtg tgatcatagg tctcttgttt gtctgggcgg ggcttaaggg tatataagtc   1620
tcttggggct aaacttggtt acacttgacc ccaatggagg cgtgggggtg cttggaggag   1680
tttgcggacg tgcgccgttt gctggacgag agctctagca atacctatac tatttggagg   1740
tatctgtggg gctctactca ggccaagttg gtttccagaa ttaagcagga ttacaagtgc   1800
gattttgaag agctttttag ttcctgcggt gagcttttgc aatccttgaa tctgggccat   1860
caggctattt tccaggaaaa ggttctctcg actttggatt tttccactcc cgggcgcacc   1920
gccgcttgtg tggcttttgt gtcttttgtg caagataaat ggagcgagga gacccacctg   1980
agtcacggct acgtactgga tttcatggcg atggctcttt ggagggctca caacaaatgg   2040
aagattcaga aggaactgta cggttccgcc ctacgtcgtc cacttctgtc gcgacagggg   2100
ctgaggtttc ccgaccatcg gcagcatcag aatctggaag acgagtcgga ggagcgagcg   2160
gaggagaaga tcagcttgag agccggcctg gaccctcctc aggaggaatg aatctcccgc   2220
aggtggttga cctgtttcca gaactgagac gggtcctgac tatcagggag gatggtcagt   2280
ttgtgaagaa gtttaagagg gatcggggtg agggagatga tgaggcggct agcaatttag   2340
cttttagtct gatgactcgc caccgaccgg aatgtattac ctatcagcag attaaggaga   2400
gttgtgccaa cgagctggat cttttgggtc agaagtatag catagaacag cttaccactt   2460
actggcttca gcctggggat gattgggaag aggcgatcag ggtgtatgca aaggtggccc   2520
tgcggcccga ttgcaagtat aagattacta agttggttaa tattagaaac tgctgctata   2580
tttctgggaa cggggccgaa gtggagatag atactcagga cagggtggct tttaggtgtt   2640
gcatgataaa catgtggccc gggatactgg ggatggatgg ggtggtattc atgaatgtga   2700
ggtttacggg ccccaacttt aatggcacgg tgttcatggg caacaccaac ttgctcctgc   2760
atggtgcgag tttctatggg tttaataaca cctgtataga ggcctggacc gatgtaaagg   2820
ttcgaggttg ttccttttat agctgttgga aggcggtggt gtgtcgccct aaaagcaggg   2880
gttctgtgaa aaaatgcttg tttgaaaggt gcaccttagg catcctctct gagggcaact   2940
ccagggtgcg ccataatgtg gcttcgaact gcggttgctt catgcaagtg aagggggtga   3000
gcgttatcaa gcataactcg gtgtgtggaa actgcgagga tcgcgcctcc cagatgctga   3060
cctgctttga tggcaactgt cacctgttga agaccattca tataagcagc caccccagaa   3120
aggcctggcc cgtgtttgag cataacatct tgacccgctg ctccttgcat ctgggggtca   3180
ggaggggtat gttcctgcct taccagtgta actttagcca cactaaaatc ctgctggaac   3240
ccgagtgcat gaccaaggtc agcctgaatg gtgtgtttga tgtgactctg aaaatctgga   3300
aggtgctgag gtatgatgag accaggacca ggtgccgacc ctgcgagtgc ggcggcaagc   3360
acatgagaaa tcagcctgtg atgttggatg tgaccgagga gcttaggcct gaccatctgg   3420
tgctggcctg caccagggcc gagtttgggt ctagcgatga ggataccgat tgaggtgggt   3480
aaggtgggcg tggctagaag ggtggggcgt gtataaattg gggggtctaag ggtctctctg   3540
ttttgtcttg caacagccgc cgccatgagc gacaccggca acagctttga tggaagcatc   3600
tttagcccct atctgacagt gcgcatgcct cactgggctg gagtgcgtca gaatgtgatg   3660
ggttccaacg tggatggacg ccccgttctg ccttcaaatt cgtctacaat ggcctacgcg   3720
accgtgggag gaactccgct ggacgccgcg acctccgccg ccgcctccgc cgccgccgcg   3780
accgcgcgca gcatggctac ggacctttac agctctttgg tggcgagcgg cgcggcctct   3840
cgcgcgtctg ctcgggatga gaaactgacc gctctgctgc ttaaactgga agacttgacc   3900
```

```
cgggagctgg gtcaactgac ccagcaggtc tccagcttgc gtgagagcag ccttgcctcc   3960
ccctaatggc ccataatata aataaaagcc agtctgtttg gattaagcaa gtgtatgttc   4020
tttatttaac tctccgcgcg cggtaagccc gggaccagcg gtctcggtcg tttagggtgc   4080
ggtggattct ttccaacacg tggtacaggt ggctctggat gtttagatac atgggcatga   4140
gtccatccct ggggtggagg tagcaccact gcagagcttc gtgctcgggg gtggtgttgt   4200
atatgatcca gtcgtagcag gagcgctggg cgtggtgctg aaaaatgtcc ttaagcaaga   4260
ggcttatagc taggggggagg cccttggtgt aagtgtttac aaatctgctc agttgggagg   4320
ggtgcatccg gggggatata atgtgcatct tggactggat ttttaggttg gctatgttcc   4380
cacccagatc ccttctggga ttcatgttgt gcaggaccac cagcacggta tatccagtgc   4440
acttgggaaa tttatcgtgg agcttagacg ggaatgcatg gaagaacttg gagacgccct   4500
tgtggcctcc cagattttcc atacattcgt ccatgatgat ggcaatgggc ccgtgggaag   4560
ctgcctgagc aaaaatgttt ctgggatcgc tcacatcgta gttatgttcc agggtgaggt   4620
catcatagga catctttacg aatcgggggc ggagggtccc ggactggggg atgatggtac   4680
cctcgggccc cggggcgtag ttcccctcac agatctgcat ctcccaggct ttcatttcag   4740
agggagggat catatccacc tgcggagcga tgaaaaacac agtttctggc gcaggggaga   4800
ttaactggga tgagagcagg tttctgagca gctgtgactt tccacagccg gtgggcccat   4860
atatcacgcc tatcaccggc tgcagctggt agttaagaga gctgcagctg ccgtcctccc   4920
ggagcagggg ggccacctcg ttcagcatat ccctgacgtg gatgttctcc ctgaccaatt   4980
ccgccagaag gcgctcgccg cccagcgaaa gcagctcttg caaggaagca aaatttttca   5040
gcggttttag gccgtcggcc gtgggcatgt ttttcagcgt ctgggtcagc agttccagcc   5100
tgtcccacag ctcggtgatg tgctctacgg catctcgatc cagcagatct cctcgtttcg   5160
cgggttgggg cggctttcgc tgtagggcac cagccgatgg gcgtccagcg gggccagagt   5220
catgtccttc catgggcgca gggtcctcgt cagggtggtc tgggtcacgg tgaaggggtg   5280
cgctccgggt tgggcgctgg ccagggtgcg cttgaggctg gttctgctgg tgctgaatcg   5340
ctgccgctct tcgccctgcg cgtcggccag gtagcatttg accatggtct cgtagtcgag   5400
accctcggcg gcgtgcccct tggcgcggag ctttcccttg gaggtggcgc cgcacgaggg   5460
gcactgcagg ctcttcaggg cgtagagctt gggagcgaga aacacggact ctggggagta   5520
ggcgtccgcg ccgcaggaag cgcagaccgt ctcgcattcc accagccaag tgagctccgg   5580
gcggtcaggg tcaaaaacca ggttgccccc atgctttttg atgcgtttct tacctcggct   5640
ctccatgagg cggtgtccct tctcggtgac gaagaggctg tccgtgtccc cgtagaccga   5700
cttcaggggc ctgtcttcca gcggagtgcc tctgtcctcc tcgtagagaa actctgacca   5760
ctctgagacg aaggcccgcg tccaggccag gacgaaggag gccacgtggg aggggtagcg   5820
gtcgttgtcc actagcgggt ccaccttctc cagggtgtgc aggcacatgt ccccctcctc   5880
cgcgtccaga aaagtgattg gcttgtaggt gtaggacacg tgaccggggg ttcccgacgg   5940
gggggtataa aagggggtgg gcgccctttc atcttcactc tcttccgcat cgctgtctgc   6000
gagggccagc tgctggggta agtattccct ctcgaaggcg ggcatgacct cagcgctcag   6060
gttgtcagtt tctaaaaatg aggaggattt gatgttcacc tgtccggagg tgataccttt   6120
gagggtacct gggtccatct ggtcagaaaa cactattttt ttgttgtcaa gcttggtggc   6180
gaacgacccg tagagggcgt tggagagcag cttggcgatg gagcgcaggg tctggttttt   6240
```

-continued

```
gtcgcggtcg gctcgctcct tggccgcgat gttgagttgc acgtactcgc gggccacgca   6300
cttccactcg gggaagacgg tggtgcgctc gtctgggatt aggcgcaccc tccagcctcg   6360
gttgtgcagg gtgaccatgt cgacgctggt ggcgacctcg ccgcgcaggc gctcgttggt   6420
ccagcagagg cggccgccct tgcgcgagca gaaggggggt agggggtcca gctggtcctc   6480
gtttgggggg tccgcgtcga tggtgaagac cccggggagc aagcgcgggt caaagtagtc   6540
gatcttgcaa gcttgcatgt ccagagcccg ctgccattcg cgggcggcga gcgcgcgctc   6600
gtaggggttg aggggcgggc cccagggcat ggggtgggtg agcgcggagg cgtacatgcc   6660
gcagatgtca tacacgtaca ggggttccct gaggatgccg aggtaggtgg ggtagcagcg   6720
ccccccgcgg atgctggcgc gcacgtagtc atagagctcg tgggaggggg ccagcatgtt   6780
gggcccgagg ttggtgcgct gggggcgctc ggcgcggaag gcgatctgcc tgaagatggc   6840
atgggagttg gaggagatgg tgggccgctg gaagacgttg aagcttgctt cttgcaagcc   6900
caccgagtcc ctgacgaagg aggcgtagga ctcgcgcagc ttgtgcacca gctcggcggt   6960
gacctggacg tcgagcgcgc agtagtcgag ggtctcgcgg atgatgtcat acttatcctc   7020
ccccttcttt ttccacagct cgcggttgag gacgaactct tcgcggtctt tccagtactc   7080
ttggagggga aacccgtccg tgtccgaacg gtaagagcct agcatgtaga actggttgac   7140
ggcctggtag gggcaacagc ccttctccac gggcagcgcg taggcctgcg ccgccttgcg   7200
gagggaggtg tgggtgaggg cgaaagtgtc cctgaccatg actttgaggt attgatgttt   7260
gaagtctgtg tcatcgcagc cgccctgttc ccacagggtg tagtccgtgc gctttttgga   7320
gcgcgggttg ggcagggaga aggtgaggtc attgaagagg atcttccccg ctcgaggcat   7380
gaagtttctg gtgatgcgaa agggccctgg gaccgaggag cggttgttga tgacctgggc   7440
ggccaggacg atctcgtcaa agccgtttat gttgtggccc acgatgtaga gctccaaaaa   7500
gcggggctgg cccttgatgg aggggagctt tttgagttcc tcgtaggtga gctcctcggg   7560
cgattccagg ccgtgctcct ccagggccca gtcttgcaag tgagggttgg ccgccaggaa   7620
ggatcgccag aggtcgcggg ccatgagggt ctgcaggcgg tcgcggaagg ttctgaactg   7680
tcgccccacg gccatctttt cgggggtgat gcagtagaag gtgagggggt ctttctccca   7740
ggggtcccat ctgagctctc gggcgaggtc gcgcgcggcg gcgaccagag cctcgtcgcc   7800
ccccagtttc atgaccagca tgaagggcac gagctgcttg ccaaaggctc ccatccaagt   7860
gtaggtctct acatcgtagg tgacaaagag gcgctccgtg cgaggatgag agccgatcgg   7920
gaagaactgg atctcccgcc accagttgga ggattggctg ttgatgtggt gaaagtagaa   7980
gtcccgtctg cgggccgagc actcgtgctg gcttttgtaa aagcgaccgc agtactggca   8040
gcgctgcacg ggttgtatat cttgcacgag gtgaacctgg cgacctctga cgaggaagcg   8100
cagcgggaat ctaagtcccc cgcctggggt cccgtgtggc tggtggtctt ctactttggt   8160
tgtctggccg ccagcatctg tctcctggag ggcgatggtg gagcagacca ccacgccgcg   8220
agagccgcag gtccagatct cggcgctcgg cgggcggagt ttgatgacga catcgcgcac   8280
attggagctg tccatggtct ccagctcccg cggcggcagg tcagctggga gttcctggag   8340
gttcacctcg cagagacggg tcaaggcgcg ggcagtgttg agatggtatc tgatttcaag   8400
gggcgtgttg gcggcggagt cgatggcttg caggaggccg cagccccggg gggccacgat   8460
ggttccccgc ggggcgcgag gggaggcgga agctgggggt gtgttcagaa gcggtgacgc   8520
gggcgggccc ccggaggtag ggggggttcc ggccccacag gcatgggcgg caggggcacg   8580
tcttcgccgc gcgcgggcag ggctggtgc tggctccgaa gagcgcttgc gtgcgcgacg   8640
```

-continued

```
acgcgacggt tggtgtcctg tatctgacgc ctctgagtga agaccacggg tcccgtgacc   8700
ttgaacctga aagagagttc gacagaatca atctcggcat cgttgacagc ggcctggcgc   8760
aggatctcct gcacgtcgcc cgagttgtcc tggtaggcga tctctgccat gaactgctcg   8820
atctcttctt cctggagatc tcctcgtccg gcgcgctcca cggtggccgc caggtcgttg   8880
gagatgcgac ccatgagctg tgagaaggcg ttgagcccgc cctcgttcca gacccggctg   8940
tagaccacgc ccccctcggc gtcgcgagcg cgcatgacca cctgggccag gttgagctcc   9000
acgtgtcgcg tgaagacggc gtagttgcgc aggcgctgga aaaggtagtt cagggtggtg   9060
gcggtgtgct cggcgacgaa gaagtacatg acccagcgcc gcaacgtgga ttcattgatg   9120
tcccccaagg cctccaggcg ctccatggcc tcgtagaagt ccacggcgaa gttgaaaaac   9180
tgggagttgc gagcggacac ggtcaactcc tcctccagaa gacggatgag ctcggcgaca   9240
gtgttgcgca cctcgcgctc gaaggccacg gggggcgctt cttcctcttc cacctcttct   9300
tccatgatcg cttcttcttc ttcctcagcc gggacgggag gggggcggcgg cggcgggggga   9360
ggggcgcggc ggcggcggcg gcgcaccggg aggcggtcga tgaagcgctc gatcatctcc   9420
ccccgcatgc ggcgcatggt ctcggtgacg gcgcggccgt tctcccgggg gcgcagctcg   9480
aagacgccgc ctctcatctc gccgcggggc gagcggccgt gaggtagcga gacggcgctg   9540
actatgcatc ttaacaattg ctgtgtaggt acaccgccga gggacctgat tgagtccaga   9600
tccaccggat ccgaaaacct ttggaggaaa gcgtctatcc agtcgcagtc gcaaggtagg   9660
ctgagcaccg tggcgggcgg gggcgggtct ggagagttcc tggcggagat gctgctgatg   9720
atgtaattaa agtaggcggt cttgagaagg cggatggtgg acaggagcac catgtctttg   9780
ggtccggcct gttggatgcg gaggcggtcg gccatgcccc aggcctcgtt ctgacaccgg   9840
cgcaggtctt tgtagtagtc ttgcatgagt ctttccaccg gcacctcttc tccttcctct   9900
tctccatctc gccggtggtt tctcgcgccg cccatgcgcg tgaccccaaa gcccctgagc   9960
ggctgcagca gggccaggtc ggcgaccacg cgctcggcca agatggcctg ctgcacctga  10020
gtgagggtcc tctcgaagtc atccatgtcc acgaagcggt ggtaggcgcc cgtgttgatg  10080
gtgtaggtgc agttggccat gacggaccag ttgacggtct ggtgtcccgg ctgcgagagc  10140
tccgtgtacc gcaggcgcga gaaggcgcgg gaatcgaaca cgtagtcgtt gcaagtccgc  10200
accagatact ggtagcccac caggaagtgc ggcggaggtt ggcgatagag gggccagcgc  10260
tgggtggcgg gggcgccggg cgccaggtct tccagcatga ggcggtggta tccgtagatg  10320
tacctggaca tccaggtgat gccggcggcg gtggtggtgg cgcgcgcgta gtcgcggacc  10380
cggttccaga tgtttcgcag ggcgagaag tgttccatgg tcggcacgct ctggccggtg  10440
aggcgcgcgc agtcgttgac gctctataca cacacaaaaa cgaaagcgtt tacagggctt  10500
tcgttctgta gcctggagga aagtaaatgg gttgggttgc ggtgtgcccc ggttcgagac  10560
caagctgagc tcggccggct gaagccgcag ctaacgtggt attggcagtc ccgtctcgac  10620
ccaggccctg tatcctccag gatacggtcg agagcccttt tgctttcttg gccaagcgcc  10680
cgtggcgcga tctgggatag atggtcgcga tgagaggaca aaagcggctc gcttccgtag  10740
tctggagaaa caatcgccag ggttgcgttg cggcgtaccc cggttcgagc ccctatggcg  10800
gcttgaatcg gccggaaccg cggctaacga gggccgtggc agccccgtcc tcaggacccc  10860
gccagccgac ttctccagtt acgggagcga gcccctttg tttttattt tttagatgca  10920
tcccgtgctg cggcagatgc gcccctcgcc ccggcccgat cagcagcagc aacagcaggc  10980
```

-continued atgcagaccc ccctctcccc tttccgcccc ggtcaccacg gccgcggcgg ccgtgtcggg 11040
cgcgggggc gcgctggagt cagatgagcc accgcggcgg cgacctaggc agtatctgga 11100
cttggaagag ggcgagggac tggcgcggct gggggcgaac tctccagagc gccacccgcg 11160
ggtgcagttg aaaagggacg cgcgcgaggc gtacctgccg cggcagaacc tgtttcgcga 11220
ccgcgggggc gaggagcccg aggagatgcg agactgcagg ttccaagcgg ggcgcgagct 11280
gcggcgcggg ctggacagac agcgcctgct gcgcgaggag gactttgagc ccgacacgca 11340
gacgggcatc agccccgcgc gcgcgcacgt agccgcggcc gacctggtga ccgcctacga 11400
gcagacggta aaccaggagc gcaacttcca aaagagcttc aacaaccacg tgcgcacgct 11460
ggtggcgcgc gaggaggtga ccctgggtct catgcatctg tgggacctgg tggaggcgat 11520
cgtgcagaac cccagcagca agcccctgac cgcgcagctg ttcctggtgg tgcagcacag 11580
cagggacaac gaggccttca gggaggcgct gctgaacatc accgagccgg aggggcgctg 11640
gctcctggac ctgataaaca tcctgcagag catagtggtg caggagcgca gcctgagcct 11700
ggccgagaag gtggcggcca tcaactactc tatgctgagc ctgggcaagt tctacgcccg 11760
caagatctac aagaccccct acgtgcccat agacaaggag gtgaagatag acagcttcta 11820
catgcgcatg gcgctgaagg tgctgaccct gagcgacgac ctgggagtgt accgcaacga 11880
gcgcatccac aaggccgtga gcgccagccg gcggcgcgag ctgagcgacc gcgagctgat 11940
gcacagtctg cagcgcgcgc tgaccggcgc gggcgagggc gacagggagg tcgagtccta 12000
cttcgacatg gggcgacc tgcactggca gccgagccgc cgcgccctgg aggcggcggg 12060
ggcgtacggc ggcccctgg cggccgatga ccaggaagag gaggactatg agctagagga 12120
gggcgagtac ctggaggact gacctggctg gtggtgtttt ggtatagatg caagatccga 12180
acgtggcgga cccggcggtc cgggcggcgc tgcaaagcca gccgtccggc attaactcct 12240
ctgacgactg ggccgcggcc atgggtcgca tcatggccct gaccgcgcgc aacccgagg 12300
ctttcaggca gcagcctcag gccaaccggc tggcggccat cttggaagcg gtagtgcccg 12360
cgcgctccaa ccccacccac gagaaggtgc tggccatagt caacgcgctg gcggagagca 12420
gggccatccg cgcggacgag gccggactgg tgtacgatgc gctgctgcag cgggtggcgc 12480
ggtacaacag cggcaacgtg cagaccaacc tggaccgcct ggtgacggac gtgcgcgagg 12540
ccgtggcgca gcgcgagcgc ttgcatcagg acggtaacct gggctcgctg gtggcgctaa 12600
acgccttcct cagcacccag ccggccaacg taccgcgggg gcaggaggac tacaccaact 12660
ttttgagcgc gctgcggctg atggtgaccg aggtccctca gagcgaggtg taccagtcgg 12720
ggcccgacta cttcttccag accagcagac agggcttgca aaccgtgaac ctgagccagg 12780
ctttcaagaa cctgcggggg ctgtggggag tgaaggcgcc caccggcgac cgggctacgg 12840
tgtccagcct gctaaccccc aactcgcgcc tgctgctgct gctgatcgcg cccttcacgg 12900
acagcgggag cgtctcgcgg gagacctatc tgggccacct gctgacgctg taccgcgagg 12960
ccatcgggca ggcgcaggtg gacgagcaca ccttccaaga gatcaccagc gtgagccacg 13020
cgctggggca ggaggacacg ggcagcctgc aggcgaccct gaactacctg ctgaccaaca 13080
ggcggcagaa gattcccacg ctgcacagcc tgacccagga ggaggagcgc atcttgcgct 13140
acgtgcagca gagcgtgagc ctgaacctga tgcgcgacgg cgtgacgccc agcgtggcgc 13200
tggacatgac cgcgcgcaac atggaaccgg gcatgtacgc ctcccaccgg ccgtttatca 13260
accgcctgat ggactacttg catcgggcgg cggccgtgaa ccccgagtac ttcactaatg 13320
ccattctgaa tccccactgg atgccccctc cgggtttcta caacggggac tttgaggtgc 13380

-continued

```
ccgaggtcaa cgacgggttc ctctgggatg acatggatga cagtgtgttc tcacccaacc 13440
cgctgcgcgc cgcgtctctg cgattgaagg agggctctga cagggaagga ccgaggagtc 13500
tggcctcctc cctggctctg ggagcggtgg gcgccacggg cgcggcggcg cggggcagta 13560
gccccttccc cagcctggca gactctctga acagcgggcg ggtgagcagg ccccgcttgc 13620
taggcgagga ggagtatctg aacaactccc tgctgcagcc cgcgagggac aagaacgctc 13680
agcggcagca gtttcccaac aatgggatag agagcctggt ggacaagatg tccagatgga 13740
agacgtatgc gcaggagtac aaggagtggg aggaccgcca gccgcggccc ttgccgcccc 13800
ctaggcagcg ctggcagcgg cgcgcgtcca accgccgctg gaggcagggg cccgaggacg 13860
atgatgactc tgcagatgac agcagcgtgt tggacctggg cgggagcggg aacccctttt 13920
cgcacctgcg cccacgcctg ggcaagatgt tttaaaagaa aaaaaaaaat aaaactcacc 13980
aaggccatgg cgacgagcgt tggttttttg ttcccttcct tagtatgcgg cgcgcggcga 14040
tgttcgagga ggggcctccc ccctcttacg agagcgcgat ggggatttct cctgcggcgc 14100
ccctgcagcc tccctacgtg cctcctcggt acctgcaacc tacagggggg agaaatagca 14160
tctgttactc tgagctgcag cccctgtacg ataccaccag actgtacctg gtggacaaca 14220
agtccgcgga cgtggcctcc ctgaactacc agaacgacca cagcgatttt ttgaccacgg 14280
tgatccaaaa caacgacttc accccaaccg aggccagcac ccagaccata aacctggata 14340
acaggtcgaa ctggggcggc gacctgaaga ccatcttgca caccaacatg cccaacgtga 14400
acgagttcat gttcaccaac tcttttaagg cgcgggtgat ggtggcgcgc gagcaggggg 14460
aggcgaagta cgagtgggtg gacttcacgc tgcccgaggg caactactca gagaccatga 14520
ctctcgacct gatgaacaat gcgatcgtgg aacactatct gaaagtgggc aggcagaacg 14580
gggtgaagga aagcgatatc ggggtcaagt ttgacaccag aaacttccgt ctgggctggg 14640
accccgtgac cgggctggtc atgccggggg tctacaccaa cgaggccttt catcccgaca 14700
tagtgcttct gcccggctgt ggggtggact tcacccagag ccggctgagc aacctgctgg 14760
gcattcgcaa gcggcagcct ttccaggagg gtttcaagat cacctatgag gatctgaagg 14820
ggggcaacat tcccgcgctc cttgatctgg acgcctacga ggagagcttg aaacccgagg 14880
agagcgctgg cgacagcggc gagagtggcg aggagcaagc cggcggcggt ggcggcgcgt 14940
cggtagaaaa cgaaagtacg cccgcagtgg cggcggacgc tgcggaggtc gagccggagg 15000
ccatgcagca ggacgcagag gagggcgcac aggagggcgc gcagaaggac atgaacgatg 15060
gggagatcag gggagacaca ttcgccaccc ggggcgaaga aaaagaggca gaggcggcgg 15120
cggcggcgac ggcggaggcc gaaaccgagg ttgaggcaga ggcagagccc gagaccgaag 15180
ttatggaaga catgaatgat ggagaacgta ggggcgacac gttcgccacc cggggcgaag 15240
agaaggcggc ggaggcagaa gccgcggctg aggaggcggc tgcggctgcg gccaagactg 15300
aggctgcggc taaggctgag gtcgaagcca atgttgcggt tgaggctcag gctgaggagg 15360
aggcggcggc tgaagcagtt aaggaaaagg cccaggcaga gcaggaagag aaaaaacctg 15420
tcattcaacc tctaaaagaa gatagcaaaa agcgcagtta caacgtcatc gagggcagca 15480
cctttaccca gtaccgcagc tggtacctgg cgtacaacta cggcgacccg gtcaaggggg 15540
tgcgctcgtg gaccctgctc tgcacgccgg acgtcacctg cggctccgag cagatgtact 15600
ggtcgctgcc gaacatgatg caagacccgg tgaccttccg ctccacgcgg caggttagca 15660
acttcccggt ggtgggcgcc gaactgctgc ccgtgcactc caagagtttt tacaacgagc 15720
```

aggccgtcta ctcccagctg atccgccagg ccacctctct gacccacgtg ttcaatcgct 15780
ttcccgagaa ccagattttg gcgcgcccgc cggcccccac catcaccacc gtgagtgaaa 15840
acgttcctgc cctcacagat cacgggacgc taccgctgcg caacagcatc tcaggagtcc 15900
agcgagtgac cattactgac gccagacgcc ggacctgccc ctacgtttac aaggccttgg 15960
gcatagtctc gccgcgcgtc ctctccagtc gcactttttta aaacacatct acccacacgt 16020
tccaaaatca tgtccgtact catctcaccc agcaacaaca ccggctgggg gctgcgcgcg 16080
cccagcaaga tgtttggagg ggcgaggaag cgctccgacc agcaccctgt gcgcgtgcgc 16140
ggccactacc gcgcgccctg gggagcgcac aagcgcgggc gcacagggcg caccactgtg 16200
gacgacgtca ttgactccgt agtggagcaa gcgcgccact acacacccgg cgcgccgacc 16260
gcccccgccg tgtccaccgt ggaccaggcg atcgaaagcg tggtacaggg cgcgcggcac 16320
tatgccaacc ttaaaagtcg ccgccgccgc gtggcccgcc gccatcgccg gagaccccgg 16380
gccaccgccg ccgcgcgcct tactaaggct ctgctcaggc gcgccaggcg aactggccac 16440
cgggccgcca tgagggccgc acggcgggct gccgctgccg caagcgtcgt ggccccgcgg 16500
gcacgaaggc gcgcggccgc tgccgccgcc gccgccattt ccagcttggc ctcgacgcgg 16560
cgcggtaaca tatactgggt gcgcgactcg gtaaccggca cgcgggtacc cgtgcgcttt 16620
cgcccccccgc ggaattagca caagacaaca tacacactga gtctcctgct gttgtgtatc 16680
ccagcggcga ccgtcagcag cggcgacatg tccaagcgca aaattaaaga agagatgctc 16740
caggtcatcg cgccggagat ctatgggccc ccgaagaagg aggaggatga ttacaagccc 16800
cgcaagctaa agcgggtcaa aaagaaaaag aaagatgatg atgacgaggc ggtggagttt 16860
gtccgccgca tggcacccag gcgccccgtg cagtggaagg gccggcgcgt gcagcgcgtt 16920
ttgcgccccg gcaccgcggt ggtcttcacg cccggcgagc gctccacgcg cactttcaag 16980
cgggtgtacg atgaggtgta cggcgacgag gacctgttgg agcaggccaa ccagcgcttt 17040
ggggagtttg catatgggaa acggccccgc gagagtctaa aagaggacct gctggcgcta 17100
ccgctggacg agggcaatcc caccccgagt ctgaagccgg taaccctgca acaggtgctg 17160
cctttgagcg cgcccagcga gcataagcga gggttgaagc gcgaaggcgg ggacctggcg 17220
cccaccgtgc agttgatggt gcccaagcgg cagaagctgg aggacgtgct ggagaaaatg 17280
aaagtagagc ccgggatcca gcccgagatc aaggtccgcc ccatcaagca ggtggcgccc 17340
ggcgtgggag tccagaccgt ggacgttagg attcccacgg aggagatgga aacccaaacc 17400
gccactccct cttcggcggc cagcgccacc accggcaccg cttcggtaga ggtgcagacg 17460
gacccctggc tacccgccac cgctgttgcc gccgccgccc cccgttcgcg cgggcgcaag 17520
agaaattatc cagcggccag cgcgctcatg ccccagtacg cactgcatcc atccatcgtg 17580
cccacccccg gctaccgcgg gtactcgtac cgcccgcgca gatcagccgg cactcgcggc 17640
cgccgccgcc gtgcgaccac aaccagccgc cgccgtcgcc gccgccgcca gccagtgctg 17700
acccccgtgt ctgtaaggaa ggtggctcgc tcggggagca cgctggtggt gcccagagcg 17760
cgctaccacc ccagcatcgt ttaaagccgg tctctgtatg gttcttgcag atatggccct 17820
cacttgtcgc ctccgcttcc cggtgccggg ataccgagga agaactcacc gccgcagagg 17880
catggcgggc agcggtctcc gcggcggccg tcgccatcgc cggcgcgcaa aaagcaggcg 17940
catgcgcggc ggtgtgctgc ctctgctaat cccgctaatc gccgcggcga tcggtgccgt 18000
acccgggatc gcctccgtgg ccctgcaggc gtcccagaaa cgttgactct tgcaaccttg 18060
caagcttgca ttttttggag gaaaaaataa aaaaaaagtc tagactctca cgctcgcttg 18120

```
gtcctgtgac tattttgtag aaaaaaagat ggaagacatc aactttgcgt cgctggcccc  18180
gcgtcacggc tcgcgcccgt tcatgggaga ctggacagat atcggcacca gcaatatgag  18240
cggtggcgcc ttcagctggg gcagtctgtg gagcggcctt aaaaattttg gttccaccat  18300
taagaactat ggcaacaaag cgtggaacag cagcacgggc cagatgctga gagacaagtt  18360
gaaagagcag aacttccagg agaaggtggc gcagggcctg gcctctggca tcagcggggt  18420
ggtggacata gctaaccagg ccgtgcagaa aaagataaac agtcatctgg acccccgtcc  18480
tcaggtggag gaaatgcctc cagcgatgga gacggtgtct cccgagggca aaggcgaaaa  18540
gcgcccgcgg cccgacagag aagagaccct ggtgtcacac accgaggagc cgccctctta  18600
cgaggaggca gtcaaggccg gcctgcccac cactcgcccc atagccccca tggccaccgg  18660
tgtggtgggc cacaggcaac acactcccgc aacactagat ctgcccccgc cgtccgagcc  18720
gccgcgccag ccaaaggcgg cgacggtgcc cgctccctcc acttccgccg ccaacagagt  18780
gcccctgcgc cgcgccgcga gcggcccccg ggcctcgcga gttagcggca actggcagag  18840
cacactgaac agcatcgtgg gcctgggagt gaggagtgtg aagcgccgcc gttgctactg  18900
aatgagcaag ctagctaacg tgttgtatgt gtgtatgcgt cctatgtcgc cgccagagga  18960
gctgttgagc cgccggcgcc gtctgcactc cagcgaattt caagatggcg accccatcga  19020
tgatgcctca gtggtcgtac atgcacatct cgggccagga cgcttcggag tacctgagcc  19080
ccgggctggt gcagttcgcc cgcgccacag acacctactt caacatgagt aacaagttca  19140
ggaaccccac tgtggcgccc acccacgatg tgaccacgga ccggtcgcag cgcctgacgc  19200
tgcggttcat ccccgtggat cgggaggaca ccgcctactc ttacaaggcg cggttcacgc  19260
tggccgtggg cgacaaccgc gtgctggaca tggcctccac ttactttgac atcagggggg  19320
tgctggacag gggccccacc ttcaagccct actcgggtac tgcctacaac tccctggccc  19380
ccaagggcgc tcccaattct tgcgagtggg aacaagatga accagctcag gcagcaatag  19440
ctgaagatga agaagaactt gaagaagaac aagctcagga cgaacaggcg cccactaaga  19500
aaacccatgt atacgcccag gcacctcttt ctggtgaaaa aattactaag gatggtttgc  19560
aaataggtgt ggatgccaca caggcgggag ataaccctat atatgctgat aaaacattcc  19620
aacccgaacc tcagataggt gagtctcagt ggaacgaggc tgatgccaca gtagcaggag  19680
gcagagtctt aaaaaagacc acccctatga gaccttgcta tggatcctat gccaaaccta  19740
ctaatgccaa tggcggtcaa gggatcatgg tggccaatga tcagggagcg cttgaatcta  19800
aagttgagat gcaatttttc tccaccacaa cgtctcttaa tgtaagggaa ggtgaaaaca  19860
atcttcagcc aaaagtagtg ctatacagcg aagatgttaa cttggaatcc cctgacactc  19920
atttgtctta caaacctaaa aaggatgaca ccaactctaa aatcatgttg ggtcagcaag  19980
ccatgcccaa cagacccaac ctcattgctt ttagggacaa ctttattgga cttatgtact  20040
acaacagcac aggcaacatg ggagtgctgg caggacaggc ctcccagcta aacgctgtgg  20100
tagacttgca agacagaaac acagagctgt cataccaact gatgcttgat tccattggag  20160
acagatcaag atacttttcc atgtggaacc aggcagtgga cagctatgac ccagatgtca  20220
gaatcattga aaaccatggg gttgaagatg agctgcccaa ctattgcttt cccctgggcg  20280
gtattggaat tacagacaca taccagtgca taaaaccaac cgcagctgct aataacacta  20340
catggtctaa ggatgaagaa tttagtgatc gcaatgaaat aggggtggga aacaacttcg  20400
ccatggagat caacatccag gccaacctct ggaggaactt cctctatgcg aacgtggggc  20460
```

-continued

```
tctacctgcc agacaagctc aagtacaacc ccaccaacgt ggacatctct gacaacccca  20520
acacctatga ctacatgaac aagcgtgtgg tggctcccgg cctggtggac tgctttgtca  20580
atgtgggagc caggtggtcc ctggactaca tggacaacgt caaccccttc aaccaccacc  20640
gcaatgcggg tctgcgctac cgctccatga tcctgggcaa cgggcgctac gtgcccttcc  20700
acattcaggt gccccagaag ttctttgcca tcaagaacct cctcctcctg ccgggctcct  20760
acacttacga gtggaacttc aggaaggatg tcaacatggt cctgcagagc tctctgggca  20820
atgaccttag ggtggacggg gccagcatca agtttgacag cgtcaccctc tatgctacct  20880
tcttccccat ggctcacaac accgcctcca cgctcgaggc catgctgagg aacgacacca  20940
acgaccagtc cttcaatgac tacctctctg gggccaacat gctctacccc atccccgcca  21000
aggccaccaa cgtgcccatc tccattccct ctcgcaactg ggccgccttc agaggctggg  21060
cctttacccg ccttaagacc aaggaaaccc cctccctggg ctcgggtttt gacccctact  21120
ttgtctactc gggatccatc cctacctgg atggcacctt ctacctcaac cacactttta  21180
agaagatatc catcatgtat gactcctccg tcagctggcc gggcaatgac cgcctgctca  21240
cccccaatga gttcgaggtc aagcgcgccg tggacggcga gggctacaac gtggcccagt  21300
gcaacatgac caaggactgg ttcctggtgc agatgctggc caactacaac ataggctacc  21360
agggcttcta catcccagag agctacaagg acaggatgta ctccttcttc agaaatttcc  21420
aacccatgag caggcaggtg gtggacgaga ccaaatacaa ggactatcag gccattggca  21480
tcactcacca gcacaacaac tcgggattcg tgggctacct ggctcccacc atgcgcgagg  21540
ggcaggccta ccccgccaac ttcccctacc cgttgatagg caaaaccgcg gtcgacagcg  21600
tcacccagaa aaagttcctc tgcgaccgca ccctctggcg catccccttc tctagcaact  21660
tcatgtccat gggtgcgctc acggacctgg gccagaacct gctctatgcc aactccgccc  21720
atgcgctgga catgactttt gaggtggacc ccatggacga gcccaccctt ctctatattg  21780
tgtttgaagt gttcgacgtg gtcagagtgc accagccgca ccgcggtgtc atcgagaccg  21840
tgtacctgcg cacgcccttc tcggccggca acgccaccac ctaaggagac agcgccgccg  21900
cctgcatgac gggttccacc gagcaagagc tcagggccat cgccagagac ctgggatgcg  21960
gaccctattt tttgggcacc tatgacaaac gcttcccggg cttcatctcc cgagacaagc  22020
tcgcctgcgc catcgtcaac acggccgcgc gcgagaccgg gggcgtgcac tggctggcct  22080
ttggctggga cccgcgctcc aaaacctgct acctcttcga ccccttggc ttctccgatc  22140
agcgcctcag acagatctat gagtttgagt acgaggggct gctgcgccgc agcgcgcttg  22200
cctcctcgcc cgaccgctgc atcacccttg agaagtccac cgagaccgtg caggggcccc  22260
actcggccgc ctgcggtctc ttctgctgca tgtttttgca cgcctttgtg cgctggcccc  22320
agagtcccat ggatcgcaac cccaccatga acttgctcaa gggagtgccc aacgccatgc  22380
tccagagccc ccaggtccag cccaccctgc gccacaacca ggaacagctc taccgcttcc  22440
tggagcgcca ctccccctac ttccgcagtc acagcgcgca catccggggg gccacctctt  22500
tctgccactt gcaagaaaac atgcaagacg gaaaatgatg tacagctcgc tttttaataa  22560
atgtaaagac tgtgcacttt atttatacac gggctctttc tggttattta ttcaacaccg  22620
ccgtcgccat ctagaaatcg aaagggttct gccgcgcgtc gccgtgcgcc acgggcagag  22680
acacgttgcg atactggaag cggctcgccc acttaaactc gggcaccacc atgcggggca  22740
gtggttcctc ggggaagttc tcgccccaca gggtgcgggt cagctgcagc gcgctcagga  22800
ggtcgggagc cgagatcttg aagtcgcagt tggggccgga accctgcgcg cgcgagttgc  22860
```

ggtacacggg gttgcagcac tggaacacca gcagggccgg attatgcacg ctggccagca 22920
ggctctcgtc gctgatcatg tcgctgtcca gatcctccgc gttgctcagg gcgaacgggg 22980
tcatcttgca gacctgcctg cccaggaaag gcggcagccc gggcttgccg ttgcagtcgc 23040
agcgcagggg catcagcagg tgcccgcggc ccgactgcgc ctgcgggtac agcgcgcgca 23100
tgaaggcttc gatctgcctg aaagccacct gcgtcttggc tccctccgaa aagaacatcc 23160
cacaggactt gctggagaac tggttcgcgg gacagctggc atcgtgcagg cagcagcgcg 23220
cgtcggtgtt ggcgatctgc accacgttgc gaccccaccg gttcttcact atcttggcct 23280
tggaagcctg ctccttcagc gcgcgctggc cgttctcgct ggtcacatcc atctctatca 23340
cctgctcctt gttgatcatg tttgtaccgt gcagacactt caggtcgccc tccgtctggg 23400
tgcagcggtg ctcccacagc gcgcaaccgg tgggctccca atttttgtgg gtcacccccg 23460
cgtaggcctg caggtaggcc tgcaagaagc gccccatcat ggccacaaag gtcttctggc 23520
tcgtaaaggt cagctgcagg ccgcgatgct cttcgttcag ccaggtcttg cagatggcgg 23580
ccagcgcctc ggtctgctcg ggcagcatcc taaaatttgt cttcaggtcg ttatccacgt 23640
ggtacttgtc catcatggcg cgcgccgcct ccatgccctt ctcccaggcg gacaccatgg 23700
gcaggcttag gggtttatc acttccaccg gcgaggacac cgtactttcg atttcttctt 23760
cctccccctc ttcccggcgc gcgcccacgc tgctgcgcgc tctcaccgcc tgcaccaagg 23820
ggtcgtcttc aggcaagcgc cgcaccgagc gcttgccgcc cttgacctgc ttaatcagca 23880
ccggcgggtt gctgaagccc accatggtca gcgccgcctg ctcttcttcg tcttcgctgt 23940
ctaccactat ctctggggaa gggcttctcc gctctgcggc ggcgcgcttc tttttttct 24000
tgggagcggc cgtgatggag tccgccacgg cgacggaggt cgagggcgtg gggctggggg 24060
tgcgcggtac cagggcctcg tcgccctcgg actcttcctc tgactccagg cggcggcgga 24120
gtcgcttctt tgggggcgcg cgcgtcagcg gcggcggaga cggggacggg gacggggacg 24180
ggacgccctc cacagggggt ggtcttcgcg cagacccgcg gccgcgctcg gggtcttct 24240
cgagctggtc ttggtcccga ctggccattg tatcctcctc ctcctaggca gagagacata 24300
aggagtctat catgcaagtc gagaaggagg agagcttaac cacccctct gagaccgccg 24360
atgcgcccgc cgtcgccgtc gccccgctg ccgccgacgc gcccgccaca ccgagcgaca 24420
cccccgcgga ccccccgcc gacgcacccc tgttcgagga agcggccgtg gagcaggacc 24480
cgggctttgt ctcggcagag gaggatttgc gagaggagga ggataaggag aagaagccct 24540
cagtgccaaa agatgataaa gagcaagacg agcacgacgc agatgcacac cagggtgaag 24600
tcgggcgggg ggacggaggg catgacggcg ccgactacct agacgaaggg aacgacgtgc 24660
tcttgaagca cctgcatcgt cagtgcgcca ttgtttgcga cgctctgcag gagcgcagcg 24720
aagtgcccct cagcgtggcg gaggtcagcc acgcctacga gctcagcctc ttctcccccc 24780
gggtgccccc ccgccgccgc gaaaacggca catgcgagcc caacccgcgc ctcaacttct 24840
accccgcctt tgtggtaccc gaggtcctgg ccacctatca catcttcttt caaaattgca 24900
agatccccct ctcgtgccgc gccaaccgta gccgcgccga taagatgctg gccctgcgcc 24960
agggcgacca catacctgat atcgccgctt tggaagatgt accaaagatc ttcgagggtc 25020
tgggtcgcaa cgagaagcgg gcagcaaact ctctgcaaca ggaaaacagc gaaaatgaga 25080
gtcacaccgg ggtactggtg gagctcgagg gcgacaacgc ccgcctggcg gtggtcaagc 25140
gcagcatcga ggtcacccac tttgcctacc ccgcgctaaa cctgcccccc aaagtcatga 25200
acgcggccat ggacgggctg atcatgcgcc gcggccggcc cctcgctcca gatgcaaact 25260
tgcatgagga gaccgaggac ggccagcccg tggtcagcga cgagcagctg gcgcgctggc 25320
tggagaccgc ggaccccgcc gaactggagg agcggcgcaa gatgatgatg gccgtggtgc 25380
tggtcaccgt agagctggag tgtctgcagc gcttcttcgg cgaccccgag atgcagagaa 25440
aggtcgagga gaccctgcac tacaccttcc gccagggcta cgtgcgccag gcttgcaaga 25500
tctccaacgt ggagctcagc aacctggtgt cctacctggg catcttgcat gagaaccgcc 25560
tcgggcagag cgtgctgcac tccaccctgc gcggggaggc gcgccgcgac tacgtgcgcg 25620
actgcgttta cctcttcctc tgctacacct ggcagacggc catgggggtc tggcagcagt 25680
gcctggagga gcgcaacctc aaggagctgg agaagctcct gcagcgcgcg ctcaaagatc 25740
tctggacggg ctacaacgag cgctcggtgg ccgccgcgct ggccgacctc atcttccccg 25800
agcgcctgct caaaaccctc cagcaggggc tgcccgactt caccagccaa agcatgttgc 25860
aaaacttcag gaactttatc ctggagcgtt ctggcatcct acccgccacc tgctgcgccc 25920
tgcccagcga ctttgtcccc ctcgtgtacc gcgagtgccc cccgccgctg tggggtcact 25980
gctacctgtt ccaactggcc aactacctgt cctaccacgc ggacctcatg gaggactcca 26040
gcggcgaggg gctcatggag tgccactgcc gctgcaacct ctgcacgccc caccgctccc 26100
tggtctgcaa cacccaactg ctcagcgaga gtcagattat cggtaccttc gagctacagg 26160
gtccgtcctc ctcagacgag aagtccgcgg ctccggggct aaaactcact ccggggctgt 26220
ggacttccgc ctacctgcgc aaatttgtac ctgaagacta ccacgcccac gagatcaggt 26280
tttacgaaga ccaatcccgc ccgcccaagg cggagctgac cgcctgcgtc atcacccagg 26340
gcgagatcct aggccaattg caagccatcc aaaaagcccg ccaagacttt ttgctgaaga 26400
agggtcgggg ggtgtatctg gacccccagt cgggtgagga gctcaacccg gttcccccgc 26460
tgccgccgcc gcgggacctt gcttcccagg ataagcatcg ccatggctcc cagaaagaag 26520
cagcagcggc cgccactgcc gccaccccac atgctggagg aagaggagga atactgggac 26580
agtcaggcag aggaggtttc ggacgaggag gagccggaga cggagatgga agagtgggag 26640
gaggacagct tagacgagga ggcttccgaa gccgaagagg cagacgcaac accgtcaccc 26700
tcggccgcag cccccctcgca ggcgcccccg aagtccgctc ccagcatcag cagcaacagc 26760
agcgctataa cctccgctcc tccaccgccg cgacccacgg ccgaccgcag acccaaccgt 26820
agatgggaca ccaccggaac cggggccggt aagtcctccg ggagaggcaa gcaagcgcag 26880
cgccaaggct accgctcgtg gcgcgctcac aagaacgcca tagtcgcttg cttgcaagac 26940
tgcgggggga acatctcctt cgcccgccgc ttcctgctct tccaccacgg tgtggccttc 27000
ccccgtaacg tcctgcatta ctaccgtcat ctctacagcc cctactgcgg cggcagtgag 27060
ccagagacgg tcggcggcgg cggcggcgcc cgtttcggcg cctaggaaga cccagggcaa 27120
gacttcagcc aagaaactcg cggcggccgc ggcgaacgcg gtcgcggggg ccctgcgcct 27180
gacggtgaac gaacccctgt cgacccgcga actgaggaac cgaatcttcc ccactctcta 27240
tgccatcttc cagcagagca gagggcagga tcaggaactg aaagtaaaaa acaggtctct 27300
gcgctccctc acccgcagct gtctgtatca caagagcgaa gaccagcttc ggcgcacgct 27360
ggaggacgct gaggcactct tcagcaaata ctgcgcgctc actcttaagg actagctccg 27420
cgcccttctc gaatttaggc gggaacgcct acgtcatcgc agcgccgccg tcatgagcaa 27480
ggacattccc acgccataca tgtggagcta tcagccgcag atgggactcg cggcgggcgc 27540
ctcccaagac tactccaccc gcatgaactg gctcagtgcc ggcccacaca tgatctcaca 27600

```
ggttaatgat atccgcaccc atcgaaacca aatattggtg gagcaggcgg caattaccac  27660
cacgccccgc aataatccca accccaggga gtggcccgcg tccctggtgt atcaggaaat  27720
tcccggcccc accaccgtac tacttccgcg tgattcccag gccgaagtcc aaatgactaa  27780
ctcaggggca cagctcgcgg gcggctgtcg tcacagggtg cggcctcctc gccagggtat  27840
aactcacctg gagatccgag gcagaggtat tcagctcaac gacgagtcgg tgagctcctc  27900
gctcggtctc agacctgacg ggaccttcca gatagccgga gccggccgat cttccttcac  27960
gccccgccag gcgtacctga ctctgcaaag ctcgtcctcg gcgccgcgct cgggcggcat  28020
cgggactctc cagttcgtgc aggagtttgt gccctcggtc tacttcaacc ccttctcggg  28080
ctctcccggt cgctacccgg accagttcat ctcgaacttt gacgccgcga gggactcggt  28140
ggacggctac gactgaatgt cgggtggacc cggtgcagag caacttcgcc tgaagcacct  28200
cgaccactgc cgccgccctc agtgctttgc ccgctgtcag accggtgagt tccagtactt  28260
ttccctgccc gactcgcacc cggacggccc ggcgcacggg gtgcgctttt tcatcccgag  28320
tcaggtgcgc tctaccctaa tcagggagtt taccgcccgt cccctactgg cggagttgga  28380
aaaggggcct tctatcctaa ccattgcctg catctgctct aaccctggat tgcaccaaga  28440
tctttgctgt catttgtgtg ctgagtataa taaaggctga gatcagaatc tactcgggct  28500
cctgtcgcca tcctgtcaac gccaccgtcc aagcccggcc cgatcagccc gaggtgaacc  28560
tcacctgcgg tctgcaccgg cgcctgagga aatacctagc ttggtactac aacagcactc  28620
cctttgtggt ttacaacagc tttgaccagg acggggtctc actgagggat aacctctcga  28680
acctgagcta ctccatcagg aagaacagca ccctcgagct acttcctcct tacctgcccg  28740
ggacttacca gtgtgtcacc ggtccctgca cccacaccca cctgttgatc gtaaacgact  28800
ctcttccgag aacagacctc aataactcct cttcgcagtt ccccagaaca ggaggtgagc  28860
tcaggaaacc ccgggtaaag aagggtggac gagagttaac acttgtgggg tttctggtgt  28920
atgtgacgct ggtggtggct cttttgatta aggcttttcc ttccatgtct gaactctccc  28980
tcttctttta tgaacaactc gactagtgct aacgggaccc tacccaacga atcgggattg  29040
aatatcggta accaggttgc agtttcactt ttgattacct tcatagtcct cttcctgcta  29100
gtgctgtcgc ttctgtgcct gcggatcggg ggctgctgca tccacgttta tatctggtgc  29160
tggctgttta gaaggttcgg agaccatcgc aggtagaata aacatgctgc tgcttaccct  29220
ctttgtcctg gcgctggccg ccagctgcca agccttttcc gaggctgact ttatagagcc  29280
ccagtgtaat gtgactttta aagcccatgc acagcgttgt catactataa tcaaatgtgc  29340
caccgaacac gatgaatacc ttatccagta taaagataaa tcacacaaag tggcacttgt  29400
tgacatctgg aaacccgaag acccctttgga atacaatgtg accgttttcc agggtgacct  29460
cttcaaaatt tacaattaca ctttcccatt tgaccagatg tgtgactttg tcatgtacat  29520
ggaaaagcag cacaagctgt ggcctccgac tccccagggc tgtgtggaaa atccaggctc  29580
tttctgcatg atctctctct gtgtaactgt gctggcacta atactcacgc ttttgtatat  29640
cagatttaaa tcaaggcaaa gcttcattga tgaaaagaaa atgccttaat cgctttcacg  29700
cttgattgct aacaccgggt ttttatccgc agaatgattg gaatcaccct actaatcacc  29760
tccctccttg cgattgccca tgggttggaa cgaatcgaag tccctgtggg ggccaatgtt  29820
accctggtgg ggcctgtcgg caatgctaca ttaatgtggg aaaaatatac taaaaatcaa  29880
tgggtctctt actgcactaa caaaaatagc cacaagccca gagccatctg cgatgggcaa  29940
```

```
aatctaacct tgattgatgt tcaattgctg gatgcgggct actattatgg gcagctgggt  30000
acaatgatta attactggag accccacaga gattacatgc tccacgtagt aaagggtccc  30060
cttagcagcc cacccactac cacctctact acccccacta ccaccactac tcccaccacc  30120
agcactgccg cccagcctcc tcatagcaga acaaccactt ttatcaattc caagtcccac  30180
tccccccaca ttgccggcgg gccctccgcc tcagactccg aaaccaccga gatctgcttc  30240
tgcaaatgct ctgacgccat tgcccaggat ttggaagatc acgaggaaga tgagcatgac  30300
ttcgcagatg catgccaggc atcagagcca gaagcgctgc cggtggccct caaacagtat  30360
gcagaccccc acaccacccc cgaccttcct ccaccttccc agaagccaag tttcctgggg  30420
gaaaatgaaa ctctgcctct ctccatactc gctctgacat ctgttgctat gttgaccgct  30480
ctgctggtgc ttctatgctc tatatgctac ctgatctgct gcagaaagaa aaaatctcac  30540
ggccatgctc accagcccct catgcacttc ccttaccctc cagagctggg cgaccacaaa  30600
ctttaagtct gcagtaacta tctgcccatc ccttgtcagt cgacagcgat gagcccccact  30660
aatctaacgg cctctggact tacaacatcg tctcttaatg agaccaccgc tcctcaagac  30720
ctgtacgatg gtgtctccgc gctggttaac cagtgggatc acctgggcat atggtggctc  30780
ctcataggag cagtgaccct gtgcctaatc ctggtctgga tcatctgctg catcaaaagc  30840
agaagaccca ggcggcggcc catctacagg cccctttgtca tcacacctga agatgatgat  30900
gacaccactt ccaggctgca gaggctaaag cagctactct tctcttttac agcatggtaa  30960
attgaatcat gcctcgcatt ttcatctact tgtctctcct tccacttttt ctgggctctt  31020
ctacattggc cgctgtgtcc cacatcgagg tagactgcct cacgcccttc acagtctacc  31080
tgcttttcgg ctttgtcatc tgcacctttg tctgcagcgt tatcactgta gtgatctgct  31140
tcatacagtg catcgactac gtctgcgtgc gggtggctta ctttagacac cacccccagt  31200
atcgcaacag ggacatagcg gctctcctaa gacttgttta aaatcatggc caaattaact  31260
gtgattggtc ttctgatcat ctgctgcgtc ctagccgcga ttgggactca agctcctacc  31320
accaccagcg ctcccagaaa gagacatgta tcctgcagct tcaagcgtcc ctggaatata  31380
ccccaatgct ttactgatga acctgaaatc tctttggctt ggtacttcag cgtcaccgcc  31440
cttcttatct tctgcagtac ggttattgcc cttgccatct acccttccct tgacctgggc  31500
tggaatgctg tcaactctat ggaatatccc accttcccag aaccagacct gccagacctg  31560
gttgttctaa acgcgtttcc tcctcctgct cccgttcaaa atcagtttcg ccctccgtcc  31620
cccacgccca ctgaggtcag ctactttaat ctaacaggcg gagatgactg aaaacctaga  31680
cctagaaatg gacggtctct gcagcgagca acgcacacta gagaggcgcc ggcaaaaaga  31740
gctcgagcgt cttaaacaag agctccaaga cgcggtggcc atacaccagt gcaaaaaagg  31800
tgtcttctgt ctggtaaaac aggccacgct cacctatgaa aaaacaggtg acacccaccg  31860
cctaggatac aagctgccca cacagcgcca aaagttcgcc ctcatgatag gcgaacaacc  31920
catcaccgtg acccagcact ccgtggagac agaaggctgc atacatgctc cctgtagggg  31980
cgctgactgc ctctacacct tgatcaaaac cctctgcggt ctcagagacc ttatcccttt  32040
caattaatca taactgtaat caataaaaaa tcacttactt gaaatctgat agcaagcctc  32100
tgtccaattt tttcagcaac acttccttcc cctcctccca actctggtac tctaggcgcc  32160
tcctagctgc aaacttcctc cacagtctga agggaatgtc agattcctcc tcctgtccct  32220
ccgcacccac gatcttcatg ttgttgcaga tgaaacgcgc gagatcgtct gacgagacct  32280
tcaaccccgt gtacccctac gataccgaga tcgctccgac ttctgtccct ttccttaccc  32340
```

```
ctccctttgt gtcatccgca ggaatgcaag aaaatccagc tggggtgctg tccctgcact  32400
tgtcagagcc ccttaccacc cacaatgggg ccctgactct aaaaatgggg ggcggcctga  32460
ccctggacaa ggaagggaat ctcacttccc aaaacatcac cagtgtcgat ccccctctca  32520
aaaaaagcaa gaacaacatc agccttcaga ccgccgcacc cctcgccgtc agctccgggg  32580
ccctaacact ttttgccact cccccccctag cggtcagtgg tgacaacctt actgtgcagt  32640
ctcaggcccc tctcactttg gaagactcaa aactaactct ggccaccaaa ggacccctaa  32700
ctgtgtccga aggcaaactt gtcctagaaa cagaggctc                          32739
```

<210> SEQ ID NO 25
<211> LENGTH: 32739
<212> TYPE: DNA
<213> ORGANISM: Artificial Sequence
<220> FEATURE:
<223> OTHER INFORMATION: Adenovirus vector nucleotide sequences

<400> SEQUENCE: 25

```
catcatcaat aatatacctt attttggatt gtggccaata tgataatgag gtgggcgggg     60
agaggcgggg cgggtgacgt aggacgcgcg agtagggttg ggaggtgtgg cggaagtgtg    120
gcatttgcaa gtgggaggag ctcacatgca agcttccgtc gcggaaaatg tgacgttttt    180
gatgagcgcc gcctacctcc ggaagtgcca attttcgcgc gcttttcacc ggatatcgta    240
gtaattttgg gcgggaccat gtaagatttg gccattttcg cgcgaaaagt gaaacgggga    300
agtgaaaact gaataatagg gcgttagtca tagtgcgtaa tatttaccga gggccgaggg    360
actttgaccg attacgtgga ggactcgccc aggtgttttt tacgtgaatt tccgcgttcc    420
gggtcaaagt ctccgtttta ttgtcaccgt catttgacgc ttaggcctga ccatctggtg    480
ctggcctgca ccagggccga gtttgggtct agcgatgagg ataccgattg aggtgggtaa    540
ggtgggcgtg gctagaaggg tggggcgtgt ataaattggg ggtctaaggg tctctctgtt    600
ttgtcttgca acagccgccg ccatgagcga caccggcaac agctttgatg gaagcatctt    660
tagcccctat ctgacagtgc gcatgcctca ctgggctgga gtgcgtcaga atgtgatggg    720
ttccaacgtg gatggacgcc ccgttctgcc ttcaaattcg tctacaatgg cctacgcgac    780
cgtgggagga actccgctgg acgccgcgac ctccgccgcc gcctccgccg ccgccgcgac    840
cgcgcgcagc atggctacgg acctttacag ctctttggtg gcgagcggcg cggcctctcg    900
cgcgtctgct cgggatgaga aactgaccgc tctgctgctt aaactggaag acttgacccg    960
ggagctgggt caactgaccc agcaggtctc cagcttgcgt gagagcagcc ttgcctcccc   1020
ctaatggccc ataatataaa taaaagccag tctgtttgga ttaagcaagt gtatgttctt   1080
tatttaactc tccgcgcgcg gtaagcccgg gaccagcggt ctcggtcgtt tagggtgcgg   1140
tggattcttt ccaacacgtg gtacaggtgg ctctggatgt ttagatacat gggcatgagt   1200
ccatccctgg ggtggaggta gcaccactgc agagcttcgt gctcgggggt ggtgttgtat   1260
atgatccagt cgtagcagga gcgctgggcg tggtgctgaa aaatgtcctt aagcaagagg   1320
cttatagcta gggggaggcc cttggtgtaa gtgtttacaa atctgctcag ttgggagggg   1380
tgcatccggg gggatataat gtgcatcttg gactggattt ttaggttggc tatgttccca   1440
cccagatccc ttctgggatt catgttgtgc aggaccacca gcacggtata tccagtgcac   1500
ttgggaaatt tatcgtggag cttagacggg aatgcatgga agaacttgga gacgcccttg   1560
tggcctccca gattttccat acattcgtcc atgatgatgg caatgggccc gtgggaagct   1620
```

-continued

```
gcctgagcaa aaatgtttct gggatcgctc acatcgtagt tatgttccag ggtgaggtca   1680
tcataggaca tctttacgaa tcgggggcgg agggtcccgg actgggggat gatggtaccc   1740
tcgggccccg gggcgtagtt cccctcacag atctgcatct cccaggcttt catttcagag   1800
ggagggatca tatccacctg cggagcgatg aaaaacacag tttctggcgc aggggagatt   1860
aactgggatg agagcaggtt tctgagcagc tgtgactttc cacagccggt gggcccatat   1920
atcacgccta tcaccggctg cagctggtag ttaagagagc tgcagctgcc gtcctcccgg   1980
agcagggggg ccacctcgtt cagcatatcc ctgacgtgga tgttctccct gaccaattcc   2040
gccagaaggc gctcgccgcc cagcgaaagc agctcttgca aggaagcaaa atttttcagc   2100
ggttttaggc cgtcggccgt gggcatgttt ttcagcgtct gggtcagcag ttccagcctg   2160
tcccacagct cggtgatgtg ctctacggca tctcgatcca gcagatctcc tcgtttcgcg   2220
ggttggggcg gctttcgctg tagggcacca gccgatgggc gtccagcggg gccagagtca   2280
tgtccttcca tgggcgcagg gtcctcgtca gggtggtctg ggtcacggtg aaggggtgcg   2340
ctccgggttg ggcgctggcc agggtgcgct tgaggctggt tctgctggtg ctgaatcgct   2400
gccgctcttc gccctgcgcg tcggccaggt agcatttgac catggtctcg tagtcgagac   2460
cctcggcggc gtgccccttg gcgcggagct ttcccttgga ggtggcgccg cacgaggggc   2520
actgcaggct cttcagggcg tagagcttgg gagcgagaaa cacggactct ggggagtagg   2580
cgtccgcgcc gcaggaagcg cagaccgtct cgcattccac cagccaagtg agctccgggc   2640
ggtcagggtc aaaaaccagg ttgcccccat gctttttgat gcgtttctta cctcggctct   2700
ccatgaggcg gtgtcccttc tcggtgacga agaggctgtc cgtgtccccg tagaccgact   2760
tcaggggcct gtcttccagc ggagtgcctc tgtcctcctc gtagagaaac tctgaccact   2820
ctgagacgaa ggcccgcgtc caggccagga cgaaggaggc cacgtgggag gggtagcggt   2880
cgttgtccac tagcgggtcc accttctcca gggtgtgcag gcacatgtcc ccctcctccg   2940
cgtccagaaa agtgattggc ttgtaggtgt aggacacgtg accgggggtt cccgacgggg   3000
gggtataaaa gggggtgggc gccctttcat cttcactctc ttccgcatcg ctgtctgcga   3060
gggccagctg ctggggtaag tattccctct cgaaggcggg catgacctca gcgctcaggt   3120
tgtcagtttc taaaaatgag gaggatttga tgttcacctg tccggaggtg atacctttga   3180
gggtacctgg gtccatctgg tcagaaaaca ctattttttt gttgtcaagc ttggtggcga   3240
acgacccgta gagggcgttg gagagcagct tggcgatgga gcgcagggtc tggtttttgt   3300
cgcggtcggc tcgctccttg gccgcgatgt tgagttgcac gtactcgcgg gccacgcact   3360
tccactcggg gaagacggtg gtgcgctcgt ctgggattag gcgcaccctc cagcctcggt   3420
tgtgcagggt gaccatgtcg acgctggtgg cgacctcgcc gcgcaggcgc tcgttggtcc   3480
agcagaggcg gccgcccttg cgcgagcaga aggggggtag ggggtccagc tggtcctcgt   3540
ttgggggggtc cgcgtcgatg gtgaagaccc cggggagcaa gcgcgggtca aagtagtcga   3600
tcttgcaagc ttgcatgtcc agagcccgct gccattcgcg ggcggcgagc gcgcgctcgt   3660
aggggttgag gggcgggccc cagggcatgg ggtgggtgag cgcggaggcg tacatgccgc   3720
agatgtcata cacgtacagg ggttccctga ggatgccgag gtaggtgggg tagcagcgcc   3780
ccccgcggat gctggcgcgc acgtagtcat agagctcgtg ggaggggggcc agcatgttgg   3840
gcccgaggtt ggtgcgctgg gggcgctcgg cgcggaaggc gatctgcctg aagatggcat   3900
gggagttgga ggagatggtg ggccgctgga agacgttgaa gcttgcttct tgcaagccca   3960
ccgagtccct gacgaaggag gcgtaggact cgcgcagctt gtgcaccagc tcggcggtga   4020
```

-continued cctggacgtc gagcgcgcag tagtcgaggg tctcgcggat gatgtcatac ttatcctccc 4080
ccttcttttt ccacagctcg cggttgagga cgaactcttc gcggtctttc cagtactctt 4140
ggaggggaaa cccgtccgtg tccgaacggt aagagcctag catgtagaac tggttgacgg 4200
cctggtaggg gcaacagccc ttctccacgg gcagcgcgta ggcctgcgcc gccttgcgga 4260
gggaggtgtg ggtgagggcg aaagtgtccc tgaccatgac tttgaggtat tgatgtttga 4320
agtctgtgtc atcgcagccg ccctgttccc acagggtgta gtccgtgcgc tttttggagc 4380
gcgggttggg cagggagaag gtgaggtcat tgaagaggat cttccccgct cgaggcatga 4440
agtttctggt gatgcgaaag ggccctggga ccgaggagcg gttgttgatg acctgggcgg 4500
ccaggacgat ctcgtcaaag ccgtttatgt tgtggcccac gatgtagagc tccaaaaagc 4560
ggggctggcc cttgatggag gggagctttt tgagttcctc gtaggtgagc tcctcgggcg 4620
attccaggcc gtgctcctcc agggcccagt cttgcaagtg agggttggcc gccaggaagg 4680
atcgccagag gtcgcgggcc atgagggtct gcaggcggtc gcggaaggtt ctgaactgtc 4740
gccccacggc catcttttcg gggtgatgc agtagaaggt gagggggtct ttctcccagg 4800
ggtcccatct gagctctcgg gcgaggtcgc gcgcggcggc gaccagagcc tcgtcgcccc 4860
ccagtttcat gaccagcatg aagggcacga gctgcttgcc aaaggctccc atccaagtgt 4920
aggtctctac atcgtaggtg acaaagaggc gctccgtgcg aggatgagag ccgatcggga 4980
agaactggat ctcccgccac cagttggagg attggctgtt gatgtggtga aagtagaagt 5040
cccgtctgcg ggccgagcac tcgtgctggc ttttgtaaaa gcgaccgcag tactggcagc 5100
gctgcacggg ttgtatatct tgcacgaggt gaacctggcg acctctgacg aggaagcgca 5160
gcgggaatct aagtcccccg cctggggtcc cgtgtggctg gtggtcttct actttggttg 5220
tctggccgcc agcatctgtc tcctggaggg cgatggtgga gcagaccacc acgccgcgag 5280
agccgcaggt ccagatctcg gcgctcggcg ggcggagttt gatgacgaca tcgcgcacat 5340
tggagctgtc catggtctcc agctcccgcg gcggcaggtc agctgggagt tcctggaggt 5400
tcacctcgca gagacgggtc aaggcgcggg cagtgttgag atggtatctg atttcaaggg 5460
gcgtgttggc ggcggagtcg atggcttgca ggaggccgca gccccggggg gccacgatgg 5520
ttccccgcgg ggcgcgaggg gaggcggaag ctgggggtgt gttcagaagc ggtgacgcgg 5580
gcgggccccc ggaggtaggg ggggttccgg ccccacaggc atgggcggca ggggcacgtc 5640
ttcgccgcgc gcgggcaggg gctggtgctg gctccgaaga gcgcttgcgt gcgcgacgac 5700
gcgacggttg gtgtcctgta tctgacgcct ctgagtgaag accacgggtc ccgtgacctt 5760
gaacctgaaa gagagttcga cagaatcaat ctcggcatcg ttgacagcgg cctggcgcag 5820
gatctcctgc acgtcgcccg agttgtcctg gtaggcgatc tctgccatga actgctcgat 5880
ctcttcttcc tggagatctc ctcgtccggc gcgctccacg gtggccgcca ggtcgttgga 5940
gatgcgaccc atgagctgtg agaaggcgtt gagcccgccc tcgttccaga cccggctgta 6000
gaccacgccc ccctcggcgt cgcgagcgcg catgaccacc tgggccaggt tgagctccac 6060
gtgtcgcgtg aagacggcgt agttgcgcag gcgctggaaa aggtagttca gggtggtggc 6120
ggtgtgctcg gcgacgaaga agtacatgac ccagcgccgc aacgtggatt cattgatgtc 6180
cccaaggcc tccaggcgct ccatggcctc gtagaagtcc acggcgaagt tgaaaaactg 6240
ggagttgcga gcggacacgg tcaactcctc ctccagaaga cggatgagct cggcgacagt 6300
gttgcgcacc tcgcgctcga aggccacggg gggcgcttct tcctcttcca cctcttcttc 6360

-continued

```
catgatcgct tcttcttctt cctcagccgg gacgggaggg ggcggcggcg gcgggggagg   6420
ggcgcggcgg cggcggcggc gcaccgggag gcggtcgatg aagcgctcga tcatctcccc   6480
ccgcatgcgg cgcatggtct cggtgacggc gcggccgttc tcccgggggc gcagctcgaa   6540
gacgccgcct ctcatctcgc cgcggggcga gcggccgtga ggtagcgaga cggcgctgac   6600
tatgcatctt aacaattgct gtgtaggtac accgccgagg gacctgattg agtccagatc   6660
caccggatcc gaaaaccttt ggaggaaagc gtctatccag tcgcagtcgc aaggtaggct   6720
gagcaccgtg gcgggcgggg gcgggtctgg agagttcctg gcggagatgc tgctgatgat   6780
gtaattaaag taggcggtct tgagaaggcg gatggtggac aggagcacca tgtctttggg   6840
tccggcctgt tggatgcgga ggcggtcggc catgccccag gcctcgttct gacaccggcg   6900
caggtctttg tagtagtctt gcatgagtct ttccaccggc acctcttctc cttcctcttc   6960
tccatctcgc cggtggtttc tcgcgccgcc catgcgcgtg accccaaagc ccctgagcgg   7020
ctgcagcagg gccaggtcgg cgaccacgcg ctcggccaag atggcctgct gcacctgagt   7080
gagggtcctc tcgaagtcat ccatgtccac gaagcggtgg taggcgcccg tgttgatggt   7140
gtaggtgcag ttggccatga cggaccagtt gacggtctgg tgtcccggct gcgagagctc   7200
cgtgtaccgc aggcgcgaga aggcgcggga atcgaacacg tagtcgttgc aagtccgcac   7260
cagatactgg tagcccacca ggaagtgcgg cggaggttgg cgatagaggg gccagcgctg   7320
ggtggcgggg gcgccgggcg ccaggtcttc cagcatgagg cggtggtatc cgtagatgta   7380
cctggacatc caggtgatgc cggcggcggt ggtggtggcg cgcgcgtagt cgcggacccg   7440
gttccagatg tttcgcaggg gcgagaagtg ttccatggtc ggcacgctct ggccggtgag   7500
gcgcgcgcag tcgttgacgc tctatacaca cacaaaaacg aaagcgttta cagggctttc   7560
gttctgtagc ctggaggaaa gtaaatgggt tgggttgcgg tgtgccccgg ttcgagacca   7620
agctgagctc ggccggctga agccgcagct aacgtggtat tggcagtccc gtctcgaccc   7680
aggccctgta tcctccagga tacggtcgag agcccttttg ctttcttggc caagcgcccg   7740
tggcgcgatc tgggatagat ggtcgcgatg agaggacaaa agcggctcgc ttccgtagtc   7800
tggagaaaca atcgccaggg ttgcgttgcg gcgtaccccg gttcgagccc ctatggcggc   7860
ttgaatcggc cggaaccgcg gctaacgagg gccgtggcag ccccgtcctc aggaccccgc   7920
cagccgactt ctccagttac gggagcgagc cccttttgtt ttttattttt tagatgcatc   7980
ccgtgctgcg gcagatgcgc ccctcgcccc ggcccgatca gcagcagcaa cagcaggcat   8040
gcagaccccc ctctcccctt tccgccccgg tcaccacggc cgcggcggcc gtgtcgggcg   8100
cggggggcgc gctggagtca gatgagccac cgcggcggcg acctaggcag tatctggact   8160
tggaagaggg cgagggactg gcgcggctgg gggcgaactc tccagagcgc cacccgcggg   8220
tgcagttgaa aagggacgcg cgcgaggcgt acctgccgcg gcagaacctg tttcgcgacc   8280
gcgggggcga ggagcccgag gagatgcgag actgcaggtt ccaagcgggg cgcgagctgc   8340
ggcgcgggct ggacagacag cgcctgctgc gcgaggagga ctttgagccc gacacgcaga   8400
cgggcatcag ccccgcgcgc gcgcacgtag ccgcggccga cctggtgacc gcctacgagc   8460
agacggtaaa ccaggagcgc aacttccaaa agagcttcaa caaccacgtg cgcacgctgg   8520
tggcgcgcga ggaggtgacc ctgggtctca tgcatctgtg ggacctggtg gaggcgatcg   8580
tgcagaaccc cagcagcaag cccctgaccg cgcagctgtt cctggtggtg cagcacagca   8640
gggacaacga ggccttcagg gaggcgctgc tgaacatcac cgagccggag gggcgctggc   8700
tcctggacct gataaacatc ctgcagagca tagtggtgca ggagcgcagc ctgagcctgg   8760
```

```
ccgagaaggt ggcggccatc aactactcta tgctgagcct gggcaagttc tacgcccgca   8820
agatctacaa gaccccctac gtgcccatag acaaggaggt gaagatagac agcttctaca   8880
tgcgcatggc gctgaaggtg ctgaccctga gcgacgacct gggagtgtac cgcaacgagc   8940
gcatccacaa ggccgtgagc gccagccggc ggcgcgagct gagcgaccgc gagctgatgc   9000
acagtctgca gcgcgcgctg accggcgcgg gcgagggcga cagggaggtc gagtcctact   9060
tcgacatggg ggccgacctg cactggcagc cgagccgccg cgccctggag gcggcggggg   9120
cgtacggcgg ccccctggcg gccgatgacc aggaagagga ggactatgag ctagaggagg   9180
gcgagtacct ggaggactga cctggctggt ggtgttttgg tatagatgca agatccgaac   9240
gtggcggacc cggcggtccg ggcggcgctg caaagccagc cgtccggcat taactcctct   9300
gacgactggg ccgcggccat gggtcgcatc atggccctga ccgcgcgcaa ccccgaggct   9360
ttcaggcagc agcctcaggc caaccggctg gcggccatct tggaagcggt agtgcccgcg   9420
cgctccaacc ccacccacga gaaggtgctg gccatagtca acgcgctggc ggagagcagg   9480
gccatccgcg cggacgaggc cggactggtg tacgatgcgc tgctgcagcg ggtggcgcgg   9540
tacaacagcg gcaacgtgca gaccaacctg gaccgcctgg tgacggacgt gcgcgaggcc   9600
gtggcgcagc gcgagcgctt gcatcaggac ggtaacctgg gctcgctggt ggcgctaaac   9660
gccttcctca gcacccagcc ggccaacgta ccgcgggggc aggaggacta caccaacttt   9720
ttgagcgcgc tgcggctgat ggtgaccgag gtccctcaga gcgaggtgta ccagtcgggg   9780
cccgactact tcttccagac cagcagacag ggcttgcaaa ccgtgaacct gagccaggct   9840
ttcaagaacc tgcgggggct gtggggagtg aaggcgccca ccggcgaccg ggctacggtg   9900
tccagcctgc taacccccaa ctcgcgcctg ctgctgctgc tgatcgcgcc cttcacggac   9960
agcgggagcg tctcgcggga gacctatctg ggccacctgc tgacgctgta ccgcgaggcc  10020
atcgggcagg cgcaggtgga cgagcacacc ttccaagaga tcaccagcgt gagccacgcg  10080
ctggggcagg aggacacggg cagcctgcag gcgaccctga actacctgct gaccaacagg  10140
cggcagaaga ttcccacgct gcacagcctg acccaggagg aggagcgcat cttgcgctac  10200
gtgcagcaga gcgtgagcct gaacctgatg cgcgacggcg tgacgcccag cgtggcgctg  10260
gacatgaccg cgcgcaacat ggaaccgggc atgtacgcct cccaccggcc gtttatcaac  10320
cgcctgatgg actacttgca tcgggcggcg gccgtgaacc ccgagtactt cactaatgcc  10380
attctgaatc cccactggat gcccccctccg ggtttctaca acggggactt tgaggtgccc  10440
gaggtcaacg acgggttcct ctgggatgac atggatgaca gtgtgttctc acccaacccg  10500
ctgcgcgccg cgtctctgcg attgaaggag ggctctgaca gggaaggacc gaggagtctg  10560
gcctcctccc tggctctggg agcggtgggc gccacgggcg cggcggcgcg gggcagtagc  10620
cccttcccca gcctggcaga ctctctgaac agcgggcggg tgagcaggcc ccgcttgcta  10680
ggcgaggagg agtatctgaa caactccctg ctgcagcccg cgagggacaa gaacgctcag  10740
cggcagcagt ttcccaacaa tgggatagag agcctggtgg acaagatgtc cagatggaag  10800
acgtatgcgc aggagtacaa ggagtgggag gaccgccagc cgcggccctt gccgcccccct  10860
aggcagcgct ggcagcggcg cgcgtccaac cgccgctgga ggcaggggcc cgaggacgat  10920
gatgactctg cagatgacag cagcgtgttg gacctgggcg ggagcgggaa ccccttttcg  10980
cacctgcgcc cacgcctggg caagatgttt taaaagaaaa aaaaaataaa actcaccaag  11040
gccatggcga cgagcgttgg ttttttgttc ccttccttag tatgcggcgc gcggcgatgt  11100
```

-continued

```
tcgaggaggg gcctcccccc tcttacgaga gcgcgatggg gatttctcct gcggcgcccc  11160
tgcagcctcc ctacgtgcct cctcggtacc tgcaacctac aggggggaga aatagcatct  11220
gttactctga gctgcagccc ctgtacgata ccaccagact gtacctggtg gacaacaagt  11280
ccgcggacgt ggcctccctg aactaccaga acgaccacag cgattttttg accacggtga  11340
tccaaaacaa cgacttcacc ccaaccgagg ccagcaccca gaccataaac ctggataaca  11400
ggtcgaactg ggcggcgac ctgaagacca tcttgcacac caacatgccc aacgtgaacg  11460
agttcatgtt caccaactct tttaaggcgc gggtgatggt ggcgcgcgag caggggggagg  11520
cgaagtacga gtgggtggac ttcacgctgc ccgagggcaa ctactcagag accatgactc  11580
tcgacctgat gaacaatgcg atcgtggaac actatctgaa agtgggcagg cagaacgggg  11640
tgaaggaaag cgatatcggg gtcaagtttg acaccagaaa cttccgtctg ggctgggacc  11700
ccgtgaccgg gctggtcatg ccgggggtct acaccaacga ggcctttcat cccgacatag  11760
tgcttctgcc cggctgtggg gtggacttca cccagagccg gctgagcaac ctgctgggca  11820
ttcgcaagcg gcagcctttc caggagggtt tcaagatcac ctatgaggat ctgaaggggg  11880
gcaacattcc cgcgctcctt gatctggacg cctacgagga gagcttgaaa cccgaggaga  11940
gcgctggcga cagcggcgag agtggcgagg agcaagccgg cggcggtggc ggcgcgtcgg  12000
tagaaaacga aagtacgccc gcagtggcgg cggacgctgc ggaggtcgag ccggaggcca  12060
tgcagcagga cgcagaggag ggcgcacagg agggcgcgca gaaggacatg aacgatgggg  12120
agatcagggg agacacattc gccacccggg gcgaagaaaa agaggcagag gcggcggcgg  12180
cggcgacggc ggaggccgaa accgaggttg aggcagaggc agagcccgag accgaagtta  12240
tggaagacat gaatgatgga gaacgtaggg gcgacacgtt cgccacccgg ggcgaagaga  12300
aggcggcgga ggcagaagcc gcggctgagg aggcggctgc ggctgcggcc aagactgagg  12360
ctgcggctaa ggctgaggtc gaagccaatg ttgcggttga ggctcaggct gaggaggagg  12420
cggcggctga agcagttaag gaaaaggccc aggcagagca ggaagagaaa aaacctgtca  12480
ttcaacctct aaaagaagat agcaaaaagc gcagttacaa cgtcatcgag ggcagcacct  12540
ttacccagta ccgcagctgg tacctggcgt acaactacgg cgacccggtc aagggggtgc  12600
gctcgtggac cctgctctgc acgccggacg tcacctgcgg ctccgagcag atgtactggt  12660
cgctgccgaa catgatgcaa gacccggtga ccttccgctc cacgcggcag gttagcaact  12720
tcccggtggt gggcgccgaa ctgctgcccg tgcactccaa gagtttttac aacgagcagg  12780
ccgtctactc ccagctgatc cgccaggcca cctctctgac ccacgtgttc aatcgctttc  12840
ccgagaacca gattttggcg cgcccgccgg cccccaccat caccaccgtg agtgaaaacg  12900
ttcctgccct cacagatcac gggacgctac cgctgcgcaa cagcatctca ggagtccagc  12960
gagtgaccat tactgacgcc agacgccgga cctgccccta cgtttacaag gccttgggca  13020
tagtctcgcc gcgcgtcctc tccagtcgca ctttttaaaa cacatctacc cacacgttcc  13080
aaaatcatgt ccgtactcat ctcacccagc aacaacaccg gctgggggct gcgcgcgccc  13140
agcaagatgt ttggaggggc gaggaagcgc tccgaccagc accctgtgcg cgtgcgcggc  13200
cactaccgcg cgccctgggg agcgcacaag cgcgggcgca cagggcgcac cactgtggac  13260
gacgtcattg actccgtagt ggagcaagcg cgccactaca cacccggcgc gccgaccgcc  13320
cccgccgtgt ccaccgtgga ccaggcgatc gaaagcgtgg tacagggcgc gcggcactat  13380
gccaacctta aaagtcgccg ccgccgcgtg gcccgccgcc atcgccggag accccgggcc  13440
accgccgccg cgcgccttac taaggctctg ctcaggcgcg ccaggcgaac tggccaccgg  13500
```

-continued gccgccatga gggccgcacg gcgggctgcc gctgccgcaa gcgtcgtggc cccgcgggca 13560
cgaaggcgcg cggccgctgc cgccgccgcc gccatttcca gcttggcctc gacgcggcgc 13620
ggtaacatat actgggtgcg cgactcggta accggcacgc gggtacccgt gcgctttcgc 13680
cccccgcgga attagcacaa gacaacatac acactgagtc tcctgctgtt gtgtatccca 13740
gcggcgaccg tcagcagcgg cgacatgtcc aagcgcaaaa ttaaagaaga gatgctccag 13800
gtcatcgcgc cggagatcta tgggcccccg aagaaggagg aggatgatta caagccccgc 13860
aagctaaagc gggtcaaaaa gaaaaagaaa gatgatgatg acgaggcggt ggagtttgtc 13920
cgccgcatgg cacccaggcg ccccgtgcag tggaagggcc ggcgcgtgca gcgcgttttg 13980
cgccccggca ccgcggtggt cttcacgccc ggcgagcgct ccacgcgcac tttcaagcgg 14040
gtgtacgatg aggtgtacgg cgacgaggac ctgttggagc aggccaacca gcgctttggg 14100
gagtttgcat atgggaaacg gccccgcgag agtctaaaag aggacctgct ggcgctaccg 14160
ctggacgagg gcaatcccac cccgagtctg aagccggtaa ccctgcaaca ggtgctgcct 14220
ttgagcgcgc ccagcgagca taagcgaggg ttgaagcgcg aaggcgggga cctggcgccc 14280
accgtgcagt tgatggtgcc caagcggcag aagctggagg acgtgctgga gaaaatgaaa 14340
gtagagcccg ggatccagcc cgagatcaag gtccgcccca tcaagcaggt ggcgcccggc 14400
gtgggagtcc agaccgtgga cgttaggatt cccacggagg agatggaaac ccaaaccgcc 14460
actccctctt cggcggccag cgccaccacc ggcaccgctt cggtagaggt gcagacggac 14520
ccctggctac ccgccaccgc tgttgccgcc gccgcccccc gttcgcgcgg gcgcaagaga 14580
aattatccag cggccagcgc gctcatgccc cagtacgcac tgcatccatc catcgtgccc 14640
acccccggct accgcgggta ctcgtaccgc ccgcgcagat cagccggcac tcgcggccgc 14700
cgccgccgtg cgaccacaac cagccgccgc cgtcgccgcc gccgccagcc agtgctgacc 14760
cccgtgtctg taaggaaggt ggctcgctcg gggagcacgc tggtggtgcc cagagcgcgc 14820
taccacccca gcatcgttta aagccggtct ctgtatggtt cttgcagata tggccctcac 14880
ttgtcgcctc cgcttcccgg tgccgggata ccgaggaaga actcaccgcc gcagaggcat 14940
ggcgggcagc ggtctccgcg gcggccgtcg ccatcgccgg cgcgcaaaaa gcaggcgcat 15000
gcgcggcggt gtgctgcctc tgctaatccc gctaatcgcc gcggcgatcg gtgccgtacc 15060
cgggatcgcc tccgtggccc tgcaggcgtc ccagaaacgt tgactcttgc aaccttgcaa 15120
gcttgcattt tttggaggaa aaataaaaaa aagtctagac tctcacgctc gcttggtcct 15180
gtgactattt tgtagaaaaa aagatggaag acatcaactt tgcgtcgctg gccccgcgtc 15240
acggctcgcg cccgttcatg ggagactgga cagatatcgg caccagcaat atgagcggtg 15300
gcgccttcag ctggggcagt ctgtggagcg gccttaaaaa ttttggttcc accattaaga 15360
actatggcaa caaagcgtgg aacagcagca cgggccagat gctgagagac aagttgaaag 15420
agcagaactt ccaggagaag gtggcgcagg gcctggcctc tggcatcagc ggggtggtgg 15480
acatagctaa ccaggccgtg cagaaaaaga taaacagtca tctggacccc cgtcctcagg 15540
tggaggaaat gcctccagcg atggagacgg tgtctcccga gggcaaaggc gaaaagcgcc 15600
cgcggcccga cagagaagag accctggtgt cacacaccga ggagccgccc tcttacgagg 15660
aggcagtcaa ggccggcctg cccaccactc gccccatagc ccccatggcc accggtgtgg 15720
tgggccacag gcaacacact cccgcaacac tagatctgcc cccgccgtcc gagccgccgc 15780
gccagccaaa ggcggcgacg gtgcccgctc cctccacttc cgccgccaac agagtgcccc 15840

-continued tgcgccgcgc cgcgagcggc ccccgggcct cgcgagttag cggcaactgg cagagcacac 15900
tgaacagcat cgtgggcctg ggagtgagga gtgtgaagcg ccgccgttgc tactgaatga 15960
gcaagctagc taacgtgttg tatgtgtgta tgcgtcctat gtcgccgcca gaggagctgt 16020
tgagccgccg gcgccgtctg cactccagcg aatttcaaga tggcgacccc atcgatgatg 16080
cctcagtggt cgtacatgca catctcgggc caggacgctt cggagtacct gagccccggg 16140
ctggtgcagt tcgcccgcgc cacagacacc tacttcaaca tgagtaacaa gttcaggaac 16200
cccactgtgg cgcccaccca cgatgtgacc acggaccggt cgcagcgcct gacgctgcgg 16260
ttcatccccg tggatcggga ggacaccgcc tactcttaca aggcgcggtt cacgctggcc 16320
gtgggcgaca accgcgtgct ggacatggcc tccacttact ttgacatcag gggggtgctg 16380
gacaggggcc ccaccttcaa gccctactcg ggtactgcct acaactccct ggccccccaag 16440
ggcgctccca attcttgcga gtgggaacaa gatgaaccag ctcaggcagc aatagctgaa 16500
gatgaagaag aacttgaaga agaacaagct caggacgaac aggcgcccac taagaaaacc 16560
catgtatacg cccaggcacc tctttctggt gaaaaaatta ctaaggatgg tttgcaaata 16620
ggtgtggatg ccacacaggc gggagataac cctatatatg ctgataaaac attccaaccc 16680
gaacctcaga taggtgagtc tcagtggaac gaggctgatg ccacagtagc aggaggcaga 16740
gtcttaaaaa agaccacccc tatgagacct tgctatggat cctatgccaa acctactaat 16800
gccaatggcg gtcaagggat catggtggcc aatgatcagg gagcgcttga atctaaagtt 16860
gagatgcaat ttttctccac cacaacgtct cttaatgtaa gggaaggtga aaacaatctt 16920
cagccaaaag tagtgctata cagcgaagat gttaacttgg aatcccctga cactcatttg 16980
tcttacaaac ctaaaaagga tgacaccaac tctaaaatca tgttgggtca gcaagccatg 17040
cccaacagac ccaacctcat tgcttttagg gacaacttta ttggacttat gtactacaac 17100
agcacaggca acatgggagt gctggcagga caggcctccc agctaaacgc tgtggtagac 17160
ttgcaagaca gaaacacaga gctgtcatac caactgatgc ttgattccat tggagacaga 17220
tcaagatact tttccatgtg gaaccaggca gtggacagct atgacccaga tgtcagaatc 17280
attgaaaacc atggggttga agatgagctg cccaactatt gctttcccct gggcggtatt 17340
ggaattacag acacatacca gtgcataaaa ccaaccgcag ctgctaataa cactacatgg 17400
tctaaggatg aagaatttag tgatcgcaat gaaatagggg tgggaaacaa cttcgccatg 17460
gagatcaaca tccaggccaa cctctggagg aacttcctct atgcgaacgt ggggctctac 17520
ctgccagaca agctcaagta caaccccacc aacgtggaca tctctgacaa ccccaacacc 17580
tatgactaca tgaacaagcg tgtggtggct cccggcctgg tggactgctt tgtcaatgtg 17640
ggagccaggt ggtccctgga ctacatggac aacgtcaacc ccttcaacca ccaccgcaat 17700
gcgggtctgc gctaccgctc catgatcctg ggcaacgggc gctacgtgcc cttccacatt 17760
caggtgcccc agaagttctt tgccatcaag aacctcctcc tcctgccggg ctcctacact 17820
tacgagtgga acttcaggaa ggatgtcaac atggtcctgc agagctctct gggcaatgac 17880
cttagggtgg acggggccag catcaagttt gacagcgtca ccctctatgc taccttcttc 17940
cccatggctc acaacaccgc ctccacgctc gaggccatgc tgaggaacga caccaacgac 18000
cagtccttca atgactacct ctctggggcc aacatgctct accccatccc cgccaaggcc 18060
accaacgtgc ccatctccat tccctctcgc aactgggccg ccttcagagg ctgggccttt 18120
acccgcctta agaccaagga aacccccctcc ctgggctcgg gttttgaccc ctactttgtc 18180
tactcgggat ccatccccta cctggatggc accttctacc tcaaccacac ttttaagaag 18240
atatccatca tgtatgactc ctccgtcagc tggccgggca atgaccgcct gctcaccccc 18300
aatgagttcg aggtcaagcg cgccgtggac ggcgagggct acaacgtggc ccagtgcaac 18360
atgaccaagg actggttcct ggtgcagatg ctggccaact acaacatagg ctaccagggc 18420
ttctacatcc cagagagcta caaggacagg atgtactcct tcttcagaaa tttccaaccc 18480
atgagcaggc aggtggtgga cgagaccaaa tacaaggact atcaggccat tggcatcact 18540
caccagcaca acaactcggg attcgtgggc tacctggctc ccaccatgcg cgaggggcag 18600
gcctaccccg ccaacttccc ctacccgttg ataggcaaaa ccgcggtcga cagcgtcacc 18660
cagaaaaagt tcctctgcga ccgcaccctc tggcgcatcc ccttctctag caacttcatg 18720
tccatgggtg cgctcacgga cctgggccag aacctgctct atgccaactc cgcccatgcg 18780
ctggacatga cttttgaggt ggaccccatg gacgagccca cccttctcta tattgtgttt 18840
gaagtgttcg acgtggtcag agtgcaccag ccgcaccgcg gtgtcatcga gaccgtgtac 18900
ctgcgcacgc ccttctcggc cggcaacgcc accacctaag gagacagcgc cgccgcctgc 18960
atgacgggtt ccaccgagca agagctcagg gccatcgcca gagacctggg atgcggaccc 19020
tattttttgg gcacctatga caaacgcttc ccgggcttca tctcccgaga caagctcgcc 19080
tgcgccatcg tcaacacggc cgcgcgcgag accgggggcg tgcactggct ggcctttggc 19140
tgggacccgc gctccaaaac ctgctacctc ttcgacccct ttggcttctc cgatcagcgc 19200
ctcagacaga tctatgagtt tgagtacgag gggctgctgc gccgcagcgc gcttgcctcc 19260
tcgcccgacc gctgcatcac ccttgagaag tccaccgaga ccgtgcaggg gccccactcg 19320
gccgcctgcg gtctcttctg ctgcatgttt ttgcacgcct ttgtgcgctg gccccagagt 19380
cccatggatc gcaaccccac catgaacttg ctcaagggag tgcccaacgc catgctccag 19440
agcccccagg tccagcccac cctgcgccac aaccaggaac agctctaccg cttcctggag 19500
cgccactccc cctacttccg cagtcacagc gcgcacatcc ggggggccac ctctttctgc 19560
cacttgcaag aaaacatgca agacggaaaa tgatgtacag ctcgcttttt aataaatgta 19620
aagactgtgc actttattta tacacgggct ctttctggtt atttattcaa caccgccgtc 19680
gccatctaga aatcgaaagg gttctgccgc gcgtcgccgt gcgccacggg cagagacacg 19740
ttgcgatact ggaagcggct cgcccactta aactcgggca ccaccatgcg gggcagtggt 19800
tcctcgggga agttctcgcc ccacagggtg cgggtcagct gcagcgcgct caggaggtcg 19860
ggagccgaga tcttgaagtc gcagttgggg ccggaaccct gcgcgcgcga gttgcggtac 19920
acggggttgc agcactggaa caccagcagg gccggattat gcacgctggc cagcaggctc 19980
tcgtcgctga tcatgtcgct gtccagatcc tccgcgttgc tcagggcgaa cggggtcatc 20040
ttgcagacct gcctgcccag gaaaggcggc agcccgggct tgccgttgca gtcgcagcgc 20100
aggggcatca gcaggtgccc gcggcccgac tgcgcctgcg ggtacagcgc gcgcatgaag 20160
gcttcgatct gcctgaaagc cacctgcgtc ttggctccct ccgaaaagaa catcccacag 20220
gacttgctgg agaactggtt cgcgggacag ctggcatcgt gcaggcagca gcgcgcgtcg 20280
gtgttggcga tctgcaccac gttgcgaccc caccggttct tcactatctt ggccttggaa 20340
gcctgctcct tcagcgcgcg ctggccgttc tcgctggtca catccatctc tatcacctgc 20400
tccttgttga tcatgtttgt accgtgcaga cacttcaggt cgccctccgt ctgggtgcag 20460
cggtgctccc acagcgcgca accggtgggc tcccaatttt tgtgggtcac cccgcgtag 20520
gcctgcaggt aggcctgcaa gaagcgcccc atcatggcca caaaggtctt ctggctcgta 20580

-continued

```
aaggtcagct gcaggccgcg atgctcttcg ttcagccagg tcttgcagat ggcggccagc  20640
gcctcggtct gctcgggcag catcctaaaa tttgtcttca ggtcgttatc cacgtggtac  20700
ttgtccatca tggcgcgcgc cgcctccatg cccttctccc aggcggacac catgggcagg  20760
cttagggggt ttatcacttc caccggcgag gacaccgtac tttcgatttc ttcttcctcc  20820
ccctcttccc ggcgcgcgcc cacgctgctg cgcgctctca ccgcctgcac caaggggtcg  20880
tcttcaggca agcgccgcac cgagcgcttg ccgcccttga cctgcttaat cagcaccggc  20940
gggttgctga agcccaccat ggtcagcgcc gcctgctctt cttcgtcttc gctgtctacc  21000
actatctctg gggaagggct tctccgctct gcggcggcgc gcttcttttt tttcttggga  21060
gcggccgtga tggagtccgc cacggcgacg gaggtcgagg gcgtggggct gggggtgcgc  21120
ggtaccaggg cctcgtcgcc ctcggactct tcctctgact ccaggcggcg gcggagtcgc  21180
ttctttgggg gcgcgcgcgt cagcggcggc ggagacgggg acggggacgg ggacgggacg  21240
ccctccacag gggtggtct tcgcgcagac ccgcggccgc gctcgggggt cttctcgagc  21300
tggtcttggt cccgactggc cattgtatcc tcctcctcct aggcagagag acataaggag  21360
tctatcatgc aagtcgagaa ggaggagagc ttaaccaccc cctctgagac cgccgatgcg  21420
cccgccgtcg ccgtcgcccc cgctgccgcc gacgcgcccg ccacaccgag cgacaccccc  21480
gcggaccccc ccgccgacgc acccctgttc gaggaagcgg ccgtggagca ggacccgggc  21540
tttgtctcgg cagaggagga tttgcgagag gaggaggata aggagaagaa gccctcagtg  21600
ccaaaagatg ataaagagca agacgagcac gacgcagatg cacaccaggg tgaagtcggg  21660
cggggggacg gagggcatga cggcgccgac tacctagacg aagggaacga cgtgctcttg  21720
aagcacctgc atcgtcagtg cgccattgtt tgcgacgctc tgcaggagcg cagcgaagtg  21780
cccctcagcg tggcggaggt cagccacgcc tacgagctca gcctcttctc cccccgggtg  21840
ccccccgcc gccgcgaaaa cggcacatgc gagcccaacc cgcgcctcaa cttctacccc  21900
gcctttgtgg tacccgaggt cctggccacc tatcacatct tctttcaaaa ttgcaagatc  21960
cccctctcgt gccgcgccaa ccgtagccgc gccgataaga tgctggccct gcgccagggc  22020
gaccacatac ctgatatcgc cgctttggaa gatgtaccaa agatcttcga gggtctgggt  22080
cgcaacgaga agcgggcagc aaactctctg caacaggaaa acagcgaaaa tgagagtcac  22140
accggggtac tggtggagct cgagggcgac aacgcccgcc tggcggtggt caagcgcagc  22200
atcgaggtca cccactttgc ctaccccgcg ctaaacctgc cccccaaagt catgaacgcg  22260
gccatggacg ggctgatcat gcgccgcggc cggcccctcg ctccagatgc aaacttgcat  22320
gaggagaccg aggacggcca gcccgtggtc agcgacgagc agctggcgcg ctggctggag  22380
accgcggacc ccgccgaact ggaggagcgg cgcaagatga tgatggccgt ggtgctggtc  22440
accgtagagc tggagtgtct gcagcgcttc ttcggcgacc ccgagatgca gagaaaggtc  22500
gaggagaccc tgcactacac cttccgccag ggctacgtgc gccaggcttg caagatctcc  22560
aacgtggagc tcagcaacct ggtgtcctac ctgggcatct tgcatgagaa ccgcctcggg  22620
cagagcgtgc tgcactccac cctgcgcggg gaggcgcgcc gcgactacgt gcgcgactgc  22680
gtttacctct tcctctgcta cacctggcag acggccatgg gggtctggca gcagtgcctg  22740
gaggagcgca acctcaagga gctggagaag ctcctgcagc gcgcgctcaa agatctctgg  22800
acgggctaca acgagcgctc ggtggccgcc gcgctggccg acctcatctt ccccgagcgc  22860
ctgctcaaaa ccctccagca ggggctgccc gacttcacca gccaaagcat gttgcaaaac  22920
ttcaggaact ttatcctgga gcgttctggc atcctacccg ccacctgctg cgccctgccc  22980
```

agcgactttg tccccctcgt gtaccgcgag tgccccccgc cgctgtgggg tcactgctac 23040
ctgttccaac tggccaacta cctgtcctac cacgcggacc tcatggagga ctccagcggc 23100
gaggggctca tggagtgcca ctgccgctgc aacctctgca cgccccaccg ctccctggtc 23160
tgcaacaccc aactgctcag cgagagtcag attatcggta ccttcgagct acagggtccg 23220
tcctcctcag acgagaagtc cgcggctccg ggctaaaac tcactccggg gctgtggact 23280
tccgcctacc tgcgcaaatt tgtacctgaa gactaccacg cccacgagat caggttttac 23340
gaagaccaat cccgcccgcc caaggcggag ctgaccgcct gcgtcatcac ccagggcgag 23400
atcctaggcc aattgcaagc catccaaaaa gcccgccaag actttttgct gaagaagggt 23460
cggggggtgt atctggaccc ccagtcgggt gaggagctca acccggttcc cccgctgccg 23520
ccgccgcggg accttgcttc ccaggataag catcgccatg gctcccagaa agaagcagca 23580
gcggccgcca ctgccgccac cccacatgct ggaggaagag gaggaatact gggacagtca 23640
ggcagaggag gtttcggacg aggaggagcc ggagacggag atggaagagt gggaggagga 23700
cagcttagac gaggaggctt ccgaagccga agaggcagac gcaacaccgt caccctcggc 23760
cgcagccccc tcgcaggcgc ccccgaagtc cgctcccagc atcagcagca acagcagcgc 23820
tataacctcc gctcctccac cgccgcgacc cacggccgac cgcagaccca accgtagatg 23880
ggacaccacc ggaaccgggg ccggtaagtc ctccgggaga ggcaagcaag cgcagcgcca 23940
aggctaccgc tcgtggcgcg ctcacaagaa cgccatagtc gcttgcttgc aagactgcgg 24000
ggggaacatc tccttcgccc gccgcttcct gctcttccac cacggtgtgg ccttcccccg 24060
taacgtcctg cattactacc gtcatctcta cagcccctac tgcggcggca gtgagccaga 24120
gacggtcggc ggcggcggcg gcgcccgttt cggcgcctag gaagacccag ggcaagactt 24180
cagccaagaa actcgcggcg gccgcggcga acgcggtcgc gggggccctg cgcctgacgg 24240
tgaacgaacc cctgtcgacc cgcgaactga ggaaccgaat cttccccact ctctatgcca 24300
tcttccagca gagcagaggg caggatcagg aactgaaagt aaaaaacagg tctctgcgct 24360
ccctcacccg cagctgtctg tatcacaaga gcgaagacca gcttcggcgc acgctggagg 24420
acgctgaggc actcttcagc aaatactgcg cgctcactct taaggactag ctccgcgccc 24480
ttctcgaatt taggcgggaa cgcctacgtc atcgcagcgc cgccgtcatg agcaaggaca 24540
ttcccacgcc atacatgtgg agctatcagc cgcagatggg actcgcggcg ggcgcctccc 24600
aagactactc cacccgcatg aactggctca gtgccggccc acacatgatc tcacaggtta 24660
atgatatccg cacccatcga aaccaaatat tggtggagca ggcggcaatt accaccacgc 24720
cccgcaataa tcccaacccc agggagtggc ccgcgtccct ggtgtatcag gaaattcccg 24780
gccccaccac cgtactactt ccgcgtgatt cccaggccga agtccaaatg actaactcag 24840
gggcacagct cgcgggcggc tgtcgtcaca gggtgcggcc tcctcgccag ggtataactc 24900
acctggagat ccgaggcaga ggtattcagc tcaacgacga gtcggtgagc tcctcgctcg 24960
gtctcagacc tgacgggacc ttccagatag ccggagccgg ccgatcttcc ttcacgcccc 25020
gccaggcgta cctgactctg caaagctcgt cctcggcgcc gcgctcgggc ggcatcggga 25080
ctctccagtt cgtgcaggag tttgtgccct cggtctactt caaccccttc tcgggctctc 25140
ccggtcgcta cccggaccag ttcatctcga actttgacgc cgcgagggac tcggtggacg 25200
gctacgactg aatgtcgggt ggacccggtg cagagcaact tcgcctgaag cacctcgacc 25260
actgccgccg ccctcagtgc tttgcccgct gtcagaccgg tgagttccag tacttttccc 25320

-continued

```
tgcccgactc gcacccggac ggcccggcgc acggggtgcg ctttttcatc ccgagtcagg  25380
tgcgctctac cctaatcagg gagtttaccg cccgtcccct actggcggag ttggaaaagg  25440
ggccttctat cctaaccatt gcctgcatct gctctaaccc tggattgcac caagatcttt  25500
gctgtcattt gtgtgctgag tataataaag gctgagatca gaatctactc gggctcctgt  25560
cgccatcctg tcaacgccac cgtccaagcc cggcccgatc agcccgaggt gaacctcacc  25620
tgcggtctgc accggcgcct gaggaaatac ctagcttggt actacaacag cactcccttt  25680
gtggtttaca acagctttga ccaggacggg gtctcactga gggataacct ctcgaacctg  25740
agctactcca tcaggaagaa cagcaccctc gagctacttc ctccttacct gcccgggact  25800
taccagtgtg tcaccggtcc ctgcacccac acccacctgt tgatcgtaaa cgactctctt  25860
ccgagaacag acctcaataa ctcctcttcg cagttcccca gaacaggagg tgagctcagg  25920
aaaccccggg taaagaaggg tggacgagag ttaacacttg tggggtttct ggtgtatgtg  25980
acgctggtgg tggctctttt gattaaggct tttccttcca tgtctgaact ctccctcttc  26040
ttttatgaac aactcgacta gtgctaacgg gaccctaccc aacgaatcgg gattgaatat  26100
cggtaaccag gttgcagttt cacttttgat taccttcata gtcctcttcc tgctagtgct  26160
gtcgcttctg tgcctgcgga tcgggggctg ctgcatccac gtttatatct ggtgctggct  26220
gtttagaagg ttcggagacc atcgcaggta gaataaacat gctgctgctt accctctttg  26280
tcctggcgct ggccgccagc tgccaagcct tttccgaggc tgactttata gagccccagt  26340
gtaatgtgac ttttaaagcc catgcacagc gttgtcatac tataatcaaa tgtgccaccg  26400
aacacgatga ataccttatc cagtataaag ataaatcaca caaagtggca cttgttgaca  26460
tctggaaacc cgaagaccct ttggaataca atgtgaccgt tttccagggt gacctcttca  26520
aaatttacaa ttacactttc ccatttgacc agatgtgtga ctttgtcatg tacatggaaa  26580
agcagcacaa gctgtggcct ccgactcccc agggctgtgt ggaaaatcca ggctctttct  26640
gcatgatctc tctctgtgta actgtgctgg cactaatact cacgcttttg tatatcagat  26700
ttaaatcaag gcaaagcttc attgatgaaa agaaaatgcc ttaatcgctt tcacgcttga  26760
ttgctaacac cgggttttta tccgcagaat gattggaatc accctactaa tcacctccct  26820
ccttgcgatt gcccatgggt tggaacgaat cgaagtccct gtgggggcca atgttaccct  26880
ggtggggcct gtcggcaatg ctacattaat gtgggaaaaa tatactaaaa atcaatgggt  26940
ctcttactgc actaacaaaa atagccacaa gcccagagcc atctgcgatg ggcaaaatct  27000
aaccttgatt gatgttcaat tgctggatgc gggctactat tatgggcagc tgggtacaat  27060
gattaattac tggagacccc acagagatta catgctccac gtagtaaagg gtccccttag  27120
cagcccaccc actaccacct ctactacccc cactaccacc actactccca ccaccagcac  27180
tgccgcccag cctcctcata gcagaacaac cacttttatc aattccaagt cccactcccc  27240
ccacattgcc ggcgggccct ccgcctcaga ctccgaaacc accgagatct gcttctgcaa  27300
atgctctgac gccattgccc aggatttgga agatcacgag gaagatgagc atgacttcgc  27360
agatgcatgc caggcatcag agccagaagc gctgccggtg gccctcaaac agtatgcaga  27420
cccccacacc acccccgacc ttcctccacc ttcccagaag ccaagtttcc tgggggaaaa  27480
tgaaactctg cctctctcca tactcgctct gacatctgtt gctatgttga ccgctctgct  27540
ggtgcttcta tgctctatat gctacctgat ctgctgcaga aagaaaaaat ctcacggcca  27600
tgctcaccag cccctcatgc acttccctta ccctccagag ctgggcgacc acaaacttta  27660
agtctgcagt aactatctgc ccatcccttg tcagtcgaca gcgatgagcc ccactaatct  27720
```

```
aacggcctct ggacttacaa catcgtctct taatgagacc accgctcctc aagacctgta  27780
cgatggtgtc tccgcgctgg ttaaccagtg ggatcacctg ggcatatggt ggctcctcat  27840
aggagcagtg accctgtgcc taatcctggt ctggatcatc tgctgcatca aaagcagaag  27900
acccaggcgg cggcccatct acaggccctt tgtcatcaca cctgaagatg atgatgacac  27960
cacttccagg ctgcagaggc taaagcagct actcttctct tttacagcat ggtaaattga  28020
atcatgcctc gcattttcat ctacttgtct ctccttccac tttttctggg ctcttctaca  28080
ttggccgctg tgtcccacat cgaggtagac tgcctcacgc ccttcacagt ctacctgctt  28140
ttcggctttg tcatctgcac ctttgtctgc agcgttatca ctgtagtgat ctgcttcata  28200
cagtgcatcg actacgtctg cgtgcgggtg gcttacttta gacaccaccc ccagtatcgc  28260
aacagggaca tagcggctct cctaagactt gtttaaaatc atggccaaat taactgtgat  28320
tggtcttctg atcatctgct gcgtcctagc cgcgattggg actcaagctc ctaccaccac  28380
cagcgctccc agaaagagac atgtatcctg cagcttcaag cgtccctgga atataccccca  28440
atgctttact gatgaacctg aaatctcttt ggcttggtac ttcagcgtca ccgcccttct  28500
tatcttctgc agtacggtta ttgcccttgc catctaccct tcccttgacc tgggctggaa  28560
tgctgtcaac tctatggaat atcccacctt cccagaacca gacctgccag acctggttgt  28620
tctaaacgcg tttcctcctc ctgctcccgt tcaaaatcag tttcgccctc cgtcccccac  28680
gcccactgag gtcagctact ttaatctaac aggcggagat gactgaaaac ctagacctag  28740
aaatggacgg tctctgcagc gagcaacgca cactagagag gcgccggcaa aaagagctcg  28800
agcgtcttaa acaagagctc caagacgcgg tggccataca ccagtgcaaa aaaggtgtct  28860
tctgtctggt aaaacaggcc acgctcacct atgaaaaaac aggtgacacc caccgcctag  28920
gatacaagct gcccacacag cgccaaaagt tcgccctcat gataggcgaa caacccatca  28980
ccgtgaccca gcactccgtg gagacagaag gctgcataca tgctccctgt aggggcgctg  29040
actgcctcta caccttgatc aaaaccctct gcggtctcag agaccttatc cctttcaatt  29100
aatcataact gtaatcaata aaaaatcact tacttgaaat ctgatagcaa gcctctgtcc  29160
aatttttttca gcaacacttc cttcccctcc tcccaactct ggtactctag gcgcctccta  29220
gctgcaaact tcctccacag tctgaaggga atgtcagatt cctcctcctg tccctccgca  29280
cccacgatct tcatgttgtt gcagatgaaa cgcgcgagat cgtctgacga gaccttcaac  29340
cccgtgtacc cctacgatac cgagatcgct ccgacttctg tccctttcct taccccctccc  29400
tttgtgtcat ccgcaggaat gcaagaaaat ccagctgggg tgctgtccct gcacttgtca  29460
gagcccctta ccacccacaa tggggccctg actctaaaaa tgggggggcgg cctgaccctg  29520
gacaaggaag ggaatctcac ttcccaaaac atcaccagtg tcgatccccc tctcaaaaaa  29580
agcaagaaca acatcagcct tcagaccgcc gcacccctcg ccgtcagctc cggggcccta  29640
acactttttg ccactccccc cctagcggtc agtggtgaca accttactgt gcagtctcag  29700
gcccctctca ctttggaaga ctcaaaacta actctggcca ccaaaggacc cctaactgtg  29760
tccgaaggca aacttgtcct agaaacagag gctcccctgc atgcaagtga cagcagcagc  29820
ctgggcctta gcgttacggc cccacttagc attaacaatg acagcctagg actagatctg  29880
caggcaccca ttgtctctca aaatggaaaa ctggctctaa atgtagcagg ccccctagct  29940
gtggccaatg gcattaatgc tttgacagta ggcacaggca aaggtattgg tctaaatgaa  30000
accagcactc acttgcaagc aaagttggtc gcccccctag gctttgatac caatggcaac  30060
```

```
attaagctaa gcgttgcagg aggcatgaga ctaaataatg acacacttat actagatgta  30120
aactacccat ttgaagctca aggccaacta agtctaagag tgggccaggg tccgctgtat  30180
gtagattcta gcagccataa cctgaccatt agatgcctta gaggattata cataacatcg  30240
tctaataacc aaaccggtct agaggccaac ataaaactaa caaaaggcct tgtctatgat  30300
ggaaatgcca tagcagtcaa tgttggtcaa ggattgcaat acagcactac tgccacatcg  30360
gaaggtgtgt atcctataca gtctaagata ggtttgggaa tggaatatga taccaacgga  30420
gccatgatga caaaactagg ctctggacta agctttgaca attcaggagc cattgtagtg  30480
ggaaacaaaa atgatgacag gcttactctg tggactacac cagacccatc tcctaactgt  30540
agaatttatt ctgaaaaaga tactaaacta accttggtgc tgactaagtg tggcagccaa  30600
atcctaggca cagtatctgc ccttgctgtc agaggcagcc ttgcgcccat cactaatgca  30660
tccagcatag tccaaatatt tctaagattt gatgaaaatg gactattgat gagcaactca  30720
tcgctagacg gtgattactg gaattacaga aatggggact ccactaatag cacaccatat  30780
acaaatgcag taggctttat gcctaatcta gcagcctatc ctaaaggtca ggctacagct  30840
gcaaaaagca gtattgtaag ccaggtatac atggatggtg acactactaa acctataaca  30900
ctaaaaataa acttcaatgg cattgatgaa acaacagaaa atacccctgt tagtaaatat  30960
tccatgacat tctcatggag ctggcccacc gcaagctaca taggccacac ttttgcaaca  31020
aactctttta ctttctccta catcgcccaa gaataaagaa agcacagaga tgcttgtttt  31080
gatttcaaaa ttgtgtgctt ttatttattt tcagcttaca gtatttccag tagtcattcg  31140
aataaagctt aatcaaactg catgagaacc cttccacata gcttaaatta gcaccagtgc  31200
aaatggagaa aagcctcgag gtcgttgcgc ggccgggatc ggtgatcacc gatccagaca  31260
tgataagata cattgatgag tttggacaaa ccacaactag aatgcagtga aaaaaatgct  31320
ttatttgtga aatttgtgat gctattgctt tatttgtaac cattataagc tgcaataaac  31380
aagttcccgg atcgcgatcc ggcccgaggc tgtagccgac gatggtgcgc caggagagtt  31440
gttgattcat tgtttgcctc cctgctgcgg tttttcaccg aagttcatgc cagtccagcg  31500
tttttgcagc agaaaagccg ccgacttcgg tttgcggtcg cgagtgaaga tccctttctt  31560
gttaccgcca acgcgcaata tgccttgcga ggtcgcaaaa tcggcgaaat tccatacctg  31620
ttcaccgacg acggcgctga cgcgatcaaa gacgcggtga tacatatcca gccatgcaca  31680
ctgatactct tcactccaca tgtcggtgta cattgagtgc agcccggcta acgtatccac  31740
gccgtattcg gtgatgataa tcggctgatg cagtttctcc tgccaggcca gaagttcttt  31800
ttccagtacc ttctctgccg tttccaaatc gccgctttgg acataccatc cgtaataacg  31860
gttcaggcac agcacatcaa agagatcgct gatggtatcg gtgtgagcgt cgcagaacat  31920
tacattgacg caggtgatcg gacgcgtcgg gtcgagttta cgcgttgctt ccgccagtgg  31980
cgcgaaatat tcccgtgcac cttgcggacg ggtatccggt tcgttggcaa tactccacat  32040
caccacgctt gggtggtttt tgtcacgcgc tatcagctct ttaatcgcct gtaagtgcgc  32100
ttgctgagtt tccccgttga ctgcctcttc gctgtacagt tctttcggct tgttgcccgc  32160
ttcgaaacca atgcctaaag agaggttaaa gccgacagca gcagtttcat caatcaccac  32220
gatgccatgt tcatctgccc agtcgagcat ctcttcagcg taagggtaat gcgaggtacg  32280
gtaggagttg gccccaatcc agtccattaa tgcgtggtcg tgcaccatca gcacgttatc  32340
gaatcctttg ccacgcaagt ccgcatcttc atgacgacca aagccagtaa agtagaacgg  32400
tttgtggtta atcaggaact gttcgccctt cactgccact gaccggatgc cgacgcgaag  32460
```

cgggtagata tcacactctg tctggctttt ggctgtgacg cacagttcat agagataacc 32520
ttcacccggt tgccagaggt gcggattcac cacttgcaaa gtcccgctag tgccttgtcc 32580
agttgcaacc acctgttgat ccgcatcacg cagttcaacg ctgacatcac cattggccac 32640
cacctgccag tcaacagacg cgtggttaca gtcttgcgcg acatgcgtca ccacggtgat 32700
atcgtccacc caggtgttcg gcgtggtgta gagcattac 32739

<210> SEQ ID NO 26
<211> LENGTH: 114
<212> TYPE: DNA
<213> ORGANISM: Artificial Sequence
<220> FEATURE:
<223> OTHER INFORMATION: IL-2 core promoter

<400> SEQUENCE: 26
acattttgac acccccataa tatttttcca gaattaacag tataaattgc atctcttgtt 60
caagagttcc ctatcactct ctttaatcac tactcacagt aacctcaact cctg 114

<210> SEQ ID NO 27
<211> LENGTH: 55
<212> TYPE: DNA
<213> ORGANISM: Artificial Sequence
<220> FEATURE:
<223> OTHER INFORMATION: IL-2 minimal promoter

<400> SEQUENCE: 27
tcaagagttc cctatcactc tctttaatca ctactcacag taacctcaac tcctg 55

<210> SEQ ID NO 28
<211> LENGTH: 380
<212> TYPE: DNA
<213> ORGANISM: Artificial Sequence
<220> FEATURE:
<223> OTHER INFORMATION: IL-2 enhancer and promoter variant

<400> SEQUENCE: 28
tgatatcttt tctgagttac ttttgtatcc ccaccccctt aaagaaagga ggaaaaactg 60
tttcatacag aaggcgttaa ttgcatgaat tagagctatc acctaagtgt gggctaatgt 120
aacaaagagg gatttcacct acatccattc agtcagtctt tgggggttta aagaaattcc 180
aaagagtcat cagaagagga aaaatgaagg taatgttttt tcagactggt aaagtctttg 240
aaaatatgtg taatatgtaa aacattttga cacccccata atatttttcc agaattaaca 300
gtataaattg catctcttgt tcaagagttc cctatcactc tctttaatca ctactcacag 360
taacctcaac tcctgccaca 380

<210> SEQ ID NO 29
<211> LENGTH: 373
<212> TYPE: DNA
<213> ORGANISM: Artificial Sequence
<220> FEATURE:
<223> OTHER INFORMATION: L-2 enhancer and promoter variant

<400> SEQUENCE: 29
ttttctgagt tacttttgta tccccacccc cttaaagaaa ggaggaaaaa ctgtttcata 60
cagaaggcgt taattgcatg aattagagct atcacctaag tgtgggctaa tgtaacaaag 120
agggatttca cctacatcca ttcagtcagt ctttgggggt ttaaagaaat tccaaagagt 180
catcagaaga ggaaaaatga aggtaatgtt ttttcagact ggtaaagtct ttgaaaatat 240

-continued

```
gtgtaatatg taaaacattt tgacaccccc ataatatttt tccagaatta acagtataaa    300

ttgcatctct tgttcaagag ttccctatca ctctctttaa tcactactca cagtaacctc    360

aactcctgcc aca                                                       373
```

<210> SEQ ID NO 30
<211> LENGTH: 161
<212> TYPE: DNA
<213> ORGANISM: Artificial Sequence
<220> FEATURE:
<223> OTHER INFORMATION: (NF-KB)1-IL2 promoter variant

<400> SEQUENCE: 30

```
aattggtccc atcgaagagg gatttcacct acataattgg tcccgggaca ttttgacacc     60

cccataatat ttttccagaa ttaacagtat aaattgcatc tcttgttcaa gagttcccta    120

tcactctctt taatcactac tcacagtaac ctcaactcct g                        161
```

<210> SEQ ID NO 31
<211> LENGTH: 201
<212> TYPE: DNA
<213> ORGANISM: Artificial Sequence
<220> FEATURE:
<223> OTHER INFORMATION: (NF-KB)3-IL2 promoter variant

<400> SEQUENCE: 31

```
aattggtccc atcgaagagg gatttcacct acataagagg gatttcacct acataagagg     60

gatttcacct acataattgg tcccgggaca ttttgacacc cccataatat ttttccagaa    120

ttaacagtat aaattgcatc tcttgttcaa gagttcccta tcactctctt taatcactac    180

tcacagtaac ctcaactcct g                                              201
```

<210> SEQ ID NO 32
<211> LENGTH: 268
<212> TYPE: DNA
<213> ORGANISM: Artificial Sequence
<220> FEATURE:
<223> OTHER INFORMATION: (NF-kB)6-IL2 promoter variant

<400> SEQUENCE: 32

```
aattggtccc atcgaagagg gatttcacct acataagagg gatttcacct acataagagg     60

gatttcacct acataattgg taagagggat ttcacctaca taagagggat ttcacctaca    120

taagagggat ttcacctaca taattggtcc cgggacattt tgacaccccc ataatatttt    180

tccagaatta acagtataaa ttgcatctct tgttcaagag ttccctatca ctctctttaa    240

tcactactca cagtaacctc aactcctg                                       268
```

<210> SEQ ID NO 33
<211> LENGTH: 177
<212> TYPE: DNA
<213> ORGANISM: Artificial Sequence
<220> FEATURE:
<223> OTHER INFORMATION: 1X NFAT response elements-IL2 promoter variant

<400> SEQUENCE: 33

```
aattggtccc atcgaattag gaggaaaaac tgtttcatac agaaggcgtc aattggtccc     60

gggacatttt gacaccccca taatattttt ccagaattaa cagtataaat tgcatctctt    120

gttcaagagt tccctatcac tctctttaat cactactcac agtaacctca actcctg       177
```

<210> SEQ ID NO 34
<211> LENGTH: 256

<212> TYPE: DNA
<213> ORGANISM: Artificial Sequence
<220> FEATURE:
<223> OTHER INFORMATION: 3X NFAT response elements-IL2 promoter variant

<400> SEQUENCE: 34
tgatatcaat tggtcccatc gaattaggag gaaaaactgt ttcatacaga aggcgtcaat 60
taggaggaaa aactgtttca tacagaaggc gtcaattagg aggaaaaact gtttcataca 120
gaaggcgtca attggtcccg ggacattttg acacccccat aatatttttc cagaattaac 180
agtataaatt gcatctcttg ttcaagagtt ccctatcact ctctttaatc actactcaca 240
gtaacctcaa ctcctg 256

<210> SEQ ID NO 35
<211> LENGTH: 249
<212> TYPE: DNA
<213> ORGANISM: Artificial Sequence
<220> FEATURE:
<223> OTHER INFORMATION: 3X NFAT response elements-IL2 promoter variant

<400> SEQUENCE: 35
aattggtccc atcgaattag gaggaaaaac tgtttcatac agaaggcgtc aattaggagg 60
aaaaactgtt tcatacagaa ggcgtcaatt aggaggaaaa actgtttcat acagaaggcg 120
tcaattggtc ccgggacatt ttgacacccc cataatattt ttccagaatt aacagtataa 180
attgcatctc ttgttcaaga gttccctatc actctcttta atcactactc acagtaacct 240
caactcctg 249

<210> SEQ ID NO 36
<211> LENGTH: 358
<212> TYPE: DNA
<213> ORGANISM: Artificial Sequence
<220> FEATURE:
<223> OTHER INFORMATION: 6X NFAT response elements-IL2 promoter variant

<400> SEQUENCE: 36
gaattaggag gaaaaactgt ttcatacaga aggcgtcaat taggaggaaa aactgtttca 60
tacagaaggc gtcaattagg aggaaaaact gtttcataca gaaggcgtca attggtccca 120
tcgaattagg aggaaaaact gtttcataca gaaggcgtca attaggagga aaaactgttt 180
catacagaag gcgtcaatta ggaggaaaaa ctgtttcata cagaaggcgt caattggtcc 240
cgggacattt tgacaccccc ataatatttt tccagaatta acagtataaa ttgcatctct 300
tgttcaagag ttccctatca ctctccttaa tcactactca cagtaacctc aactcctg 358

<210> SEQ ID NO 37
<211> LENGTH: 374
<212> TYPE: DNA
<213> ORGANISM: Artificial Sequence
<220> FEATURE:
<223> OTHER INFORMATION: 6X NFAT response elements-IL2 promoter variant

<400> SEQUENCE: 37
tgatatcgaa ttaggaggaa aaactgtttc atacagaagg cgtcaattag gaggaaaaac 60
tgtttcatac agaaggcgtc aattaggagg aaaaactgtt tcatacagaa ggcgtcaatt 120
ggtcccatcg aattaggagg aaaaactgtt tcatacagaa ggcgtcaatt aggaggaaaa 180
actgtttcat acagaaggcg tcaattagga ggaaaaactg tttcatacag aaggcgtcaa 240
ttggtcccgg gacattttga cacccccata atatttttcc agaattaaca gtataaattg 300

-continued catctcttgt tcaagagttc cctatcactc tctttaatca ctactcacag taacctcaac 360
tcctgaattc catg 374

<210> SEQ ID NO 38
<211> LENGTH: 358
<212> TYPE: DNA
<213> ORGANISM: Artificial Sequence
<220> FEATURE:
<223> OTHER INFORMATION: 6X NFAT response elements-IL2 promoter variant

<400> SEQUENCE: 38
gaattaggag gaaaaactgt ttcatacaga aggcgtcaat taggaggaaa aactgtttca 60
tacagaaggc gtcaattagg aggaaaaact gtttcataca gaaggcgtca attggtccca 120
tcgaattagg aggaaaaact gtttcataca gaaggcgtca attaggagga aaaactgttt 180
catacagaag gcgtcaatta ggaggaaaaa ctgtttcata cagaaggcgt caattggtcc 240
cgggacattt tgacaccccc ataatatttt tccagaatta acagtataaa ttgcatctct 300
tgttcaagag ttccctatca ctctctttaa tcactactca cagtaacctc aactcctg 358

<210> SEQ ID NO 39
<211> LENGTH: 365
<212> TYPE: DNA
<213> ORGANISM: Artificial Sequence
<220> FEATURE:
<223> OTHER INFORMATION: 6X NFAT response elements-IL2 promoter variant

<400> SEQUENCE: 39
tgatatcgaa ttaggaggaa aaactgtttc atacagaagg cgtcaattag gaggaaaaac 60
tgtttcatac agaaggcgtc aattaggagg aaaaactgtt tcatacagaa ggcgtcaatt 120
ggtcccatcg aattaggagg aaaaactgtt tcatacagaa ggcgtcaatt aggaggaaaa 180
actgtttcat acagaaggcg tcaattagga ggaaaaactg tttcatacag aaggcgtcaa 240
ttggtcccgg gacattttga cacccccata atatttttcc agaattaaca gtataaattg 300
catctcttgt tcaagagttc cctatcactc tctttaatca ctactcacag taacctcaac 360
tcctg 365

<210> SEQ ID NO 40
<211> LENGTH: 244
<212> TYPE: DNA
<213> ORGANISM: Artificial Sequence
<220> FEATURE:
<223> OTHER INFORMATION: human EEF1A1 promoter variant

<400> SEQUENCE: 40
gagcgtgcgt gaggctccgg tgcccgtcag tgggcagagc gcacatcgcc cacagtcccc 60
gagaagttgg ggggaggggg tcggcgattg aaccggtgcc tagagaaggt ggcgcggggt 120
aaactgggaa agtgatgtcg tgtactggct ccgccttttt cccgagggtg ggggagaacc 180
gtatataagt gcagtagtcg ccgtgaacgt tctttttcgc aacgggtttg ccgccagaac 240
acag 244

<210> SEQ ID NO 41
<211> LENGTH: 236
<212> TYPE: DNA
<213> ORGANISM: Artificial Sequence
<220> FEATURE:
<223> OTHER INFORMATION: human EEF1A1 promoter variant

<400> SEQUENCE: 41
gcgtgaggct ccggtgcccg tcagtgggca gagcgcacat cgcccacagt ccccgagaag 60 ttgggggggag gggtcggcaa ttgaaccggt gcctagagaa ggtggcgcgg ggtaaactgg 120
gaaagtgatg tcgtgtactg gctccgcctt tttcccgagg gtgggggaga accgtatata 180
agtgcagtag tcgccgtgaa cgttcttttt cgcaacgggt ttgccgccag aacaca 236

<210> SEQ ID NO 42
<211> LENGTH: 1266
<212> TYPE: DNA
<213> ORGANISM: Artificial Sequence
<220> FEATURE:
<223> OTHER INFORMATION: human EEF1A1 promoter and enhancer

<400> SEQUENCE: 42
gagctttgca aagatggata aagttttaaa cagagaggaa tctttgcagc taatggacct 60
tctaggtctt gaaaggagtg ggaattggct ccggtgcccg tcagtgggca gagcgcacat 120
cgcccacagt ccccgagaag ttgggggggag gggtcggcaa ttgaaccggt gcctagagaa 180
ggtggcgcgg ggtaaactgg gaaagtgatg tcgtgtactg gctccgcctt tttcccgagg 240
gtgggggaga accgtatata agtgcagtag tcgccgtgaa cgttcttttt cgcaacgggt 300
ttgccgccag aacacaggta agtgccgtgt gtggttcccg cgggcctggc ctctttacgg 360
gttatggccc ttgcgtgcct tgaattactt ccacctggct gcagtacgtg attcttgatc 420
ccgagcttcg ggttggaagt gggtgggaga gttcgaggcc ttgcgcttaa ggagcccctt 480
cgcctcgtgc ttgagttgag gcctggcctg ggcgctgggg ccgccgcgtg cgaatctggt 540
ggcaccttcg cgcctgtctc gctgctttcg ataagtctct agccatttaa aatttttgat 600
gacctgctgc gacgcttttt ttctggcaag atagtcttgt aaatgcgggc caagatctgc 660
acactggtat ttcggttttt ggggccgcgg gcggcgacgg ggcccgtgcg tcccagcgca 720
catgttcggc gaggcggggc ctgcgagcgc ggccaccgag aatcggacgg gggtagtctc 780
aagctggccg gcctgctctg gtgcctggcc tcgcgccgcc gtgtatcgcc ccgccctggg 840
cggcaaggct ggcccggtcg gcaccagttg cgtgagcgga aagatggccg cttcccggcc 900
ctgctgcagg gagctcaaaa tggaggacgc ggcgctcggg agagcgggcg ggtgagtcac 960
ccacacaaag gaaaagggcc tttccgtcct cagccgtcgc ttcatgtgac tccacggagt 1020
accgggcgcc gtccaggcac ctcgattagt tctcgagctt ttggagtacg tcgtctttag 1080
gttgggggga ggggttttat gcgatggagt ttccccacac tgagtgggtg gagactgaag 1140
ttaggccagc ttggcacttg atgtaattct ccttggaatt tgcccttttt gagtttggat 1200
cttggttcat tctcaagcct cagacagtgg ttcaaagttt ttttcttcca tttcaggtgt 1260
cgtgag 1266

<210> SEQ ID NO 43
<211> LENGTH: 571
<212> TYPE: DNA
<213> ORGANISM: Artificial Sequence
<220> FEATURE:
<223> OTHER INFORMATION: human UBC promoter

<400> SEQUENCE: 43
ggcctccgcg ccgggttttg gcgcctcccg cgggcgcccc cctcctcacg gcgagcgctg 60
ccacgtcaga cgaagggcgc agcgagcgtc ctgatccttc cgcccggacg ctcaggacag 120
cggcccgctg ctcataagac tcggccttag aaccccagta tcagcagaag gacattttag 180
gacgggactt gggtgactct agggcactgg ttttctttcc agagagcgga acaggcgagg 240
aaaagtagtc ccttctcggc gattctgcgg agggatctcc gtggggcggt gaacgccgat 300
gattatataa ggacgcgccg ggtgtggcac agctagttcc gtcgcagccg ggatttgggt 360
cgcggttctt gtttgtggat cgctgtgatc gtcacttggt gagtagcggg ctgctgggct 420
gggtacgtgc gctcggggtt ggcgagtgtg ttttgtgaag ttttttaggc accttttgaa 480
atgtaatcat ttgggtcaat atgtaatttt cagtgttaga ctagtaaatt gtccgctaaa 540
ttctggccgt ttttggcttt tttgttagac g 571

<210> SEQ ID NO 44
<211> LENGTH: 81
<212> TYPE: DNA
<213> ORGANISM: Artificial Sequence
<220> FEATURE:
<223> OTHER INFORMATION: synthetic minimal promoter 1

<400> SEQUENCE: 44
aggtctatat aagcagagct cgtttagtga accctcattc tggagacgga tcccgagccg 60
agtgttttga cctccataga a 81

<210> SEQ ID NO 45
<211> LENGTH: 10
<212> TYPE: PRT
<213> ORGANISM: Artificial Sequence
<220> FEATURE:
<223> OTHER INFORMATION: HBV Peptides from Core 1

<400> SEQUENCE: 45

Phe Leu Pro Ser Asp Phe Phe Pro Ser Val
1 5 10

<210> SEQ ID NO 46
<211> LENGTH: 8
<212> TYPE: PRT
<213> ORGANISM: Artificial Sequence
<220> FEATURE:
<223> OTHER INFORMATION: HBV Peptides from Core 2

<400> SEQUENCE: 46

Cys Trp Gly Glu Leu Met Thr Leu
1 5

<210> SEQ ID NO 47
<211> LENGTH: 9
<212> TYPE: PRT
<213> ORGANISM: Artificial Sequence
<220> FEATURE:
<223> OTHER INFORMATION: HBV Peptides from Core 3

<400> SEQUENCE: 47

Gly Val Trp Ile Arg Thr Pro Pro Ala
1 5

<210> SEQ ID NO 48
<211> LENGTH: 11
<212> TYPE: PRT
<213> ORGANISM: Artificial Sequence
<220> FEATURE:
<223> OTHER INFORMATION: HBV Peptides from Core 4

<400> SEQUENCE: 48

Ser Thr Leu Pro Glu Thr Thr Val Val Arg Arg
1 5 10

<210> SEQ ID NO 49
<211> LENGTH: 11
<212> TYPE: PRT
<213> ORGANISM: Artificial Sequence
<220> FEATURE:
<223> OTHER INFORMATION: HBV Peptides from Core 5

<400> SEQUENCE: 49

Leu Thr Phe Gly Arg Glu Thr Val Leu Glu Tyr
1 5 10

<210> SEQ ID NO 50
<211> LENGTH: 10
<212> TYPE: PRT
<213> ORGANISM: Artificial Sequence
<220> FEATURE:
<223> OTHER INFORMATION: HBV Peptides from Core 6

<400> SEQUENCE: 50

Asp Leu Leu Asp Thr Ala Ser Ala Leu Tyr
1 5 10

<210> SEQ ID NO 51
<211> LENGTH: 10
<212> TYPE: PRT
<213> ORGANISM: Artificial Sequence
<220> FEATURE:
<223> OTHER INFORMATION: HBV Peptides from Core 7

<400> SEQUENCE: 51

Leu Trp Phe His Ile Ser Cys Leu Thr Phe
1 5 10

<210> SEQ ID NO 52
<211> LENGTH: 9
<212> TYPE: PRT
<213> ORGANISM: Artificial Sequence
<220> FEATURE:
<223> OTHER INFORMATION: HBV Peptides from Core 8

<400> SEQUENCE: 52

Glu Tyr Leu Val Ser Phe Gly Val Trp
1 5

<210> SEQ ID NO 53
<211> LENGTH: 9
<212> TYPE: PRT
<213> ORGANISM: Artificial Sequence
<220> FEATURE:
<223> OTHER INFORMATION: HBV Peptides from Polymerase 1

<400> SEQUENCE: 53

Phe Leu Lys Gln Gln Tyr Met Asn Leu
1 5

<210> SEQ ID NO 54
<211> LENGTH: 9
<212> TYPE: PRT
<213> ORGANISM: Artificial Sequence
<220> FEATURE:
<223> OTHER INFORMATION: HBV Peptides from Polymerase 2

<400> SEQUENCE: 54

Phe Leu Ser Lys Gln Tyr Met Asp Leu
1 5

<210> SEQ ID NO 55
<211> LENGTH: 9
<212> TYPE: PRT
<213> ORGANISM: Artificial Sequence
<220> FEATURE:
<223> OTHER INFORMATION: HBV Peptides from Polymerase 3

<400> SEQUENCE: 55

Thr Val Ser Thr Lys Leu Cys Lys Ile
1               5

<210> SEQ ID NO 56
<211> LENGTH: 9
<212> TYPE: PRT
<213> ORGANISM: Artificial Sequence
<220> FEATURE:
<223> OTHER INFORMATION: HBV Peptides from Polymerase 4

<400> SEQUENCE: 56

Gly Leu Ser Arg Tyr Val Ala Arg Leu
1               5

<210> SEQ ID NO 57
<211> LENGTH: 9
<212> TYPE: PRT
<213> ORGANISM: Artificial Sequence
<220> FEATURE:
<223> OTHER INFORMATION: HBV Peptides from Polymerase 5

<400> SEQUENCE: 57

Lys Leu His Leu Tyr Ser His Pro Ile
1               5

<210> SEQ ID NO 58
<211> LENGTH: 9
<212> TYPE: PRT
<213> ORGANISM: Artificial Sequence
<220> FEATURE:
<223> OTHER INFORMATION: HBV Peptides from Polymerase 6

<400> SEQUENCE: 58

Phe Leu Leu Ser Leu Gly Ile His Leu
1               5

<210> SEQ ID NO 59
<211> LENGTH: 9
<212> TYPE: PRT
<213> ORGANISM: Artificial Sequence
<220> FEATURE:
<223> OTHER INFORMATION: HBV Peptides from Polymerase 7

<400> SEQUENCE: 59

Ser Leu Tyr Ala Asp Ser Pro Ser Val
1               5

<210> SEQ ID NO 60
<211> LENGTH: 9
<212> TYPE: PRT
<213> ORGANISM: Artificial Sequence
<220> FEATURE:
<223> OTHER INFORMATION: HBV Peptides from Polymerase 8

<400> SEQUENCE: 60

Ala Leu Met Pro Leu Tyr Ala Cys Ile
1               5

<210> SEQ ID NO 61
<211> LENGTH: 10410
<212> TYPE: DNA
<213> ORGANISM: Artificial Sequence
<220> FEATURE:
<223> OTHER INFORMATION: GCAd-RTS-IL12 design 1

<400> SEQUENCE: 61

```
ttcaaatatg tatccgctca tgagacaata accctgataa atgcttcaat aatattgaaa     60
aaggaagagt atgagtattc aacatttccg tgtcgccctt attccctttt ttgcggcatt    120
ttgccttcct gtttttgctc acccagaaac gctggtgaaa gtaaaagatg ctgaagatca    180
gttgggtgca cgagtgggtt acatcgaact ggatctcaac agcggtaaga tccttgagag    240
ttttcgcccc gaagaacgtt ttccaatgat gagcactttt aaagttctgc tatgtggcgc    300
ggtattatcc cgtattgacg ccgggcaaga gcaactcggt cgccgcatac actattctca    360
gaatgacttg gttgagtact caccagtcac agaaaagcat cttacggatg gcatgacagt    420
aagagaatta tgcagtgctg ccataaccat gagtgataac actgcggcca acttacttct    480
gacaacgatc ggaggaccga aggagctaac cgcttttttg cacaacatgg gggatcatgt    540
aactcgcctt gatcgttggg aaccggagct gaatgaagcc ataccaaacg acgagcgtga    600
caccacgatg cctgtagcaa tggcaacaac gttgcgcaaa ctattaactg gcgaactact    660
tactctagct tcccggcaac aattaataga ctggatggag gcggataaag ttgcaggacc    720
acttctgcgc tcggcccttc cggctggctg gtttattgct gataaatctg gagccggtga    780
gcgtgggtct cgcggtatca ttgcagcact ggggccagat ggtaagccct cccgtatcgt    840
agttatctac acgacgggga gtcaggcaac tatggatgaa cgaaatagac agatcgctga    900
gataggtgcc tcactgatta agcattggta actgtcagac caagtttact catatatact    960
ttagattgat ttaaaacttc atttttaatt taaaaggatc taggtgaaga tcctttttga   1020
taatctcatg accaaaatcc cttaacgtga gttttcgttc cactgagcgt cagaccccgt   1080
agaaaagatc aaaggatctt cttgagatcc tttttttctg cgcgtaatct gctgcttgca   1140
aacaaaaaaa ccaccgctac cagcggtggt ttgtttgccg gatcaagagc taccaactct   1200
ttttccgaag gtaactggct tcagcagagc gcagatacca aatactgttc ttctagtgta   1260
gccgtagtta ggccaccact tcaagaactc tgtagcaccg cctacatacc tcgctctgct   1320
aatcctgtta ccagtggctg ctgccagtgg cgataagtcg tgtcttaccg ggttggactc   1380
aagacgatag ttaccggata aggcgcagcg gtcgggctga acggggggtt cgtgcacaca   1440
gcccagcttg gagcgaacga cctacaccga actgagatac ctacagcgtg agctatgaga   1500
aagcgccacg cttcccgaag ggagaaaggc ggacaggtat ccggtaagcg gcagggtcgg   1560
aacaggagag cgcacgaggg agcttccagg gggaaacgcc tggtatcttt atagtcctgt   1620
cgggtttcgc cacctctgac ttgagcgtcg atttttgtga tgctcgtcag gggggcggag   1680
cctatggaaa aacgccagca acgcggcctt tttacggttc ctggcctttt gctggccttt   1740
tgctcacatg ttctttcctg cgttatcccc tgattctgtg gataaccgta ttaccgcctt   1800
tgagtgagct gataccgctc gccgcagccg aacgaccgag cgcagcgagt cagtgagcga   1860
ggaagcggaa gagcgcccaa tacgcaaacc gcctctcccc gcgcgttggc cgattcatta   1920
atgcagctgg cacgacaggt ttcccgactg gaaagcgggc agtgagcgca acgcaattaa   1980
tgtgagttag ctcactcatt aggcacccca ggctttacac tttatgcttc cggctcgtat   2040
gttgtgtgga attgtgagcg gataacaatt tcacacagga aacagctatg accatgatta   2100
```

```
cgccaagctg ggtcaagtct tccagtttaa gcagcagagc ggtcagtttc tcatcccgag   2160
cagacgcgcg agaggccgcg ccgctcgcca ccaaagagct gtaaaggtcc gtagccatgc   2220
tgcgcgcggt cgcggcggcg gcggaggcgg cggcggaggt cgcggcgtcc agcggagttc   2280
ctcccacggt cgcgtaggcc attgtagacg aatttgaagg cagaacgggg cgtccatcca   2340
cgttggaacc catcacattc tgacgcactc cagcccagtg aggcatgcgc actgtcagat   2400
aggggctaaa gatgcttcca tcaaagctgt tgccggtgtc gctcatggcg gcggctgttg   2460
caagacaaaa cagagagacc cttagacccc caatttatac acgccccacc cttctagcca   2520
cgcccacctt acccacctca atcggtatcc tcatcgctag acccaaactc ggccctggtg   2580
caggccagca ccagatggtc aggcctgcag gccgcaataa aatatcttta ttttcattac   2640
atctgtgtgt tggttttttg tgtgaatcga tagtactaac atacgctctc catcaaaaca   2700
aaacgaaaca aaacaaacta gcaaaatagg ctgtccccag tgcaagtgca ggtgccagaa   2760
catttctcta tcgataatgc aggtcggagt actgtcctcc gagcggagta ctgtcctccg   2820
agcggagtac tgtcctccga gcggagtact gtcctccgag cggagtactg tcctccgagc   2880
ggagtactgt cctccgagcg gagactcttc gaaggaagag gggcggggtc gatcgacccc   2940
gcccctcttc cttcgaagga agaggggcgg ggtcgaagac ctagagggta tataatgggt   3000
gccttagctg gtgtgtgagc tcatcttcct gtagatcacg cgtgccacca tgggtcacca   3060
gcagttggtc atctcttggt tttccctggt tttctggca tctcccctcg tggccatatg   3120
ggaactgaag aaagatgttt atgtcgtaga attggattgg tatccggatg cccctggaga   3180
aatggtggtc ctcacctgtg acacccctga agaagatggt atcacctgga ccttggacca   3240
gagcagtgag gtcttaggct ctggcaaaac cctgaccatc caagtcaaag agtttggaga   3300
tgctggccag tacacctgtc acaaaggagg cgaggttcta agccattcgc tcctgctgct   3360
tcacaaaaag gaagatggaa tttggtccac tgatatttta aaggaccaga aagaacccaa   3420
aaataagacc tttctaagat gcgaggccaa gaattattct ggacgtttca cctgctggtg   3480
gctgacgaca atcagtactg atttgacatt cagtgtcaaa agcagcagag gctcttctga   3540
cccccaaggg gtgacgtgcg gagctgctac actctctgca gagagagtca gaggggacaa   3600
caaggagtat gagtactcag tggagtgcca ggaggacagt gcctgcccag ctgctgagga   3660
gagtctgccc attgaggtca tggtggatgc cgttcacaag ctcaagtatg aaaactacac   3720
cagcagcttc ttcatcaggg acatcatcaa acctgaccca cccaagaact tgcagctgaa   3780
gccattaaag aattctcggc aggtggaggt cagctgggag taccctgaca cctggagtac   3840
tccacattcc tacttctccc tgacattctg cgttcaggtc cagggcaaga gcaagagaga   3900
aaagaaagat agagtcttca cggacaagac ctcagccacg gtcatctgcc gcaaaaatgc   3960
cagcattagc gtgcgggccc aggaccgcta ctatagctca tcttggagcg aatgggcatc   4020
tgtgccctgc agttaggttg ggcgagctcg aattcattga tccccccggc tgcaggaatt   4080
cgatatcaag ctcgggatcc gaattccgcc cccccccccc cccccccccct aacgttactg   4140
gccgaagccg cttggaataa ggccggtgtg cgtttgtcta tatgttattt tccaccatat   4200
tgccgtcttt tggcaatgtg agggcccgga aacctggccc tgtcttcttg acgagcattc   4260
ctaggggtct ttcccctctc gccaaaggaa tgcaaggtct gttgaatgtc gtgaaggaag   4320
cagttcctct ggaagcttct tgaagacaaa caacgtctgt agcgaccctt tgcaggcagc   4380
ggaacccccc acctggcgac aggtgcctct gcggccaaaa gccacgtgta taagatacac   4440
ctgcaaaggc ggcacaaccc cagtgccacg ttgtgagttg gatagttgtg gaaagagtca   4500
```

aatggctctc ctcaagcgta ttcaacaagg ggctgaagga tgcccagaag gtaccccatt 4560
gtatgggatc tgatctgggg cctcggtgca catgctttac atgtgtttag tcgaggttaa 4620
aaaaacgtct aggccccccg aaccacgggg acgtggtttt cctttgaaaa acacgatgat 4680
aatatggcca caaccatggg tccagcgcgc agcctcctcc ttgtggctac cctggtcctc 4740
ctggaccacc tcagtttggc cagaaacctc cccgtggcca ctccagaccc aggaatgttc 4800
ccatgccttc accactccca aaacctgctg agggccgtca gcaacatgct ccagaaggcc 4860
agacaaactc tagaatttta cccttgcact tctgaagaga ttgatcatga agatatcaca 4920
aaagataaaa ccagcacagt ggaggcctgt ttaccattgg aattaaccaa gaatgagagt 4980
tgcctaaatt ccagagagac ctctttcata actaatggga gttgcctggc ctccagaaag 5040
acctctttta tgatggccct gtgccttagt agtatttatg aagacttgaa gatgtaccag 5100
gtggagttca agaccatgaa tgcaaagctt ctgatggatc ctaagaggca gatctttcta 5160
gatcaaaaca tgctggcagt tattgatgag ctgatgcagg ccctgaattt caacagtgag 5220
actgtgccac aaaaatcctc ccttgaagaa ccggattttt ataaaactaa aatcaagctc 5280
tgcatacttc ttcatgcttt cagaattcgg gcagtgacta ttgatagagt gatgagctat 5340
ctgaatgctt cctaacgtac gtcgacatcg agaacttgtt tattgcagct tataatggtt 5400
acaaataaag caatagcatc acaaatttca caaataaagc atttttttca ctgcattcta 5460
gttgtggttt gtccaaactc atcaatgtat cttatcatgt ctgggcgcgc cggcctccgc 5520
gccgggtttt ggcgcctccc gcgggcgccc ccctcctcac ggcgagcgct gccacgtcag 5580
acgaagggcg cagcgagcgt cctgatcctt ccgcccggac gctcaggaca gcggcccgct 5640
gctcataaga ctcggcctta gaaccccagt atcagcagaa ggacatttta ggacgggact 5700
tgggtgactc tagggcactg gttttctttc cagagagcgg aacaggcgag gaaaagtagt 5760
cccttctcgg cgattctgcg gagggatctc cgtggggcgg tgaacgccga tgattatata 5820
aggacgcgcc gggtgtggca cagctagttc cgtcgcagcc gggatttggg tcgcggttct 5880
tgtttgtgga tcgctgtgat cgtcacttgg tgagtagcgg gctgctgggc tgggtacgtg 5940
cgctcggggt tggcgagtgt gttttgtgaa gtttttttagg caccttttga aatgtaatca 6000
tttgggtcaa tatgtaattt tcagtgttag actagtaaat tgtccgctaa attctggccg 6060
tttttggctt ttttgttaga cgagctagcg ccgccaccat gggccctaaa aagaagcgta 6120
aagtcgcccc cccgaccgat gtcagcctgg gggacgagct ccacttagac ggcgaggacg 6180
tggcgatggc gcatgccgac gcgctagacg atttcgatct ggacatgttg ggggacgggg 6240
attccccggg tccgggattt accccccacg actccgcccc ctacggcgct ctggatatgg 6300
ccgacttcga gtttgagcag atgtttaccg atgcccttgg aattgacgag tacggtgggg 6360
aattcgagat gcctgtggac aggatcctgg aggcagagct tgctgtggaa cagaagagtg 6420
accagggcgt tgagggtcct gggggaaccg ggggtagcgg cagcagccca aatgaccctg 6480
tgactaacat ctgtcaggca gctgacaaac agctattcac gcttgttgag tgggcgaaga 6540
ggatcccaca cttttcctcc ttgcctctgg atgatcaggt catattgctg cgggcaggct 6600
ggaatgaact cctcattgcc tccttttcac accgatccat tgatgttcga gatggcatcc 6660
tccttgccac aggtcttcac gtgcaccgca actcagccca ttcagcagga gtaggagcca 6720
tctttgatcg ggtgctgaca gagctagtgt ccaaaatgcg tgacatgagg atggacaaga 6780
cagagcttgg ctgcctgagg gcaatcattc tgtttaatcc agaggtgagg ggtttgaaat 6840

```
ccgcccagga agttgaactt ctacgtgaaa aagtatatgc cgctttggaa gaatatacta   6900
gaacaacaca tcccgatgaa ccaggaagat ttgcaaaact tttgcttcgt ctgccttctt   6960
tacgttccat aggccttaag tgtttggagc atttgttttt ctttcgcctt attggagatg   7020
ttccaattga tacgttcctg atggagatgc ttgaatcacc ttctgattca taatctagcc   7080
tagcccccct ctccctcccc ccccccctaac gttactggcc gaagccgctt ggaataaggc   7140
cggtgtgcgt ttgtctatat gttattttcc accatattgc cgtcttttgg caatgtgagg   7200
gcccggaaac ctggccctgt cttcttgacg agcattccta ggggtctttc ccctctcgcc   7260
aaaggaatgc aaggtctgtt gaatgtcgtg aaggaagcag ttcctctgga agcttcttga   7320
agacaaacaa cgtctgtagc gaccctttgc aggcagcgga acccccccacc tggcgacagg   7380
tgcctctgcg gccaaaagcc acgtgtataa gatacacctg caaaggcggc acaaccccag   7440
tgccacgttg tgagttggat agttgtggaa agagtcaaat ggctctcctc aagcgtattc   7500
aacaaggggc tgaaggatgc ccagaaggta ccccattgta tgggatctga tctggggcct   7560
cggtgcacat gctttacatg tgtttagtcg aggttaaaaa acgtctaggc cccccgaacc   7620
acggggacgt ggttttcctt tgaaaaacac gatctctagg cgccaccatg aagctactgt   7680
cttctatcga acaagcatgc gatatttgcc gacttaaaaa gctcaagtgc tccaaagaaa   7740
aaccgaagtg cgccaagtgt ctgaagaaca actgggagtg tcgctactct cccaaaacca   7800
aaaggtctcc gctgactagg gcacatctga cagaagtgga atcaaggcta gaaagactgg   7860
aacagctatt tctactgatt tttcctcgag aagaccttga catgattttg aaaatggatt   7920
ctttacagga tataaaagca ttgttaacag gattatttgt acaagataat gtgaataaag   7980
atgccgtcac agatagattg gcttcagtgg agactgatat gcctctaaca ttgagacagc   8040
atagaataag tgcgacatca tcatcggaag agagtagtaa caaaggtcaa agacagttga   8100
ctgtatcgcc ggaattcccg gggatccggc ctgagtgcgt agtacccgag actcagtgcg   8160
ccatgaagcg gaaagagaag aaagcacaga aggagaagga caaactgcct gtcagcacga   8220
cgacggtgga cgaccacatg ccgcccatta tgcagtgtga acctccacct cctgaagcag   8280
caaggattca cgaagtggtc ccaaggtttc tctccgacaa gctgttggtg acaaaccggc   8340
agaaaaacat cccccagttg acagccaacc agcagttcct tatcgccagg ctcatctggt   8400
accaggacgg gtacgagcag ccttctgatg aagatttgaa gaggattacg cagacgtggc   8460
agcaagcgga cgatgaaaac gaagagtcgg acactcccctt ccgccagatc acagagatga   8520
ctatcctcac ggtccaactt atcgtggagt tcgcgaaggg attgccaggg ttcgccaaga   8580
tctcgcagcc tgatcaaatt acgctgctta aggcttgctc aagtgaggta atgatgctcc   8640
gagtcgcgcg acgatacgat gcggcctcag acagtattct gttcgcgaac aaccaagcgt   8700
acactcgcga caactaccgc aaggctggca tggccgaggt catcgaggat ctactgcact   8760
tctgccggtg catgtactct atggcgttgg acaacatcca ttacgcgctg ctcacggctg   8820
tcgtcatctt ttctgaccgg ccagggttgg agcagccgca actggtggaa gagatccagc   8880
ggtactacct gaatacgctc cgcatctata tcctgaacca gctgagcggg tcggcgcgtt   8940
cgtccgtcat atacggcaag atcctctcaa tcctctctga gctacgcacg ctcggcatgc   9000
aaaactccaa catgtgcatc tccctcaagc tcaagaacag aaagctgccg cctttcctcg   9060
aggagatctg ggatgtggcg gacatgtcgc acacccaacc gccgcctatc ctcgagtccc   9120
ccacgaatct ctaggcggcc tctagagcgg ccgccaccgc ggggagatcc agacatgata   9180
agatacattg atgagtttgg acaaaccaca actagaatgc agtgaaaaaa atgctttatt   9240
```

tgtgaaattt gtgatgctat tgctttattt gtaaccatta taagctgcaa taaacaagtt 9300
aacaacaaca attgcattca ttttatgttt caggttcagg gggaggtgtg ggaggttttt 9360
taaagcaagt aaaacctcta caaatgtggt atggctgatt atgatcaccg gtcaaatgac 9420
ggtgacaata aaacggagac tttgacccgg aacgcggaaa ttcacgtaaa aaacacctgg 9480
gcgagtcctc cacgtaatcg gtcaaagtcc ctcggccctc ggtaaatatt acgcactatg 9540
actaacgccc tattattcag ttttcacttc cccgtttcac ttttcgcgcg aaaatggcca 9600
aatcttacat ggtcccgccc aaaattacta cgatatccgg tgaaaagcgc gcgaaaattg 9660
gcacttccgg aggtaggcgg cgctcatcaa aaacgtcaca ttttccgcga cggaagcttg 9720
catgtgagct cctcccactt gcaaatgcca cacttccgcc acacctccca accctactcg 9780
cgcgtcctac gtcacccgcc ccgcctctcc ccgcccacct cattatcata ttggccacaa 9840
tccaaaataa ggtatattat tgatgatggt ttaaacgccc aattcactgg ccgtcgtttt 9900
acaacgtcgt gactgggaaa accctggcgt tacccaactt aatcgccttg cagcacatcc 9960
ccctttcgcc agctggcgta atagcgaaga ggcccgcacc gatcgccctt cccaacagtt 10020
gcgcagcctg aatggcgaat ggcgcctgat gcggtatttt ctccttacgc atctgtgcgg 10080
tatttcacac cgcatatggt gcactctcag tacaatctgc tctgatgccg catagttaag 10140
ccagccccga cacccgccaa cacccgctga cgcgccctga cgggcttgtc tgctcccggc 10200
atccgcttac agacaagctg tgaccgtctc cgggagctgc atgtgtcaga ggttttcacc 10260
gtcatcaccg aaacgcgcga gacgaaaggg cctcgtgata cgcctatttt tataggttaa 10320
tgtcatgata ataatggttt cttagacgtc aggtggcact tttcggggaa atgtgcgcgg 10380
aacccctatt tgtttatttt tctaaataca 10410

<210> SEQ ID NO 62
<211> LENGTH: 10040
<212> TYPE: DNA
<213> ORGANISM: Artificial Sequence
<220> FEATURE:
<223> OTHER INFORMATION: GCAd-RTS-IL12 design 2

<400> SEQUENCE: 62
ttcaaatatg tatccgctca tgagacaata accctgataa atgcttcaat aatattgaaa 60
aaggaagagt atgagtattc aacatttccg tgtcgccctt attccctttt ttgcggcatt 120
ttgccttcct gtttttgctc acccagaaac gctggtgaaa gtaaaagatg ctgaagatca 180
gttgggtgca cgagtgggtt acatcgaact ggatctcaac agcggtaaga tccttgagag 240
ttttcgcccc gaagaacgtt ttccaatgat gagcactttt aaagttctgc tatgtggcgc 300
ggtattatcc cgtattgacg ccgggcaaga gcaactcggt cgccgcatac actattctca 360
gaatgacttg gttgagtact caccagtcac agaaaagcat cttacggatg gcatgacagt 420
aagagaatta tgcagtgctg ccataaccat gagtgataac actgcggcca acttacttct 480
gacaacgatc ggaggaccga aggagctaac cgcttttttg cacaacatgg gggatcatgt 540
aactcgcctt gatcgttggg aaccggagct gaatgaagcc ataccaaacg acgagcgtga 600
caccacgatg cctgtagcaa tggcaacaac gttgcgcaaa ctattaactg gcgaactact 660
tactctagct tcccggcaac aattaataga ctggatggag gcggataaag ttgcaggacc 720
acttctgcgc tcggcccttc cggctggctg gtttattgct gataaatctg gagccggtga 780
gcgtgggtct cgcggtatca ttgcagcact ggggccagat ggtaagccct cccgtatcgt 840
agttatctac acgacgggga gtcaggcaac tatggatgaa cgaaatagac agatcgctga 900
gataggtgcc tcactgatta agcattggta actgtcagac caagtttact catatatact 960
ttagattgat ttaaaacttc atttttaatt taaaaggatc taggtgaaga tcctttttga 1020
taatctcatg accaaaatcc cttaacgtga gttttcgttc cactgagcgt cagaccccgt 1080
agaaaagatc aaaggatctt cttgagatcc tttttttctg cgcgtaatct gctgcttgca 1140
aacaaaaaaa ccaccgctac cagcggtggt ttgtttgccg gatcaagagc taccaactct 1200
ttttccgaag gtaactggct tcagcagagc gcagatacca aatactgttc ttctagtgta 1260
gccgtagtta ggccaccact tcaagaactc tgtagcaccg cctacatacc tcgctctgct 1320
aatcctgtta ccagtggctg ctgccagtgg cgataagtcg tgtcttaccg ggttggactc 1380
aagacgatag ttaccggata aggcgcagcg gtcgggctga acggggggtt cgtgcacaca 1440
gcccagcttg gagcgaacga cctacaccga actgagatac ctacagcgtg agctatgaga 1500
aagcgccacg cttcccgaag ggagaaaggc ggacaggtat ccggtaagcg gcagggtcgg 1560
aacaggagag cgcacgaggg agcttccagg gggaaacgcc tggtatcttt atagtcctgt 1620
cgggtttcgc cacctctgac ttgagcgtcg atttttgtga tgctcgtcag gggggcggag 1680
cctatggaaa aacgccagca acgcggcctt tttacggttc ctggcctttt gctggccttt 1740
tgctcacatg ttctttcctg cgttatcccc tgattctgtg gataaccgta ttaccgcctt 1800
tgagtgagct gataccgctc gccgcagccg aacgaccgag cgcagcgagt cagtgagcga 1860
ggaagcggaa gagcgcccaa tacgcaaacc gcctctcccc gcgcgttggc cgattcatta 1920
atgcagctgg cacgacaggt ttcccgactg gaaagcgggc agtgagcgca acgcaattaa 1980
tgtgagttag ctcactcatt aggcacccca ggctttacac tttatgcttc cggctcgtat 2040
gttgtgtgga attgtgagcg gataacaatt tcacacagga aacagctatg accatgatta 2100
cgccaagctg ggtcaagtct tccagtttaa gcagcagagc ggtcagtttc tcatcccgag 2160
cagacgcgcg agaggccgcg ccgctcgcca ccaaagagct gtaaaggtcc gtagccatgc 2220
tgcgcgcggt cgcggcggcg gcggaggcgg cggcggaggt cgcggcgtcc agcggagttc 2280
ctcccacggt cgcgtaggcc attgtagacg aatttgaagg cagaacgggg cgtccatcca 2340
cgttggaacc catcacattc tgacgcactc cagcccagtg aggcatgcgc actgtcagat 2400
aggggctaaa gatgcttcca tcaaagctgt tgccggtgtc gctcatggcg gcggctgttg 2460
caagacaaaa cagagagacc cttagacccc caatttatac acgccccacc cttctagcca 2520
cgcccacctt acccacctca atcggtatcc tcatcgctag acccaaactc ggccctggtg 2580
caggccagca ccagatggtc aggcctgcag gtacgtagcc gcaataaaat atctttattt 2640
tcattacatc tgtgtgttgg tttttgtgt gaatccatag tactaacata cgctctccat 2700
caaaacaaaa cgaaacaaaa caaactagca aaataggctg tccccagtgc aagtccaggt 2760
gccagaacat ttctctatcc ataatgcagg ggtaccggaa ggaagagggg cggggtcgat 2820
cgaccccgcc cctcttcctt cgaaggaaga ggggcggggt ccaattgcgg agtactgtcc 2880
tccgagcgga gtactgtcct ccgagcggag tactgtcctc cgagcggagt actgtcctcc 2940
gagcggagta ctgtcctccg agcggagtac tgtcctccga gcggagagtc cccggggacc 3000
tagagggtat ataatgggtg ccttagctgg tgtgtgacct catcttcctg tacgcccctg 3060
caggagatca cgcgtgccac catgggtcac cagcagttgg tcatctcttg gttttccctg 3120
gtttttctgg catctcccct cgtggccata tgggaactga agaaagatgt ttatgtcgta 3180
gaattggatt ggtatccgga tgcccctgga gaaatggtgg tcctcacctg tgacacccct 3240

```
gaagaagatg gtatcacctg gaccttggac cagagcagtg aggtcttagg ctctggcaaa   3300
accctgacca tccaagtcaa agagtttgga gatgctggcc agtacacctg tcacaaagga   3360
ggcgaggttc taagccattc gctcctgctg cttcacaaaa aggaagatgg aatttggtcc   3420
actgatattt taaaggacca gaaagaaccc aaaaataaga cctttctaag atgcgaggcc   3480
aagaattatt ctggacgttt cacctgctgg tggctgacga caatcagtac tgatttgaca   3540
ttcagtgtca aaagcagcag aggctcttct gacccccaag ggtgacgtg cggagctgct    3600
acactctctg cagagagagt cagaggggac aacaaggagt atgagtactc agtggagtgc   3660
caggaggaca gtgcctgccc agctgctgag gagagtctgc ccattgaggt catggtggat   3720
gccgttcaca agctcaagta tgaaaactac accagcagct tcttcatcag ggacatcatc   3780
aaacctgacc cacccaagaa cttgcagctg aagccattaa agaattctcg gcaggtggag   3840
gtcagctggg agtaccctga cacctggagt actccacatt cctacttctc cctgacattc   3900
tgcgttcagg tccagggcaa gagcaagaga gaaaagaaag atagagtctt cacggacaag   3960
acctcagcca cggtcatctg ccgcaaaaat gccagcatta gcgtgcgggc ccaggaccgc   4020
tactatagct catcttggag cgaatgggca tctgtgccct gcagtctcga gggcggcgga   4080
gagggcagag gaagtcttct aacatgcggt gacgtggagg agaatcccgg ccctaggatg   4140
ggtccagcgc gcagcctcct ccttgtggct accctggtcc tcctggacca cctcagtttg   4200
gccagaaacc tccccgtggc cactccagac ccaggaatgt tcccatgcct tcaccactcc   4260
caaaacctgc tgagggccgt cagcaacatg ctccagaagg ccagacaaac tctagaattt   4320
tacccttgca cttctgaaga gattgatcat gaagatatca caaaagataa aaccagcaca   4380
gtggaggcct gtttaccatt ggaattaacc aagaatgaga gttgcctaaa ttccagagag   4440
acctctttca taactaatgg gagttgcctg gcctccagaa agacctcttt tatgatggcc   4500
ctgtgcctta gtagtattta tgaagacttg aagatgtacc aggtggagtt caagaccatg   4560
aatgcaaagc ttctgatgga tcctaagagg cagatctttc tagatcaaaa catgctggca   4620
gttattgatg agctgatgca ggccctgaat ttcaacagtg agactgtgcc acaaaaatcc   4680
tcccttgaag aaccggattt ttataaaact aaaatcaagc tctgcatact tcttcatgct   4740
ttcagaattc gggcagtgac tattgataga gtgatgagct atctgaatgc ttcctaaatc   4800
gatttattta tcggcataaa taattttttt gaagaagtaa tactattttt cttttttttt   4860
gtaaataaat gggttaaggg atgtaacatt gtttgttgtt tggtgggggt tggggcctcc   4920
gcgccgggtt ttggcgcctc ccgcgggcgc ccccctcctc acggcgagcg ctgccacgtc   4980
agacgaaggg cgcagcgagc gtcctgatcc ttccgcccgg acgctcagga cagcggcccg   5040
ctgctcataa gactcggcct tagaacccca gtatcagcag aaggacattt taggacggga   5100
cttgggtgac tctagggcac tggttttctt tccagagagc ggaacaggcg aggaaaagta   5160
gtcccttctc ggcgattctg cggagggatc tccgtggggc ggtgaacgcc gatgattata   5220
taaggacgcg ccgggtgtgg cacagctagt tccgtcgcag ccgggatttg ggtcgcggtt   5280
cttgtttgtg gatcgctgtg atcgtcactt ggtgagtagc gggctgctgg gctgggtacg   5340
tgcgctcggg gttggcgagt gtgttttgtg aagtttttta ggcacctttt gaaatgtaat   5400
catttgggtc aatatgtaat tttcagtgtt agactagtaa attgtccgct aaattctggc   5460
cgtttttggc tttttgtta gacgagctag cgccgccacc atgggcccta aaaagaagcg    5520
taaagtcgcc cccccgaccg atgtcagcct gggggacgag ctccacttag acggcgagga   5580
```

```
cgtggcgatg gcgcatgccg acgcgctaga cgatttcgat ctggacatgt tgggggacgg   5640
ggattccccg ggtccgggat ttacccccca cgactccgcc ccctacggcg ctctggatat   5700
ggccgacttc gagtttgagc agatgtttac cgatgccctt ggaattgacg agtacggtgg   5760
ggaattcgag atgcctgtgg acaggatcct ggaggcagag cttgctgtgg aacagaagag   5820
tgaccagggc gttgagggtc ctgggggaac cgggggtagc ggcagcagcc caaatgaccc   5880
tgtgactaac atctgtcagg cagctgacaa acagctattc acgcttgttg agtgggcgaa   5940
gaggatccca cacttttcct ccttgcctct ggatgatcag gtcatattgc tgcgggcagg   6000
ctggaatgaa ctcctcattg cctccttttc acaccgatcc attgatgttc gagatggcat   6060
cctccttgcc acaggtcttc acgtgcaccg caactcagcc cattcagcag gagtaggagc   6120
catctttgat cgggtgctga cagagctagt gtccaaaatg cgtgacatga ggatggacaa   6180
gacagagctt ggctgcctga gggcaatcat tctgtttaat ccagaggtga ggggtttgaa   6240
atccgcccag gaagttgaac ttctacgtga aaaagtatat gccgctttgg aagaatatac   6300
tagaacaaca catcccgatg aaccaggaag atttgcaaaa cttttgcttc gtctgccttc   6360
tttacgttcc ataggcctta agtgtttgga gcatttgttt ttctttcgcc ttattggaga   6420
tgttccaatt gatacgttcc tgatggagat gcttgaatca ccttctgatt cataatctag   6480
cctagccccc ctctccctcc cccccccta acgttactgg ccgaagccgc ttggaataag   6540
gccggtgtgc gtttgtctat atgttatttt ccaccatatt gccgtctttt ggcaatgtga   6600
gggcccggaa acctggccct gtcttcttga cgagcattcc taggggtctt tcccctctcg   6660
ccaaaggaat gcaaggtctg ttgaatgtcg tgaaggaagc agttcctctg gaagcttctt   6720
gaagacaaac aacgtctgta gcgacccttt gcaggcagcg gaacccccca cctggcgaca   6780
ggtgcctctg cggccaaaag ccacgtgtat aagatacacc tgcaaaggcg gcacaacccc   6840
agtgccacgt tgtgagttgg atagttgtgg aaagagtcaa atggctctcc tcaagcgtat   6900
tcaacaaggg gctgaaggat gcccagaagg taccccattg tatgggatct gatctggggc   6960
ctcggtgcac atgctttaca tgtgtttagt cgaggttaaa aaacgtctag gccccccgaa   7020
ccacggggac gtggttttcc tttgaaaaac acgatctcta ggcgccacca tgaagctact   7080
gtcttctatc gaacaagcat gcgatatttg ccgacttaaa aagctcaagt gctccaaaga   7140
aaaaccgaag tgcgccaagt gtctgaagaa caactgggag tgtcgctact ctcccaaaac   7200
caaaaggtct ccgctgacta gggcacatct gacagaagtg gaatcaaggc tagaaagact   7260
ggaacagcta tttctactga tttttcctcg agaagacctt gacatgattt tgaaaatgga   7320
ttctttacag gatataaaag cattgttaac aggattattt gtacaagata atgtgaataa   7380
agatgccgtc acagatagat tggcttcagt ggagactgat atgcctctaa cattgagaca   7440
gcatagaata agtgcgacat catcatcgga agagagtagt aacaaaggtc aaagacagtt   7500
gactgtatcg ccggaattcc cggggatccg gcctgagtgc gtagtacccg agactcagtg   7560
cgccatgaag cggaaagaga agaaagcaca gaaggagaag gacaaactgc ctgtcagcac   7620
gacgacggtg gacgaccaca tgccgcccat tatgcagtgt gaacctccac ctcctgaagc   7680
agcaaggatt cacgaagtgg tcccaaggtt tctctccgac aagctgttgg tgacaaaccg   7740
gcagaaaaac atcccccagt tgacagccaa ccagcagttc cttatcgcca ggctcatctg   7800
gtaccaggac gggtacgagc agccttctga tgaagatttg aagaggatta cgcagacgtg   7860
gcagcaagcg gacgatgaaa acgaagagtc ggacactccc ttccgccaga tcacagagat   7920
gactatcctc acggtccaac ttatcgtgga gttcgcgaag ggattgccag ggttcgccaa   7980
```

gatctcgcag cctgatcaaa ttacgctgct taaggcttgc tcaagtgagg taatgatgct 8040
ccgagtcgcg cgacgatacg atgcggcctc agacagtatt ctgttcgcga acaaccaagc 8100
gtacactcgc gacaactacc gcaaggctgg catggccgag gtcatcgagg atctactgca 8160
cttctgccgg tgcatgtact ctatggcgtt ggacaacatc cattacgcgc tgctcacggc 8220
tgtcgtcatc ttttctgacc ggccagggtt ggagcagccg caactggtgg aagagatcca 8280
gcggtactac ctgaatacgc tccgcatcta tatcctgaac cagctgagcg ggtcggcgcg 8340
ttcgtccgtc atatacggca agatcctctc aatcctctct gagctacgca cgctcggcat 8400
gcaaaactcc aacatgtgca tctccctcaa gctcaagaac agaaagctgc cgcctttcct 8460
cgaggagatc tgggatgtgg cggacatgtc gcacacccaa ccgccgccta tcctcgagtc 8520
ccccacgaat ctctaaatcg attacgctcc tctactcttt gagacatcac tggcctataa 8580
taaatgggtt aatttatgta acaaaattgc cttggcttgt taactttatt agacattctg 8640
atgtttgcat tgtgtaaata ctgttgtatt ggaaaagcgt gccaagatgg attattgtaa 8700
ttcagtgtct tttttagtag cgtcacgtgc caaacactgt tagtcacaga gggcatgaga 8760
cagcctgtgc tggaacagct cagttcatag ggctatggag atggggagaa aggggcgctt 8820
ctgtcagaga caagctgtgg tctgggaagg ccttagcact aaaagcacca caatgagaag 8880
caaccgccag aagcagggcc cgcaggcctt tgttccagct gcaaagagaa aggaaaaagt 8940
ggggaataag agttggggct gcggaggggg tggggagcat tgtgcaggtt ccgtacttga 9000
acagaaagca gggaccaaca caaggaaggg cgcgccaccg gtcaaatgac ggtgacaata 9060
aaacggagac tttgacccgg aacgcggaaa ttcacgtaaa aaacacctgg gcgagtcctc 9120
cacgtaatcg gtcaaagtcc ctcggccctc ggtaaatatt acgcactatg actaacgccc 9180
tattattcag ttttcacttc cccgtttcac ttttcgcgcg aaaatggcca aatcttacat 9240
ggtcccgccc aaaattacta cgatatccgg tgaaaagcgc gcgaaaattg gcacttccgg 9300
aggtaggcgg cgctcatcaa aaacgtcaca ttttccgcga cggaagcttg catgtgagct 9360
cctcccactt gcaaatgcca cacttccgcc acacctccca accctactcg cgcgtcctac 9420
gtcacccgcc ccgcctctcc ccgcccacct cattatcata ttggccacaa tccaaaataa 9480
ggtatattat tgatgatggt ttaaacgccc aattcactgg ccgtcgtttt acaacgtcgt 9540
gactgggaaa accctggcgt tacccaactt aatcgccttg cagcacatcc ccctttcgcc 9600
agctggcgta atagcgaaga ggcccgcacc gatcgccctt cccaacagtt gcgcagcctg 9660
aatggcgaat ggcgcctgat gcggtatttt ctccttacgc atctgtgcgg tatttcacac 9720
cgcatatggt gcactctcag tacaatctgc tctgatgccg catagttaag ccagccccga 9780
cacccgccaa cacccgctga cgcgccctga cgggcttgtc tgctcccggc atccgcttac 9840
agacaagctg tgaccgtctc cgggagctgc atgtgtcaga ggttttcacc gtcatcaccg 9900
aaacgcgcga gacgaaaggg cctcgtgata cgcctatttt tataggttaa tgtcatgata 9960
ataatggttt cttagacgtc aggtggcact tttcggggaa atgtgcgcgg aacccctatt 10020
tgtttatttt tctaaataca 10040

<210> SEQ ID NO 63
<211> LENGTH: 9949
<212> TYPE: DNA
<213> ORGANISM: Artificial Sequence
<220> FEATURE:
<223> OTHER INFORMATION: GCAd-RTS-IL12 design 3

<400> SEQUENCE: 63
ttcaaatatg tatccgctca tgagacaata accctgataa atgcttcaat aatattgaaa 60
aaggaagagt atgagtattc aacatttccg tgtcgccctt attccctttt ttgcggcatt 120
ttgccttcct gtttttgctc acccagaaac gctggtgaaa gtaaaagatg ctgaagatca 180
gttgggtgca cgagtgggtt acatcgaact ggatctcaac agcggtaaga tccttgagag 240
ttttcgcccc gaagaacgtt ttccaatgat gagcactttt aaagttctgc tatgtggcgc 300
ggtattatcc cgtattgacg ccgggcaaga gcaactcggt cgccgcatac actattctca 360
gaatgacttg gttgagtact caccagtcac agaaaagcat cttacggatg gcatgacagt 420
aagagaatta tgcagtgctg ccataaccat gagtgataac actgcggcca acttacttct 480
gacaacgatc ggaggaccga aggagctaac cgcttttttg cacaacatgg gggatcatgt 540
aactcgcctt gatcgttggg aaccggagct gaatgaagcc ataccaaacg acgagcgtga 600
caccacgatg cctgtagcaa tggcaacaac gttgcgcaaa ctattaactg gcgaactact 660
tactctagct tcccggcaac aattaataga ctggatggag gcggataaag ttgcaggacc 720
acttctgcgc tcggcccttc cggctggctg gtttattgct gataaatctg gagccggtga 780
gcgtgggtct cgcggtatca ttgcagcact ggggccagat ggtaagccct cccgtatcgt 840
agttatctac acgacgggga gtcaggcaac tatggatgaa cgaaatagac agatcgctga 900
gataggtgcc tcactgatta agcattggta actgtcagac caagtttact catatatact 960
ttagattgat ttaaaacttc atttttaatt taaaaggatc taggtgaaga tcctttttga 1020
taatctcatg accaaaatcc cttaacgtga gttttcgttc cactgagcgt cagaccccgt 1080
agaaaagatc aaaggatctt cttgagatcc tttttttctg cgcgtaatct gctgcttgca 1140
aacaaaaaaa ccaccgctac cagcggtggt ttgtttgccg gatcaagagc taccaactct 1200
ttttccgaag gtaactggct tcagcagagc gcagatacca aatactgttc ttctagtgta 1260
gccgtagtta ggccaccact tcaagaactc tgtagcaccg cctacatacc tcgctctgct 1320
aatcctgtta ccagtggctg ctgccagtgg cgataagtcg tgtcttaccg ggttggactc 1380
aagacgatag ttaccggata aggcgcagcg gtcgggctga acggggggtt cgtgcacaca 1440
gcccagcttg gagcgaacga cctacaccga actgagatac ctacagcgtg agctatgaga 1500
aagcgccacg cttcccgaag ggagaaaggc ggacaggtat ccggtaagcg gcagggtcgg 1560
aacaggagag cgcacgaggg agcttccagg gggaaacgcc tggtatcttt atagtcctgt 1620
cgggtttcgc cacctctgac ttgagcgtcg atttttgtga tgctcgtcag gggggcggag 1680
cctatggaaa aacgccagca acgcggcctt tttacggttc ctggcctttt gctggccttt 1740
tgctcacatg ttctttcctg cgttatcccc tgattctgtg gataaccgta ttaccgcctt 1800
tgagtgagct gataccgctc gccgcagccg aacgaccgag cgcagcgagt cagtgagcga 1860
ggaagcggaa gagcgcccaa tacgcaaacc gcctctcccc gcgcgttggc cgattcatta 1920
atgcagctgg cacgacaggt ttcccgactg gaaagcgggc agtgagcgca acgcaattaa 1980
tgtgagttag ctcactcatt aggcacccca ggctttacac tttatgcttc cggctcgtat 2040
gttgtgtgga attgtgagcg gataacaatt tcacacagga aacagctatg accatgatta 2100
cgccaagctg ggtcaagtct tccagtttaa gcagcagagc ggtcagtttc tcatcccgag 2160
cagacgcgcg agaggccgcg ccgctcgcca ccaaagagct gtaaaggtcc gtagccatgc 2220
tgcgcgcggt cgcggcggcg gcggaggcgg cggcggaggt cgcggcgtcc agcggagttc 2280
ctcccacggt cgcgtaggcc attgtagacg aatttgaagg cagaacgggg cgtccatcca 2340
cgttggaacc catcacattc tgacgcactc cagcccagtg aggcatgcgc actgtcagat 2400
aggggctaaa gatgcttcca tcaaagctgt tgccggtgtc gctcatggcg gcggctgttg 2460
caagacaaaa cagagagacc cttagacccc caatttatac acgccccacc cttctagcca 2520
cgcccacctt acccacctca atcggtatcc tcatcgctag acccaaactc ggccctggtg 2580
caggccagca ccagatggtc aggcctgcag gtacgtagcc gcaataaaat atctttattt 2640
tcattacatc tgtgtgttgg tttttttgtgt gaatccatag tactaacata cgctctccat 2700
caaaacaaaa cgaaacaaaa caaactagca aaataggctg tccccagtgc aagtccaggt 2760
gccagaacat ttctctatcc ataatgcagg ggtaccggaa ggaagagggg cggggtcgat 2820
cgaccccgcc cctcttcctt cgaaggaaga ggggcggggt ccaattgcgg agtactgtcc 2880
tccgagcgga gtactgtcct ccgagcggag tactgtcctc cgagcggagt actgtcctcc 2940
gagcggagta ctgtcctccg agcggagtac tgtcctccga gcggagagtc cccggggacc 3000
tagagggtat ataatgggtg ccttagctgg tgtgtgacct catcttcctg tacgcccctg 3060
caggcagccg ctaaatccaa ggtaaggtca gaagagctag cgccaccatg tgtcaccagc 3120
agttggtcat ctcttggttc agcctggttt ttctggcatc tcccctcgtg gccatctggg 3180
aactgaagaa agatgtttat gtcgtagaat tggattggta tcccgacgcc cctggagaaa 3240
tggtggtcct gacatgtgac acccctgaag aagatggtat cacctggacc ttggaccaga 3300
gcagtgaggt cttaggctct ggcaagaccc tgaccatcca agtcaaagag tttggagatg 3360
ctggccagta cacctgtcac aaaggaggcg aggttctaag ccattcgctc ctgctgcttc 3420
acaaaaagga agatggaatt tggtccactg acattctgaa ggaccagaaa gaacccaaga 3480
ataagacctt tctaagatgc gaggccaaga attattctgg acgtttcacc tgctggtggc 3540
tgacgacaat cagtactgat ttgacattca gtgtcaaaag cagcagaggc tcttctgacc 3600
cccaaggggt gacgtgcgga gctgctacac tcagcgccga gagagtcaga ggggacaaca 3660
aggagtatga gtactcagtg gagtgccagg aggacagtgc ctgcccagct gctgaggaga 3720
gtctgcccat tgaggtcatg gtggatgccg ttcacaagct caagtatgaa aactacacca 3780
gcagcttctt catcagggac atcatcaaac ctgacccacc caagaacttg cagctgaagc 3840
ccctgaagaa cagcagacag gtggaggtca gctgggagta ccctgacacc tggagtactc 3900
cacattccta cttctccctg acattctgcg ttcaggtcca gggcaagagc aagagagaaa 3960
agaaagatag agtcttcacg gacaagacct cagccacggt catctgccgc aaaaatgcca 4020
gcattagcgt gcgggcccag gaccgctact atagctcatc ttggagcgaa tgggcatctg 4080
tgccctgctc cggtggcggt ggcggcggat ctagaaacct ccccgtggcc actccagacc 4140
caggaatgtt cccatgcctt caccacagcc agaacctgct gagggccgtc agcaacatgc 4200
tccagaaggc cagacaaact ctagaatttt acccttgcac ttctgaagag attgatcatg 4260
aagatatcac aaaagataaa accagcacag tggaggcctg tttaccattg gaattaacca 4320
agaatgagag ttgcctaaat tccagagaga cctctttcat aactaatggg agttgcctgg 4380
cctccagaaa gacctctttt atgatggccc tgtgccttag tagtatttat gaagacttga 4440
agatgtacca ggtggagttc aagaccatga atgcaaagct gctgatggac cccaagaggc 4500
agatctttct agatcaaaac atgctggcag ttattgatga gctgatgcag gccctgaatt 4560
tcaacagtga gactgtgcca caaaaatcct ccccttgaaga accggatttt tataaaacta 4620
aaatcaagct ctgcatactt cttcatgctt tcagaatcag agcagtgact attgatagag 4680

-continued

```
tgatgagcta tctgaatgct tcctaaatcg atttatttat cggcataaat aatttttttg   4740
aagaagtaat actatttttc tttttttttg taaataaatg ggttaaggga tgtaacattg   4800
tttgttgttt ggtgggggtt ggggcctccg cgccgggttt tggcgcctcc cgcgggcgcc   4860
cccctcctca cggcgagcgc tgccacgtca gacgaagggc gcagcgagcg tcctgatcct   4920
tccgcccgga cgctcaggac agcggcccgc tgctcataag actcggcctt agaaccccag   4980
tatcagcaga aggacatttt aggacgggac ttgggtgact ctagggcact ggttttcttt   5040
ccagagagcg gaacaggcga ggaaaagtag tcccttctcg gcgattctgc ggagggatct   5100
ccgtggggcg gtgaacgccg atgattatat aaggacgcgc cgggtgtggc acagctagtt   5160
ccgtcgcagc cgggatttgg gtcgcggttc ttgtttgtgg atcgctgtga tcgtcacttg   5220
gtgagtagcg ggctgctggg ctgggtacgt gcgctcgggg ttggcgagtg tgttttgtga   5280
agtttttttag gcaccttttg aaatgtaatc atttgggtca atatgtaatt ttcagtgtta   5340
gactagtaaa ttgtccgcta aattctggcc gtttttggct tttttgttag acgagctagc   5400
gccgccacca tgggccctaa aaagaagcgt aaagtcgccc ccccgaccga tgtcagcctg   5460
ggggacgagc tccacttaga cggcgaggac gtggcgatgg cgcatgccga cgcgctagac   5520
gatttcgatc tggacatgtt gggggacggg gattccccgg gtccgggatt tacccccccac   5580
gactccgccc cctacggcgc tctggatatg gccgacttcg agtttgagca gatgtttacc   5640
gatgcccttg gaattgacga gtacggtggg gaattcgaga tgcctgtgga caggatcctg   5700
gaggcagagc ttgctgtgga acagaagagt gaccagggcg ttgagggtcc tgggggaacc   5760
gggggtagcg gcagcagccc aaatgaccct gtgactaaca tctgtcaggc agctgacaaa   5820
cagctattca cgcttgttga gtgggcgaag aggatcccac acttttcctc cttgcctctg   5880
gatgatcagg tcatattgct gcgggcaggc tggaatgaac tcctcattgc ctccttttca   5940
caccgatcca ttgatgttcg agatggcatc ctccttgcca caggtcttca cgtgcaccgc   6000
aactcagccc attcagcagg agtaggagcc atctttgatc gggtgctgac agagctagtg   6060
tccaaaatgc gtgacatgag gatggacaag acagagcttg gctgcctgag ggcaatcatt   6120
ctgtttaatc cagaggtgag gggtttgaaa tccgcccagg aagttgaact tctacgtgaa   6180
aaagtatatg ccgctttgga agaatatact agaacaacac atcccgatga accaggaaga   6240
tttgcaaaac ttttgcttcg tctgccttct ttacgttcca taggccttaa gtgtttggag   6300
catttgtttt tctttcgcct tattggagat gttccaattg atacgttcct gatggagatg   6360
cttgaatcac cttctgattc ataatctagc ctagcccccc tctccctccc ccccccctaa   6420
cgttactggc cgaagccgct tggaataagg ccggtgtgcg tttgtctata tgttattttc   6480
caccatattg ccgtcttttg gcaatgtgag ggcccggaaa cctggccctg tcttcttgac   6540
gagcattcct aggggtcttt cccctctcgc caaaggaatg caaggtctgt tgaatgtcgt   6600
gaaggaagca gttcctctgg aagcttcttg aagacaaaca acgtctgtag cgaccctttg   6660
caggcagcgg aaccccccac ctggcgacag gtgcctctgc ggccaaaagc cacgtgtata   6720
agatacacct gcaaaggcgg cacaacccca gtgccacgtt gtgagttgga tagttgtgga   6780
aagagtcaaa tggctctcct caagcgtatt caacaagggg ctgaaggatg cccagaaggt   6840
accccattgt atgggatctg atctggggcc tcggtgcaca tgctttacat gtgtttagtc   6900
gaggttaaaa aacgtctagg ccccccgaac cacggggacg tggttttcct ttgaaaaaca   6960
cgatctctag gcgccaccat gaagctactg tcttctatcg aacaagcatg cgatatttgc   7020
cgacttaaaa agctcaagtg ctccaaagaa aaaccgaagt gcgccaagtg tctgaagaac   7080
```

```
aactgggagt gtcgctactc tcccaaaacc aaaaggtctc cgctgactag ggcacatctg   7140
acagaagtgg aatcaaggct agaaagactg gaacagctat ttctactgat ttttcctcga   7200
gaagaccttg acatgatttt gaaaatggat tctttacagg atataaaagc attgttaaca   7260
ggattatttg tacaagataa tgtgaataaa gatgccgtca cagatagatt ggcttcagtg   7320
gagactgata tgcctctaac attgagacag catagaataa gtgcgacatc atcatcggaa   7380
gagagtagta acaaaggtca aagacagttg actgtatcgc cggaattccc ggggatccgg   7440
cctgagtgcg tagtacccga gactcagtgc gccatgaagc ggaaagagaa gaaagcacag   7500
aaggagaagg acaaactgcc tgtcagcacg acgacggtgg acgaccacat gccgcccatt   7560
atgcagtgtg aacctccacc tcctgaagca gcaaggattc acgaagtggt cccaaggttt   7620
ctctccgaca agctgttggt gacaaaccgg cagaaaaaca tcccccagtt gacagccaac   7680
cagcagttcc ttatcgccag gctcatctgg taccaggacg ggtacgagca gccttctgat   7740
gaagatttga agaggattac gcagacgtgg cagcaagcgg acgatgaaaa cgaagagtcg   7800
gacactccct tccgccagat cacagagatg actatcctca cggtccaact tatcgtggag   7860
ttcgcgaagg gattgccagg gttcgccaag atctcgcagc ctgatcaaat tacgctgctt   7920
aaggcttgct caagtgaggt aatgatgctc cgagtcgcgc gacgatacga tgcggcctca   7980
gacagtattc tgttcgcgaa caaccaagcg tacactcgcg acaactaccg caaggctggc   8040
atggccgagg tcatcgagga tctactgcac ttctgccggt gcatgtactc tatggcgttg   8100
gacaacatcc attacgcgct gctcacggct gtcgtcatct ttctgaccg gccagggttg   8160
gagcagccgc aactggtgga agagatccag cggtactacc tgaatacgct ccgcatctat   8220
atcctgaacc agctgagcgg gtcggcgcgt tcgtccgtca tatacggcaa gatcctctca   8280
atcctctctg agctacgcac gctcggcatg caaaactcca acatgtgcat ctccctcaag   8340
ctcaagaaca gaaagctgcc gcctttcctc gaggagatct gggatgtggc ggacatgtcg   8400
cacacccaac cgccgcctat cctcgagtcc cccacgaatc tctaaatcga ttacgctcct   8460
ctactctttg agacatcact ggcctataat aaatgggtta atttatgtaa caaaattgcc   8520
ttggcttgtt aactttatta gacattctga tgtttgcatt gtgtaaatac tgttgtattg   8580
gaaaagcgtg ccaagatgga ttattgtaat tcagtgtctt ttttagtagc gtcacgtgcc   8640
aaacactgtt agtcacagag ggcatgagac agcctgtgct ggaacagctc agttcatagg   8700
gctatggaga tggggagaaa ggggcgcttc tgtcagagac aagctgtggt ctgggaaggc   8760
cttagcacta aaagcaccac aatgagaagc aaccgccaga agcagggccc gcaggccttt   8820
gttccagctg caaagagaaa ggaaaaagtg gggaataaga gttggggctg cggagggggt   8880
ggggagcatt gtgcaggttc cgtacttgaa cagaaagcag ggaccaacac aaggaagggc   8940
gcgccaccgg tcaaatgacg gtgacaataa aacggagact ttgacccgga acgcggaaat   9000
tcacgtaaaa aacacctggg cgagtcctcc acgtaatcgg tcaaagtccc tcggccctcg   9060
gtaaatatta cgcactatga ctaacgccct attattcagt tttcacttcc ccgtttcact   9120
tttcgcgcga aaatggccaa atcttacatg gtcccgccca aaattactac gatatccggt   9180
gaaaagcgcg cgaaaattgg cacttccgga ggtaggcggc gctcatcaaa aacgtcacat   9240
tttccgcgac ggaagcttgc atgtgagctc ctcccacttg caaatgccac acttccgcca   9300
cacctcccaa ccctactcgc gcgtcctacg tcacccgccc cgcctctccc cgcccacctc   9360
attatcatat tggccacaat ccaaaataag gtatattatt gatgatggtt taaacgccca   9420
```

-continued

```
attcactggc cgtcgtttta caacgtcgtg actgggaaaa ccctggcgtt acccaactta   9480

atcgccttgc agcacatccc cctttcgcca gctggcgtaa tagcgaagag gcccgcaccg   9540

atcgcccttc ccaacagttg cgcagcctga atggcgaatg gcgcctgatg cggtattttc   9600

tccttacgca tctgtgcggt atttcacacc gcatatggtg cactctcagt acaatctgct   9660

ctgatgccgc atagttaagc cagccccgac acccgccaac acccgctgac gcgccctgac   9720

gggcttgtct gctcccggca tccgcttaca gacaagctgt gaccgtctcc gggagctgca   9780

tgtgtcagag gttttcaccg tcatcaccga aacgcgcgag acgaaagggc ctcgtgatac   9840

gcctattttt ataggttaat gtcatgataa taatggtttc ttagacgtca ggtggcactt   9900

ttcggggaaa tgtgcgcgga acccctattt gtttattttt ctaaataca              9949
```

<210> SEQ ID NO 64
<211> LENGTH: 54
<212> TYPE: DNA
<213> ORGANISM: Artificial Sequence
<220> FEATURE:
<223> OTHER INFORMATION: Whitlow Linker

<400> SEQUENCE: 64

```
ggcagcacct ccggcagcgg caagcctggc agcggcgagg gcagcaccaa gggc          54
```

<210> SEQ ID NO 65
<211> LENGTH: 78
<212> TYPE: DNA
<213> ORGANISM: Artificial Sequence
<220> FEATURE:
<223> OTHER INFORMATION: Linker

<400> SEQUENCE: 65

```
tctggcggag gatctggagg aggcggatct ggaggaggag gcagtggagg cggaggatct    60

ggcggaggat ctctgcag                                                  78
```

<210> SEQ ID NO 66
<211> LENGTH: 9
<212> TYPE: DNA
<213> ORGANISM: Artificial Sequence
<220> FEATURE:
<223> OTHER INFORMATION: GSG linker

<400> SEQUENCE: 66

```
ggaagcgga                                                             9
```

<210> SEQ ID NO 67
<211> LENGTH: 12
<212> TYPE: DNA
<213> ORGANISM: Artificial Sequence
<220> FEATURE:
<223> OTHER INFORMATION: SGSG linker

<400> SEQUENCE: 67

```
agtggcagcg gc                                                        12
```

<210> SEQ ID NO 68
<211> LENGTH: 45
<212> TYPE: DNA
<213> ORGANISM: Artificial Sequence
<220> FEATURE:
<223> OTHER INFORMATION: (G4S)3 linker

<400> SEQUENCE: 68

```
ggtggcggtg gctcgggcgg tggtgggtcg ggtggcggcg gatct                    45
```

<210> SEQ ID NO 69
<211> LENGTH: 12
<212> TYPE: DNA
<213> ORGANISM: Artificial Sequence
<220> FEATURE:
<223> OTHER INFORMATION: Furin cleavage site

<400> SEQUENCE: 69
cgtgcaaagc gt 12

<210> SEQ ID NO 70
<211> LENGTH: 84
<212> TYPE: DNA
<213> ORGANISM: Artificial Sequence
<220> FEATURE:
<223> OTHER INFORMATION: Fmdv

<400> SEQUENCE: 70
agagccaaga gggcaccggt gaaacagact ttgaattttg accttctgaa gttggcagga 60
gacgttgagt ccaaccctgg gccc 84

<210> SEQ ID NO 71
<211> LENGTH: 54
<212> TYPE: DNA
<213> ORGANISM: Artificial Sequence
<220> FEATURE:
<223> OTHER INFORMATION: Thosea asigna virus 2A region (T2A)

<400> SEQUENCE: 71
gagggcagag gaagtctgct aacatgcggt gacgtcgagg agaatcctgg acct 54

<210> SEQ ID NO 72
<211> LENGTH: 75
<212> TYPE: DNA
<213> ORGANISM: Artificial Sequence
<220> FEATURE:
<223> OTHER INFORMATION: Furin-GSG-T2A

<400> SEQUENCE: 72
agagctaaga ggggaagcgg agagggcaga ggaagtctgc taacatgcgg tgacgtcgag 60
gagaatcctg gacct 75

<210> SEQ ID NO 73
<211> LENGTH: 78
<212> TYPE: DNA
<213> ORGANISM: Artificial Sequence
<220> FEATURE:
<223> OTHER INFORMATION: Furin-SGSG-T2A

<400> SEQUENCE: 73
agggccaaga ggagtggcag cggcgagggc agaggaagtc ttctaacatg cggtgacgtg 60
gaggagaatc ccggccct 78

<210> SEQ ID NO 74
<211> LENGTH: 57
<212> TYPE: DNA
<213> ORGANISM: Artificial Sequence
<220> FEATURE:
<223> OTHER INFORMATION: Porcine teschovirus-1 2A region (P2A)

<400> SEQUENCE: 74
gcaacgaact tctctctcct aaaacaggct ggtgatgtgg aggagaatcc tggtcca 57

<210> SEQ ID NO 75
<211> LENGTH: 66
<212> TYPE: DNA
<213> ORGANISM: Artificial Sequence
<220> FEATURE:
<223> OTHER INFORMATION: GSG-P2A

<400> SEQUENCE: 75
ggaagcggag ctactaactt cagcctgctg aagcaggctg gagacgtgga ggagaaccct 60
ggacct 66

<210> SEQ ID NO 76
<211> LENGTH: 60
<212> TYPE: DNA
<213> ORGANISM: Artificial Sequence
<220> FEATURE:
<223> OTHER INFORMATION: Equine rhinitis A virus 2A region (E2A)

<400> SEQUENCE: 76
cagtgtacta attatgctct cttgaaattg gctggagatg ttgagagcaa ccctggacct 60

<210> SEQ ID NO 77
<211> LENGTH: 66
<212> TYPE: DNA
<213> ORGANISM: Artificial Sequence
<220> FEATURE:
<223> OTHER INFORMATION: Foot-and-mouth disease virus 2A region (F2A)

<400> SEQUENCE: 77
gtcaaacaga ccctaaactt tgatctgcta aaactggccg gggatgtgga aagtaatccc 60
ggcccc 66

<210> SEQ ID NO 78
<211> LENGTH: 93
<212> TYPE: DNA
<213> ORGANISM: Artificial Sequence
<220> FEATURE:
<223> OTHER INFORMATION: FP2A

<400> SEQUENCE: 78
cgtgcaaagc gtgcaccggt gaaacaggga agcggagcta ctaacttcag cctgctgaag 60
caggctggag acgtggagga gaaccctgga cct 93

<210> SEQ ID NO 79
<211> LENGTH: 24
<212> TYPE: DNA
<213> ORGANISM: Artificial Sequence
<220> FEATURE:
<223> OTHER INFORMATION: Linker-GSG

<400> SEQUENCE: 79
gcaccggtga aacagggaag cgga 24

<210> SEQ ID NO 80
<211> LENGTH: 15
<212> TYPE: DNA
<213> ORGANISM: Artificial Sequence
<220> FEATURE:
<223> OTHER INFORMATION: Linker

<400> SEQUENCE: 80
gcaccggtga aacag 15

<210> SEQ ID NO 81
<211> LENGTH: 18
<212> TYPE: PRT
<213> ORGANISM: Artificial Sequence
<220> FEATURE:
<223> OTHER INFORMATION: Whitlow Linker Amino Acid Sequence

<400> SEQUENCE: 81

Gly Ser Thr Ser Gly Ser Gly Lys Pro Gly Ser Gly Glu Gly Ser Thr
1 5 10 15

Lys Gly

<210> SEQ ID NO 82
<211> LENGTH: 26
<212> TYPE: PRT
<213> ORGANISM: Artificial Sequence
<220> FEATURE:
<223> OTHER INFORMATION: Linker Amino Acid Sequence

<400> SEQUENCE: 82

Ser Gly Gly Gly Ser Gly Gly Gly Gly Ser Gly Gly Gly Gly Ser Gly
1 5 10 15

Gly Gly Gly Ser Gly Gly Gly Ser Leu Gln
20 25

<210> SEQ ID NO 83
<211> LENGTH: 3
<212> TYPE: PRT
<213> ORGANISM: Artificial Sequence
<220> FEATURE:
<223> OTHER INFORMATION: GSG Linker Amino Acid Sequence

<400> SEQUENCE: 83

Gly Ser Gly
1

<210> SEQ ID NO 84
<211> LENGTH: 4
<212> TYPE: PRT
<213> ORGANISM: Artificial Sequence
<220> FEATURE:
<223> OTHER INFORMATION: SGSG Linker Amino Acid Sequence

<400> SEQUENCE: 84

Ser Gly Ser Gly
1

<210> SEQ ID NO 85
<211> LENGTH: 15
<212> TYPE: PRT
<213> ORGANISM: Artificial Sequence
<220> FEATURE:
<223> OTHER INFORMATION: G4S LINKER Amino Acid Sequence

<400> SEQUENCE: 85

Gly Gly Gly Gly Ser Gly Gly Gly Gly Ser Gly Gly Gly Gly Ser
1 5 10 15

<210> SEQ ID NO 86
<211> LENGTH: 4
<212> TYPE: PRT
<213> ORGANISM: Artificial Sequence
<220> FEATURE:
<223> OTHER INFORMATION: Furin Cleavage site Amino Acid Sequence

<400> SEQUENCE: 86

Arg Ala Lys Arg
1

<210> SEQ ID NO 87
<211> LENGTH: 28
<212> TYPE: PRT
<213> ORGANISM: Artificial Sequence
<220> FEATURE:
<223> OTHER INFORMATION: FMDV Amino Acid Sequence

<400> SEQUENCE: 87

Arg Ala Lys Arg Ala Pro Val Lys Gln Thr Leu Asn Phe Asp Leu Leu
1 5 10 15

Lys Leu Ala Gly Asp Val Glu Ser Asn Pro Gly Pro
20 25

<210> SEQ ID NO 88
<211> LENGTH: 18
<212> TYPE: PRT
<213> ORGANISM: Artificial Sequence
<220> FEATURE:
<223> OTHER INFORMATION: Thosea asigna virus 2a Region (T2A) Amino Acid Sequence

<400> SEQUENCE: 88

Glu Gly Arg Gly Ser Leu Leu Thr Cys Gly Asp Val Glu Glu Asn Pro
1 5 10 15

Gly Pro

<210> SEQ ID NO 89
<211> LENGTH: 25
<212> TYPE: PRT
<213> ORGANISM: Artificial Sequence
<220> FEATURE:
<223> OTHER INFORMATION: FURIN-SGSG-T2A Amino Acid Sequence

<400> SEQUENCE: 89

Arg Ala Lys Arg Gly Ser Gly Glu Gly Arg Gly Ser Leu Leu Thr Cys
1 5 10 15

Gly Asp Val Glu Glu Asn Pro Gly Pro
20 25

<210> SEQ ID NO 90
<211> LENGTH: 26
<212> TYPE: PRT
<213> ORGANISM: Artificial Sequence
<220> FEATURE:
<223> OTHER INFORMATION: FURIN-SGSG-T2A Amino Acid Sequence

<400> SEQUENCE: 90

Arg Ala Lys Arg Ser Gly Ser Gly Glu Gly Arg Gly Ser Leu Leu Thr
1 5 10 15

Cys Gly Asp Val Glu Glu Asn Pro Gly Pro
20 25

<210> SEQ ID NO 91
<211> LENGTH: 19
<212> TYPE: PRT
<213> ORGANISM: Artificial Sequence
<220> FEATURE:
<223> OTHER INFORMATION: Porcine teschovirus-1 2A region (P2A) Amino Acid Sequence

<400> SEQUENCE: 91

Ala Thr Asn Phe Ser Leu Leu Lys Gln Ala Gly Asp Val Glu Glu Asn

-continued

```
1               5                   10                  15

Pro Gly Pro


<210> SEQ ID NO 92
<211> LENGTH: 22
<212> TYPE: PRT
<213> ORGANISM: Artificial Sequence
<220> FEATURE:
<223> OTHER INFORMATION: GSG-P2A Amino Acid Sequence

<400> SEQUENCE: 92

Gly Ser Gly Ala Thr Asn Phe Ser Leu Leu Lys Gln Ala Gly Asp Val
1               5                   10                  15

Glu Glu Asn Pro Gly Pro
            20


<210> SEQ ID NO 93
<211> LENGTH: 20
<212> TYPE: PRT
<213> ORGANISM: Artificial Sequence
<220> FEATURE:
<223> OTHER INFORMATION: GSG-P2A Amino Acid Sequence

<400> SEQUENCE: 93

Gln Cys Thr Asn Tyr Ala Leu Leu Lys Leu Ala Gly Asp Val Glu Ser
1               5                   10                  15

Asn Pro Gly Pro
            20


<210> SEQ ID NO 94
<211> LENGTH: 22
<212> TYPE: PRT
<213> ORGANISM: Artificial Sequence
<220> FEATURE:
<223> OTHER INFORMATION: Foot-and-motuh disease virus 2A region (F2A)
      Amino Acid Sequence

<400> SEQUENCE: 94

Val Lys Gln Thr Leu Asn Phe Asp Leu Leu Lys Leu Ala Gly Asp Val
1               5                   10                  15

Glu Ser Asn Pro Gly Pro
            20


<210> SEQ ID NO 95
<211> LENGTH: 31
<212> TYPE: PRT
<213> ORGANISM: Artificial Sequence
<220> FEATURE:
<223> OTHER INFORMATION: FP2A Amino Acid Sequence

<400> SEQUENCE: 95

Arg Ala Lys Arg Ala Pro Val Lys Gln Gly Ser Gly Ala Thr Asn Phe
1               5                   10                  15

Ser Leu Leu Lys Gln Ala Gly Asp Val Glu Glu Asn Pro Gly Pro
            20                  25                  30


<210> SEQ ID NO 96
<211> LENGTH: 8
<212> TYPE: PRT
<213> ORGANISM: Artificial Sequence
<220> FEATURE:
<223> OTHER INFORMATION: LINKER-GSG Amino Acid Sequence

<400> SEQUENCE: 96
```

Ala Pro Val Lys Gln Gly Ser Gly
1 5

<210> SEQ ID NO 97
<211> LENGTH: 5
<212> TYPE: PRT
<213> ORGANISM: Artificial Sequence
<220> FEATURE:
<223> OTHER INFORMATION: LINKER Amino Acid Sequence

<400> SEQUENCE: 97

Ala Pro Val Lys Gln
1 5

<210> SEQ ID NO 98
<211> LENGTH: 154
<212> TYPE: PRT
<213> ORGANISM: Artificial Sequence
<220> FEATURE:
<223> OTHER INFORMATION: HBV HBx domain of HBV design 1

<400> SEQUENCE: 98

Met Ala Ala Arg Leu Cys Cys Gln Leu Asp Pro Ala Arg Asp Val Leu
1 5 10 15

Cys Leu Arg Pro Val Gly Ala Glu Ser Arg Gly Arg Pro Phe Ser Gly
20 25 30

Pro Leu Gly Ala Leu Ser Ser Ser Ser Pro Pro Ala Val Pro Thr Asp
35 40 45

His Gly Ala His Leu Ser Leu Arg Gly Leu Pro Val Cys Ala Phe Ser
50 55 60

Ser Ala Gly Pro Cys Ala Leu Arg Phe Thr Ser Ala Arg Arg Met Glu
65 70 75 80

Thr Thr Val Asn Ala His Gln Phe Leu Pro Lys Val Leu His Lys Arg
85 90 95

Thr Leu Gly Leu Ser Ala Met Ser Thr Thr Asp Leu Glu Ala Tyr Phe
100 105 110

Lys Asp Cys Leu Phe Lys Asp Trp Glu Glu Leu Gly Glu Glu Leu Arg
115 120 125

Leu Lys Val Phe Val Leu Gly Gly Cys Arg His Lys Leu Val Cys Ala
130 135 140

Pro Ala Pro Cys Asn Phe Phe Thr Ser Ala
145 150

<210> SEQ ID NO 99
<211> LENGTH: 454
<212> TYPE: PRT
<213> ORGANISM: Artificial Sequence
<220> FEATURE:
<223> OTHER INFORMATION: HBV Pol domain of HBV design 1

<400> SEQUENCE: 99

Gly Pro Cys Ala Glu His Gly Glu His His Ile Arg Ile Pro Arg Thr
1 5 10 15

Pro Ala Arg Val Thr Gly Gly Val Phe Leu Val Asp Lys Asn Pro His
20 25 30

Asn Thr Ala Glu Ser Arg Leu Val Val Asp Phe Ser Gln Phe Ser Arg
35 40 45

Gly Asn Tyr Arg Val Ser Trp Pro Lys Phe Ala Val Pro Asn Leu Gln
50 55 60

Ser Leu Thr Asn Leu Leu Ser Ser Asn Leu Cys Trp Leu Ser Leu Asp

```
65                  70                  75                  80

Val Ser Ala Ala Phe Tyr His Leu Pro Leu His Pro Ala Ala Met Pro
                85                  90                  95

His Leu Leu Val Gly Ser Ser Gly Leu Ser Arg Tyr Val Ala Arg Leu
            100                 105                 110

Ser Ser Asn Ser Arg Ile Ile Asn His Gln His Gly Thr Leu Gln Asn
        115                 120                 125

Leu His Asp Ser Cys Ser Arg Asn Leu Tyr Val Ser Leu Leu Leu Leu
    130                 135                 140

Tyr Lys Thr Phe Gly Trp Lys Leu His Leu Tyr Ser His Pro Ile Ile
145                 150                 155                 160

Leu Gly Phe Arg Lys Ile Pro Met Gly Val Gly Leu Ser Pro Phe Leu
                165                 170                 175

Leu Ala Gln Phe Thr Ser Ala Ile Cys Ser Val Val Arg Arg Ala Phe
            180                 185                 190

Pro His Cys Leu Ala Phe Ser Gly Ala Lys Ser Val Gln His Leu Glu
        195                 200                 205

Ser Leu Phe Thr Ala Val Thr Asn Phe Leu Leu Ser Leu Gly Ile His
    210                 215                 220

Leu Asn Pro Asn Lys Thr Lys Arg Trp Gly Tyr Ser Leu Asn Phe Met
225                 230                 235                 240

Gly Tyr Val Ile Gly Ser Trp Gly Ser Leu Pro Gln Asp His Ile Arg
                245                 250                 255

His Lys Ile Lys Glu Cys Phe Arg Lys Leu Pro Val His Arg Pro Ile
            260                 265                 270

Asp Trp Lys Val Cys Gln Arg Ile Val Gly Leu Leu Gly Phe Ala Ala
        275                 280                 285

Pro Phe Thr Gln Cys Gly Tyr Pro Ala Leu Met Pro Leu Tyr Ala Cys
    290                 295                 300

Ile Gln Ser Lys Gln Ala Phe Thr Phe Ser Pro Thr Tyr Lys Ala Phe
305                 310                 315                 320

Leu Cys Lys Gln Tyr Leu Asn Leu Tyr Pro Val Ala Arg Gln Arg Pro
                325                 330                 335

Gly Leu Cys Gln Val Phe Ala Asp Ala Thr Pro Thr Gly Trp Gly Leu
            340                 345                 350

Val Met Gly His Gln Arg Met Arg Gly Thr Phe Ser Ser Arg Lys Tyr
        355                 360                 365

Thr Ser Phe Pro Trp Leu Leu Gly Cys Ala Ala Asn Trp Ile Leu Arg
    370                 375                 380

Gly Thr Ser Phe Val Tyr Val Pro Ser Ala Leu Asn Pro Ala Asp Asp
385                 390                 395                 400

Pro Ser Arg Gly Arg Leu Gly Pro Cys Arg Pro Leu Leu His Leu Pro
                405                 410                 415

Phe Arg Pro Thr Thr Gly Arg Thr Ser Leu Tyr Ala Asp Ser Pro Ser
            420                 425                 430

Val Pro Ser His Leu Pro Asp Arg Val His Phe Ala Ser Pro Leu His
        435                 440                 445

Val Ala Trp Arg Pro Pro
    450
```

<210> SEQ ID NO 100
<211> LENGTH: 226
<212> TYPE: PRT
<213> ORGANISM: Artificial Sequence
<220> FEATURE:
<223> OTHER INFORMATION: HBV Surface (Env1) domain of HBV domain 1

<400> SEQUENCE: 100

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Ser Phe Leu Gly Gly Thr Thr Val Cys
        35                  40                  45

Leu Gly Gln Asn Ser Gln Ser Pro Thr Ser Asn His Ser Pro Thr Ser
    50                  55                  60

Cys Pro Pro Thr Cys Val Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Arg Thr Cys Thr Thr Pro Ala
        115                 120                 125

Gln Gly Thr Ser Met Tyr Pro Ser Cys Cys Cys Thr Lys Pro Ser Asp
    130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Asn Thr
        195                 200                 205

Leu Ser Pro Phe Leu Pro Leu Leu Pro Ile Phe Phe Tyr Leu Trp Val
    210                 215                 220

Tyr Ile
225

<210> SEQ ID NO 101
<211> LENGTH: 180
<212> TYPE: PRT
<213> ORGANISM: Artificial Sequence
<220> FEATURE:
<223> OTHER INFORMATION: HBV Core domain of HBV design 1

<400> SEQUENCE: 101

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Asp Met Asp Ile
            20                  25                  30

Asp Pro Tyr Lys Glu Phe Gly Ala Ser Val Glu Leu Leu Ser Phe Leu
        35                  40                  45

Pro Ser Asp Phe Phe Pro Ser Val Arg Asp Leu Leu Asp Thr Ala Thr
    50                  55                  60

Ala Leu Tyr Arg Asp Ala Leu Glu Ser Pro Glu His Cys Thr Pro His
65                  70                  75                  80

His Thr Ala Leu Arg His Val Cys Leu Cys Trp Gly Asp Leu Met Asn
                85                  90                  95

Leu Ala Thr Trp Val Gly Thr Asn Leu Glu Asp Gln Ala Ser Arg Asp

-continued

```
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Asp Leu Val
    130                 135                 140

Leu Glu Tyr Leu Val Ser Phe Gly Val Trp Ile Arg Thr Pro Pro Ala
145                 150                 155                 160

Tyr Arg Pro Ser Asn Ala Pro Ile Leu Ser Thr Leu Pro Glu Thr Thr
                165                 170                 175

Val Val Arg Gln
            180
```

<210> SEQ ID NO 102
<211> LENGTH: 226
<212> TYPE: PRT
<213> ORGANISM: Artificial Sequence
<220> FEATURE:
<223> OTHER INFORMATION: SHB(Env) domain

<400> SEQUENCE: 102

```
Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Ser Phe Leu Gly Gly Thr Thr Val Cys
        35                  40                  45

Leu Gly Gln Asn Ser Gln Ser Pro Thr Ser Asn His Ser Pro Thr Ser
    50                  55                  60

Cys Pro Pro Thr Cys Val Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Arg Thr Cys Thr Thr Pro Ala
        115                 120                 125

Gln Gly Thr Ser Met Tyr Pro Ser Cys Cys Cys Thr Lys Pro Ser Asp
    130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Asn Thr
        195                 200                 205

Leu Ser Pro Phe Leu Pro Leu Leu Pro Ile Phe Phe Tyr Leu Trp Val
    210                 215                 220

Tyr Ile
225
```

<210> SEQ ID NO 103
<211> LENGTH: 180
<212> TYPE: PRT
<213> ORGANISM: Artificial Sequence
<220> FEATURE:
<223> OTHER INFORMATION: HBeAg domain

<400> SEQUENCE: 103

```
Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Asp Met Asp Ile
            20                  25                  30

Asp Pro Tyr Lys Glu Phe Gly Ala Ser Val Glu Leu Leu Ser Phe Leu
        35                  40                  45

Pro Ser Asp Phe Phe Pro Ser Val Arg Asp Leu Leu Asp Thr Ala Thr
    50                  55                  60

Ala Leu Tyr Arg Asp Ala Leu Glu Ser Pro Glu His Cys Thr Pro His
65                  70                  75                  80

His Thr Ala Leu Arg His Val Cys Leu Cys Trp Gly Asp Leu Met Asn
                85                  90                  95

Leu Ala Thr Trp Val Gly Thr Asn Leu Glu Asp Gln Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Asp Leu Val
    130                 135                 140

Leu Glu Tyr Leu Val Ser Phe Gly Val Trp Ile Arg Thr Pro Pro Ala
145                 150                 155                 160

Tyr Arg Pro Ser Asn Ala Pro Ile Leu Ser Thr Leu Pro Glu Thr Thr
                165                 170                 175

Val Val Arg Gln
            180
```

<210> SEQ ID NO 104
<211> LENGTH: 154
<212> TYPE: PRT
<213> ORGANISM: Artificial Sequence
<220> FEATURE:
<223> OTHER INFORMATION: HBx domain

<400> SEQUENCE: 104

```
Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Phe Ser Gly
            20                  25                  30

Pro Leu Gly Ala Leu Ser Ser Ser Ser Pro Pro Ala Val Pro Thr Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala His Gln Phe Leu Pro Lys Val Leu His Lys Arg
                85                  90                  95

Thr Leu Gly Leu Ser Ala Met Ser Thr Thr Asp Leu Glu Ala Tyr Phe
            100                 105                 110

Lys Asp Cys Leu Phe Lys Asp Trp Glu Glu Leu Gly Glu Glu Leu Arg
        115                 120                 125

Leu Lys Val Phe Val Leu Gly Gly Cys Arg His Lys Leu Val Cys Ala
    130                 135                 140

Pro Ala Pro Cys Asn Phe Phe Thr Ser Ala
145                 150
```

<210> SEQ ID NO 105
<211> LENGTH: 454
<212> TYPE: PRT
<213> ORGANISM: Artificial Sequence
<220> FEATURE:
<223> OTHER INFORMATION: Pol domain

<400> SEQUENCE: 105

```
Gly Pro Cys Ala Glu His Gly Glu His His Ile Arg Ile Pro Arg Thr
1               5                   10                  15

Pro Ala Arg Val Thr Gly Gly Val Phe Leu Val Asp Lys Asn Pro His
            20                  25                  30

Asn Thr Ala Glu Ser Arg Leu Val Val Asp Phe Ser Gln Phe Ser Arg
        35                  40                  45

Gly Asn Tyr Arg Val Ser Trp Pro Lys Phe Ala Val Pro Asn Leu Gln
    50                  55                  60

Ser Leu Thr Asn Leu Leu Ser Ser Asn Leu Cys Trp Leu Ser Leu Asp
65                  70                  75                  80

Val Ser Ala Ala Phe Tyr His Leu Pro Leu His Pro Ala Ala Met Pro
                85                  90                  95

His Leu Leu Val Gly Ser Ser Gly Leu Ser Arg Tyr Val Ala Arg Leu
            100                 105                 110

Ser Ser Asn Ser Arg Ile Ile Asn His Gln His Gly Thr Leu Gln Asn
        115                 120                 125

Leu His Asp Ser Cys Ser Arg Asn Leu Tyr Val Ser Leu Leu Leu Leu
    130                 135                 140

Tyr Lys Thr Phe Gly Trp Lys Leu His Leu Tyr Ser His Pro Ile Ile
145                 150                 155                 160

Leu Gly Phe Arg Lys Ile Pro Met Gly Val Gly Leu Ser Pro Phe Leu
                165                 170                 175

Leu Ala Gln Phe Thr Ser Ala Ile Cys Ser Val Val Arg Arg Ala Phe
            180                 185                 190

Pro His Cys Leu Ala Phe Ser Gly Ala Lys Ser Val Gln His Leu Glu
        195                 200                 205

Ser Leu Phe Thr Ala Val Thr Asn Phe Leu Leu Ser Leu Gly Ile His
    210                 215                 220

Leu Asn Pro Asn Lys Thr Lys Arg Trp Gly Tyr Ser Leu Asn Phe Met
225                 230                 235                 240

Gly Tyr Val Ile Gly Ser Trp Gly Ser Leu Pro Gln Asp His Ile Arg
                245                 250                 255

His Lys Ile Lys Glu Cys Phe Arg Lys Leu Pro Val His Arg Pro Ile
            260                 265                 270

Asp Trp Lys Val Cys Gln Arg Ile Val Gly Leu Leu Gly Phe Ala Ala
        275                 280                 285

Pro Phe Thr Gln Cys Gly Tyr Pro Ala Leu Met Pro Leu Tyr Ala Cys
    290                 295                 300

Ile Gln Ser Lys Gln Ala Phe Thr Phe Ser Pro Thr Tyr Lys Ala Phe
305                 310                 315                 320

Leu Cys Lys Gln Tyr Leu Asn Leu Tyr Pro Val Ala Arg Gln Arg Pro
                325                 330                 335

Gly Leu Cys Gln Val Phe Ala Asp Ala Thr Pro Thr Gly Trp Gly Leu
            340                 345                 350

Val Met Gly His Gln Arg Met Arg Gly Thr Phe Ser Ser Arg Lys Tyr
        355                 360                 365
```

```
Thr Ser Phe Pro Trp Leu Leu Gly Cys Ala Ala Asn Trp Ile Leu Arg
    370                 375                 380

Gly Thr Ser Phe Val Tyr Val Pro Ser Ala Leu Asn Pro Ala Asp Asp
385                 390                 395                 400

Pro Ser Arg Gly Arg Leu Gly Pro Cys Arg Pro Leu Leu His Leu Pro
                405                 410                 415

Phe Arg Pro Thr Thr Gly Arg Thr Ser Leu Tyr Ala Asp Ser Pro Ser
            420                 425                 430

Val Pro Ser His Leu Pro Asp Arg Val His Phe Ala Ser Pro Leu His
        435                 440                 445

Val Ala Trp Arg Pro Pro
    450


<210> SEQ ID NO 106
<211> LENGTH: 1014
<212> TYPE: PRT
<213> ORGANISM: Artificial Sequence
<220> FEATURE:
<223> OTHER INFORMATION: HBV design 1

<400> SEQUENCE: 106

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Ser Phe Leu Gly Gly Thr Thr Val Cys
        35                  40                  45

Leu Gly Gln Asn Ser Gln Ser Pro Thr Ser Asn His Ser Pro Thr Ser
    50                  55                  60

Cys Pro Pro Thr Cys Val Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Arg Thr Cys Thr Thr Pro Ala
        115                 120                 125

Gln Gly Thr Ser Met Tyr Pro Ser Cys Cys Cys Thr Lys Pro Ser Asp
    130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Asn Thr
        195                 200                 205

Leu Ser Pro Phe Leu Pro Leu Leu Pro Ile Phe Phe Tyr Leu Trp Val
    210                 215                 220

Tyr Ile Met Gln Leu Phe His Leu Cys Leu Ile Ile Ser Cys Ser Cys
225                 230                 235                 240

Pro Thr Val Gln Ala Ser Lys Leu Cys Leu Gly Trp Leu Trp Asp Met
                245                 250                 255

Asp Ile Asp Pro Tyr Lys Glu Phe Gly Ala Ser Val Glu Leu Leu Ser
            260                 265                 270
```

-continued

```
Phe Leu Pro Ser Asp Phe Phe Pro Ser Val Arg Asp Leu Leu Asp Thr
        275                 280                 285

Ala Thr Ala Leu Tyr Arg Asp Ala Leu Glu Ser Pro Glu His Cys Thr
    290                 295                 300

Pro His His Thr Ala Leu Arg His Val Cys Leu Cys Trp Gly Asp Leu
305                 310                 315                 320

Met Asn Leu Ala Thr Trp Val Gly Thr Asn Leu Glu Asp Gln Ala Ser
                325                 330                 335

Arg Asp Leu Val Val Ser Tyr Val Asn Thr Asn Met Gly Leu Lys Phe
            340                 345                 350

Arg Gln Leu Leu Trp Phe His Ile Ser Cys Leu Thr Phe Gly Arg Asp
        355                 360                 365

Leu Val Leu Glu Tyr Leu Val Ser Phe Gly Val Trp Ile Arg Thr Pro
    370                 375                 380

Pro Ala Tyr Arg Pro Ser Asn Ala Pro Ile Leu Ser Thr Leu Pro Glu
385                 390                 395                 400

Thr Thr Val Val Arg Gln Met Ala Ala Arg Leu Cys Cys Gln Leu Asp
                405                 410                 415

Pro Ala Arg Asp Val Leu Cys Leu Arg Pro Val Gly Ala Glu Ser Arg
            420                 425                 430

Gly Arg Pro Phe Ser Gly Pro Leu Gly Ala Leu Ser Ser Ser Pro
        435                 440                 445

Pro Ala Val Pro Thr Asp His Gly Ala His Leu Ser Leu Arg Gly Leu
    450                 455                 460

Pro Val Cys Ala Phe Ser Ser Ala Gly Pro Cys Ala Leu Arg Phe Thr
465                 470                 475                 480

Ser Ala Arg Arg Met Glu Thr Thr Val Asn Ala His Gln Phe Leu Pro
                485                 490                 495

Lys Val Leu His Lys Arg Thr Leu Gly Leu Ser Ala Met Ser Thr Thr
            500                 505                 510

Asp Leu Glu Ala Tyr Phe Lys Asp Cys Leu Phe Lys Asp Trp Glu Glu
        515                 520                 525

Leu Gly Glu Glu Leu Arg Leu Lys Val Phe Val Leu Gly Gly Cys Arg
    530                 535                 540

His Lys Leu Val Cys Ala Pro Ala Pro Cys Asn Phe Phe Thr Ser Ala
545                 550                 555                 560

Gly Pro Cys Ala Glu His Gly Glu His His Ile Arg Ile Pro Arg Thr
                565                 570                 575

Pro Ala Arg Val Thr Gly Gly Val Phe Leu Val Asp Lys Asn Pro His
            580                 585                 590

Asn Thr Ala Glu Ser Arg Leu Val Val Asp Phe Ser Gln Phe Ser Arg
        595                 600                 605

Gly Asn Tyr Arg Val Ser Trp Pro Lys Phe Ala Val Pro Asn Leu Gln
    610                 615                 620

Ser Leu Thr Asn Leu Leu Ser Ser Asn Leu Cys Trp Leu Ser Leu Asp
625                 630                 635                 640

Val Ser Ala Ala Phe Tyr His Leu Pro Leu His Pro Ala Ala Met Pro
                645                 650                 655

His Leu Leu Val Gly Ser Ser Gly Leu Ser Arg Tyr Val Ala Arg Leu
            660                 665                 670

Ser Ser Asn Ser Arg Ile Ile Asn His Gln His Gly Thr Leu Gln Asn
        675                 680                 685

Leu His Asp Ser Cys Ser Arg Asn Leu Tyr Val Ser Leu Leu Leu Leu
```

690 695 700

Tyr Lys Thr Phe Gly Trp Lys Leu His Leu Tyr Ser His Pro Ile Ile
705 710 715 720

Leu Gly Phe Arg Lys Ile Pro Met Gly Val Gly Leu Ser Pro Phe Leu
725 730 735

Leu Ala Gln Phe Thr Ser Ala Ile Cys Ser Val Val Arg Arg Ala Phe
740 745 750

Pro His Cys Leu Ala Phe Ser Gly Ala Lys Ser Val Gln His Leu Glu
755 760 765

Ser Leu Phe Thr Ala Val Thr Asn Phe Leu Leu Ser Leu Gly Ile His
770 775 780

Leu Asn Pro Asn Lys Thr Lys Arg Trp Gly Tyr Ser Leu Asn Phe Met
785 790 795 800

Gly Tyr Val Ile Gly Ser Trp Gly Ser Leu Pro Gln Asp His Ile Arg
805 810 815

His Lys Ile Lys Glu Cys Phe Arg Lys Leu Pro Val His Arg Pro Ile
820 825 830

Asp Trp Lys Val Cys Gln Arg Ile Val Gly Leu Leu Gly Phe Ala Ala
835 840 845

Pro Phe Thr Gln Cys Gly Tyr Pro Ala Leu Met Pro Leu Tyr Ala Cys
850 855 860

Ile Gln Ser Lys Gln Ala Phe Thr Phe Ser Pro Thr Tyr Lys Ala Phe
865 870 875 880

Leu Cys Lys Gln Tyr Leu Asn Leu Tyr Pro Val Ala Arg Gln Arg Pro
885 890 895

Gly Leu Cys Gln Val Phe Ala Asp Ala Thr Pro Thr Gly Trp Gly Leu
900 905 910

Val Met Gly His Gln Arg Met Arg Gly Thr Phe Ser Ser Arg Lys Tyr
915 920 925

Thr Ser Phe Pro Trp Leu Leu Gly Cys Ala Ala Asn Trp Ile Leu Arg
930 935 940

Gly Thr Ser Phe Val Tyr Val Pro Ser Ala Leu Asn Pro Ala Asp Asp
945 950 955 960

Pro Ser Arg Gly Arg Leu Gly Pro Cys Arg Pro Leu Leu His Leu Pro
965 970 975

Phe Arg Pro Thr Thr Gly Arg Thr Ser Leu Tyr Ala Asp Ser Pro Ser
980 985 990

Val Pro Ser His Leu Pro Asp Arg Val His Phe Ala Ser Pro Leu His
995 1000 1005

Val Ala Trp Arg Pro Pro
1010

<210> SEQ ID NO 107
<211> LENGTH: 1021
<212> TYPE: PRT
<213> ORGANISM: Artificial Sequence
<220> FEATURE:
<223> OTHER INFORMATION: HBV design 2

<400> SEQUENCE: 107

Ser Val Glu Leu Leu Ser Phe Leu Pro Ser Asp Phe Phe Pro Ser Val
1 5 10 15

Arg Asp Leu Leu Asp Thr Ala Thr Ala Leu Tyr Arg Asp Ala Leu Glu
20 25 30

Ser Pro Glu His Cys Thr Pro His His Thr Ala Leu Arg His Val Cys

-continued

```
        35                  40                  45

Leu Cys Trp Gly Asp Leu Met Asn Leu Ala Thr Trp Val Gly Thr Asn
    50                  55                  60

Leu Glu Asp Gln Ala Ser Arg Asp Leu Val Val Ser Tyr Val Asn Thr
65                  70                  75                  80

Asn Met Gly Leu Lys Phe Arg Gln Leu Leu Trp Phe His Ile Ser Cys
                85                  90                  95

Leu Thr Phe Gly Arg Asp Leu Val Leu Glu Tyr Leu Val Ser Phe Gly
            100                 105                 110

Val Trp Ile Arg Thr Pro Pro Ala Tyr Arg Pro Ser Asn Ala Pro Ile
        115                 120                 125

Leu Ser Thr Leu Pro Glu Thr Thr Val Val Arg Gln Arg Gly Arg Thr
    130                 135                 140

Ile Val Leu His Lys Arg Thr Leu Gly Leu Met Gly Gln Asn Leu Ser
145                 150                 155                 160

Thr Ser Asn Pro Leu Gly Phe Phe Pro Asp His Gln Leu Asp Pro Ala
                165                 170                 175

Phe Arg Ala Asn Thr Asn Asn Pro Asp Trp Asp Phe Asn Pro Asn Lys
            180                 185                 190

Asp Thr Trp Pro Asp Ala Asn Lys Val Gly Ala Gly Ala Phe Gly Leu
        195                 200                 205

Gly Phe Thr Pro Pro His Gly Gly Leu Leu Gly Trp Ser Pro Gln Ala
    210                 215                 220

Gln Gly Ile Met Gln Thr Leu Pro Ala Asn Pro Pro Pro Ala Ser Thr
225                 230                 235                 240

Asn Arg Gln Ser Gly Arg Gln Pro Thr Pro Leu Leu Pro Lys Val Leu
                245                 250                 255

His Lys Arg Thr Leu Met Pro Leu Ser Tyr Gln His Phe Arg Lys Leu
            260                 265                 270

Leu Leu Leu Asp Asn Glu Ala Gly Pro Leu Glu Glu Glu Leu Pro Arg
        275                 280                 285

Leu Ala Asp Glu Asp Leu Asn Arg Arg Val Ala Glu Asp Leu Asn Leu
    290                 295                 300

Gly Asn Leu Asn Val Ser Ile Pro Trp Thr His Lys Val Gly Asn Phe
305                 310                 315                 320

Thr Gly Leu Tyr Ser Ser Ser Val Pro Val Phe Asn Pro His Trp Lys
                325                 330                 335

Thr Pro Ser Phe Pro Asn Ile His Leu His Gln Asp Ile Ile Lys Lys
            340                 345                 350

Cys Glu Gln Phe Val Gly Pro Leu Thr Val Asn Glu Lys Arg Arg Leu
        355                 360                 365

Lys Leu Ile Met Pro Ala Arg Phe Tyr Pro Asn Phe Thr Lys Tyr Leu
    370                 375                 380

Pro Leu Asp Lys Gly Ile Lys Pro Tyr Tyr Pro Glu His Leu Val Asn
385                 390                 395                 400

His Tyr Phe His Thr Arg His Tyr Leu His Thr Leu Trp Lys Ala Gly
                405                 410                 415

Ile Leu Tyr Lys Arg Val Ser Thr His Ser Ala Ser Phe Cys Gly Ser
            420                 425                 430

Pro Tyr Ser Trp Glu Gln Glu Leu Gln His Gly Ala Glu Ser Phe His
        435                 440                 445

Gln Gln Ser Ser Gly Ile Leu Ser Arg Pro Ser Val Gly Ser Ser Leu
    450                 455                 460
```

-continued

```
Gln Ser Lys His Gln Gln Ser Arg Leu Gly Leu Gln Ser Gln Gln Gly
465                 470                 475                 480

His Leu Ala Arg Arg Gln Gln Gly Arg Ser Trp Ser Ile Arg Thr Arg
                485                 490                 495

Val His Pro Thr Ala Arg Arg Pro Ser Gly Val Glu Pro Ser Gly Ser
            500                 505                 510

Gly His Asn Ala Asn Leu Ala Ser Lys Ser Ala Ser Cys Leu Tyr Gln
        515                 520                 525

Ser Thr Val Arg Thr Ala Ala Tyr Pro Ala Val Ser Thr Ser Glu Asn
    530                 535                 540

His Ser Ser Ser Gly His Ala Val Glu Leu His Asn Leu Pro Pro Asn
545                 550                 555                 560

Ser Ala Arg Ser Gln Ser Glu Arg Pro Val Ser Pro Cys Trp Trp Leu
                565                 570                 575

Gln Phe Arg Asn Ser Lys Pro Cys Ser Asp Tyr Cys Leu Ser His Ile
            580                 585                 590

Val Asn Leu Leu Glu Asp Trp Gly Pro Cys His Lys Arg Thr Leu Gly
        595                 600                 605

Leu Ser Ala Met Ser Pro Pro Leu Arg Thr Thr His Pro Gln Ala Met
    610                 615                 620

Gln Trp Asn Ser Thr Thr Phe His Gln Thr Leu Gln Asp Pro Arg Val
625                 630                 635                 640

Arg Gly Leu Tyr Leu Pro Ala Gly Gly Ser Ser Ser Gly Thr Val Asn
                645                 650                 655

Pro Val Pro Thr Thr Ala Ser Pro Thr Leu Ser Thr Ser Ser Arg Ile
            660                 665                 670

Gly Asp Pro Ala Leu Asn Gln Phe Leu Pro Lys Val Leu His Lys Arg
        675                 680                 685

Ser Arg Gly Asn Tyr Arg Val Ser Trp Pro Lys Phe Ala Val Pro Asn
    690                 695                 700

Leu Gln Ser Leu Thr Asn Leu Leu Ser Ser Asn Leu Cys Trp Leu Ser
705                 710                 715                 720

Leu Asp Val Ser Ala Ala Phe Tyr His Leu Pro Leu His Pro Ala Ala
                725                 730                 735

Met Pro His Leu Leu Val Gly Ser Ser Gly Leu Ser Arg Tyr Val Ala
            740                 745                 750

Arg Leu Ser Ser Asn Ser Arg Ile Ile Asn His Gln His Gly Thr Leu
        755                 760                 765

Gln Asn Leu His Asp Ser Cys Ser Arg Asn Leu Tyr Val Ser Leu Leu
    770                 775                 780

Leu Leu Tyr Lys Thr Phe Gly Trp Lys Leu His Leu Tyr Ser His Pro
785                 790                 795                 800

Ile Ile Leu Gly Phe Arg Lys Ile Pro Met Gly Val Gly Leu Ser Pro
                805                 810                 815

Phe Leu Leu Ala Gln Phe Thr Ser Ala Ile Thr Val Asn Ala His Gln
            820                 825                 830

Phe Leu Pro Lys Gln Asn Ser Gln Ser Pro Thr Ser Asn His Ser Pro
        835                 840                 845

Thr Ser Cys Pro Pro Thr Cys Val Gly Tyr Arg Trp Met Cys Leu Arg
    850                 855                 860

Arg Phe Ile Ile Phe Leu Phe Ile Leu Leu Leu Cys Leu Ile Phe Leu
865                 870                 875                 880
```

Leu Val Leu Leu Asp Tyr Gln Gly Met Leu Pro Val Cys Pro Leu Ile
885 890 895

Pro Gly Ser Ser Thr Thr Ser Thr Gly Pro Cys Arg Thr Cys Thr Thr
900 905 910

Pro Ala Gln Gly Thr Ser Met Tyr Pro Ser Cys Cys Cys Thr Lys Pro
915 920 925

Ser Asp Gly Asn Cys Thr Cys Ile Pro Ile Pro Ser Ser Trp Ala Phe
930 935 940

Gly Lys Phe Leu Trp Glu Trp Ala Ser Ala Arg Phe Ser Trp Leu Ser
945 950 955 960

Leu Leu Val Pro Phe Val Gln Trp Phe Val Gly Leu Ser Pro Thr Val
965 970 975

Trp Leu Ser Val Ile Trp Met Met Trp Tyr Trp Gly Pro Ser Leu Tyr
980 985 990

Asn Thr Leu Ser Pro Phe Leu Pro Leu Leu Pro Ile Phe Phe Tyr Leu
995 1000 1005

Trp Val Tyr Ile Leu Ser Ala Met Ser Thr Thr Asp Leu
1010 1015 1020

<210> SEQ ID NO 108
<211> LENGTH: 532
<212> TYPE: PRT
<213> ORGANISM: Artificial Sequence
<220> FEATURE:
<223> OTHER INFORMATION: HBV design 3

<400> SEQUENCE: 108

Met Gln Thr Asp Arg Thr Gly Glu Thr Ala Leu His Leu Ala Ala Arg
1 5 10 15

Tyr Ser Arg Ser Asp Phe Leu Pro Ser Asp Phe Phe Pro Ser Val Ala
20 25 30

Asp Ala Gly Val Trp Ile Arg Thr Pro Pro Ala Asp Asn Met Glu Tyr
35 40 45

Leu Val Ser Phe Gly Val Trp Pro Leu His Ala Ala Val Ser Ala Asp
50 55 60

Cys Trp Gly Glu Leu Met Thr Leu Arg Asn Arg Ala Thr Asp Leu Gly
65 70 75 80

Gly Pro Asn Leu Asp Asn Ile Leu Met His Asp Ile Leu Arg Ser Phe
85 90 95

Ile Pro Leu Leu Pro Leu Ile Leu Ala Ala Arg Leu Ala Val Ser Thr
100 105 110

Leu Pro Glu Thr Thr Val Val Arg Arg Ser His Ala Asp Val Phe Leu
115 120 125

Gly Gly Pro Pro Val Cys Leu Asp Asp Leu Phe Leu Leu Thr Arg Ile
130 135 140

Leu Thr Ile Ala Leu His Trp Ala Ala Ala Val Asn Asn Val Leu Thr
145 150 155 160

Phe Gly Arg Glu Thr Val Leu Glu Tyr Gly Ala Asn Lys Trp Leu Ser
165 170 175

Leu Leu Val Pro Phe Val Asn Asn Arg Phe Leu Lys Gln Gln Tyr Met
180 185 190

Asn Leu Pro Leu Phe Leu Ala Ala Arg Glu Gly Ser Tyr Glu Asp Leu
195 200 205

Leu Asp Thr Ala Ser Ala Leu Tyr Ala Asn Arg Phe Leu Ser Lys Gln
210 215 220

```
Tyr Met Asp Leu Asp His Met Thr Val Ser Thr Lys Leu Cys Lys Ile
225                 230                 235                 240

Pro Arg Asp Leu Trp Phe His Ile Ser Cys Leu Thr Phe Ile Val Arg
                245                 250                 255

Leu Leu Asp Leu Glu Val Ser Gln Thr Ser Lys Leu Thr Arg Gln Thr
            260                 265                 270

Asp Arg Thr Gly Glu Thr Ala Leu His Leu Ala Ala Arg Tyr Ser Arg
        275                 280                 285

Ser Asp Leu Thr Thr Val Pro Ala Ala Ser Leu Leu Ala Ala Asp Ala
    290                 295                 300

Gly Leu Ser Arg Tyr Val Ala Arg Leu Asp Asn Met Lys Leu His Leu
305                 310                 315                 320

Tyr Ser His Pro Ile Pro Leu His Ala Ala Val Ser Ala Asp Gly Leu
                325                 330                 335

Ser Pro Thr Val Trp Leu Ser Val Arg Asn Arg Ala Thr Asp Leu Phe
            340                 345                 350

Leu Leu Ser Leu Gly Ile His Leu Met His Asp Ser Leu Tyr Ala Asp
        355                 360                 365

Ser Pro Ser Val Pro Leu Ile Leu Ala Ala Arg Leu Ala Val His Lys
    370                 375                 380

Arg Thr Leu Gly Leu Ser Ala Met Ser His Ala Asp Val Thr Leu Cys
385                 390                 395                 400

Ile Pro His Val Ala Val Asp Asp Leu Leu Leu Leu Lys Ala Thr Leu
                405                 410                 415

Cys Ile Ala Leu His Trp Ala Ala Ala Val Asn Asn Val Gln Phe Leu
            420                 425                 430

Pro Lys Val Leu His Lys Arg Gly Ala Asn Lys Ala Leu Met Pro Leu
        435                 440                 445

Tyr Ala Cys Ile Asn Asn Arg Thr Val Asn Ala His Gln Phe Leu Pro
    450                 455                 460

Lys Pro Leu Phe Leu Ala Ala Arg Glu Gly Ser Tyr Glu Leu Pro Lys
465                 470                 475                 480

Val Leu His Lys Arg Thr Leu Ala Asn Arg Val Leu His Lys Arg Thr
                485                 490                 495

Leu Gly Leu Asp His Met Leu Ser Ala Met Ser Thr Thr Asp Leu Pro
            500                 505                 510

Arg Asp Leu Leu Val Pro Phe Val Gln Trp Phe Val Ile Val Arg Leu
        515                 520                 525

Leu Asp Leu Glu
    530


<210> SEQ ID NO 109
<211> LENGTH: 368
<212> TYPE: PRT
<213> ORGANISM: Artificial Sequence
<220> FEATURE:
<223> OTHER INFORMATION: HBV design 4

<400> SEQUENCE: 109

Lys Lys Phe Leu Pro Ser Asp Phe Phe Pro Ser Val Lys Lys Cys Trp
1               5                   10                  15

Gly Glu Leu Met Thr Leu Lys Lys Gly Val Trp Ile Arg Thr Pro Pro
            20                  25                  30

Ala Lys Lys Ser Thr Leu Pro Glu Thr Thr Val Val Arg Arg Lys Lys
        35                  40                  45
```

-continued

```
Leu Thr Phe Gly Arg Glu Thr Val Leu Glu Tyr Lys Lys Asp Leu Leu
    50                  55                  60

Asp Thr Ala Ser Ala Leu Tyr Lys Lys Leu Trp Phe His Ile Ser Cys
65                  70                  75                  80

Leu Thr Phe Lys Lys Glu Tyr Leu Val Ser Phe Gly Val Trp Lys Lys
                85                  90                  95

Gly Gly Pro Asn Leu Asp Asn Ile Leu Lys Lys Leu Thr Thr Val Pro
            100                 105                 110

Ala Ala Ser Leu Leu Ala Lys Lys Ile Leu Arg Ser Phe Ile Pro Leu
        115                 120                 125

Leu Lys Lys Phe Leu Gly Gly Pro Pro Val Cys Leu Lys Lys Phe Leu
    130                 135                 140

Leu Thr Arg Ile Leu Thr Ile Lys Lys Trp Leu Ser Leu Leu Val Pro
145                 150                 155                 160

Phe Val Lys Lys Gly Leu Ser Pro Thr Val Trp Leu Ser Val Lys Lys
                165                 170                 175

Leu Leu Val Pro Phe Val Gln Trp Phe Val Lys Lys Phe Leu Lys Gln
            180                 185                 190

Gln Tyr Met Asn Leu Lys Lys Phe Leu Ser Lys Gln Tyr Met Asp Leu
        195                 200                 205

Lys Lys Thr Val Ser Thr Lys Leu Cys Lys Ile Lys Lys Gly Leu Ser
    210                 215                 220

Arg Tyr Val Ala Arg Leu Lys Lys Lys Leu His Leu Tyr Ser His Pro
225                 230                 235                 240

Ile Lys Lys Phe Leu Leu Ser Leu Gly Ile His Leu Lys Lys Ser Leu
                245                 250                 255

Tyr Ala Asp Ser Pro Ser Val Lys Lys Ala Leu Met Pro Leu Tyr Ala
            260                 265                 270

Cys Ile Lys Lys Leu Leu Leu Lys Ala Thr Leu Cys Ile Lys Lys Thr
        275                 280                 285

Leu Cys Ile Pro His Val Ala Val Lys Lys Val Leu His Lys Arg Thr
    290                 295                 300

Leu Gly Leu Lys Lys Leu Pro Lys Val Leu His Lys Arg Thr Leu Lys
305                 310                 315                 320

Lys His Lys Arg Thr Leu Gly Leu Ser Ala Met Lys Lys Gln Phe Leu
                325                 330                 335

Pro Lys Val Leu His Lys Arg Lys Lys Thr Val Asn Ala His Gln Phe
            340                 345                 350

Leu Pro Lys Lys Lys Leu Ser Ala Met Ser Thr Thr Asp Leu Lys Lys
        355                 360                 365
```

<210> SEQ ID NO 110
<211> LENGTH: 20
<212> TYPE: PRT
<213> ORGANISM: Artificial Sequence
<220> FEATURE:
<223> OTHER INFORMATION: splice primer

<400> SEQUENCE: 110

```
Thr Gly Cys Cys Ala Ala Gly Ala Gly Thr Gly Ala Cys Gly Thr Gly
1               5                   10                  15

Thr Cys Cys Ala
            20
```

<210> SEQ ID NO 111
<211> LENGTH: 9

<212> TYPE: PRT
<213> ORGANISM: Artificial Sequence
<220> FEATURE:
<223> OTHER INFORMATION: Cleavable linker

<400> SEQUENCE: 111

Val Ser Gln Thr Ser Lys Leu Thr Arg
1               5

<210> SEQ ID NO 112
<211> LENGTH: 9
<212> TYPE: PRT
<213> ORGANISM: Artificial Sequence
<220> FEATURE:
<223> OTHER INFORMATION: HBV Peptides from Surface 1

<400> SEQUENCE: 112

Gly Gly Pro Asn Leu Asp Asn Ile Leu
1               5

<210> SEQ ID NO 113
<211> LENGTH: 11
<212> TYPE: PRT
<213> ORGANISM: Artificial Sequence
<220> FEATURE:
<223> OTHER INFORMATION: HBV Peptides from Surface 2

<400> SEQUENCE: 113

Leu Thr Thr Val Pro Ala Ala Ser Leu Leu Ala
1               5                   10

<210> SEQ ID NO 114
<211> LENGTH: 9
<212> TYPE: PRT
<213> ORGANISM: Artificial Sequence
<220> FEATURE:
<223> OTHER INFORMATION: HBV Peptides from Surface 3

<400> SEQUENCE: 114

Ile Leu Arg Ser Phe Ile Pro Leu Leu
1               5

<210> SEQ ID NO 115
<211> LENGTH: 9
<212> TYPE: PRT
<213> ORGANISM: Artificial Sequence
<220> FEATURE:
<223> OTHER INFORMATION: HBV Peptides from Surface 4

<400> SEQUENCE: 115

Phe Leu Gly Gly Pro Pro Val Cys Leu
1               5

<210> SEQ ID NO 116
<211> LENGTH: 9
<212> TYPE: PRT
<213> ORGANISM: Artificial Sequence
<220> FEATURE:
<223> OTHER INFORMATION: HBV Peptides from Surface 5

<400> SEQUENCE: 116

Phe Leu Leu Thr Arg Ile Leu Thr Ile
1               5

<210> SEQ ID NO 117
<211> LENGTH: 9
<212> TYPE: PRT

<213> ORGANISM: Artificial Sequence
<220> FEATURE:
<223> OTHER INFORMATION: HBV Peptides from Surface 6

<400> SEQUENCE: 117

Trp Leu Ser Leu Leu Val Pro Phe Val
1 5

<210> SEQ ID NO 118
<211> LENGTH: 10
<212> TYPE: PRT
<213> ORGANISM: Artificial Sequence
<220> FEATURE:
<223> OTHER INFORMATION: HBV Peptides from Surface 7

<400> SEQUENCE: 118

Gly Leu Ser Pro Thr Val Trp Leu Ser Val
1 5 10

<210> SEQ ID NO 119
<211> LENGTH: 10
<212> TYPE: PRT
<213> ORGANISM: Artificial Sequence
<220> FEATURE:
<223> OTHER INFORMATION: HBV Peptides from Surface 8

<400> SEQUENCE: 119

Leu Leu Val Pro Phe Val Gln Trp Phe Val
1 5 10

<210> SEQ ID NO 120
<211> LENGTH: 9
<212> TYPE: PRT
<213> ORGANISM: Artificial Sequence
<220> FEATURE:
<223> OTHER INFORMATION: Hepatitis B Spliced Protein 1

<400> SEQUENCE: 120

Leu Leu Leu Lys Ala Thr Leu Cys Ile
1 5

<210> SEQ ID NO 121
<211> LENGTH: 9
<212> TYPE: PRT
<213> ORGANISM: Artificial Sequence
<220> FEATURE:
<223> OTHER INFORMATION: Hepatitis B Spliced Protein 2

<400> SEQUENCE: 121

Thr Leu Cys Ile Pro His Val Ala Val
1 5

<210> SEQ ID NO 122
<211> LENGTH: 9
<212> TYPE: PRT
<213> ORGANISM: Artificial Sequence
<220> FEATURE:
<223> OTHER INFORMATION: HBx protein

<400> SEQUENCE: 122

Val Leu His Lys Arg Thr Leu Gly Leu
1 5

<210> SEQ ID NO 123
<211> LENGTH: 10
<212> TYPE: PRT
<213> ORGANISM: Artificial Sequence
<220> FEATURE:
<223> OTHER INFORMATION: HBx protein

<400> SEQUENCE: 123

Leu Pro Lys Val Leu His Lys Arg Thr Leu
1 5 10

<210> SEQ ID NO 124
<211> LENGTH: 10
<212> TYPE: PRT
<213> ORGANISM: Artificial Sequence
<220> FEATURE:
<223> OTHER INFORMATION: HBx protein

<400> SEQUENCE: 124

His Lys Arg Thr Leu Gly Leu Ser Ala Met
1 5 10

<210> SEQ ID NO 125
<211> LENGTH: 10
<212> TYPE: PRT
<213> ORGANISM: Artificial Sequence
<220> FEATURE:
<223> OTHER INFORMATION: HBx protein

<400> SEQUENCE: 125

Gln Phe Leu Pro Lys Val Leu His Lys Arg
1 5 10

<210> SEQ ID NO 126
<211> LENGTH: 10
<212> TYPE: PRT
<213> ORGANISM: Artificial Sequence
<220> FEATURE:
<223> OTHER INFORMATION: HBx protein

<400> SEQUENCE: 126

Thr Val Asn Ala His Gln Phe Leu Pro Lys
1 5 10

<210> SEQ ID NO 127
<211> LENGTH: 9
<212> TYPE: PRT
<213> ORGANISM: Artificial Sequence
<220> FEATURE:
<223> OTHER INFORMATION: HBx protein

<400> SEQUENCE: 127

Leu Ser Ala Met Ser Thr Thr Asp Leu
1 5

<210> SEQ ID NO 128
<211> LENGTH: 21
<212> TYPE: PRT
<213> ORGANISM: Artificial Sequence
<220> FEATURE:
<223> OTHER INFORMATION: splice probe

<400> SEQUENCE: 128

Cys Cys Cys Ala Gly Gly Thr Cys Cys Ala Ala Cys Thr Gly Cys Ala
1 5 10 15

Gly Cys Cys Gly Gly
20

<210> SEQ ID NO 129
<211> LENGTH: 10

<212> TYPE: PRT
<213> ORGANISM: Artificial Sequence
<220> FEATURE:
<223> OTHER INFORMATION: Rigid Linker

<400> SEQUENCE: 129

Glu Ala Ala Ala Lys Glu Ala Ala Ala Lys
1 5 10

<210> SEQ ID NO 130
<211> LENGTH: 12
<212> TYPE: DNA
<213> ORGANISM: Artificial Sequence
<220> FEATURE:
<223> OTHER INFORMATION: Furin Linker

<400> SEQUENCE: 130
agagctaaga gg 12

<210> SEQ ID NO 131
<211> LENGTH: 5
<212> TYPE: PRT
<213> ORGANISM: Artificial Sequence
<220> FEATURE:
<223> OTHER INFORMATION: Rigid linker

<400> SEQUENCE: 131

Glu Ala Ala Ala Lys
1 5

<210> SEQ ID NO 132
<211> LENGTH: 212
<212> TYPE: PRT
<213> ORGANISM: Artificial Sequence
<220> FEATURE:
<223> OTHER INFORMATION: Synthetic sequence

<400> SEQUENCE: 132

Met Gln Leu Phe His Leu Cys Leu Ile Ile Ser Cys Ser Cys Pro Thr
1 5 10 15

Val Gln Ala Ser Lys Leu Cys Leu Gly Trp Leu Trp Gly Met Asp Ile
20 25 30

Asp Pro Tyr Lys Glu Phe Gly Ala Ser Val Glu Leu Leu Ser Phe Leu
35 40 45

Pro Ser Asp Phe Phe Pro Ser Ile Arg Asp Leu Leu Asp Thr Ala Ser
50 55 60

Ala Leu Tyr Arg Glu Ala Leu Glu Ser Pro Glu His Cys Ser Pro His
65 70 75 80

His Thr Ala Leu Arg Gln Ala Ile Leu Cys Trp Gly Glu Leu Met Asn
85 90 95

Leu Ala Thr Trp Val Gly Ser Asn Leu Glu Asp Pro Ala Ser Arg Glu
100 105 110

Leu Val Val Ser Tyr Val Asn Val Asn Met Gly Leu Lys Ile Arg Gln
115 120 125

Leu Leu Trp Phe His Ile Ser Cys Leu Thr Phe Gly Arg Glu Thr Val
130 135 140

Leu Glu Tyr Leu Val Ser Phe Gly Val Trp Ile Arg Thr Pro Pro Ala
145 150 155 160

Tyr Arg Pro Pro Asn Ala Pro Ile Leu Ser Thr Leu Pro Glu Thr Thr
165 170 175

Val Val Arg Arg Arg Gly Arg Ser Pro Arg Arg Arg Thr Pro Ser Pro

```
            180                 185                 190

Arg Arg Arg Arg Ser Gln Ser Pro Arg Arg Arg Arg Ser Gln Ser Arg
        195                 200                 205

Glu Ser Gln Cys
    210
```

<210> SEQ ID NO 133
<211> LENGTH: 214
<212> TYPE: PRT
<213> ORGANISM: Artificial Sequence
<220> FEATURE:
<223> OTHER INFORMATION: Synthetic sequence

<400> SEQUENCE: 133

```
Leu Gln Leu Phe His Leu Cys Leu Ile Ile Phe Cys Thr Cys Ser Thr
1               5                   10                  15

Phe Gln Ala Ser Lys Leu Cys Leu Gly Trp Leu Trp Asp Met Asp Ile
            20                  25                  30

Asp Thr Tyr Lys Glu Phe Gly Ala Thr Ala Glu Leu Leu Ser Phe Leu
        35                  40                  45

Pro Ala Asp Phe Phe Pro Ser Val Arg Asp Leu Leu Asp Thr Ala Ala
    50                  55                  60

Ala Leu Tyr Arg Asp Ala Leu Glu Ser Pro Glu His Cys Thr Pro Asn
65                  70                  75                  80

His Thr Ala Ile Arg Gln Ala Val Val Cys Trp Val Asp Leu Met Thr
                85                  90                  95

Leu Ala Ser Trp Val Gly Asn Asn Leu Gln Asp Gln Ile Ala Arg Asp
            100                 105                 110

Leu Ile Val Asn Tyr Val Asn Thr Asn Val Gly Leu Lys Phe Arg Gln
        115                 120                 125

Ile Leu Trp Phe His Ile Ser Cys Leu Thr Phe Gly Arg Asp Thr Val
    130                 135                 140

Ile Glu Tyr Leu Val Ser Phe Gly Val Trp Ile Arg Thr Pro Thr Pro
145                 150                 155                 160

Tyr Arg Pro Gln Asn Ala Pro Ile Leu Ser Thr Leu Pro Glu Asn Cys
                165                 170                 175

Val Ile Arg Gln Arg Asp Arg Cys Arg Thr Pro Arg Arg Arg Thr Pro
            180                 185                 190

Ser Pro Arg Arg Arg Arg Ser Gln Ser Pro Arg Arg Arg Arg Ser Lys
        195                 200                 205

Ser Pro Ala Pro Gln Cys
    210
```

<210> SEQ ID NO 134
<211> LENGTH: 212
<212> TYPE: PRT
<213> ORGANISM: Artificial Sequence
<220> FEATURE:
<223> OTHER INFORMATION: Synthetic sequence

<400> SEQUENCE: 134

```
Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Ser Val Glu Leu Leu Ser Phe Leu
        35                  40                  45
```

```
Pro Thr Asp Phe Phe Pro Ser Ile Arg Asp Leu Leu Asp Thr Ala Thr
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Asn
                85                  90                  95

Leu Ala Thr Trp Val Gly Val Asn Leu Asp Asp Pro Thr Ser Arg Glu
            100                 105                 110

Leu Val Val Gly Tyr Val Asn Val Asn Met Gly Leu Lys Leu Arg Gln
        115                 120                 125

Leu Leu Trp Phe His Ile Ser Cys Leu Thr Phe Gly Arg Glu Thr Val
    130                 135                 140

Leu Glu Tyr Leu Val Ser Phe Gly Val Trp Ile Arg Thr Pro Gln Ala
145                 150                 155                 160

Tyr Arg Pro Pro Asn Ala Pro Ile Leu Ser Thr Leu Pro Glu Thr Thr
                165                 170                 175

Val Val Arg Cys Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Gly Ser Gln Cys
    210


<210> SEQ ID NO 135
<211> LENGTH: 212
<212> TYPE: PRT
<213> ORGANISM: Artificial Sequence
<220> FEATURE:
<223> OTHER INFORMATION: Synthetic sequence

<400> SEQUENCE: 135

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Ser Val Glu Leu Leu Ser Phe Leu
        35                  40                  45

Pro Ser Asp Phe Phe Pro Ser Ile Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Asn
                85                  90                  95

Leu Ala Thr Trp Val Gly Gly Asn Leu Glu Asp Pro Ala Ser Arg Glu
            100                 105                 110

Leu Val Val Ser Tyr Val Asn Val Asn Met Gly Leu Lys Ile Arg Gln
        115                 120                 125

Leu Leu Trp Phe His Ile Ser Cys Leu Thr Phe Gly Arg Glu Thr Val
    130                 135                 140

Leu Glu Tyr Leu Val Ser Phe Gly Val Trp Ile Arg Thr Pro Leu Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190
```

```
Arg Arg Arg Arg Ser Gln Ser Pro Arg Arg Arg Arg Ser Gln Ser Arg
        195                 200                 205

Glu Ser Gln Cys
    210


<210> SEQ ID NO 136
<211> LENGTH: 212
<212> TYPE: PRT
<213> ORGANISM: Artificial Sequence
<220> FEATURE:
<223> OTHER INFORMATION: Synthetic sequence

<400> SEQUENCE: 136

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Ser Val Glu Leu Leu Ser Phe Leu
        35                  40                  45

Pro Ser Asp Phe Phe Pro Ser Ile Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Asn
                85                  90                  95

Leu Ala Thr Trp Val Gly Thr Asn Leu Glu Asp Pro Ala Ser Arg Glu
            100                 105                 110

Leu Val Val Ser Tyr Val Asn Val Asn Met Gly Leu Lys Ile Arg Gln
        115                 120                 125

Leu Leu Trp Phe His Ile Ser Cys Leu Thr Phe Gly Arg Glu Thr Val
    130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 137
<211> LENGTH: 15
<212> TYPE: PRT
<213> ORGANISM: Artificial Sequence
<220> FEATURE:
<223> OTHER INFORMATION: HBV Pre S1 peptide

<400> SEQUENCE: 137

His Gln Leu Asp Pro Ala Phe Gly Ala Asn Ser Thr Asn Pro Asp
1               5                   10                  15


<210> SEQ ID NO 138
<211> LENGTH: 23
<212> TYPE: PRT
<213> ORGANISM: Artificial Sequence
<220> FEATURE:
<223> OTHER INFORMATION: HBV Pre S2 peptide
```

<400> SEQUENCE: 138

Asn Ser Thr Thr Phe His Gln Ala Leu Leu Asp Pro Arg Val Arg Gly
1 5 10 15

Leu Tyr Phe Pro Ala Gly Gly
20

<210> SEQ ID NO 139
<211> LENGTH: 14
<212> TYPE: PRT
<213> ORGANISM: Artificial Sequence
<220> FEATURE:
<223> OTHER INFORMATION: HBV HBx peptide

<400> SEQUENCE: 139

Ile Leu Pro Lys Val Leu His Lys Arg Thr Leu Gly Leu Ser
1 5 10

<210> SEQ ID NO 140
<211> LENGTH: 26
<212> TYPE: PRT
<213> ORGANISM: Artificial Sequence
<220> FEATURE:
<223> OTHER INFORMATION: HBV HBx peptide

<400> SEQUENCE: 140

Glu Tyr Ile Lys Asp Cys Val Phe Lys Asp Trp Glu Glu Leu Gly Glu
1 5 10 15

Glu Ile Arg Leu Lys Val Phe Val Leu Gly
20 25

<210> SEQ ID NO 141
<211> LENGTH: 9
<212> TYPE: PRT
<213> ORGANISM: Artificial Sequence
<220> FEATURE:
<223> OTHER INFORMATION: HBV core peptide

<400> SEQUENCE: 141

Val Cys Trp Gly Glu Leu Met Asn Leu
1 5

<210> SEQ ID NO 142
<211> LENGTH: 9
<212> TYPE: PRT
<213> ORGANISM: Artificial Sequence
<220> FEATURE:
<223> OTHER INFORMATION: HBV core peptide

<400> SEQUENCE: 142

Ser Thr Leu Pro Glu Thr Thr Val Val
1 5

<210> SEQ ID NO 143
<211> LENGTH: 360
<212> TYPE: PRT
<213> ORGANISM: Artificial Sequence
<220> FEATURE:
<223> OTHER INFORMATION: TG1050 (MOD-1755595) HBV D Core

<400> SEQUENCE: 143

Met Asp Ile Asp Pro Tyr Lys Glu Phe Gly Ala Ser Val Glu Leu Leu
1 5 10 15

Ser Phe Leu Pro Ser Asp Phe Phe Pro Ser Val Arg Asp Leu Leu Asp
20 25 30

```
Thr Ala Thr Ala Leu Tyr Arg Asp Ala Leu Glu Ser Pro Glu His Cys
        35                  40                  45

Thr Pro His His Thr Ala Leu Arg His Val Cys Leu Cys Trp Gly Asp
    50                  55                  60

Leu Met Asn Leu Ala Thr Trp Val Gly Thr Asn Leu Glu Asp Gln Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Asp Leu Val Leu Glu Tyr Leu Val Ser Phe Gly Val Trp Ile Arg Thr
        115                 120                 125

Pro Pro Ala Tyr Arg Pro Ser Asn Ala Pro Ile Leu Ser Thr Leu Pro
    130                 135                 140

Glu Thr Thr Val Met Pro Leu Ser Tyr Gln His Phe Arg Arg Leu Leu
145                 150                 155                 160

Leu Leu Asp Asp Glu Ala Gly Pro Leu Glu Glu Glu Leu Pro Arg Leu
                165                 170                 175

Ala Asp Glu Gly Leu Asn Arg Arg Val Ala Glu Asp Leu Asn Leu Gly
            180                 185                 190

Asn Leu Asn Val Ser Ile Pro Trp Thr His Lys Val Gly Asn Phe Thr
        195                 200                 205

Gly Leu Tyr Ser Ser Thr Val Pro Val Phe Asn Pro His Trp Lys Thr
    210                 215                 220

Pro Ser Phe Pro Asn Ile His Leu His Gln Asp Ile Ile Lys Lys Cys
225                 230                 235                 240

Glu Gln Phe Val Gly Pro Leu Thr Val Asn Glu Lys Arg Arg Leu Gln
                245                 250                 255

Leu Ile Met Pro Ala Arg Phe Tyr Pro Asn Val Thr Lys Tyr Leu Pro
            260                 265                 270

Leu Asp Lys Gly Ile Lys Pro Tyr Tyr Pro Glu His Leu Val Asn His
        275                 280                 285

Tyr Phe Gln Thr Arg His Tyr Leu His Thr Leu Trp Lys Ala Gly Ile
    290                 295                 300

Leu Tyr Lys Arg Glu Thr Thr His Ser Ala Ser Phe Cys Gly Ser Pro
305                 310                 315                 320

Tyr Ser Trp Glu Gln Lys Leu Gln His Gly Ala Glu Ser Phe His Gln
                325                 330                 335

Gln Ser Ser Gly Ile Leu Ser Arg Pro Pro Val Gly Ser Ser Leu Gln
            340                 345                 350

Ser Lys His Arg Lys Ser Arg Leu
        355                 360
```

<210> SEQ ID NO 144
<211> LENGTH: 148
<212> TYPE: PRT
<213> ORGANISM: Artificial Sequence
<220> FEATURE:
<223> OTHER INFORMATION: TG1050 GB Y07587.1

<400> SEQUENCE: 144

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30
```

```
Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Gly Asn Leu Glu Asp Pro Ile
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val
145


<210> SEQ ID NO 145
<211> LENGTH: 1051
<212> TYPE: PRT
<213> ORGANISM: Artificial Sequence
<220> FEATURE:
<223> OTHER INFORMATION: (MOD-1755595) HBV D Core 1 148 P

<400> SEQUENCE: 145

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Val Arg Asp Leu Leu Asp
            20                  25                  30

Thr Ala Thr Ala Leu Tyr Arg Asp Ala Leu Glu Ser Pro Glu His Cys
        35                  40                  45

Thr Pro His His Thr Ala Leu Arg His Val Cys Leu Cys Trp Gly Asp
    50                  55                  60

Leu Met Asn Leu Ala Thr Trp Val Gly Thr Asn Leu Glu Asp Gln Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Asp Leu Val Leu Glu Tyr Leu Val Ser Phe Gly Val Trp Ile Arg Thr
        115                 120                 125

Pro Pro Ala Tyr Arg Pro Ser Asn Ala Pro Ile Leu Ser Thr Leu Pro
    130                 135                 140

Glu Thr Thr Val Met Pro Leu Ser Tyr Gln His Phe Arg Arg Leu Leu
145                 150                 155                 160

Leu Leu Asp Asp Glu Ala Gly Pro Leu Glu Glu Glu Leu Pro Arg Leu
                165                 170                 175

Ala Asp Glu Gly Leu Asn Arg Arg Val Ala Glu Asp Leu Asn Leu Gly
            180                 185                 190

Asn Leu Asn Val Ser Ile Pro Trp Thr His Lys Val Gly Asn Phe Thr
        195                 200                 205

Gly Leu Tyr Ser Ser Thr Val Pro Val Phe Asn Pro His Trp Lys Thr
    210                 215                 220

Pro Ser Phe Pro Asn Ile His Leu His Gln Asp Ile Ile Lys Lys Cys
225                 230                 235                 240
```

```
Glu Gln Phe Val Gly Pro Leu Thr Val Asn Glu Lys Arg Arg Leu Gln
                245                 250                 255

Leu Ile Met Pro Ala Arg Phe Tyr Pro Asn Val Thr Lys Tyr Leu Pro
            260                 265                 270

Leu Asp Lys Gly Ile Lys Pro Tyr Tyr Pro Glu His Leu Val Asn His
        275                 280                 285

Tyr Phe Gln Thr Arg His Tyr Leu His Thr Leu Trp Lys Ala Gly Ile
    290                 295                 300

Leu Tyr Lys Arg Glu Thr Thr His Ser Ala Ser Phe Cys Gly Ser Pro
305                 310                 315                 320

Tyr Ser Trp Glu Gln Lys Leu Gln His Gly Ala Glu Ser Phe His Gln
                325                 330                 335

Gln Ser Ser Gly Ile Leu Ser Arg Pro Pro Val Gly Ser Ser Leu Gln
            340                 345                 350

Ser Lys His Arg Lys Ser Arg Leu Gly Leu Gln Ser Gln Gln Gly His
        355                 360                 365

Leu Ala Arg Arg Gln Gln Gly Arg Ser Trp Ser Ile Arg Ala Gly Ile
    370                 375                 380

His Pro Thr Ala Arg Arg Ser Phe Gly Val Glu Pro Ser Gly Ser Gly
385                 390                 395                 400

His Ser Thr Asn Leu Ala Ser Lys Ser Ala Ser Cys Leu Tyr Gln Ser
                405                 410                 415

Pro Val Arg Lys Ala Ala Tyr Pro Ala Val Ser Thr Phe Glu Lys His
            420                 425                 430

Ser Ser Ser Gly His Ala Val Glu Leu His Asn Leu Pro Pro Asn Ser
        435                 440                 445

Ala Arg Ser Gln Ser Glu Arg Pro Val Phe Pro Cys Trp Trp Leu Gln
    450                 455                 460

Phe Arg Asn Ser Lys Pro Cys Ser Asp Tyr Cys Leu Ser His Ile Val
465                 470                 475                 480

Asn Leu Leu Glu Asp Trp Gly Pro Cys Ala Glu His Gly Glu His His
                485                 490                 495

Ile Arg Ile Pro Arg Thr Pro Ala Arg Val Thr Gly Gly Val Phe Leu
            500                 505                 510

Val Asp Lys Asn Pro His Asn Thr Ala Glu Ser Arg Leu Val Val Asp
        515                 520                 525

Phe Ser Gln Phe Ser Arg Gly Asn Tyr Arg Val Ser Trp Pro Lys Phe
    530                 535                 540

Ala Val Pro Asn Leu Gln Ser Leu Thr Asn Leu Leu Ser Ser Asn Leu
545                 550                 555                 560

Ser Trp Leu Ser Leu Asp Val Ser Ala Ala Phe Tyr His Leu Pro Leu
                565                 570                 575

His Pro Ala Ala Met Pro His Leu Leu Val Gly Ser Ser Gly Leu Ser
            580                 585                 590

Arg Tyr Val Ala Arg Leu Ser Ser Asn Ser Arg Ile Phe Asn Tyr Gln
        595                 600                 605

His Gly Thr Met Gln Asn Leu His Asp Ser Cys Ser Arg Asn Leu Tyr
    610                 615                 620

Val Ser Leu Leu Leu Leu Tyr Gln Thr Phe Gly Arg Lys Leu His Val
625                 630                 635                 640

Leu Gln Ala Gly Phe Phe Leu Leu Thr Arg Ile Leu Thr Ile Pro Gln
                645                 650                 655

Ser Leu Asp Ser Trp Trp Thr Ser Leu Ser Phe Leu Gly Gly Thr Thr
```

```
            660                 665                 670

Val Cys Leu Gly Gln Trp Gly Leu Ser Pro Phe Leu Leu Ala Gln Phe
        675                 680                 685

Thr Ser Ala Ile Cys Ser Val Val Arg Arg Ala Phe Pro His Cys Leu
    690                 695                 700

Ala Phe Ser Phe Pro Asp His Gln Leu Asp Pro Ala Phe Arg Ala Asn
705                 710                 715                 720

Thr Ala Asn Pro Asp Trp Asp Phe Asn Pro Asn Lys Asp Thr Trp Pro
                725                 730                 735

Asp Ala Asn Lys Val Gly Ala Gly Ala Gly Ala Lys Ser Val Gln His
            740                 745                 750

Leu Glu Ser Leu Phe Thr Ala Val Thr Asn Phe Leu Leu Ser Leu Gly
        755                 760                 765

Ile His Leu Asn Pro Asn Lys Thr Lys Arg Trp Gly Tyr Ser Leu His
    770                 775                 780

Phe Met Gly Tyr Val Ile Gly Cys Tyr Gly Ser Leu Pro Gln Asp His
785                 790                 795                 800

Ile Ile Gln Lys Ile Lys Glu Cys Phe Arg Lys Leu Pro Val Asn Arg
                805                 810                 815

Pro Ile Asp Trp Lys Val Cys Gln Arg Ile Val Gly Leu Leu Gly Phe
            820                 825                 830

Ala Ala Pro Phe Thr Gln Cys Gly Tyr Pro Ala Leu Met Pro Leu Tyr
        835                 840                 845

Ala Cys Ile Gln Ser Trp Ala Ser Ala Arg Phe Ser Trp Leu Ser Leu
    850                 855                 860

Leu Val Pro Phe Val Gln Trp Phe Val Gly Leu Ser Pro Thr Val Trp
865                 870                 875                 880

Leu Ser Val Tyr Lys Ala Phe Leu Cys Lys Gln Tyr Leu Asn Leu Tyr
                885                 890                 895

Pro Val Ala Arg Gln Arg Pro Gly Leu Cys Gln Val Phe Ala His Ala
            900                 905                 910

Thr Pro Thr Gly Trp Gly Leu Val Met Gly His Gln Arg Met Arg Gly
        915                 920                 925

Thr Phe Leu Glu Asn Ile Thr Ser Gly Phe Leu Gly Pro Leu Leu Val
    930                 935                 940

Leu Gln Ala Gly Phe Phe Leu Leu Thr Arg Ile Leu Thr Ile Pro Gln
945                 950                 955                 960

Ser Ser Arg Lys Tyr Thr Ser Phe Pro Trp Leu Leu Gly Cys Ala Ala
                965                 970                 975

Asn Trp Ile Leu Arg Gly Thr Ser Phe Val Tyr Tyr Pro Ser Ala Leu
            980                 985                 990

Asn Pro Tyr His Asp Pro Ser Arg  Gly Arg Leu Gly Leu  Ser Arg Pro
        995                 1000                1005

Leu Leu  Arg Leu Pro Phe Arg  Pro Thr Thr Gly Arg  Thr Ser Leu
    1010                1015                1020

Tyr Ala  Asp Ser Pro Ser Val  Pro Ser His Leu Pro  Asp Arg Val
    1025                1030                1035

His Phe  Ala Ser Pro Leu His  Val Ala Trp Arg Pro  Pro
    1040                1045                1050
```

<210> SEQ ID NO 146
<211> LENGTH: 903
<212> TYPE: PRT
<213> ORGANISM: Artificial Sequence

<220> FEATURE:
<223> OTHER INFORMATION: GB Y07587.1

<400> SEQUENCE: 146

```
Met Pro Leu Ser Tyr Gln His Phe Arg Arg Leu Leu Leu Leu Asp Asp
1               5                   10                  15

Glu Ala Gly Pro Leu Glu Glu Glu Leu Pro Arg Leu Ala Asp Glu Gly
            20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
    50                  55                  60

Ser Thr Val Pro Val Phe Asn Pro His Trp Lys Thr Pro Ser Phe Pro
65                  70                  75                  80

Asn Ile His Leu His Gln Asp Ile Ile Lys Lys Cys Glu Gln Phe Val
                85                  90                  95

Gly Pro Leu Thr Val Asn Glu Lys Arg Arg Leu Gln Leu Ile Met Pro
            100                 105                 110

Ala Arg Phe Tyr Pro Asn Val Thr Lys Tyr Leu Pro Leu Asp Lys Gly
        115                 120                 125

Ile Lys Pro Tyr Tyr Pro Glu His Leu Val Asn His Tyr Phe Gln Thr
    130                 135                 140

Arg His Tyr Leu His Thr Leu Trp Lys Ala Gly Ile Leu Tyr Lys Arg
145                 150                 155                 160

Glu Thr Thr His Ser Ala Ser Phe Cys Gly Ser Pro Tyr Ser Trp Glu
                165                 170                 175

Gln Lys Leu Gln His Gly Ala Glu Ser Phe His Gln Gln Ser Ser Gly
            180                 185                 190

Ile Leu Ser Arg Pro Pro Val Gly Ser Ser Leu Gln Ser Lys His Arg
        195                 200                 205

Lys Ser Arg Leu Gly Leu Gln Ser Gln Gln Gly His Leu Ala Arg Arg
    210                 215                 220

Gln Gln Gly Arg Ser Trp Ser Ile Arg Ala Gly Ile His Pro Thr Ala
225                 230                 235                 240

Arg Arg Ser Phe Gly Val Glu Pro Ser Gly Ser Gly His Ser Thr Asn
                245                 250                 255

Leu Ala Ser Lys Ser Ala Ser Cys Leu Tyr Gln Ser Pro Val Arg Lys
            260                 265                 270

Ala Ala Tyr Pro Ala Val Ser Thr Phe Glu Lys His Ser Ser Ser Gly
        275                 280                 285

His Ala Val Glu Leu His Asn Leu Pro Pro Asn Ser Ala Arg Ser Gln
    290                 295                 300

Ser Glu Arg Pro Val Phe Pro Cys Trp Trp Leu Gln Phe Arg Asn Ser
305                 310                 315                 320

Lys Pro Cys Ser Asp Tyr Cys Leu Ser His Ile Val Asn Leu Leu Glu
                325                 330                 335

Asp Trp Gly Pro Cys Ala Glu His Gly Glu His His Ile Arg Ile Pro
            340                 345                 350

Arg Thr Pro Ala Arg Val Thr Gly Gly Val Phe Leu Val Asp Lys Asn
        355                 360                 365

Pro His Asn Thr Ala Glu Ser Arg Leu Val Val Asp Phe Ser Gln Phe
    370                 375                 380

Ser Arg Gly Asn Tyr Arg Val Ser Trp Pro Lys Phe Ala Val Pro Asn
385                 390                 395                 400
```

-continued

```
Leu Gln Ser Leu Thr Asn Leu Leu Ser Ser Asn Leu Ser Trp Leu Ser
                405                 410                 415

Leu Asp Val Ser Ala Ala Phe Tyr His Leu Pro Leu His Pro Ala Ala
            420                 425                 430

Met Pro His Leu Leu Val Gly Ser Ser Gly Leu Ser Arg Tyr Val Ala
        435                 440                 445

Arg Leu Ser Ser Asn Ser Arg Ile Phe Asn Tyr Gln His Gly Thr Met
    450                 455                 460

Gln Asn Leu His Asp Ser Cys Ser Arg Asn Leu Tyr Val Ser Leu Leu
465                 470                 475                 480

Leu Leu Tyr Gln Thr Phe Gly Arg Lys Leu His Val Leu Gln Ala Gly
                485                 490                 495

Phe Phe Leu Leu Thr Arg Ile Leu Thr Ile Pro Gln Ser Leu Asp Ser
            500                 505                 510

Trp Trp Thr Ser Leu Ser Phe Leu Gly Gly Thr Thr Val Cys Leu Gly
        515                 520                 525

Gln Trp Gly Leu Ser Pro Phe Leu Leu Ala Gln Phe Thr Ser Ala Ile
    530                 535                 540

Cys Ser Val Val Arg Arg Ala Phe Pro His Cys Leu Ala Phe Ser Phe
545                 550                 555                 560

Pro Asp His Gln Leu Asp Pro Ala Phe Arg Ala Asn Thr Ala Asn Pro
                565                 570                 575

Asp Trp Asp Phe Asn Pro Asn Lys Asp Thr Trp Pro Asp Ala Asn Lys
            580                 585                 590

Val Gly Ala Gly Ala Gly Ala Lys Ser Val Gln His Leu Glu Ser Leu
        595                 600                 605

Phe Thr Ala Val Thr Asn Phe Leu Leu Ser Leu Gly Ile His Leu Asn
    610                 615                 620

Pro Asn Lys Thr Lys Arg Trp Gly Tyr Ser Leu His Phe Met Gly Tyr
625                 630                 635                 640

Val Ile Gly Cys Tyr Gly Ser Leu Pro Gln Asp His Ile Ile Gln Lys
                645                 650                 655

Ile Lys Glu Cys Phe Arg Lys Leu Pro Val Asn Arg Pro Ile Asp Trp
            660                 665                 670

Lys Val Cys Gln Arg Ile Val Gly Leu Leu Gly Phe Ala Ala Pro Phe
        675                 680                 685

Thr Gln Cys Gly Tyr Pro Ala Leu Met Pro Leu Tyr Ala Cys Ile Gln
    690                 695                 700

Ser Trp Ala Ser Ala Arg Phe Ser Trp Leu Ser Leu Leu Val Pro Phe
705                 710                 715                 720

Val Gln Trp Phe Val Gly Leu Ser Pro Thr Val Trp Leu Ser Val Tyr
                725                 730                 735

Lys Ala Phe Leu Cys Lys Gln Tyr Leu Asn Leu Tyr Pro Val Ala Arg
            740                 745                 750

Gln Arg Pro Gly Leu Cys Gln Val Phe Ala Asp Ala Thr Pro Thr Gly
        755                 760                 765

Trp Gly Leu Val Met Gly His Gln Arg Met Arg Gly Thr Phe Leu Glu
    770                 775                 780

Asn Ile Thr Ser Gly Phe Leu Gly Pro Leu Leu Val Leu Gln Ala Gly
785                 790                 795                 800

Phe Phe Leu Leu Thr Arg Ile Leu Thr Ile Pro Gln Ser Ser Arg Lys
                805                 810                 815
```

Tyr Thr Ser Phe Pro Trp Leu Leu Gly Cys Ala Ala Asn Trp Ile Leu
820 825 830

Arg Gly Thr Ser Phe Val Tyr Val Pro Ser Ala Leu Asn Pro Thr Asp
835 840 845

Asp Pro Ser Arg Gly Arg Leu Gly Leu Ser Arg Pro Leu Leu Arg Leu
850 855 860

Pro Phe Arg Pro Thr Thr Gly Arg Thr Ser Leu Tyr Ala Asp Ser Pro
865 870 875 880

Ser Val Pro Ser His Leu Pro Asp Arg Val His Phe Ala Ser Pro Leu
885 890 895

His Val Ala Trp Arg Pro Pro
900

<210> SEQ ID NO 147
<211> LENGTH: 1014
<212> TYPE: PRT
<213> ORGANISM: Artificial Sequence
<220> FEATURE:
<223> OTHER INFORMATION: (MOD-1755596) HBV D SHB(Env) HBe

<400> SEQUENCE: 147

Met Glu Asn Ile Thr Ser Gly Phe Leu Gly Pro Leu Leu Val Leu Gln
1 5 10 15

Ala Gly Phe Phe Leu Leu Thr Arg Ile Leu Thr Ile Pro Gln Ser Leu
20 25 30

Asp Ser Trp Trp Thr Ser Leu Ser Phe Leu Gly Gly Thr Thr Val Cys
35 40 45

Leu Gly Gln Asn Ser Gln Ser Pro Thr Ser Asn His Ser Pro Thr Ser
50 55 60

Cys Pro Pro Thr Cys Val Gly Tyr Arg Trp Met Cys Leu Arg Arg Phe
65 70 75 80

Ile Ile Phe Leu Phe Ile Leu Leu Leu Cys Leu Ile Phe Leu Leu Val
85 90 95

Leu Leu Asp Tyr Gln Gly Met Leu Pro Val Cys Pro Leu Ile Pro Gly
100 105 110

Ser Ser Thr Thr Ser Thr Gly Pro Cys Arg Thr Cys Thr Thr Pro Ala
115 120 125

Gln Gly Thr Ser Met Tyr Pro Ser Cys Cys Cys Thr Lys Pro Ser Asp
130 135 140

Gly Asn Cys Thr Cys Ile Pro Ile Pro Ser Ser Trp Ala Phe Gly Lys
145 150 155 160

Phe Leu Trp Glu Trp Ala Ser Ala Arg Phe Ser Trp Leu Ser Leu Leu
165 170 175

Val Pro Phe Val Gln Trp Phe Val Gly Leu Ser Pro Thr Val Trp Leu
180 185 190

Ser Val Ile Trp Met Met Trp Tyr Trp Gly Pro Ser Leu Tyr Asn Thr
195 200 205

Leu Ser Pro Phe Leu Pro Leu Leu Pro Ile Phe Phe Tyr Leu Trp Val
210 215 220

Tyr Ile Met Gln Leu Phe His Leu Cys Leu Ile Ile Ser Cys Ser Cys
225 230 235 240

Pro Thr Val Gln Ala Ser Lys Leu Cys Leu Gly Trp Leu Trp Asp Met
245 250 255

Asp Ile Asp Pro Tyr Lys Glu Phe Gly Ala Ser Val Glu Leu Leu Ser
260 265 270

-continued

```
Phe Leu Pro Ser Asp Phe Phe Pro Ser Val Arg Asp Leu Leu Asp Thr
        275                 280                 285

Ala Thr Ala Leu Tyr Arg Asp Ala Leu Glu Ser Pro Glu His Cys Thr
    290                 295                 300

Pro His His Thr Ala Leu Arg His Val Cys Leu Cys Trp Gly Asp Leu
305                 310                 315                 320

Met Asn Leu Ala Thr Trp Val Gly Thr Asn Leu Glu Asp Gln Ala Ser
                325                 330                 335

Arg Asp Leu Val Val Ser Tyr Val Asn Thr Asn Met Gly Leu Lys Phe
            340                 345                 350

Arg Gln Leu Leu Trp Phe His Ile Ser Cys Leu Thr Phe Gly Arg Asp
        355                 360                 365

Leu Val Leu Glu Tyr Leu Val Ser Phe Gly Val Trp Ile Arg Thr Pro
    370                 375                 380

Pro Ala Tyr Arg Pro Ser Asn Ala Pro Ile Leu Ser Thr Leu Pro Glu
385                 390                 395                 400

Thr Thr Val Val Arg Gln Met Ala Ala Arg Leu Cys Cys Gln Leu Asp
                405                 410                 415

Pro Ala Arg Asp Val Leu Cys Leu Arg Pro Val Gly Ala Glu Ser Arg
            420                 425                 430

Gly Arg Pro Phe Ser Gly Pro Leu Gly Ala Leu Ser Ser Ser Pro
        435                 440                 445

Pro Ala Val Pro Thr Asp His Gly Ala His Leu Ser Leu Arg Gly Leu
    450                 455                 460

Pro Val Cys Ala Phe Ser Ser Ala Gly Pro Cys Ala Leu Arg Phe Thr
465                 470                 475                 480

Ser Ala Arg Arg Met Glu Thr Thr Val Asn Ala His Gln Phe Leu Pro
                485                 490                 495

Lys Val Leu His Lys Arg Thr Leu Gly Leu Ser Ala Met Ser Thr Thr
            500                 505                 510

Asp Leu Glu Ala Tyr Phe Lys Asp Cys Leu Phe Lys Asp Trp Glu Glu
        515                 520                 525

Leu Gly Glu Glu Leu Arg Leu Lys Val Phe Val Leu Gly Gly Cys Arg
    530                 535                 540

His Lys Leu Val Cys Ala Pro Ala Pro Cys Asn Phe Phe Thr Ser Ala
545                 550                 555                 560

Gly Pro Cys Ala Glu His Gly Glu His His Ile Arg Ile Pro Arg Thr
                565                 570                 575

Pro Ala Arg Val Thr Gly Gly Val Phe Leu Val Asp Lys Asn Pro His
            580                 585                 590

Asn Thr Ala Glu Ser Arg Leu Val Val Asp Phe Ser Gln Phe Ser Arg
        595                 600                 605

Gly Asn Tyr Arg Val Ser Trp Pro Lys Phe Ala Val Pro Asn Leu Gln
    610                 615                 620

Ser Leu Thr Asn Leu Leu Ser Ser Asn Leu Cys Trp Leu Ser Leu Asp
625                 630                 635                 640

Val Ser Ala Ala Phe Tyr His Leu Pro Leu His Pro Ala Ala Met Pro
                645                 650                 655

His Leu Leu Val Gly Ser Ser Gly Leu Ser Arg Tyr Val Ala Arg Leu
            660                 665                 670

Ser Ser Asn Ser Arg Ile Ile Asn His Gln His Gly Thr Leu Gln Asn
        675                 680                 685

Leu His Asp Ser Cys Ser Arg Asn Leu Tyr Val Ser Leu Leu Leu Leu
```

```
    690                 695                 700

Tyr Lys Thr Phe Gly Trp Lys Leu His Leu Tyr Ser His Pro Ile Ile
705                 710                 715                 720

Leu Gly Phe Arg Lys Ile Pro Met Gly Val Gly Leu Ser Pro Phe Leu
                725                 730                 735

Leu Ala Gln Phe Thr Ser Ala Ile Cys Ser Val Val Arg Arg Ala Phe
            740                 745                 750

Pro His Cys Leu Ala Phe Ser Gly Ala Lys Ser Val Gln His Leu Glu
        755                 760                 765

Ser Leu Phe Thr Ala Val Thr Asn Phe Leu Leu Ser Leu Gly Ile His
    770                 775                 780

Leu Asn Pro Asn Lys Thr Lys Arg Trp Gly Tyr Ser Leu Asn Phe Met
785                 790                 795                 800

Gly Tyr Val Ile Gly Ser Trp Gly Ser Leu Pro Gln Asp His Ile Arg
                805                 810                 815

His Lys Ile Lys Glu Cys Phe Arg Lys Leu Pro Val His Arg Pro Ile
            820                 825                 830

Asp Trp Lys Val Cys Gln Arg Ile Val Gly Leu Leu Gly Phe Ala Ala
        835                 840                 845

Pro Phe Thr Gln Cys Gly Tyr Pro Ala Leu Met Pro Leu Tyr Ala Cys
    850                 855                 860

Ile Gln Ser Lys Gln Ala Phe Thr Phe Ser Pro Thr Tyr Lys Ala Phe
865                 870                 875                 880

Leu Cys Lys Gln Tyr Leu Asn Leu Tyr Pro Val Ala Arg Gln Arg Pro
                885                 890                 895

Gly Leu Cys Gln Val Phe Ala Asp Ala Thr Pro Thr Gly Trp Gly Leu
            900                 905                 910

Val Met Gly His Gln Arg Met Arg Gly Thr Phe Ser Ser Arg Lys Tyr
        915                 920                 925

Thr Ser Phe Pro Trp Leu Leu Gly Cys Ala Ala Asn Trp Ile Leu Arg
    930                 935                 940

Gly Thr Ser Phe Val Tyr Val Pro Ser Ala Leu Asn Pro Ala Asp Asp
945                 950                 955                 960

Pro Ser Arg Gly Arg Leu Gly Pro Cys Arg Pro Leu Leu His Leu Pro
                965                 970                 975

Phe Arg Pro Thr Thr Gly Arg Thr Ser Leu Tyr Ala Asp Ser Pro Ser
            980                 985                 990

Val Pro Ser His Leu Pro Asp Arg  Val His Phe Ala Ser  Pro Leu His
        995                 1000                1005

Val Ala  Trp Arg Pro Pro
    1010


<210> SEQ ID NO 148
<211> LENGTH: 1054
<212> TYPE: PRT
<213> ORGANISM: Artificial Sequence
<220> FEATURE:
<223> OTHER INFORMATION: HBV DB elements AB048701

<400> SEQUENCE: 148

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Ser Phe Leu Gly Gly Thr Thr Val Cys
```

-continued

```
        35                  40                  45

Leu Gly Gln Asn Ser Gln Ser Pro Thr Ser Asn His Ser Pro Thr Ser
    50                  55                  60

Cys Pro Pro Thr Cys Val Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Arg Thr Cys Thr Thr Pro Ala
        115                 120                 125

Gln Gly Thr Ser Met Tyr Pro Ser Cys Cys Cys Thr Lys Pro Ser Asp
    130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Asn Thr
        195                 200                 205

Leu Ser Pro Phe Leu Pro Leu Leu Pro Ile Phe Phe Tyr Leu Trp Val
    210                 215                 220

Tyr Ile Met Gln Leu Phe His Leu Cys Leu Ile Ile Ser Cys Ser Cys
225                 230                 235                 240

Pro Thr Val Gln Ala Ser Lys Leu Cys Leu Gly Trp Leu Trp Asp Met
                245                 250                 255

Asp Ile Asp Pro Tyr Lys Glu Phe Gly Ala Ser Val Glu Leu Leu Ser
            260                 265                 270

Phe Leu Pro Ser Asp Phe Phe Pro Ser Val Arg Asp Leu Leu Asp Thr
        275                 280                 285

Ala Thr Ala Leu Tyr Arg Asp Ala Leu Glu Ser Pro Glu His Cys Thr
    290                 295                 300

Pro His His Thr Ala Leu Arg His Val Cys Leu Cys Trp Gly Asp Leu
305                 310                 315                 320

Met Asn Leu Ala Thr Trp Val Gly Thr Asn Leu Glu Asp Gln Ala Ser
                325                 330                 335

Arg Asp Leu Val Val Ser Tyr Val Asn Thr Asn Met Gly Leu Lys Phe
            340                 345                 350

Arg Gln Leu Leu Trp Phe His Ile Ser Cys Leu Thr Phe Gly Arg Asp
        355                 360                 365

Leu Val Leu Glu Tyr Leu Val Ser Phe Gly Val Trp Ile Arg Thr Pro
    370                 375                 380

Pro Ala Tyr Arg Pro Ser Asn Ala Pro Ile Leu Ser Thr Leu Pro Glu
385                 390                 395                 400

Thr Thr Val Val Arg Gln Met Ala Ala Arg Leu Cys Cys Gln Leu Asp
                405                 410                 415

Pro Ala Arg Asp Val Leu Cys Leu Arg Pro Val Gly Ala Glu Ser Arg
            420                 425                 430

Gly Arg Pro Phe Ser Gly Pro Leu Gly Ala Leu Ser Ser Ser Ser Pro
        435                 440                 445

Pro Ala Val Pro Thr Asp His Gly Ala His Leu Ser Leu Arg Gly Leu
    450                 455                 460
```

Pro Val Cys Ala Phe Ser Ser Ala Gly Pro Cys Ala Leu Arg Phe Thr
465 470 475 480

Ser Ala Arg Arg Met Glu Thr Thr Val Asn Ala His Gln Phe Leu Pro
485 490 495

Lys Val Leu His Lys Arg Thr Leu Gly Leu Ser Ala Met Ser Thr Thr
500 505 510

Asp Leu Glu Ala Tyr Phe Lys Asp Cys Leu Phe Lys Asp Trp Glu Glu
515 520 525

Leu Gly Glu Glu Leu Arg Leu Lys Val Phe Val Leu Gly Gly Cys Arg
530 535 540

His Lys Leu Val Cys Ala Pro Ala Pro Cys Asn Phe Phe Thr Ser Ala
545 550 555 560

Gly Pro Cys Ala Glu His Gly Glu His His Ile Arg Ile Pro Arg Thr
565 570 575

Pro Ala Arg Val Thr Gly Gly Val Phe Leu Val Asp Lys Asn Pro His
580 585 590

Asn Thr Ala Glu Ser Arg Leu Val Val Asp Phe Ser Gln Phe Ser Arg
595 600 605

Gly Asn Tyr Arg Val Ser Trp Pro Lys Phe Ala Val Pro Asn Leu Gln
610 615 620

Ser Leu Thr Asn Leu Leu Ser Ser Asn Leu Cys Trp Leu Ser Leu Asp
625 630 635 640

Val Ser Ala Ala Phe Tyr His Leu Pro Leu His Pro Ala Ala Met Pro
645 650 655

His Leu Leu Val Gly Ser Ser Gly Leu Ser Arg Tyr Val Ala Arg Leu
660 665 670

Ser Ser Asn Ser Arg Ile Ile Asn His Gln His Gly Thr Leu Gln Asn
675 680 685

Leu His Asp Ser Cys Ser Arg Asn Leu Tyr Val Ser Leu Leu Leu Leu
690 695 700

Tyr Lys Thr Phe Gly Trp Lys Leu His Leu Tyr Ser His Pro Ile Ile
705 710 715 720

Leu Gly Phe Arg Lys Ile Pro Met Gly Val Gly Leu Ser Pro Phe Leu
725 730 735

Leu Ala Gln Phe Thr Ser Ala Ile Cys Ser Val Val Arg Arg Ala Phe
740 745 750

Pro His Cys Leu Ala Phe Ser Tyr Met Asp Asp Val Val Leu Gly Ala
755 760 765

Lys Ser Val Gln His Leu Glu Ser Leu Phe Thr Ala Val Thr Asn Phe
770 775 780

Leu Leu Ser Leu Gly Ile His Leu Asn Pro Asn Lys Thr Lys Arg Trp
785 790 795 800

Gly Tyr Ser Leu Asn Phe Met Gly Tyr Val Ile Gly Ser Trp Gly Ser
805 810 815

Leu Pro Gln Asp His Ile Arg His Lys Ile Lys Glu Cys Phe Arg Lys
820 825 830

Leu Pro Val His Arg Pro Ile Asp Trp Lys Val Cys Gln Arg Ile Val
835 840 845

Gly Leu Leu Gly Phe Ala Ala Pro Phe Thr Gln Cys Gly Tyr Pro Ala
850 855 860

Leu Met Pro Leu Tyr Ala Cys Ile Gln Ser Lys Gln Ala Phe Thr Phe
865 870 875 880

-continued

```
Ser Pro Thr Tyr Lys Ala Phe Leu Cys Lys Gln Tyr Leu Asn Leu Tyr
                885                 890                 895

Pro Val Ala Arg Gln Arg Pro Gly Leu Cys Gln Val Phe Ala Asp Ala
            900                 905                 910

Thr Pro Thr Gly Trp Gly Leu Val Met Gly His Gln Arg Met Arg Gly
        915                 920                 925

Thr Phe Ser Ala Pro Leu Pro Ile His Thr Ala Glu Leu Leu Ala Ala
    930                 935                 940

Cys Phe Ala Arg Ser Arg Ser Gly Ala Asn Ile Leu Gly Thr Asp Asn
945                 950                 955                 960

Ser Val Val Leu Ser Arg Lys Tyr Thr Ser Phe Pro Trp Leu Leu Gly
                965                 970                 975

Cys Ala Ala Asn Trp Ile Leu Arg Gly Thr Ser Phe Val Tyr Val Pro
            980                 985                 990

Ser Ala Leu Asn Pro Ala Asp Asp  Pro Ser Arg Gly Arg  Leu Gly Pro
        995                 1000                1005

Cys Arg  Pro Leu Leu His Leu  Pro Phe Arg Pro Thr  Thr Gly Arg
    1010                1015                1020

Thr Ser  Leu Tyr Ala Asp Ser  Pro Ser Val Pro Ser  His Leu Pro
    1025                1030                1035

Asp Arg  Val His Phe Ala Ser  Pro Leu His Val Ala  Trp Arg Pro
    1040                1045                1050

Pro
```

HEPATITIS B VACCINES AND USES OF THE SAME

REFERENCE TO SEQUENCE LISTING

The content of the electronically submitted sequence listing (Name: 2584_1610001_Seqlisting_ST25; Size: 423,230 bytes; Date of Creation: Aug. 3, 2022) filed with this application is incorporated herein by reference in its entirety.

FIELD OF THE DISCLOSURE

The present disclosure relates to improved, broad-spectrum HBV molecular vaccines designed via use of advanced principles in bioinformatics and protein engineering.

BACKGROUND OF THE DISCLOSURE

Chronic hepatitis B is a disease involving multiple viral (HepB or HBV) genotypes. HBV genotypes/subgenotypes have been increasingly associated with differences in clinical and virological characteristics, such as severity of liver disease and response to antiviral therapies. Infection with HBV causes hepatitis that can result in cirrhosis, liver failure and hepatocellular carcinoma (HCC). The diagnosis of HBV is based on the serological findings. There is no cure for chronic HBV infection. Currently available treatment options are aimed at slowing the progression of cirrhosis and viral replication, reducing the incidence of HCC and liver failures.

The present disclosure relates to improved, broad-spectrum HBV molecular vaccines designed via use of advanced principles in bioinformatics and protein engineering. These novel HBV vaccines can be used as a therapeutic vaccine against HBV related diseases.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE DISCLOSURE

Provided herein is a non-naturally occurring polynucleotide encoding a polypeptide comprising at least one or more immune response-inducing hepatitis B virus (HBV) polypeptides.

In some embodiments, said non-naturally occurring polynucleotide encodes a polypeptide comprising said one or more HBV polypeptides. In some embodiments, said one or more HBV polypeptides comprises an HBV Core peptide. In some embodiments, said HBV Core peptide has any one of Core peptide sequences as shown in Table 3. In some embodiments, said one or more HBV peptides comprises an HBV Surface peptide. In some embodiments, said HBV Surface peptide has any one of Surface peptide sequences as shown in Table 3. In some embodiments, said one or more HBV peptides comprises an HBV Pol peptide. In some embodiments, said HBV Pol peptide has any one of Pol peptide sequences as shown in Table 3. In some embodiments, said one or more HBV peptides comprises an HBV HBSP/HBx peptide. In some embodiments, said HBV HBSP/HBx peptide has any one of HBSP/HBx peptide sequences as shown in Table 3. In some embodiments, said one or more HBV peptides comprises a KK linker. In some embodiments, said KK linker connects any one of peptide sequences as shown in Table 3 to any other peptide sequences as shown in Table 3.

Provided herein is a polynucleotide comprising any of the polynucleotides provided herein, further comprising one or more polynucleotides encoding a gene switch system for inducible control of heterologous gene expression, wherein heterologous gene expression is regulated by said gene switch system; and, wherein said heterologous gene comprises any of the polynucleotide described herein. In some embodiments, said gene switch system is an ecdysone receptor-based (EcR-based) gene switch system. In some embodiments, said one or more HBV polypeptides is for use in a vaccine.

Provided herein is a vector comprising any of the polynucleotides provided herein. In some embodiments, said vector is an adenoviral vector. In some embodiments, said adenoviral vector is a gorilla adenoviral vector.

Provided herein is a method of regulating the expression of a heterologous gene in a cell, the method comprising: introducing into said cell one or more polynucleotides that comprise (i) an repressible or inducible gene switch, and (ii) a heterologous immune response-inducing gene, wherein expression of said heterologous immune response-inducing gene is regulated by said gene switch, wherein said heterologous immune response-inducing gene encodes at least one of one or more HBV polypeptides; and exposing said cell to a compound in an amount sufficient to repress or induce expression of said heterologous immune response-inducing gene.

In some embodiments, said target cell is a mammalian cell in a method of regulating the expression of a heterologous gene in a cell described herein. In some embodiments, said gene switch comprises a ligand binding domain derived from at least one of an ecdysone receptor (EcR), a ubiquitous receptor, an orphan receptor 1, an NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a famesol receptor.

Provided herein is a polynucleotide encoding any of the presently described polypeptide constructs. Also provided herein is a vector comprising said polynucleotide. In some embodiments, said vector is an adenoviral vector. In some embodiments, said adenoviral vector is a gorilla adenoviral vector.

Provided herein is a vector, wherein said vector comprises a polynucleotide that encodes at least one HBV peptide, wherein said vector is an adenoviral vector.

Provided herein is a vector, wherein said vector comprises a polynucleotide that encodes at least one HBV peptide, wherein said vector is an adenoviral vector, wherein said adenoviral vector is a gorilla adenoviral vector.

Provided herein is a polypeptide construct, wherein said polypeptide construct comprises an HBV HBx domain and at least one of an HBV Pol domain, an HBV Core domain, an HBV pre-Core domain or an HBV Surface domain. Also provided herein is a polypeptide construct, wherein said polypeptide construct comprises a pre-Core domain and at least one of an HBV Pol domain, an HBV HBx domain or an HBV Surface domain. In some embodiments, said HBV HBx domain has a sequence as shown in SEQ ID NO: 98. In some embodiments, said HBV Pol domain comprises a deletion of at least one amino acid as compared to a wildtype HBV Pol domain. In some embodiments, said deletion comprises a deleted portion of said wildtype HBV Pol domain, wherein said deleted portion comprises at least one of amino acids 538-544 or amino acids 710-742. In some embodiments, said deleted portion comprises both of amino acids 538-544 and amino acids 710-742. In some embodiments, said HBV Pol domain has a sequence as shown in SEQ ID NO: 99. In some embodiments, said HBV Surface domain comprises at least one of a PreS1 domain, a PreS2 domain and an S domain. In some embodiments, said HBV Surface domain comprises an HBV S domain. In some embodiments, said Surface domain has a sequence as shown in SEQ ID NO: 100. In some embodiments, said polypeptide construct further comprises an HBV Core domain. In some embodiments, said polypeptide construct comprises a Core portion, wherein said Core portion comprises said HBV Core domain and said HBV pre-Core domain. In some embodiments, said Core portion has a sequence as shown in SEQ ID NO: 101. In some embodiments, said polypeptide construct comprises each of SHB(Env), HBeAg, HBx, and Pol domains. In some embodiments, said polypeptide construct comprises a structure, from N-terminus to C-terminus, of said SHB(Env), HBeAg, HBx, and Pol domains. In some embodiments, said SHB(Env) domain has a sequence as shown in SEQ ID NO: 102. In some embodiments, said HBeAg domain has a sequence as shown in SEQ ID NO: 103. In some embodiments, said HBx domain has a sequence as shown in SEQ ID NO: 104. In some embodiments, said Pol domain has a sequence as shown in SEQ ID NO: 105. In some embodiments, said polypeptide construct has a sequence as shown in SEQ ID NO: 106.

Provided herein is a polypeptide construct, wherein said polypeptide construct comprises one or more HBV HBx linkers and at least one of a Core domain, a Surface domain and a Pol domain, wherein one of said Core domain, said Surface domain and said Pol domain is connected to another of said Core domain, said Surface domain and said Pol domain by said one or more HBx linkers. In some embodiments, said Surface domain comprises at least one of an HBV PreS1 domain, an HBV PreS2 domain and an HBV S domain. In some embodiments, said one or more HBV HBx linkers comprises multiple HBV HBx linkers. In some embodiments, at least two of said multiple HBV HBx linkers differ in an amino acid sequence. In some embodiments, said HBV HBx linker has a sequence as shown in any one of HBx-1, HBx-2, HBx-3, HBx-4, HBx-5 or HBx-6 of Table 3. In some embodiments, said Core domain is adjacent to said Surface domain. In some embodiments, said Surface domain comprises a PreS1 domain. In some embodiments, said Surface domain is connected to said Core domain by one of said one or more HBx linkers. In some embodiments, said Pol domain is adjacent to a Surface domain. In some embodiments, said Surface domain comprises at least one of a PreS1 domain, a PreS2 domain and an S domain. In some embodiments, said Surface domain comprises said PreS1 domain, and an N-terminal portion of said Pol domain is adjacent to said PreS1 domain. In some embodiments, said N-terminal portion of said Pol domain is connected to said PreS1 domain by one of said one or more HBx linkers. In some embodiments, said Surface domain comprises said PreS2 domain, and an N-terminal portion of said Pol domain is adjacent to said PreS2 domain. In some embodiments, said N-terminal portion of said Pol domain is connected to said PreS2 domain by one of said one or more HBx linkers. In some embodiments, said Surface domain comprises said PreS2 domain, and a C-terminal portion of said Pol domain is adjacent to said PreS2 domain. In some embodiments, said C-terminal portion of said Pol domain is connected to said PreS2 domain by one of said one or more HBx linkers. In some embodiments, said Surface domain comprises said S domain, and a C-terminal portion of said Pol domain is adjacent to said S domain. In some embodiments, said C-terminal portion of said Pol domain is connected to said S domain by one of said one or more HBx linkers. In some embodiments, said polypeptide construct has a sequence as shown in SEQ ID NO: 107.

Provided herein is a polypeptide construct comprising an ankyrin-like repeat domain and one or more HBV peptides. In some embodiments, said ankyrin-like repeat protein is a human ankyrin-like repeat protein. In some embodiments, said one or more HBV peptides has a sequence as shown in any one of the amino acid sequences of Table 3. In some embodiments, said one or more HBV peptides comprises one or more of a Core peptide, a Surface peptide, a Pol peptide and an HBSP/HBx peptide. In some embodiments, said one or more HBV peptides comprises a Core peptide, and said Core peptide has a sequence as shown in any one of the Core amino acid sequences of Table 3. In some embodiments, said one or more HBV peptides comprises a Surface peptide, and said Surface peptide has a sequence as shown in any one of the Surface amino acid sequences of Table 3. In some embodiments, said one or more HBV peptides comprises a Pol peptide, and said Pol peptide has a sequence as shown in any one of the Pol amino acid sequences of Table 3. In some embodiments, said one or more HBV peptides comprises an HBSP/HBx peptide, and said HBSP/HBx peptide has a sequence as shown in any one of the HBSP/HBx amino acid sequences of Table 3. In some embodiments, said polypeptide construct has a sequence as shown in SEQ ID NO: 108.

Provided herein is a polypeptide construct, wherein said polypeptide construct comprises at least two HBV amino acid sequences as shown in Table 3, wherein said at least two HBV amino acid sequences are connected by a peptide linker, wherein said peptide linker is a KK linker. In some embodiments, said comprises at least two HBV amino acid sequences comprise at least one of a Core peptide, a Surface peptide, a Pol peptide and an HBSP/HBx peptide as shown in Table 3. In some embodiments, said at least two HBV amino acid sequences comprise each of the amino acid sequences as shown in Table 3. In some embodiments, said each of the amino acid sequences is connected to another of said each of the amino acid sequences by said KK linker. In some embodiments, said polypeptide construct has a sequence as shown in SEQ ID NO: 109. In some embodiments, any of the polypeptide constructs described herein is for use in a vaccine. Also provided herein is a polynucleotide encoding any of the polypeptide constructs presently described. Also provided herein is a vector comprising said polynucleotide. In some embodiments, said vector is an adenoviral vector. In some embodiments, said adenoviral vector is a gorilla adenoviral vector.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 15A shows core sequence comparisons of HBV design 1 and TG1050 control (SEQ ID NOs: 143-144).

DETAILED DESCRIPTION OF THE DISCLOSURE

Figure 1:
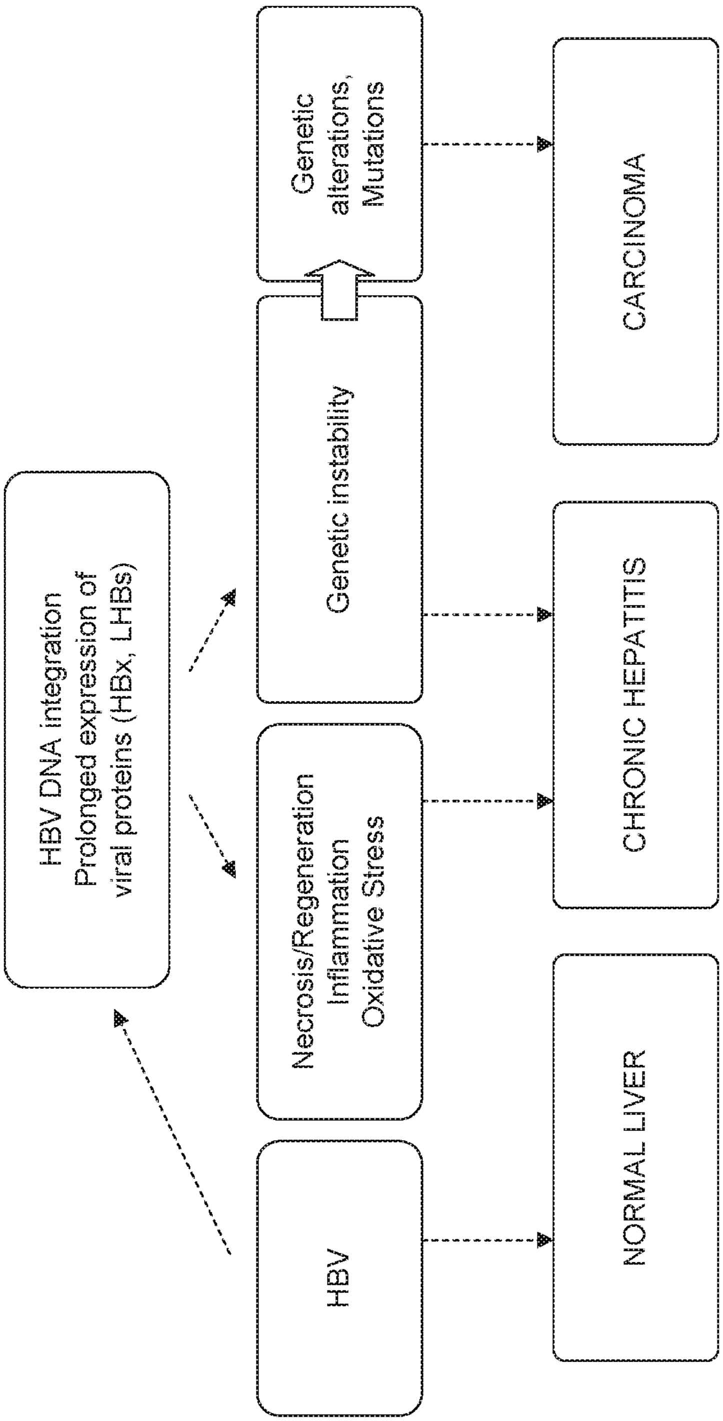
FIG. 1 is a schematic of chronic HBV infection.

The following description and examples illustrate embodiments of the present disclosure in detail.

It is to be understood that the present disclosure is not limited to the particular embodiments described herein and as such can vary. Those of skill in the art will recognize that there are variations and modifications of the present disclosure, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the disclosure can be described in the context of a single embodiment, the features can also be provided separately or in any suitable combination. Conversely, although the present disclosure can be described herein in the context of separate embodiments for clarity, the present disclosure can also be implemented in a single embodiment.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

Definitions

In this application, the use of the singular includes the plural unless specifically stated otherwise. It must be noted that, as used in the specification, the singular forms "a," "an" and "the" include plural referents unless the context clearly dictates otherwise.

In this application, the use of "or" means "and/or" unless stated otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively, unless the context specifically refers to a disjunctive use.

Furthermore, use of the term "including" as well as other forms, such as "include," "includes," and "included," is not limiting.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the disclosure, and vice versa. Furthermore, compositions of the present disclosure can be used to achieve methods of the present disclosure.

The term "about" in relation to a reference numerical value and its grammatical equivalents as used herein can include the numerical value itself and a range of values plus or minus 10% from that numerical value.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. In another example, the amount "about 10" includes 10 and any amounts from 9 to 11. In yet another example, the term "about" in relation to a reference numerical value can also include a range of values plus or minus 10%, 9%, 8%, 7%, 6%, 5%, 4%, 3%, 2%, or 1% from that value. Alternatively, particularly with respect to biological systems or processes, the term "about" can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "isolated" and its grammatical equivalents as used herein refer to the removal of a nucleic acid from its natural environment. The term "purified" and its grammatical equivalents as used herein refer to a molecule or composition, whether removed from nature (including genomic DNA and mRNA) or synthesized (including cDNA) and/or amplified under laboratory conditions, that has been increased in purity, wherein "purity" is a relative term, not "absolute purity." It is to be understood, however, that nucleic acids and proteins can be formulated with diluents or adjuvants and still for practical purposes be isolated. For example, nucleic acids typically are mixed with an acceptable carrier or diluent when used for introduction into cells. The term "substantially purified" and its grammatical equivalents as used herein refer to a nucleic acid sequence, polypeptide, protein or other compound which is essentially free, i.e., is more than about 50% free of, more than about 70% free of, more than about 90% free of, the polynucleotides, proteins, polypeptides and other molecules that the nucleic acid, polypeptide, protein or other compound is naturally associated with.

"Polynucleotide", "oligonucleotide", "polynucleotide construct", "gene", "gene construct", "heterologous gene" and their grammatical equivalents as used herein refer to a polymeric form of nucleotides or nucleic acids of any length, either ribonucleotides or deoxyribonucleotides. This term refers only to the primary structure of the molecule. Thus, this term includes double and single stranded DNA, triplex DNA, as well as double and single stranded RNA. It also includes modified, for example, by methylation and/or by capping, and unmodified forms of the polynucleotide. The term is also meant to include molecules that include non-naturally occurring or synthetic nucleotides as well as nucleotide analogs. The nucleic acid sequences and vectors disclosed or contemplated herein can be introduced into a cell by, for example, transfection, transformation, or transduction.

"Transfection," "transformation," or "transduction" as used herein refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), Methods in Molecular Biology, Vol. 7, Gene Transfer and Expression Protocols, Humana Press (1991)); DEAE-dextran; electroporation; cationic liposome-mediated transfection; tungsten particle-facilitated microparticle bombardment (Johnston, *Nature,* 346:776-777 (1990)); and strontium phosphate DNA co-precipitation (Brash et al., *Mol. Cell Biol.,* 7:2031-2034 (1987)). Phage or viral vectors can be introduced into host cells, after growth of infectious particles in suitable packaging cells, many of which are commercially available.

"Polypeptide", "peptide" "polypeptide construct" and "peptide construct" and their grammatical equivalents as used herein refer to a polymer of amino acid residues. A "mature protein" is a protein which is full-length and which, optionally, includes glycosylation or other modifications typical for the protein in a given cellular environment. Polypeptides and proteins disclosed herein (including functional portions and functional variants thereof) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, 5-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenyl serine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine. The present disclosure further contemplates that expression of polypeptides described herein in an engineered cell can be associated with post-translational modifications of one or more amino acids of the polypeptide constructs. Non-limiting examples of post-translational modifications include phosphorylation, acylation including acetylation and formylation, glycosylation (including N-linked and O-linked), amidation, hydroxylation, alkylation including methylation and ethylation, ubiquitylation, addition of pyrrolidone carboxylic acid, formation of disulfide bridges, sulfation, myristoylation, palmitoylation, isoprenylation, farnesylation, geranylation, glypiation, lipoylation and iodination.

Nucleic acids and/or nucleic acid sequences are "homologous" when they are derived, naturally or artificially, from a common ancestral nucleic acid or nucleic acid sequence. Proteins and/or protein sequences are "homologous" when their encoding DNAs are derived, naturally or artificially, from a common ancestral nucleic acid or nucleic acid sequence. The homologous molecules can be termed homologs. For example, any naturally occurring proteins, as described herein, can be modified by any available mutagenesis method. When expressed, this mutagenized nucleic acid encodes a polypeptide that is homologous to the protein encoded by the original nucleic acid. Homology is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95% or 99% or more can also be used to establish homology. Methods for determining sequence identity percentages (e.g., BLASTP and BLASTN using default parameters) are described herein and are generally available.

The term "identical" and its grammatical equivalents as used herein or "sequence identity" in the context of two nucleic acid sequences or amino acid sequences of polypeptides refers to the residues in the two sequences which are the same when aligned for maximum correspondence over a specified comparison window. A "comparison window", as used herein, refers to a segment of at least about 20 contiguous positions, usually about 50 to about 200, more usually about 100 to about 150 in which a sequence can be compared to a reference sequence of the same number of contiguous positions after the two sequences are aligned optimally. Methods of alignment of sequences for comparison are well-known in the art. Optimal alignment of sequences for comparison can be conducted by the local homology algorithm of Smith and Waterman, *Adv. Appl. Math.,* 2:482 (1981); by the alignment algorithm of Needleman and Wunsch, *J. Mol. Biol.,* 48:443 (1970); by the search for similarity method of Pearson and Lipman, *Proc. Nat. Acad. Sci U.S.A.,* 85:2444 (1988); by computerized implementations of these algorithms (including, but not limited to CLUSTAL in the PC/Gene program by Intelligentics, Mountain View Calif., GAP, BESTFIT, BLAST, FASTA, and TFASTA in the Wisconsin Genetics Software Package, Genetics Computer Group (GCG), 575 Science Dr., Madison, Wis., U.S.A.); the CLUSTAL program is well described by Higgins and Sharp, *Gene,* 73:237-244 (1988) and Higgins and Sharp, *CABIOS,* 5:151-153 (1989); Corpet et al., *Nucleic Acids Res.,* 16:10881-10890 (1988); Huang et al., *Computer Applications in the Biosciences,* 8:155-165 (1992); and Pearson et al., *Methods in Molecular Biology,* 24:307-331 (1994). Alignment is also often performed by inspection and manual alignment. In one class of embodiments, the polypeptides herein are at least 80%, 85%, 90%, 98% 99% or 100% identical to a reference polypeptide, or a fragment thereof, e.g., as measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 98%, 99% or 100% identical to a reference nucleic acid or a fragment thereof, e.g., as measured by BLASTN (or CLUSTAL, or any other available alignment software) using default parameters. When one molecule is said to have certain percentage of sequence identity with a larger molecule, it means that when the two molecules are optimally aligned, said percentage of residues in the smaller molecule finds a match residue in the larger molecule in accordance with the order by which the two molecules are optimally aligned.

The term "substantially identical" and its grammatical equivalents as applied to nucleic acid or amino acid sequences mean that a nucleic acid or amino acid sequence comprises a sequence that has at least 90% sequence identity or more, at least 95%, at least 98% and at least 99%, compared to a reference sequence using the programs described above, e.g., BLAST, using standard parameters. For example, the BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, Proc. Natl. Acad. Sci. USA 89:10915 (1992)). Percentage of sequence identity is determined by comparing two optimally aligned sequences over a comparison window, wherein the portion of the polynucleotide sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. In embodiments, the substantial identity exists over a region of the sequences that is at least about 50 residues in length, over a region of at least about 100 residues, and in embodiments, the sequences are substantially identical over at least about 150 residues. In embodiments, the sequences are substantially identical over the entire length of the coding regions.

An "expression vector" or "vector" is any genetic element, e.g., a plasmid, chromosome, virus, transposon, behaving either as an autonomous unit of polynucleotide replication within a cell. (i.e. capable of replication under its own control) or being rendered capable of replication by insertion into a host cell chromosome, having attached to it another polynucleotide segment, so as to bring about the replication and/or expression of the attached segment. Suitable vectors include, but are not limited to, plasmids, transposons, bacteriophages and cosmids. Vectors can contain polynucleotide sequences which are necessary to effect ligation or insertion of the vector into a desired host cell and to effect the expression of the attached segment. Such sequences differ depending on the host organism; they include promoter sequences to effect transcription, enhancer sequences to increase transcription, ribosomal binding site sequences and transcription and translation termination sequences. Alternatively, expression vectors can be capable of directly expressing nucleic acid sequence products encoded therein without ligation or integration of the vector into host cell DNA sequences. In some embodiments, the vector is an "episomal expression vector" or "episome," which is able to replicate in a host cell, and persists as an extrachromosomal segment of DNA within the host cell in the presence of appropriate selective pressure (see, e.g., Conese et al., *Gene Therapy,* 11:1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP. Vector also can comprise a selectable marker gene.

The term "adenovirus," as used herein, refers to an adenovirus that retains the ability to participate in the adenovirus life cycle and has not been physically inactivated by, for example, disruption (e.g., sonication), denaturing (e.g., using heat or solvents), or cross-linkage (e.g., via formalin cross-linking). The "adenovirus life cycle" includes (1) virus binding and entry into cells, (2) transcription of the adenoviral genome and translation of adenovirus proteins, (3) replication of the adenoviral genome, and (4) viral particle assembly (see, e.g., Fields Virology, $5^{th}$ ed., Knipe et al. (eds.), Lippincott Williams & Wilkins, Philadelphia, Pa. (2006)). The term "adenoviral vector," as used herein, refers to an adenovirus in which the adenoviral genome has been manipulated to accommodate a nucleic acid sequence that is non-native with respect to the adenoviral genome. Typically, an adenoviral vector is generated by introducing one or more mutations (e.g., a deletion, insertion, or substitution) into the adenoviral genome of the adenovirus so as to accommodate the insertion of a non-native nucleic acid sequence, for example, for gene transfer, into the adenovirus.

The term "selectable marker gene" as used herein refers to a nucleic acid sequence that allows cells expressing the nucleic acid sequence to be specifically selected for or against, in the presence of a corresponding selective agent. Suitable selectable marker genes are known in the art and described in, e.g., International Patent Application Publications WO 1992/08796 and WO 1994/28143; Wigler et al., *Proc. Natl. Acad. Sci. USA,* 77: 3567 (1980); O'Hare et al., *Proc. Natl. Acad. Sci. USA,* 78: 1527 (1981); Mulligan & Berg, *Proc. Natl. Acad. Sci. USA,* 78: 2072 (1981); Colberre-Garapin et al., *J. Mol. Biol.,* 150:1 (1981); Santerre et al., *Gene,* 30: 147 (1984); Kent et al., *Science,* 237: 901-903 (1987); Wigler et al., *Cell,* 11: 223 (1977); Szybalska & Szybalski, *Proc. Natl. Acad. Sci. USA,* 48: 2026 (1962); Lowy et al., *Cell,* 22: 817 (1980); and U.S. Pat. Nos. 5,122,464 and 5,770,359.

The term "coding sequence" as used herein refers to a segment of a polynucleotide that codes for protein. The region or sequence is bounded nearer the 5' end by a start codon and nearer the 3' end with a stop codon. Coding sequences can also be referred to as open reading frames.

The term "operably linked" as used herein refers to refers to the physical and/or functional linkage of a DNA segment to another DNA segment in such a way as to allow the segments to function in their intended manners. A DNA sequence encoding a gene product is operably linked to a regulatory sequence when it is linked to the regulatory sequence, such as, for example, promoters, enhancers and/or silencers, in a manner which allows modulation of transcription of the DNA sequence, directly or indirectly. For example, a DNA sequence is operably linked to a promoter when it is ligated to the promoter downstream with respect to the transcription initiation site of the promoter, in the correct reading frame with respect to the transcription initiation site and allows transcription elongation to proceed through the DNA sequence. An enhancer or silencer is operably linked to a DNA sequence coding for a gene product when it is ligated to the DNA sequence in such a manner as to increase or decrease, respectively, the transcription of the DNA sequence. Enhancers and silencers can be located upstream, downstream or embedded within the coding regions of the DNA sequence. A DNA for a signal sequence is operably linked to DNA coding for a polypeptide if the signal sequence is expressed as a pre-protein that participates in the secretion of the polypeptide. Linkage of DNA sequences to regulatory sequences is typically accomplished by ligation at suitable restriction sites or via adapters or linkers inserted in the sequence using restriction endonucleases known to one of skill in the art.

The terms "induce", "induction" and its grammatical equivalents as used herein refer to an increase in nucleic acid sequence transcription, promoter activity and/or expression brought about by a transcriptional regulator, relative to some basal level of transcription.

The term "transcriptional regulator" refers to a biochemical element that acts to prevent or inhibit the transcription of a promoter-driven DNA sequence under certain environmental conditions (e.g., a repressor or nuclear inhibitory protein), or to permit or stimulate the transcription of the promoter-driven DNA sequence under certain environmental conditions (e.g., an inducer or an enhancer).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. The term "Ig enhancers" refers to enhancer elements derived from enhancer regions mapped within the immunoglobulin (Ig) locus (such enhancers include for example, the heavy chain (mu) 5' enhancers, light chain (kappa) 5' enhancers, kappa and mu intronic enhancers, and 3' enhancers (see generally Paul W. E. (ed), Fundamental Immunology, 3rd Edition, Raven Press, New York (1993), pages 353-363; and U.S. Pat. No. 5,885,827).

The term "promoter" refers to a region of a polynucleotide that initiates transcription of a coding sequence. Promoters are located near the transcription start sites of genes, on the same strand and upstream on the DNA (towards the 5' region of the sense strand). Some promoters are constitutive as they are active in all circumstances in the cell, while others are regulated becoming active in response to specific stimuli, e.g., an inducible promoter. The term "promoter activity" and its grammatical equivalents as used herein refer to the extent of expression of nucleotide sequence that is operably linked to the promoter whose activity is being measured. Promoter activity can be measured directly by determining the amount of RNA transcript produced, for example by Northern blot analysis or indirectly by determining the amount of product coded for by the linked nucleic acid sequence, such as a reporter nucleic acid sequence linked to the promoter.

"Inducible promoter" as used herein refers to a promoter which is induced into activity by the presence or absence of transcriptional regulators, e.g., biotic or abiotic factors. Inducible promoters are useful because the expression of genes operably linked to them can be turned on or off at certain stages of development of an organism or in a particular tissue. Non-limiting examples of inducible promoters include alcohol-regulated promoters, tetracycline-regulated promoters, steroid-regulated promoters, metal-regulated promoters, pathogenesis-regulated promoters, temperature-regulated promoters and light-regulated promoters. The inducible promoter can be part of a gene switch or genetic switch. The inducible promoter can be a gene switch ligand inducible promoter. In some cases, an inducible promoter can be a small molecule ligand-inducible two polypeptide ecdysone receptor-based gene switch. In some cases, a gene switch can be selected from ecdysone-based receptor components as described in, but without limitation to, any of the systems described in: International Patent Applications WO 2001/070816; WO 2002/029075; WO 2002/066613; WO 2002/066614; WO 2002/066612; WO 2002/066615; WO 2003/027266; WO 2003/027289; WO 2005/108617; WO 2009/045370; WO 2009/048560; WO 2010/042189; WO 2010/042189; WO 2011/119773; and WO 2012/122025; and U.S. Pat. Nos. 7,091,038; 7,776,587; 7,807,417; 8,202,718; 8,105,825; 8,168,426; 7,531,326; 8,236,556; 8,598,409; 8,715,959; 7,601,508; 7,829,676; 7,919,269; 8,030,067; 7,563,879; 8,021,878; 8,497,093; 7,935,510; 8,076,454; 9,402,919; 9,493,540; 9,249,207; and 9,492,482, each of which is incorporated by reference in its entirety).

The term "gene switch" or "genetic switch" refers to the combination of a response element associated with a promoter, and for instance, an EcR based system, which, in the presence of one or more ligands, modulates the expression of a gene into which the response element and promoter are incorporated. Tightly regulated inducible gene expression systems or gene switches are useful for various applications such as gene therapy, large scale production of proteins in cells, cell based high throughput screening assays, functional genomics and regulation of traits in transgenic plants and animals. Such inducible gene expression systems can include ligand inducible heterologous gene expression systems.

"Sleeping Beauty (SB) Transposon System" refers a synthetic DNA transposon system for to introducing DNA sequences into the chromosomes of vertebrates. Some exemplary embodiments of the system are described, for example, in U.S. Pat. Nos. 6,489,458, 8,227,432, 9,228,180 and WO/2016/145146. The Sleeping Beauty transposon system is composed of a Sleeping Beauty (SB) transposase and a SB transposon. In embodiments, the Sleeping Beauty transposon system can include the SB11 transposon system, the SB100X transposon system, or the SB110 transposon system.

"Transposon" or "transposable element" (TE) is a vector DNA sequence that can change its position within the genome, sometimes creating or reversing mutations and altering the cell's genome size. Transposition often results in duplication of the TE. Class I TEs are copied in two stages: first they are transcribed from DNA to RNA, and the RNA produced is then reverse transcribed to DNA. This copied DNA is then inserted at a new position into the genome. The reverse transcription step is catalyzed by a reverse transcriptase, which can be encoded by the TE itself. The characteristics of retrotransposons are similar to retroviruses, such as HIV. The cut-and-paste transposition mechanism of class II TEs does not involve an RNA intermediate. The transpositions are catalyzed by several transposase enzymes. Some transposases non-specifically bind to any target site in DNA, whereas others bind to specific DNA sequence targets. The transposase makes a staggered cut at the target site resulting in single-strand 5' or 3' DNA overhangs (sticky ends). This step cuts out the DNA transposon, which is then ligated into a new target site; this process involves activity of a DNA polymerase that fills in gaps and of a DNA ligase that closes the sugar-phosphate backbone. This results in duplication of the target site. The insertion sites of DNA transposons can be identified by short direct repeats which can be created by the staggered cut in the target DNA and filling in by DNA polymerase, followed by a series of inverted repeats important for the TE excision by transposase. Cut-and-paste TEs can be duplicated if their transposition takes place during S phase of the cell cycle when a donor site has already been replicated, but a target site has not yet been replicated. Transposition can be classified as either autonomous or non-autonomous in both Class I and Class II TEs. Autonomous TEs can move by themselves while non-autonomous TEs require the presence of another TE to move. This is often because non-autonomous TEs lack transposase (for class II) or reverse transcriptase (for class I).

"Transposase" refers an enzyme that binds to the end of a transposon and catalyzes the movement of the transposon to another part of the genome by a cut and paste mechanism or a replicative transposition mechanism.

"T cell" or "T lymphocyte" as used herein is a type of lymphocyte that plays a central role in cell-mediated immunity. They can be distinguished from other lymphocytes, such as B cells and natural killer cells (NK cells), by the presence of a T-cell receptor (TCR) on the cell surface.

"T helper cells" ($T_H$ cells) assist other white blood cells in immunologic processes, including maturation of B cells into plasma cells and memory B cells, and activation of cytotoxic T cells and macrophages. These cells are also known as CD4+ T cells because they express the CD4 glycoprotein on their surfaces. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H9$, $T_H17$, $T_H22$ or $T_{FH}$ (T follicular helper cells), which secrete different cytokines to facilitate different types of immune responses. Signaling from the APCs directs T cells into particular subtypes.

"Cytotoxic T cells" (TC cells, or CTLs) or "cytotoxic T lymphocytes" destroy virus-infected cells and tumor cells, and are also implicated in transplant rejection. These cells are also known as CD8+ T cells since they express the CD8 glycoprotein at their surfaces. These cells recognize their targets by binding to antigen associated with MHC class I molecules, which are present on the surface of all nucleated cells. Through IL-10, adenosine, and other molecules secreted by regulatory T cells, the CD8+ cells can be inactivated to an anergic state, which prevents autoimmune diseases.

"Memory T cells" are a subset of antigen-specific T cells that persist long-term after an infection has resolved. They quickly expand to large numbers of effector T cells upon re-exposure to their cognate antigen, thus providing the immune system with memory against past infections. Memory T cells comprise three subtypes: central memory T cells ($T_{CM}$ cells) and two types of effector memory T cells ($T_{EM}$ cells and $T_{EMRA}$ cells). Memory cells can be either CD4+ or CD8+. Memory T cells typically express the cell surface proteins CD45RO, CD45RA and/or CCR7.

"Regulatory T cells" (Treg cells), formerly known as suppressor T cells, play a role in the maintenance of immunological tolerance. Their major role is to shut down T cell-mediated immunity toward the end of an immune reaction and to suppress autoreactive T cells that escaped the process of negative selection in the thymus.

"Natural killer T cells" (NKT cells—not to be confused with natural killer cells of the innate immune system) bridge the adaptive immune system with the innate immune system. Unlike conventional T cells that recognize peptide antigens presented by major histocompatibility complex (MHC) molecules, NKT cells recognize glycolipid antigen presented by a molecule called CD1d. Once activated, these cells can perform functions ascribed to both T helper ($T_H$) and cytotoxic T (TC) cells (i.e., cytokine production and release of cytolytic/cell killing molecules). They are also able to recognize and eliminate some tumor cells and cells infected with herpes viruses.

"Adoptive T cell transfer" refers to the isolation and ex vivo expansion of tumor specific T cells to achieve greater number of T cells than what could be obtained by vaccination alone or the patient's natural tumor response. The tumor specific T cells are then infused into patients with cancer in an attempt to give their immune system the ability to overwhelm remaining tumor via T cells which can attack and kill cancer. There are many forms of adoptive T cell therapy being used for cancer treatment; culturing tumor infiltrating lymphocytes or TIL, isolating and expanding one particular T cell or clone, and even using T cells that have been engineered to potently recognize and attack tumors.

"Antibody" as used herein refers to monoclonal or polyclonal antibodies. The term "monoclonal antibodies," as used herein, refers to antibodies that are produced by a single clone of B-cells and bind to the same epitope. In contrast, "polyclonal antibodies" refer to a population of antibodies that are produced by different B-cells and bind to different epitopes of the same antigen. A whole antibody typically consists of four polypeptides: two identical copies of a heavy (H) chain polypeptide and two identical copies of a light (L) chain polypeptide. Each of the heavy chains contains one N-terminal variable (VH) region and three C-terminal constant (CH1, CH2 and CH3) regions, and each light chain contains one N-terminal variable (VL) region and one C-terminal constant (CL) region. The variable regions of each pair of light and heavy chains form the antigen binding site of an antibody. The VH and VL regions have a similar general structure, with each region comprising four framework regions, whose sequences are relatively conserved. The framework regions are connected by three complementarity determining regions (CDRs). The three CDRs, known as CDR1, CDR2, and CDR3, form the "hypervariable region" of an antibody, which is responsible for antigen binding.

"Antibody like molecules" can be for example proteins that are members of the Ig-superfamily which are able to selectively bind a partner. MHC molecules and T cell receptors are such molecules. In one embodiment, the antibody-like molecule is an TCR. In one embodiment, the TCR has been modified to increase its MHC binding affinity.

The terms "fragment of an antibody," "antibody fragment," "functional fragment of an antibody," "antigen-binding portion" or its grammatical equivalents are used interchangeably herein to mean one or more fragments or portions of an antibody that retain the ability to specifically bind to an antigen (see, generally, Holliger et al., *Nat. Biotech.,* 23(9):1126-1129 (2005)). The antibody fragment desirably comprises, for example, one or more CDRs, the variable region (or portions thereof), the constant region (or portions thereof), or combinations thereof. Non-limiting examples of antibody fragments include (i) a Fab fragment, which is a monovalent fragment consisting of the VL, VH, CL, and CH1 domains; (ii) a F(ab')2 fragment, which is a bivalent fragment comprising two Fab fragments linked by a disulfide bridge at the stalk region; (iii) a Fv fragment consisting of the VL and VH domains of a single arm of an antibody; (iv) a single chain Fv (scFv), which is a monovalent molecule consisting of the two domains of the Fv fragment (i.e., VL and VH) joined by a synthetic linker which enables the two domains to be synthesized as a single polypeptide chain (see, e.g., Bird et al., *Science,* 242: 423-426 (1988); Huston et al., *Proc. Natl. Acad. Sci. USA,* 85: 5879-5883 (1988); and Osbourn et al., *Nat. Biotechnol.,* 16: 778 (1998)) and (v) a diabody, which is a dimer of polypeptide chains, wherein each polypeptide chain comprises a VH connected to a VL by a peptide linker that is too short to allow pairing between the VH and VL on the same polypeptide chain, thereby driving the pairing between the complementary domains on different VH-VL polypeptide chains to generate a dimeric molecule having two functional antigen binding sites. Antibody fragments are known in the art and are described in more detail in, e.g., U.S. Pat. No. 8,603,950.

"Antigen recognition moiety" or "antigen recognition domain" refers to a molecule or portion of a molecule that specifically binds to an antigen. In one embodiment, the antigen recognition moiety is an antibody, antibody like molecule or fragment thereof and the antigen is a tumor antigen.

The term "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and Schirmer, R. H., Principles of Protein Structure, Springer-Verlag, New York (1979)). According to such analyses, groups of amino acids can be defined where amino acids within a group exchange preferentially with each other, and therefore resemble each other most in their impact on the overall protein structure (Schulz, G. E. and Schirmer, R. H., supra). Examples of conservative mutations include amino acid substitutions of amino acids within the sub-groups above, for example, lysine for arginine and vice versa such that a positive charge can be maintained; glutamic acid for aspartic acid and vice versa such that a negative charge can be maintained; serine for threonine such that a free —OH can be maintained; and glutamine for asparagine such that a free —$NH_2$ can be maintained. Alternatively or additionally, the functional variants can comprise the amino acid sequence of the reference protein with at least one non-conservative amino acid substitution.

The term "non-conservative mutations" involve amino acid substitutions between different groups, for example, lysine for tryptophan, or phenylalanine for serine, etc. In this case, it is preferable for the non-conservative amino acid substitution to not interfere with, or inhibit the biological activity of, the functional variant. The non-conservative amino acid substitution can enhance the biological activity of the functional variant, such that the biological activity of the functional variant is increased as compared to the homologous parent protein.

The term "ankyrin" refers to a family of adaptor proteins that mediate the attachment of integral membrane proteins to the spectrin-actin based membrane cytoskeleton. Ankyrins have binding sites for the beta subunit of spectrin and at least 12 families of integral membrane proteins. This linkage is required to maintain the integrity of the plasma membranes and to anchor specific ion channels, ion exchangers and ion transporters in the plasma membrane. Ankyrins contain four functional domains: an N-terminal domain that contains 24 tandem ankyrin repeats, a central domain that binds to spectrin, a death domain that binds to proteins involved in apoptosis, and a C-terminal regulatory domain that is highly variable between different ankyrin proteins. The 24 tandem ankyrin repeats are responsible for the recognition of a wide range of membrane proteins. These 24 repeats contain 3 structurally distinct binding sites ranging from repeat 1-14. These binding sites are quasi-independent of each other and can be used in combination. The interactions the sites use to bind to membrane proteins are non-specific and consist of: hydrogen bonding, hydrophobic interactions and electrostatic interactions. These non-specific interactions gives ankyrin the property to recognize a large range of proteins as the sequence doesn't have to be conserved just the properties of the amino acids. The quasi-independence means that if a binding site is not used, it won't have a large effect on the overall binding. These two properties in combination give rise to large repertoire of proteins ankyrin can recognize. Ankyrins are encoded by three genes (ANK1, ANK2 and ANK3) in mammals. Each gene in turn produces multiple proteins through alternative splicing.

The term "proliferative disease" as referred to herein refers to a unifying concept in which excessive proliferation of cells and/or turnover of cellular matrix contributes significantly to the pathogenesis of the disease, including cancer.

"Patient" or "subject" as used herein refers to a mammalian subject diagnosed with or suspected of having or developing a proliferative disorder such as cancer. In some embodiments, the term "patient" refers to a mammalian subject with a higher than average likelihood of developing a proliferative disorder such as cancer. Exemplary patients can be humans, apes, dogs, pigs, cattle, cats, horses, goats, sheep, rodents and other mammalians that can benefit from the therapies disclosed herein. Exemplary human patients can be male and/or female. "Patient in need thereof" or "subject in need thereof" is referred to herein as a patient diagnosed with or suspected of having a disease or disorder, for instance, but not restricted to chronic hepatitis B infection.

"Administering" is referred to herein as providing one or more compositions described herein to a patient or a subject. By way of example and not limitation, composition administration, e.g., injection, can be performed by intravenous (i.v.) injection, sub-cutaneous (s.c.) injection, intradermal (i.d.) injection, intraperitoneal (i.p.) injection, or intramuscular (i.m.) injection. One or more such routes can be employed. Parenteral administration can be, for example, by bolus injection or by gradual perfusion over time. Alternatively, or concurrently, administration can be by the oral route. Additionally, administration can also be by surgical deposition of a bolus or pellet of cells, or positioning of a medical device. In an embodiment, a composition of the present disclosure can comprise engineered cells or host cells expressing nucleic acid sequences described herein, or a vector comprising at least one nucleic acid sequence described herein, in an amount that is effective to treat or prevent proliferative disorders. A pharmaceutical composition can comprise a target cell population as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

As used herein, the term "treatment", "treating", or its grammatical equivalents refers to obtaining a desired pharmacologic and/or physiologic effect. In embodiments, the effect is therapeutic, i.e., the effect partially or completely cures a disease and/or adverse symptom attributable to the disease. To this end, the inventive method comprises administering a therapeutically effective amount of the composition comprising the host cells expressing the inventive nucleic acid sequence, or a vector comprising the inventive nucleic acid sequences.

The term "therapeutically effective amount", therapeutic amount", "immunologically effective amount", "anti-tumor effective amount", "tumor-inhibiting effective amount" or its grammatical equivalents refers to an amount effective, at dosages and for periods of time necessary, to achieve a desired therapeutic result. The therapeutically effective amount can vary according to factors such as the disease state, age, sex, and weight of the individual, and the ability of a composition described herein to elicit a desired response in one or more subjects. The precise amount of the compositions of the present disclosure to be administered can be determined by a physician with consideration of individual differences in age, weight, tumor size, extent of infection or metastasis, and condition of the patient (subject).

Alternatively, the pharmacologic and/or physiologic effect of administration of one or more compositions described herein to a patient or a subject of can be "prophylactic," i.e., the effect completely or partially prevents a disease or symptom thereof. A "prophylactically effective amount" refers to an amount effective, at dosages and for periods of time necessary, to achieve a desired prophylactic result (e.g., prevention of disease onset).

HBV Molecular Vaccine

Hepatitis B (HepB) is a potentially life-threatening liver infection caused by the hepatitis B virus (HBV). HBV can cause chronic infection and puts people at high risk of death from cirrhosis and liver cancer. The evolution of HBV is strikingly highlighted by the geographical distribution of the genotypes. HBV genotypes/subgenotypes have been increasingly associated with differences in clinical and virological characteristics, such as severity of liver disease and response to antiviral therapies. When comparing sequences, HBV is classified into eight genotypes (A to H), each with a distinct geographic distribution. Researchers have correlated an association between the different HBV genotypes and the severity and outcome of HBV disease.

HBV is a double stranded DNA virus with high liver tropism. HBV DNA is 3.2 kb circular, enveloped, partially double strand DNA genome (FIGS. 3A-3D). HBV has four genes (S, C, P, and X). The S gene codes for envelope (lipid bilayer) surface protein (HBsAg) consisting of small surface protein (S), medium surface protein (S+PreS2), and large surface protein (S+PreS2+PreS1). The C gene codes for the capsid or core proteins. The C gene has a precore and a core region. If translation is initiated at the precore region, the protein is HBeAg. If translation is initiated at the core region, the protein is HBcAg. The P gene codes for the DNA polymerase (Pol). The X gene codes for the x protein (HBxAg) (FIGS. 3A-3D). The HBV genome comprises Pol (832 amino acids) comprising TP, SP, RT and RH; PreS1 (108 amino acids); PreS2 (55 amino acids); S (226 amino acids); PreC (29 amino acids); C (183 amino acids); and HBx (154 amino acids) (FIGS. 3A-3D).

Acute HBV infection is characterized by the presence of hepatitis B surface antigen (HBsAg) and immunoglobulin M (IgM) antibody to the core antigen, HBcAg. During the initial phase of infection, patients are also seropositive for hepatitis B e antigen (HBeAg). HBeAg is usually a marker of high levels of replication of the virus. The presence of HBeAg indicates that the blood and body fluids of the infected individual are highly infectious. Chronic infection is characterized by the persistence of HBsAg for at least 6 months (with or without concurrent HBeAg). Persistence of HBsAg is the principal marker of risk for developing chronic liver disease and liver cancer (hepatocellular carcinoma) later in life.

The hepatitis B virus can survive outside the body for at least 7 days. During this time, the virus can still cause infection if it enters the body of a person who is not protected by the vaccine. The incubation period of the hepatitis B virus is 75 days on average, but can vary from 30 to 180 days. The virus can be detected within 30 to 60 days after infection and can persist and develop into chronic hepatitis B. In highly endemic areas, hepatitis B is most commonly spread from mother to child at birth (perinatal transmission), or through horizontal transmission (exposure to infected blood), especially from an infected child to an uninfected child during the first 5 years of life. The development of chronic infection is very common in infants infected from their mothers or before the age of 5 years. Hepatitis B is also spread by percutaneous or mucosal exposure to infected blood and various body fluids, as well as through saliva, menstrual, vaginal, and seminal fluids. Sexual transmission of hepatitis B can also commonly occur. Infection in adulthood leads to chronic hepatitis in less than 5% of cases. Transmission of the virus can also occur through the reuse of needles and syringes either in health-care settings or among persons who inject drugs. In addition, infection can occur during medical, surgical and dental procedures, through tattooing, or through the use of razors and similar objects that are contaminated with infected blood.

Figure 2:
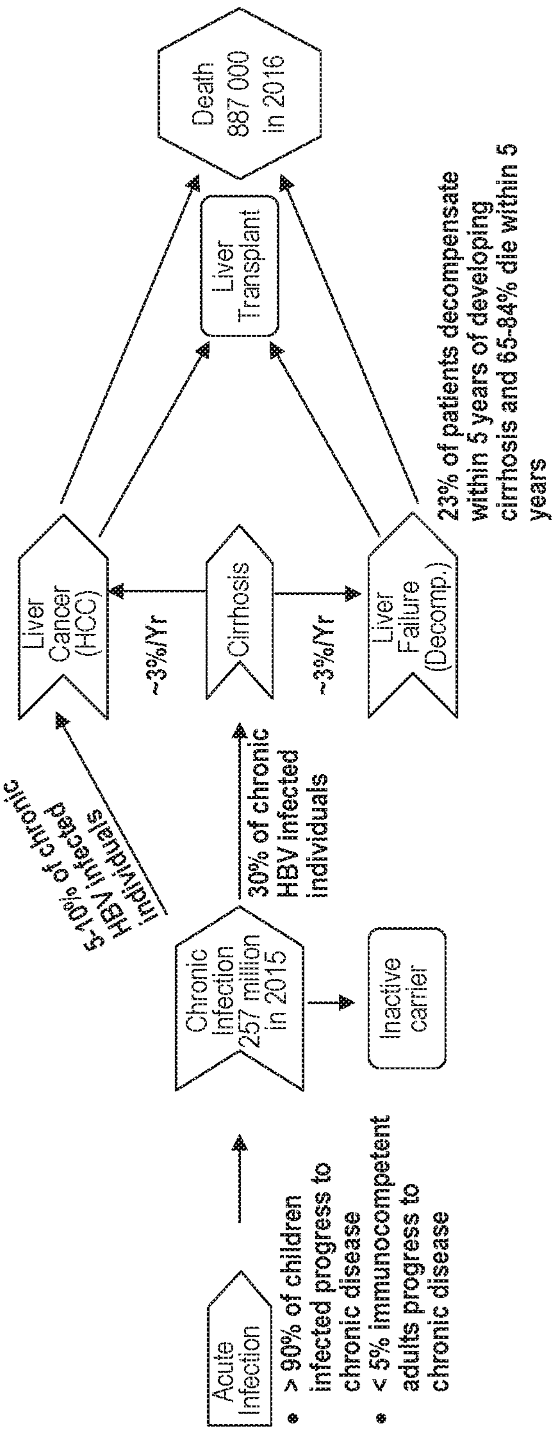
FIG. 2 is a schematic showing history of chronic HBV infection.
Figure 3A:
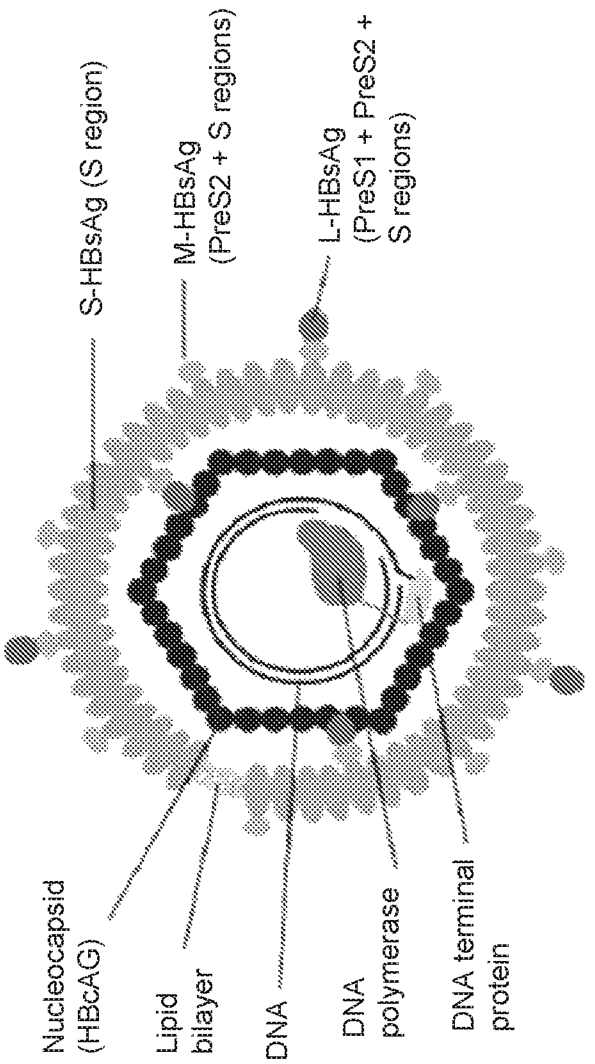
FIG. 3A is a schematic overview of hepatitis B virus. HBV DNA is 3.2 kb circular, enveloped, partially double strand DNA genome. HBV has four genes (S, C, P, and X). The S gene codes for envelope (lipid bilayer) surface protein (HBsAg) consisting of small surface protein (S), medium surface protein (S+PreS2), and large surface protein (S+PreS2+PreS1). The C gene codes for the capsid or core proteins. The C gene has a precore and a core region. If translation is initiated at the precore region, the protein is HBeAg. If translation is initiated at the core region, the protein is HBcAg. The P gene codes for the DNA polymerase (Pol). The X gene codes for the x protein (HBxAg).
Figure 3B:
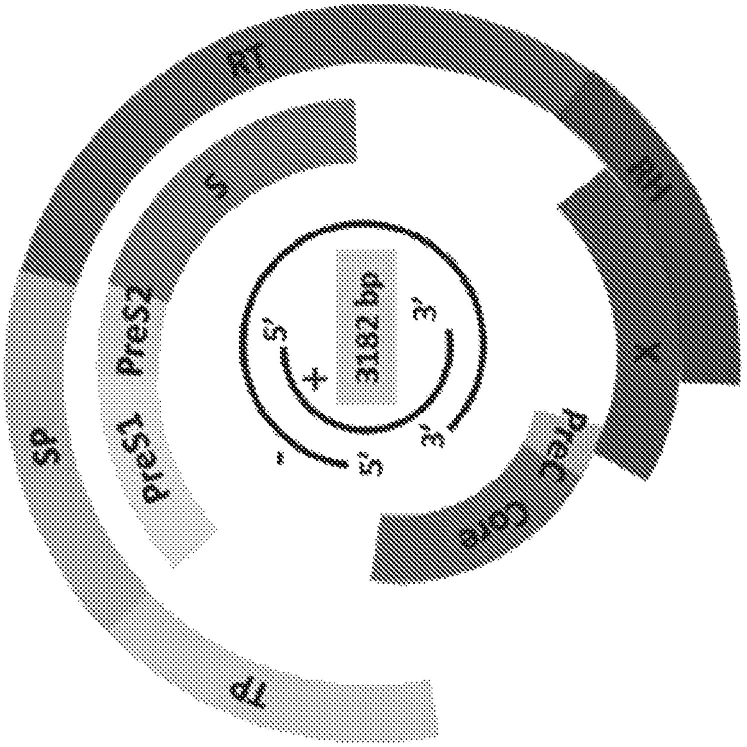
FIG. 3B is an overview of hepatitis B virus genome. The HBV genome comprises Pol (832 amino acids) comprising TP, SP, RT and RH; PreS1 (108 amino acids); PreS2 (55 amino acids); S (226 amino acids); PreC (29 amino acids); C (183 amino acids); and HBx (154 amino acids).
Figure 3C:
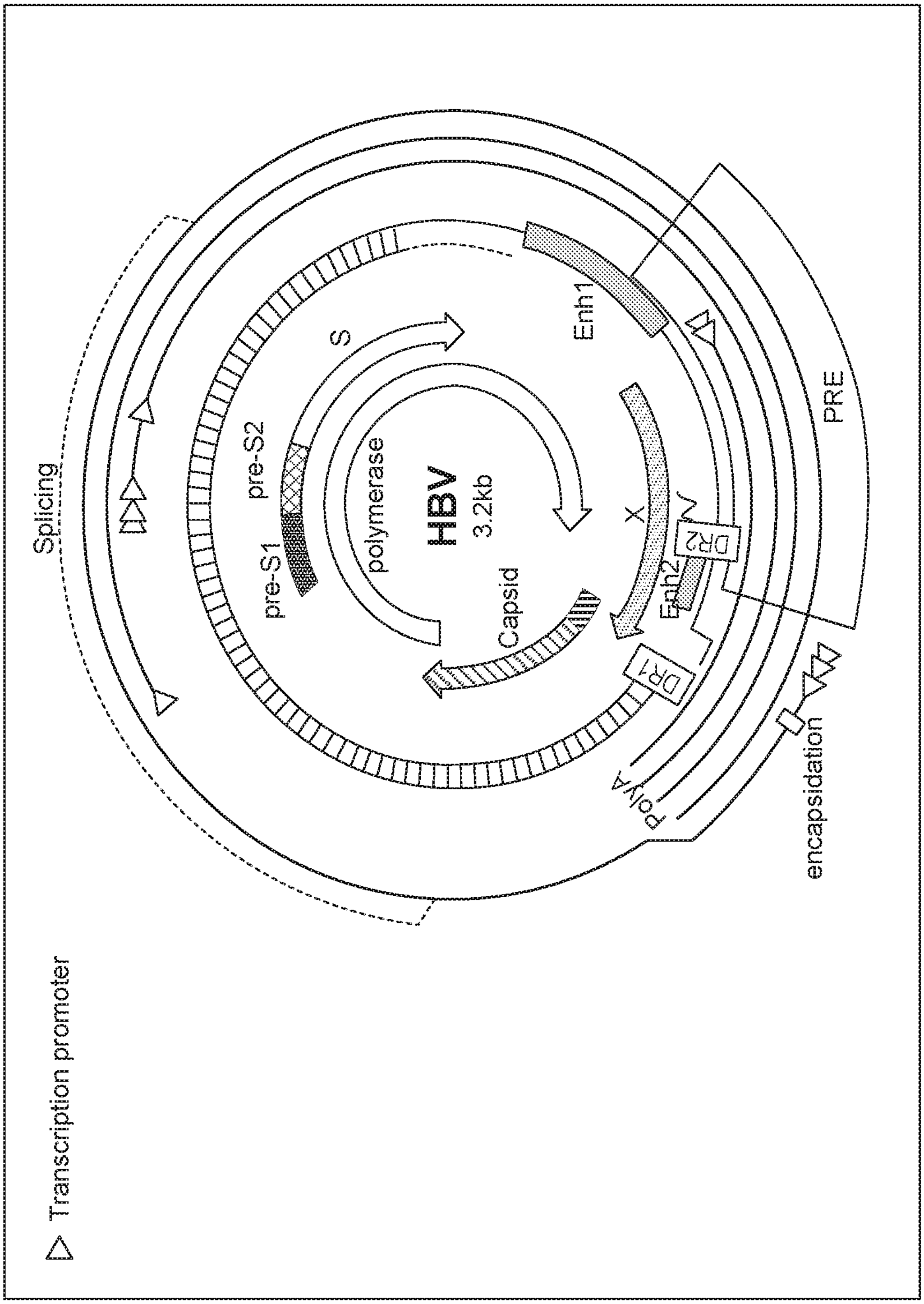
FIG. 3C shows a schematic of the HBV genome encoding several overlapping viral proteins, including the polymerase core, core envelop (Pre-S1, S2, S), HBe, and HBx proteins.
Figure 3D:
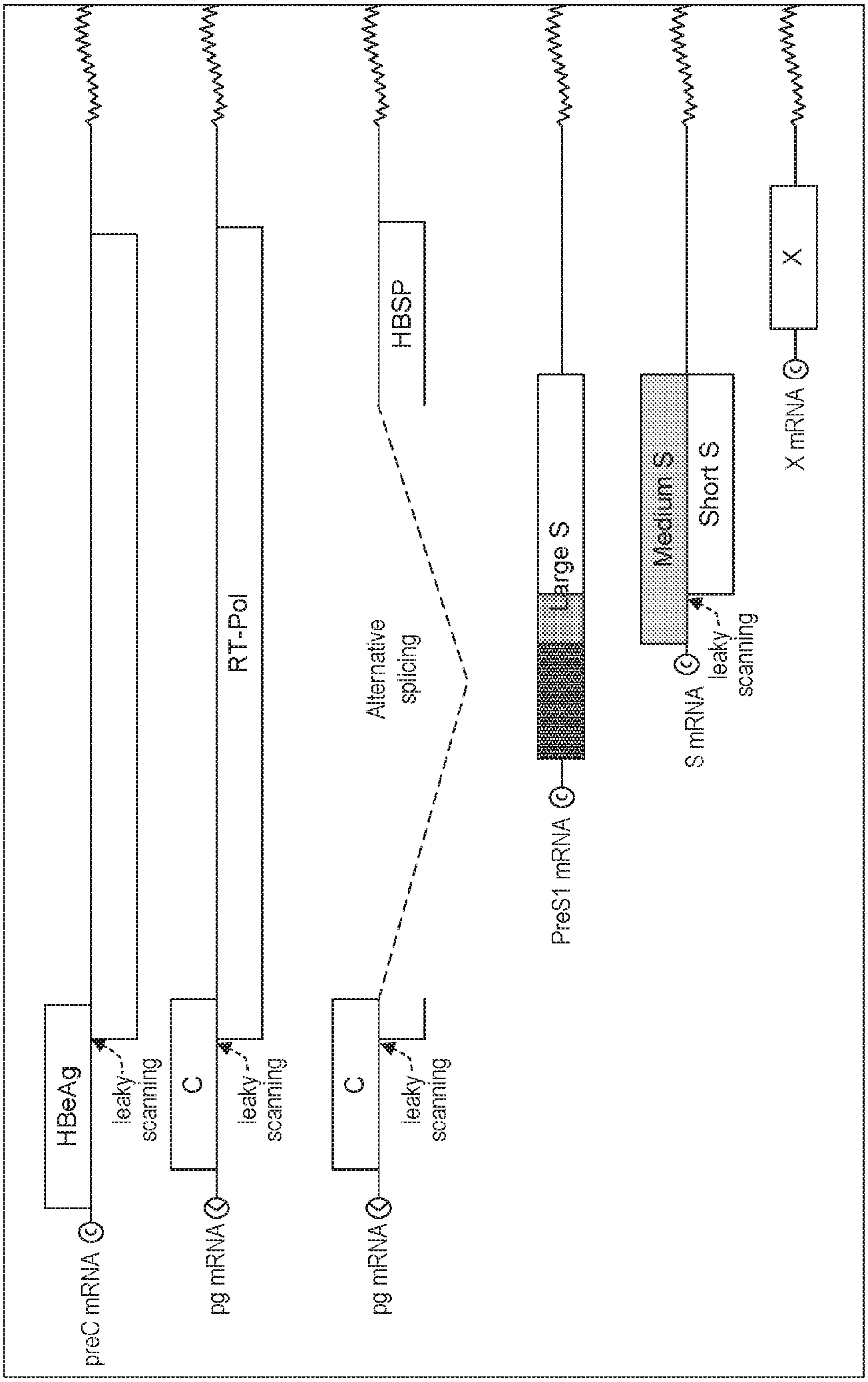
FIG. 3D shows a schematic of the HBV genome encoding several overlapping viral proteins, including the polymerase core, core envelop (Pre-S1, S2, S), HBe, and HBx proteins.

Most people do not experience any symptoms during the acute infection phase. However, some people have acute illness with symptoms that last several weeks, including yellowing of the skin and eyes (jaundice), dark urine, extreme fatigue, nausea, vomiting and abdominal pain. A small subset of persons with acute hepatitis can develop acute liver failure, which can lead to death. In some people, the hepatitis B virus can also cause a chronic liver infection that can later develop into cirrhosis (a scarring of the liver) or liver cancer. The likelihood that infection becomes chronic depends upon the age at which a person becomes infected. Children less than 6 years of age who become infected with the hepatitis B virus are the most likely to develop chronic infections. 80-90% of infants infected during the first year of life develop chronic infections; and 30-50% of children infected before the age of 6 years develop chronic infections. In adults, less than 5% of otherwise healthy persons who are infected as adults will develop chronic infection; and 20-30% of adults who are chronically infected will develop cirrhosis and/or liver cancer (FIG. 1 and FIG. 2).

There is no specific treatment for acute hepatitis B. Therefore, care is aimed at maintaining comfort and adequate nutritional balance, including replacement of fluids lost from vomiting and diarrhea. Chronic hepatitis B infection can be treated with medicines, including oral antiviral agents. Treatment (e.g., liver transplant or IFN-α nucleotide analogs) can slow the progression of cirrhosis, reduce incidence of liver cancer and improve long term survival. Recent more advanced therapeutic vaccines (i.e., GS-4777, Gilead; ABX203, Abivax) have failed in clinical trial phase 2/3. In most people, however, the treatment does not cure hepatitis B infection, but only suppresses the replication of the virus. Therefore, most people who start hepatitis B treatment must continue it for life. There is still limited access to diagnosis and treatment of hepatitis B in many resource-constrained settings.

An estimated 257 million people are living with chronic hepatitis B virus (HBV) infection (positive confirmation through surface antigen detection). In 2015, hepatitis B infection resulted in 887,000 deaths, with liver failure or liver cancer as the leading cause of death. Currently, HBV vaccines prevent infection in 95% of the cases, thereby preventing infection, liver cancer, and chronic diseases due to hepatitis B. However, there is still a large need for developing a HBV vaccine with broad coverage against multiple HBV subtypes and functionality against liver cancer. The present disclosure relates to novel HBV vaccine antigens based on bioinformatics methods and protein engineering approaches. These novel HBV vaccine candidates can be used as therapeutic vaccines against HBV and HBV-related diseases.

Treatment Options

Figure 4:
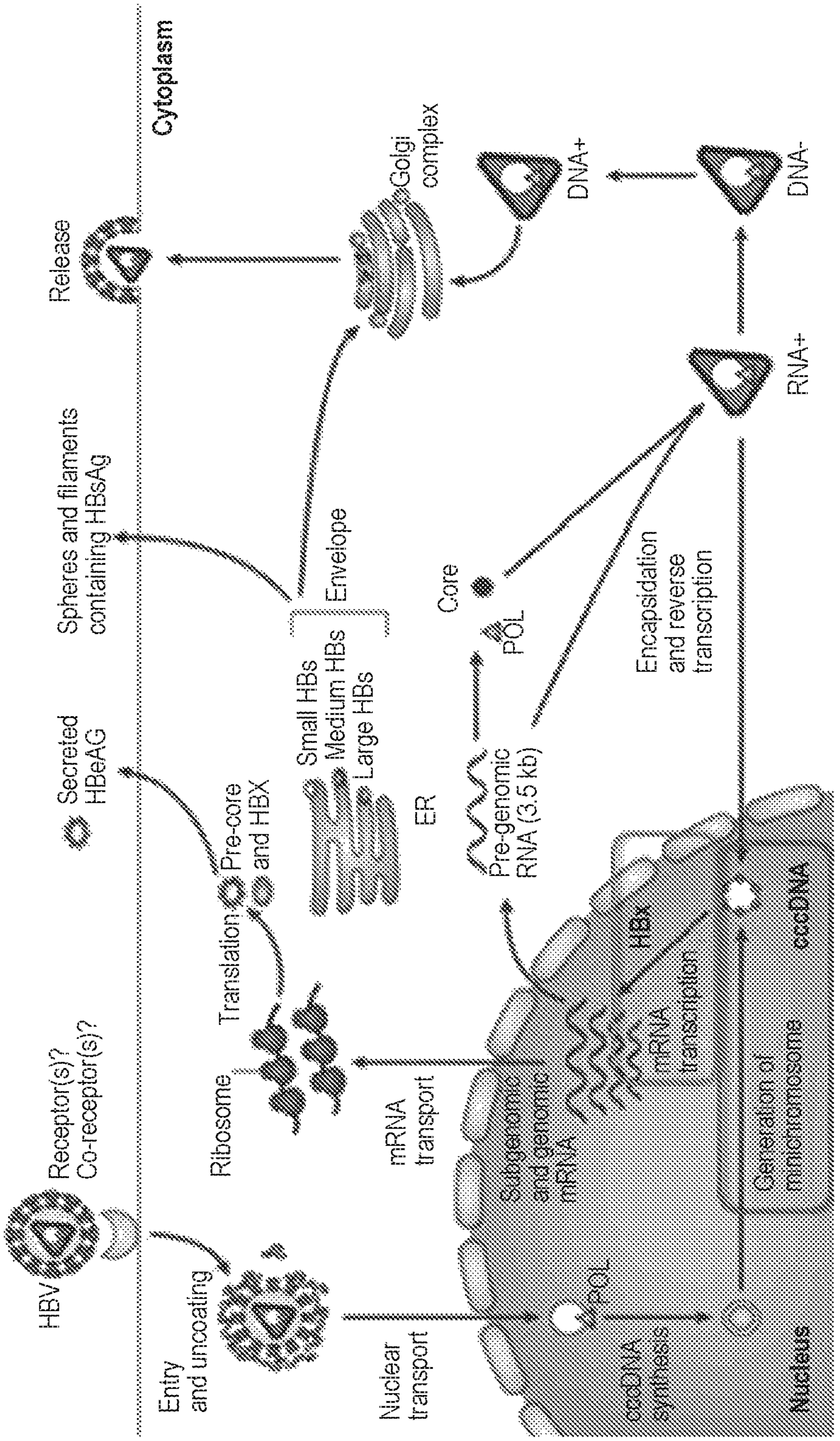
FIG. 4 shows a schematic overview of HBV infection mechanism.

Standard of care (SOC) for chronic hepatitis B infection include PEG-IFN, and/or nucleotide analogues. However, cccDNA and immune tolerance and exhaustion can persist (FIG. 4). Infection with HBV causes hepatitis that can result in cirrhosis, liver failure and hepatocellular carcinoma (HCC). The diagnosis of HBV is based on the serological findings. In fact, viral DNA, antigens and their respective antibodies can be found in the serum. HBV is subdivided into four major serotypes (adr, adw, ayr, ayw) based on a based on a common antigenic determinant (a) and two mutually exclusive determinant pairs (d/y and w/r) found on the HBsAg. There exist ten known genotypes (A-J) and forty known subgenotypes according to overall nucleotide sequence variation of the genome. The genotypes have a distinct geographical distribution and different genotypes are associated with different disease severity, course and likelihood of complications, and response to treatment and possibly vaccination. The serotypes and genotypes do not necessarily correspond (e.g., genotype D has 10 subgenotypes).

Currently, there is no cure for chronic HBV infection. Treatment options are aimed at slowing the progression of cirrhosis and viral replication, reducing the incidence of HCC and liver failures. Current treatments are divided into two major categories: (1) immune modulator drugs, i.e., mainly type I interferon (interferon alpha and pegylated interferon alpha) designed to boost the immune system to fight viral infected cells; and (2) antiviral drugs, which include nucleoside analogues (lamivudine, entecavir and telbivudine) and nucleotide analogues (adefovir, dipivoxil and tenofovir), and aimed at interfering with viral replication. The death toll to HBV infection currently is almost 0.7 million/year on par with HIV and tuberculosis. Although the rate of new HBV infection is decreasing, the increase in overall death from hepatitis requires urgent need of the development of new treatment options.

Therapeutic Approaches

HBV epitopes from surface (S), core (C), and polymerase (Pol) proteins are targeted by T cells during infection which mediate cellular immune responses to HBV. The HBV X protein (HBx), which includes MHC-I and MHC-II epitopes, is a multifunctional regulatory protein involved in viral pathogenesis and carcinogenesis. The HBV vaccine designs described herein include all major components that have potential T cell epitopes. Specifically, provided herein are the HBV vaccines comprising two different unique designs with genetic modifications (in the form of point mutations) and truncations in Pol, Core, Env and HBx. Also provided herein are uniquely designed multi-epitope constructs (i.e., cytotoxic T lymphocytes) with specific peptides grafted onto a human protein scaffold and linked by charged dipeptide that can stimulate the cellular immune responses required for controlling and clearing HBV infection.

Provided herein are various gene therapeutic approaches to treat HBV infection. For example, described in Table 1 are some of the strategies used to improve the immune system-mediated control of HBV. Also provided herein is an HBV therapeutic vaccine, intelligent design of a prime/boost DNA-based vaccine encompassing the combination of immunogenic regions of the main component of the HBV (HBsAg, HBcAg, HBxAg, HBeAg and HB PolAg) for priming and a combination of agonist CD8 T cell epitope for boosting.

Figure 5:
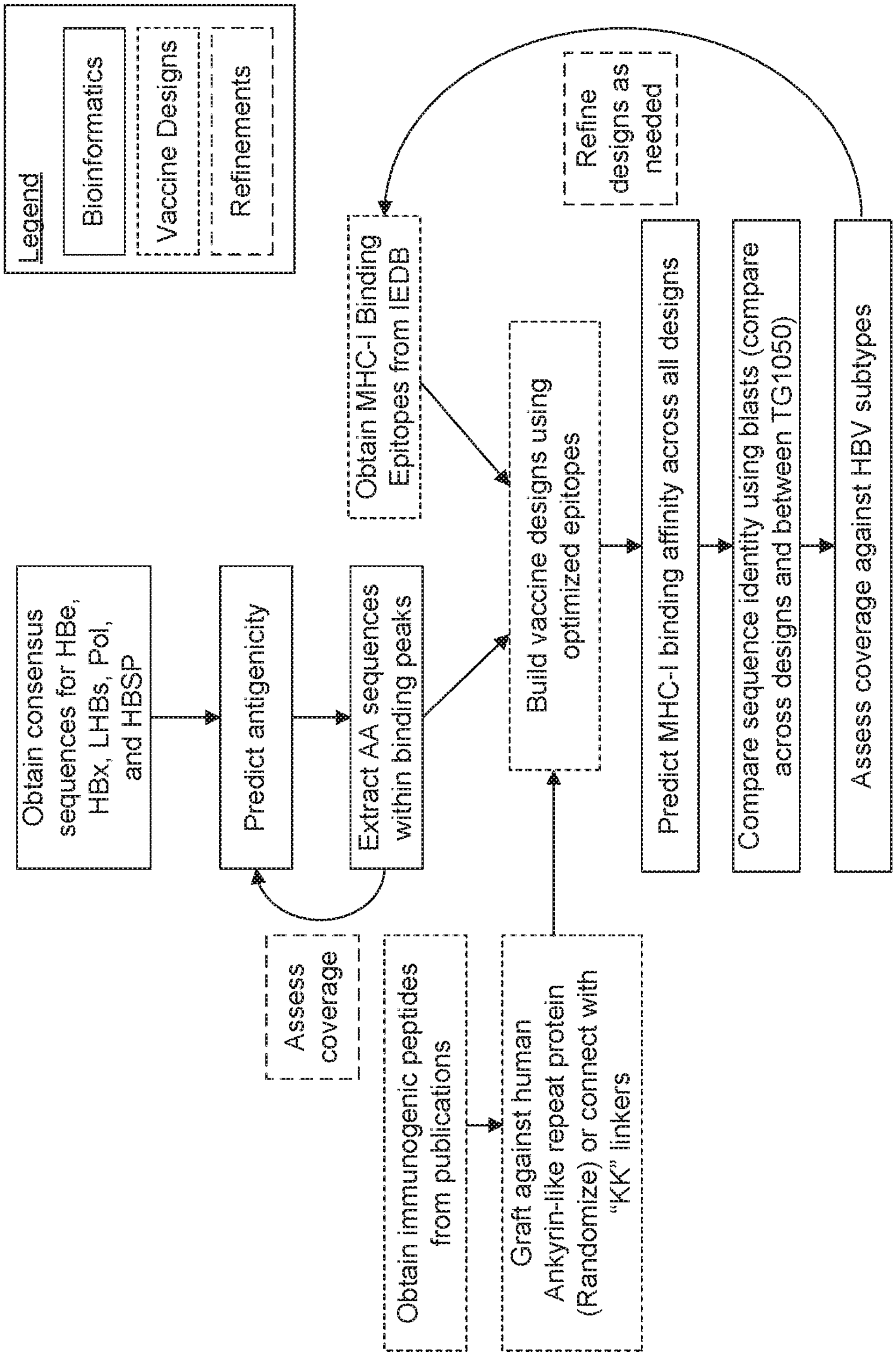
FIG. 5 is schematic overall workflow implemented for designing HBV vaccine antigens.

Provided herein are compositions, kits, and systems comprising and methods of making HBV recombinant vaccines. The HBV recombinant vaccines (e.g., HBV designs 1-5) in the present disclosure are engineered through protein engineering of HBe, HBx, LHBs, Pol, and HBSP. Each HBV vaccine antigen design was inspired via inventor-selected combinatorial guidance using bioinformatics analyses and in silico protein engineering methods (e.g., selection of antigenic sequences that match closer to consensus sequences, antigenicity predictions, and T cell epitope mapping, which could lead to MHC-I binding and cytokine production following T cell activation). The overall workflow of the presently disclosed HBV vaccine designs is shown in FIG. 5, and further detailed in Example 1. The present disclosure provides five HBV antigen designs (HBV designs 1-5) constructed in a multi-deleted gorilla adenovector (GC46).

Figure 6:
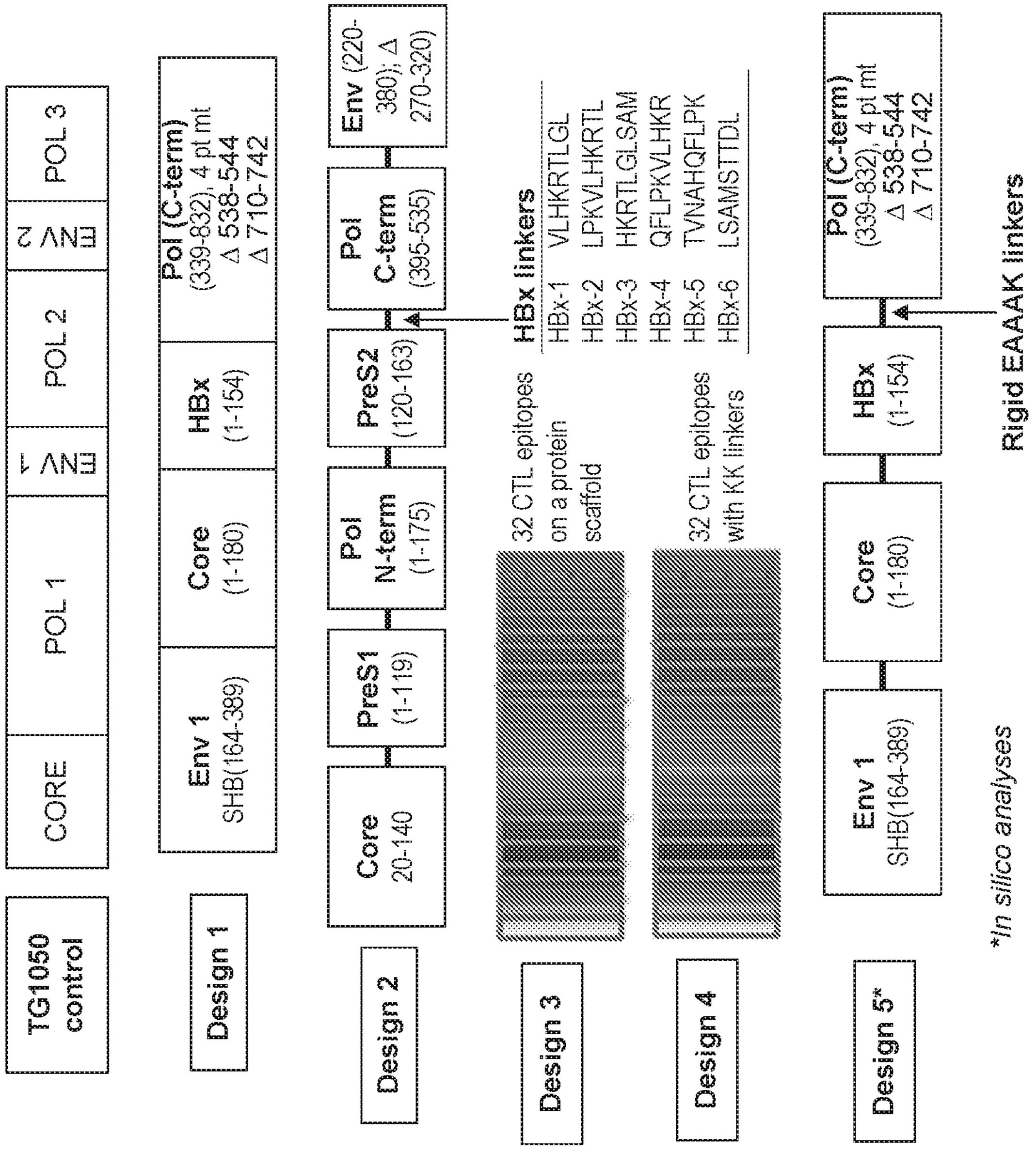
FIG. 6 shows schematic structural diagrams of HBV designs 1-5. HBV designs 1 and 2 were designed based on clade D consensus. For HBV design 3, human ankyrin-like repeat (ALR) protein scaffold (PDB code 1QYM) peptides were grafted at the helical and loop regions in a tandem manner. Two ALR scaffolds were used, connected by a cleavable linker (VSQTSKLTR). HBV design 4 epitopes were separated by KK linkers. Different linkers, such as EAAAK linkers (SEQ ID NO: 131), were used in HBV design 5 to connect the peptides.
Figure 14:
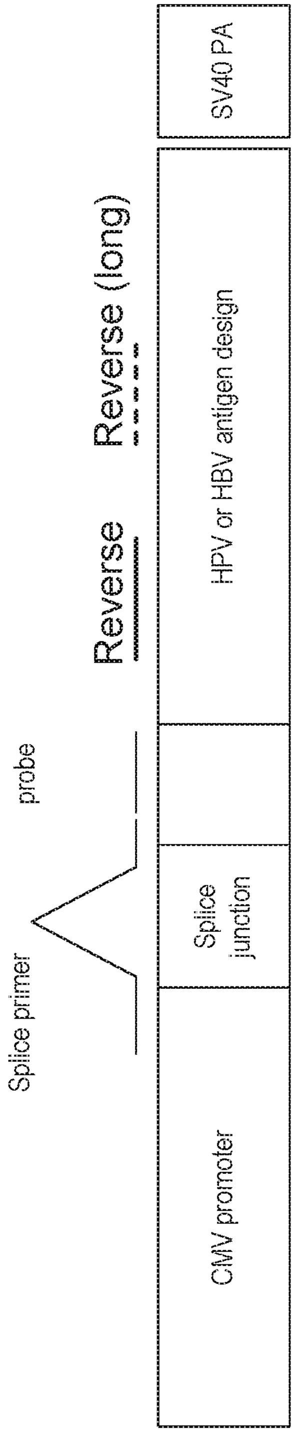
FIG. 14 is a schematic illustration showing short and long primer and probe sets generated for RNA qPCR relative expression assay. Specific primers were designed for each HBV antigen design.

Four antigen designs (HBV designs 1-4) and a control antigen were synthesized and cloned into expression plasmids—pAdShuttles for adenovector construction (FIG. 6). HBV design was analyzed to assess whether different linkers cause prediction of different epitopes. Initial antigen screening evaluated in vitro antigen expression in transient transfection, in vitro antigen processing and presentation in transient transfection studies of monocyte-derived dendritic cells. As shown in FIG. 6, HBV designs 1 and 2 were designed based on clade D consensus. 32 HBV peptides from Core (8), Surface (8), Polymerase (8), HBx (6) and HBPS (2) were curated from literature that have experimental and functional data, such as immunogenicity data, Mass-spec. etc. (Table 4). For HBV design 3, human ankyrin-like repeat (ALR) protein scaffold (PDB code 1QYM) peptides were grafted at the helical and loop regions in a tandem manner. Two ALR scaffolds were used, connected by a cleavable linker VSQTSKLTR (SEQ ID NO: 111). ALR proteins have generally high expression and high stability. Thus, ALR proteins were used as a scaffold for the HBV peptides to create novel CTLs. HBV design 4 epitopes were separated by KK linkers (FIG. 6). For RNA qPCR relative expression assay, 5'-TGCCAAGAGTGACGTGTCCA-3' (SEQ ID NO: 110) was used as a splice primer, and 5'-CCCAGGTCCAACTGCAGCCGG-3' (SEQ ID NO: 128) was used as a splice probe. Specific primers designed for each antigen were used as reverse primers (FIG. 14).

TABLE 1

Strategies to Improve the Immune Mediated Control of HBV

| Characteristics of chronic HBV infection | Therapeutic goals | Tools | Expected effects |
|---|---|---|---|
| High viral load | To decrease viral and antigen loads | Nucleoside analogs | Transient restoration of T-cell functions |
| High levels of PD-1 expression on HBV-specific T cells | To decrease the inhibitory signal | Anti-PD-L1 antibody | Restoration of T-cell functions |
| HBV-specific T-cell exhaustion | To reactivate/activate functional HBV-specific T cells in vivo<br>To activate T cells ex vivo | Vaccines<br>Novel adjuvants<br>DNA vaccines<br>Viral vaccines<br>Ag/Ab IC<br>Cytokines<br>Modified DCs<br>Stimulation of PBMCs | Reactivation of Th1 responses<br>De novo activation of CD4 and CD8 T cells<br>Improvement of antigen presentation<br>T-cell expansion<br>Improvement of antigen presentation<br>Activation of killer cells |
| HBV-specific T-cell deletion | To engineer new HBV-specific T cells | TCR-redirected T cells | Non exhausted, functional HBV-specific T cells<br>Recognition of HBV-infected cells |
| Suppressive environment | To target functional non HBV-specific T cells to the liver | Liver gene therapy | Elimination of HBV-infected hepatocytes |

Delivery System

Gorilla Adenovirus Shuttle Vector

Certain aspects of the present disclosure are directed to a vector comprising a polynucleotide encoding a polypeptide comprising one or more immune response-inducing HBV polypeptides. In certain embodiments, the vector is a viral vector. In particular embodiments, the vector is an adenoviral vector. Adenoviruses are generally associated with benign pathologies in humans, and the genomes of adenoviruses isolated from a variety of species, including humans, have been extensively studied. Adenovirus is a medium-sized (90-100 nm), non-enveloped icosahedral virus containing approximately 36 kb of double-stranded DNA. The adenovirus capsid mediates the key interactions of the early stages of the infection of a cell by the virus, and is required for packaging adenovirus genomes at the end of the adenovirus life cycle. The capsid comprises 252 capsomeres, which includes 240 hexons, 12 penton base proteins, and 12 fibers (Ginsberg et al., *Virology,* 28: 782-83 (1966)). The hexon comprises three identical proteins, namely polypeptide II (Roberts et al., *Science,* 232: 1148-51 (1986)). The penton base comprises five identical proteins and the fiber comprises three identical proteins. Proteins Ma, VI, and IX are present in the adenoviral coat and are believed to stabilize the viral capsid (Stewart et al., *Cell,* 67: 145-54 (1991), and Stewart et al., *EMBO J.,* 12(7): 2589-99 (1993)). The expression of the capsid proteins, with the exception of pIX, is dependent on the adenovirus polymerase protein. Therefore, major components of an adenovirus particle are expressed from the genome only when the polymerase protein gene is present and expressed.

Several features of adenoviruses make them ideal vehicles for transferring genetic material to cells for therapeutic applications (i.e., "gene therapy"), or for use as antigen delivery systems for vaccine applications. For example, adenoviruses can be produced in high titers (e.g., about $10^{13}$ particle units (pu)), and can transfer genetic material to non-replicating and replicating cells. The adenoviral genome can be manipulated to carry a large amount of exogenous DNA (up to about 8 kb), and the adenoviral capsid can potentiate the transfer of even longer sequences (Curiel et al., *Hum. Gene Ther.,* 3: 147-154 (1992)). Additionally, adenoviruses generally do not integrate into the host cell chromosome, but rather are maintained as a linear episome, thereby minimizing the likelihood that a recombinant adenovirus will interfere with normal cell function.

In some embodiments, the adenovirus described herein is isolated from a gorilla. There are four widely recognized gorilla subspecies within the two species of Eastern Gorilla (*Gorilla beringei*) and Western Gorilla (*Gorilla gorilla*). The Western Gorilla species includes the subspecies Western Lowland Gorilla (*Gorilla gorilla gorilla*) and Cross River Gorilla (*Gorilla gorilla diehli*). The Eastern Gorilla species includes the subspecies Mountain Gorilla (*Gorilla beringei beringei*) and Eastern Lowland Gorilla (*Gorilla beringei graueri*) (see, e.g., Wilson and Reeder, eds., *Mammalian Species of the World,* 3rd ed., Johns Hopkins University Press, Baltimore, Md. (2005)). In some embodiments, the adenovirus of the present disclosure is isolated from Mountain Gorilla (*Gorilla beringei beringei*).

Various Gorilla adenoviruses or adenoviral vectors are described in International Patent Application Publications WO 2013/052832; WO 2013/052811; and WO 2013 052799, each of which is herein incorporated by reference in its entirety.

The genomes of several such adenoviruses have been analyzed, and it has been determined that the adenovirus can have the nucleic acid sequence of, for example, SEQ ID NO: 21, SEQ ID NO: 22, SEQ ID NO: 23, SEQ ID NO: 24, or SEQ ID NO: 25, each of which includes a number of sub-sequences that serve to uniquely define the adenovirus, namely the nucleic acid sequences SEQ ID NOs: 1-10, and amino acid sequences SEQ ID NOs: 11-20. SEQ ID NOs: 6-10 encode the amino acid sequences of SEQ ID NOs: 16-20, respectively. SEQ ID NOs: 1-5 are a subset of the nucleic acid sequences of SEQ ID NOs: 6-10, respectively. SEQ ID NOs: 11-15 are a subset of the amino acid sequences of SEQ ID NOs: 16-20, respectively.

The adenovirus can be modified in the same manner as previously known adenoviruses to be used as an adenoviral vector, e.g., a gene delivery vehicle. The adenovirus and adenoviral vector can be replication-competent, conditionally replication-competent, or replication-deficient.

A replication-competent adenovirus or adenoviral vector can replicate in typical host cells, i.e., cells typically capable of being infected by an adenovirus. A replication-competent adenovirus or adenoviral vector can have one or more mutations as compared to the wild-type adenovirus (e.g., one or more deletions, insertions, and/or substitutions) in the adenoviral genome that do not inhibit viral replication in host cells. For example, the adenovirus or adenoviral vector can have a partial or entire deletion of the adenoviral early region known as the E3 region, which is not essential for propagation of the adenovirus or adenoviral genome.

A conditionally-replicating adenovirus or adenoviral vector is an adenovirus or adenoviral vector that has been engineered to replicate under pre-determined conditions. For example, replication-essential gene functions, e.g., gene functions encoded by the adenoviral early regions, can be operably linked to an inducible, repressible, or tissue-specific transcription control sequence, e.g., promoter. In such an embodiment, replication requires the presence or absence of specific factors that interact with the transcription control sequence. Conditionally-replicating adenoviral vectors are further described in U.S. Pat. No. 5,998,205.

A replication-deficient adenovirus or adenoviral vector is an adenovirus or adenoviral vector that requires complementation of one or more gene functions or regions of the adenoviral genome that are required for replication, as a result of, for example, a deficiency in one or more replication-essential gene function or regions, such that the adenovirus or adenoviral vector does not replicate in typical host cells, especially those in a human to be infected by the adenovirus or adenoviral vector.

A deficiency in a gene function or genomic region, as used herein, is defined as a disruption (e.g., deletion) of sufficient genetic material of the adenoviral genome to obliterate or impair the function of the gene (e.g., such that the function of the gene product is reduced by at least about 2-fold, 5-fold, 10-fold, 20-fold, 30-fold, or 50-fold) whose nucleic acid sequence was disrupted (e.g., deleted) in whole or in part. Deletion of an entire gene region often is not required for disruption of a replication-essential gene function. However, for the purpose of providing sufficient space in the adenoviral genome for one or more transgenes, removal of a majority of one or more gene regions can be desirable. While deletion of genetic material is preferred, mutation of genetic material by addition or substitution also is appropriate for disrupting gene function. Replication-essential gene functions are those gene functions that are required for adenovirus replication (e.g., propagation) and are encoded by, for example, the adenoviral early regions (e.g., the E1, E2, and E4 regions), late regions (e.g., the L1, L2, L3, L4, and L5 regions), genes involved in viral packaging (e.g., the IVa2 gene), and virus-associated RNAs (e.g., VA-RNA-1 and/or VA-RNA-2).

Whether the adenovirus or adenoviral vector is replication-competent or replication-deficient, the adenovirus or adenoviral vector retains at least a portion of the adenoviral genome. The adenovirus or adenoviral vector can comprise any portion of the adenoviral genome, including protein coding and non-protein coding regions. Desirably, the adenovirus or adenoviral vector comprises at least one nucleic acid sequence that encodes an adenovirus protein. The adenovirus or adenoviral vector can comprise a nucleic acid sequence that encodes any suitable adenovirus protein, such as, for example, a protein encoded by any one of the early region genes (i.e., E1A, E1B, E2A, E2B, E3, and/or E4 regions), or a protein encoded by any one of the late region genes, which encode the virus structural proteins (i.e., L1, L2, L3, L4, and L5 regions).

The adenovirus or adenoviral vector desirably comprises one or more nucleic acid sequences that encode the pIX protein, the DNA polymerase protein, the penton protein, the hexon protein, and/or the fiber protein. The adenovirus or adenoviral vector can comprise a full-length nucleic acid sequence that encodes a full-length amino acid sequence of an adenovirus protein. Alternatively, the adenovirus or adenoviral vector can comprise a portion of a full-length nucleic acid sequence that encodes a portion of a full-length amino acid sequence of an adenovirus protein.

A "portion" of a nucleic acid sequence comprises at least ten nucleotides (e.g., about 10 to about 5000 nucleotides). Preferably, a "portion" of a nucleic acid sequence comprises 10 or more (e.g., 15 or more, 20 or more, 25 or more, 30 or more, 35 or more, 40 or more, 45 or more, 50 or more, or 100 or more) nucleotides, but less than 5,000 (e.g., 4900 or less, 4000 or less, 3000 or less, 2000 or less, 1000 or less, 800 or less, 500 or less, 300 or less, or 100 or less) nucleotides. Preferably, a portion of a nucleic acid sequence is about 10 to about 3500 nucleotides (e.g., about 10, 20, 30, 50, 100, 300, 500, 700, 1000, 1500, 2000, 2500, or 3000 nucleotides), about 10 to about 1000 nucleotides (e.g., about 25, 55, 125, 325, 525, 725, or 925 nucleotides), or about 10 to about 500 nucleotides (e.g., about 15, 30, 40, 50, 60, 70, 80, 90, 150, 175, 250, 275, 350, 375, 450, 475, 480, 490, 495, or 499 nucleotides), or a range defined by any two of the foregoing values. More preferably, a "portion" of a nucleic acid sequence comprises no more than about 3200 nucleotides (e.g., about 10 to about 3200 nucleotides, about 10 to about 3000 nucleotides, or about 30 to about 500 nucleotides, or a range defined by any two of the foregoing values).

A "portion" of an amino acid sequence comprises at least three amino acids (e.g., about 3 to about 1,200 amino acids). Preferably, a "portion" of an amino acid sequence comprises 3 or more (e.g., 5 or more, 10 or more, 15 or more, 20 or more, 25 or more, 30 or more, 40 or more, or 50 or more) amino acids, but less than 1,200 (e.g., 1,000 or less, 800 or less, 700 or less, 600 or less, 500 or less, 400 or less, 300 or less, 200 or less, or 100 or less) amino acids. Preferably, a portion of an amino acid sequence is about 3 to about 500 amino acids (e.g., about 10, 100, 200, 300, 400, or 500 amino acids), about 3 to about 300 amino acids (e.g., about 20, 50, 75, 95, 150, 175, or 200 amino acids), or about 3 to about 100 amino acids (e.g., about 15, 25, 35, 40, 45, 60, 65, 70, 80, 85, 90, 95, or 99 amino acids), or a range defined by any two of the foregoing values. More preferably, a "portion" of an amino acid sequence comprises no more than about 500 amino acids (e.g., about 3 to about 400 amino acids, about 10 to about 250 amino acids, or about 50 to about 100 amino acids, or a range defined by any two of the foregoing values).

The adenovirus pIX protein is present in the adenovirus capsid, has been shown to strengthen hexon nonamer interactions, and is essential for the packaging of full-length genomes (see, e.g., Boulanger et al., *J. Gen. Virol.,* 44: 783-800 (1979); Horwitz M. S., "Adenoviridae and their replication" in *Virology,* $2^{nd}$ ed., B. N. Fields et al. (eds.), Raven Press, Ltd., New York, pp. 1679-1721 (1990), Ghosh-Choudhury et al., *EMBO J.,* 6: 1733-1739 (1987), and van Oostrum et al, *J. Virol.,* 56: 439-448 (1985)). In addition to its contribution to adenovirus structure, pIX also has been shown to exhibit transcriptional properties, such as stimulation of adenovirus major late promoter (MLP) activity (see, e.g., Lutz et al., *J. Virol.,* 71(7): 5102-5109 (1997)). Nucleic acid sequences that encode all or a portion of an adenovirus pIX protein include, for example, SEQ ID NO: 6 and SEQ ID NO: 1. Amino acid sequences that comprise a full-length pIX protein, or a portion thereof, include, for example, SEQ ID NO: 16 and SEQ ID NO: 11.

The adenovirus DNA polymerase protein is essential for viral DNA replication both in vitro and in vivo. The polymerase co-purifies in a complex with the precursor (pTP) of the terminal protein (TP), which is covalently attached to the 5' ends of adenovirus DNA (Field et al., *J. Biol. Chem.,* 259: 9487-9495 (1984)). Both the adenovirus DNA polymerase and pTP are encoded by the E2 region. The polymerase protein is required for the expression of all the structural proteins except for pIX. Without the gene sequence for polymerase protein, polymerase protein is not produced. As a result, the viral genome is not replicated, the Major Late Promoter is not activated, and the capsid proteins are not expressed. Nucleic acid sequences that encode all or a portion of an adenovirus DNA polymerase protein include, for example, SEQ ID NO: 7 and SEQ ID NO: 2. Amino acid sequences that comprise a full-length adenovirus DNA polymerase, or a portion thereof, include, for example, SEQ ID NO: 17 and SEQ ID NO: 12.

The adenovirus hexon protein is the largest and most abundant protein in the adenovirus capsid. The hexon protein is essential for virus capsid assembly, determination of the icosahedral symmetry of the capsid (which in turn defines the limits on capsid volume and DNA packaging size), and integrity of the capsid. In addition, hexon is a primary target for modification in order to reduce neutralization of adenoviral vectors (see, e.g., Gall et al., *J. Virol.,* 72: 10260-264 (1998), and Rux et al., *J. Virol.,* 77(17): 9553-9566 (2003)). The major structural features of the hexon protein are shared by adenoviruses across serotypes, but the hexon protein differs in size and immunological properties between serotypes (Jornvall et al., *J. Biol. Chem.,* 256(12): 6181-6186 (1981)). A comparison of 15 adenovirus hexon proteins revealed that the predominant antigenic and serotype-specific regions of the hexon appear to be in loops 1 and 2 (i.e., LI or l1, and LII or l2, respectively), within which are seven discrete hypervariable regions (HVR1 to HVR7) varying in length and sequence between adenoviral serotypes (Crawford-Miksza et al., *J. Virol.,* 70(3): 1836-1844 (1996)). Nucleic acid sequences that encode all or a portion of an adenovirus hexon protein include, for example, SEQ ID NO: 9 and SEQ ID NO: 4. Amino acid sequences that comprise a full-length adenovirus hexon protein, or a portion thereof, include, for example, SEQ ID NO: 19 and SEQ ID NO: 14.

The adenovirus fiber protein is a homotrimer of the adenoviral polypeptide IV that has three domains: the tail, shaft, and knob. (Devaux et al., *J. Molec. Biol.,* 215: 567-88 (1990), Yeh et al., *Virus Res.,* 33: 179-98 (1991)). The fiber protein mediates primary viral binding to receptors on the cell surface via the knob and the shaft domains (Henry et al., *J. Virol.,* 68(8): 5239-46 (1994)). The amino acid sequences for trimerization are located in the knob, which appears necessary for the amino terminus of the fiber (the tail) to properly associate with the penton base (Novelli et al., *Virology,* 185: 365-76 (1991)). In addition to recognizing cell receptors and binding the penton base, the fiber contributes to serotype identity. Fiber proteins from different adenoviral serotypes differ considerably (see, e.g., Green et al., *EMBO J.,* 2: 1357-65 (1983), Chroboczek et al., *Virology,* 186: 280-85 (1992), and Signas et al., *J. Virol.,* 53: 672-78 (1985)). Thus, the fiber protein has multiple functions key to the life cycle of adenovirus. Nucleic acid sequences that encode all or a portion of an adenovirus fiber protein include, for example, SEQ ID NO: 10 and SEQ ID NO: 5. Amino acid sequences that comprise a full-length adenovirus fiber protein, or a portion thereof, include, for example, SEQ ID NO: 20 and SEQ ID NO: 15.

The adenovirus penton base protein is located at the vertices of the icosahedral capsid and comprises five identical monomers. The penton base protein provides a structure for bridging the hexon proteins on multiple facets of the icosahedral capsid, and provides the essential interface for the fiber protein to be incorporated in the capsid. Each monomer of the penton base contains an RGD tripeptide motif (Neumann et al., *Gene,* 69: 153-157 (1988)). The RGD tripeptide mediates binding to αv integrins and adenoviruses that have point mutations in the RGD sequence of the penton base are restricted in their ability to infect cells (Bai et al.,

*J. Virol.*, 67: 5198-5205 (1993)). Thus, the penton base protein is essential for the architecture of the capsid and for maximum efficiency of virus-cell interaction. Nucleic acid sequences that encode all or a portion of an adenovirus penton base protein include, for example, SEQ ID NO: 8 and SEQ ID NO: 3. Amino acid sequences that comprise a full-length adenovirus penton base protein, or a portion thereof, include, for example, SEQ ID NO: 18 and SEQ ID NO: 13.

Nucleic acid or amino acid sequence "identity," as described herein, can be determined by comparing a nucleic acid or amino acid sequence of interest to a reference nucleic acid or amino acid sequence. The numbers of nucleotides or amino acid residues that have been changed and/or modified (such as, e.g., by point mutations, insertions, or deletions) in the reference sequence so as to result in the sequence of interest are counted. The total number of such changes is subtracted from the total length of the sequence of interest, and the difference is divided by the length of the sequence of interest and expressed as a percentage. A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FASTM, and SSEARCH) (for sequence alignment and sequence similarity searches). Sequence alignment algorithms also are disclosed in, for example, Altschul et al., *J. Molecular Biol.*, 215(3): 403-410 (1990), Beigert et al., *Proc. Natl. Acad. Sci. USA*, 106(10): 3770-3775 (2009), Durbin et al., eds., *Biological Sequence Analysis: Probabilistic Models of Proteins and Nucleic Acids*, Cambridge University Press, Cambridge, UK (2009), Soding, *Bioinformatics*, 21(7): 951-960 (2005), Altschul et al., *Nucleic Acids Res.*, 25(17): 3389-3402 (1997), and Gusfield, *Algorithms on Strings, Trees and Sequences*, Cambridge University Press, Cambridge UK (1997)).

The adenovirus or adenoviral vector can comprise one, two, three, four, or all five of the aforementioned sequences alone or in any combination. In this respect, the adenovirus or adenoviral vector can comprise any combination of any two of the aforementioned sequences, any combination of any three of the aforementioned sequences, any combination of any four of the aforementioned sequences, or all five of the aforementioned sequences.

As discussed herein, the adenovirus or adenoviral vector can be replication-competent, conditionally-replicating, or replication-deficient. Preferably, the adenovirus or adenoviral vector is replication-deficient, such that the replication-deficient adenovirus or adenoviral vector requires complementation of at least one replication-essential gene function of one or more regions of the adenoviral genome for propagation (e.g., to form adenoviral vector particles).

The replication-deficient adenovirus or adenoviral vector can be modified in any suitable manner to cause the deficiencies in the one or more replication-essential gene functions in one or more regions of the adenoviral genome for propagation. The complementation of the deficiencies in the one or more replication-essential gene functions of one or more regions of the adenoviral genome refers to the use of exogenous means to provide the deficient replication-essential gene functions. Such complementation can be effected in any suitable manner, for example, by using complementing cells and/or exogenous DNA (e.g., helper adenovirus) encoding the disrupted replication-essential gene functions.

The adenovirus or adenoviral vector can be deficient in one or more replication-essential gene functions of only the early regions (i.e., E1-E4 regions) of the adenoviral genome, only the late regions (i.e., L1-L5 regions) of the adenoviral genome, both the early and late regions of the adenoviral genome, or all adenoviral genes (i.e., a high capacity adenovector (HC-Ad). See Morsy et al., *Proc. Natl. Acad. Sci. USA*, 95: 965-976 (1998); Chen et al., *Proc. Natl. Acad. Sci. USA*, 94: 1645-1650 (1997); and Kochanek et al., *Hum. Gene Ther.*, 10: 2451-2459 (1999). Examples of replication-deficient adenoviral vectors are disclosed in U.S. Pat. Nos. 5,837,511; 5,851,806; 5,994,106; 6,127,175; 6,482,616; and 7,195,896, and International Patent Application Publications WO 1994/028152, WO 1995/002697, WO 1995/016772, WO 1995/034671, WO 1996/022378, WO 1997/012986, WO 1997/021826, and WO 2003/022311.

The early regions of the adenoviral genome include the E1, E2, E3, and E4 regions. The E1 region comprises the E1A and E1B subregions, and one or more deficiencies in replication-essential gene functions in the E1 region can include one or more deficiencies in replication-essential gene functions in either or both of the E1A and E1B subregions, thereby requiring complementation of the E1A subregion and/or the E1B subregion of the adenoviral genome for the adenovirus or adenoviral vector to propagate (e.g., to form adenoviral vector particles). The E2 region comprises the E2A and E2B subregions, and one or more deficiencies in replication-essential gene functions in the E2 region can include one or more deficiencies in replication-essential gene functions in either or both of the E2A and E2B subregions, thereby requiring complementation of the E2A subregion and/or the E2B subregion of the adenoviral genome for the adenovirus or adenoviral vector to propagate (e.g., to form adenoviral vector particles).

The E3 region does not include any replication-essential gene functions, such that a deletion of the E3 region in part or in whole does not require complementation of any gene functions in the E3 region for the adenovirus or adenoviral vector to propagate (e.g., to form adenoviral vector particles). In the context of the present disclosure, the E3 region is defined as the region that initiates with the open reading frame that encodes a protein with high homology to the 12.5K protein from the E3 region of human adenovirus 5 (NCBI reference sequence AP_000218) and ends with the open reading frame that encodes a protein with high homology to the 14.7K protein from the E3 region of human adenovirus 5 (NCBI reference sequence AP_000224.1). The E3 region can be deleted in whole or in part, or retained in whole or in part. The size of the deletion can be tailored so as to retain an adenovirus or adenoviral vector whose genome closely matches the optimum genome packaging size. A larger deletion will accommodate the insertion of larger heterologous nucleic acid sequences in the adenovirus or adenoviral genome. In one embodiment of the present disclosure, the L4 polyadenylation signal sequences, which reside in the E3 region, are retained.

The E4 region comprises multiple open reading frames (ORFs). An adenovirus or adenoviral vector with a deletion of all of the open reading frames of the E4 region except ORF6, and in some cases ORF3, does not require complementation of any gene functions in the E4 region for the adenovirus or adenoviral vector to propagate (e.g., to form adenoviral vector particles). Conversely, an adenovirus or adenoviral vector with a disruption or deletion of ORF6, and in some cases ORF3, of the E4 region (e.g., with a deficiency in a replication-essential gene function based in ORF6 and/or ORF3 of the E4 region), with or without a disruption or deletion of any of the other open reading frames of the E4 region or the native E4 promoter, polyadenylation sequence, and/or the right-side inverted terminal repeat (ITR), requires complementation of the E4 region (specifically, of ORF6 and/or ORF3 of the E4 region) for the adenovirus or adenoviral vector to propagate (e.g., to form adenoviral vector particles). The late regions of the adenoviral genome include the L1, L2, L3, L4, and L5 regions. The adenovirus or adenoviral vector also can have a mutation in the major late promoter (MLP), as discussed in International Patent Application Publication WO 2000/000628, which can render the adenovirus or adenoviral vector replication-deficient if desired.

The one or more regions of the adenoviral genome that contain one or more deficiencies in replication-essential gene functions desirably are one or more early regions of the adenoviral genome, i.e., the E1, E2, and/or E4 regions, optionally with the deletion in part or in whole of the E3 region.

The replication-deficient adenovirus or adenoviral vector also can have one or more mutations as compared to the wild-type adenovirus (e.g., one or more deletions, insertions, and/or substitutions) in the adenoviral genome that do not inhibit viral replication in host cells. Thus, in addition to one or more deficiencies in replication-essential gene functions, the adenovirus or adenoviral vector can be deficient in other respects that are not replication-essential. For example, the adenovirus or adenoviral vector can have a partial or entire deletion of the adenoviral early region known as the E3 region, which is not essential for propagation of the adenovirus or adenoviral genome.

In one embodiment, the adenovirus or adenoviral vector is replication-deficient and requires, at most, complementation of the E1 region or the E4 region of the adenoviral genome, for propagation (e.g., to form adenoviral vector particles). Thus, the replication-deficient adenovirus or adenoviral vector requires complementation of at least one replication-essential gene function of the E1A subregion and/or the E1B region of the adenoviral genome (denoted an E1-deficient adenoviral vector) or the E4 region of the adenoviral genome (denoted an E4-deficient adenoviral vector) for propagation (e.g., to form adenoviral vector particles). The adenovirus or adenoviral vector can be deficient in at least one replication-essential gene function (desirably all replication-essential gene functions) of the E1 region of the adenoviral genome and at least one gene function of the nonessential E3 region of the adenoviral genome (denoted an E1/E3-deficient adenoviral vector). The adenovirus or adenoviral vector can be deficient in at least one replication-essential gene function (desirably all replication-essential gene functions) of the E4 region of the adenoviral genome and at least one gene function of the nonessential E3 region of the adenoviral genome (denoted an E3/E4-deficient adenoviral vector).

In one embodiment, the adenovirus or adenoviral vector is replication-deficient and requires, at most, complementation of the E2 region, preferably the E2A subregion, of the adenoviral genome, for propagation (e.g., to form adenoviral vector particles). Thus, the replication-deficient adenovirus or adenoviral vector requires complementation of at least one replication-essential gene function of the E2A subregion of the adenoviral genome (denoted an E2A-deficient adenoviral vector) for propagation (e.g., to form adenoviral vector particles). The adenovirus or adenoviral vector can be deficient in at least one replication-essential gene function (desirably all replication-essential gene functions) of the E2A region of the adenoviral genome and at least one gene function of the nonessential E3 region of the adenoviral genome (denoted an E2A/E3-deficient adenoviral vector).

In one embodiment, the adenovirus or adenoviral vector is replication-deficient and requires, at most, complementation of the E1 and E4 regions of the adenoviral genome for propagation (e.g., to form adenoviral vector particles). Thus, the replication-deficient adenovirus or adenoviral vector requires complementation of at least one replication-essential gene function of both the E1 and E4 regions of the adenoviral genome (denoted an E1/E4-deficient adenoviral vector) for propagation (e.g., to form adenoviral vector particles). The adenovirus or adenoviral vector can be deficient in at least one replication-essential gene function (desirably all replication-essential gene functions) of the E1 region of the adenoviral genome, at least one replication-essential gene function of the E4 region of the adenoviral genome, and at least one gene function of the nonessential E3 region of the adenoviral genome (denoted an E1/E3/E4-deficient adenoviral vector). The adenovirus or adenoviral vector preferably requires, at most, complementation of the E1 region of the adenoviral genome for propagation, and does not require complementation of any other deficiency of the adenoviral genome for propagation. More preferably, the adenovirus or adenoviral vector requires, at most, complementation of the E1 and E4 regions of the adenoviral genome for propagation, and does not require complementation of any other deficiency of the adenoviral genome for propagation.

The adenovirus or adenoviral vector, when deficient in multiple replication-essential gene functions of the adenoviral genome (e.g., an E1/E4-deficient adenoviral vector), can include a spacer sequence to provide viral growth in a complementing cell line similar to that achieved by adenoviruses or adenoviral vectors deficient in a single replication-essential gene function (e.g., an E1-deficient adenoviral vector). The spacer sequence can contain any nucleotide sequence or sequences which are of a desired length, such as sequences at least about 15 base pairs (e.g., between about 15 nucleotides and about 12,000 nucleotides), preferably about 100 nucleotides to about 10,000 nucleotides, more preferably about 500 nucleotides to about 8,000 nucleotides, even more preferably about 1,500 nucleotides to about 6,000 nucleotides, and most preferably about 2,000 to about 3,000 nucleotides in length, or a range defined by any two of the foregoing values. The spacer sequence can be coding or non-coding and native or non-native with respect to the adenoviral genome, but does not restore the replication-essential function to the deficient region. The spacer also can contain an expression cassette. More preferably, the spacer comprises a polyadenylation sequence and/or a gene that is non-native with respect to the adenovirus or adenoviral vector. The use of a spacer in an adenoviral vector is further described in, for example, U.S. Pat. No. 5,851,806 and International Patent Application Publication WO 1997/021826.

By removing all or part of the adenoviral genome, for example, the E1, E3, and E4 regions of the adenoviral genome, the resulting adenovirus or adenoviral vector is able to accept inserts of exogenous nucleic acid sequences while retaining the ability to be packaged into adenoviral capsids. An exogenous nucleic acid sequence can be inserted at any position in the adenoviral genome so long as insertion in the position allows for the formation of adenovirus or the adenoviral vector particle. The exogenous nucleic acid sequence preferably is positioned in the E1 region, the E3 region, or the E4 region of the adenoviral genome.

The replication-deficient adenovirus or adenoviral vector of the present disclosure can be produced in complementing cell lines that provide gene functions not present in the replication-deficient adenovirus or adenoviral vector, but required for viral propagation, at appropriate levels in order to generate high titers of viral vector stock. Such complementing cell lines are known and include, but are not limited to, 293 cells (described in, e.g., Graham et al., *J. Gen. Virol.,* 36: 59-72 (1977)), PER.C6 cells (described in, e.g., International Patent Application Publication WO 1997/000326, and U.S. Pat. Nos. 5,994,128 and 6,033,908), and 293-ORF6 cells (described in, e.g., International Patent Application Publication WO 95/34671 and Brough et al., *J. Virol.,* 71: 9206-9213 (1997)). Other suitable complementing cell lines to produce the replication-deficient adenovirus or adenoviral vector of the present disclosure include complementing cells that have been generated to propagate adenoviral vectors encoding transgenes whose expression inhibits viral growth in host cells (see, e.g., U.S. Patent Application Publication No. 2008/0233650). Additional suitable complementing cells are described in, for example, U.S. Pat. Nos. 6,677,156 and 6,682,929, and International Patent Application Publication WO 2003/020879. In some instances, the cellular genome need not comprise nucleic acid sequences, the gene products of which complement for all of the deficiencies of a replication-deficient adenoviral vector. One or more replication-essential gene functions lacking in a replication-deficient adenoviral vector can be supplied by a helper virus, e.g., an adenoviral vector that supplies in trans one or more essential gene functions required for replication of the replication-deficient adenovirus or adenoviral vector. Alternatively, the inventive adenovirus or adenoviral vector can comprise a non-native replication-essential gene that complements for the one or more replication-essential gene functions lacking in the inventive replication-deficient adenovirus or adenoviral vector. For example, an E1/E4-deficient adenoviral vector can be engineered to contain a nucleic acid sequence encoding E4 ORF 6 that is obtained or derived from a different adenovirus (e.g., an adenovirus of a different serotype than the inventive adenovirus or adenoviral vector, or an adenovirus of a different species than the inventive adenovirus or adenoviral vector).

The adenovirus or adenoviral vector can further comprise a transgene. The term "transgene" is defined herein as a non-native nucleic acid sequence that is operably linked to appropriate regulatory elements (e.g., a promoter), such that the non-native nucleic acid sequence can be expressed to produce a protein (e.g., peptide or polypeptide). The regulatory elements (e.g., promoter) can be native or non-native to the adenovirus or adenoviral vector.

A "non-native" nucleic acid sequence is any nucleic acid sequence (e.g., DNA, RNA, or cDNA sequence) that is not a naturally occurring nucleic acid sequence of an adenovirus in a naturally occurring position. Thus, the non-native nucleic acid sequence can be naturally found in an adenovirus, but located at a non-native position within the adenoviral genome and/or operably linked to a non-native promoter. The terms "non-native nucleic acid sequence," "heterologous nucleic acid sequence," and "exogenous nucleic acid sequence" are synonymous and can be used interchangeably in the context of the present disclosure. The non-native nucleic acid sequence preferably is DNA and preferably encodes a protein (i.e., one or more nucleic acid sequences encoding one or more proteins).

The non-native nucleic acid sequence can encode a therapeutic protein that can be used to prophylactically or therapeutically treat a mammal for a disease. Examples of suitable therapeutic proteins include cytokines, toxins, tumor suppressor proteins, growth factors, hormones, receptors, mitogens, immunoglobulins, neuropeptides, neurotransmitters, and enzymes. Alternatively, the non-native nucleic acid sequence can encode an antigen of a pathogen (e.g., a bacterium or a virus), and the adenovirus or adenoviral vector can be used as a vaccine.

Viral Based Delivery System

The present disclosure also provides delivery systems, such as viral-based systems, in which a nucleic acid described herein is inserted. Representative viral expression vectors include, but are not limited to, adeno-associated viral vectors, adenovirus-based vectors, lentivirus-based vectors, retroviral vectors, and herpes virus-based vectors. In an embodiment, the viral vector is a lentivirus vector. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In an additional embodiment, the viral vector is an adeno-associated viral vector. In a further embodiment, the viral vector is a retroviral vector. In general, and in embodiments, a suitable vector contains an origin of replication functional in at least one organism, a promoter sequence, convenient restriction endonuclease sites, and one or more selectable markers.

Additional suitable vectors include integrating expression vectors, which can randomly integrate into the host cell's DNA, or can include a recombination site to enable the specific recombination between the expression vector and the host cell's chromosome. Such integrating expression vectors can utilize the endogenous expression control sequences of the host cell's chromosomes to effect expression of the desired protein. Examples of vectors that integrate in a site specific manner include, for example, components of the flp-in system from Invitrogen (Carlsbad, Calif.) (e.g., pcDNATM5/FRT), or the cre-lox system, such as can be found in the pExchange-6 Core Vectors from Stratagene (La Jolla, Calif.). Examples of vectors that randomly integrate into host cell chromosomes include, for example, pcDNA3.1 (when introduced in the absence of T-antigen) from Invitrogen (Carlsbad, Calif.), and pCI or pFN10A (ACT) FLEXI™ from Promega (Madison, Wis.). Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto.

However, other constitutive promoter sequences can also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the present disclosure should not be limited to the use of constitutive promoters. Inducible promoters are also contemplated as part of the present disclosure. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Reporter genes can be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes can include genes encoding luciferase, beta-galactosidase, chloramphenicol acetyl transferase, secreted alkaline phosphatase, or the green fluorescent protein gene (e.g., Ui-Tei et al., *FEBS Letters* 479: 79-82 (2000)). Suitable expression systems are well known and can be prepared using known techniques or obtained commercially. In general, the construct with the minimal 5' flanking region showing the highest level of expression of reporter gene is identified as the promoter. Such promoter regions can be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (Molecular Cloning: A Laboratory Manual, Cold Spring Harbor Laboratory, New York (2001)). In embodiments, a method for the introduction of a polynucleotide into a host cell is calcium phosphate transfection or polyethylenimine (PEI) Transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Non-Viral Based Delivery System

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

The use of lipid formulations is contemplated for the introduction of the nucleic acids into a host cell (in vitro, ex vivo or in vivo). In another aspect, the nucleic acid can be associated with a lipid. The nucleic acid associated with a lipid can be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they can be present in a bilayer structure, as micelles, or with a "collapsed" structure. They can also simply be interspersed in a solution, possibly forming aggregates that are not uniform in size or shape. Lipids are fatty substances which can be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids can be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., *Glycobiology* 5: 505-10 (1991)). However, compositions that have different structures in solution than the normal vesicular structure are also encompassed. For example, the lipids can assume a micellar structure or merely exist as nonuniform aggregates of lipid molecules. Also contemplated are lipofectamine-nucleic acid complexes.

In some instances, polynucleotides encoding polypeptides can also be introduced into cells using non-viral based delivery systems, such as the "Sleeping Beauty (SB) Transposon System," which refers a synthetic DNA transposon system for introducing DNA sequences into the chromosomes of vertebrates. Some exemplary embodiments of the system are described, for example, in U.S. Pat. Nos. 6,489, 458 and 8,227,432. The Sleeping Beauty transposon system is composed of a Sleeping Beauty (SB) transposase and a SB transposon. In embodiments, the Sleeping Beauty transposon system can include the SB11 transposon system, the SB100X transposon system, or the SB110 transposon system.

DNA transposons translocate from one DNA site to another in a simple, cut-and-paste manner. Transposition is a precise process in which a defined DNA segment is excised from one DNA molecule and moved to another site in the same or different DNA molecule or genome. As do other Tc1/mariner-type transposases, SB transposase inserts a transposon into a TA dinucleotide base pair in a recipient DNA sequence. The insertion site can be elsewhere in the same DNA molecule, or in another DNA molecule (or chromosome). In mammalian genomes, including humans, there are approximately 200 million TA sites. The TA insertion site is duplicated in the process of transposon integration. This duplication of the TA sequence is a hallmark of transposition and used to ascertain the mechanism in some experiments. The transposase can be encoded either within the transposon or the transposase can be supplied by another source, for instance a DNA or mRNA source, in which case the transposon becomes a non-autonomous element. Non-autonomous transposons are most useful as genetic tools because after insertion they cannot independently continue to excise and re-insert. SB transposons envisaged to be used as non-viral vectors for introduction of genes into genomes of vertebrate animals and for gene therapy.

Regardless of the method used to introduce exogenous nucleic acids into a host cell or otherwise expose a cell to the inhibitor of the present disclosure, in order to confirm the presence of the recombinant DNA sequence in the host cell, a variety of assays can be performed. Such assays include, for example, molecular assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the present disclosure.

In embodiments, a modified effector cell described herein and other genetic elements are delivered to a cell using the SB11 transposon system, the SB100X transposon system, the SB110 transposon system, the piggyBac transposon system (see, e.g., Wilson et al, "PiggyBac Transposon-mediated Gene Transfer in Human Cells," *Molecular Therapy* 15:139-145 (2007), incorporated herein by reference in its entirety) and/or the piggyBac transposon system (see, e.g., Mitra et al., "Functional characterization of piggyBac from the bat *Myotis lucifugus* unveils an active mammalian DNA transposon," *Proc. Natl. Acad. Sci USA* 110:234-239 (2013). Additional transposases and transposon systems are provided in U.S. Pat. Nos. 6,489,458; 6,613,752, 7,148,203; 7,985,739; 8,227,432; 9,228,180; U.S. Patent Publn. No. 2011/0117072; Mates et al., *Nat Genet.*, 41(6):753-61 (2009). doi: 10.1038/ng.343. Epub 2009 May 3, *Gene Ther.*, 18(9):849-56 (2011). doi: 10.1038/gt.2011.40. Epub 2011 Mar. 31 and in Ivies et al., *Cell.* 91(4):501-10, (1997), each of which is incorporated herein by reference in their entirety.

Additional suitable non-viral systems can include integrating expression vectors, which can randomly integrate into the host cell's DNA, or can include a recombination site to enable the specific recombination between the expression vector and the host cell's chromosome. Targeted integration of transgenes into predefined genetic loci is a desirable goal for many applications. First, a first recombination site for a site-specific recombinase is inserted at a genomic site, either at a random or at a predetermined location. Subsequently, the cells are transfected with a plasmid carrying the gene or DNA of interest and the second recombination site and a source for recombinase (expression plasmid, RNA, protein, or virus-expressing recombinase). Recombination between the first and second recombination sites leads to integration of plasmid DNA.

Such integrating expression vectors can utilize the endogenous expression control sequences of the host cell's chromosomes to effect expression of the desired protein. In some embodiments, targeted integration is promoted by the presence of sequences on the donor polynucleotide that are homologous to sequences flanking the integration site. For example, targeted integration using the donor polynucleotides described herein can be achieved following conventional transfection techniques, e.g. techniques used to create gene knockouts or knockins by homologous recombination. In other embodiments, targeted integration is promoted both by the presence of sequences on the donor polynucleotide that are homologous to sequences flanking the integration site, and by contacting the cells with donor polynucleotide in the presence of a site-specific recombinase. By a site-specific recombinase, or simply a recombinase, it is meant is a polypeptide that catalyzes conservative site-specific recombination between its compatible recombination sites. As used herein, a site-specific recombinase includes native polypeptides as well as derivatives, variants and/or fragments that retain activity, and native polynucleotides, derivatives, variants, and/or fragments that encode a recombinase that retains activity.

Also provided herein is a system for integrating heterologous genes in a host cell, said system comprising one or more gene expression cassettes. In some instances, the system includes a first gene expression cassette comprising a first polynucleotide encoding a first polypeptide construct. In other instances, the system can include a second gene expression cassette comprising a second polynucleotide encoding a second polypeptide construct. In yet other instances, the system can include a third gene expression cassette. In one embodiment, one of the gene expression cassettes can comprise a gene switch polynucleotide encoding one or more of: (i) a transactivation domain; (ii) nuclear receptor ligand binding domain; (iii) a DNA-binding domain; and (iv) ecdysone receptor binding domain. In another embodiment, the system further includes recombinant attachment sites; and a serine recombinase; such that upon contacting said host cell with at least said first gene expression cassette, in the presence of said serine recombinase, said heterologous genes are integrated in said host cell.

In some instances, the system further comprises a ligand; such that upon contacting said host cell, in the presence of said ligand, said heterologous gene are expressed in said host cell. In one instance, the system also includes recombinant attachment sites. In some instances, one recombination attachment site is a phage genomic recombination attachment site (attP) or a bacterial genomic recombination attachment site (attB). In one instance, the host cell is an eukaryotic cell. In another instance, the host cell is a human cell. In further instances, the host cell is a T cell or NK cell.

Promoters

"Promoter" refers to a region of a polynucleotide that initiates transcription of a coding sequence. Promoters are located near the transcription start sites of genes, on the same strand and upstream on the DNA (towards the 5' region of the sense strand). Some promoters are constitutive as they are active in all circumstances in the cell, while others are regulated becoming active in response to specific stimuli, e.g., an inducible promoter. Yet other promoters are tissue specific or activated promoters, including but not limited to T-cell specific promoters.

The term "promoter activity" and its grammatical equivalents as used herein refer to the extent of expression of nucleotide sequence that is operably linked to the promoter whose activity is being measured. Promoter activity can be measured directly by determining the amount of RNA transcript produced, for example by Northern blot analysis or indirectly by determining the amount of product coded for by the linked nucleic acid sequence, such as a reporter nucleic acid sequence linked to the promoter.

"Inducible promoter" as used herein refers to a promoter which is induced into activity by the presence or absence of transcriptional regulators, e.g., biotic or abiotic factors. Inducible promoters are useful because the expression of genes operably linked to them can be turned on or off at certain stages of development of an organism or in a particular tissue. Examples of inducible promoters are alcohol-regulated promoters, tetracycline-regulated promoters, steroid-regulated promoters, metal-regulated promoters, pathogenesis-regulated promoters, temperature-regulated promoters and light-regulated promoters. In one embodiment, the inducible promoter is part of a genetic switch. The inducible promoter can be a gene switch ligand inducible promoter. In some cases, an inducible promoter can be a small molecule ligand-inducible two polypeptide ecdysone receptor-based gene switch, such as RHEOSWITCH® gene switch. In some cases, a gene switch can be selected from ecdysone-based receptor components as described in, but without limitation to, any of the systems described in: PCT/US2001/009050 (WO 2001/070816); U.S. Pat. Nos. 7,091,038; 7,776,587; 7,807,417; 8,202,718; PCT/US2001/030608 (WO 2002/029075); U.S. Pat. Nos. 8,105,825; 8,168,426; PCT/1J52002/005235 (WO 2002/066613); U.S. application Ser. No. 10/468,200 (U.S. Pub. No. 20120167239); PCT/US2002/005706 (WO 2002/066614); U.S. Pat. Nos. 7,531,326; 8,236,556; 8,598,409; PCT/US2002/005090 (WO 2002/066612); U.S. Pat. No. 8,715,959 (U.S. Pub. No. 20060100416); PCT/US2002/005234 (WO 2003/027266); U.S. Pat. Nos. 7,601,508; 7,829,676; 7,919,269; 8,030,067; PCT/US2002/005708 (WO 2002/066615); U.S. application Ser. No. 10/468,192 (U.S. Pub. No. 20110212528); PCT/US2002/005026 (WO 2003/027289); U.S. Pat. Nos. 7,563,879; 8,021,878; 8,497,093; PCT/US2005/015089 (WO 2005/108617); U.S. Pat. Nos. 7,935,510; 8,076,454; PCT/US2008/011270 (WO 2009/045370); U.S. application Ser. No. 12/241,018 (U.S. Pub. No. 20090136465); PCT/US2008/011563 (WO 2009/048560); U.S. application Ser. No. 12/247,738 (U.S. Pub. No. 20090123441); PCT/US2009/005510 (WO 2010/042189); U.S. application Ser. No. 13/123,129 (U.S. Pub. No. 20110268766); PCT/US2011/029682 (WO 2011/119773); U.S. application Ser. No. 13/636,473 (U.S. Pub. No. 20130195800); PCT/US2012/027515 (WO 2012/122025); and, U.S. Pat. No. 9,402,919 each of which is incorporated by reference in its entirety).

Provided herein are methods comprising administering to a subject at least one non-viral vector comprising a polynucleotide encoding a polypeptide sequence described herein comprising at least two functional proteins or portions thereof; at least one promoter; and at least one engineered recombination site; wherein said at least one promoter drives expression of said at least two functional proteins. In some cases, at least one promoter can be constitutive. In some cases, at least one promoter can be tissue-specific. In some cases, at least one promoter can be inducible. In some cases, an inducible promoter is a small molecule ligand-inducible two polypeptide ecdysone receptor-based gene switch. In other cases, a combination of promoters wherein at least one promoter can be inducible and at least one promoter can be activation specific can be utilized.

An inducible promoter utilizes a ligand for dose-regulated control of expression of said at least two genes. In some cases, a ligand can be selected from a group consisting of ecdysteroid, 9-cis-retinoic acid, synthetic analogs of retinoic acid, N,N'-diacylhydrazines, oxadiazolines, dibenzoylalkyl cyanohydrazines, N-alkyl-N,N'-diaroylhydrazines, N-acyl-N-alkylcarbonylhydrazines, N-aroyl-N-alkyl-N'-aroylhydrazines, arnidoketones, 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, framesol, bile acids, 1,1-biphosphonate esters, juvenile hormone III, RG-115819 (3,5-Dimethyl-benzoic acid N-(1-ethyl-2,2-dimethyl-propyl)-N'-(2-methyl-3-methoxy-benzoyl)-hydrazide-), RG-115932 ((R)-3,5-Dimethyl-benzoic acid N-(1-tert-butyl-butyl)-N'-(2-ethyl-3-methoxy-benzoyl)-hydrazide), and RG-115830 (3,5-Dimethyl-benzoic acid N-(1-tert-butyl-butyl)-N'-(2-ethyl-3-methoxy-benzoyl)-hydrazide), and any combination thereof.

In some embodiments, a promoter is an inducible promoter. In some embodiments, a promoter is a non-inducible promoter. In some cases, a promoter can be a tissue-specific promoter. Herein "tissue-specific" refers to regulated expression of a gene in a subset of tissues or cell types. In some cases, a tissue-specific promoter can be regulated spatially such that the promoter drives expression only in certain tissues or cell types of an organism. In other cases, a tissue-specific promoter can be regulated temporally such that the promoter drives expression in a cell type or tissue differently across time, including during development of an organism. In some cases, a tissue-specific promoter is regulated both spatially and temporally. In certain embodiments, a tissue-specific promoter is activated in certain cell types either constitutively or intermittently at particular times or stages of the cell type. For example, a tissue-specific promoter can be a promoter that is activated when a specific cell such as a T cell or a NK cell is activated. T cells can be activated in a variety of ways, for example, when presented with peptide antigens by MEW class II molecules.

In one case, at least one promoter is an engineered promoter or variants thereof. As described herein, the promoter can incorporate minimal promoter sequences from IL-2 and one or more of the following: nuclear factor of activated T-cells (NFAT) response element(s); NFIL2D response element, NFkB/TCF response element, NF_AT/NFIL2B response element or NFIL2A/OCT response element. Examples of response elements are described in Mattila et al., *EMBO J.* 9(13):4425-33 (1990); incorporated herein in its entirety.

In some embodiments, at least one promoter comprises IL-2 core promoter (SEQ ID NO: 26). In one embodiment, at least one promoter comprises IL-2 minimal promoter (SEQ ID NO: 27). In another embodiment, at least one promoter comprises IL-2 enhancer and promoter variant (SEQ ID NOS: 26-28). In yet another embodiment, at least one promoter comprises NF-κB binding site (SEQ ID NOS: 30-32). In some embodiments, at least one promoter comprises $(NF-\kappa B)_1$-IL2 promoter variant (SEQ ID NO: 30). In some embodiments, at least one promoter comprises $(NF-\kappa B)_3$-IL2 promoter variant (SEQ ID NO: 31). In some embodiments, at least one promoter comprises $(NF-\kappa B)_6$-IL2 promoter variant (SEQ ID NO: 32). In one embodiment, at least one promoter comprises 1× nuclear factor of activated T-cells (NFAT) response elements-IL2 promoter variant (SEQ ID NO: 33). In another embodiment, at least one promoter comprises 3×NFAT response element (SEQ ID NOS: 34-35). In yet another embodiment, at least one promoter comprises 6×NFAT response elements-IL2 promoter variant (SEQ ID NOS: 36-39). In some embodiments, at least one promoter comprises human EF1A1 promoter variant (SEQ ID NOS: 40-41). In some embodiment, at least one promoter comprises human EF1A1 promoter and enhancer (SEQ ID NO: 42). In some embodiments, at least one promoter comprises human UBC promoter (SEQ ID NO: 43). In some embodiments, at least one promoter comprises 6 site GAL4-inducible proximal factor binding element (PFB). In some embodiment, at least one promoter comprises synthetic minimal promoter 1 (inducible promoter) (SEQ ID NO: 44).

Use of gene switch for ligand inducible control of IL-12 expression described herein can improve the safety profile of IL-12 by for example allowing for regulated expression and improving therapeutic index. However, a condition for ligand dose dependent expression of IL-12 using gene switch(es) is the presence or absence of activator ligand (e.g. veledimex). In certain embodiments, an additional conditional control for induction of IL-12 expression is contemplated. Gene switch components under the control of T cell activated specific promoters are provided. This results in conditional expression (e.g., T cell activation) of gene switch components necessary for veledimex controlled expression of transgene(s) under control of a gene switch. In some embodiments, this results in preferential expression of cytokines such as IL-12 or IL-15 by tumor specific T cells when veledimex is present and T cells are activated. This can lead to increased localized levels of gene switch controlled transgene expression.

For example, T cell activation specific expression of gene switch components can be controlled by promoter comprising Nuclear Factor of Activated T-cells (NFAT) response element(s). NFAT transcription factors are key modulators of effector T-cell states. NFATs are early transcriptional checkpoint progressively driving exhaustion. NFATs are quickly activated in T cells following TCR stimulation and form a protein complex with AP-1 induced by appropriate co-stimulation signaling and regulate effector genes and T-cell functions. NFAT response element(s) can be fused with other minimal promoter sequences (e.g. IL2 minimal promoter) to drive expression of transgenes in response to T cell activation.

Other examples of activation specific promoters include but are not limited to interleukin-2 (IL2) promoter and Programmed Death (PD)-1 (CD279) promoter. Gene switch components can also be conditionally expressed upon immune cell activation by fusing binding sites for other nuclear factors like NF-κB of proinflammatory signaling pathway to minimal promoter sequence (e.g. IL2).

In certain embodiments, the promoter can be any one or more of: IL-2 core promoter, IL-2 minimal promoter, IL-2 enhancer and promoter variant, (NF-κB)i-IL2 promoter variant, $(NF-\kappa B)_3$-IL2 promoter variant, $(NF-\kappa B)_6$-IL2 promoter variant, 1× NFAT response elements-IL2 promoter variant, 3×NFAT response elements-IL2 promoter variant, 6×NFAT response elements-IL2 promoter variant, human EEF1A1 promoter variant, human EEF1A1 promoter and enhancer, human UBC promoter and synthetic minimal promoter 1. In certain embodiments, the promoter nucleotides can comprise SEQ ID NOs: 26-44.

Gene Switch

Provided herein are gene switch polypeptides, polynucleotides encoding ligand-inducible gene switch polypeptides, and methods and systems incorporating these polypeptides and/or polynucleotides. In certain aspects, the present disclosure is directed to a polynucleotide comprising one or more polynucleotides encoding a gene switch system for inducible control of heterologous gene expression, wherein the heterologous gene expression is regulated by said gene switch system; and, wherein said heterologous gene comprises a polynucleotide encoding a polypeptide comprising one or more immune response-inducing hepatitis B virus (HBV) polypeptides, disclosed herein.

The term “gene switch” refers to the combination of a response element associated with a promoter, and for instance, an EcR based system which, in the presence of one or more ligands, modulates the expression of a gene into which the response element and promoter are incorporated. Tightly regulated inducible gene expression systems or gene switches are useful for various applications such as gene therapy, large scale production of proteins in cells, cell based high throughput screening assays, functional genomics and regulation of traits in transgenic plants and animals. Such inducible gene expression systems can include ligand inducible heterologous gene expression systems.

An early version of EcR-based gene switch used *Drosophila melanogaster* EcR (DmEcR) and *Mus musculus* RXR (MmRXR) polypeptides and showed that these receptors in the presence of steroid, ponasteroneA, transactivate reporter genes in mammalian cell lines and transgenic mice (Christopherson et al., *Proc. Natl. Acad. Sci. USA* 89(14):6314-18 (1992); No et al., *Proc. Natl. Acad. Sci. USA* 93(8):3346-51 (1996)). Later, Suhr et al. (*Proc. Natl. Acad. Sci. USA* 95(14):7999-8004 (1998)) showed that non-steroidal ecdysone agonist, tebufenozide, induced high level of transactivation of reporter genes in mammalian cells through *Bombyx mori* EcR (BmEcR) in the absence of exogenous heterodimer partner.

International Patent Applications No. PCT/US97/05330 (WO 97/38117) and PCT/US99/08381 (WO99/58155) disclose methods for modulating the expression of an exogenous gene in which a DNA construct comprising the exogenous gene and an ecdysone response element is activated by a second DNA construct comprising an ecdysone receptor that, in the presence of a ligand therefor, and optionally in the presence of a receptor capable of acting as a silent partner, binds to the ecdysone response element to induce gene expression. In this example, the ecdysone receptor was isolated from *Drosophila melanogaster*. Typically, such systems require the presence of the silent partner, preferably retinoid X receptor (RXR), in order to provide optimum activation. In mammalian cells, insect ecdysone receptor (EcR) is capable of heterodimerizing with mammalian retinoid X receptor (RXR) and, thereby, be used to regulate expression of target genes or heterologous genes in a ligand dependent manner. International Patent Application No. PCT/US98/14215 (WO 99/02683) discloses that the ecdysone receptor isolated from the silk moth *Bombyx mori* is functional in mammalian systems without the need for an exogenous dimer partner.

U.S. Pat. No. 6,265,173 discloses that various members of the steroid/thyroid superfamily of receptors can combine with *Drosophila melanogaster* ultraspiracle receptor (USP)

or fragments thereof comprising at least the dimerization domain of USP for use in a gene expression system. U.S. Pat. No. 5,880,333 discloses a *Drosophila melanogaster* EcR and ultraspiracle (USP) heterodimer system used in plants in which the transactivation domain and the DNA binding domain are positioned on two different hybrid proteins. In each of these cases, the transactivation domain and the DNA binding domain (either as native EcR as in International Patent Application No. PCT/US98/14215 or as modified EcR as in International Patent Application No. PCT/US97/05330) were incorporated into a single molecule and the other heterodimeric partners, either USP or RXR, were used in their native state.

International Patent Application No. PCT/US01/0905 discloses an ecdysone receptor-based inducible gene expression system in which the transactivation and DNA binding domains are separated from each other by placing them on two different proteins results in greatly reduced background activity in the absence of a ligand and significantly increased activity over background in the presence of a ligand. This two-hybrid system is a significantly improved inducible gene expression modulation system compared to the two systems disclosed in applications PCT/US97/05330 and PCT/US98/14215. The two-hybrid system is believed to exploit the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). The two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, it is believed that a conformational change is induced which promotes interaction of the first polypeptide with the second polypeptide thereby resulting in dimerization of the DNA binding domain and the transactivation domain. Since the DNA binding and transactivation domains reside on two different molecules, the background activity in the absence of ligand is greatly reduced.

Another surprising discovery was that certain modifications of the two-hybrid system could also provide improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provided higher gene transcription activity at a lower ligand concentration. Furthermore, the two-hybrid system avoids some side effects due to overexpression of RXR that can occur when unmodified RXR is used as a switching partner. In a preferred two-hybrid system, native DNA binding and transactivation domains of EcR or RXR are eliminated and as a result, these hybrid molecules have less chance of interacting with other steroid hormone receptors present in the cell, thereby resulting in reduced side effects.

The ecdysone receptor (EcR) is a member of the nuclear receptor superfamily and is classified into subfamily 1, group H (referred to herein as "Group H nuclear receptors"). The members of each group share 40-60% amino acid identity in the E (ligand binding) domain (Laudet et al., A Unified Nomenclature System for the Nuclear Receptor Subfamily, 1999; *Cell* 97: 161-163). In addition to the ecdysone receptor, other members of this nuclear receptor subfamily 1, group H include: ubiquitous receptor (UR), Orphan receptor 1 (OR-1), steroid hormone nuclear receptor 1 (NER-1), RXR interacting protein-15 (RIP-15), liver x receptor β (LXRβ), steroid hormone receptor like protein (RLD-1), liver x receptor (LXR), liver x receptor α (LXRα), farnesoid x receptor (FXR), receptor interacting protein 14 (RIP-14), and farnesol receptor (HRR-1).

In some cases, an inducible promoter can be a small molecule ligand-inducible two polypeptide ecdysone receptor-based gene switch, such as Intrexon Corporation's RHEOSWITCH® gene switch. In some cases, a gene switch can be selected from ecdysone-based receptor components as described in, but without limitation to, any of the systems described in: PCT/US2001/009050 (WO 2001/070816); U.S. Pat. Nos. 7,091,038; 7,776,587; 7,807,417; 8,202,718; PCT/US2001/030608 (WO 2002/029075); U.S. Pat. Nos. 8,105,825; 8,168,426; PCT/1J52002/005235 (WO 2002/066613); U.S. application Ser. No. 10/468,200 (U.S. Pub. No. 20120167239); PCT/US2002/005706 (WO 2002/066614); U.S. Pat. Nos. 7,531,326; 8,236,556; 8,598,409; PCT/US2002/005090 (WO 2002/066612); U.S. Pat. No. 8,715,959 (U.S. Pub. No. 20060100416); PCT/US2002/005234 (WO 2003/027266); U.S. Pat. Nos. 7,601,508; 7,829,676; 7,919,269; 8,030,067; PCT/US2002/005708 (WO 2002/066615); U.S. application Ser. No. 10/468,192 (U.S. Pub. No. 20110212528); PCT/US2002/005026 (WO 2003/027289); U.S. Pat. Nos. 7,563,879; 8,021,878; 8,497,093; PCT/US2005/015089 (WO 2005/108617); U.S. Pat. Nos. 7,935,510; 8,076,454; PCT/US2008/011270 (WO 2009/045370); U.S. application Ser. No. 12/241,018 (U.S. Pub. No. 20090136465); PCT/US2008/011563 (WO 2009/048560); U.S. application Ser. No. 12/247,738 (U.S. Pub. No. 20090123441); PCT/US2009/005510 (WO 2010/042189); U.S. application Ser. No. 13/123,129 (U.S. Pub. No. 20110268766); PCT/US2011/029682 (WO 2011/119773); U.S. application Ser. No. 13/636,473 (U.S. Pub. No. 20130195800); PCT/US2012/027515 (WO 2012/122025); and, U.S. Pat. No. 9,402,919 each of which is incorporated by reference in its entirety.

Provided are systems for modulating the expression of a heterologous gene and an interleukin in a host cell, comprising polynucleotides expressing gene-switch polypeptides disclosed herein.

In some embodiments are systems for modulating the expression of a heterologous gene and a cytokine in a host cell, comprising a first gene expression cassette comprising a first polynucleotide encoding a first polypeptide; a second gene expression cassette comprising a second polynucleotide encoding a second polypeptide; and a ligand; wherein said first and second polypeptides comprise one or more of: (i) a transactivation domain; (ii) a DNA-binding domain; and (iii) a ligand binding domain; (iv) said heterologous gene; and (vi) said cytokine such that upon contacting said host cell with said first gene expression cassette and said second gene expression cassette in the presence of said ligand, said heterologous gene and said cytokine are expressed in said host cell. In some cases, the heterologous gene comprises an antigen binding polypeptide described herein. In some cases, the cytokine comprises at least one chemokine, interferon, interleukin, lymphokine, tumor necrosis factor, or variant or combination thereof. In some cases, the cytokine is an interleukin. In some cases the interleukin is at least one of IL12, IL2, IL15, IL21, and functional variants and fragments thereof. In some embodiments, the cytokines can be membrane bound or secreted. In other embodiments, the cytokines can be intracellular. The interleukin can comprise membrane bound IL-15 (mbIL-15) or a fusion of IL-15 and IL-15Rα. In some embodiments, a mbIL-15 is a membrane-bound chimeric IL-15 which can be co-expressed with a modified effector cell described herein. In some embodiments, the mbIL-15 comprises a full-length IL-15 (e.g., a native IL-15 polypeptide) or fragment or variant thereof, fused in frame with a full length IL-15Rα, functional fragment or variant thereof. In some cases, the IL-15 is indirectly linked to the IL-15Rα through a linker. In some instances, the mbIL-15 is as described in Hurton et al., "Tethered IL-15 augments antitumor activity and promotes a stem-cell memory subset in tumor-specific T cells," *Proc. Natl. Acad. Sci. USA* 113(48):E7788-E7797 (2016). In another aspect, the interleukin can comprise IL-12. In some embodiments, the IL-12 is a single chain IL-12 (scIL-12), protease sensitive IL-12, destabilized IL-12, membrane bound IL-12, intercalated IL-12. In some instances, the IL-12 variants are as described in WO2015/095249, WO2016/048903, WO2017/062953, all of which is incorporated by reference in their entireties.

Provided herein are polynucleotides encoding gene switch polypeptides, wherein said gene switch polypeptides comprise: a) a first gene switch polypeptide comprising a DNA-binding domain fused to a nuclear receptor ligand binding domain, and b) a second gene switch polypeptide comprising a transactivation domain fused to a nuclear receptor ligand binding domain, wherein the first gene switch polypeptide and the second gene switch polypeptide are connected by a linker. In some cases, the linker can be a linker described herein, for instance GSG linker, furinlink, a 2A linker such as F/T2A, T2A, p2A, GSG-p2A, variants and derivatives thereof. In other instances, the linker can be an IRES.

In some cases, the DNA binding domain (DBD) comprises a DBD described herein, for instance at least one of GAL4 (GAL4 DBD), a LexA DBD, a transcription factor DBD, a steroid/thyroid hormone nuclear receptor superfamily member DBD, a bacterial LacZ DBD, and a yeast DBD. The transactivation domain can comprise a transactivation domain described herein, for instance one of a VP16 transactivation domain, a p53 transactivation domain and a B42 acidic activator transactivation domain. The Nuclear receptor ligand binding domain can comprise at least one of a ecdysone receptor (EcR), a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a famesol receptor.

In some cases, the gene switch polypeptides connected by a polypeptide linker or ribosome-skipping sequence exhibit improved dose-dependent ligand-inducible control of gene expression compared to a ligand-inducible gene switch wherein the gene switch polypeptides are connected by non-coding sequences, such as an IRES. In some cases, the gene switch polypeptides connected by a 2A linker can exhibit improved dose-dependent ligand-inducible control of heterologous gene expression compared to a gene switch wherein said gene switch polypeptides are separated by an IRES.

In some embodiments, the gene switch comprises a VP16 transactivation domain. In one embodiment, the gene switch comprises at least one of an ecdysone receptor (EcR), a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a famesol receptor. In another embodiment, a DNA-binding domain (DBD) of the gene switch comprises at least one of GAL4 (GAL4 DBD), a LexA DBD, a transcription factor DBD, a steroid/thyroid hormone nuclear receptor superfamily member DBD, a bacterial LacZ DBD, and a yeast DBD. In yet another case, the gene switch further comprises at least one of ultraspiracle protein (USP), retinoid receptor X (RXR), functional fragments and variants thereof wherein said functional fragments and variants are capable of binding to an EcR.

The polypeptides and polynucleotides as described herein can be expressed in an engineered cell. Herein an engineered cell is a cell which has been modified from its natural or endogenous state. An example of an engineered cell is a cell described herein which has been modified (e.g., by transfection of a polynucleotide into the cell) to encode for example, gene switch polypeptides, gene of interest (GOO, cell tags, heterologous genes and any other polypeptides and polynucleotides described herein.

Ligands

In some embodiments, a ligand used for inducible gene switch regulation can be selected from any of, but without limitation to, following: N-[(1R)-1-(1,1-dimethylethyl)butyl]-N'-(2-ethyl-3-methoxybenzoyl)-3,5-dimethylbenzohydrazide (also referred to as veledimex), (2S,3R,5R,9R,10R,13R,14S,17R)-17-[(2S,3R)-3,6-dihydroxy-6-methylheptan-2-yl]-2,3,14-trihydroxy-10,13-dimethyl-2,3,4,5,9,11,12,15,16,17-decahydro-1H-cyclopenta[a]phenanthren-6-one; N'-(3,5-Dimethylbenzoyl)-N'-[(3R)-2,2-dimethyl-3-hexanyl]-2-ethyl-3-methoxybenzohydrazide; 5-Methyl-2,3-dihydro-benzo[1,4]dioxine-6-carboxylic acid N'-(3,5-dimethyl-benzoyl)-N'-(1-ethyl-2,2-dimethyl-propyl)-hydrazide; 5-Methyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide; 5-Methyl-2,3-dihydro-benzo[1,4]dioxine-6-carboxylic acid N'-(1-tert-butyl-butyl)-N'-(3,5-dimethyl-benzoyl)-hydrazide; 5-Methyl-2,3-dihydro-benzo[1,4]dioxine-6-carboxylic acid N'-(1-tert-butyl-butyl)-N'-(3,5-dimethoxy-4-methyl-benzoyl)-hydrazide; 5-Ethyl-2,3-dihydro-benzo[1,4]dioxine-6-carboxylic acid N'-(3,5-dimethyl-benzoyl)-N'-(1-ethyl-2,2-dimethyl-propyl)-hydrazide; 5-Ethyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide; 5-Ethyl-2,3-dihydro-benzo[1,4]dioxine-6-carboxylic acid N'-(1-tert-butyl-butyl)-N'-(3,5-dimethyl-benzoyl)-hydrazide; 5-Ethyl-2,3-dihydro-benzo[1,4]dioxine-6-carboxylic acid N'-(1-tert-butyl-butyl)-N'-(3,5-dimethoxy-4-methyl-benzoyl)-hydrazide; 3,5-Dimethyl-benzoic acid N-(1-ethyl-2,2-dimethyl-propyl)-N'-(3-methoxy-2-methyl-benzoyl)-hydrazide; 3,5-Dimethoxy-4-methyl-benzoic acid N-(1-ethyl-2,2-dimethyl-propyl)-N'-(3-methoxy-2-methyl-benzoyl)-hydrazide; 3,5-Dimethyl-benzoic acid N-(1-tert-butyl-butyl)-N'-(3-methoxy-2-methyl-benzoyl)-hydrazide; 3,5-Dimethoxy-4-methyl-benzoic acid N-(1-tert-butyl-butyl)-N'-(3-methoxy-2-methyl-benzoyl)-hydrazide; 3,5-Dimethyl-benzoic acid N-(1-ethyl-2,2-dimethyl-propyl)-N'-(2-ethyl-3-methoxy-benzoyl)-hydrazide; 3,5-Dimethoxy-4-methyl-benzoic acid N-(1-ethyl-2,2-dimethyl-propyl)-N'-(2-ethyl-3-methoxy-benzoyl)-hydrazide; 3,5-Dimethyl-benzoic acid N-(1-tert-butyl-butyl)-N'-(2-ethyl-3-methoxy-benzoyl)-hydrazide; 3,5-Dimethoxy-4-methyl-benzoic acid N-(1-tert-butyl-butyl)-N'-(2-ethyl-3-methoxy-benzoyl)-hydrazide; 2-Methoxy-nicotinic acid N-(1-tert-butyl-pentyl)-N'-(4-ethyl-benzoyl)-hydrazide; 3,5-Dimethyl-benzoic acid N-(2,2-dimethyl-1-phenyl-propyl)-N'-(4-ethyl-benzoyl)-hydrazide; 3,5-Dimethyl-benzoic acid N-(1-tert-butyl-pentyl)-N'-(3-methoxy-2-methyl-benzoyl)-hydrazide; and 3,5-Dimethoxy-4-methyl-benzoic acid N-(1-tert-butyl-pentyl)-N'-(3-methoxy-2-methyl-benzoyl)-hydrazide.

In some cases, a ligand used for dose-regulated control of ecdysone receptor-based inducible gene switch can be selected from any of, but without limitation to, an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726 and U.S. Published Application Nos. 2005/0209283 and 2006/0020146; oxadiazolines as described in U.S. Published Application No. 2004/0171651; dibenzoylalkyl cyanohydrazines such as those disclosed in European Application No. 461,809; N-alkyl-N,N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; arnidoketones such as those described in U.S. Published Application No. 2004/0049037; each of which is incorporated herein by reference and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, framesol, bile acids, 1,1-biphosphonate esters, juvenile hormone III, and the like. Examples of diacylhydrazine ligands useful in the present disclosure include RG-115819 (3,5-Dimethyl-benzoic acid N-(1-ethyl-2,2-dimethyl-propyl)-N'-(2-methyl-3-methoxy-benzoyl)-hydrazide-), RG-115932 ((R)-3,5-Dimethyl-benzoic acid N-(1-tert-butyl-butyl)-N'-(2-ethyl-3-methoxy-benzoyl)-hydrazide), and RG-115830 (3,5-Dimethyl-benzoic acid N-(1-tert-butyl-butyl)-N'-(2-ethyl-3-methoxy-benzoyl)-hydrazide). See, e.g., U.S. patent application Ser. No. 12/155,111, and PCT Appl. No. PCT/US2008/006757, both of which are incorporated herein by reference in their entireties.

Cytokines

In certain embodiments, HBV vaccine antigens provided herein may be co-delivered and/or co-expressed (e.g., as part of the same HBV antigen delivery vector or via a separate vector) along with other cytokines. Provided herein are polynucleotides encoding gene-switch polypeptides and a cytokine, or variant or derivative thereof, and methods and systems incorporating the same. Cytokine is a category of small proteins between about 5-20 kDa that are involved in cell signaling. In some instances, cytokines include chemokines, interferons, interleukins, colony-stimulating factors or tumor necrosis factors. In some embodiments, chemokines play a role as a chemoattractant to guide the migration of cells, and is classified into four subfamilies: CXC, CC, CX3C, and XC. Exemplary chemokines include chemokines from the CC subfamily: CCL1, CCL2 (MCP-1), CCL3, CCL4, CCL5 (RANTES), CCL6, CCL7, CCL8, CCL9 (or CCL10), CCL11, CCL12, CCL13, CCL14, CCL15, CCL16, CCL17, CCL18, CCL19, CCL20, CCL21, CCL22, CCL23, CCL24, CCL25, CCL26, CCL27, and CCL28; the CXC subfamily: CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, and CXCL17; the XC subfamily: XCL1 and XCL2; and the CX3C subfamily CX3CL1.

In certain embodiments, HBV vaccine antigens provided herein may be co-delivered and/or co-expressed (e.g., as part of the same HBV antigen delivery vector or via a separate vector) along with other interferons. Interferons (IFNs) comprise interferon type I (e.g. IFN-α, IFN-β, IFN-ε, IFN-κ, and IFN-ω), interferon type II (e.g. IFN-γ), and interferon type III. In some embodiments, IFN-α is further classified into about 13 subtypes including IFNA1, IFNA2, IFNA4, IFNA5, IFNA6, IFNA7, IFNA8, IFNA10, IFNA13, IFNA14, IFNA16, IFNA17, and IFNA21.

In certain embodiments, HBV vaccine antigens provided herein may be co-delivered and/or co-expressed (e.g., as part of the same HBV antigen delivery vector or via a separate vector) along with other interleukins. Interleukins are expressed by leukocytes or white blood cells and they promote the development and differentiation of T and B lymphocytes and hematopoietic cells. Exemplary interleukines include IL-1, IL-2, IL-3, IL-4, IL-5, IL-6, IL-7, IL-8 (CXCL8), IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35, and IL-36. In some embodiments, interleukins are IL-2, IL-12, IL-15, IL-21 or a fusion of IL-15 and IL-15a.

In some aspects, the interleukin can comprise IL12. In some embodiments, the IL-12 is a single chain IL-12 (scIL-12), protease sensitive IL-12, destabilized IL-12, membrane bound IL-12, intercalated IL-2. In some instances, the IL-12 variants are as described in WO2015/095249, WO2016/048903, WO2017/062953, all of which is incorporated by reference in their entireties.

In some embodiments, an interleukin comprises mbIL-15. In some embodiments, a mbIL-15 is a membrane-bound chimeric IL-15 which can be co-expressed with a modified effector cell described herein. In some embodiments, the mbIL-15 comprises a full-length IL-15 (e.g., a native IL-15 polypeptide) or fragment or variant thereof, fused in frame with a full length IL-15Rα, functional fragment or variant thereof. In some cases, the IL-15 is indirectly linked to the IL-15Rα through a linker. In some instances, the mbIL-15 is as described in Hurton et al., 2016.

In certain embodiments, HBV vaccine antigens provided herein may be co-delivered and/or co-expressed (e.g., as part of the same HBV antigen delivery vector or via a separate vector) along with other tumor necrosis factors. Tumor necrosis factors (TNFs) are a group of cytokines that modulate apoptosis. In some instances, there are about 19 members within the TNF family, including, not limited to, TNFα, lymphotoxin-alpha (LT-alpha), lymphotoxin-beta (LT-beta), T cell antigen gp39 (CD40L), CD27L, CD30L, FASL, 4-1BBL, OX40L, and TNF-related apoptosis inducing ligand (TRAIL).

In certain embodiments, HBV vaccine antigens provided herein may be co-delivered and/or co-expressed (e.g., as part of the same HBV antigen delivery vector or via a separate vector) along with other colony stimulating factors. Colony-stimulating factors (CSFs) are secreted glycoproteins that interact with receptor proteins on the surface of hemopoietic stem cells, which subsequently modulates cell proliferation and differentiation into specific kind of blood cells. In some instances, a CSF comprises macrophage colony-stimulating factor, granulocyte macrophage colony-stimulating factor (GM-CSF), granulocyte colony-stimulating factor (G-CSF) or promegapoietin.

In some embodiments, the cytokine is a membrane-bound cytokine, which is co-expressed with a chimeric antigen receptor described herein. In some embodiments, one or more methods described herein further comprise administration of a cytokine. In some instances, the cytokine comprises a chemokine, an interferon, an interleukin, a colony-stimulating factor or a tumor necrosis factor. In some instances, one or more methods described herein further comprise administration of a cytokine selected from a chemokine, an interferon, an interleukin, a colony-stimulating factor or a tumor necrosis factor. In some instances, one or more methods described herein further comprise administration of a cytokine selected from IL2, IL7, IL12, IL15, a fusion of IL-15 and IL-15Rα, IL21, IFNγ or TNF-α.

Interleukin-12

Figure 7:
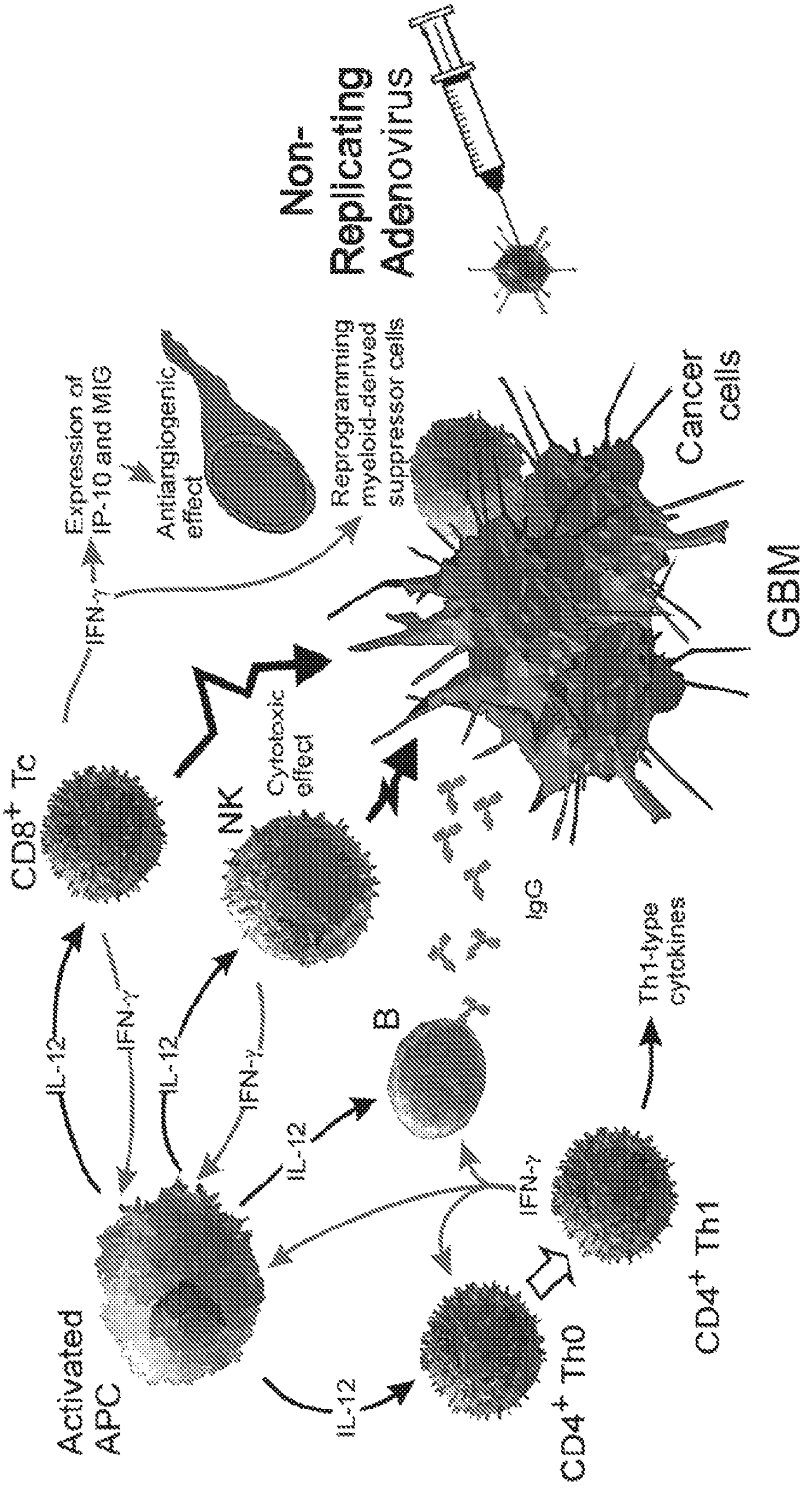
FIG. 7 shows an overview of IL-12 promoting immune response by activating NK cells and T cells.

In particular embodiments, HBV vaccine antigens provided herein may be co-delivered and/or co-expressed (e.g., as part of the same HBV antigen delivery vector or via a separate vector) along with Interleukin-12. Interleukin 12 (IL-12) is an interleukin that is naturally produced by dendritic cells, macrophages, neutrophils, and human B-lymphoblastoid cells (NC-37) in response to antigenic stimulation. IL-12 is composed of a bundle of four alpha helices. It is a heterodimeric cytokine encoded by two separate genes, IL-12A (p35) and IL-12B (p40). The active heterodimer (referred to as p70), and a homodimer of p40 are formed following protein synthesis. IL-12 is the master regulator of the immune system. IL-12 promotes immune response by activating NK cells and T cells (FIG. 7).

Figure 8:
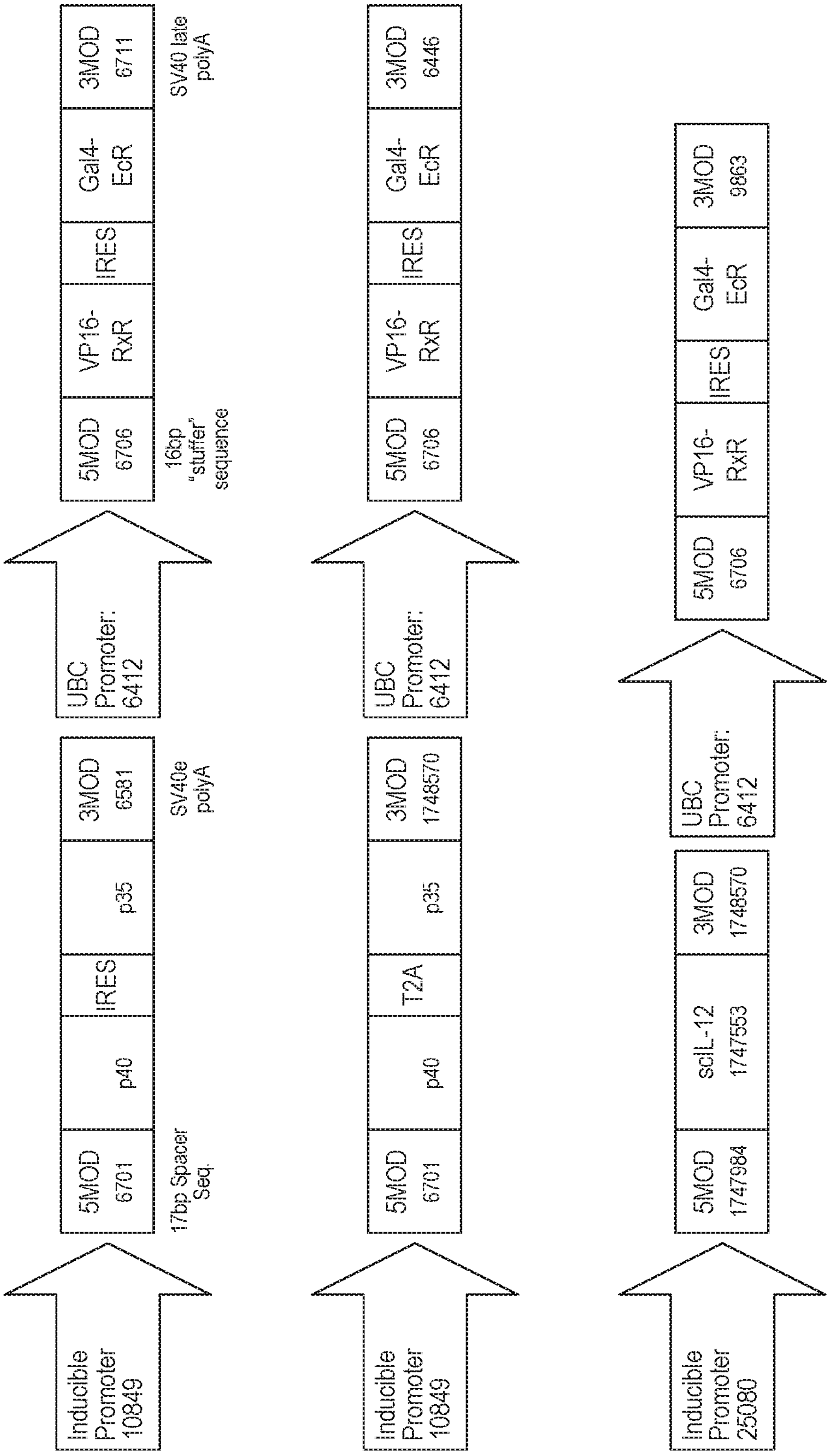
FIG. 8 shows various structural components of diverse IL-12 ligand-inducible gene switch vector systems.

Provided herein are compositions, kits, and system comprising and methods of making HBV recombinant vaccines. The present disclosure provides HBV antigen designs (HBV designs 1-5) constructed in a multi-deleted gorilla adenovector (GC46) (SEQ ID NOS: 61-63). Also provided herein are polynucleotides encoding gene-switch polypeptides and IL-12 or variant or derivative thereof, and methods and systems incorporating the same (FIG. 8).

Linkers

Also disclosed are constructs comprising a linker to facilitate the expression and functionality of the polynucleotides and polypeptides described herein. In some embodiments, a polynucleotide linker can be utilized in a polynucleotide described herein. A polynucleotide linker can be a double-stranded segment of DNA containing desired restriction sites that can be added to create end structures that are compatible with a vector comprising a polynucleotide described herein. In some cases, a polynucleotide linker can be useful for modifying vectors comprising polynucleotides described herein. For example, a vector modification comprising a polynucleotide linker can be a change in a multiple cloning site, or the addition of a poly-histidine tail. Polynucleotide linkers can also be used to adapt the ends of blunt insert DNA for cloning into a vector cleaved with a restriction enzyme with cohesive end termini. The use of polynucleotide linkers can be more efficient than a blunt ligation into a vector and can provide a method of releasing an insert from a vector in downstream applications. In some cases an insert can be a polynucleotide sequence encoding polypeptides useful for therapeutic applications. In some cases, a linker can be a cleavable linker.

A polynucleotide linker can be an oligomer. A polynucleotide linker can be a DNA double strand, single strand, or a combination thereof. In some cases, a linker can be RNA. A polynucleotide linker can be ligated into a vector comprising a polynucleotide described herein by a T4 ligase in some cases. To facilitate a ligation an excess of polynucleotide linkers can be added to a composition comprising an insert and a vector. In some cases, an insert and vector are pre-treated before a linker is introduced. For example, pre-treatment with a methylase can prevent unwanted cleavage of insert DNA.

In certain embodiments, two or more polypeptides encoded by a polynucleotide described herein can be separated by an intervening sequence encoding an intervening linker polypeptide. Herein the term "intervening linker polypeptide" referring to an amino acid sequence separating two or more polypeptides encoded by a polynucleotide is distinguished from the term "peptide linker" which refers to the sequence of amino acids which is optionally included in a polypeptide construct disclosed herein to connect the transmembrane domain to the cell surface polypeptide (e.g., comprising a truncated variant of a natural polypeptide). In certain cases, the intervening linker is a cleavage-susceptible intervening linker polypeptide. In some embodiments, the linker is a cleavable or ribosome skipping linker. In some embodiments, the cleavable linker or ribosome skipping linker sequence is selected from the group consisting of 2A, GSG-2A, GSG linker, SGSG linker, furinlink variants and derivatives thereof. In some embodiments, the 2A linker is a p2A linker, a T2A linker, F2A linker or E2A linker. In some embodiments, polypeptides of interest are expressed as fusion proteins linked by a cleavage-susceptible intervening linker polypeptide. In certain embodiments, cleavage-susceptible intervening linker polypeptide(s) can be any one or more of: F/T2A, T2A, p2A, 2A, GSG-p2A, GSG linker, and furinlink variants. Linkers (polynucleotide and polypeptide sequences) as disclosed in PCT/US2016/061668 (WO2017083750) published 18 May 2017 are incorporated by reference herein. In certain embodiments, the linker polypeptide comprises disclosed in the table below:

TABLE 2

Linker amino acid sequences and polynucleotide sequences

| Linker Name | SEQ ID NO: | Polynucleotide Sequence (5' to 3' where applicable) | SEQ ID NO: | Amino Acids Sequence (5' to 3' where applicable) |
|---|---|---|---|---|
| Whitlow Linker | 64 | GGCAGCACCTCCGGCAGCGGCAAGCCTGGCAGCGGCGAGGGCAGCACCAAGGGC | 81 | GSTSGSGKPGSGEGSTKG |
| Linker | 65 | TCTGGCGGAGGATCTGGAGGAGGCGGATCTGGAGGAGGAGGCAGTGGAGGCGGAGGATCTGGCGGAGGATCTCTGCAG | 82 | SGGGSGGGGSGGGGSGGGGSGGGSLQ |
| GSG linker | 66 | GGAAGCGGA | 83 | GSG |
| SGSG linker | 67 | AGTGGCAGCGGC | 84 | SGSG |

TABLE 2-continued

Linker amino acid sequences and polynucleotide sequences

| Linker Name | SEQ ID NO: | Polynucleotide Sequence (5' to 3' where applicable) | SEQ ID NO: | Amino Acids Sequence (5' to 3' where applicable) |
|---|---|---|---|---|
| (G4S)3 linker | 68 | GGTGGCGGTGGCTCGGGCG GTGGTGGGTCGGGTGGCGG CGGATCT | 85 | GGGGSGGGGSGGGGS |
| Furin cleavage site/ Furinlink1 | 69 | CGTGCAAAGCGT | 86 | RAKR |
| Fmdv | 70 | AGAGCCAAGAGGGCACCGG TGAAACAGACTTTGAATTTT GACCTTCTGAAGTTGGCAG GAGACGTTGAGTCCAACCC TGGGCCC | 87 | RAKRAPVKQTLNFDLLKL AGDVESNPGP |
| Thosea asigna virus 2A region (T2A) | 71 | GAGGGCAGAGGAAGTCTGC TAACATGCGGTGACGTCGA GGAGAATCCTGGACCT | 88 | EGRGSLLTCGDVEENPGP |
| Furin-GSG-T2A | 72 | AGAGCTAAGAGGGGAAGCG GAGAGGGCAGAGGAAGTCT GCTAACATGCGGTGACGTC GAGGAGAATCCTGGACCT | 89 | RAKRGSGEGRGSLLTCGD VEENPGP |
| Furin-SGSG-T2A | 73 | AGGGCCAAGAGGAGTGGCA GCGGCGAGGGCAGAGGAA GTCTTCTAACATGCGGTGAC GTGGAGGAGAATCCCGGCC CT | 90 | RAKRSGSGEGRGSLLTCG DVEENPGP |
| Porcine teschovirus-1 2A region (P2A) | 74 | GCAACGAACTTCTCTCTCCT AAAACAGGCTGGTGATGTG GAGGAGAATCCTGGTCCA | 91 | ATNFSLLKQAGDVEENPG P |
| GSG-P2A | 75 | GGAAGCGGAGCTACTAACT TCAGCCTGCTGAAGCAGGC TGGAGACGTGGAGGAGAAC CCTGGACCT | 92 | GSGATNFSLLKQAGDVEE NPGP |
| Equine rhinitis A virus 2A region (E2A) | 76 | CAGTGTACTAATTATGCTCT CTTGAAATTGGCTGGAGAT GTTGAGAGCAACCCTGGAC CT | 93 | QCTNYALLKLAGDVESNP GP |
| Foot-and-mouth disease virus 2A region (F2A) | 77 | GTCAAACAGACCCTAAACT TTGATCTGCTAAAACTGGCC GGGGATGTGGAAAGTAATC CCGGCCCC | 94 | VKQTLNFDLLKLAGDVES NPGP |
| FP2A | 78 | CGTGCAAAGCGTGCACCGG TGAAACAGGGAAGCGGAGC TACTAACTTCAGCCTGCTGA AGCAGGCTGGAGACGTGGA GGAGAACCCTGGACCT | 95 | RAKRAPVKQGSGATNFSL LKQAGDVEENPGP |
| Linker-GSG | 79 | GCACCGGTGAAACAGGGAA GCGGA | 96 | APVKQGSG |
| Linker | 80 | GCACCGGTGAAACAG | 97 | APVKQ |

In some embodiments, an intervening linker polypeptide comprises an amino acid sequence having at least 70%, 75%, 80%, 85%, 90%, 95%, 99%, 99.5% or 100% identity with the amino acid sequence of Whitlow linker (SEQ ID NO: 64), GSG linker (SEQ ID NO: 66), SGSG linker (SEQ ID NO: 67), (G4S)3 linker (SEQ ID NO: 68), Furin cleavage site/Furlink1 (SEQ ID NO: 69), Fmdv linker (SEQ ID NO: 70), Thosea asigna virus 2A region (T2A) (SEQ ID NO: 71), Furin-GSG-T2A (SEQ ID NO: 72), Furin-SGSG-T2A (SEQ ID NO: 73), porcine teschovirus-1 2A region (P2A) (SEQ ID NO: 74), GSG-P2A (SEQ ID NO: 75), equine rhinitis A virus 2A region (E2A) (SEQ ID NO: 76), or foot-and-mouth disease virus 2A region (F2A) (SEQ ID NO: 78) (Table 2). In some cases, an intervening linker polypeptide comprises an amino acid sequence having at least 70%, 75%, 80%, 85%, 90%, 95%, 99%, 99.5% or 100% identity with the amino acid sequence of linkers (SEQ ID NOS: 65, 79 80) In some cases, a viral 2A sequence can be used. 2A elements can be shorter than IRES, having from 5 to 100 base pairs. In some cases, a 2A sequence can have 5, 10, 15, 20, 25, 30, 35, 40, 45, 50, 55, 60, 65, 70, 75, 80, 85, 90, or 100 nucleotides in length. 2A linked genes can be expressed in one single open reading frame and "self-cleavage" can occur co-translationally between the last two amino acids, GP, at the C-terminus of the 2A polypeptide, giving rise to equal amounts of co-expressed proteins.

A viral 2A sequence can be about 20 amino acids. In some cases, a viral 2A sequence can contain a consensus motif Asp-Val/Ile-Glu-X-Asn-Pro-Gly-Pro. A consensus motif sequence can act co-translationally. For example, formation of a normal peptide bond between a glycine and proline residue can be prevented, which can result in ribosomal skipping and cleavage of a nascent polypeptide. This effect can produce multiple genes at equimolar levels.

A 2A peptide can allow translation of multiple proteins in a single open reading frame into a polypeptide that can be subsequently cleaved into individual polypeptide through a ribosome-skipping mechanism (Funston et al., *J. Gen. Virol.* 89(Pt 2):389-96 (2008)). In some embodiments, a 2A sequence can include: F/T2A, T2A, p2A, 2A, T2A, E2A, F2A, and BmCPV2A, BmIFV2A, and any combination thereof.

In some cases, a vector can comprise an IRES sequence and a 2A linker sequence. In other cases, expression of multiple genes linked with 2A peptides can be facilitated by a spacer sequence (GSG) ahead of the 2A peptides. In some cases, constructs can combine a spacers, linkers, adaptors, promoters, or combinations thereof. For example, a linker can have a spacer (SGSG or GSG or Whitlow linker) and furin linker (R-A-K-R) cleavage site with different 2A peptides. A spacer can be an I-Ceui. In some cases, a linker can be engineered. For example, a linker can be designed to comprise chemical characteristics such as hydrophobicity. In some cases, at least two linker sequences can produce the same protein. In other cases, multiple linkers can be used in a vector. For example, genes of interest can be separated by at least two linkers.

In certain embodiments, two or more polypeptides encoded by a polynucleotide described herein can be separated by an intervening sequence encoding a linker polypeptide. In certain cases, the linker is a cleavage-susceptible linker. In some embodiments, polypeptides of interest are expressed as fusion proteins linked by a cleavage-susceptible linker polypeptide. In certain embodiments, cleavage-susceptible linker polypeptide(s) can be any one or two of: Furinlink, fmdv, p2a, GSG-p2a, and/or fp2a described below. In some cases, a linker is APVKQGSG (SEQ ID NO: 96).

In certain cases, a linker polypeptide can comprise an amino acid sequence "RAKR" (SEQ ID NO: 86). In certain cases, a Furin linker polypeptide can be encoded by a polynucleotide sequence polynucleotide sequence comprising "CGTGCAAAGCGT" (SEQ ID NO: 69) or "AGAGCTAAGAGG." (SEQ ID NO: 130).

In some embodiments, a linker can be utilized in a polynucleotide described herein. A linker can be a flexible linker, a rigid linker, an in vivo cleavable linker, or any combination thereof. In some cases, a linker can link functional domains together (as in flexible and rigid linkers) or releasing free functional domain in vivo as in in vivo cleavable linkers.

Linkers can improve biological activity, increase expression yield, and achieving desirable pharmacokinetic profiles. A linker can also comprise hydrazone, peptide, disulfide, or thioesther.

In some cases, a linker sequence described herein can include a flexible linker. Flexible linkers can be applied when a joined domain requires a certain degree of movement or interaction. Flexible linkers can be composed of small, non-polar (e.g., Gly) or polar (e.g., Ser or Thr) amino acids. A flexible linker can have sequences consisting primarily of stretches of Gly and Ser residues ("GS" linker). An example of a flexible linker can have the sequence of (Gly-Gly-Gly-Gly-Ser)n (SEQ ID NO: 85). By adjusting the copy number "n", the length of this exemplary GS linker can be optimized to achieve appropriate separation of functional domains, or to maintain necessary inter-domain interactions. Besides GS linkers, other flexible linkers can be utilized for recombinant fusion proteins. In some cases, flexible linkers can also be rich in small or polar amino acids such as Gly and Ser, but can contain additional amino acids such as Thr and Ala to maintain flexibility. In other cases, polar amino acids such as Lys and Glu can be used to improve solubility.

Flexible linkers included in linker sequences described herein, can be rich in small or polar amino acids such as Gly and Ser to provide good flexibility and solubility. Flexible linkers can be suitable choices when certain movements or interactions are desired for fusion protein domains. In addition, although flexible linkers cannot have rigid structures, they can serve as a passive linker to keep a distance between functional domains. The length of flexible linkers can be adjusted to allow for proper folding or to achieve optimal biological activity of the fusion proteins.

A linker described herein can further include a rigid linker in some cases. A rigid linker can be utilized to maintain a fixed distance between domains of a polypeptide. Examples of rigid linkers can be: Alpha helix-forming linkers, Pro-rich sequence, (XP)n, X-Pro backbone, A(EAAAK)nA (n=2-5), to name a few. Rigid linkers can exhibit relatively stiff structures by adopting α-helical structures or by containing multiple Pro residues in some cases.

A linker described herein can be cleavable in some cases. In other cases a linker is not cleavable. Linkers that are not cleavable can covalently join functional domains together to act as one molecule throughout an in vivo processes or an ex vivo process. A linker can also be cleavable in vivo. A cleavable linker can be introduced to release free functional domains in vivo. A cleavable linker can be cleaved by the presence of reducing reagents, proteases, to name a few. For example, a reduction of a disulfide bond can be utilized to produce a cleavable linker. In the case of a disulfide linker, a cleavage event through disulfide exchange with a thiol, such as glutathione, could produce a cleavage. In other cases, an in vivo cleavage of a linker in a recombinant fusion protein can also be carried out by proteases that can be expressed in vivo under pathological conditions (e.g. cancer or inflammation), in specific cells or tissues, or constrained within certain cellular compartments. In some cases, a cleavable linker can allow for targeted cleavage. For example, the specificity of many proteases can offer slower cleavage of a linker in constrained compartments. A cleavable linker can also comprise hydrazone, peptides, disulfide, or thioesther. For example, a hydrazone can confer serum stability. In other cases, a hydrazone can allow for cleavage in an acidic compartment. An acidic compartment can have a pH up to 7. A linker can also include a thioether. A thioether can be nonreducible A thioether can be designed for intracellular proteolytic degradation.

In certain embodiments, an fmdv linker polypeptide comprises a sequence that can be at least about 45%, 50%, 55%, 60%, 65%, 70%, 75%, 80%, 85%, 90%, 95%, 97%, 98%, 99% or 100% identical to SEQ ID NO: 87. In certain embodiments, an fmdv linker polypeptide is one or more of the linkers encoded in a single vector linking two or more fusion proteins. In certain cases, an fmdv linker polypeptide can be encoded by a polynucleotide open reading frame (ORF) nucleic acid sequence. In some cases, an ORF encoding fmdv comprises or consists of a sequence of SEQ ID NO: 70). In certain embodiments, a polynucleotide encoding fmdv is at least 45%, 50%, 55%, 60%, 65%, 70%, 75%, 80%, 85%, 90%, 95%, 97%, 98%, 99% or 100% identical to SEQ ID NO: 70).

In certain cases, a linker polypeptide can be a "p2a" linker. In certain embodiments, a p2a polypeptide can comprise a sequence that can be about at least 45%, 50%, 55%, 60%, 65%, 70%, 75%, 80%, 85%, 90%, 95%, 97%, 98%, 99% or 100% identical to SEQ ID NO: 91). In certain embodiments, the p2a linker polypeptide can be one or more of the linkers encoded in a single vector linking two or more fusion proteins. In some cases, a p2a linker polypeptide can be encoded by a polynucleotide open reading frame (ORF) nucleic acid sequence. In certain embodiments, an ORF encoding p2a comprises or consists of the sequence of SEQ ID NO: 74). In certain cases, a polynucleotide encoding p2a can be or can be about at least 45%, 50%, 55%, 60%, 65%, 70%, 75%, 80%, 85%, 90%, 95%, 97%, 98%, 99% or 100% identical to SEQ ID NO: 74).

In some cases, a linker polypeptide can be a "GSG-p2a" linker. In certain embodiments, a GSG-p2a linker polypeptide can comprise a sequence that can be about at least 45%, 50%, 55%, 60%, 65%, 70%, 75%, 80%, 85%, 90%, 95%, 97%, 98%, 99% or 100% identical to SEQ ID NO: 92). In certain embodiments, a GSG-p2a linker polypeptide can be one or more of the linkers encoded in a single vector linking two or more fusion proteins. In some cases, a GSG-p2a linker polypeptide can be encoded by a polynucleotide open-reading frame (ORF) nucleic acid sequence. An ORF encoding GSG p2a can comprise the sequence of SEQ ID NO: 75). In some cases, a polynucleotide encoding GSG-p2a can be or can be about at least 45%, 50%, 55%, 60%, 65%, 70%, 75%, 80%, 85%, 90%, 95%, 97%, 98%, 99% or 100% identical to SEQ ID NO: 75).

A linker polypeptide can be an "fp2a" linker as provided herein. In certain embodiments, a fp2a linker polypeptide can comprise a sequence that can be about at least 45%, 50%, 55%, 60%, 65%, 70%, 75%, 80%, 85%, 90%, 95%, 97%, 98%, 99% or 100% identical to SEQ ID NO: 95). In certain cases, an fp2a linker polypeptide can be one or more of the linkers encoded in a single vector linking two or more fusion proteins. In some cases, a fp2a linker polypeptide can be encoded by a polynucleotide open reading frame (ORF) nucleic acid sequence. In certain embodiments, a polynucleotide encoding an fp2a linker can be or can be about at least 45%, 50%, 55%, 60%, 65%, 70%, 75%, 80%, 85%, 90%, 95%, 97%, 98%, 99% or 100% identical to SEQ ID NO: 78).

In some cases, a linker can be engineered. For example, a linker can be designed to comprise chemical characteristics such as hydrophobicity. In some cases, at least two linker sequences can produce the same protein. A sequence can be or can be about 45%, 50%, 55%, 60%, 65%, 70%, 75%, 80%, 85%, 90%, 95%, 96%, 97%, 98%, 99%, or 100% identical to a polypeptide sequence of SEQ ID NOS: 82, 96 or 97. In other cases, multiple linkers can be used in a vector. For example, genes of interest, and one or more gene switch polypeptide sequences described herein can be separated by at least two linkers. In some cases, genes can be separated by 2, 3, 4, 5, 6, 7, 8, 9, or up to 10 linkers.

A linker can be an engineered linker. Methods of designing linkers can be computational. In some cases, computational methods can include graphic techniques. Computation methods can be used to search for suitable peptides from libraries of three-dimensional peptide structures derived from databases. For example, a Brookhaven Protein Data Bank (PDB) can be used to span the distance in space between selected amino acids of a linker.

In some embodiments are polynucleotides encoding a polypeptide construct comprising a furin polypeptide and a 2A polypeptide, wherein the furin polypeptide and the 2A polypeptide are connected by a polypeptide linker comprising at least three hydrophobic amino acids. In some cases, at least three hydrophobic amino acids are selected from the list consisting of glycine (Gly)(G), alanine (Ala)(A), valine (Val)(V), leucine (Leu)(L), isoleucine (Ile)(I), proline (Pro) (P), phenylalanine (Phe)(F), methionine (Met)(M), tryptophan (Trp)(W). In some cases, a polypeptide linker can also include one or more GS linker sequences, for instance (GS)n, (SG)n, (GSG)n, and (SGSG)n, wherein n can be any number from zero to fifteen.

Provided are methods of obtaining an improved expression of a polypeptide construct comprising: providing a polynucleotide encoding said polypeptide construct comprising a first functional polypeptide and a second functional polypeptide, wherein said first functional polypeptide and second functional polypeptide are connected by a linker polypeptide comprising a sequence with at least 60% identity to the sequence APVKQ; and expressing said polynucleotide in a host cell, wherein said expressing results in an improved expression of the polypeptide construct as compared to a corresponding polypeptide construct that does not have a linker polypeptide comprising a sequence with at least 60% identity to the sequence APVKQ.

IRES Elements

Also disclosed herein are constructs comprising an IRES element to facilitate the expression and functionality of the polynucleotides and polypeptides described herein. The term "internal ribosome entry site (IRES)" as used herein can be intended to mean internal ribosomal entry site. In a vector comprising an IRES sequence, a first gene can be translated by a cap-dependent, ribosome scanning, mechanism with its own 5'-UTR, whereas translation of a subsequent gene can be accomplished by direct recruitment of a ribosome to an IRES in a cap-independent manner. An IRES sequence can allow eukaryotic ribosomes to bind and begin translation without binding to a 5' capped end. An IRES sequence can allow expression of multiple genes from one transcript (Mountford and Smith 1995).

The term "CAP" or "cap" as used herein refers to a modified nucleotide, generally a 7-methyl guanosine, linked 3' to 5' (7meG-ppp-G), to the 5' end of a eukaryotic mRNA, that serves as a required element in the normal translation initiation pathway during expression of protein from that mRNA.

In certain cases, an IRES region can be derived from a virus, such as picornavirus, encephalomyocarditis virus, hepatitis C virus IRES sequence. In other cases, an IRES sequence can be derived from an encephalomyocarditis virus. The term "EMCV" or "encephalomyocarditis virus" as used herein refers to any member isolate or strain of the encephalomyocarditis virus species of the genus of the family Picornaviridae. Examples are: EMCV-R (Rueckert) strain virus, Columbia-SK virus. In some cases, a cellular IRES element, such as eukaryotic initiation factor 4G, immunoglobulin heavy chain binding protein, c-myc proto-oncogene, vascular endothelial growth factor, fibroblast growth factor-1 IRES, or any combination or modification thereof can be used. In some cases, a cellular IRES can have increased gene expression when compared to a viral IRES.

An IRES sequence of viral, cellular or a combination thereof can be utilized in a vector. An IRES can be from encephalomyocarditis (EMCV) or poliovirus (PV). In some cases, an IRES element is selected from a group consisting of Poliovirus (PV), Encephalomyelitis virus (EMCV), Footand-mouth disease virus (FMDV), Porcine teschovirus-1 (PTV-1), Aichivirus (AiV), Seneca Valley virus (SVV), Hepatitis C virus (HCV), Classical swine fever virus (CSFV), Human immunodeficiency virus-2 (HIV-2), Human immunodeficiency virus-1 (HIV-1), Moloney murine leukemia virus (MoMLV), Feline immunodeficiency virus (FIV), Mouse mammary tumor virus (MMTV), Human cytomegalovirus latency (pUL138), Epstein-Barr virus (EBNA-1), Herpes virus Marek's disease (MDV RLORF9), SV40 polycistronic 19S (SV40 19S), Rhopalosiphum padi virus (RhPV), Cricket paralysis virus (CrPV), Ectropis obliqua picorna-like virus (EoPV), Plautia stali intestine virus (PSIV), Triatoma virus (TrV), Bee paralysis dicistrovirus (IAPV, KBV), Black currant reversion virus (BRV), Pelargonium flower break virus (PFBV), Hibiscus chlorotic ringspot virus (HCRSV), Crucifer-infecting tobamovirus (CrTMV), Potato leaf roll polerovirus (PLRV), Tobacco etch virus (TEV), Giardiavirus (GLV), Leishmania RNA virus-1 (LRV-1), and combinations or modifications thereof. In some cases, an IRES is selected from a group consisting of Apaf-1, XIAP, HIAP2/c-IAP1, DAP5, Bcl-2, c-myc, CAT-1, INR, Differentiation LEF-1, PDGF2, HIF-1a, VEGF, FGF2, BiP, BAG-1, CIRP, p53, SHMT1, PITSLREp58, CDK1, Rpr, hid, hsp70, grim, skl, Antennapedia, dFoxO, dInR, Adh-Adhr, HSP101, ADH, URE-2, GPR1, NCE102, YMR181a, MSN1, BOI1, FLO8, GIC1, and any combination or modification thereof. When an IRES element is included between two open reading frames (ORFs), initiation of translation can occur by a canonical 5'-m7GpppN cap-dependent mechanism in a first ORF and a cap-independent mechanism in a second ORF downstream of the IRES element.

In some cases, genes can be linked by an internal ribosomal entry site (IRES). An IRES can allow simultaneous expression of multiple genes. For example, an IRES sequence can permit production of multiple proteins from a single mRNA transcript. A ribosome can bind to an IRES in a 5'-cap independent manner and initiate translation.

In some cases, an IRES sequence can be or can be about 500 base pairs. An IRES sequence can be from 300 base pairs to 1000 base pairs. For example, an IRES can be 300, 350, 400, 450, 500, 550, 600, 650, 700, 750, 800, 850, 900, 950, or 1000 base pairs long.

In some cases, expression of a downstream gene within a vector comprising an IRES sequence can be reduced. For example, a gene following an IRES sequence can have reduced expression over a gene preceding an IRES sequence. Reduced expression can be from 1% to 99% reduction over a preceding gene.

Methods of Regulating Expression

In one embodiment, a method of regulating the expression of a heterologous gene in an engineered cell is provided. Polynucleotides encoding for gene switch polypeptides for ligand inducible control of a heterologous gene expression, an antigen binding polypeptide and a heterologous gene is provided. In some instances, the polynucleotides are in one or more gene expression cassettes as depicted in any one of FIGS. 1 through 16. In another instance, the polynucleotides are incorporated into an engineered cell via viral or non-viral vectors. Viral vectors can include lentiviral vectors, retroviral vectors or adenoviral vectors. Non-viral vectors can include Sleeping Beauty transposons. In other instances, the polynucleotides are incorporated into an engineered cell via recombinases or gene editing techniques. Examples of recombinases are serine recombinases as described herein. Examples of gene editing techniques can include CRISPR or Argonaute systems. Herein a "CRISPR gene editing system" of "CRISPR system" refers to any RNA-guided Cas protein-mediated process for targeting a change in DNA sequence to a specific region of a genome. Herein "Argonaute gene editing system" refers to any single-stranded DNA guided Argonaute endonuclease-mediated process for targeting a change in DNA sequence to a specific region of a genome.

Pharmaceutical Compostions and Dosage

The present disclosure provides a composition comprising the adenovirus or adenoviral vector described herein and a carrier therefor (e.g., a pharmaceutically acceptable carrier). The composition desirably is a physiologically acceptable (e.g., pharmaceutically acceptable) composition, which comprises a carrier, preferably a physiologically (e.g., pharmaceutically) acceptable carrier, and the adenovirus or adenoviral vector. Any suitable carrier can be used within the context of the present disclosure, and such carriers are well known in the art. The choice of carrier will be determined, in part, by the particular use of the composition (e.g., administration to an animal) and the particular method used to administer the composition. Ideally, in the context of replication-deficient adenoviral vectors, the pharmaceutical composition preferably is free of replication-competent adenovirus. The pharmaceutical composition optionally can be sterile.

Suitable compositions include aqueous and non-aqueous isotonic sterile solutions, which can contain anti-oxidants, buffers, and bacteriostats, and aqueous and non-aqueous sterile suspensions that can include suspending agents, solubilizers, thickening agents, stabilizers, and preservatives. The composition can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. More preferably, the adenovirus or adenoviral vector is part of a composition formulated to protect the adenovirus or adenoviral vector from damage prior to administration. For example, the composition can be formulated to reduce loss of the adenovirus or adenoviral vector on devices used to prepare, store, or administer the adenovirus or adenoviral vector, such as glassware, syringes, or needles. The composition can be formulated to decrease the light sensitivity and/or temperature sensitivity of the adenovirus or adenoviral vector. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the adenovirus or adenoviral vector, and facilitate its administration. Formulations for adenovirus or adenoviral vector-containing compositions are further described in, for example, U.S. Pat. Nos. 6,225,289, 6,514,943, and International Patent Application Publication WO 2000/034444.

The composition also can be formulated to enhance transduction efficiency. In addition, one of ordinary skill in the art will appreciate that the adenovirus or adenoviral vector can be present in a composition with other therapeutic or biologically-active agents. For example, factors that control inflammation, such as ibuprofen or steroids, can be part of the composition to reduce swelling and inflammation associated with in vivo administration of the adenovirus or adenoviral vector. If the adenovirus or adenoviral vector is used to deliver an antigen-encoding nucleic acid sequence to a host, immune system stimulators or adjuvants, e.g., interleukins, lipopolysaccharide, or double-stranded RNA, can be administered to enhance or modify any immune response to the antigen. Antibiotics, i.e., microbicides and fungicides, can be present to treat existing infection and/or reduce the risk of future infection, such as infection associated with gene transfer procedures.

In some embodiments, disclosed herein are compositions comprising a polynucleotide or polypeptide disclosed herein for administration in a subject. In some instances, are modified effector cell compositions encoding a polynucleotide or polypeptide disclosed herein, and optionally containing a cytokine and/or an additional therapeutic agent. In some instances, also included herein are vectors encoding gene-switch polypeptides for regulating expression of a chimeric antigen receptor for modification of an effector cell.

In some instances, pharmaceutical compositions of a modified effector cell or a vector encoding gene-switch polypeptides and a chimeric antigen receptor are formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Pharmaceutical compositions are optionally manufactured in a conventional manner, such as, by way of example only, by means of conventional mixing, dissolving, granulating, dragee-making, levigating, emulsifying, encapsulating, entrapping or compression processes.

In certain embodiments, compositions can also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions can also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The pharmaceutical compositions described herein are administered by any suitable administration route, including but not limited to, oral, parenteral (e.g., intravenous, subcutaneous, intramuscular, intracerebral, intracerebroventricular, intra-articular, intraperitoneal, or intracranial), intranasal, buccal, sublingual, or rectal administration routes. In some instances, the pharmaceutical composition is formulated for parenteral (e.g., intravenous, subcutaneous, intramuscular, intracerebral, intracerebroventricular, intraarticular, intraperitoneal, or intracranial) administration.

The pharmaceutical compositions described herein are formulated into any suitable dosage form, including but not limited to, aqueous oral dispersions, liquids, gels, syrups, elixirs, slurries, suspensions and the like, for oral ingestion by an individual to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In some embodiments, the pharmaceutical compositions are formulated into capsules. In some embodiments, the pharmaceutical compositions are formulated into solutions (for example, for IV administration). In some cases, the pharmaceutical composition is formulated as an infusion. In some cases, the pharmaceutical composition is formulated as an injection.

The pharmaceutical solid dosage forms described herein optionally include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

In still other aspects, using standard coating procedures, such as those described in Remington's Pharmaceutical Sciences, 20th Edition (2000), a film coating is provided around the compositions. In some embodiments, the compositions are formulated into particles (for example for administration by capsule) and some or all of the particles are coated. In some embodiments, the compositions are formulated into particles (for example for administration by capsule) and some or all of the particles are microencapsulated. In some embodiments, the compositions are formulated into particles (for example for administration by capsule) and some or all of the particles are not microencapsulated and are uncoated.

In certain embodiments, compositions provided herein can also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

Formulations described herein can benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v.

polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of ibrutinib and An anticancer agent, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" can include, but are not limited to, acacia, gelatin, colloidal silicon dioxide, calcium glycerophosphate, calcium lactate, maltodextrin, glycerine, magnesium silicate, polyvinylpyrollidone (PVP), cholesterol, cholesterol esters, sodium caseinate, soy lecithin, taurocholic acid, phosphatidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, poly sorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants can be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

A kit typically includes labels listing contents and/or instructions for use, and package inserts with instructions for use. A set of instructions will also typically be included.

In some embodiments, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

EXAMPLES

These examples are provided for illustrative purposes only and not to limit the scope of the claims provided herein.

Example 1

Antigenicity Bioinformatics Workflow for HBV Vaccine Designs

The HBV vaccine antigen designs provided herein were inspired via inventor-selected combinatorial guidance provided via use of bioinformatics analysis and in silico protein engineering methods. HBV antigen sequences were selected based on genotype D protein sequences, antigenicity predictions and T cell epitope mapping with broad coverages, which could lead to MHC-I binding and cytokine production following T cell activation. The overall workflow of the HBV vaccine designs provided herein is shown in FIG. 5 and is further detailed below.

Obtaining Consensus Sequences

The HBV genome encodes several overlapping viral proteins, including the polymerase, core, envelope (Pre-S1, S2, S), HBe, and HBx proteins (FIGS. 3A-3D). Consensus AA sequences were obtained from the Hepatitis B Virus database (HBVdb) for A, C, and D subtypes.

Predicting Binding Affinity

Figure 9A:
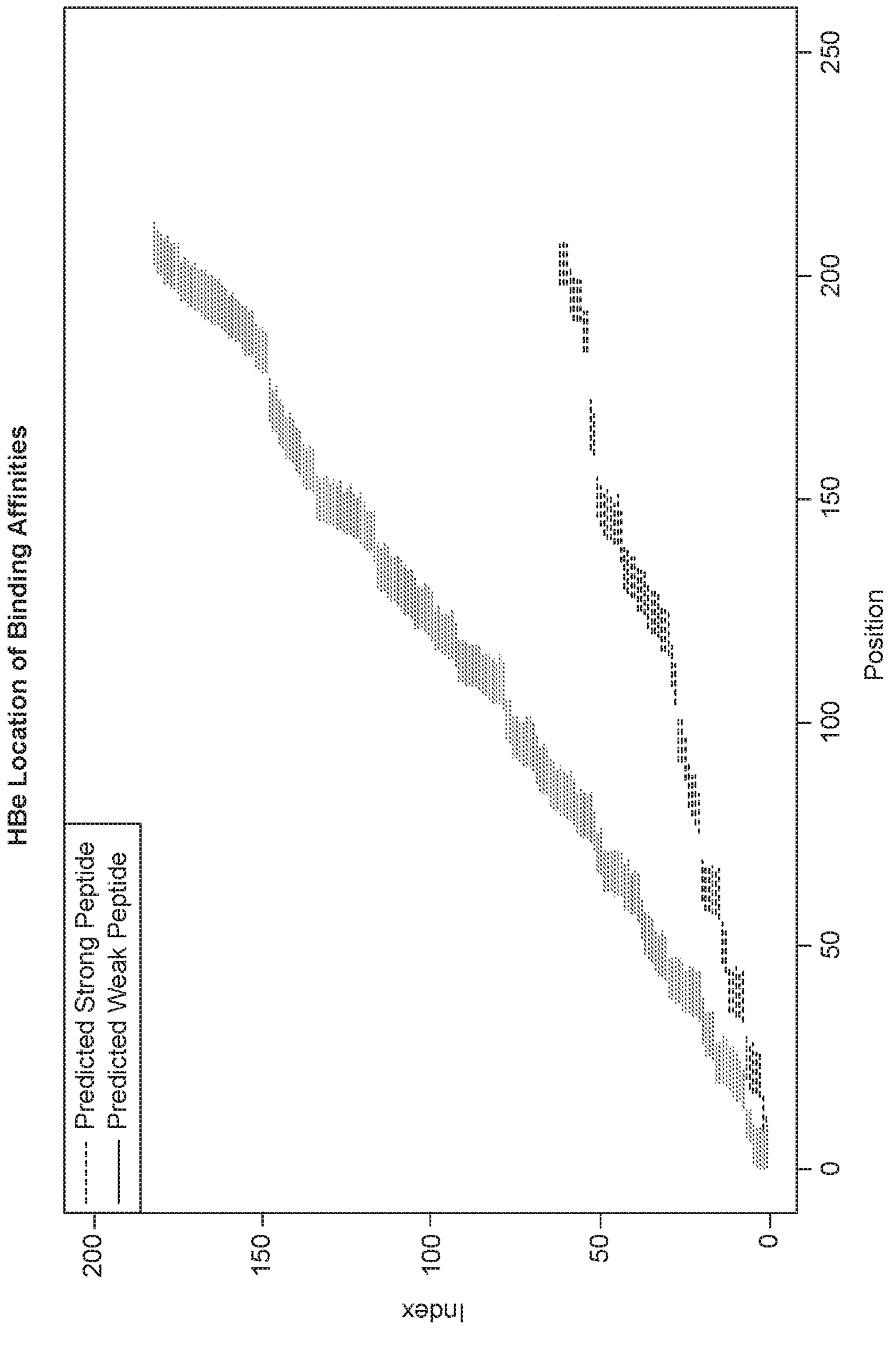
FIG. 9A shows NetMHC4.0 antigenicity predictions for HBe. Predicted strong and weak binding peptides indices were plated against peptide locations.
Figure 9B:
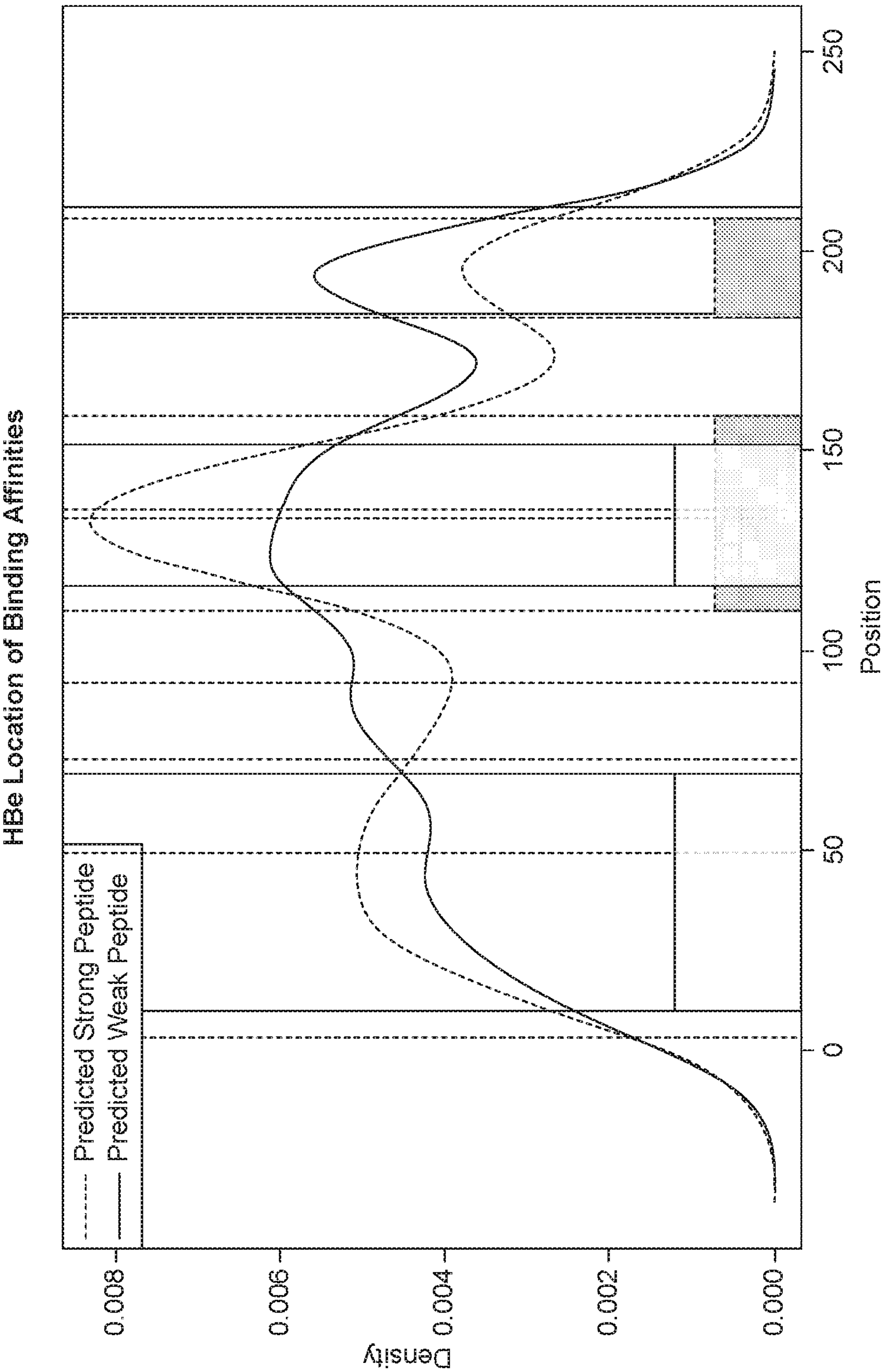
FIG. 9B shows NetMHC4.0 antigenicity predictions for HBe. First and second order differentials were employed on density plots in order to identify peaks.
Figure 9C:
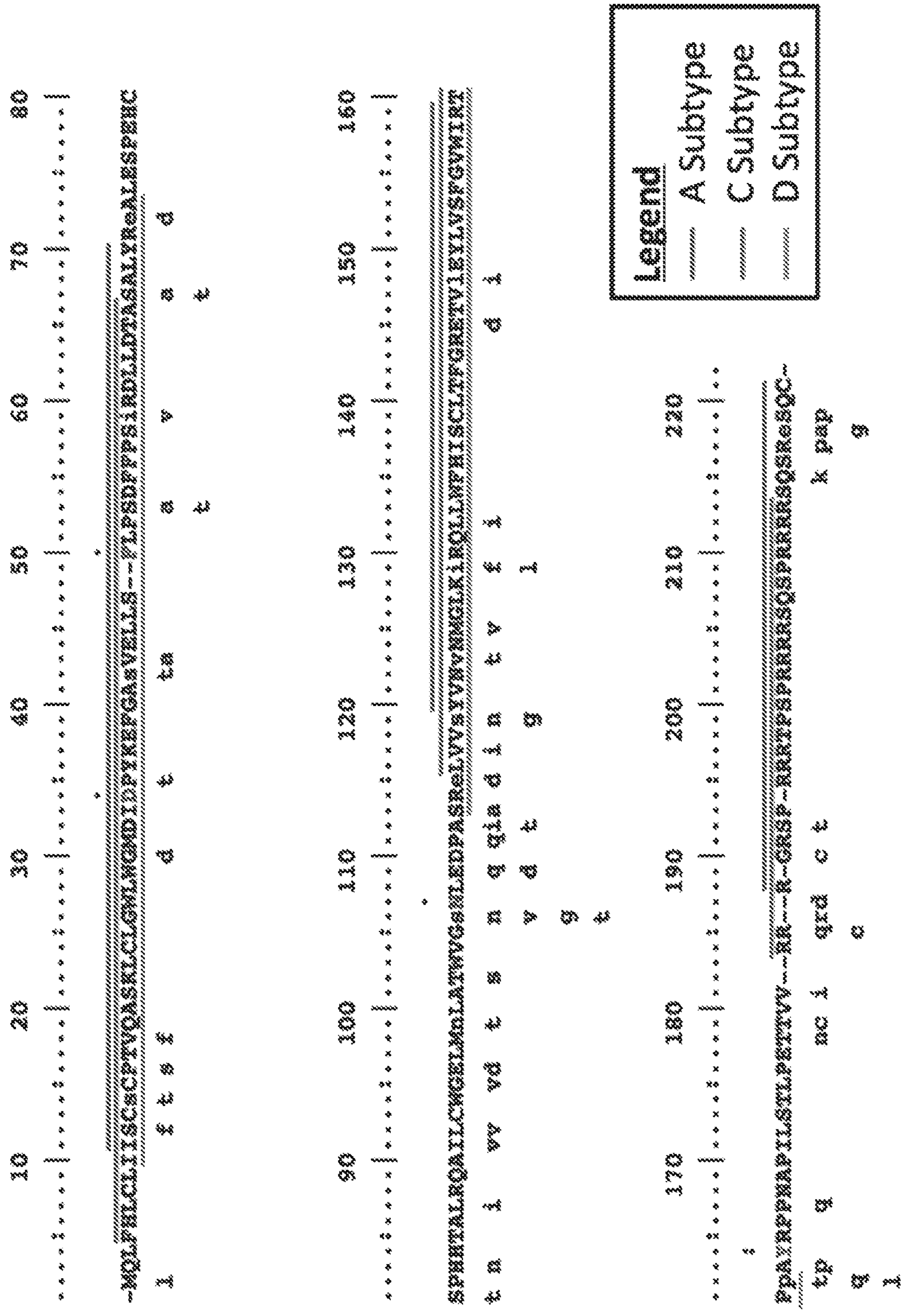
FIG. 9C shows amino acid sequences aligned against consensus sequences in order to determine coverage across HBV subtypes (SEQ ID NOs: 132-136).

NetMHC 4.0 was applied to each consensus sequence to predict binding affinity against all major MHC-I alleles (HLA-A0101, HLA-A0201, HLA-A0301, HLA-A2402, HLA-A2601, HLA-B0702, HLA-B0801, HLA-B2705, HLA-B3901, HLA-B4001, HLA-B5801, and HLA-B1501). NetMHC 4.0 uses artificial neural networks to predict the binding affinity of peptide sequences. This analysis was performed across HBV genotypes A, C, and D. Thresholds were arbitrarily established at 0.5% (strong binders) and 2% (weak binders) ranks. Peptides with predicted binding affinity greater than 99.5% were classified as strong binders and peptides with predicted binding affinity greater than 98% were classified as weak binders. The position of each AA within the peptide sequences were extracted and used to generate density curves (FIG. 9A). Using these density curves, first and second order differentials were calculated to determine peaks for strong and weak binders (FIG. 9B). Finally, the union of these positions was used to extract AA sequences likely to elicit a response (FIG. 9C).

Example 2

HBV Molecular Vaccine Designs

The HBV vaccines described herein include the following HBV designs 1-5 engineered proteins (peptides with genetic modifications). Once the designs were finalized the entire sequence for each design was subjected to NetMHC prediction to assess antigenicity and coverage against A, C, and D genotypes (Example 1). The vaccines described herein were compared against TG1050, an adenovirus-based immunotherapeutic HBV vaccine currently in clinical trials, that encodes a unique large fusion protein composed of: (a) a truncated core, (b) a modified polymerase, and (c) two envelope domains. The core region of TG1050 lacked the pre-core and its polymerase was split into three segments along with four point mutations to improve the vaccine construct stability (Pol1, Plo2 and Pol3; Δ AA 538-544 and Δ AA 710-742 and mutations D689H, V769Y, T776Y, D777H). The two selected envelope domains were inserted in between those polymerase segments as shown in FIG. 5. TG1050 polymerase, Env1 and Env2 sequences were obtained from Genbank (Y07587.1), and the TG1050 core sequences were obtained from HBV DB (AB048701).

Five antigen designs (HBV designs 1-5) and a control antigen were synthesized and cloned into expression plasmids—pAdShuttles for adenovector construction (FIG. 6). Initial antigen screening evaluated in vitro antigen expression in transient transfection, in vitro antigen processing and presentation in transient transfection studies of monocyte-derived dendritic cells. As shown in FIG. 6, HBV designs 1 and 2 were designed based on clade D consensus. 32 HBV peptides from Core (8), Surface (8), Polymerase (8), HBx (6) and HBPS (2) were curated from literature that have experimental and functional data, such as immunogenicity data, Mass-spec. etc. (Table 3). For HBV design 3, human ankyrin-like repeat (ALR) protein scaffold (PDB code 1QYM) peptides were grafted at the helical and loop regions in a tandem manner. Two ALR scaffolds were used, connected by a cleavable linker (VSQTSKLTR; SEQ ID NO:111). ALR proteins have generally high expression and high stability. Thus, ALR proteins were used as a scaffold for the HBV peptides to create novel CTLs. HBV design 4 epitopes were separated by KK linkers (FIG. 6).

HBV Design 1

Figure 10:
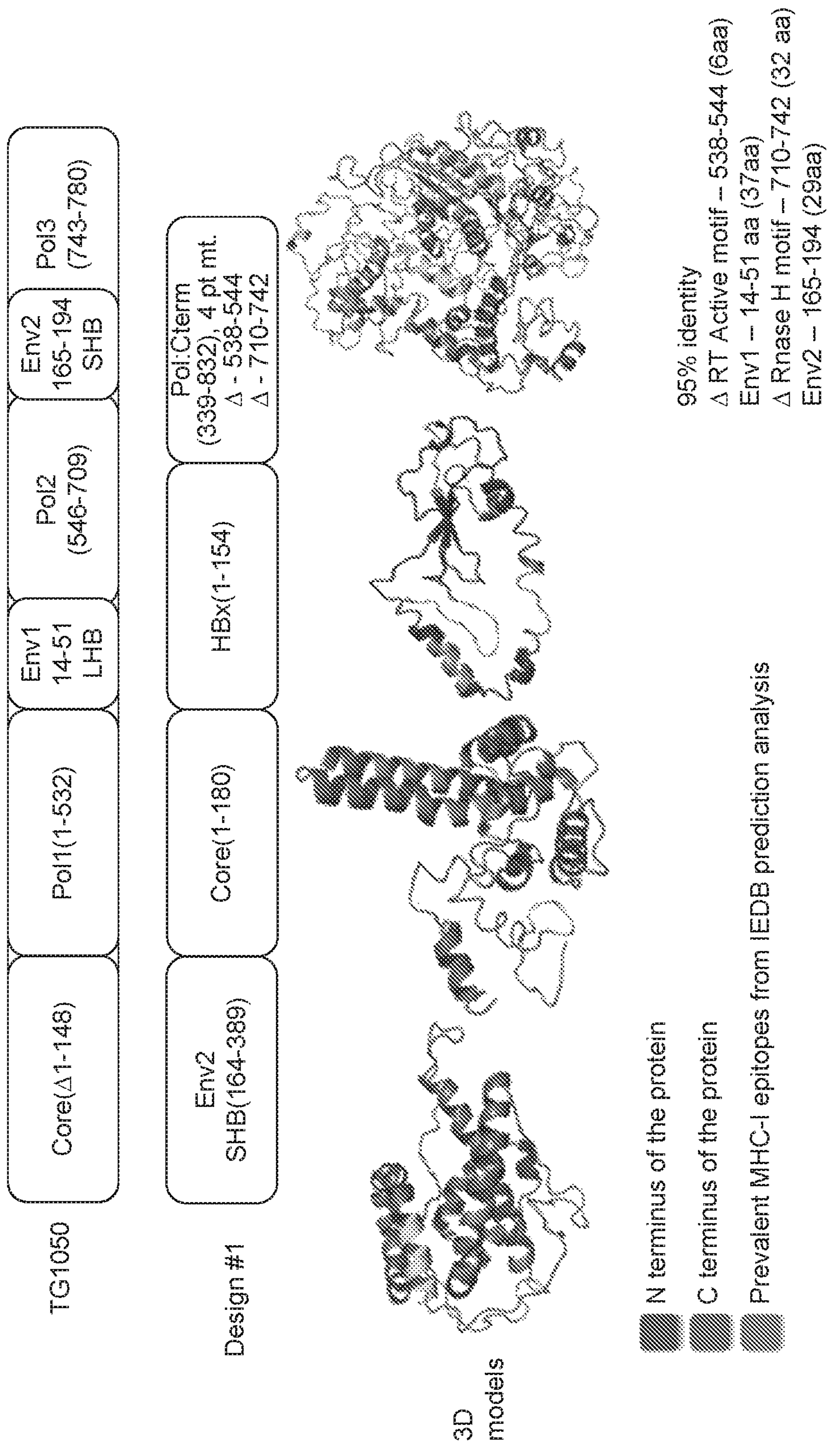
FIG. 10 is a schematic representation of TG1050 and HBV design 1 highlighting the fused domains of different HBV protein. Homology models were used to further assess the design.
Figure 15B:
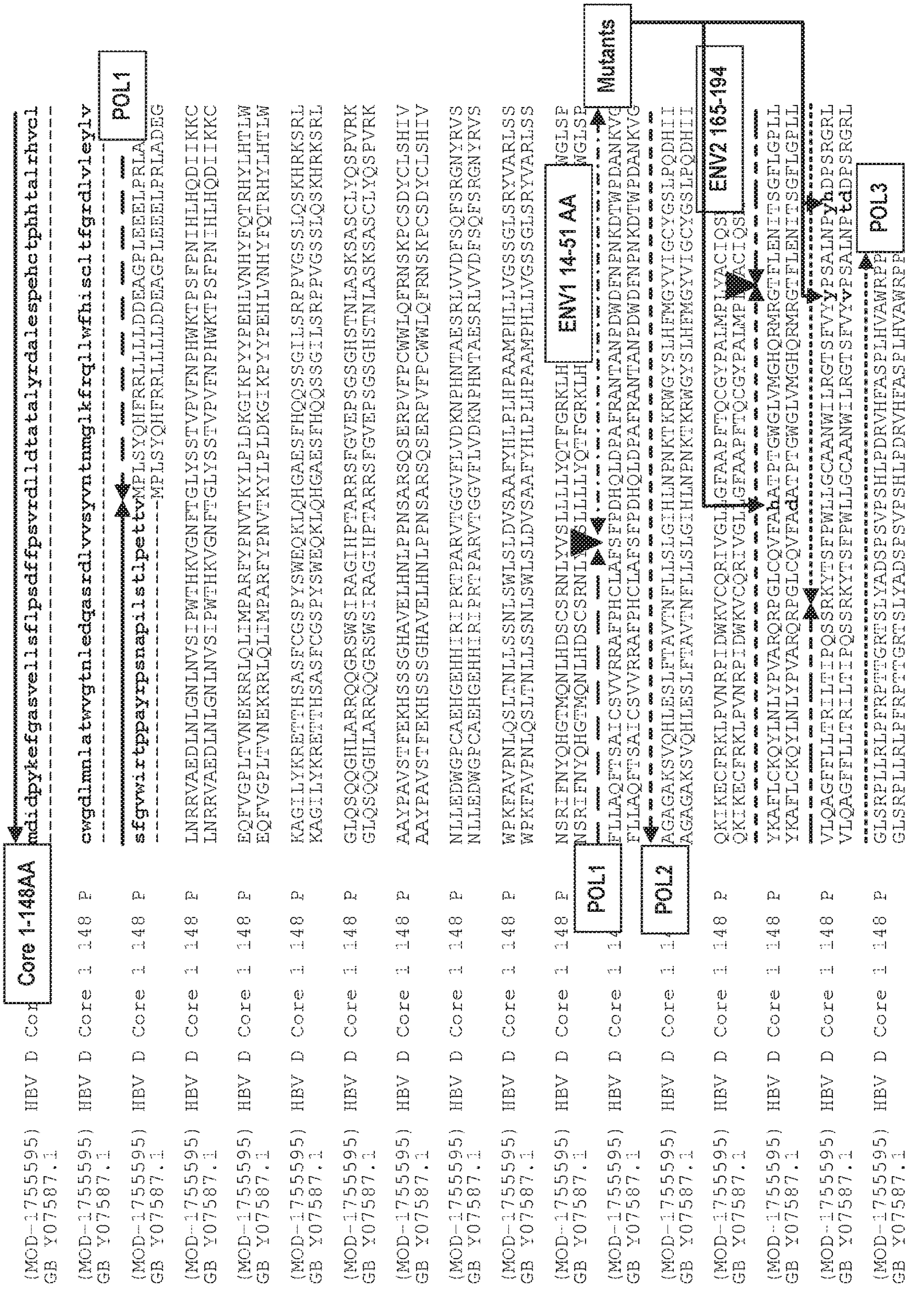
FIG. 15B shows sequence comparisons of HBV design 1 and TG1050 control (SEQ ID NOs: 145-146).
Figure 15C:
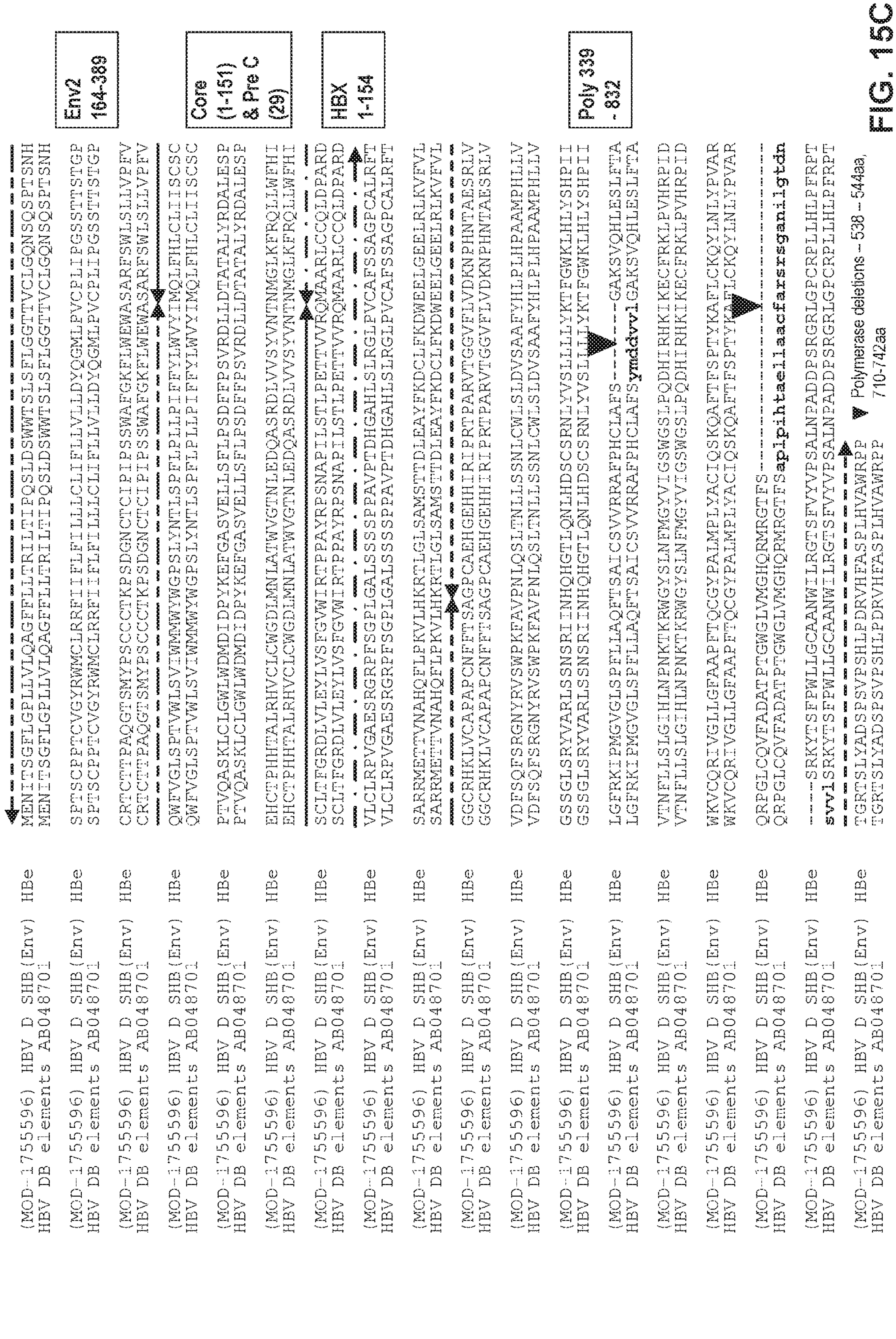
FIG. 15C shows sequence comparisons of HBV design 1 and TG1050 control (SEQ ID NOs: 147-148).

HBV D genotype protein sequence (HBV DB: AB048701) was used in this design. Antigenicity prediction analysis (Example 1) and homology models of HBV proteins guided this Design. Comparison of HBV Design 1 and TG1050 along with homology models of protein antigens is shown in FIG. 10, and sequence comparisons are shown in FIGS. 15A-15C. This design contained four native HBV antigens: (1) extended Env2/S region 165-382 AA; (2) core region 1-151 AA and pre-core region; (3) HBx region 1-154 AA; and (4) Polymerase (339-832 AA), del 538-544, 710-742 AA. The TG1050 comparator had two HBV antigens with a third envelope peptide fused to polymerase.

This design encompassed entire protein domains from envelope, core, HBx and the reverse transcriptase domain of polymerase. The TG1050 comparator had truncated core and envelope peptides fused into the modified polymerase domain, but did not encode any HBx sequences.

Different HBV domains were seamlessly fused together as a one long open reading frame. The TG1050 comparator had only two domains (core and polymerase) with truncations as well as deletions. The TG1050 comparator had random insertion of envelope peptides within the polymerase domain.

Truncations were made in the envelope protein and polymerase domains. Only the C terminus region of the envelope protein was used in this design. Only the C terminus region of reverse transcriptase was included. The entire RNaseH domain was included. Truncations were made to inactivate the reverse transcriptase function in ΔRT active motif (538-544: baa) and in ΔRNase H motif (710-742: 32 aa).

HBV design 1 novelty: Overall, HBV design 1 had an extended Env2/S region along with both pre-core and core regions compared to TG1050. Unlike TG1050, it also contained the HBx domain. The N-term truncated polymerase along with deletions similar to TG1050 was also used.

HBV Design 2

Figure 11:
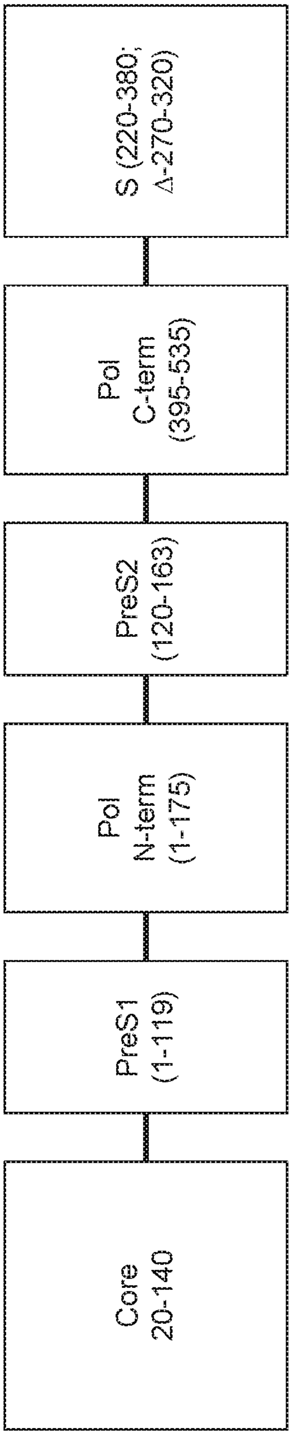
FIG. 11 is a schematic representation of the HBV design 2 consisting of all three major proteins (core, surface splice variants, and polymerase) linked with HBx peptides.
Figure 12A:
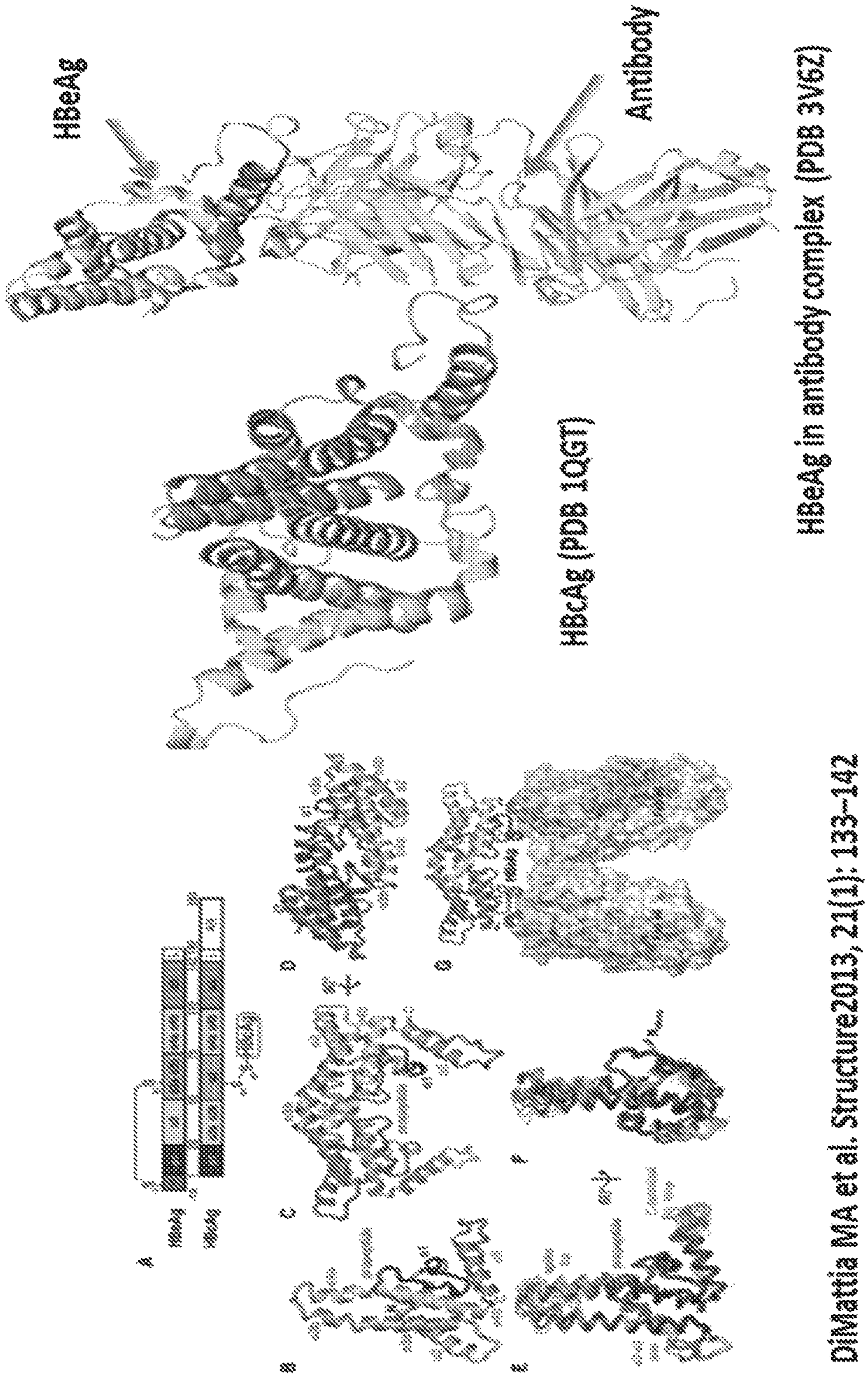
FIG. 12A shows a structure of core HBV protein domain.
Figure 12B:
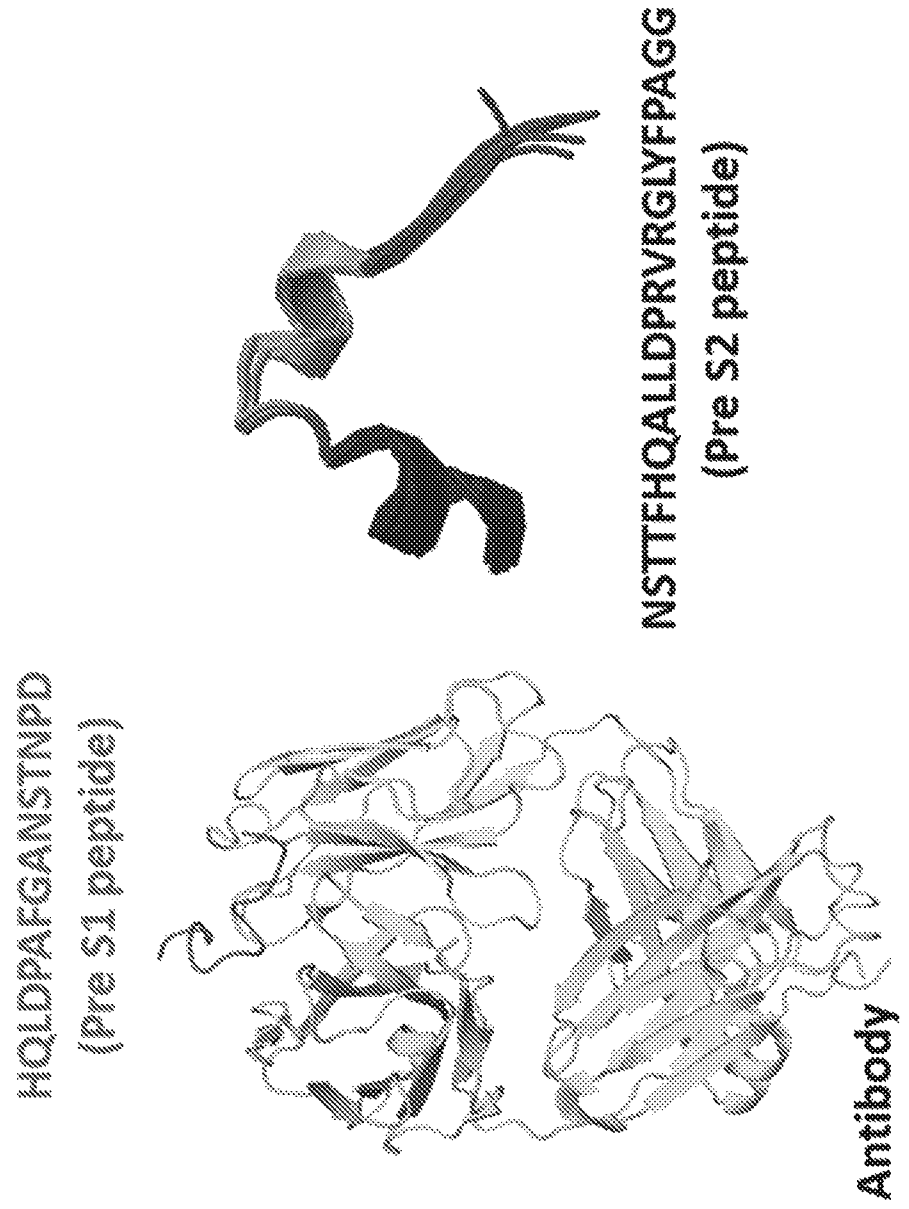
FIG. 12B shows a structure of HBV preS1 and S2 peptides (SEQ ID NOs: 137-138).
Figure 12C:
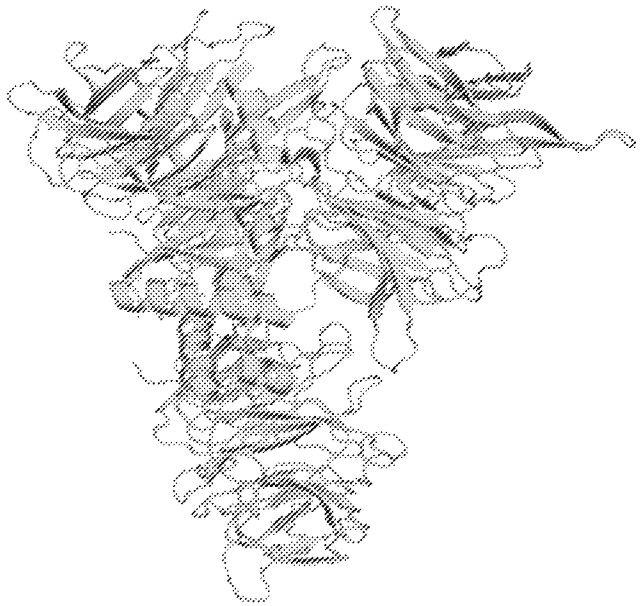
FIG. 12C shows structures of HBV HBx (SEQ ID NOs: 139-140).
Figure 12C:
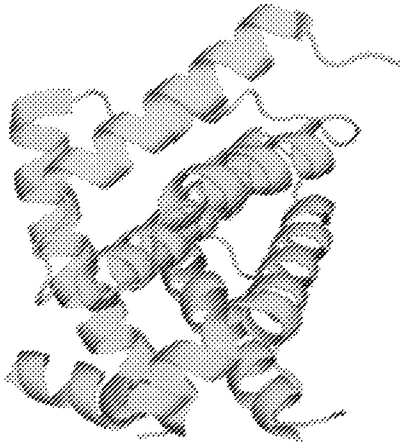
Figure 12D:
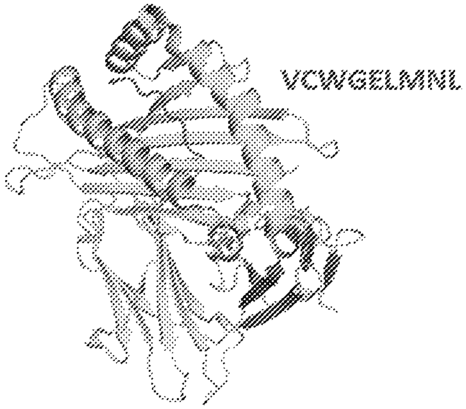
FIG. 12D shows structures of four core peptides-MHC complexes (SEQ ID NOs: 141-142).
Figure 12D:
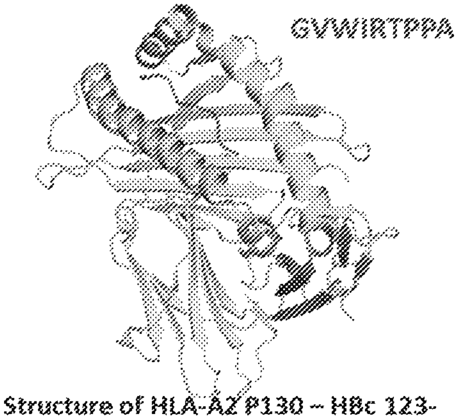
Figure 12D:
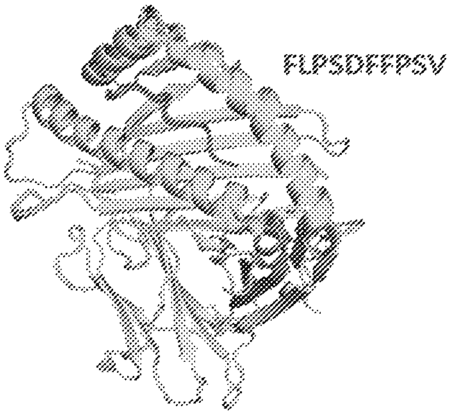
Figure 12D:
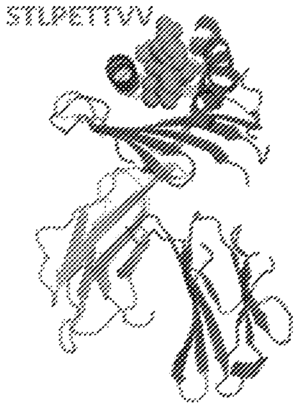
Figure 13:
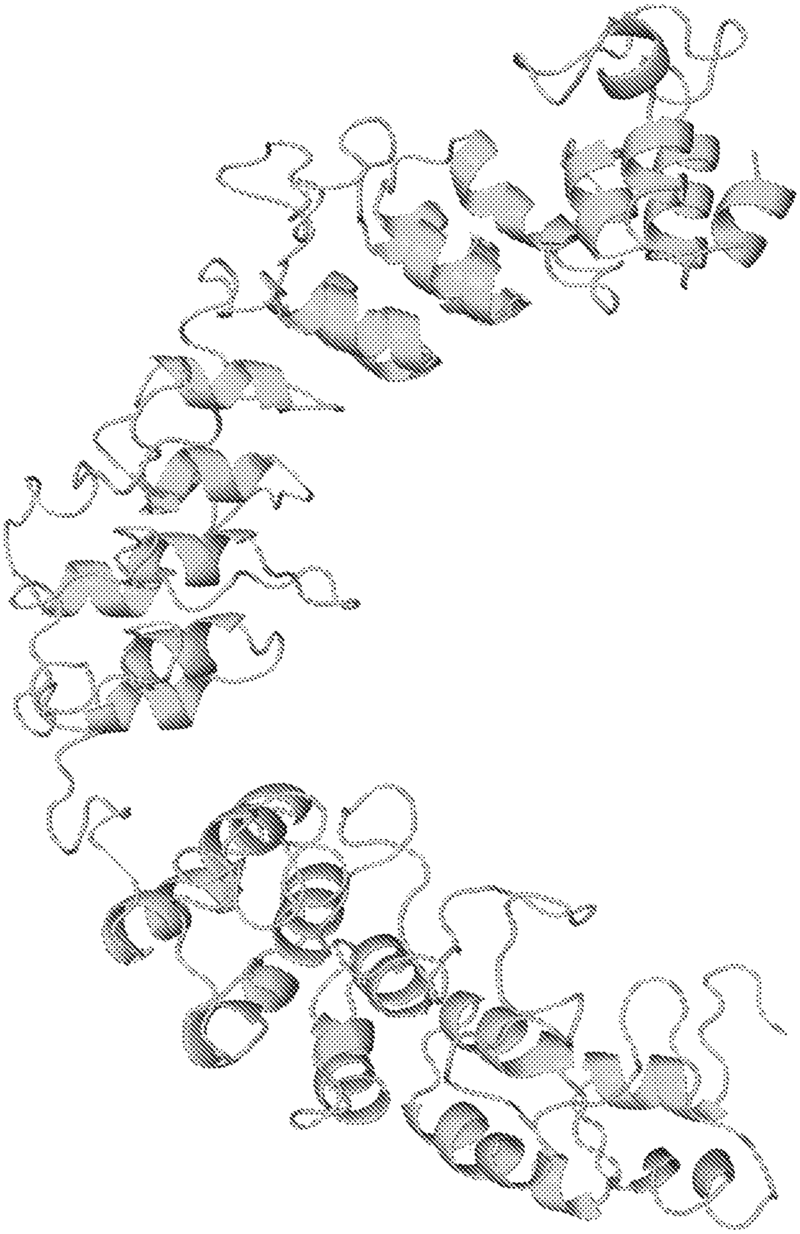
FIG. 13 shows a homology model of HBV design 4 based on multi-epitope antigens.

This design consisted of all three major proteins including Core, Surface splice variants, and Polymerase that were linked with HBx peptides as depicted in FIG. 11. Selected protein components were fused together to make a one long open reading frame. This design was based on the following: (a) functional genomics data (HBVdb: AB048701); (b) T cell epitope predictions (Example 1); and (c) analysis of available HBV protein structures as illustrated in FIGS. 12A-12D. When compared to the TG1050 comparator and HBV design design 1, this design has additional and/or modified protein domains as follows: (a) truncated C terminus; (b) spliced variants of surface proteins (PreS1 and PreS2, S); (c) split Pol N- and C-terminus fragments; and (d) six HBx peptides. The protein domains were shuffled to avoid any HBV infectivity, and HBV design 2 used a different ordering scheme than the TG1050 comparator and HBV design 1.

HBV Design 3

This design was based on multi-epitopes containing a total of 32 CTL specific epitopes (Table 3) and was selected from the following: (1) literature review based on multiple immunological assays and immunoproteomics; and (2) the IEDB; (3) NetMHC 4.0 epitope predictions. Human Ankyrin-like repeat protein (PDB code 1QYM) was selected as a scaffold on to which the 32 peptides were grafted replacing the repeat regions. A homology model of the this design (FIG. 13) was generated, which suggested that ankyrin scaffold with grafted peptides can retain the overall tertiary structure. Scaffold backbone amino acids connecting the 32 grafted CTL epitopes can serve as adequate linkers.

HBV Design 4

This design was comprised of the same 32 CTL epitopes from Core, Surface, Pol, HBx and HBSP as Design 3 (Table 3). The peptides were assembled with charged dipeptide KK residue linkers instead of grafting onto a scaffold.

TABLE 3

| 32 HBV Peptides from Core, Surface, Polymerase, HBx, and HBPS | | | | | | | |
|---|---|---|---|---|---|---|---|
| Source | Sequence | SEQ | Length | Source | Sequence | SEQ | Length |
| Core-1 | FLPSDFFPSV | #45 | 10 | Surface-1 | GGPNLDNIL | #112 | 9 |
| Core-2 | CWGELMTL | #46 | 8 | Surface-2 | LTTVPAASLLA | #113 | 11 |
| Core-3 | GVWIRTPPA | #47 | 9 | Surface-3 | ILRSFIPLL | #114 | 9 |
| Core-4 | STLPETTVVRR | #48 | 11 | Surface-4 | FLGGPPVCL | #115 | 9 |
| Core-5 | LTFGRETVLEY | #49 | 11 | Surface-5 | FLLTRILTI | #116 | 9 |
| Core-6 | DLLDTASALY | #50 | 10 | Surface-6 | WLSLLVPFV | #117 | 9 |
| Core-7 | LWFHISCLTF | #51 | 10 | Surface-7 | GLSPTVWLSV | #118 | 10 |
| Core-8 | EYLVSFGVW | #52 | 9 | Surface-8 | LLVPFVQWFV | #119 | 10 |
| Pol-1 | FLKQQYMNL | #53 | 9 | HBSP-1 | LLLKATLCI | #120 | 9 |
| Pol-2 | FLSKQYMDL | #54 | 9 | HBSP-2 | TLCIPHVAV | #121 | 9 |
| Pol-3 | TVSTKLCKI | #55 | 9 | HBx-1 | VLHKRTLGL | #122 | 9 |
| Pol-4 | GLSRYVARL | #56 | 9 | HBx-2 | LPKVLHKRTL | #123 | 10 |
| Pol-5 | KLHLYSHPI | #57 | 9 | HBx-3 | HKRTLGLSAM | #124 | 10 |
| Pol-6 | FLLSLGIHL | #58 | 9 | HBx-4 | QFLPKVLHKR | #25 | 10 |
| Pol-7 | SLYADSPSV | #59 | 9 | HBx-5 | TVNAHQFLPK | #126 | 10 |
| Pol-8 | ALMPLYACI | #60 | 9 | HBx-6 | LSAMSTTDL | #127 | 9 |

HBV Design 5

Figure 16:
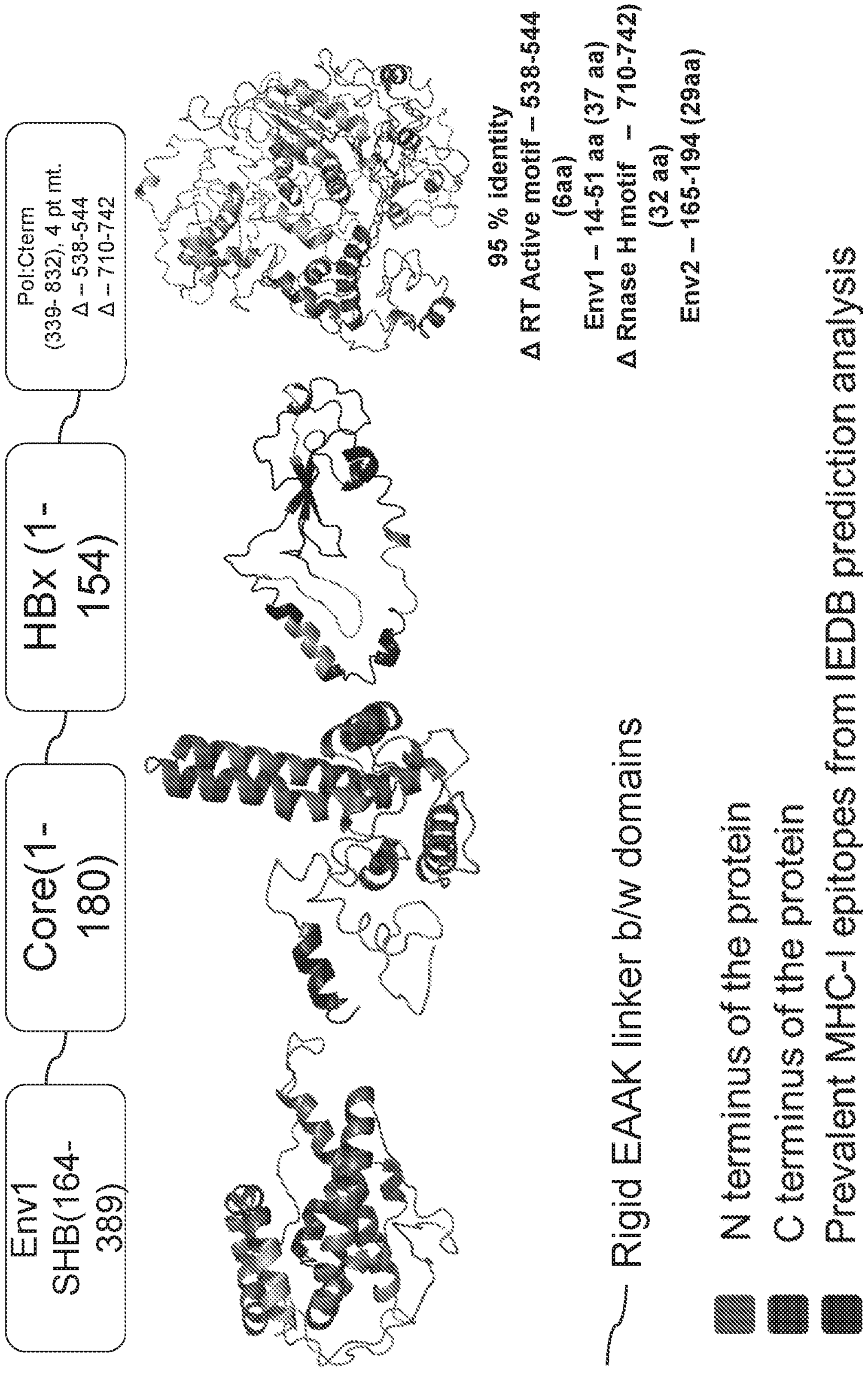
FIG. 16 is a schematic representation of HBV design 5.

This design is similar to design 1 and has rigid linker (EAAAK)2 (SEQ ID NO: 129) between the fusion components (SEQ ID NOs: 112 and 113; Table 6; FIG. 16).

For RNA qPCR relative expression assay, 5'-TGCCAAGAGTGACGTGTCCA-3' (SEQ ID NO: 110) was used as a splice primer, and 5'-CCCAGGTCCAACTGCAGCCGG-3' (SEQ ID NO: 128) was used as a splice probe.

Specific primers designed for each antigen were used as reverse primers (FIG. 14). A549 cells were lipotransfected (Table 4), and HT1080 cells were nucleofected (Table 5).

TABLE 4

| qPCR Expression Assay (A549 Cells) | | | | | | | | |
|---|---|---|---|---|---|---|---|---|
| | One-step qPCR 0.1 ng total RNA | | | | Two-step qPCR 0.2 ng cDNA | | | |
| Sample | Short Amplicon bp | GOI Ave. Ct | HPRT1 Ave. Ct | Fold difference in GOI relative to untreated | long Amplicon bp | GOI Ave. Ct | HPRT1 Ave. Ct | Fold difference in GOI relative to untreated |
| Mock | | 40.0 | 31.1 | 1 | | 40.0 | 31.3 | 1 |
| 4825853 | 141 | 23.1 | 31.3 | 145618 | 993 | 32.0 | 31.6 | 300 |
| Mock | | 40.0 | 31.1 | 1 | | 40.0 | 31.3 | 1 |
| 4825811 | 162 | 23.2 | 31.4 | 138449 | 948 | 31.2 | 31.6 | 531 |
| Mock | | 40.0 | 31.1 | 1 | | 40.0 | 31.3 | 1 |
| 4825790 | 125 | 22.5 | 31.5 | 241891 | 839 | 29.0 | 31.3 | 2016 |
| Mock | | 40.0 | 31.1 | 1 | | 40.0 | 31.3 | 1 |
| 4825791 | 127 | 22.3 | 31.6 | 304806 | 895 | 28.1 | 31.4 | 3882 |
| Mock | | 40.0 | 31.1 | 1 | | 40.0 | 31.3 | 1 |
| 4825852 | 143 | 20.8 | 31.6 | 827615 | 777 | 24.5 | 31.7 | 58169 |

TABLE 5

| qPCR Expression Assay (HT1080 Cells) | | | | | | | | |
|---|---|---|---|---|---|---|---|---|
| | One-step qPCR 5 ng total RNA | | | | Two-step qPCR 5 ng cDNA | | | |
| Sample | Short Amplicon bp | GOI Ave. Ct | HPRT1 Ave. Ct | Fold difference in GOI relative to untreated | long Amplicon bp | GOI Ave. Ct | HPRT1 Ave. Ct | Fold difference in GOI relative to untreated |
| Mock | | 40.0 | 25.5 | 1 | | 40.0 | 25.5 | 1 |
| 4825853 | 141 | 26.5 | 25.7 | 13981 | 993 | 32.4 | 25.1 | 143 |
| Mock | | 40.0 | 25.5 | 1 | | 40.0 | 25.5 | 1 |
| 4825811 | 162 | 23.9 | 25.5 | 71179 | 948 | 27.5 | 25.5 | 5564 |
| Mock | | 40.0 | 25.5 | 1 | | 40.0 | 25.5 | 1 |
| 4825790 | 125 | 25.5 | 25.6 | 24556 | 839 | 29.6 | 25.2 | 1114 |
| Mock | | 40.0 | 25.5 | 1 | | 40.0 | 25.5 | 1 |
| 4825791 | 127 | 24.4 | 26.1 | 78118 | 895 | 26.0 | 25.4 | 15042 |
| Mock | | 40.0 | 25.5 | 1 | | 40.0 | 25.5 | 1 |
| 4825852 | 143 | 21.8 | 25.7 | 360074 | 777 | 22.9 | 25.2 | 113697 |

Example 3

Immunogenicity Testing of HBV Vaccine

All of the antigens were constructed in multi-deleted gorilla adenovectors and produced to generate research materials for experimentation as well as pre-GMP stocks that can move to GMP manufacture for clinical studies (FIG. 6).

Optimum plasmid concentration for dendritic cell transfection is determined. The ability of different antigen designs to activate T cells from chronic PHBV patients is assessed. The immunogenicity of antigen design on HBV infected patient samples is assessed. The in vivo testing plan is to conduct in vivo immunogenicity studies in mice (e.g., single administration studies, repeat administration studies, including a "boost at home" proof of feasibility, route of administration (IM vs SC)), and mouse model of chronic HBV infection and eventually HCC.

Monocyte-derived dendritic cells are generated with GM-CSF and IL-4 according to standard protocol. The monocyte-derived dendritic cells are infected with different HBV antigen constructs and incubated with the vectors for 24 hours at 37° C. The cells are washed and matured overnight with 10 ng/ml rhuTNF-α. The cell maturation is assessed by flow cytometry (CD40, CD80, CD83, CD86, HLA-DR). Cytokine production is assessed for IL-1β, TNF-α, IL-6, IL-12p40, and MCP1. The monocyte-derived dendritic cells are co-cultured with autologous T cells for 10 days 1:10 ratio. Exogenous rhuIL-2 (200U/ml), rhuIL-7 and rHuIL-15 (10 ng/ml) are added on day 3, 5 and 7. Cytokine secretions for IFN-γ, TNF-α, CXCL-10, CXCL-9, IL-10, IL-6, IL-4, IL-5, IL-12p70, and MCP1 are assessed. Activation markers for T cells are CD25, CD69, CD45RA, CD45RO, PD1, CTLA-4, TIGIT, and LAG3. Antigen design with the most immunogenicity based on dendritic cells and T cell activation is selected, and the immunogenicity of the antigen design on HBV infected patient samples is assessed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The present application claims benefit to U.S. Provisional Application No. 62/639,354 filed Mar. 6, 2018, which is incorporated herein by reference in its entirety.

Embodiments

E1. A non-naturally occurring polynucleotide encoding a polypeptide comprising at least one or more immune response-inducing hepatitis B virus (HBV) polypeptides.

E2. The polynucleotide of E1, wherein said one or more HBV polypeptides comprises an HBV Core peptide.

E3. The polynucleotide of E2, wherein said HBV Core peptide has any one of the Core peptide sequences as shown in Table 3.

E4. The polynucleotide of any one of E1 to E3, wherein said one or more HBV polypeptides comprises an HBV Surface peptide.

E5. The polynucleotide of E4, wherein said HBV Surface peptide has any one of the Surface peptide sequences as shown in Table 3.

E6. The polynucleotide of any one of E1 to E5, wherein said one or more HBV polypeptides comprises an HBV Pol peptide.

E7. The polynucleotide of E6, wherein said HBV Pol peptide has any one of the Pol peptide sequences as shown in Table 3.

E8. The polynucleotide of any one of E1 to E7, wherein said one or more HBV polypeptides comprises an HBV HBSP/HBx peptide.

E9. The polynucleotide of E8, wherein said HBV HBSP/HBx peptide has any one of the HBSP/HBx peptide sequences as shown in Table 3.

E10. The polynucleotide of any one of E1 to E9, wherein said one or more HBV polypeptides comprises a KK linker.

E11. The polynucleotide of E10, wherein said KK linker connects any one of the peptide sequences as shown in Table 3 to any other peptide sequences as shown in Table 3.

E12. A polynucleotide comprising the polynucleotide of any one of E1 to E11, further comprising one or more polynucleotides encoding a gene switch system for inducible control of heterologous gene expression, wherein heterologous gene expression is regulated by said gene switch system; and, wherein said heterologous gene comprises the polynucleotide of any one of E1 to E11.

E13. The polynucleotide of any one of E1 to E12, wherein said gene switch system is an ecdysone receptor-based (EcR-based) gene switch system.

E14. The polynucleotide of any one of E1 to E13, wherein said one or more HBV polypeptides is for use in a vaccine.

E15. A vector comprising the polynucleotide of any one of E1 to E14.

E16. The vector of E15, wherein said vector is an adenoviral vector.

E17. The vector of E16, wherein said adenoviral vector is a gorilla adenoviral vector.

E18. A method of regulating the expression of a heterologous gene in a cell, the method comprising: introducing into said cell one or more polynucleotides that comprise (i) an repressible or inducible gene switch, and (ii) a heterologous immune response-inducing gene, wherein expression of said heterologous immune response-inducing gene is regulated by said gene switch, wherein said heterologous immune response-inducing gene encodes at least one of one or more HBV polypeptides; and exposing said cell to a compound in an amount sufficient to repress or induce expression of said heterologous immune response-inducing gene.

E19. The method of E18, wherein said target cell is a mammalian cell.

E20. The method of E18 or E19, wherein said gene switch comprises a ligand binding domain derived from at least one of an ecdysone receptor (EcR), a ubiquitous receptor, an orphan receptor 1, an NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a famesol receptor.

E21. A vector, wherein said vector comprises a polynucleotide that encodes at least one HBV peptide, wherein said vector is an adenoviral vector.

E22. A vector, wherein said vector comprises a polynucleotide that encodes at least one HBV peptide, wherein said vector is an adenoviral vector, wherein said adenoviral vector is a gorilla adenoviral vector.

E23. A polypeptide construct, wherein said polypeptide construct comprises an HBV HBx domain and at least one of an HBV Pol domain, an HBV Core domain, an HBV pre-Core domain or an HBV Surface domain.

E24. A polypeptide construct, wherein said polypeptide construct comprises a pre-Core domain and at least one of an HBV Pol domain, an HBV HBx domain or an HBV Surface domain.

E25. The polypeptide construct of E23 or E24, wherein said HBV HBx domain has a sequence as shown in SEQ ID NO: 98.

E26. The polypeptide construct of any one of E23 to E25, wherein said HBV Pol domain comprises a deletion of at least one amino acid as compared to a wildtype HBV Pol domain.

E27. The polypeptide construct of E26, wherein said deletion comprises a deleted portion of said wildtype HBV Pol domain, wherein said deleted portion comprises at least one of amino acids 538-544 or amino acids 710-742.

E28. The polypeptide construct of E27, wherein said deleted portion comprises both of amino acids 538-544 and amino acids 710-742.

E29. The polypeptide construct of E28, wherein said HBV Pol domain has a sequence as shown in SEQ ID NO: 99.

E30. The polypeptide construct of any one of E23 to E29, wherein said HBV Surface domain comprises at least one of a PreS1 domain, a PreS2 domain and an S domain.

E31. The polypeptide construct of E30, wherein said HBV Surface domain comprises an HBV S domain.

E32. The polypeptide construct of E30 or E31, wherein said HBV Surface domain has a sequence as shown in SEQ ID NO: 100.

E33. The polypeptide construct of any one of E24 to E32, wherein said polypeptide construct further comprises an HBV Core domain.

E34. The polypeptide of E23 or E33, wherein said polypeptide construct comprises a Core portion, wherein said Core portion comprises said HBV Core domain and said HBV pre-Core domain.

E35. The polypeptide construct of E34, wherein said Core portion has a sequence as shown in SEQ ID NO: 101.

E36. The polypeptide construct of E23 or E33, wherein said polypeptide construct comprises each of SHB(Env), HBeAg, HBx, and Pol domains.

E37. The polypeptide construct of E36, wherein said polypeptide construct comprises a structure, from N-terminus to C-terminus, of said SHB(Env), HBeAg, HBx, and Pol domains.

E38. The polypeptide construct of E36 or E37, wherein said SHB(Env) domain has a sequence as shown in SEQ ID NO: 102.

E39. The polypeptide construct of E36 or E37, wherein said HBeAg domain has a sequence as shown in SEQ ID NO: 103.

E40. The polypeptide construct of E36 or E37, wherein said HBx domain has a sequence as shown in SEQ ID NO: 104.

E41. The polypeptide construct of E36 or E37, wherein said Pol domain has a sequence as shown in SEQ ID NO: 105.

E42. The polypeptide construct of E36 or E37, wherein said polypeptide construct has a sequence as shown in SEQ ID NO: 106.

E43. The polypeptide construct of E36 or E37, further comprising a rigid linker.

E44. The polypeptide construct of E36 or E37, wherein said polypeptide has a sequence as shown in SEQ ID NO: 112.

E45. A polypeptide construct, wherein said polypeptide construct comprises one or more HBV HBx linkers and at least one of a Core domain, a Surface domain and a Pol domain, wherein one of said Core domain, said Surface domain and said Pol domain is connected to another of said Core domain, said Surface domain and said Pol domain by said one or more HBx linkers.

E46. The polypeptide construct of E45, wherein said Surface domain comprises at least one of an HBV PreS1 domain, an HBV PreS2 domain and an HBV S domain.

E47. The polypeptide construct of E45 or E46, wherein said one or more HBV

HBx linkers comprises multiple HBV HBx linkers.

E48. The polypeptide construct of E47, wherein at least two of said multiple HBV HBx linkers differ in an amino acid sequence.

E49. The polypeptide construct of any one of E45 to E48, wherein said HBV HBx linker has a sequence as shown in any one of HBx-1, HBx-2, HBx-3, HBx-4, HBx-5 or HBx-6 of Table 3.

E50. The polypeptide construct of any one of E45 to E49, wherein said Core domain is adjacent to said Surface domain.

E51. The polypeptide construct of E50, wherein said Surface domain comprises a PreS1 domain.

E52. The polypeptide construct of E50 or E51, wherein said Surface domain is connected to said Core domain by one of said one or more HBx linkers.

E53. The polypeptide construct of any one of E45 to E52, wherein said Pol domain is adjacent to a Surface domain.

E54. The polypeptide construct of E53, wherein said Surface domain comprises at least one of a PreS1 domain, a PreS2 domain and an S domain.

E55. The polypeptide construct of E54, wherein said Surface domain comprises said PreS1 domain, and an N-terminal portion of said Pol domain is adjacent to said PreS1 domain.

E56. The polypeptide construct of E55, wherein said N-terminal portion of said Pol domain is connected to said PreS1 domain by one of said one or more HBx linkers.

E57. The polypeptide construct of E56, wherein said Surface domain comprises said PreS2 domain, and an N-terminal portion of said Pol domain is adjacent to said PreS2 domain.

E58. The polypeptide construct of E57, wherein said N-terminal portion of said Pol domain is connected to said PreS2 domain by one of said one or more HBx linkers.

E59. The polypeptide construct of E58, wherein said Surface domain comprises said PreS2 domain, and a C-terminal portion of said Pol domain is adjacent to said PreS2 domain.

E60. The polypeptide construct of E59, wherein said C-terminal portion of said Pol domain is connected to said PreS2 domain by one of said one or more HBx linkers.

E61. The polypeptide construct of E60, wherein said Surface domain comprises said S domain, and a C-terminal portion of said Pol domain is adjacent to said S domain.

E62. The polypeptide construct of E61, wherein said C-terminal portion of said Pol domain is connected to said S domain by one of said one or more HBx linkers.

E63. The polypeptide construct of any one of E45 to E62, wherein said polypeptide construct has a sequence as shown in SEQ ID NO: 107.

E64. A polypeptide construct comprising an ankyrin-like repeat domain and one or more HBV peptides.

E65. The polypeptide construct of E64, wherein said ankyrin-like repeat protein is a human ankyrin-like repeat protein.

E66. The polypeptide construct of E64 or E65, wherein said one or more HBV peptides has a sequence as shown in any one of the amino acid sequences of Table 3.

E67. The polypeptide construct of any one of E64 to E66, wherein said one or more HBV peptides comprises one or more of a Core peptide, a Surface peptide, a Pol peptide and an HBSP/HBx peptide.

E68. The polypeptide construct of E67, wherein said one or more HBV peptides comprises a Core peptide, and said Core peptide has a sequence as shown in any one of the Core amino acid sequences of Table 3.

E69. The polypeptide construct of E67, wherein said one or more HBV peptides comprises a Surface peptide, and said Surface peptide has a sequence as shown in any one of the Surface amino acid sequences of Table 3.

E70. The polypeptide construct of E67, wherein said one or more HBV peptides comprises a Pol peptide, and said Pol peptide has a sequence as shown in any one of the Pol amino acid sequences of Table 3.

E71. The polypeptide construct of E67, wherein said one or more HBV peptides comprises an HBSP/HBx peptide, and said HBSP/HBx peptide has a sequence as shown in any one of the HBSP/HBx amino acid sequences of Table 3.

E72. The polypeptide construct of any one of E65 to E71, wherein said polypeptide construct has a sequence as shown in SEQ ID NO: 108.

E73. A polypeptide construct, wherein said polypeptide construct comprises at least two HBV amino acid sequences as shown in Table 3, wherein said at least two HBV amino acid sequences are connected by a peptide linker, wherein said peptide linker is a KK linker.

E74. The polypeptide construct of E73, wherein said comprises at least two HBV amino acid sequences comprise at least one of a Core peptide, a Surface peptide, a Pol peptide and an HBSP/HBx peptide as shown in Table 3.

E75. The polypeptide construct of E73 or E74, wherein said at least two HBV amino acid sequences comprise each of the amino acid sequences as shown in Table 3.

E76. The polypeptide construct of E75, wherein said each of the amino acid sequences is connected to another of said each of the amino acid sequences by said KK linker.

E77. The polypeptide construct of any one of E73 to E75, wherein said polypeptide construct has a sequence as shown in SEQ ID NO: 109.

E78. The polypeptide construct of any one of E23 to E77 for use in a vaccine.

E79. A polynucleotide encoding the polypeptide construct of any one of E25 to E78.

E80. A vector comprising the polynucleotide of E79.

E81. The vector of E80, wherein said vector is an adenoviral vector.

E82. The vector of E81, wherein said adenoviral vector is a gorilla adenoviral vector.

SEQUENCES

Provided herein is a representative list of certain sequences included in embodiments provided herein (Table 6).

TABLE 6

| Polynucleotide/Amino Acid Sequences | |
|---|---|
| SEQ ID NO: | Description |
| 1 | Adenovirus pIX fragment nucleotides |
| 2 | Adenovirus DNA polymerase fragment nucleotides |
| 3 | Adenovirus penton base protein fragment nucleotides |

TABLE 6-continued

| SEQ ID NO: | Description |
|---|---|
| Polynucleotide/Amino Acid Sequences | |
| 4 | Adenovirus hexon protein fragment nucleotides |
| 5 | Adenovirus fiber protein fragment nucleotides |
| 6 | Adenovirus pIX nucleotides |
| 7 | Adenovirus DNA polymerase nucleotides |
| 8 | Adenovirus penton base protein nucleotides |
| 9 | Adenovirus hexon protein nucleotides |
| 10 | Adenovirus fiber protein nucleotides |
| 11 | Adenovirus pIX protein fragment |
| 12 | Adenovirus DNA polymerase fragment |
| 13 | Adenovirus penton base protein fragment |
| 14 | Adenovirus hexon protein fragment |
| 15 | Adenovirus fiber protein fragment |
| 16 | Adenovirus pIX amino acids |
| 17 | Adenovirus DNA polymerase amino acids |
| 18 | Adenovirus penton base protein |
| 19 | Adenovirus hexon protein |
| 20 | Adenovirus fiber protein |
| 21 | Adenovirus vector nucleotide sequences |
| 22 | Adenovirus vector nucleotide sequences |
| 23 | Adenovirus vector nucleotide sequences |
| 24 | Adenovirus vector nucleotide sequences |
| 25 | Adenovirus vector nucleotide sequences |
| 26 | IL-2 core promoter |
| 27 | IL-2 minimal promoter |
| 28 | IL-2 enhancer and promoter variant |
| 29 | L-2 enhancer and promoter variant |
| 30 | $(NF\text{-}\kappa B)_1$-IL2 promoter variant |
| 31 | $(NF\text{-}\kappa B)_3$-IL2 promoter variant |
| 32 | $(NF\text{-}\kappa B)_6$-IL2 promoter variant |

TABLE 6-continued

| SEQ ID NO: | Description |
|---|---|
| Polynucleotide/Amino Acid Sequences | |
| 33 | 1X NFAT response elements-IL2 promoter variant |
| 34 | 3X NFAT response elements-IL2 promoter variant |
| 35 | 3X NFAT response elements-IL2 promoter variant |
| 36 | 6X NFAT response elements-IL2 promoter variant |
| 37 | 6X NFAT response elements-IL2 promoter variant |
| 38 | 6X NFAT response elements-IL2 promoter variant |
| 39 | 6X NFAT response elements-IL2 promoter variant |
| 40 | human EEF1A1 promoter variant |
| 41 | human EEF1A1 promoter variant |
| 42 | human EEF1A1 promoter and enhancer |
| 43 | human UBC promoter |
| 44 | synthetic minimal promoter 1 |
| 61 | GCAd-RTS-IL12 design 1 |
| 62 | GCAd-RTS-IL12 design 2 |
| 63 | GCAd-RTS-IL12 design 3 |
| 98 | HBV HBx domain of HBV design 1 |
| 99 | HBV Pol domain of HBV design 1 |
| 100 | HBV Surface (Env1) domain of HBV domain 1 |
| 101 | HBV Core domain of HBV design 1 |
| 102 | SHB(Env) domain |
| 103 | HBeAg domain |
| 104 | HBx domain |
| 105 | Pol domain |
| 106 | HBV design 1 |
| 107 | HBV design 2 |
| 108 | HBV design 3 |
| 109 | HBV design 4 |
| 112 | HBV design 5 |

What is claimed is:

1. A polypeptide construct, wherein said polypeptide construct comprises:

(a) an HBV HBx domain, an HBV Pol domain, an HBV Core domain, and an HBV Surface domain; or (b) a pre-Core domain, an HBV Pol domain, an HBV HBx domain, and an HBV Surface domain, wherein the HBV Pol domain comprises the amino acid sequence set forth in SEQ ID NO: 99.

2. The polypeptide construct of claim 1, wherein said HBV HBx domain comprises the amino acid sequence set forth in SEQ ID NO: 104.

3. The polypeptide construct of claim 2, wherein said HBV Core domain comprises the amino acid sequence set forth in SEQ ID NO: 101.

4. The polypeptide construct of claim 1, further comprising a rigid linker.

5. A polynucleotide encoding the polypeptide construct of claim 1.

6. A vector comprising the polynucleotide of claim 5.

7. The polynucleotide of claim 5 for use in a vaccine.

8. The polypeptide construct of claim 3, wherein

Surface domain comprises the amino acid sequence set forth in SEQ ID NO: 100.

9. The polypeptide of claim 8, further comprising a rigid linker between one or more of said HBV Pol domain, said HBV Core domain, said HBV Surface domain, and said HBV HBx domain.

10. The polypeptide construct of claim 9, wherein the rigid linker comprises the amino acid sequence set forth in SEQ ID NO: 129.

11. A polypeptide construct, wherein the polypeptide construct comprises:

(i) an HBV Pol domain comprising the amino acid sequence set forth in SEQ ID NO: 99;

(ii) an HBV Surface domain comprising the amino acid sequence set forth in SEQ ID NO: 100;

(iii) an HBV Core domain comprising the amino acid sequence set forth in SEQ ID NO: 101; and (iv) an HBV HBx domain comprising the amino acid sequence set forth in SEQ ID NO: 104.

12. The polypeptide construct of claim 11, wherein one or more of the HBV domains are connected by a rigid linker.

13. The polypeptide construct of claim 12, wherein one or more of the rigid linkers comprise the amino acid sequence set forth in SEQ ID NO: 129.

14. A polynucleotide encoding the polypeptide construct in any one of claims 11 to 13.

15. A vector comprising the polynucleotide of claim 14.

16. The polynucleotide of claim 14 for use in a vaccine.

* * * * *